(12) United States Patent
Jo

(10) Patent No.: US 10,774,123 B2
(45) Date of Patent: *Sep. 15, 2020

(54) CELL-PERMEABLE BONE MORPHOGENETIC PROTEIN (CP-BMP) RECOMBINANT PROTEIN AND USE THEREOF

(71) Applicant: CELLIVERY THERAPEUTICS, INC., Seoul (KR)

(72) Inventor: Daewoong Jo, Brentwood, TN (US)

(73) Assignee: CELLIVERY THERAPEUTICS, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,884

(22) Filed: Jan. 31, 2018

(65) Prior Publication Data

US 2018/0237485 A1 Aug. 23, 2018

Related U.S. Application Data

(63) Continuation of application No. PCT/KR2016/009405, filed on Aug. 25, 2016, which is a continuation of application No. 14/838,318, filed on Aug. 27, 2015, now abandoned.

(51) Int. Cl.
| | | |
|---|---|---|
| C07K 14/51 | (2006.01) |
| C07K 7/08 | (2006.01) |
| C07K 14/47 | (2006.01) |
| A61K 38/17 | (2006.01) |
| A61K 38/00 | (2006.01) |
| C07K 7/06 | (2006.01) |
| A61K 38/08 | (2019.01) |
| A61K 38/10 | (2006.01) |

(52) U.S. Cl.
CPC .......... *C07K 14/51* (2013.01); *A61K 38/1761* (2013.01); *C07K 7/08* (2013.01); *C07K 14/47* (2013.01); *C07K 14/4703* (2013.01); *A61K 38/00* (2013.01); *A61K 38/08* (2013.01); *A61K 38/10* (2013.01); *A61K 38/1709* (2013.01); *C07K 7/06* (2013.01); *C07K 14/4702* (2013.01); *C07K 2319/00* (2013.01); *C07K 2319/01* (2013.01); *C07K 2319/10* (2013.01); *C07K 2319/21* (2013.01); *C07K 2319/40* (2013.01)

(58) Field of Classification Search
None
See application file for complete search history.

(56) References Cited

U.S. PATENT DOCUMENTS

| | | |
|---|---|---|
| 2003/0104622 A1 | 6/2003 | Robbins et al. |
| 2004/0197867 A1 | 10/2004 | Titus et al. |
| 2010/0197598 A1 | 8/2010 | Jo et al. |
| 2010/0209447 A1 | 8/2010 | Kumar-Singh et al. |
| 2014/0141452 A1 | 5/2014 | Watt et al. |
| 2014/0186379 A1 | 7/2014 | Jo et al. |
| 2016/0060310 A1* | 3/2016 | Jo .............. C07K 7/08 530/350 |
| 2016/0060311 A1* | 3/2016 | Jo .............. C07K 7/08 530/327 |
| 2016/0060312 A1* | 3/2016 | Jo .............. C07K 7/08 530/327 |
| 2016/0060313 A1* | 3/2016 | Jo .............. C07K 7/08 530/327 |
| 2016/0060314 A1* | 3/2016 | Jo .............. C07K 7/08 530/327 |
| 2016/0060319 A1* | 3/2016 | Jo .............. C07K 7/08 530/327 |
| 2016/0068825 A1* | 3/2016 | Jo .......... C12N 9/0065 424/94.3 |
| 2016/0083441 A1* | 3/2016 | Jo ........... C07K 14/47 514/19.3 |
| 2017/0029798 A1* | 2/2017 | Jo .............. C12N 9/93 |
| 2017/0137482 A1* | 5/2017 | Jo .............. C07K 7/08 |
| 2017/0190754 A1* | 7/2017 | Jo .............. C07K 7/08 |
| 2017/0198019 A1* | 7/2017 | Jo ............. C07K 14/47 |
| 2017/0226168 A1* | 8/2017 | Jo ........... C07K 14/4703 |
| 2017/0240598 A1* | 8/2017 | Jo .............. C07K 7/08 |
| 2018/0051060 A1* | 2/2018 | Jo ........... C07K 14/4703 |
| 2018/0171322 A1* | 6/2018 | Jo .............. C12N 9/93 |
| 2018/0195047 A1* | 7/2018 | Jo ........... C07K 14/435 |
| 2018/0230444 A1* | 8/2018 | Jo .............. C12N 9/00 |
| 2018/0291073 A1* | 10/2018 | Jo .............. C07K 7/08 |

FOREIGN PATENT DOCUMENTS

| | | |
|---|---|---|
| EP | 1 362 917 A3 | 11/2003 |
| EP | 2 784 081 A1 | 10/2014 |
| JP | 2010-516758 A | 5/2010 |
| KR | 10-2008-0044710 A | 5/2008 |
| KR | 10-1258279 B1 | 4/2013 |

(Continued)

OTHER PUBLICATIONS

GenBank entry ACV32593, downloaded Feb. 25, 2019.*
European Patent Office; Communication dated Aug. 9, 2018 in European application No. 16839619.0.
Hamed Alborzinia et al., "Quantitative kinetics analysis of BMP2 uptake into cells and its modulation by BMP antagonists", Journal of Cell Science, vol. 126, No. 1, pp. 117-127, XP055495837, Oct. 17, 2012, 11 pages.
International Searching Authority, Communication dated Nov. 16, 2015 in PCT/KR2015/008544.
Australian Patent Office, Communication dated Oct. 13, 2017 by the Australian Patent Office in Application No. 2015304194.

(Continued)

*Primary Examiner* — Fred H Reynolds
(74) *Attorney, Agent, or Firm* — Sughrue Mion, PLLC

(57) ABSTRACT

The present invention provides the CP-BMP recombinant protein with technical advantages as an intracellular protein therapy for the treatment of bone defects caused by osteogenesis imperfecta, osteoporosis, fracture and osteoctomy in that it could resolve cell-/tissue-permeability and bio-transfer function.

12 Claims, 99 Drawing Sheets

Specification includes a Sequence Listing.

(56) References Cited

FOREIGN PATENT DOCUMENTS

| WO | 01/27154 A3 | 4/2001 | | |
|---|---|---|---|---|
| WO | 03/097671 A1 | 11/2003 | | |
| WO | 2008/093982 A1 | 8/2008 | | |
| WO | 2009/139599 A2 | 11/2009 | | |
| WO | 2012/050402 A2 | 4/2012 | | |
| WO | 2012/072088 A1 | 6/2012 | | |
| WO | 2016/028036 A1 | 2/2016 | | |
| WO | WO-2016028036 A1 * | 2/2016 | ............... | C07K 7/08 |
| WO | WO-2017026776 A1 * | 2/2017 | ........... | C07K 14/435 |
| WO | WO-2017026779 A1 * | 2/2017 | ............... | C12N 9/00 |
| WO | WO-2017030323 A1 * | 2/2017 | ............... | C07K 7/08 |

OTHER PUBLICATIONS

European Patent Office, communication dated Nov. 27, 2017 by the European Patent Office in Application No. 15 833 496.1.

Japanese Patent Office; Communication dated Feb. 20, 2018 in counterpart Japanese application No. 2017-510405.

European Patent Office; Communication dated Feb. 9, 2018 in European application No. 15833496.1.

ChemPages. Hydrophobic Amino Acids. Datasheet [online], ChemPages Netorials. [retrieved on Jun. 15, 2018], Retrieved from the internet: URL:https://www.chem.wisc.edu/deptfiles/genchem/neotorial/modules/biomolecules/modules/protein1/prot13.htm, 1 page.

Medical Physiology/Basic Biochemistry/Amino Acids. Classification of Amino Acids, [retrieved on Jun. 15, 2018], Retrieved from the internet: URL:https://en.wikibooks.org/w/index.php?title=MedicaLPhysiology/Basic_Biochemistry/Amino_Acids_and_Proteins & oldid=3436225. Last edited on Jun. 15, 2018, 4 pages total.

ExPASy. ProtParam.Gasteiger, E et al. Protein identification and analysis tools on the ExPASy server. In: The Proteomics Protocols Handbook; Ed.: John M. Walker. Copyright 2005 Humana Press, [retrieved on Jun. 15, 2018],Retrieved from the internet <https://web.expasy.org/cgi-bin/protparam/protparam, 6 pages.

Christopher L Murriel et al., "Influence of protein transduction domains on intracellular delivery of macromolecules", Expert Opinion, Drug Deli, informa healthcare, vol. 3, No. 6, pp. 739-746, Nov. 1, 2006, XP008107388, 8 pages.

Dror Ben-David et al., "Low dose BMP-2 treatment for bone repair using a PEGylated fibrinogen hydrogel matrix", Biomaterials, vol. 34, No. 12, pp. 2902-2910, Jan. 31, 2013, XP028971197, 9 pages.

Xiaojun Zhou et al., "BIV1P-2 Derived Peptide and Dexamethasone Incorporated Mesoporous Silica Nanoparticles for Enhanced Osteogenic Differentiation of Bone Mesenchymal Stem Cells", ACS Applied Materials & Interfaces, vol. 7, No. 29, Jul. 14, 2015, pp. 15777-15789, XP055495881, 13 pages.

Jacek Hawiger, "Noninvasive intracellular delivery of functional peptides and proteins", Current Opinion in Chemical Biology, vol. 3, pp. 89-94, Feb. 1, 1999, XP001009450, 6 pages.

Janette N. Zara et al., "High Doses of Bone Morphogenetic Protein 2 Induce Structurally Abnormal Bone and Inflammation In Vivo", Tissue Engineering: Part A, vol. 17, Nos. 9 and 10, May 1, 2011, pp. 1389-1399, XP055495878, 11 pages.

International Search Report for PCT/KR2016/009405, dated Nov. 25, 2016 (PCT/ISA/210).

Written Opinion of the International Searching Authority for PCT/KR2016/009405, dated Nov. 25, 2016 (PCT/ISA/237).

* cited by examiner

[Figure 1]
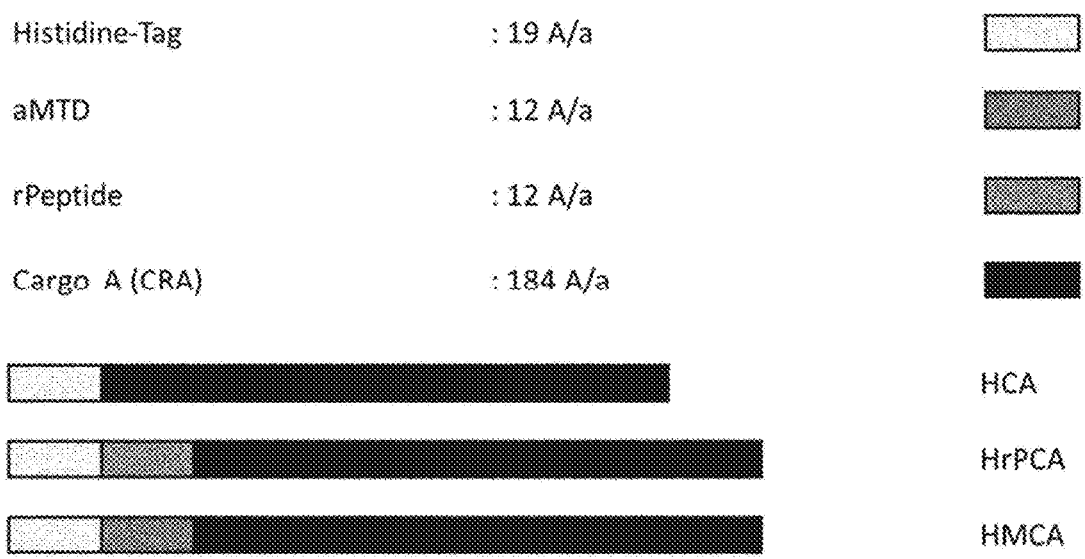
[Figure 2a]
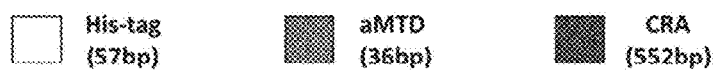
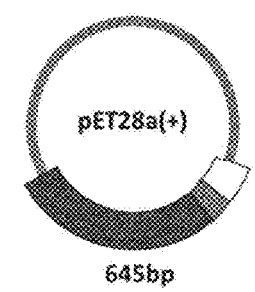

[Figure 2b]
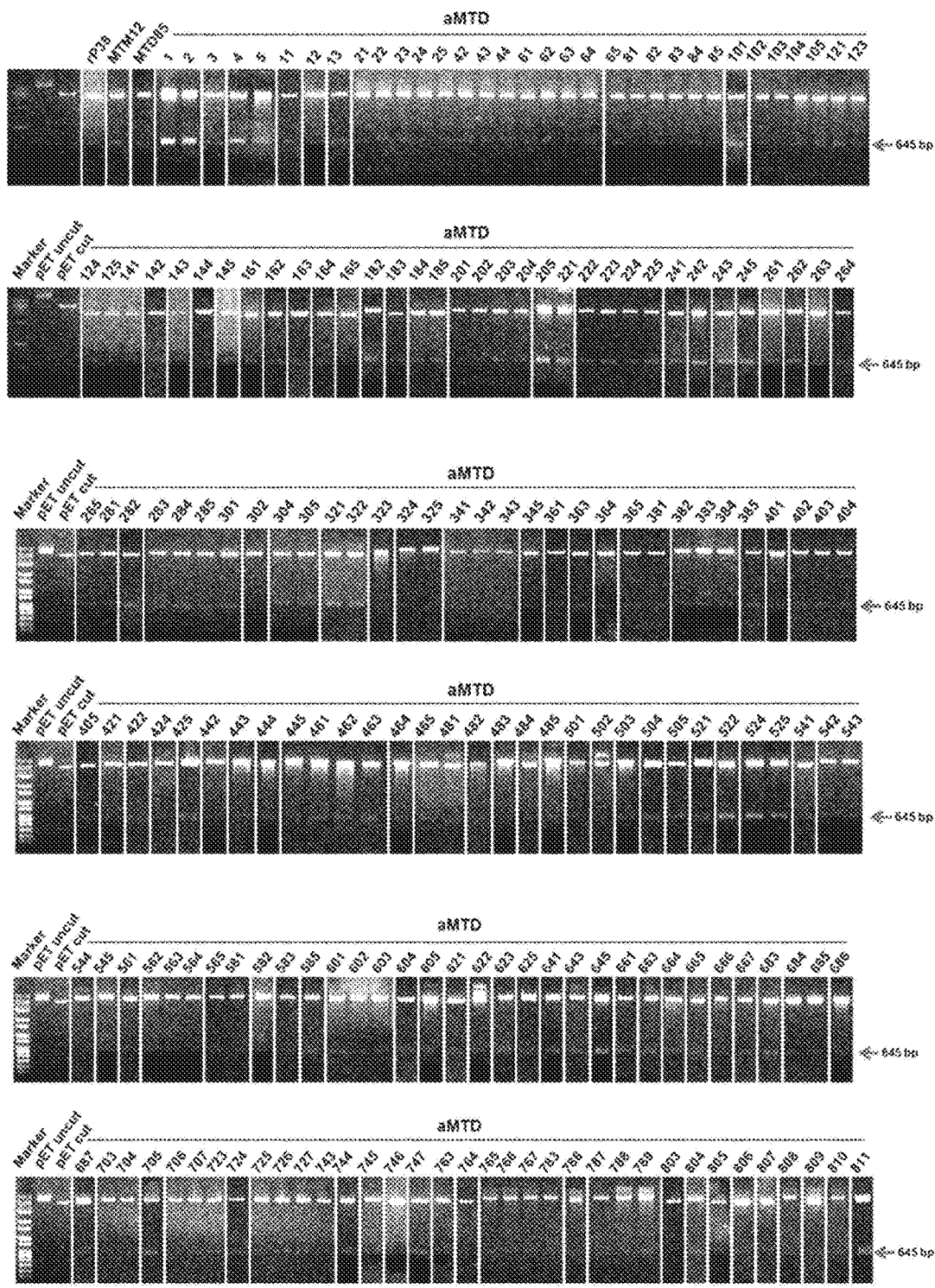

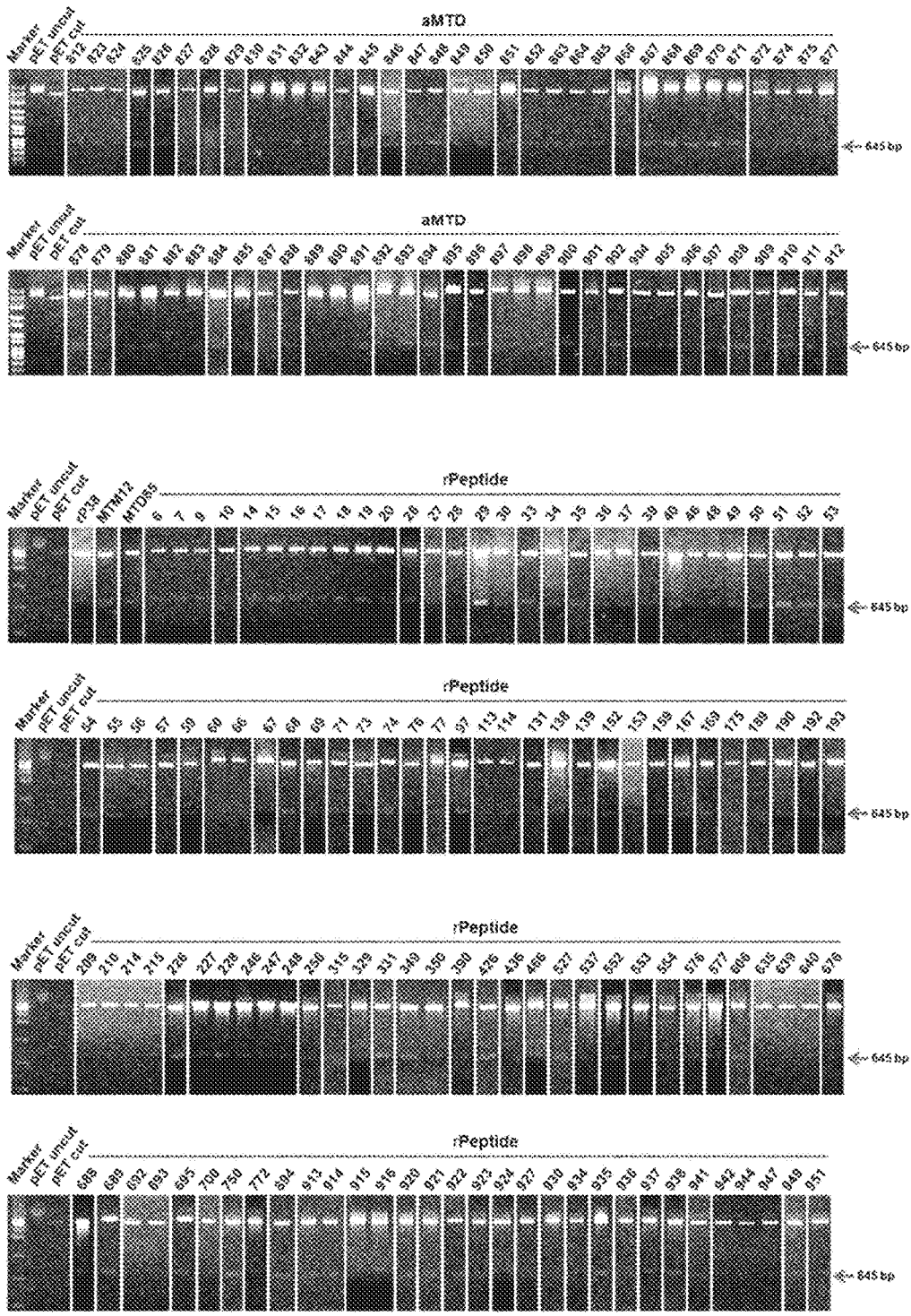
[Figure 2c]

[Figure 3a]
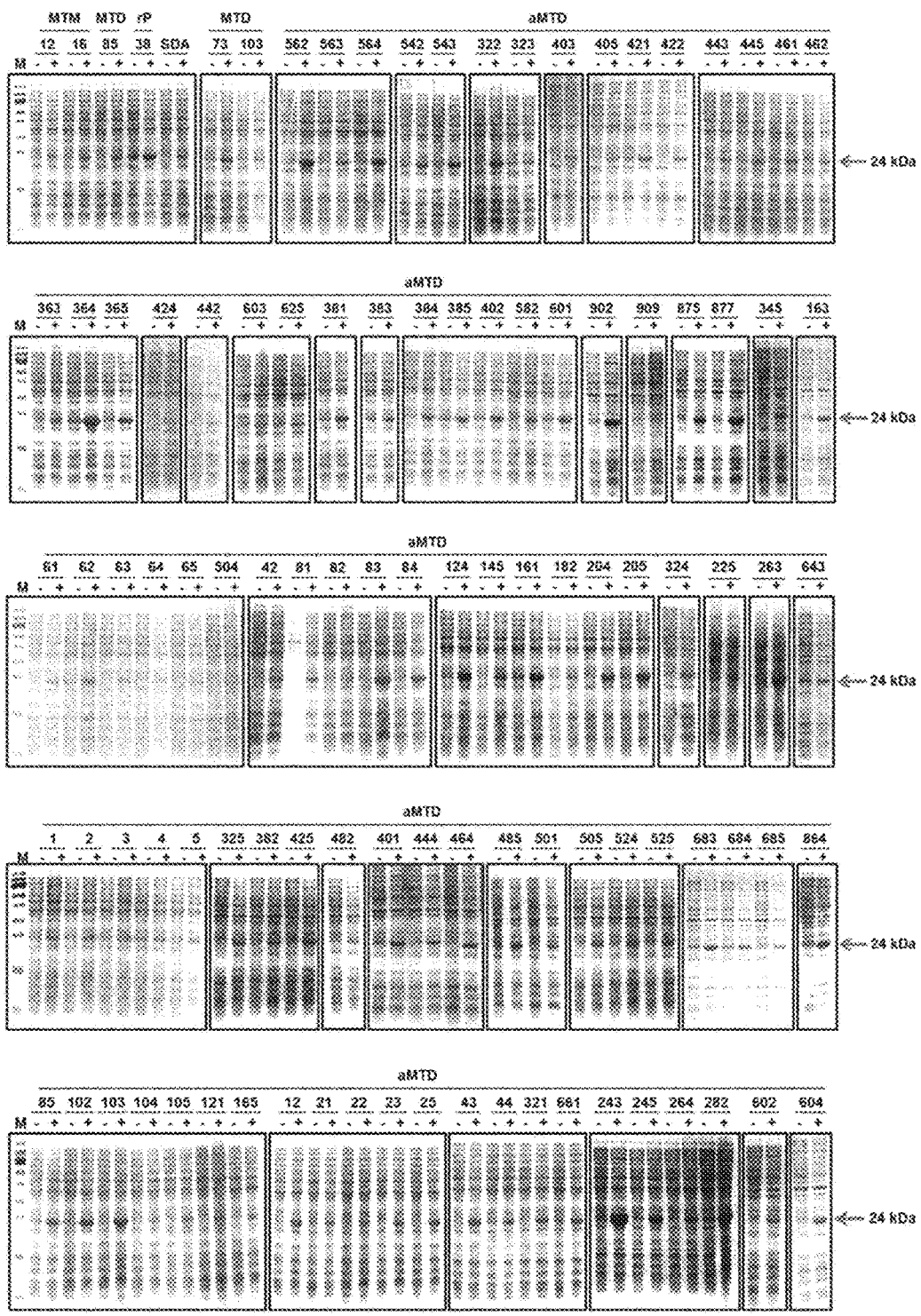

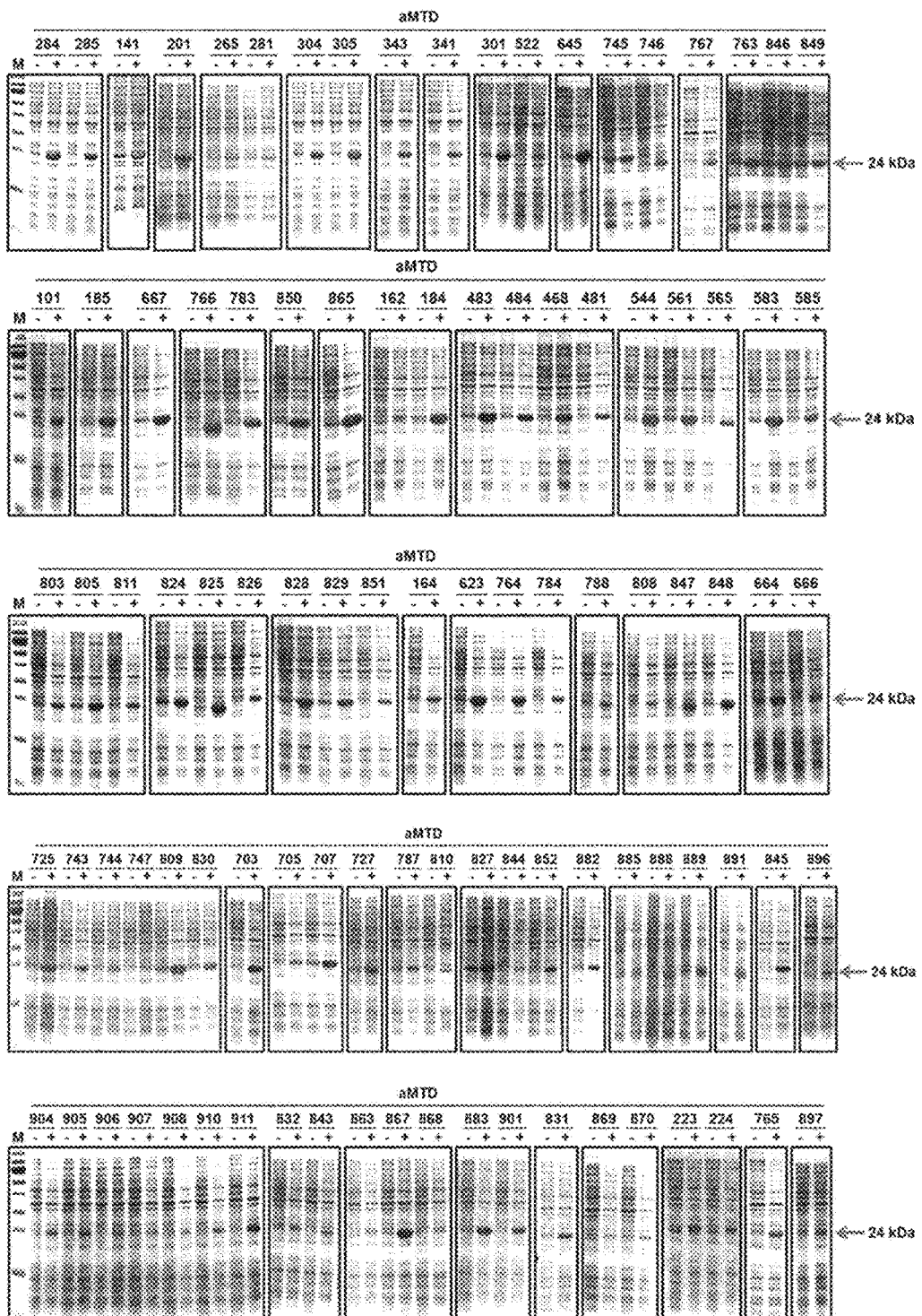
[Figure 3b]

[Figure 3c]
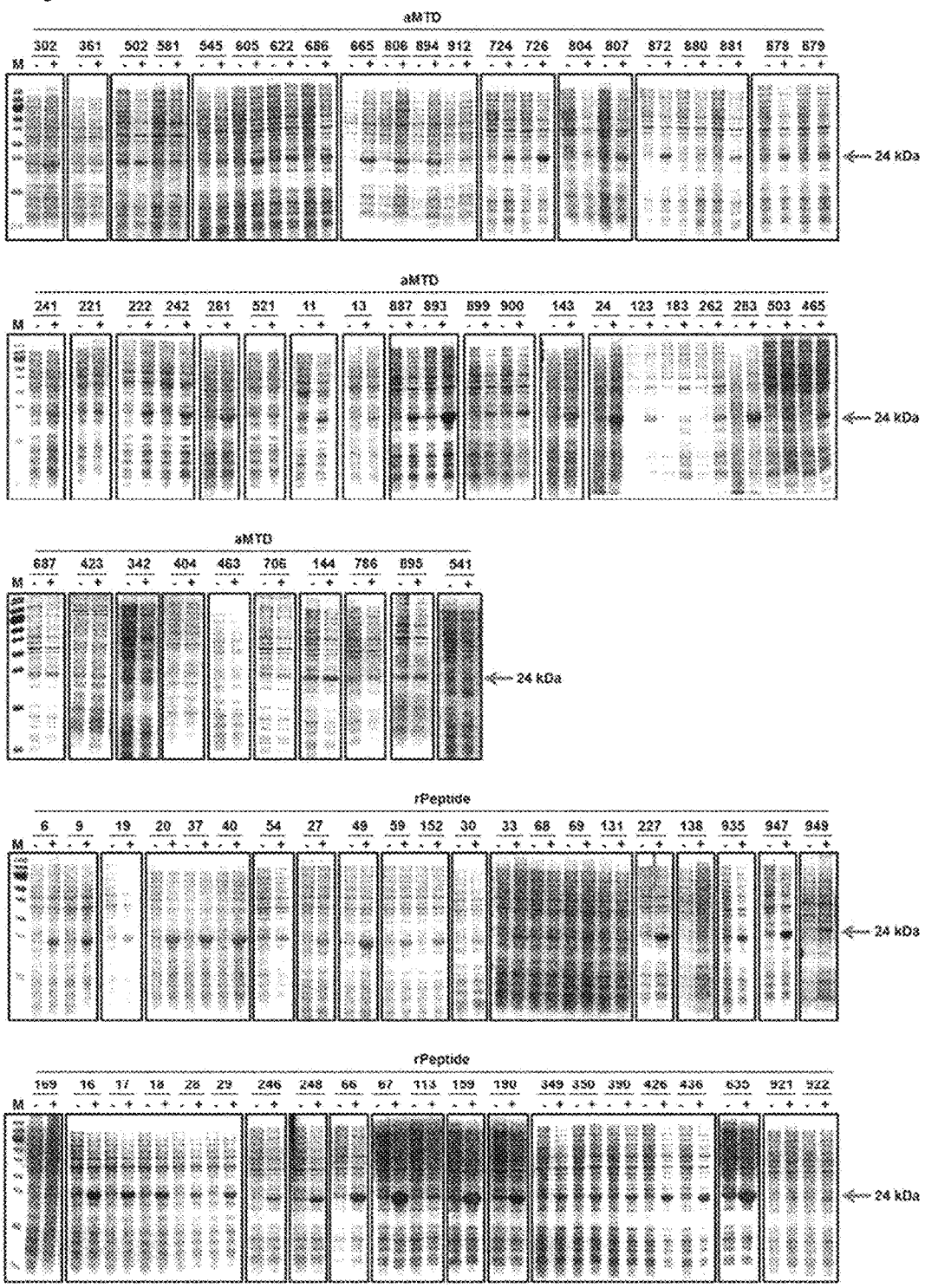

[Figure 3d]
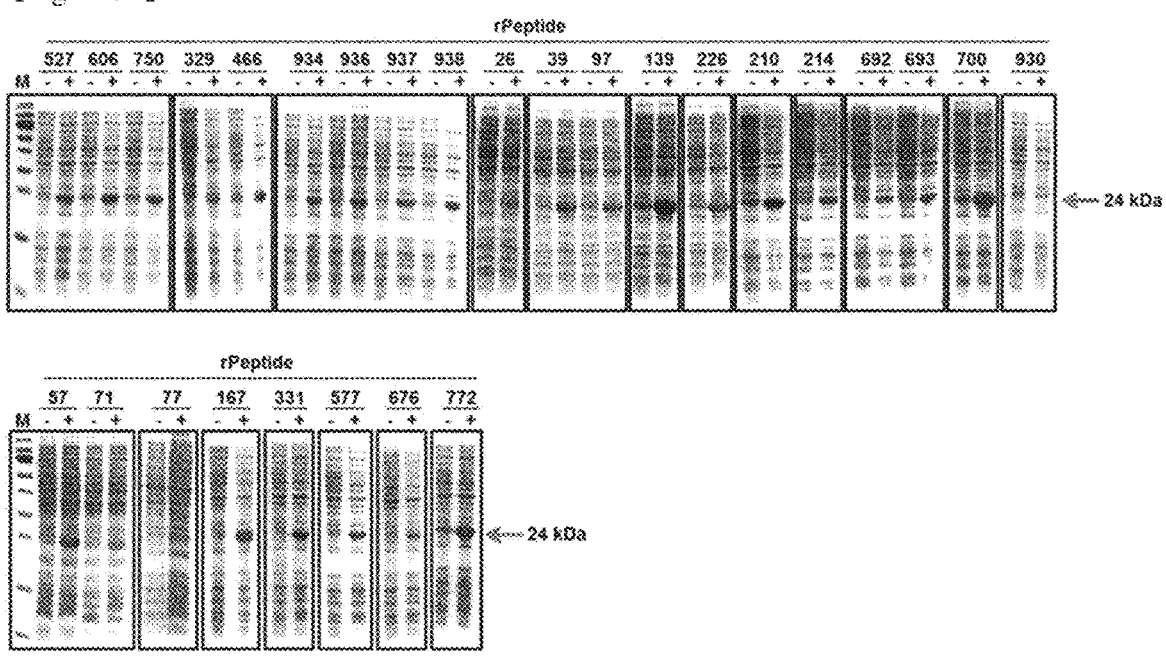

[Figure 4a]
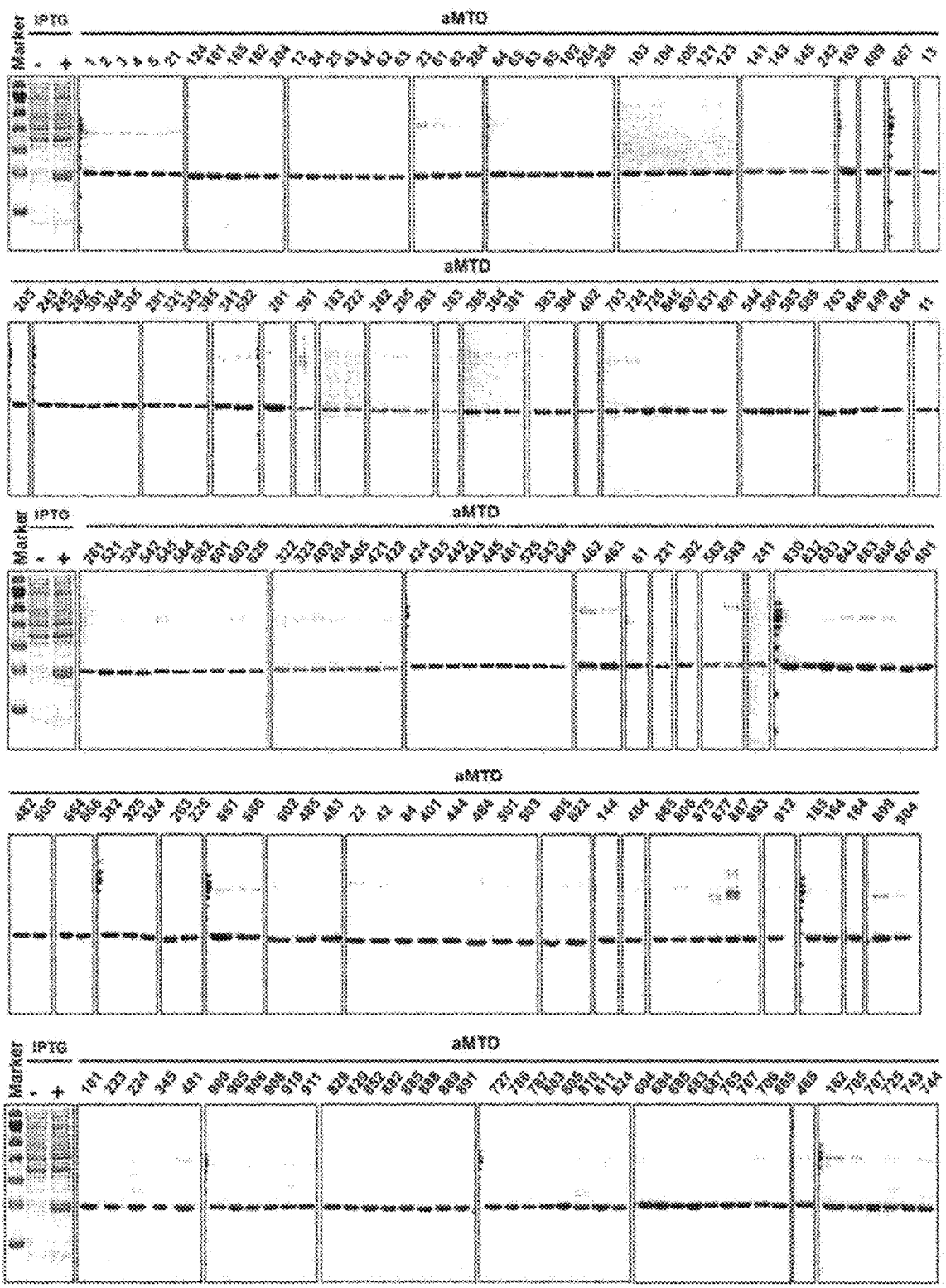

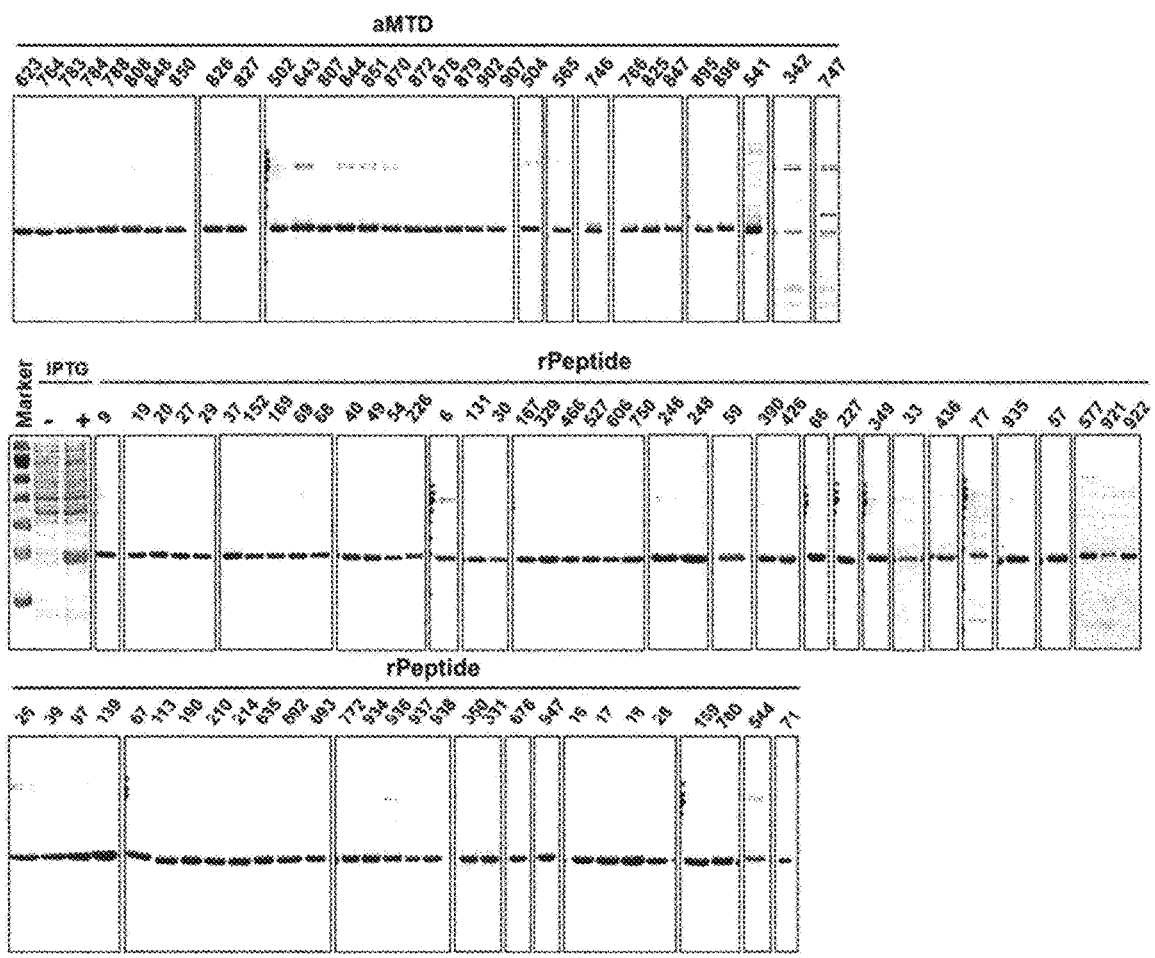

[Figure 5a]
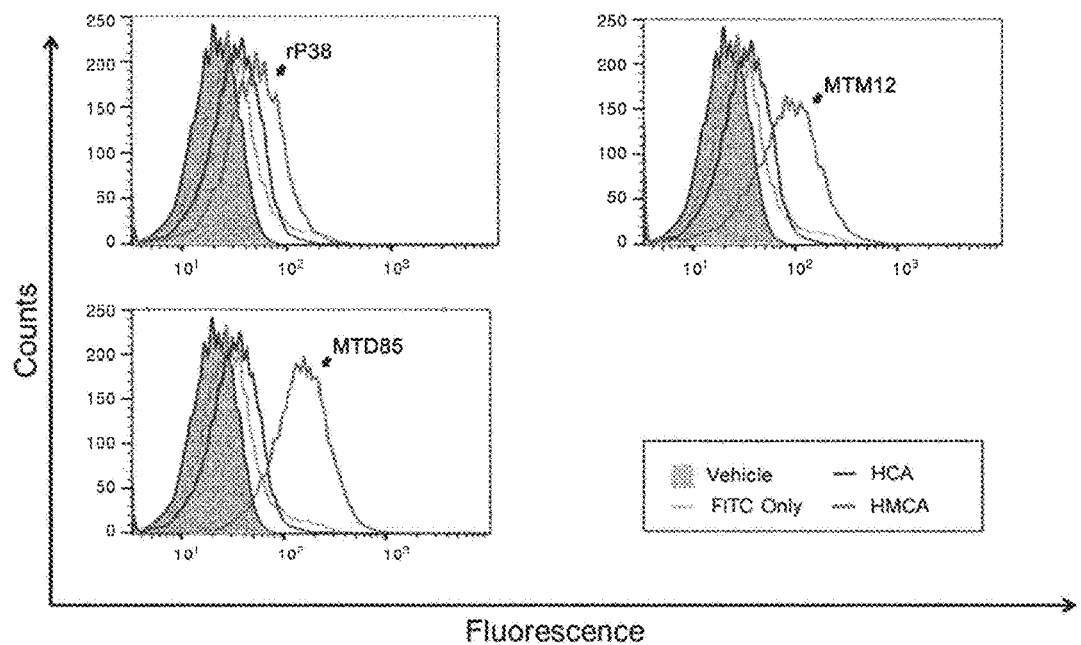
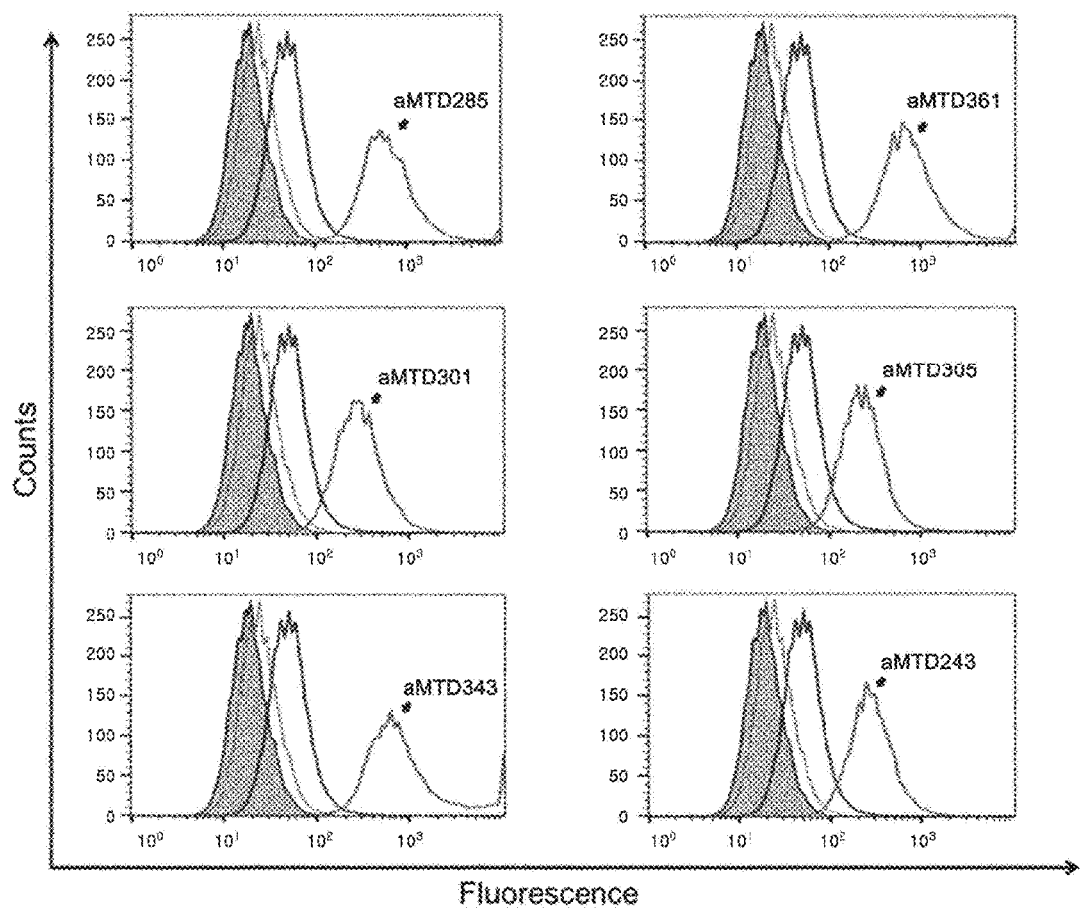

[Figure 5b]
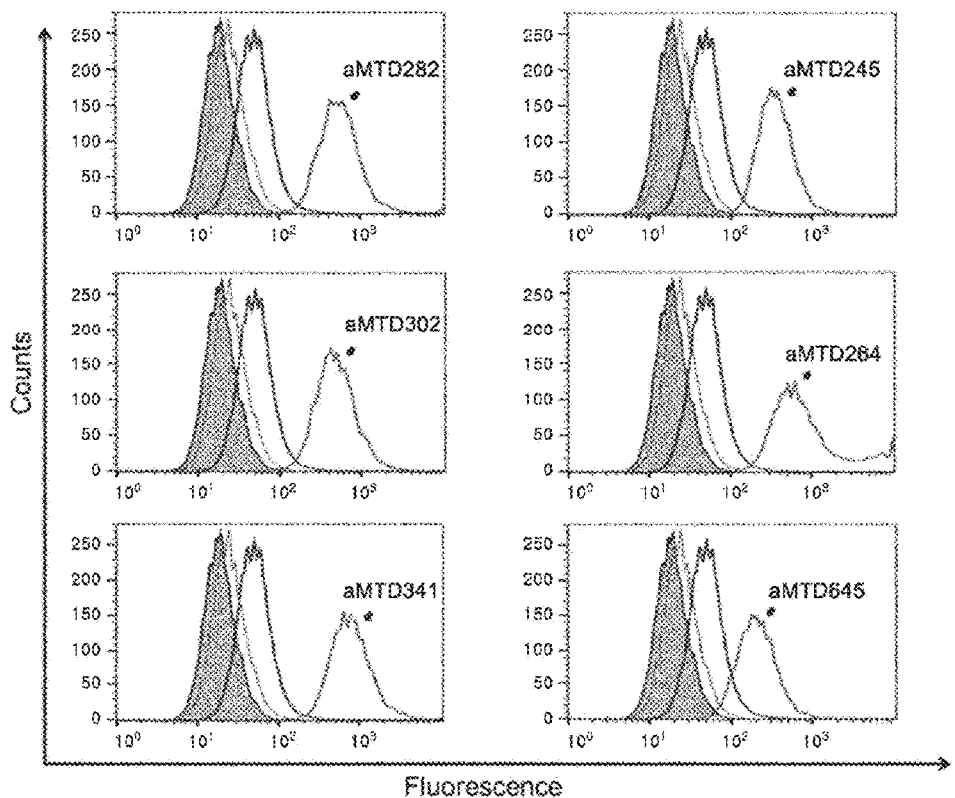
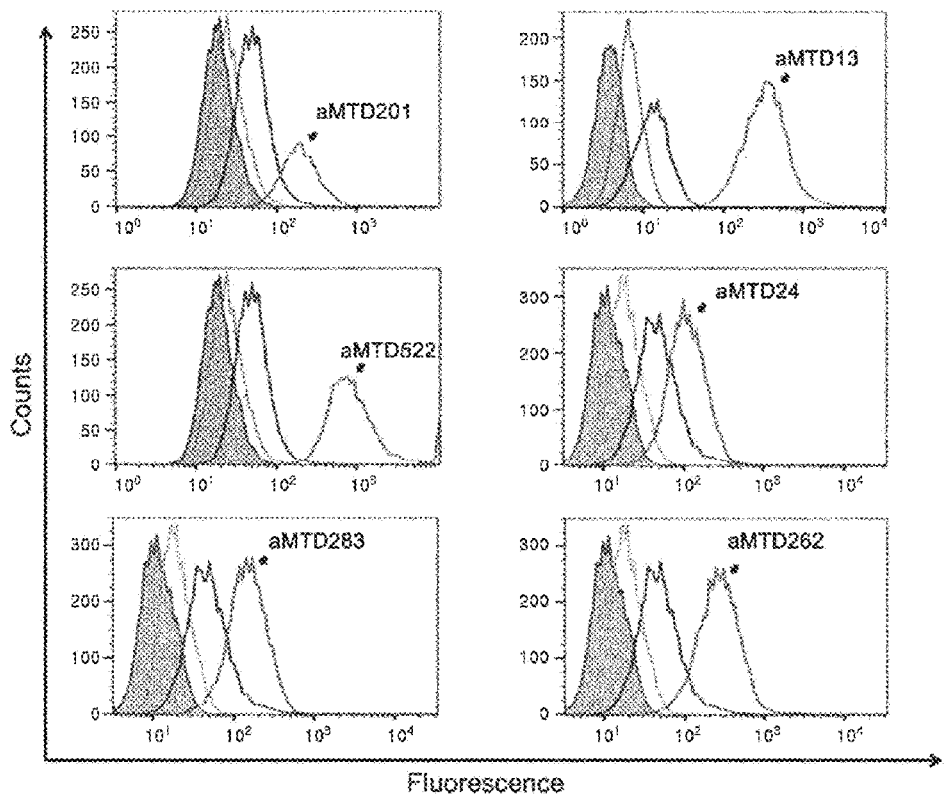

[Figure 5c]
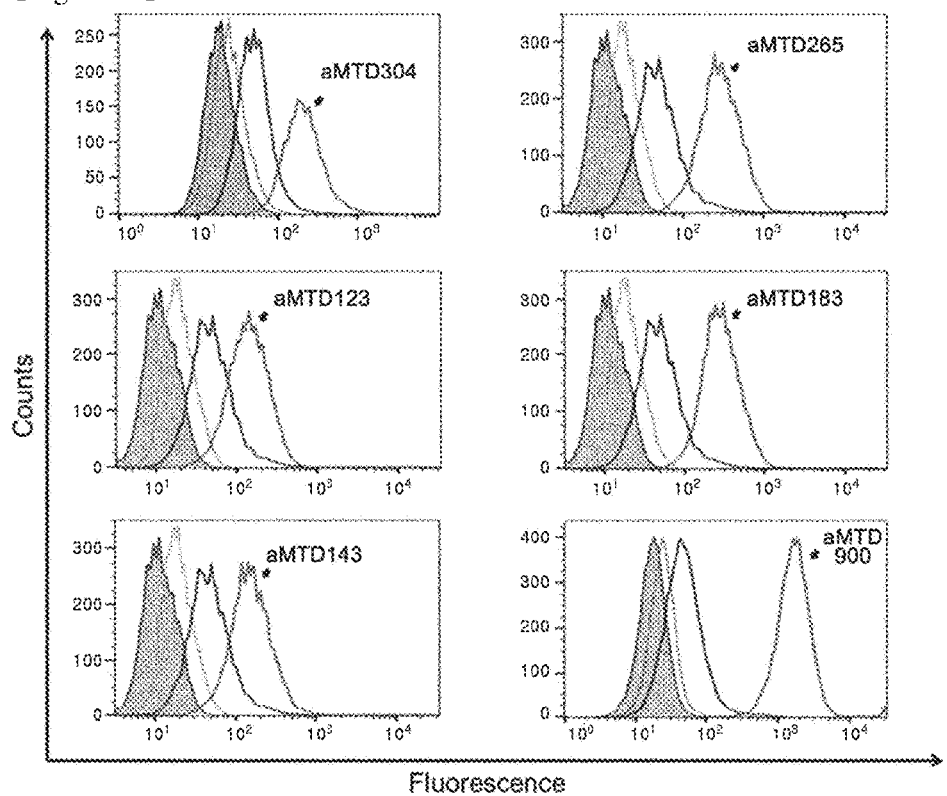
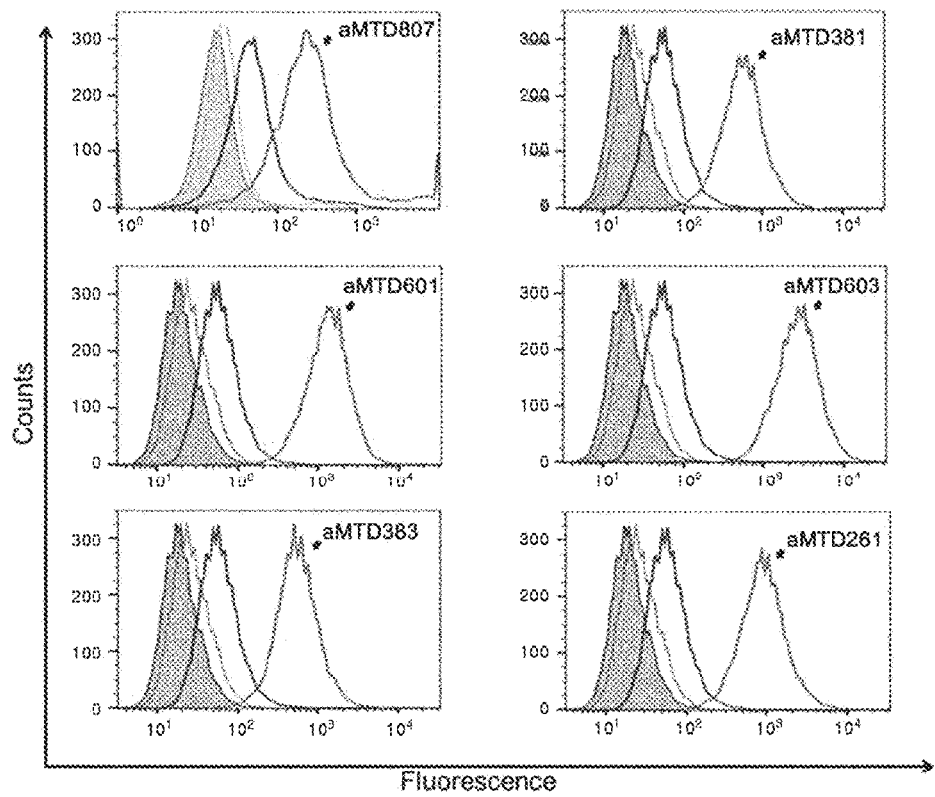

[Figure 5d]
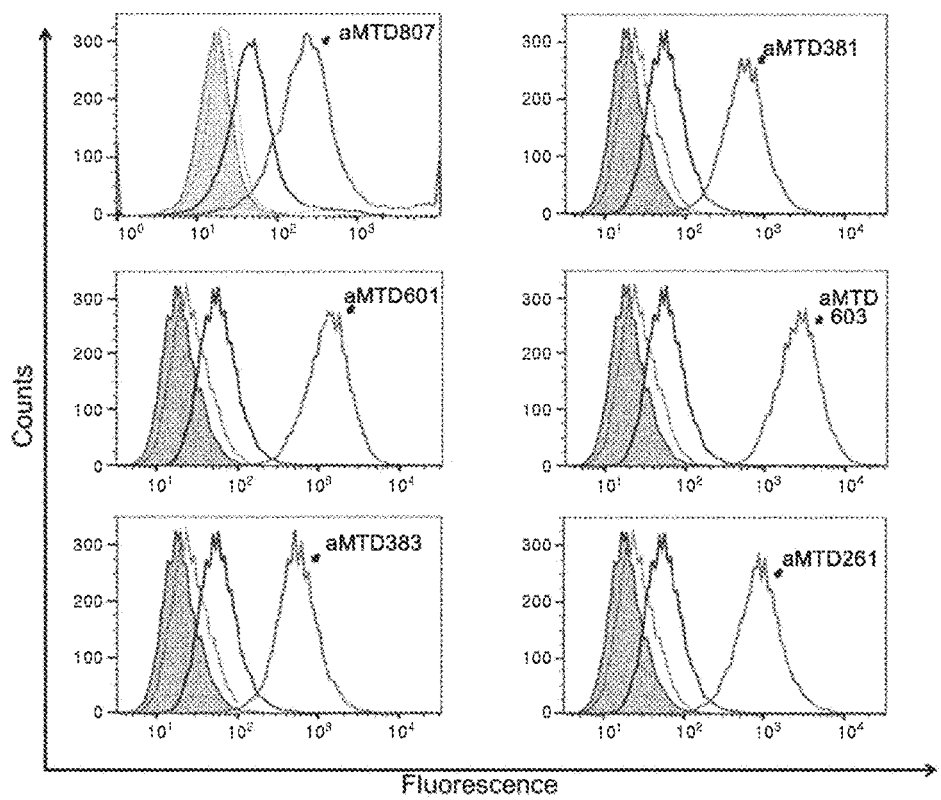
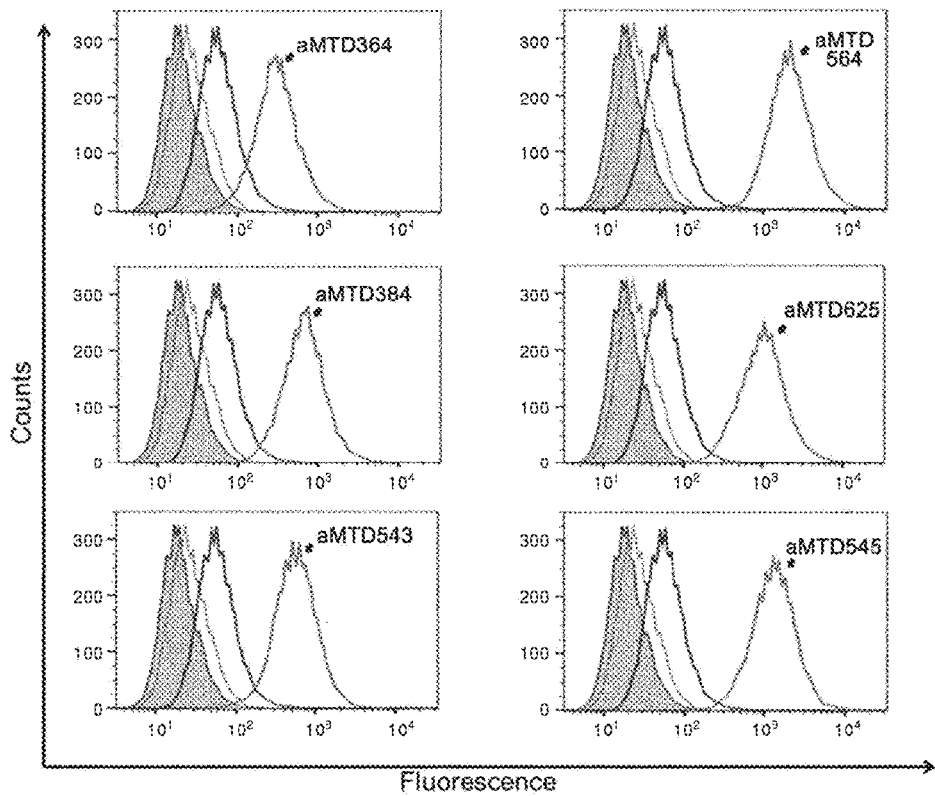

[Figure 5e]
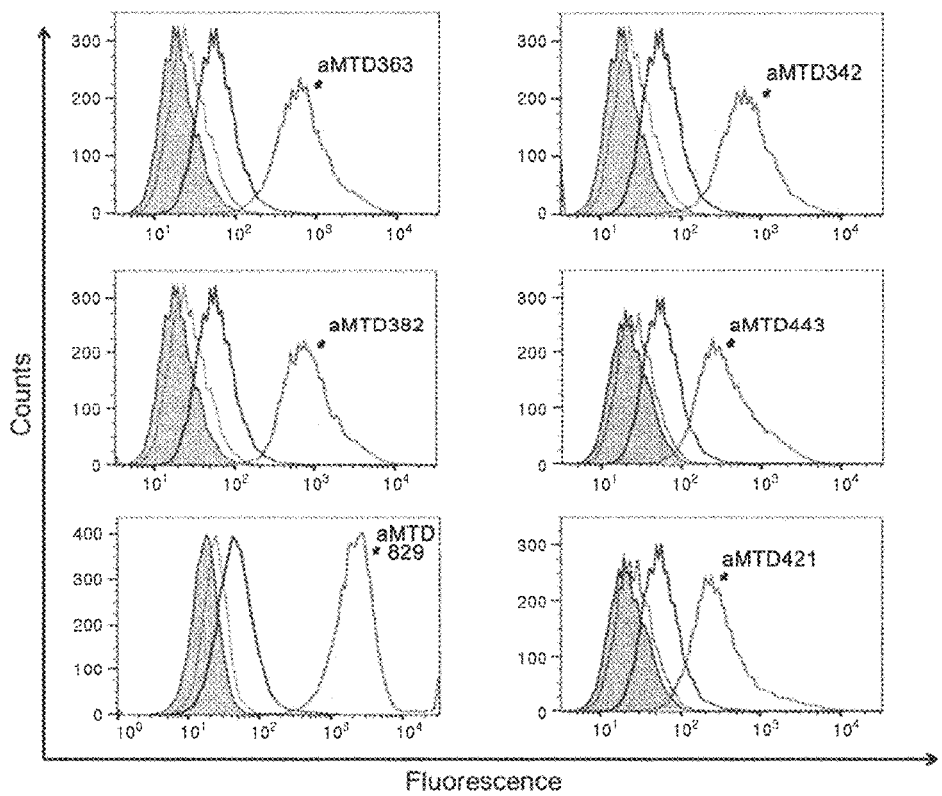
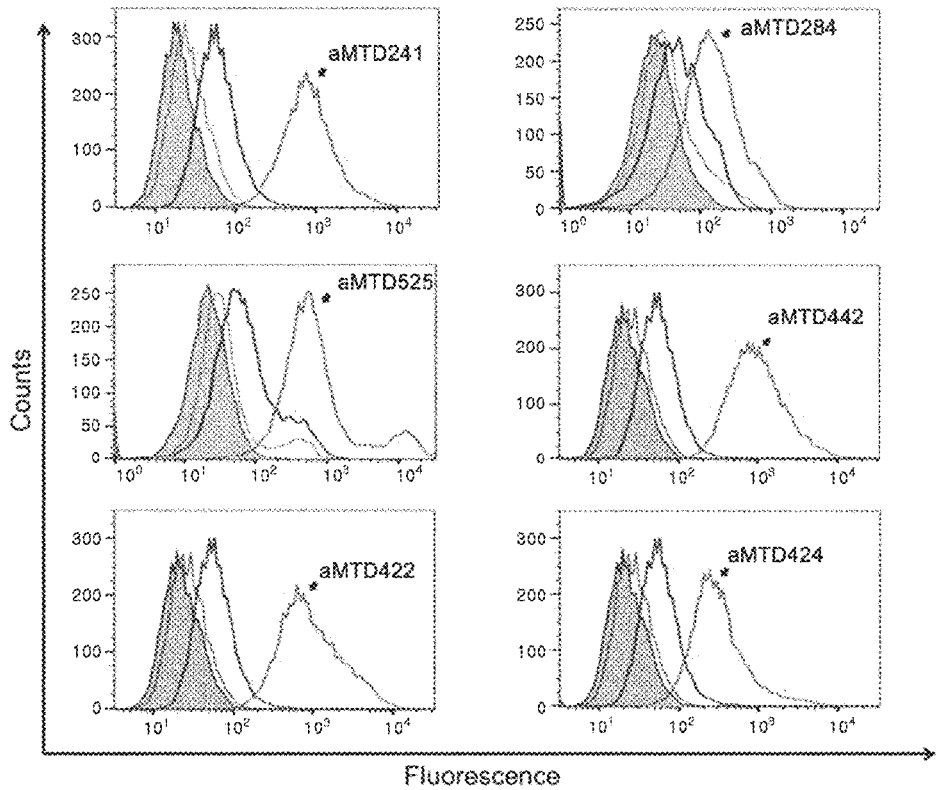

[Figure 5f]
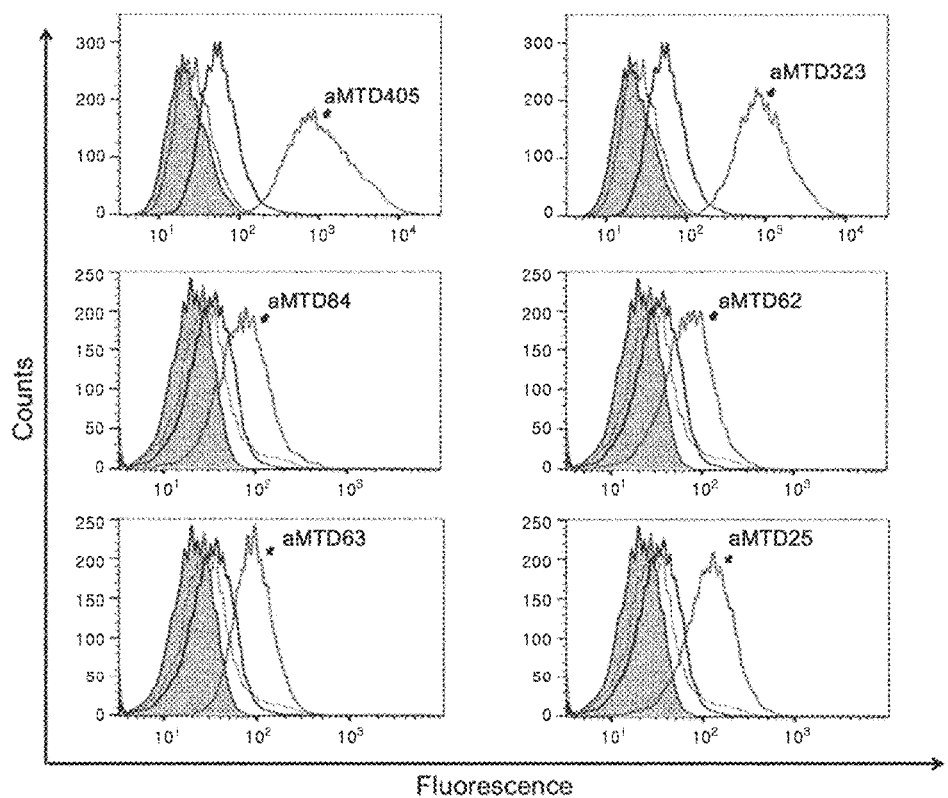
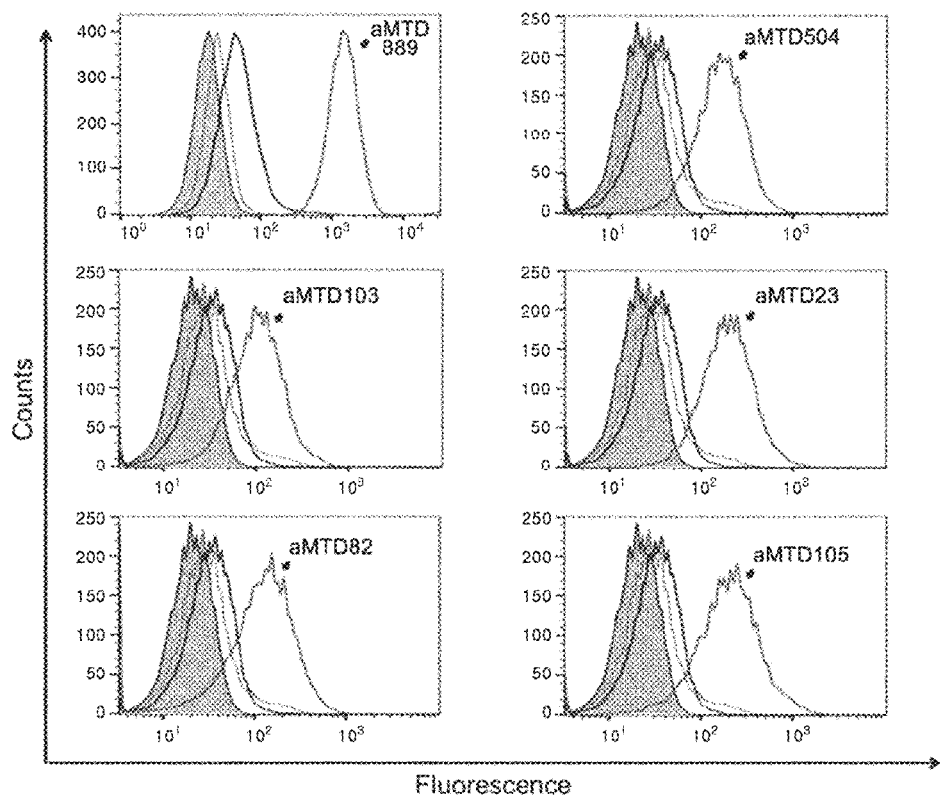

[Figure 5g]
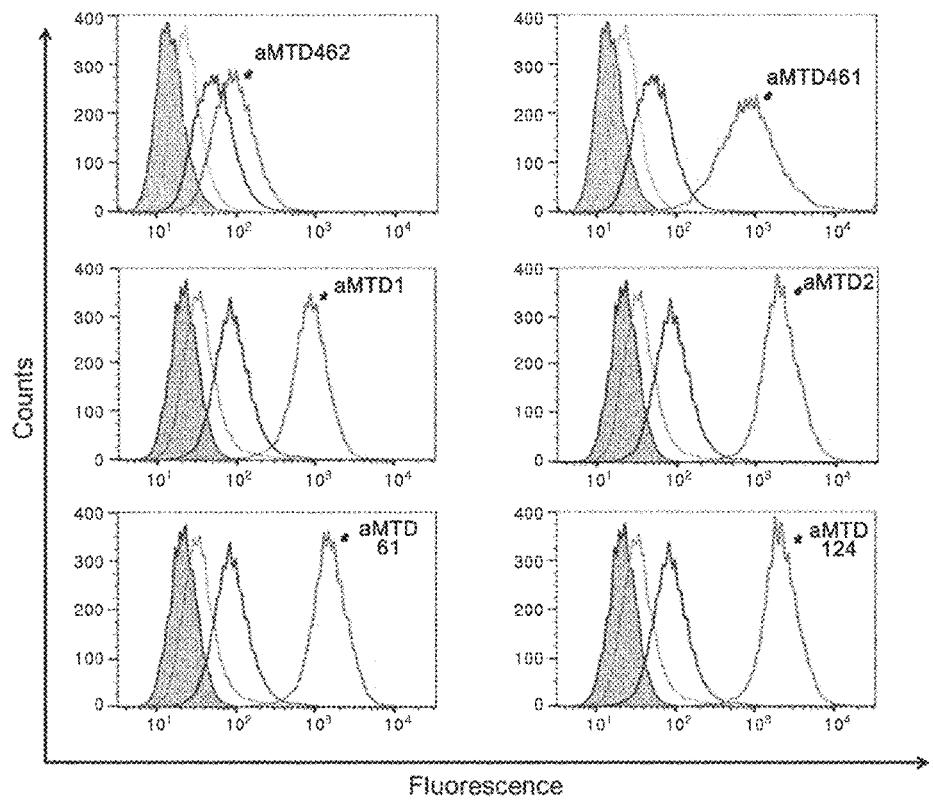
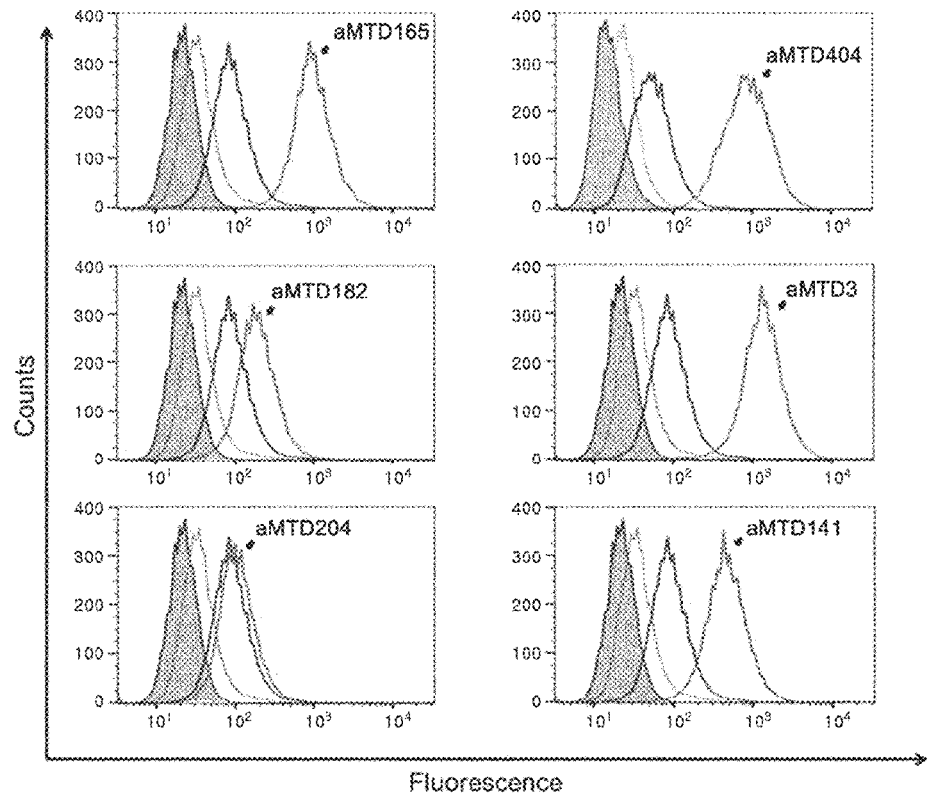

[Figure 5h]
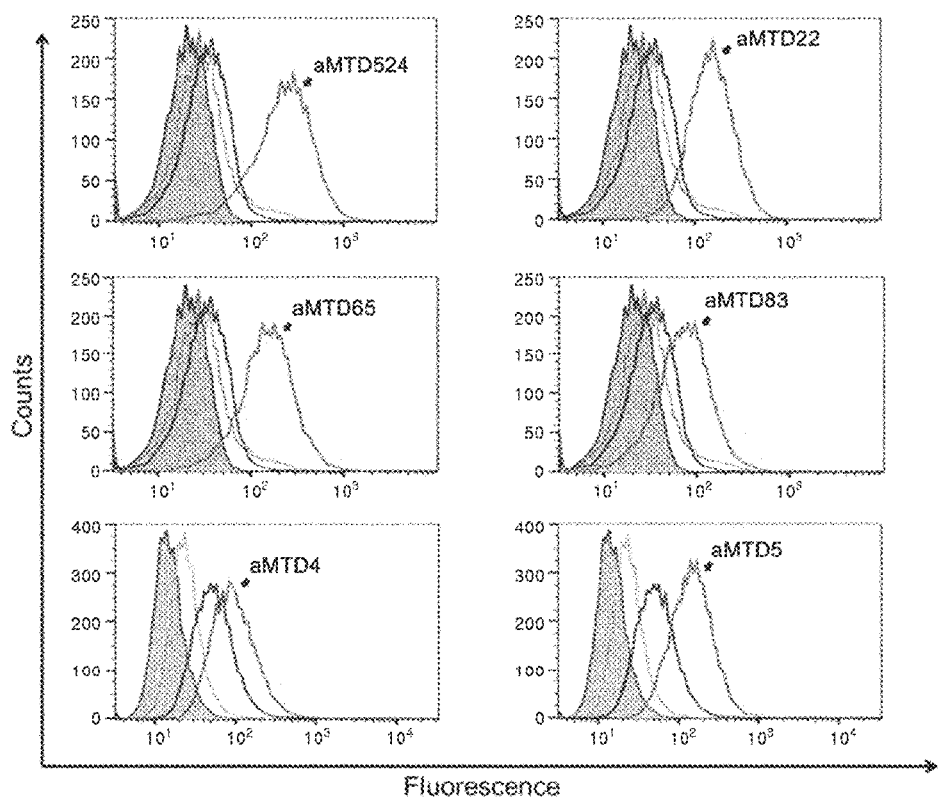
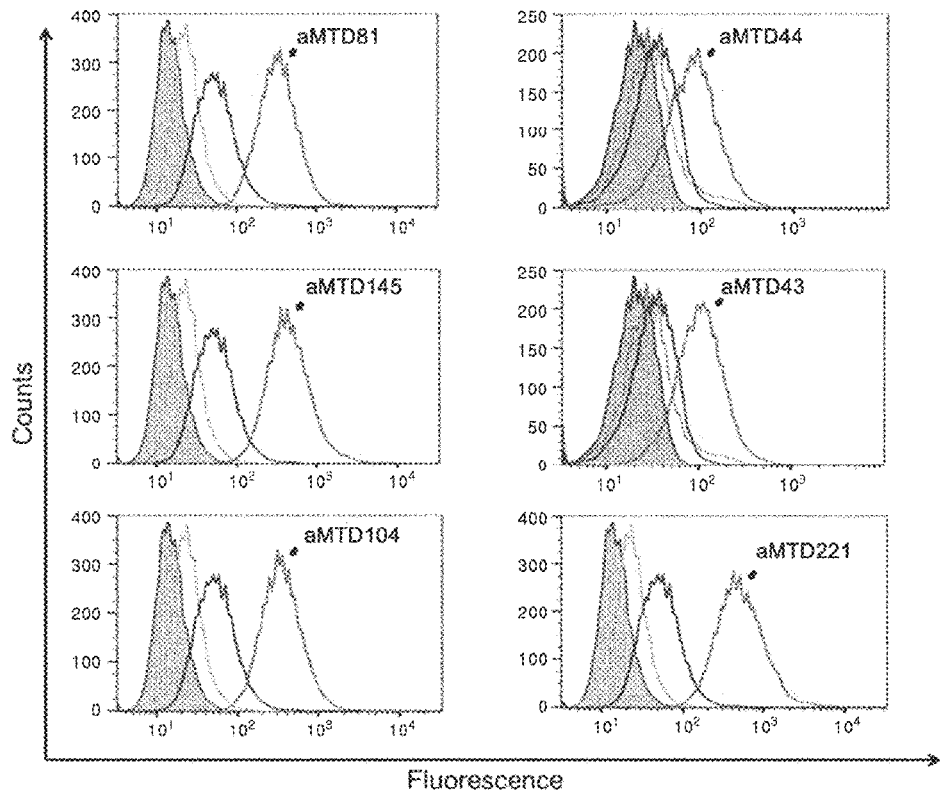

[Figure 5i]
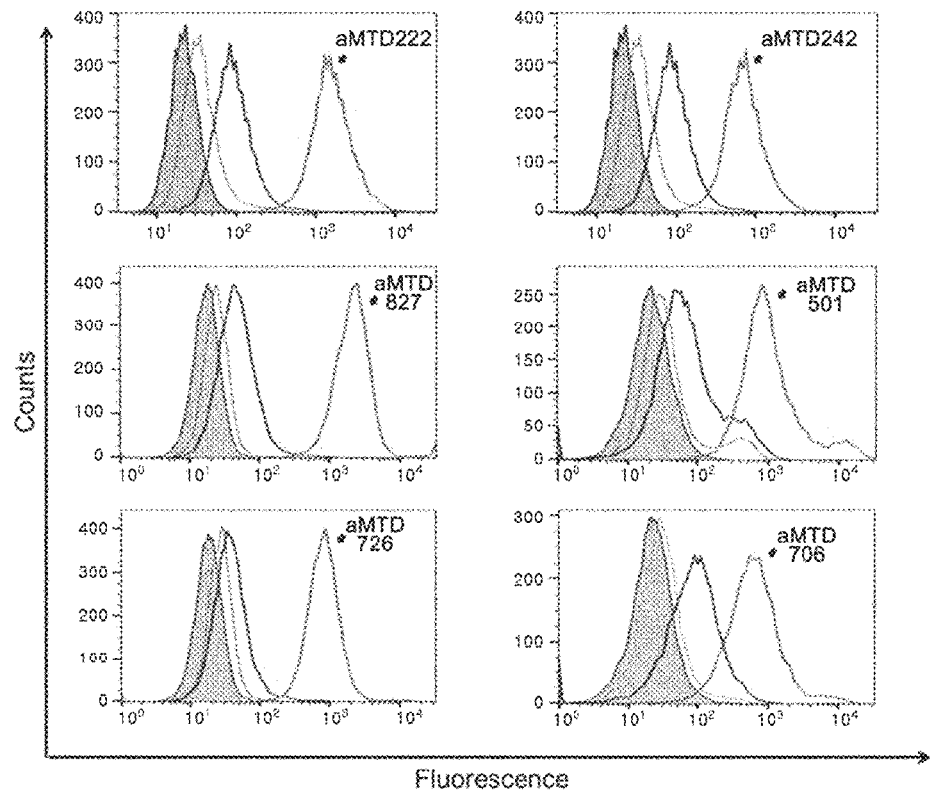
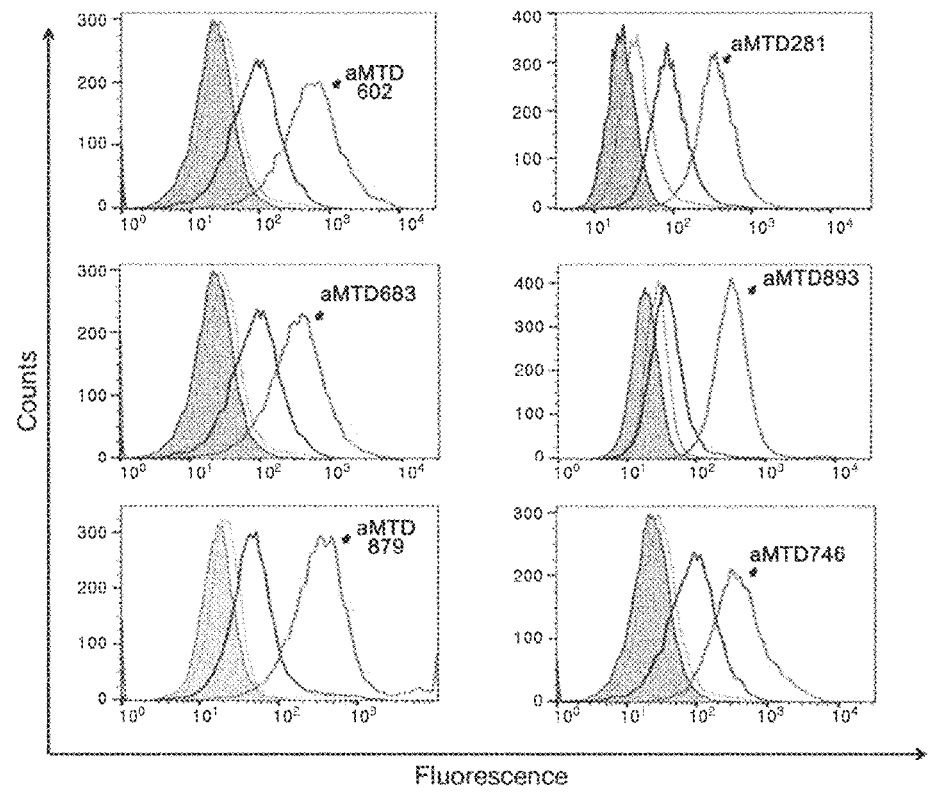

[Figure 5j]
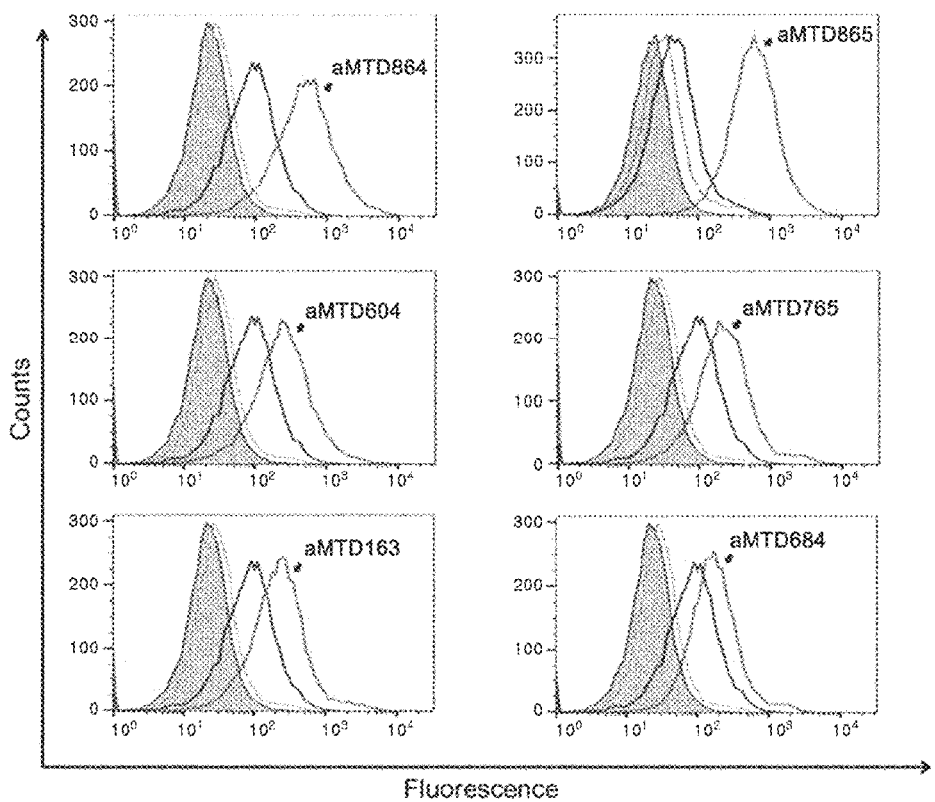
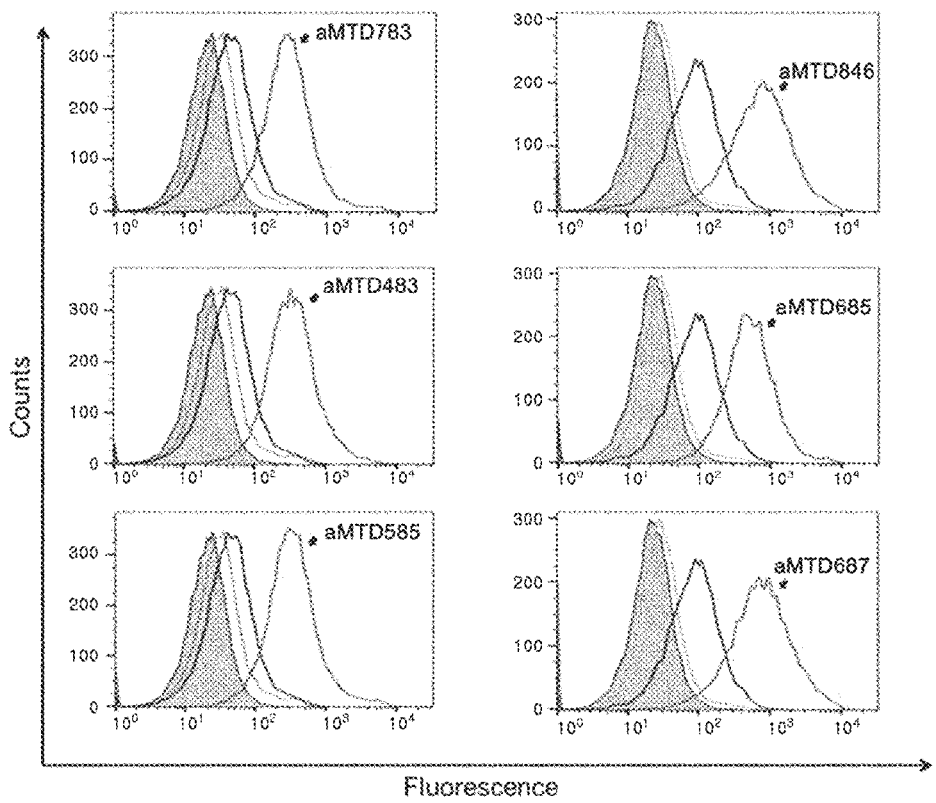

[Figure 5k]
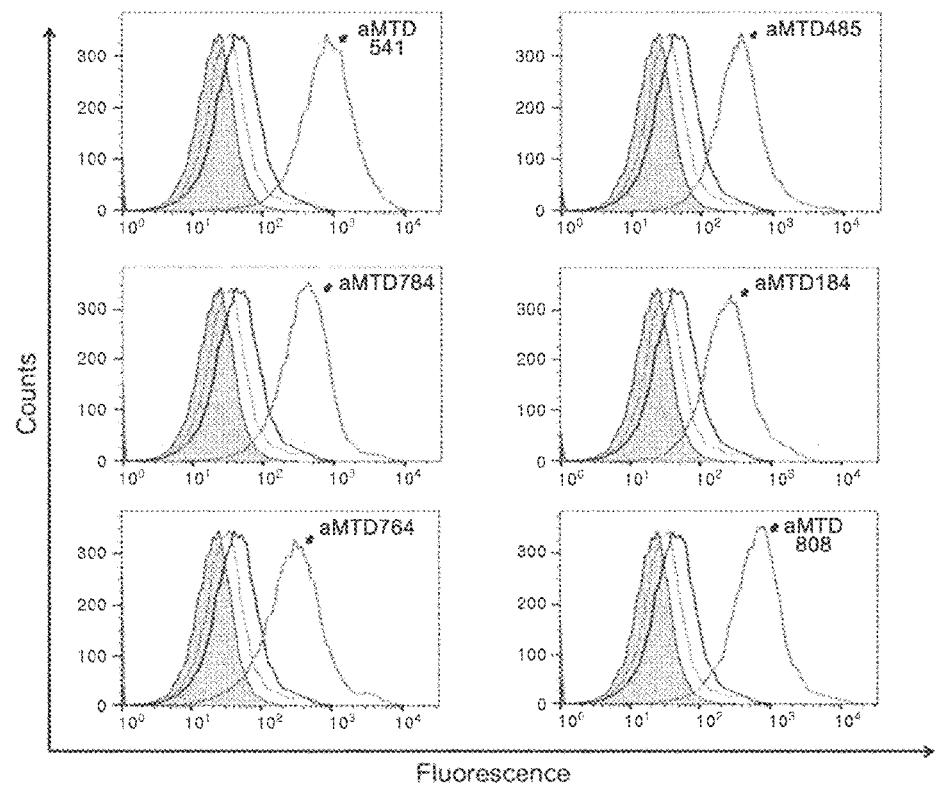
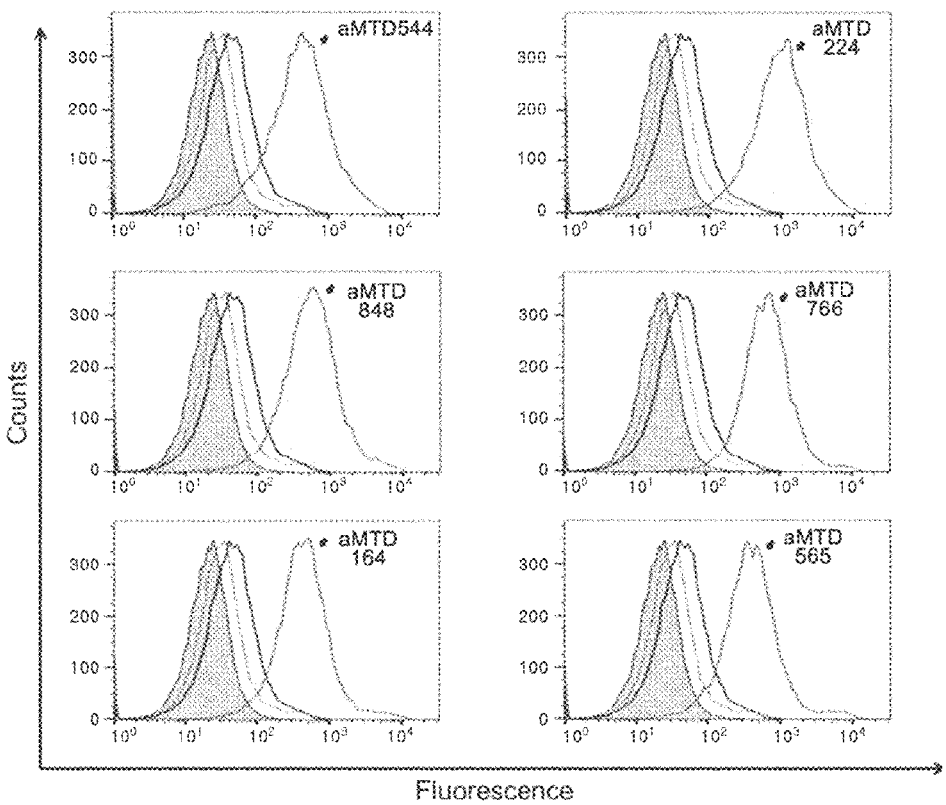

[Figure 51]
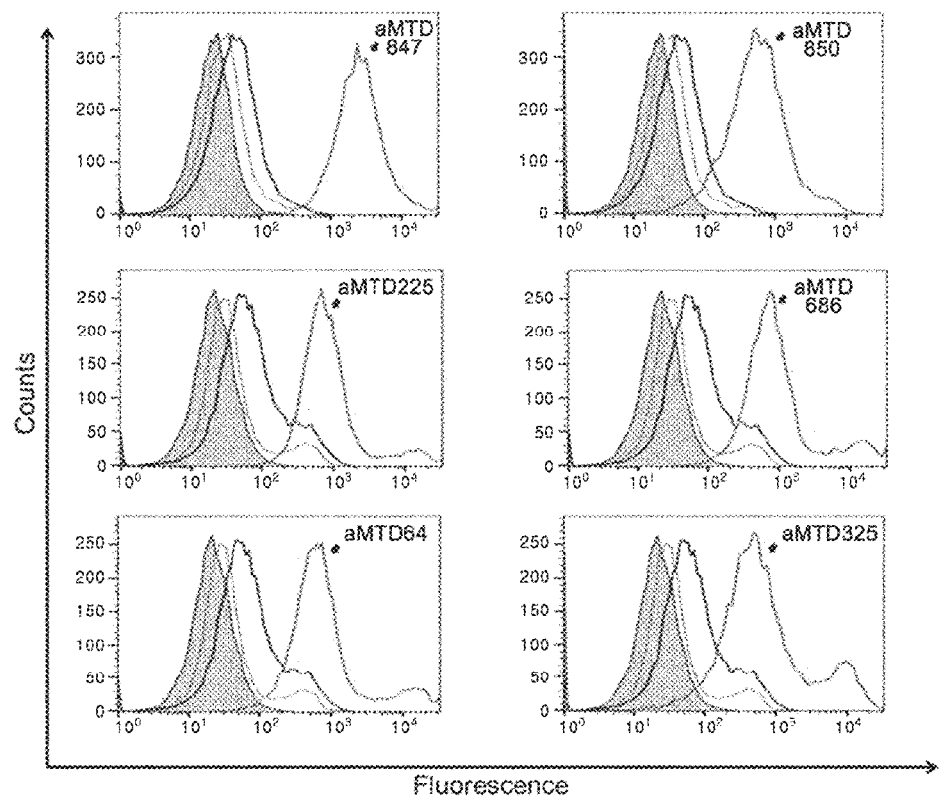
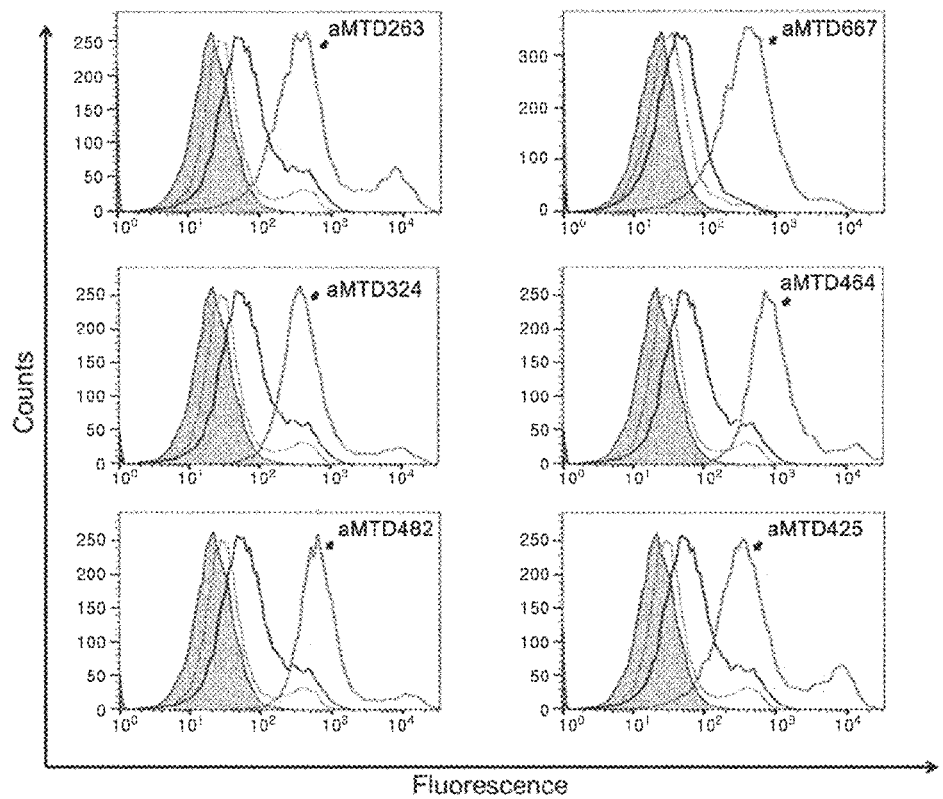

[Figure 5m]
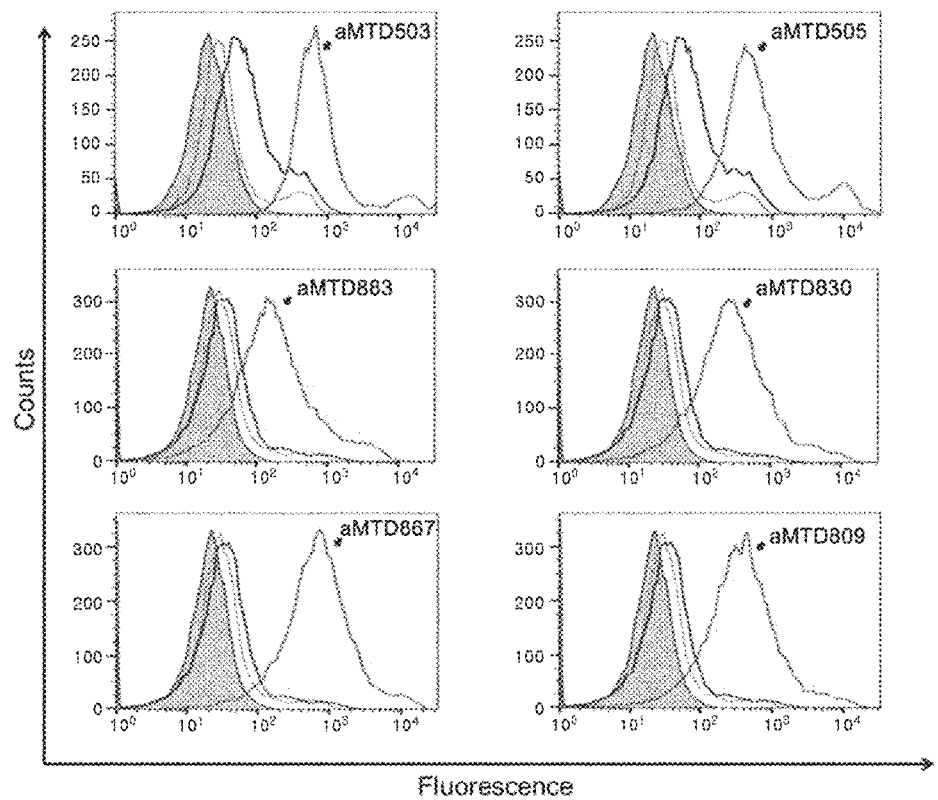
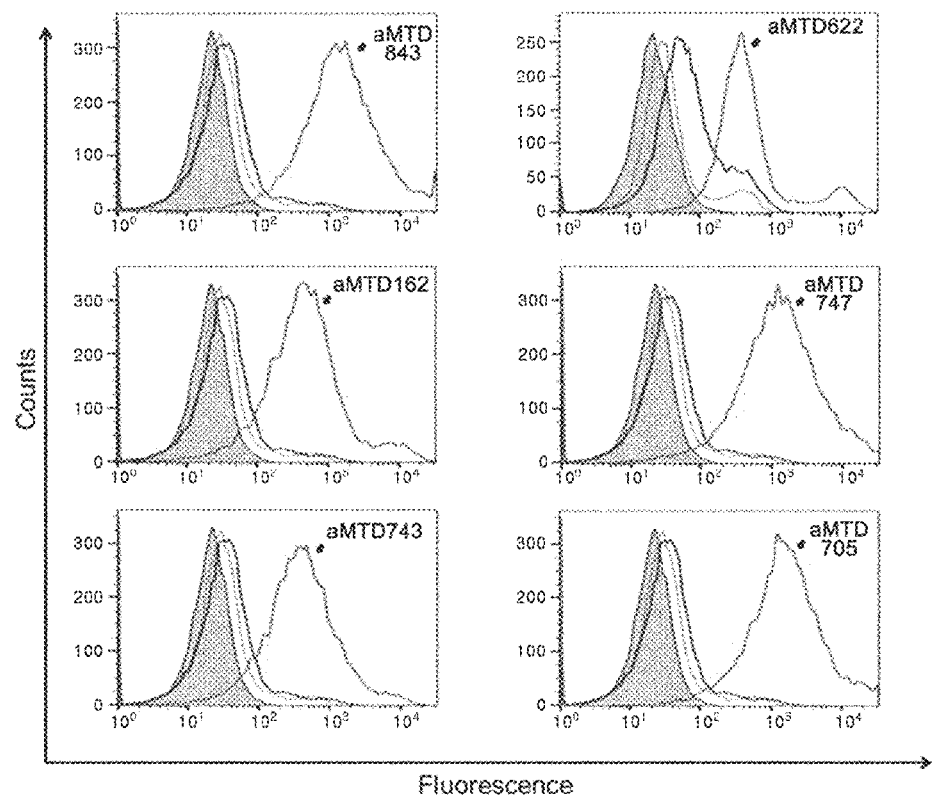

[Figure 5n]
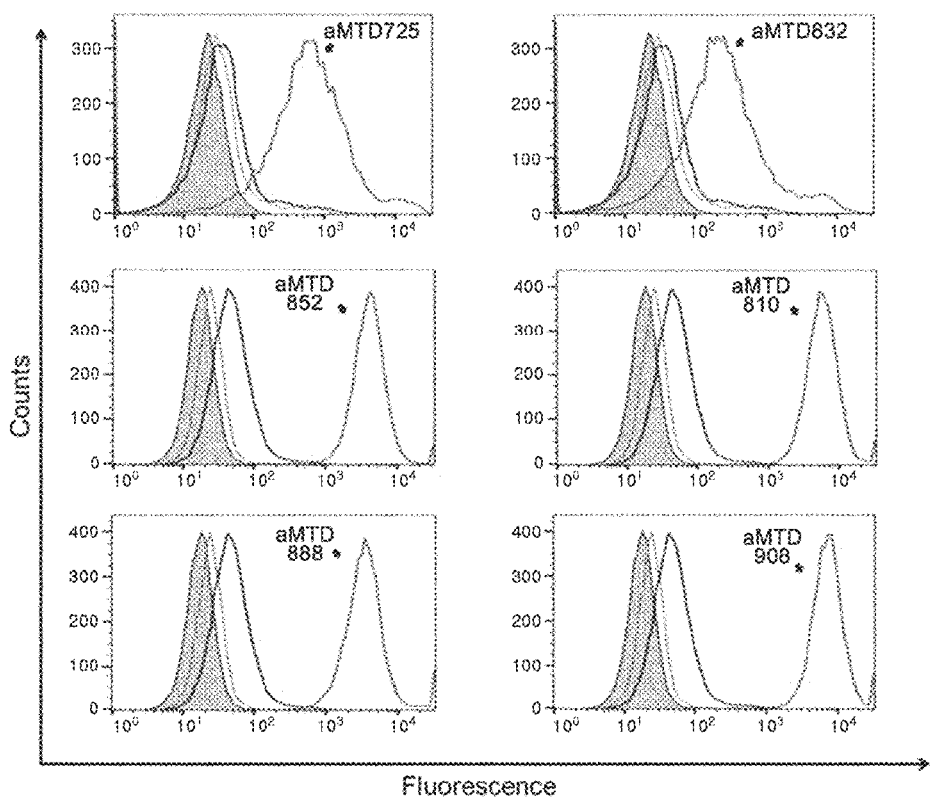
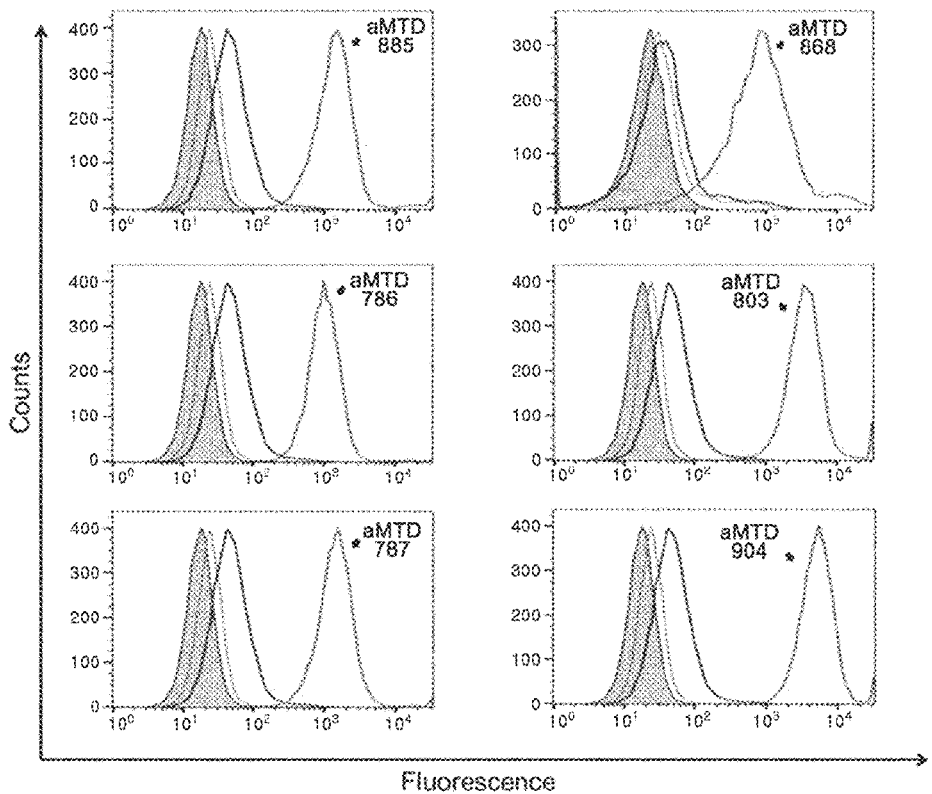

[Figure 5o]
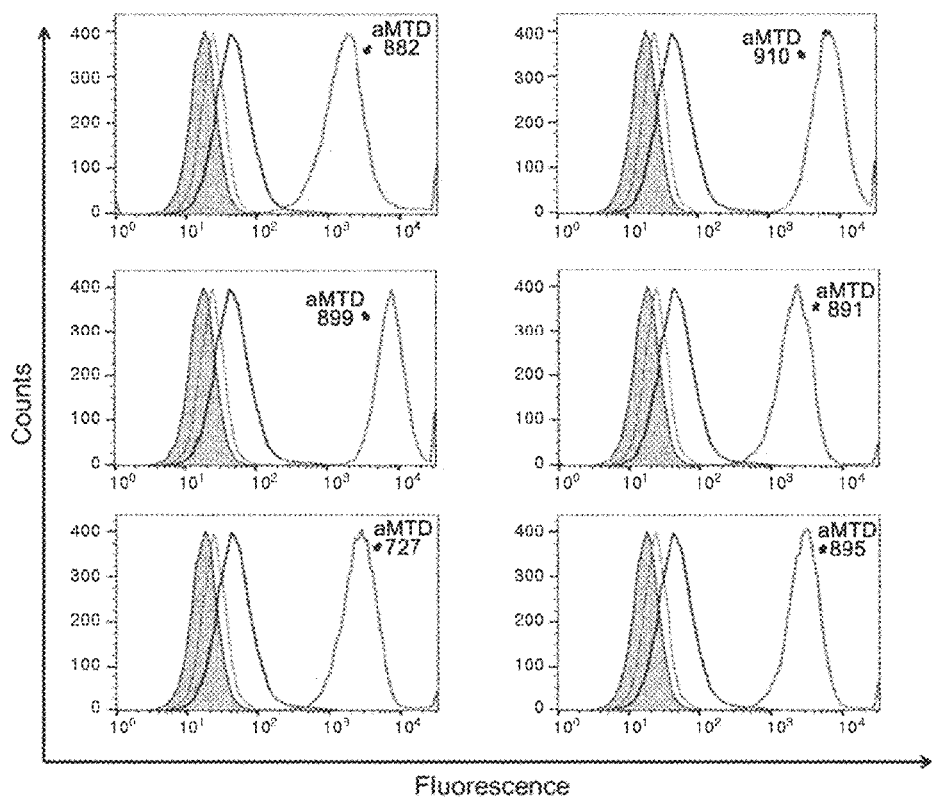
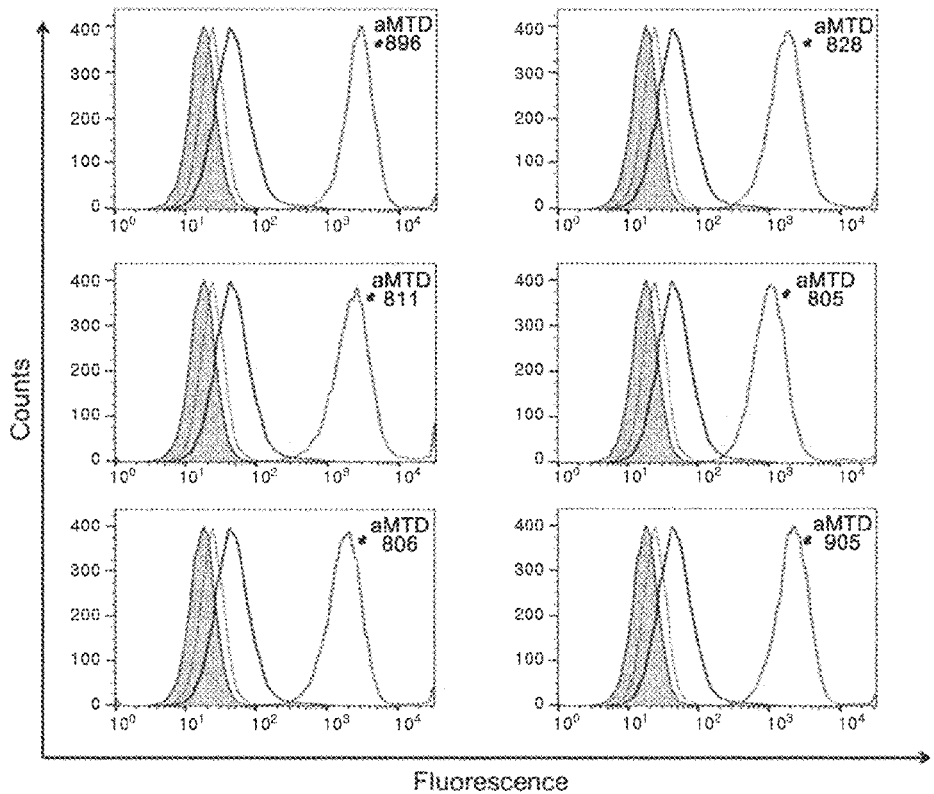

[Figure 5p]
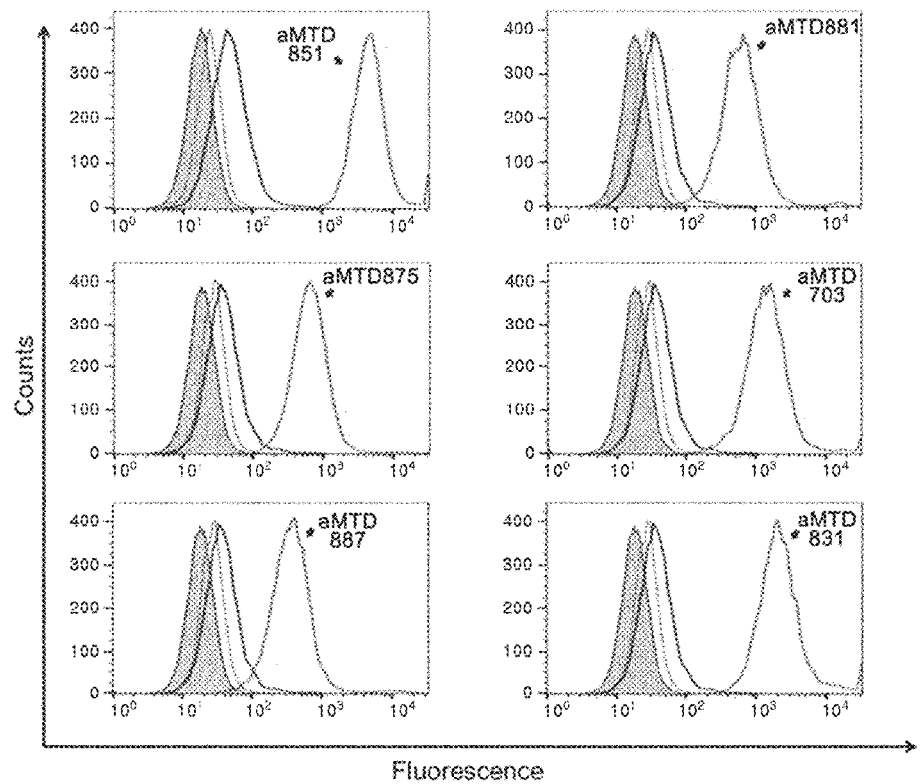
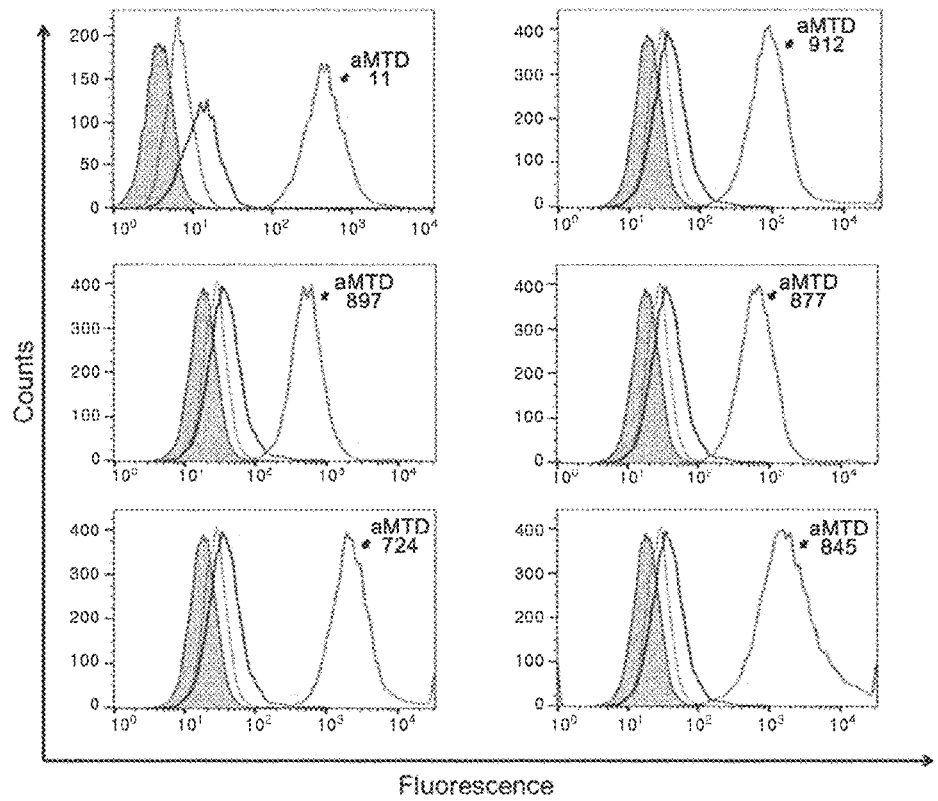

[Figure 5q]
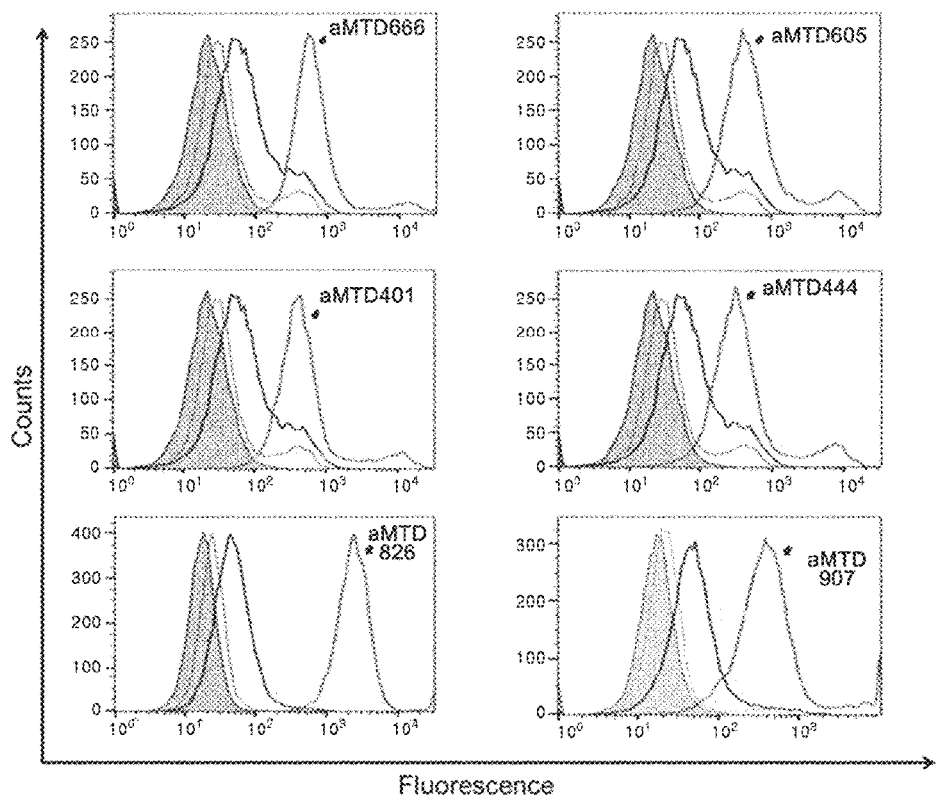
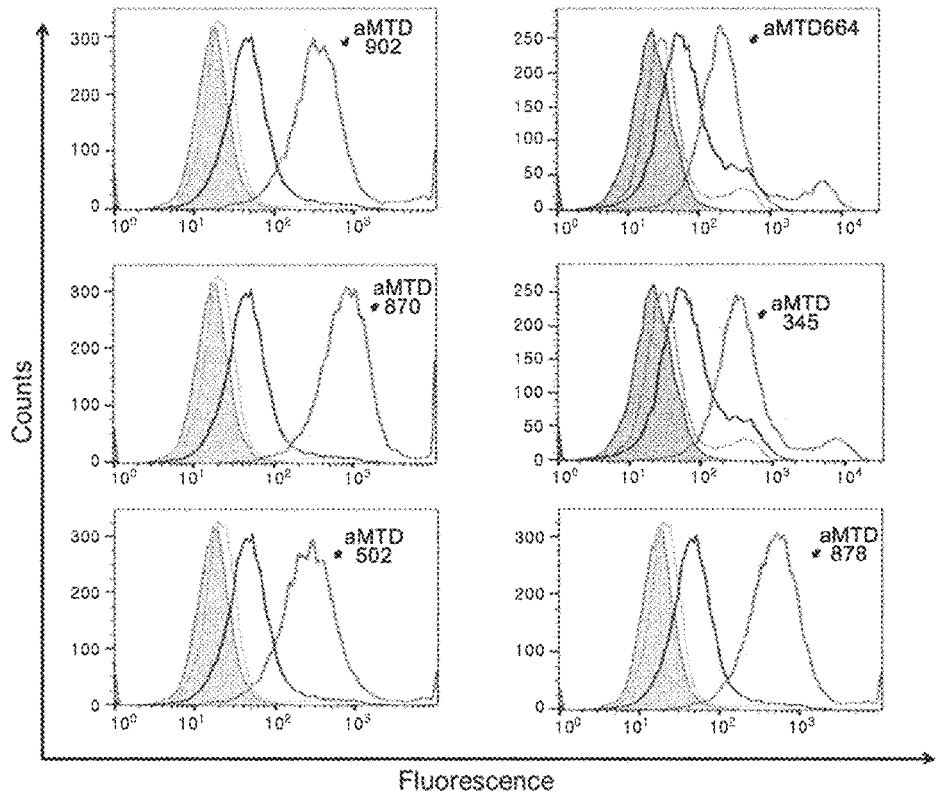

[Figure 5r]
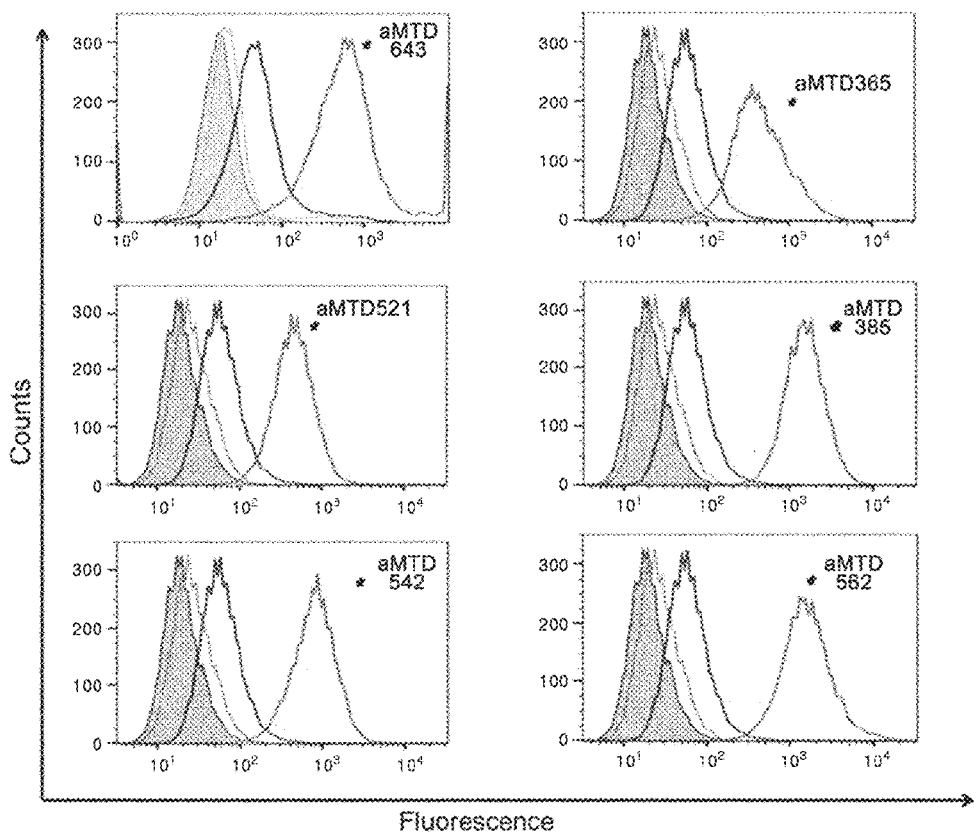
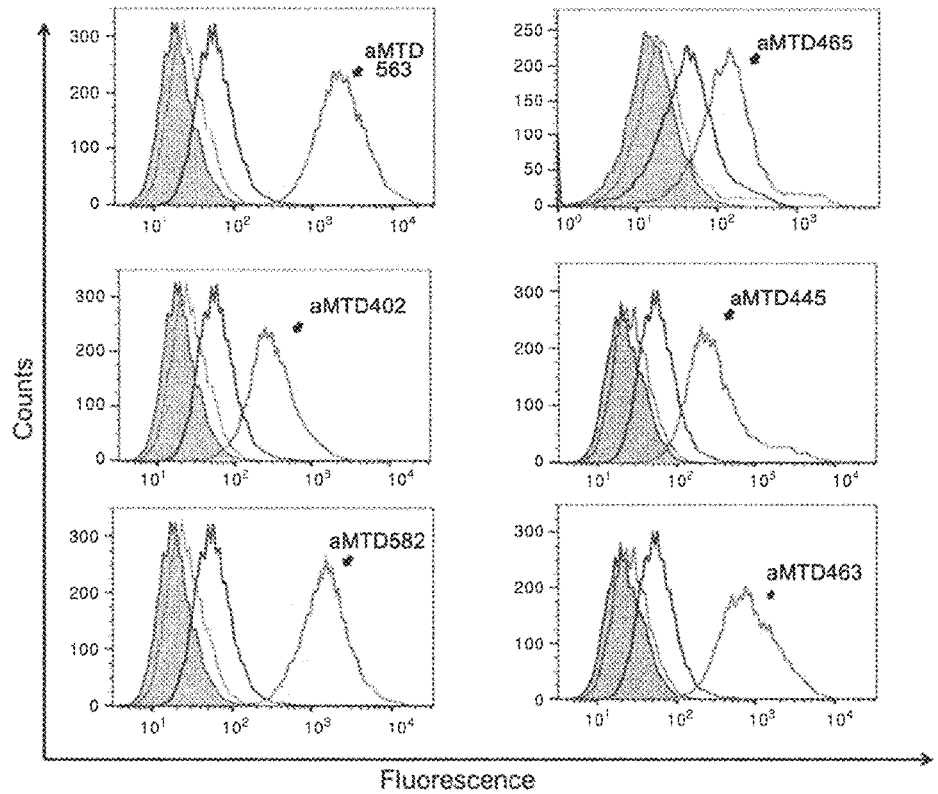

[Figure 5s]
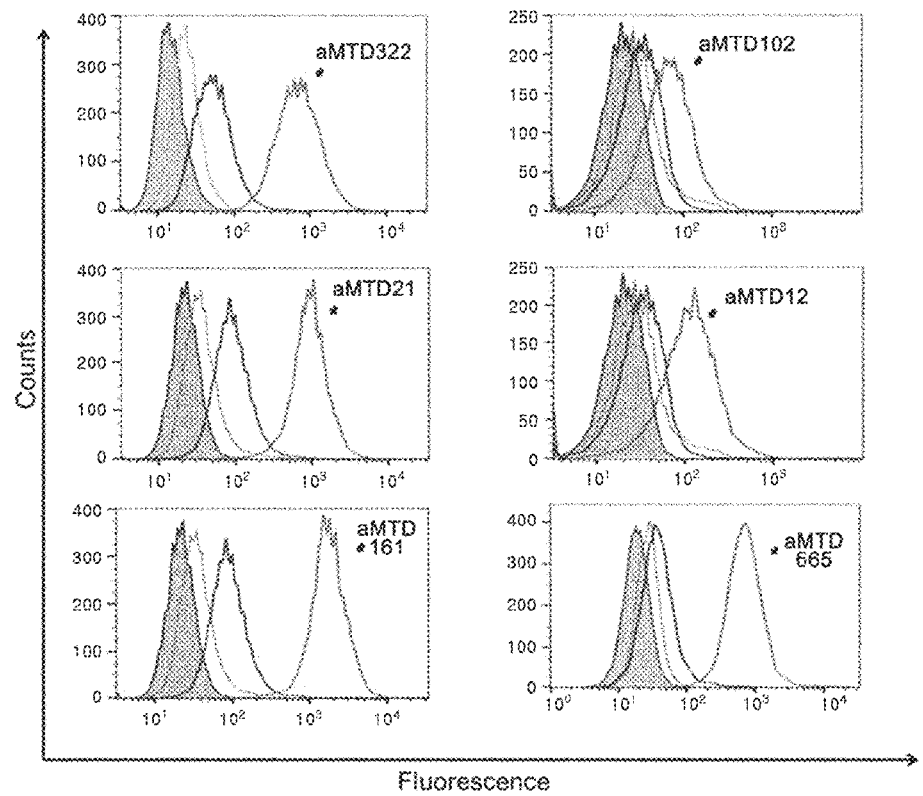
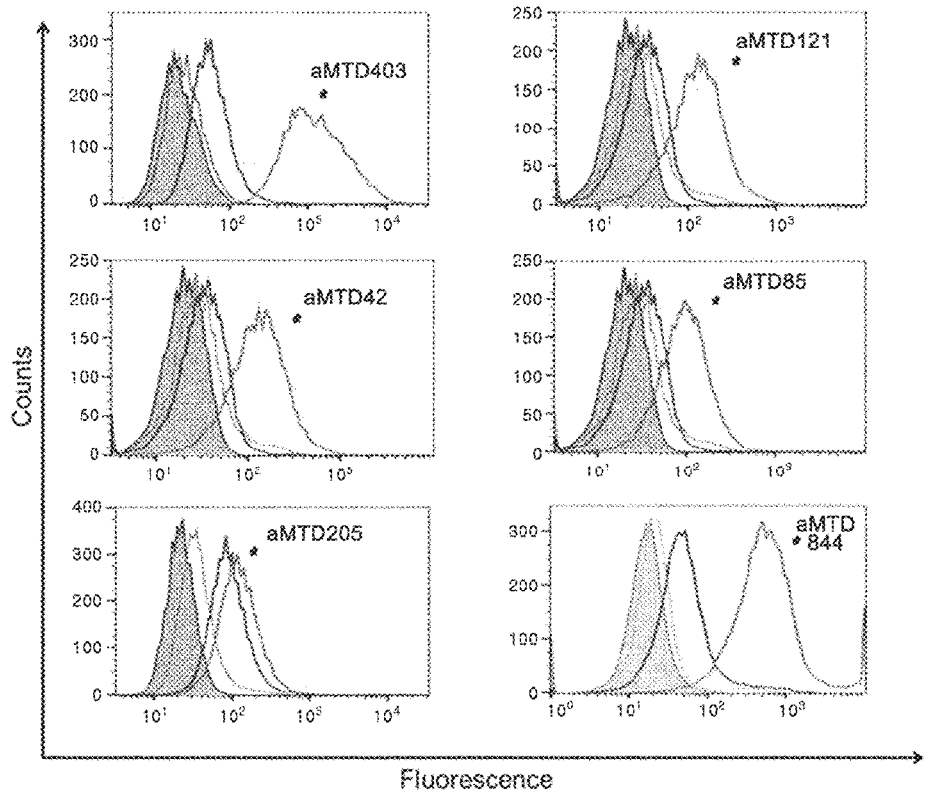

[Figure 5t]
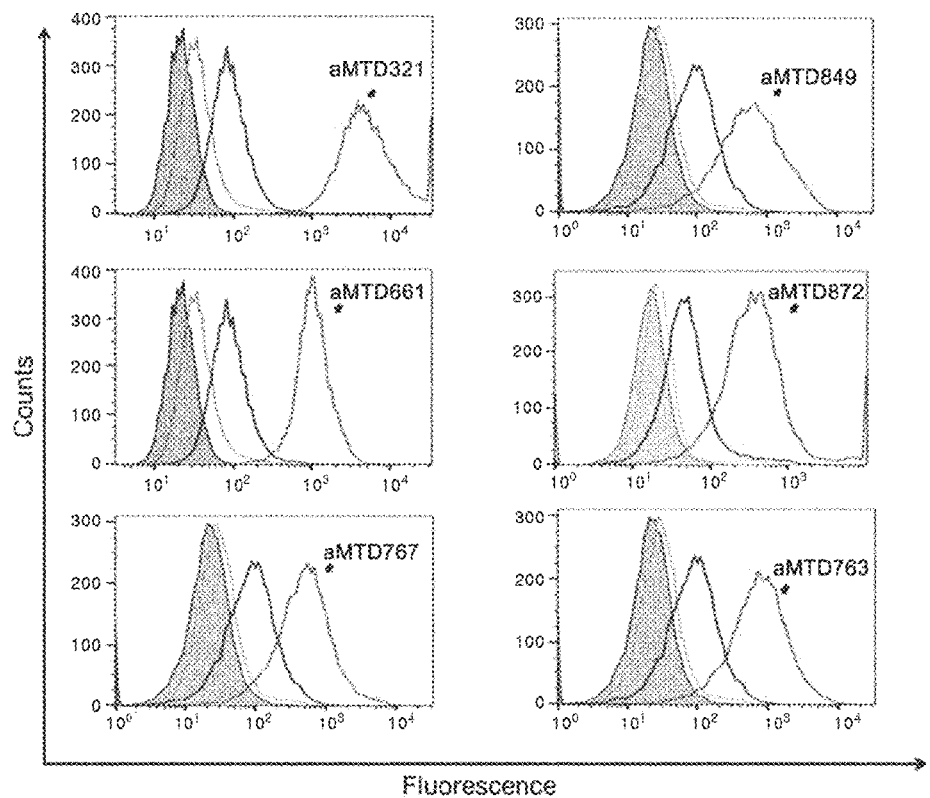
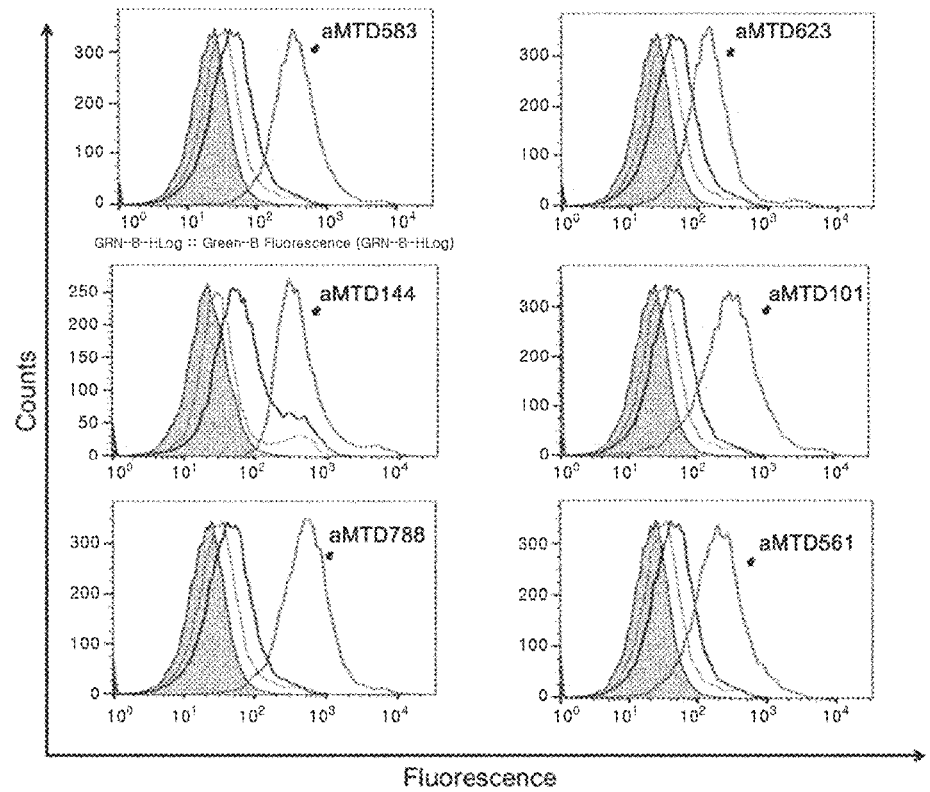

[Figure 5u]
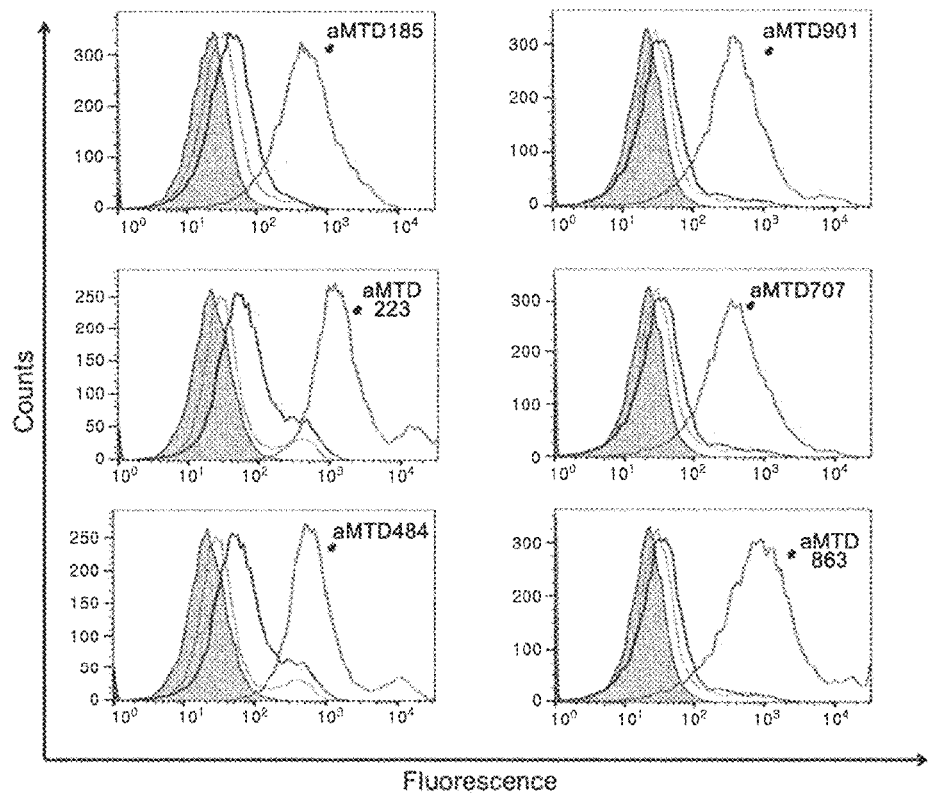
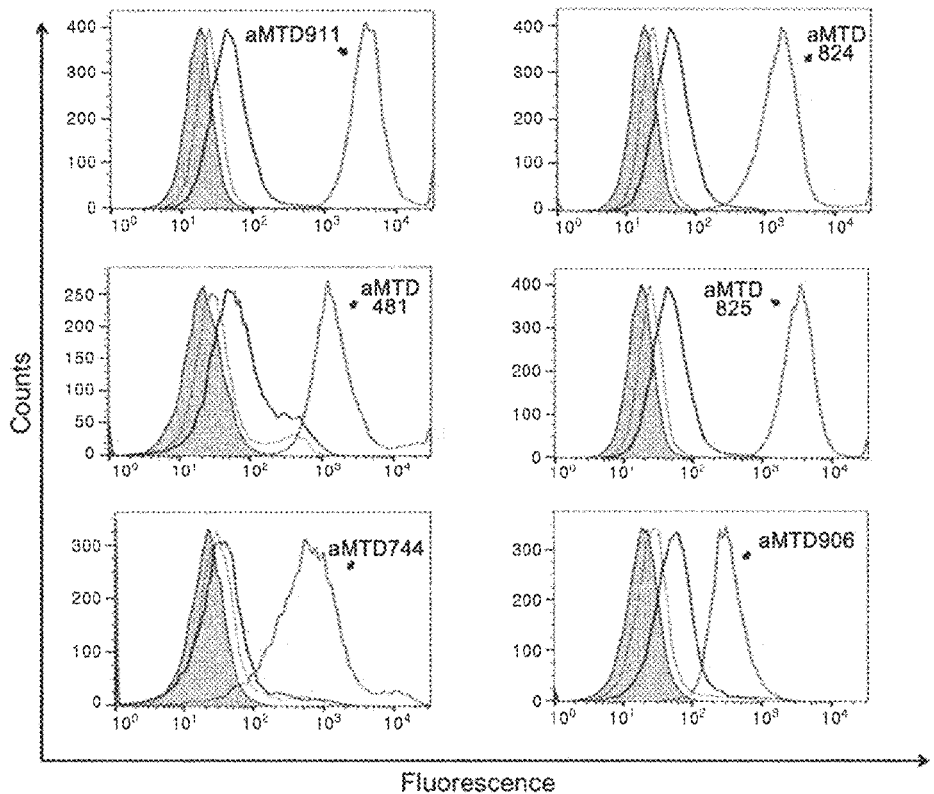

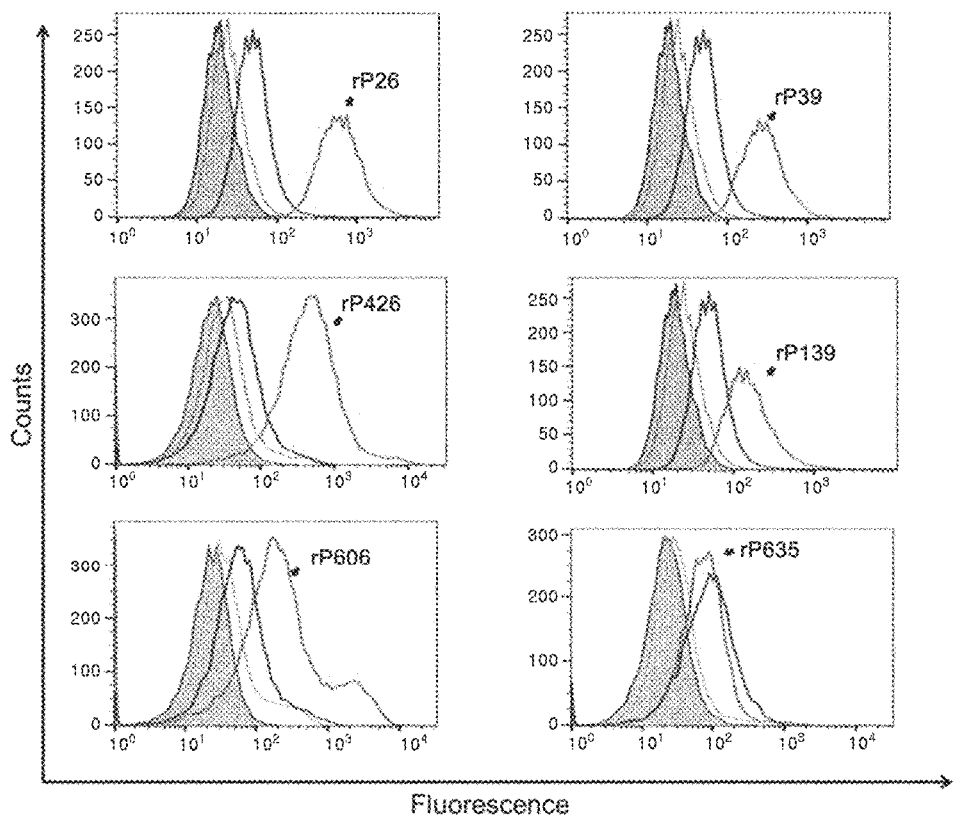
[Figure 6a]

[Figure 6b]
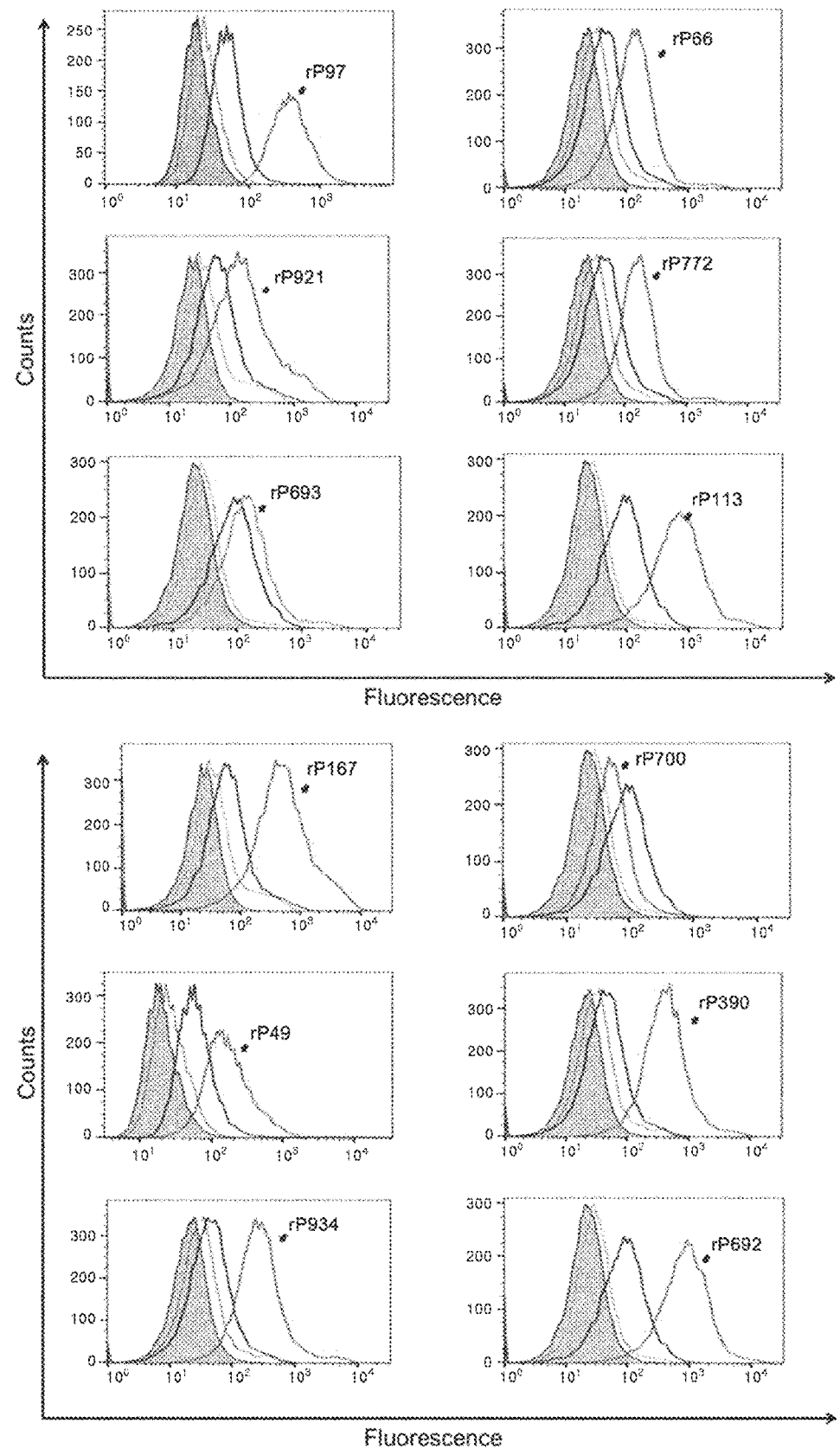

[Figure 6c]
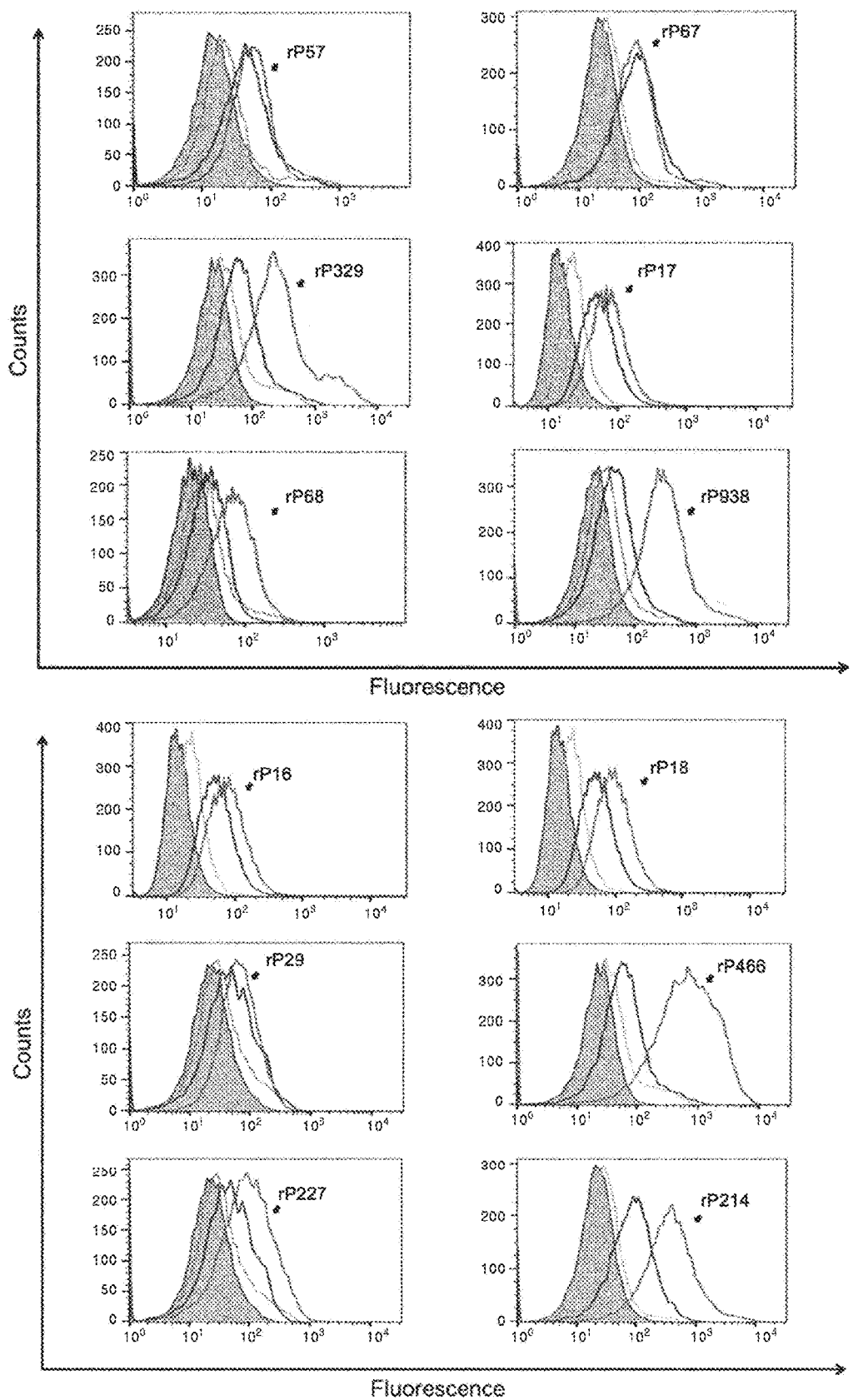

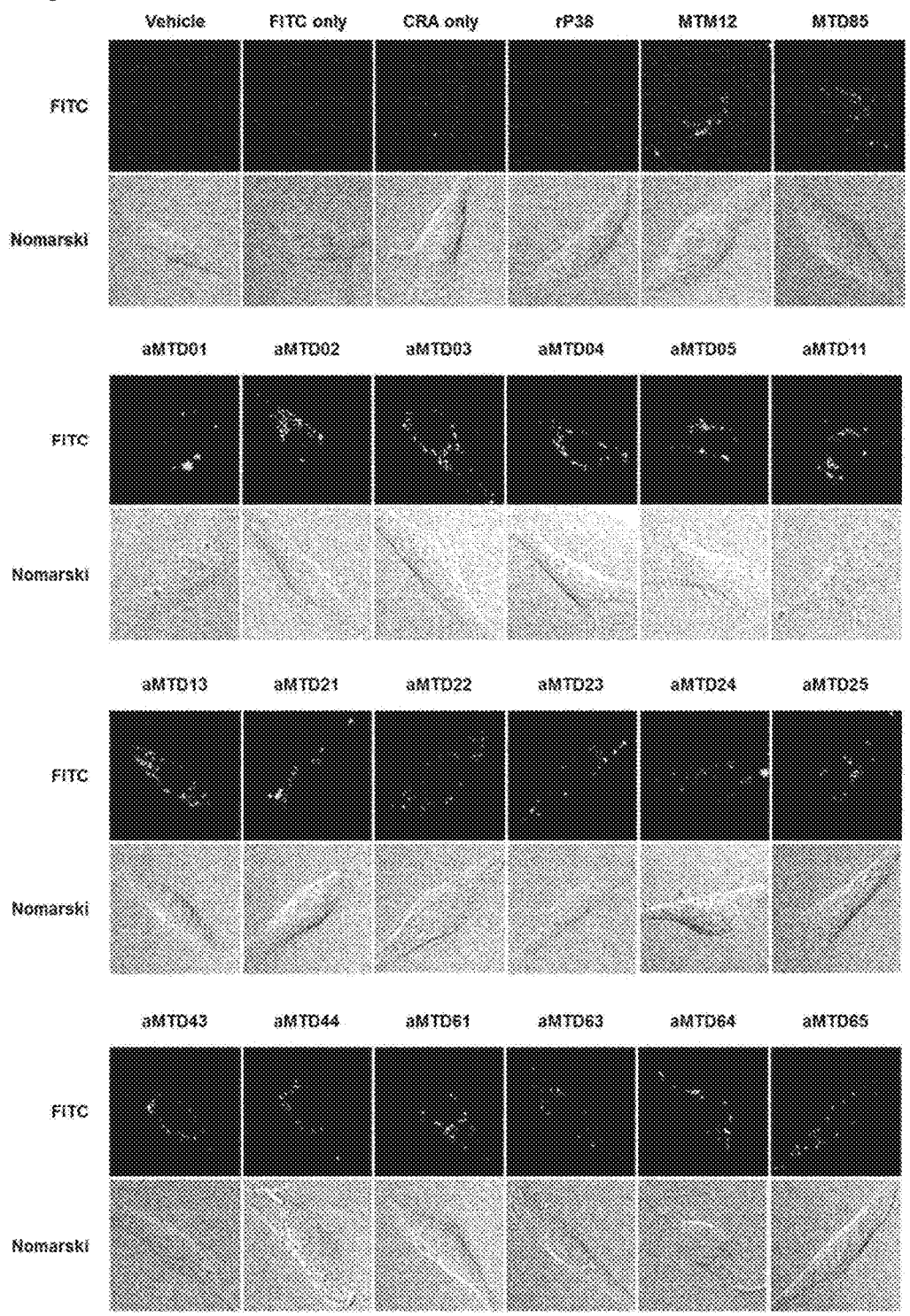
[Figure 7a]

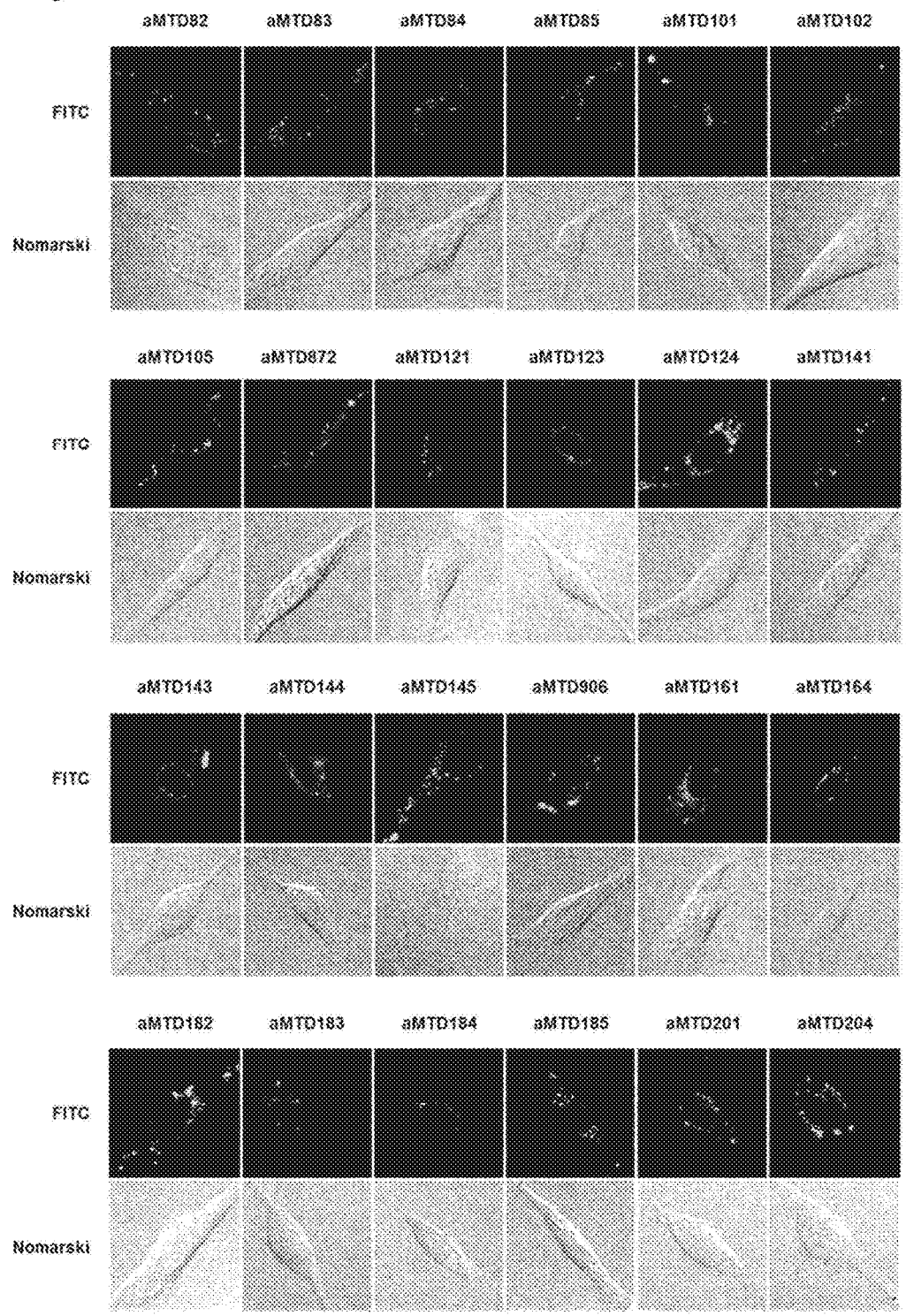
[Figure 7b]

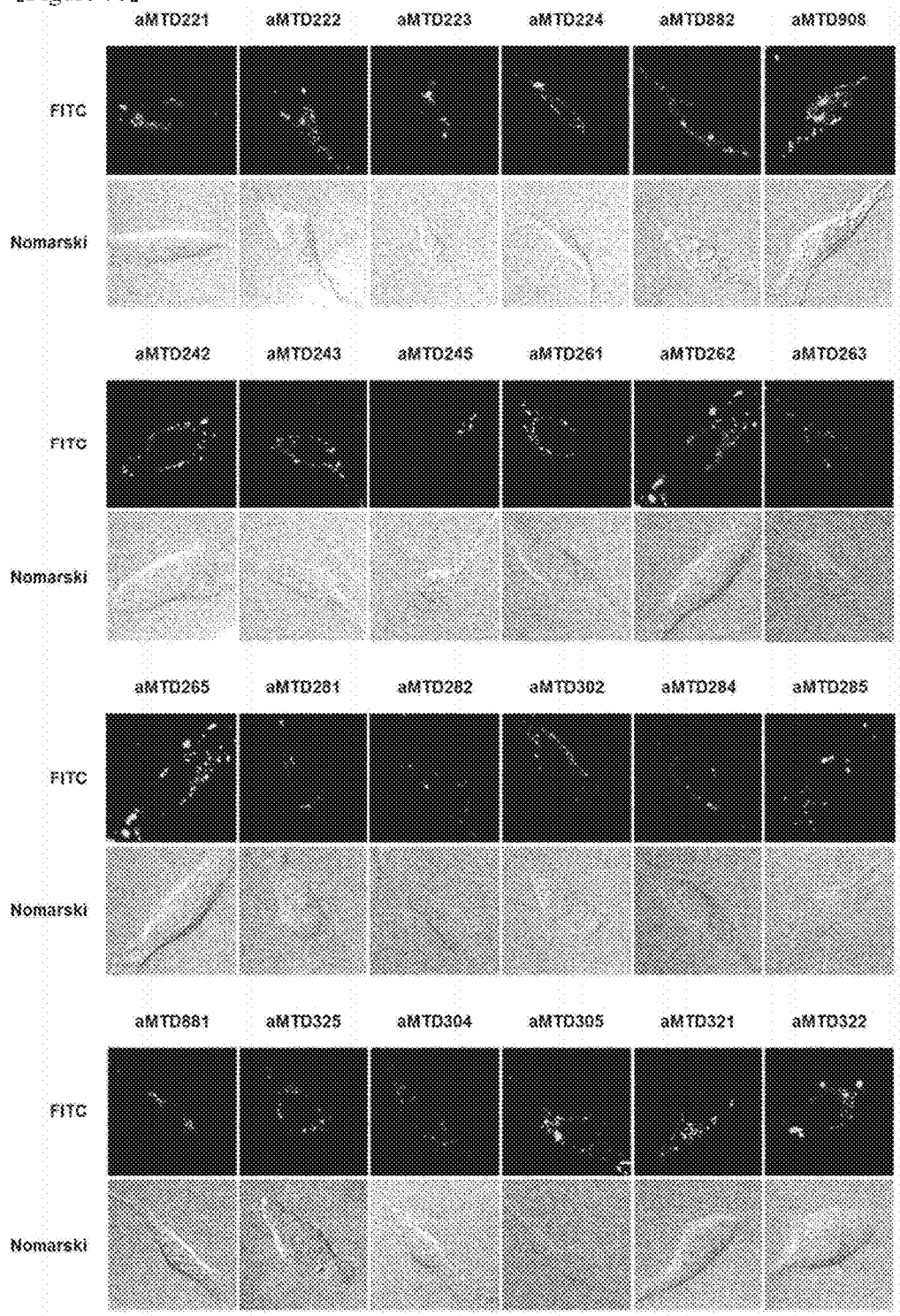
[Figure 7c]

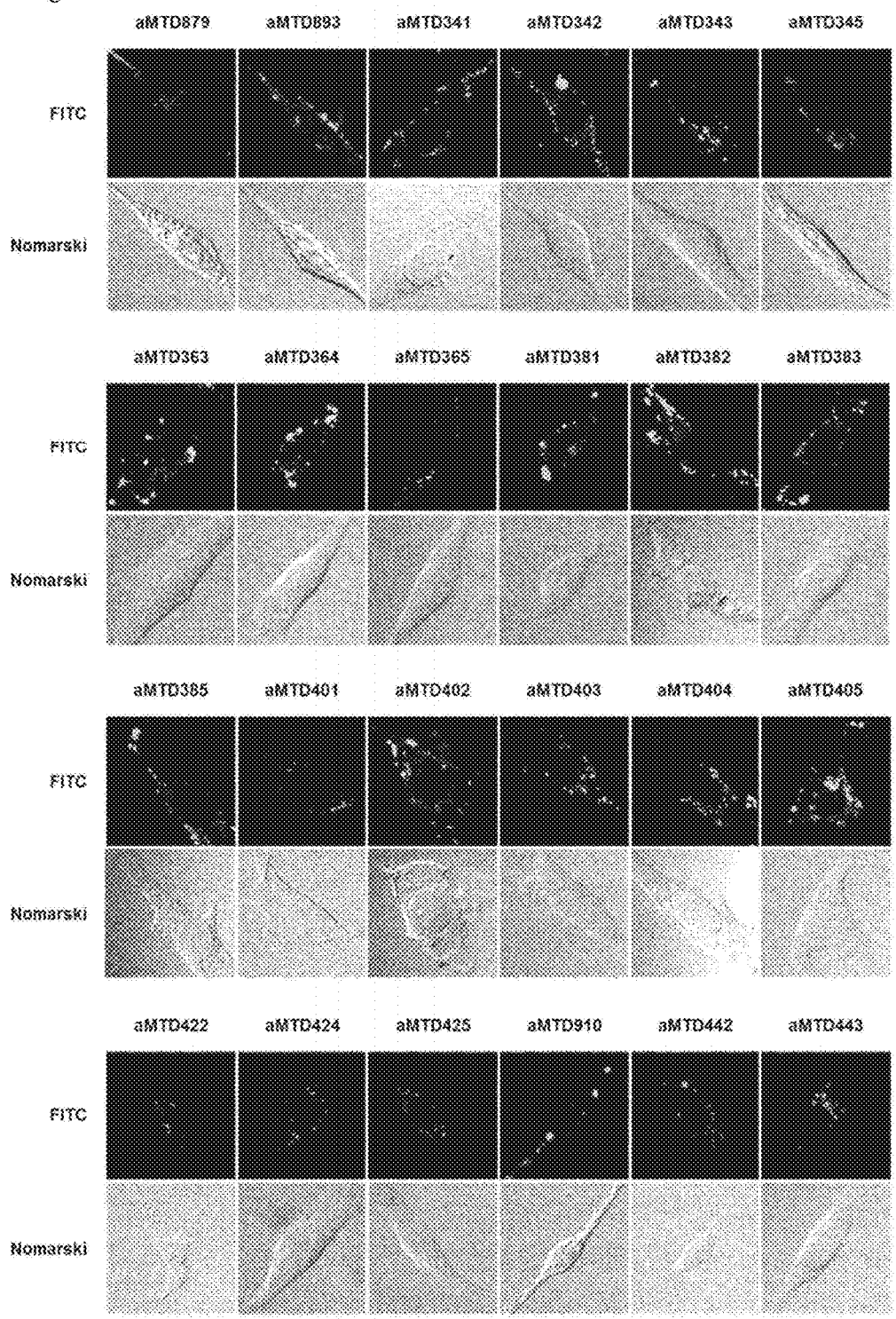
[Figure 7d]

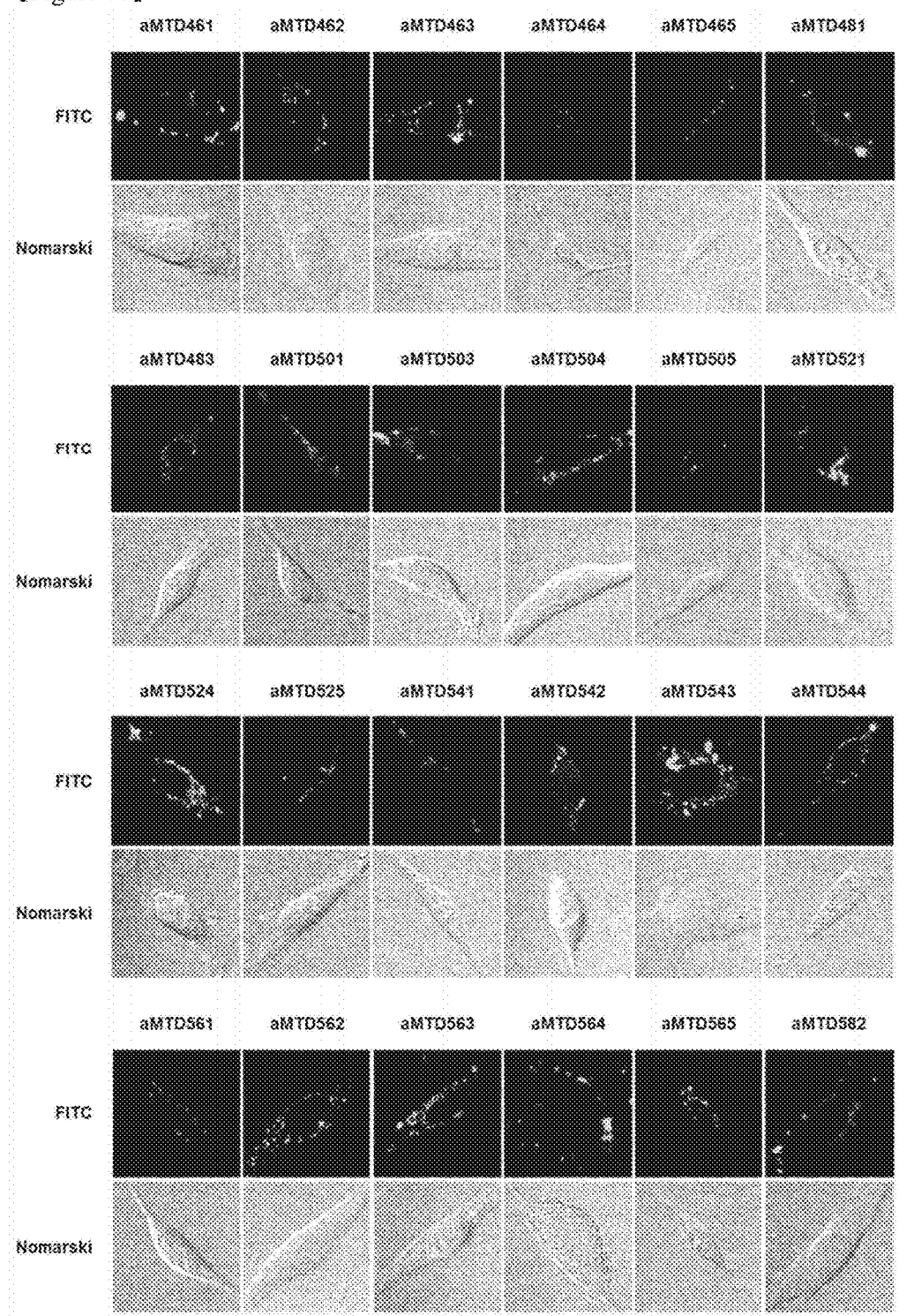
[Figure 7e]

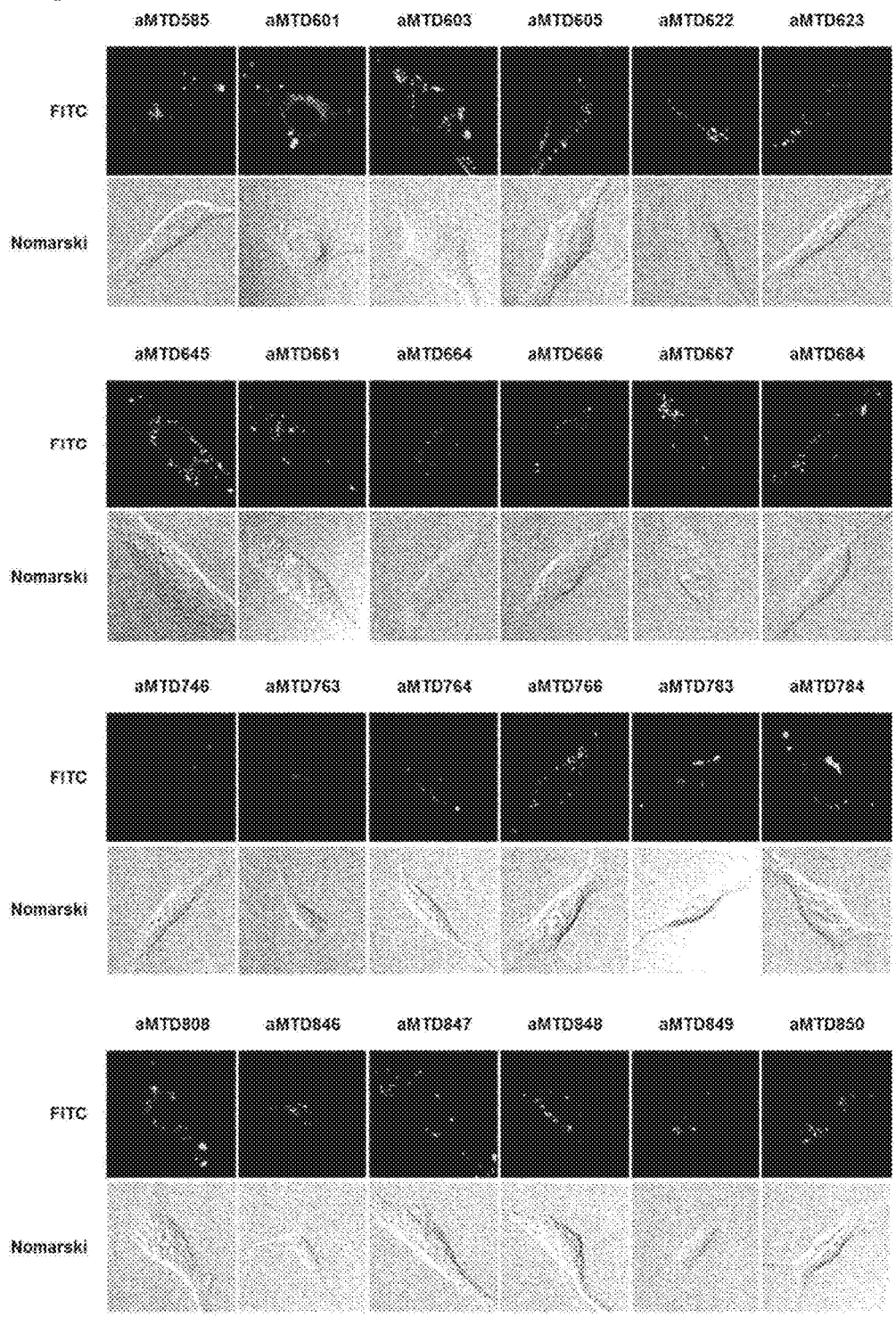
[Figure 7f]

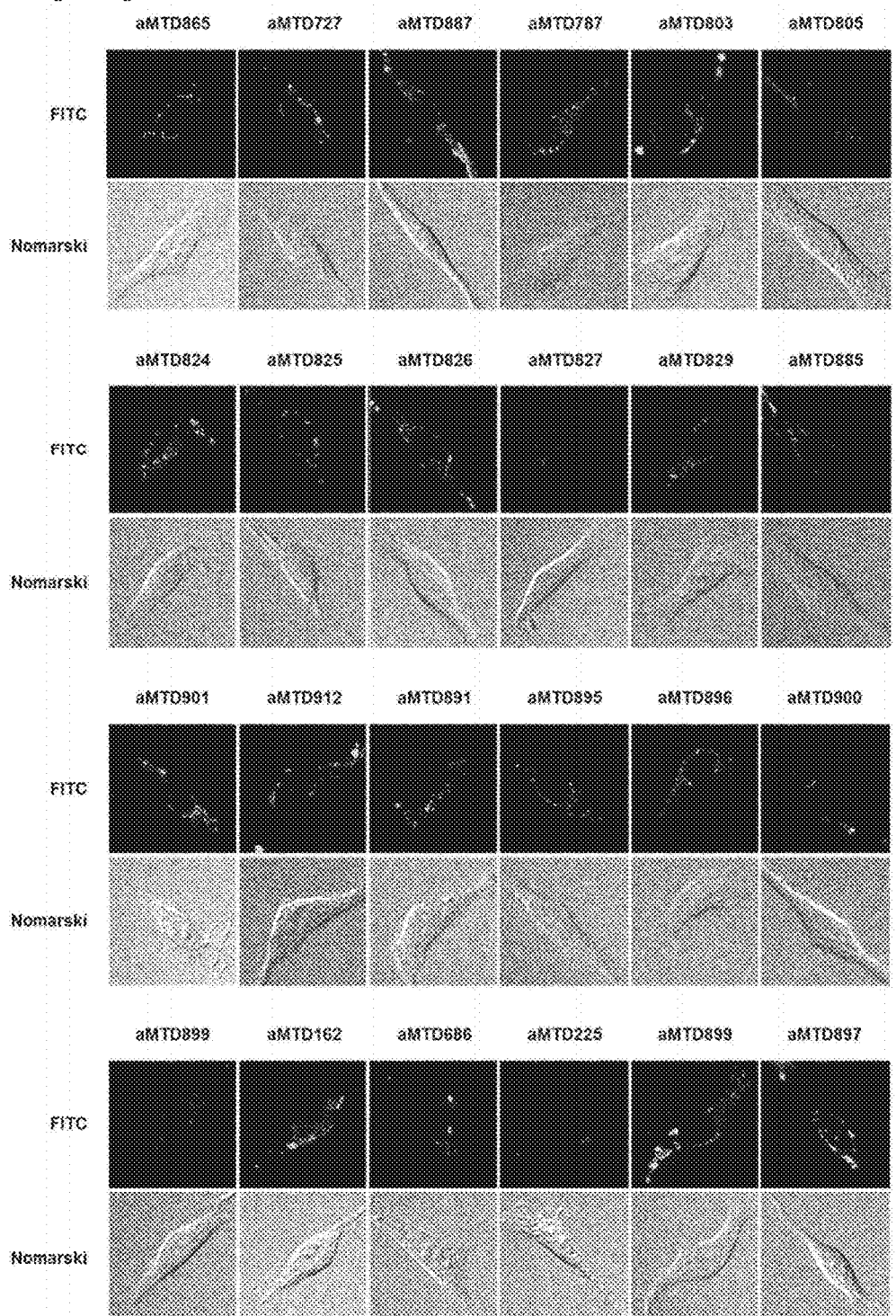
[Figure 7g]

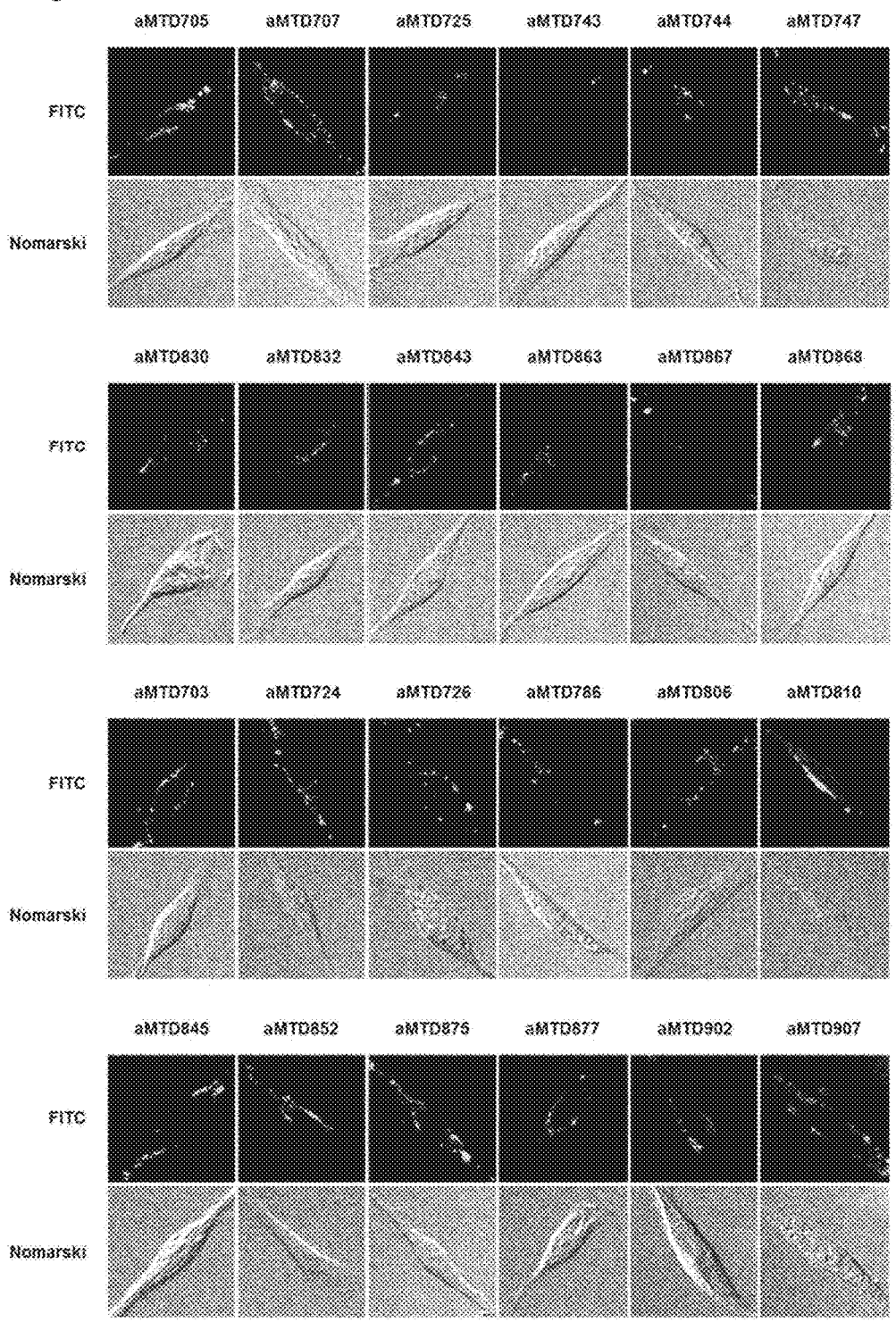
[Figure 7h]

[Figure 7i]
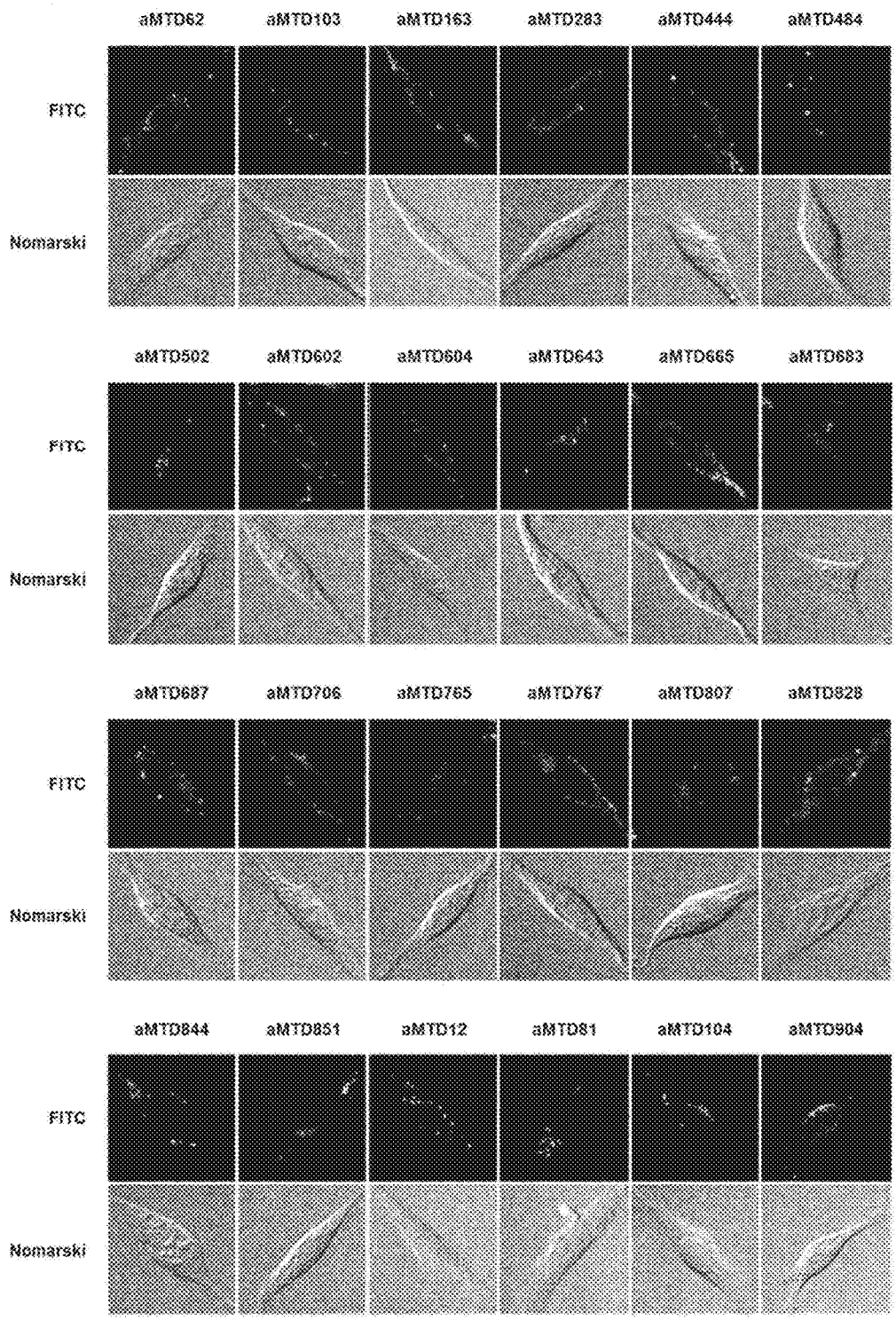

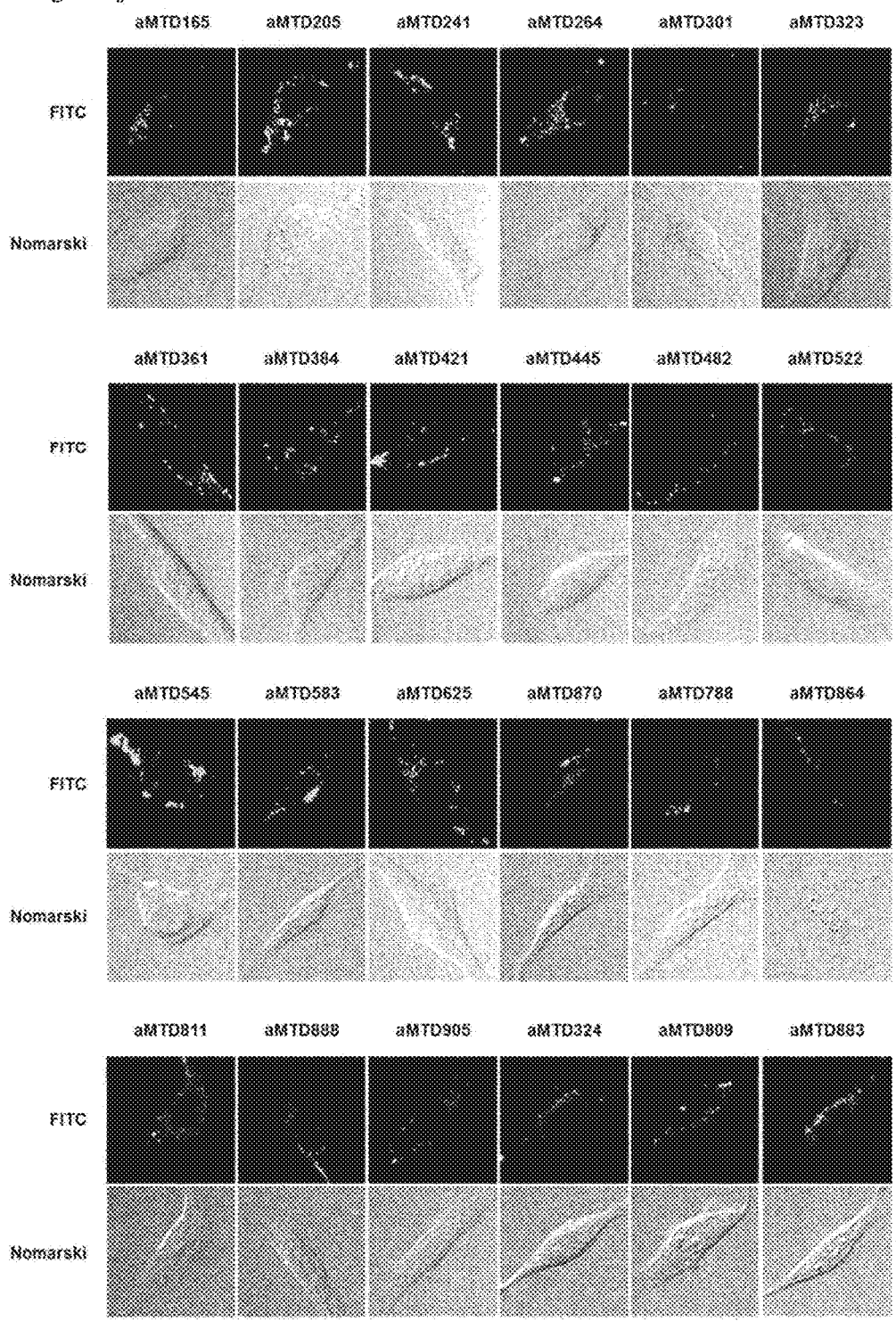

[Figure 7k]
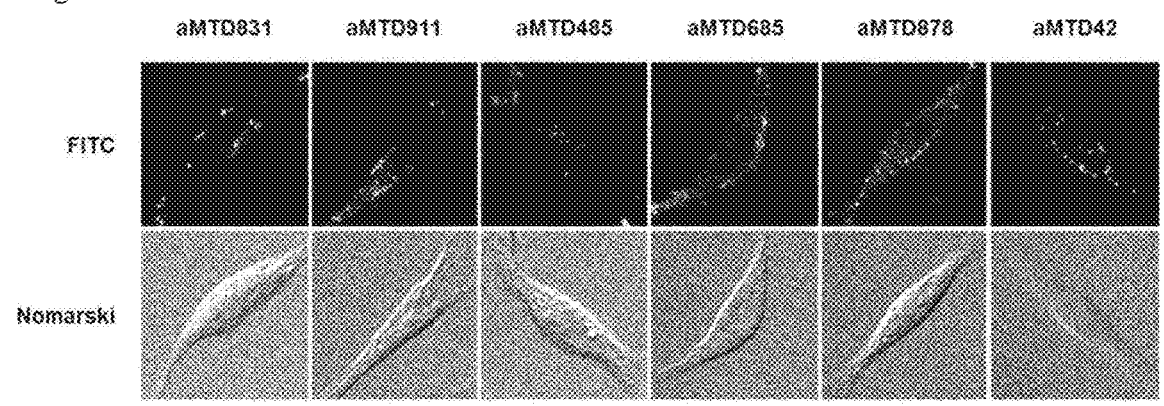

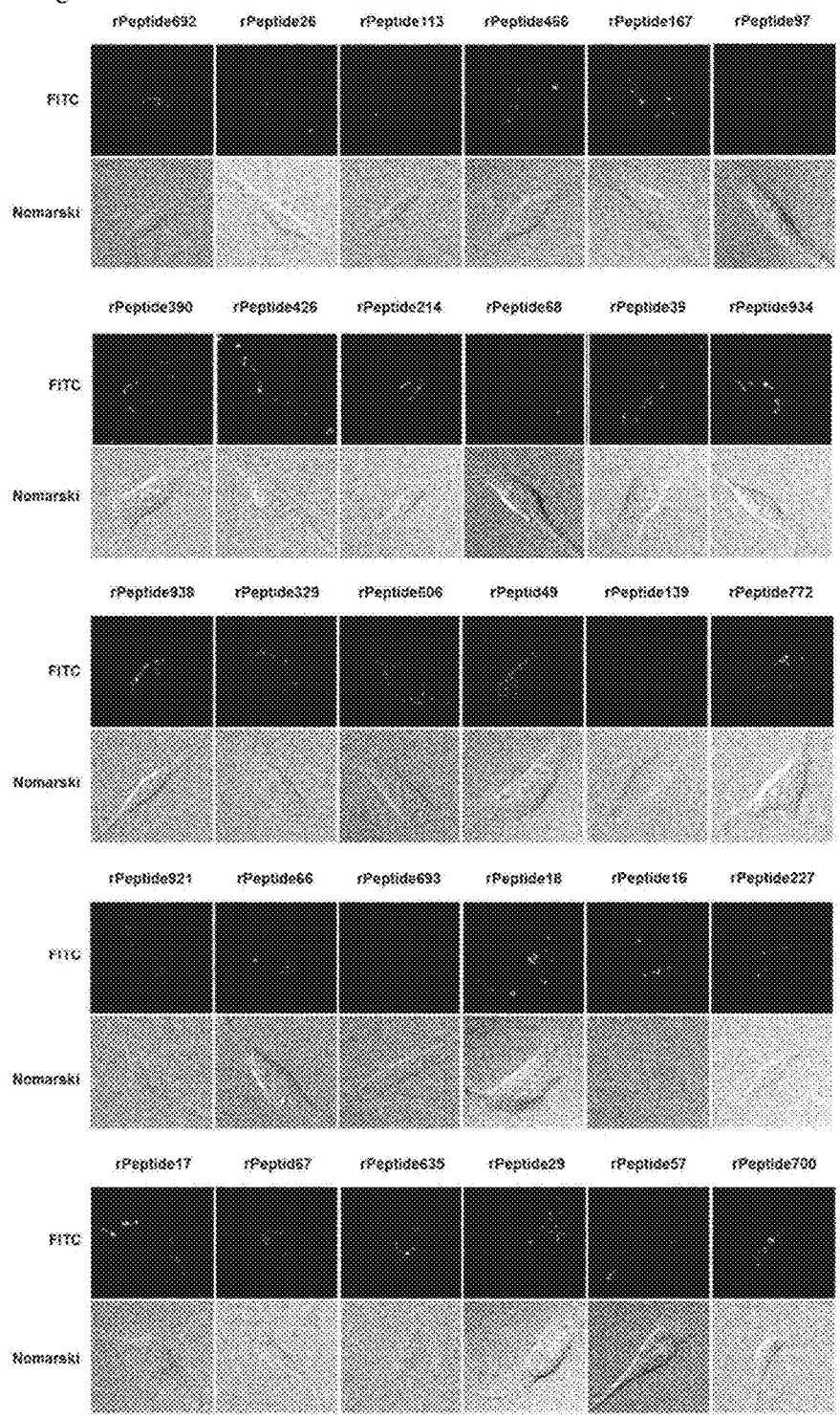
[Figure 8]

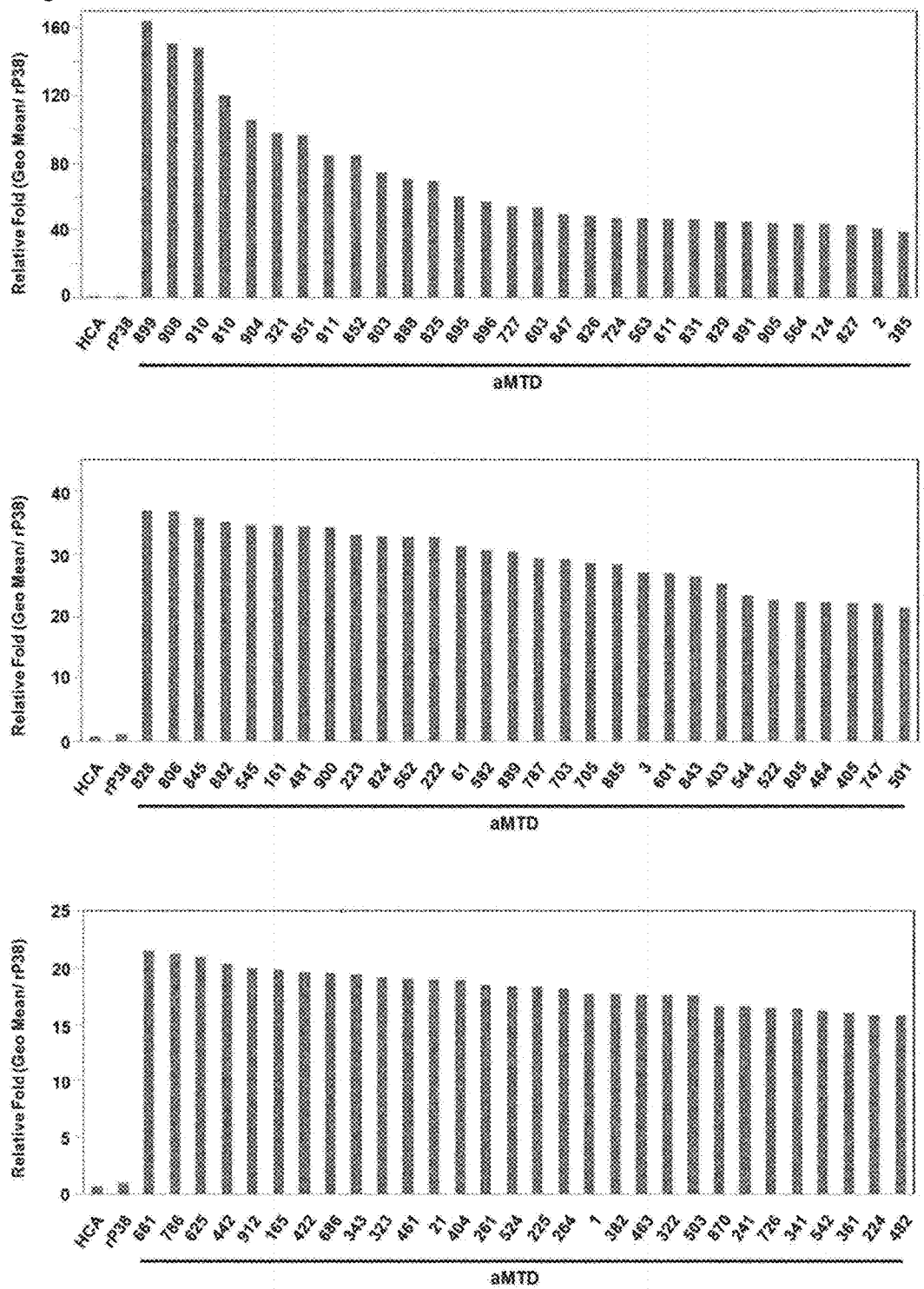
[Figure 9a]

[Figure 9b]
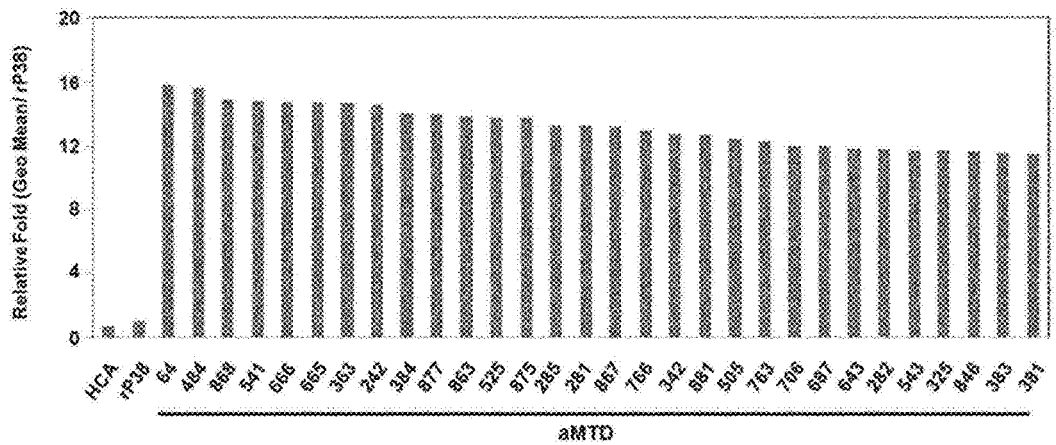
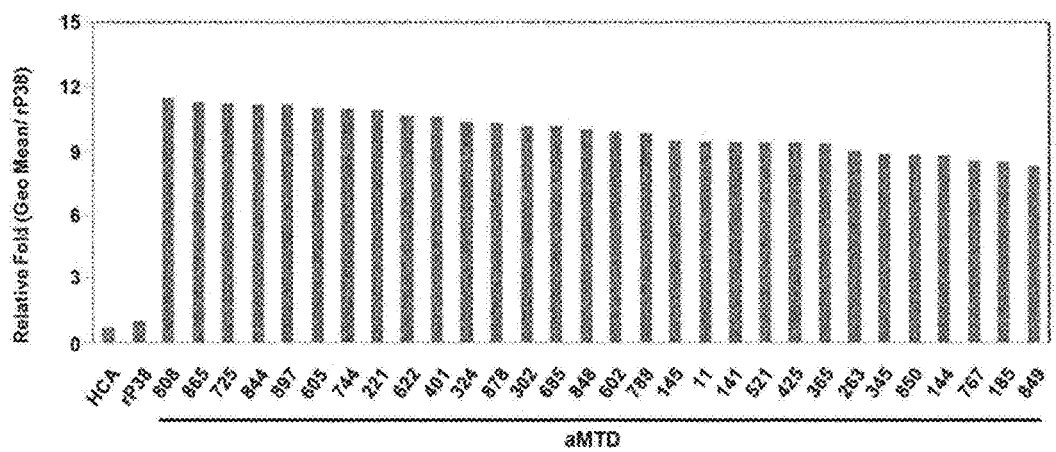
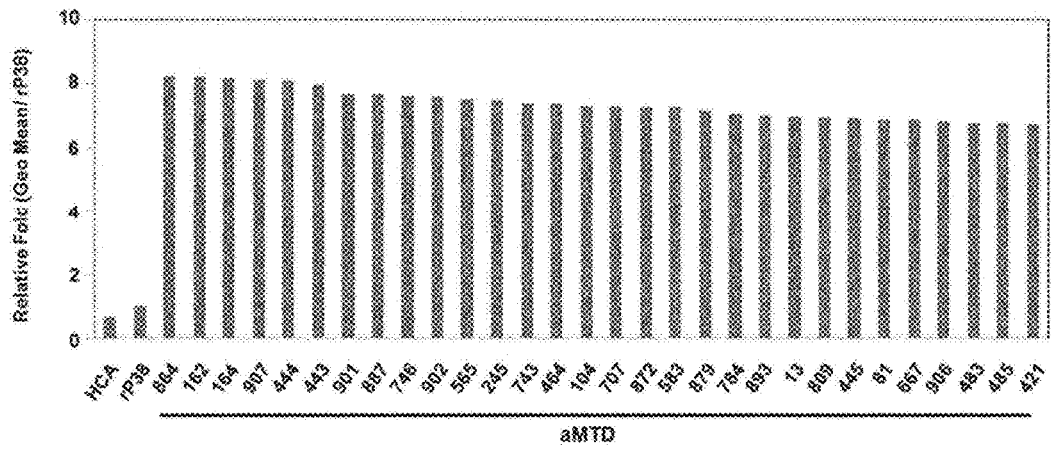

[Figure 9c]
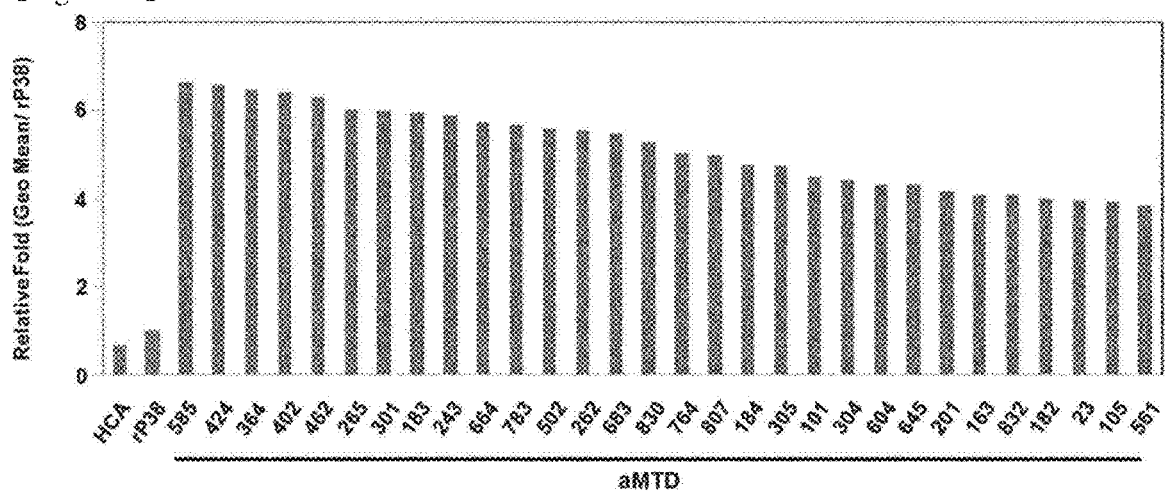
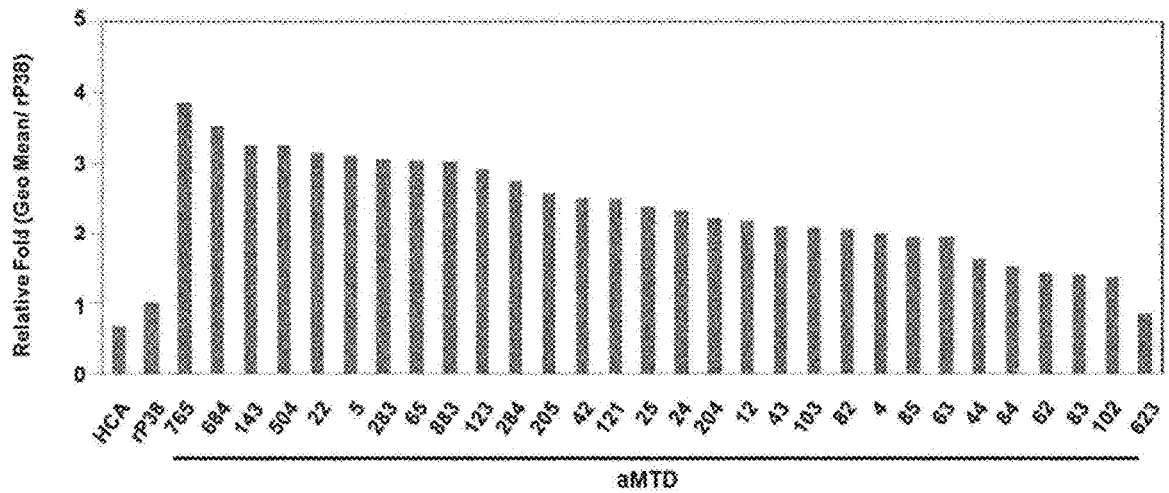

[Figure 10a]
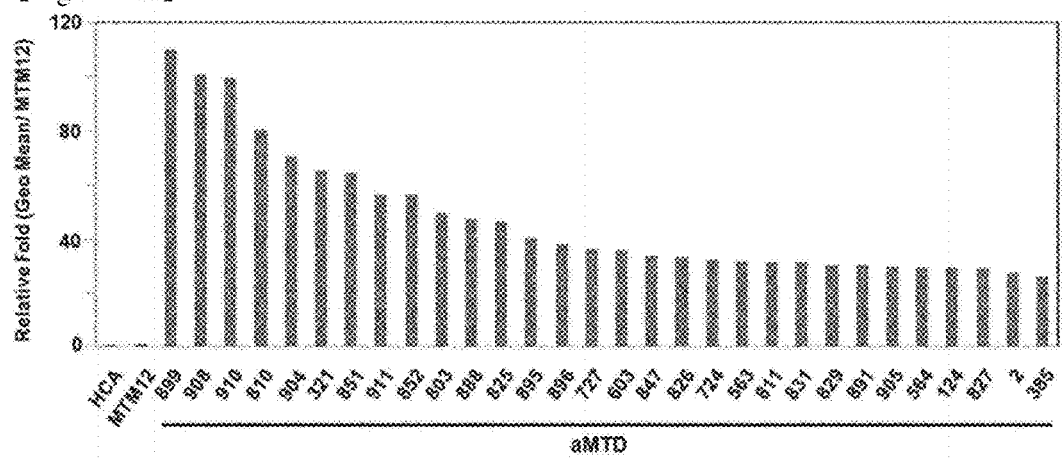
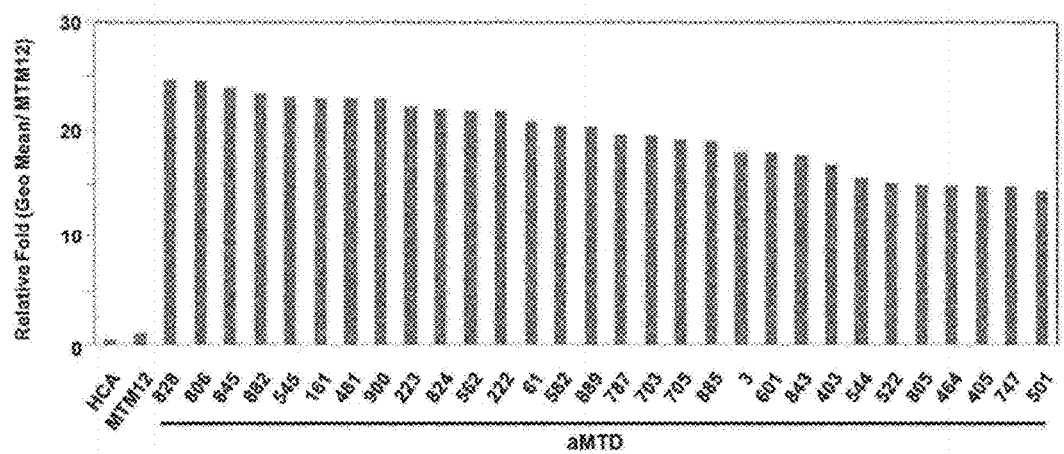
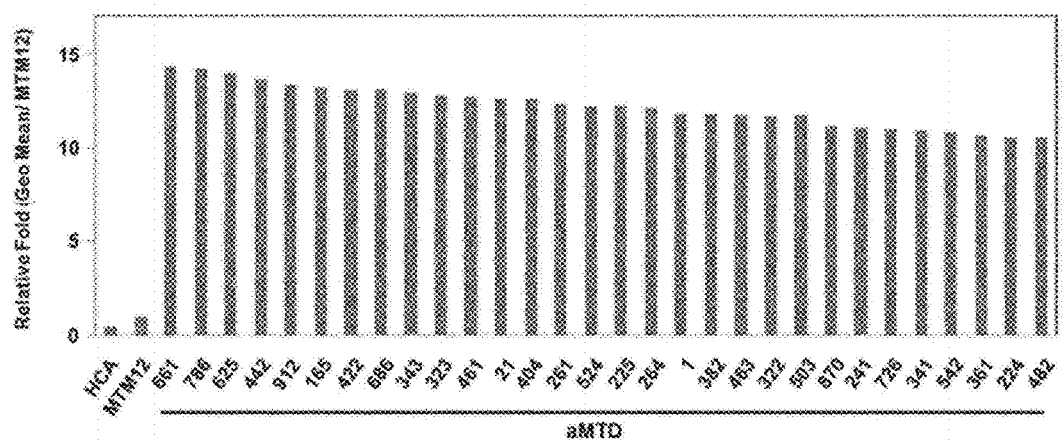

[Figure 10b]
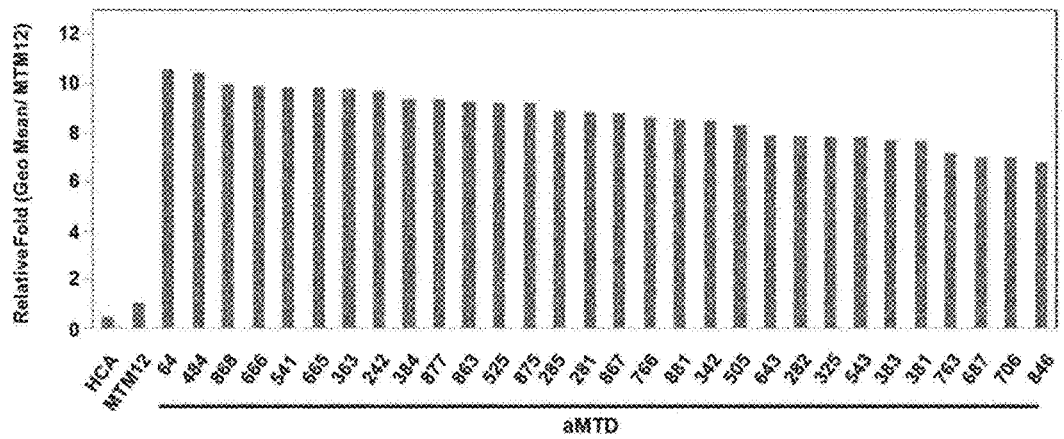
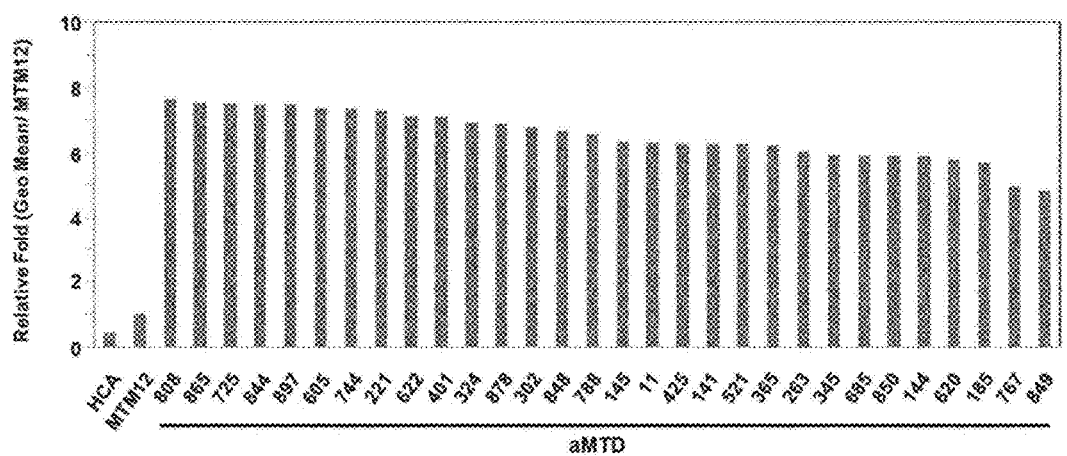
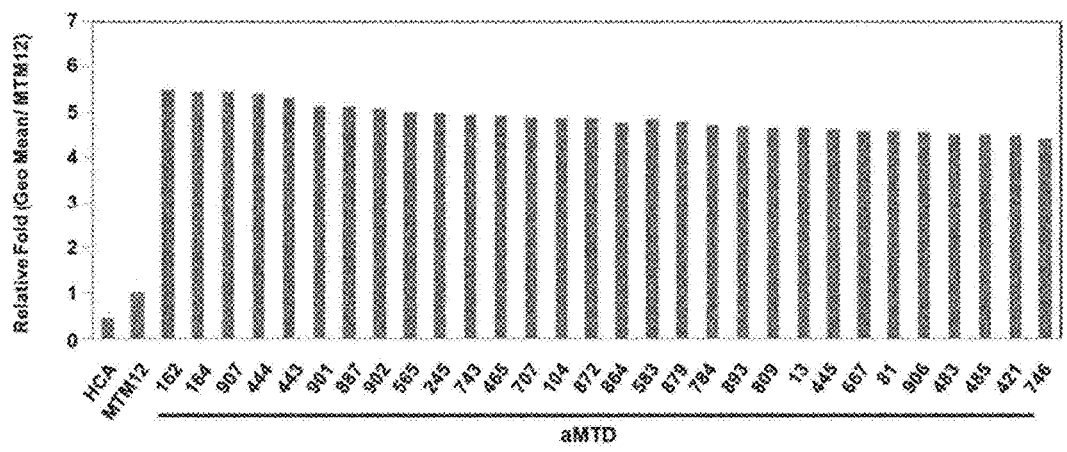

[Figure 10c]
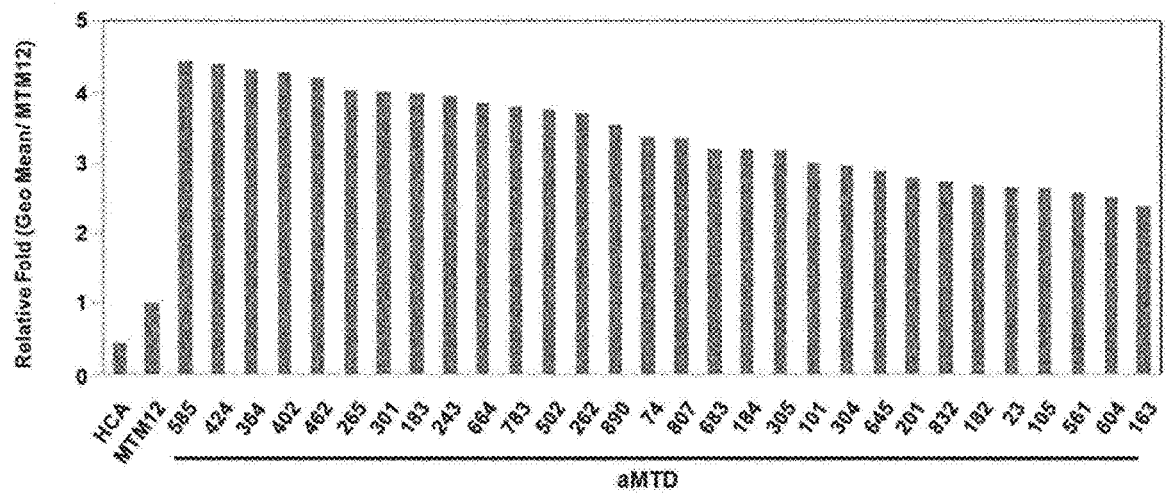
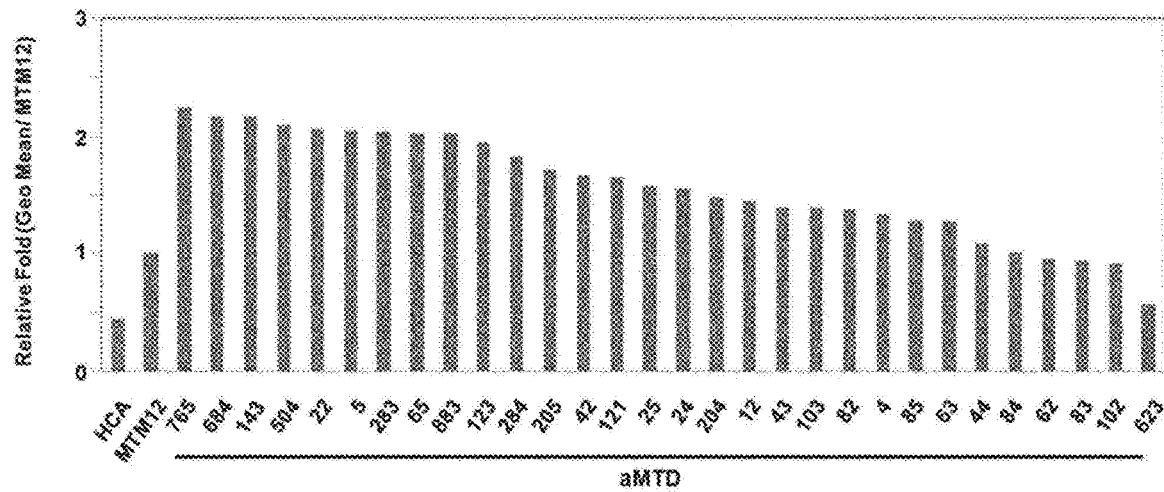

[Figure 11a]
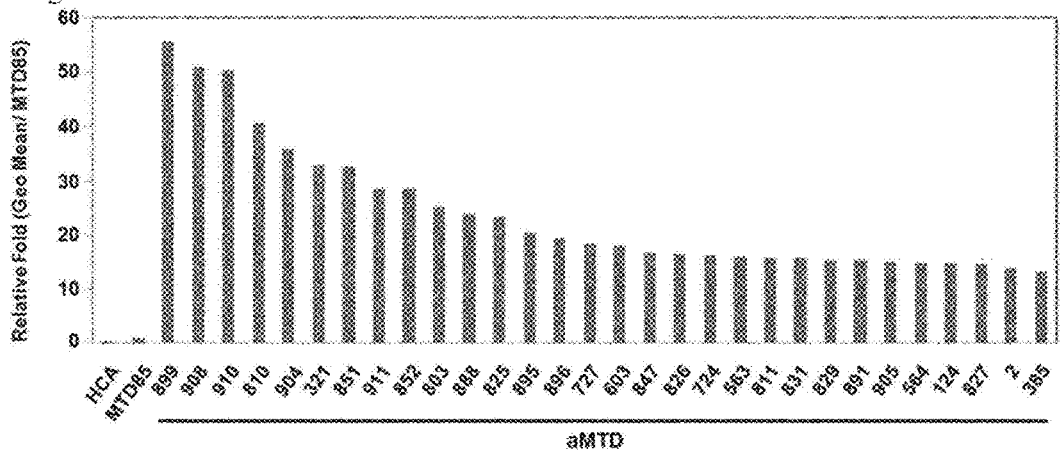
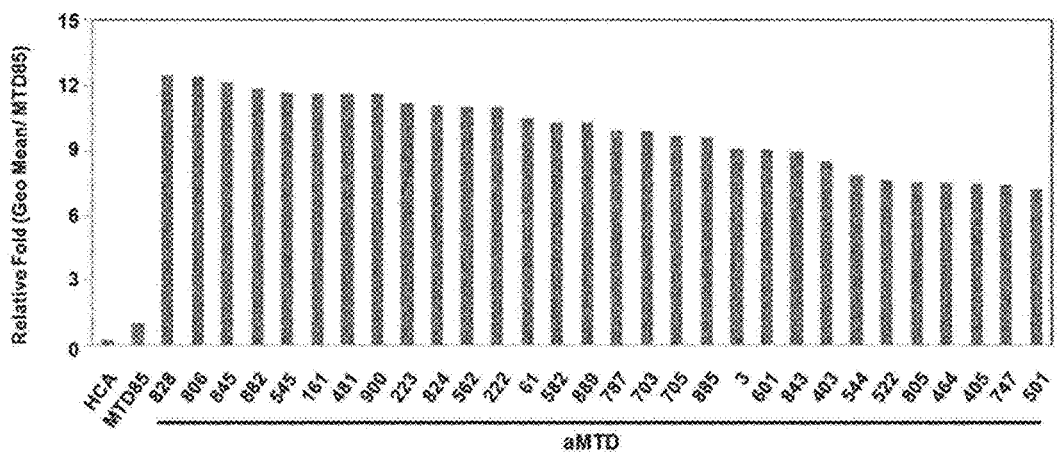
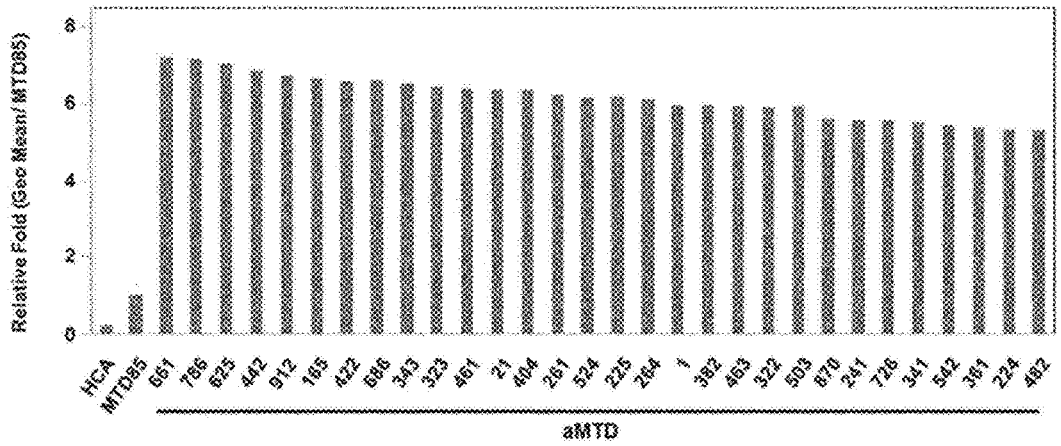

[Figure 11b]
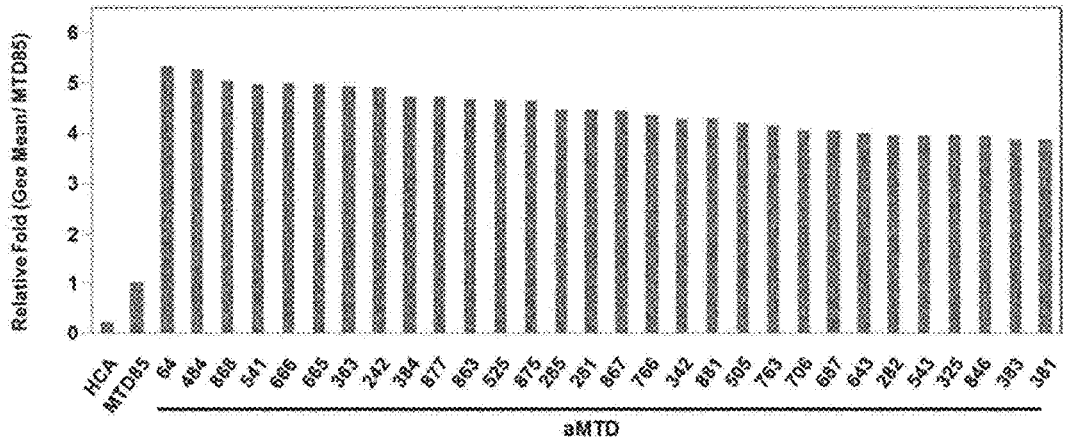
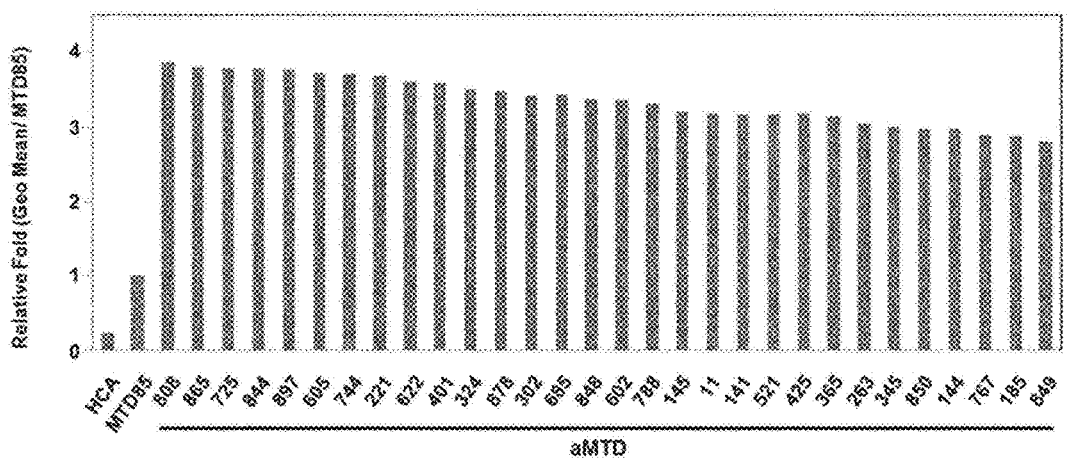
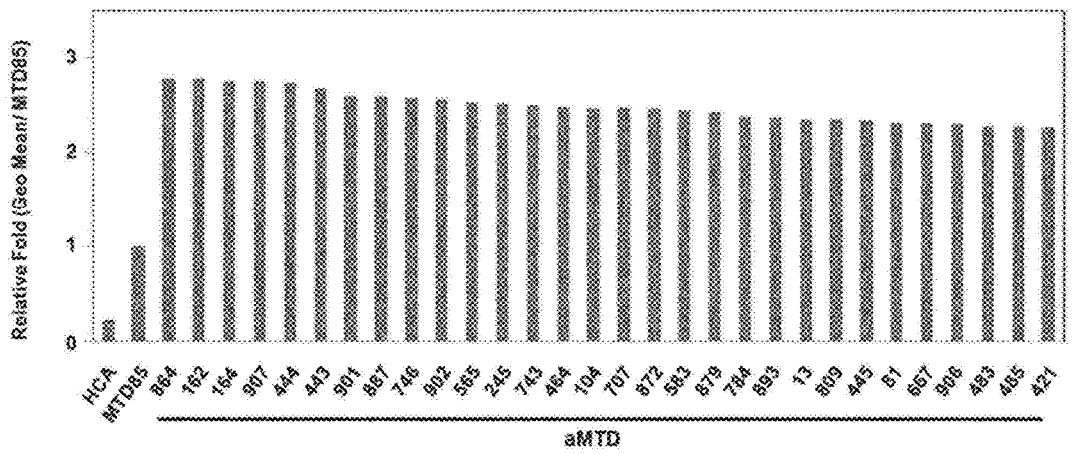

[Figure 11c]
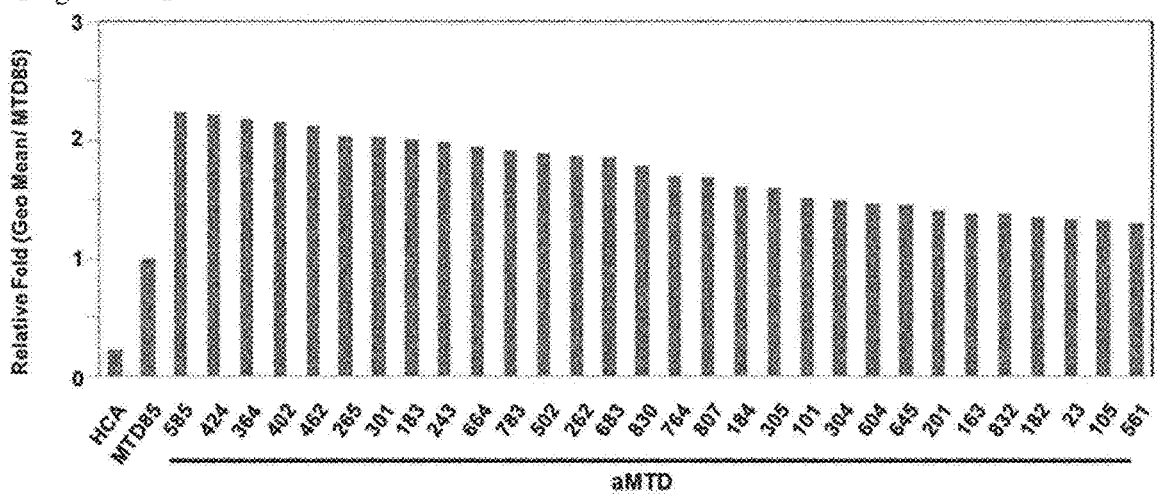
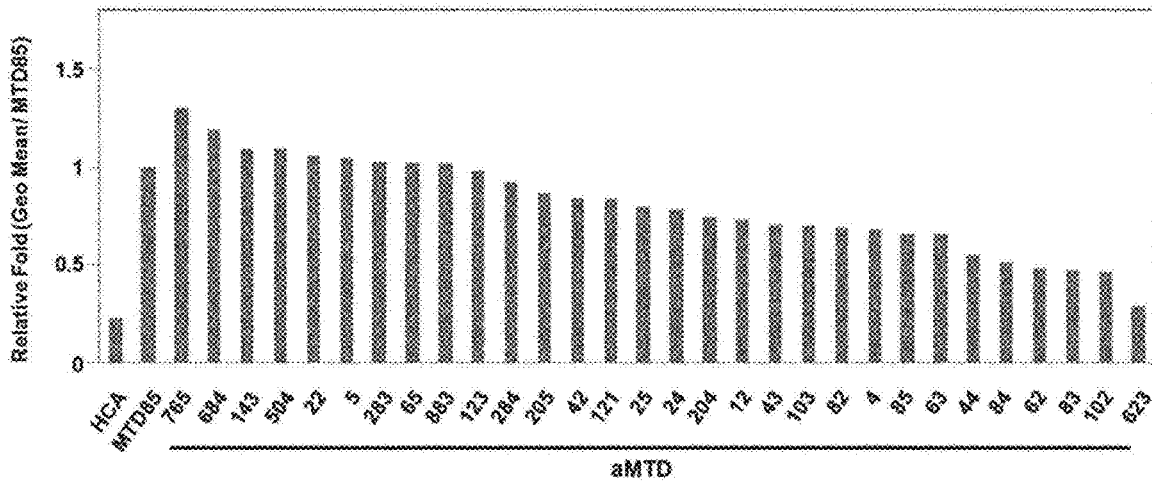

[Figure 12]
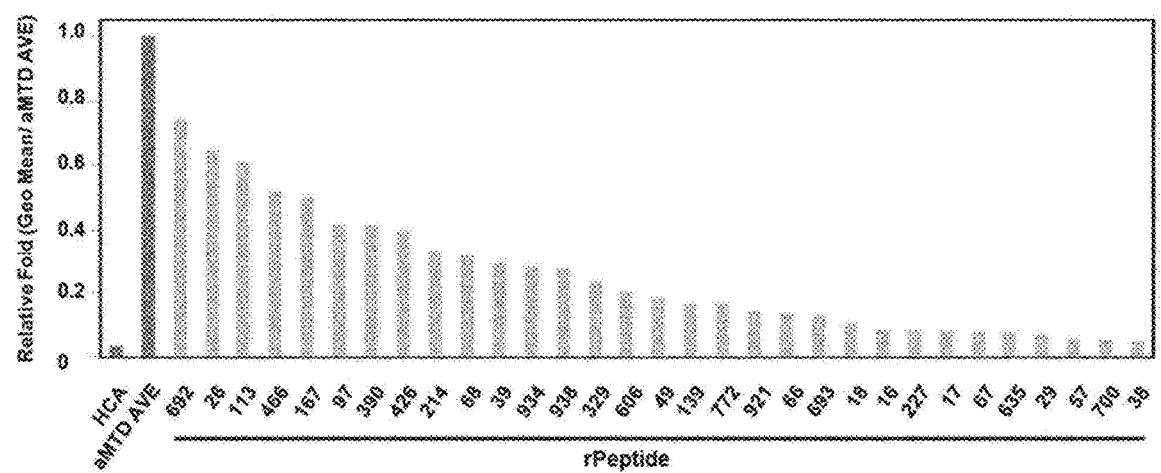

[Figure 13a]
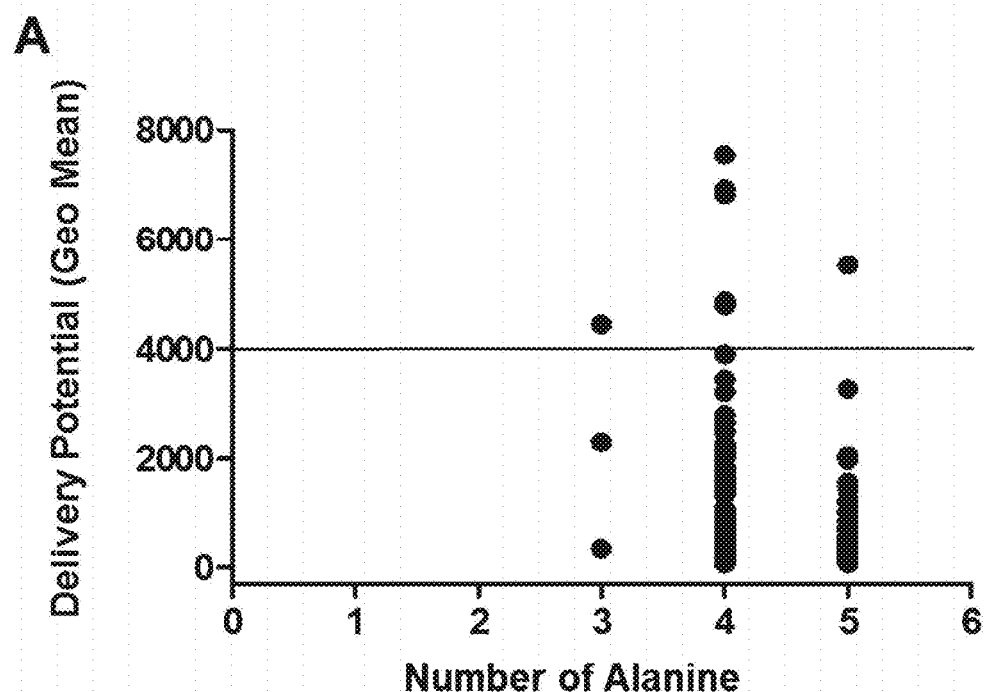
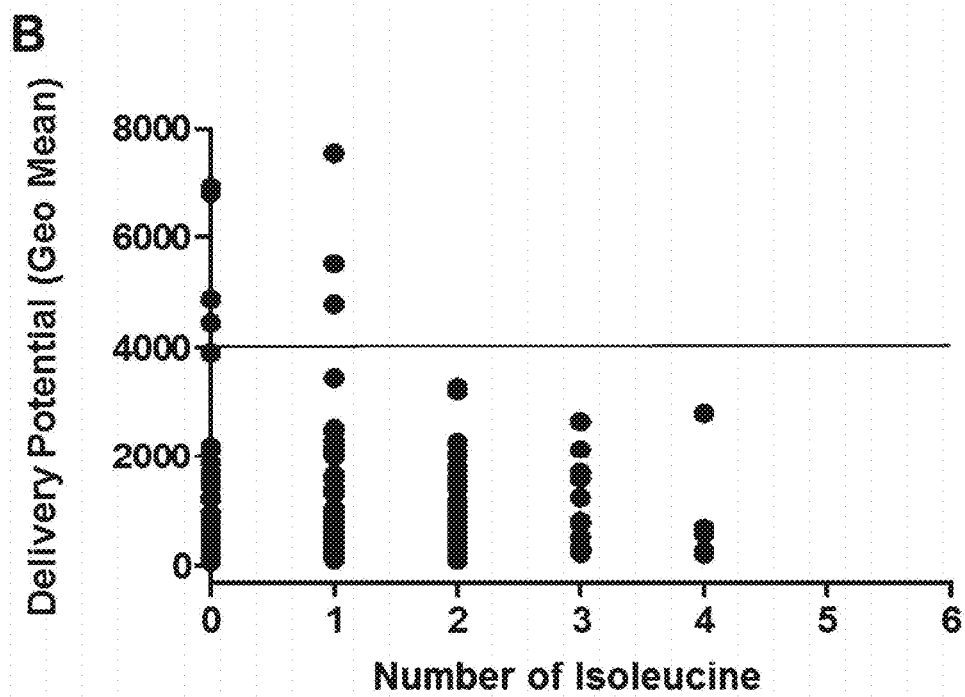

[Figure 13b]
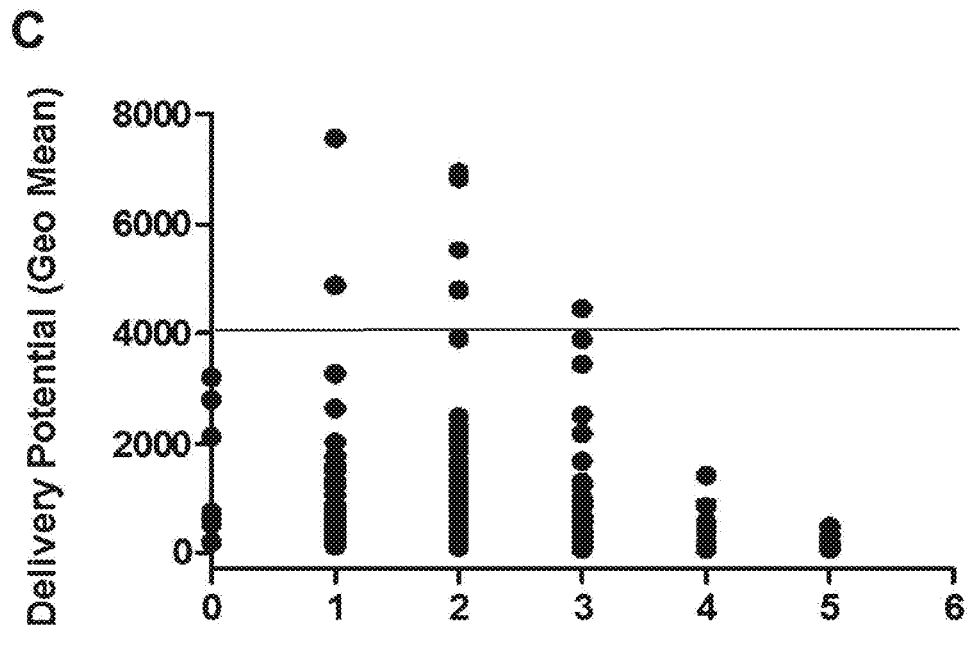
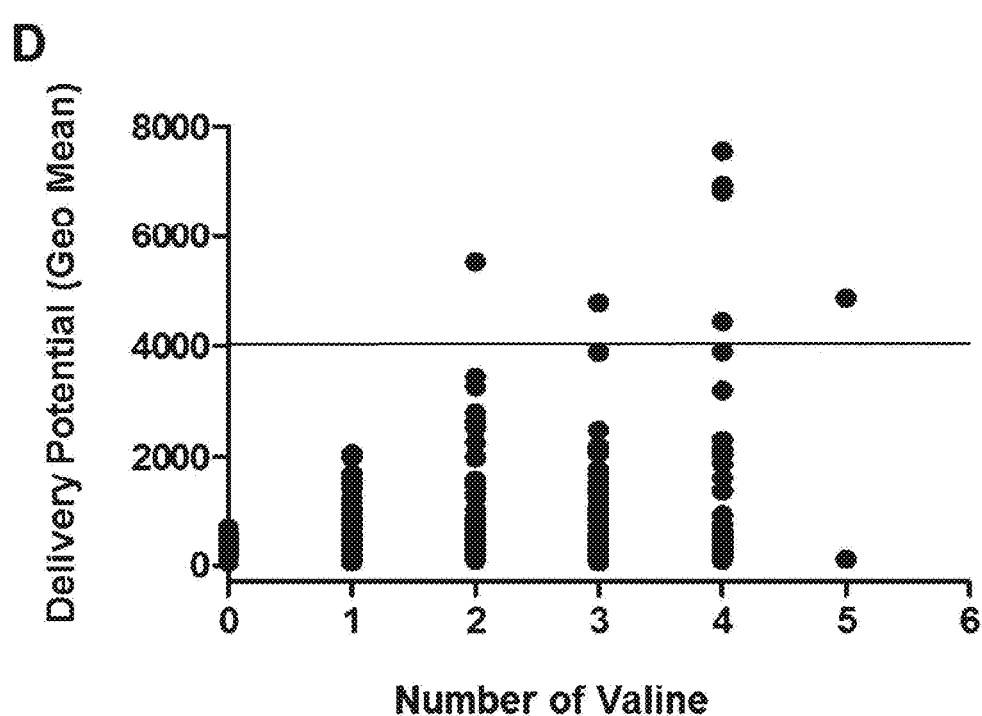

[Figure 14a]
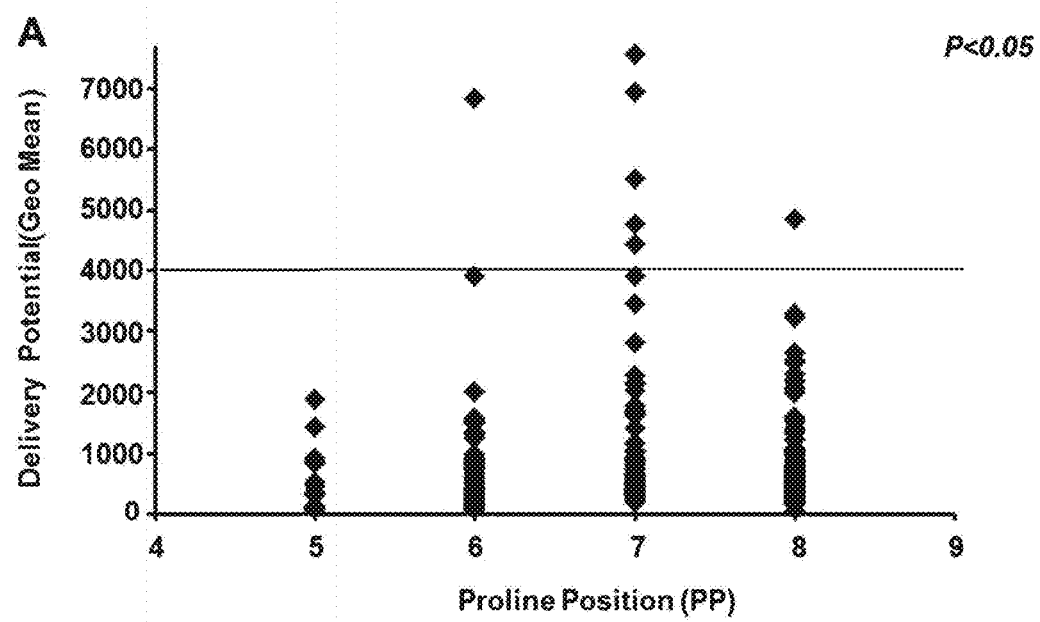
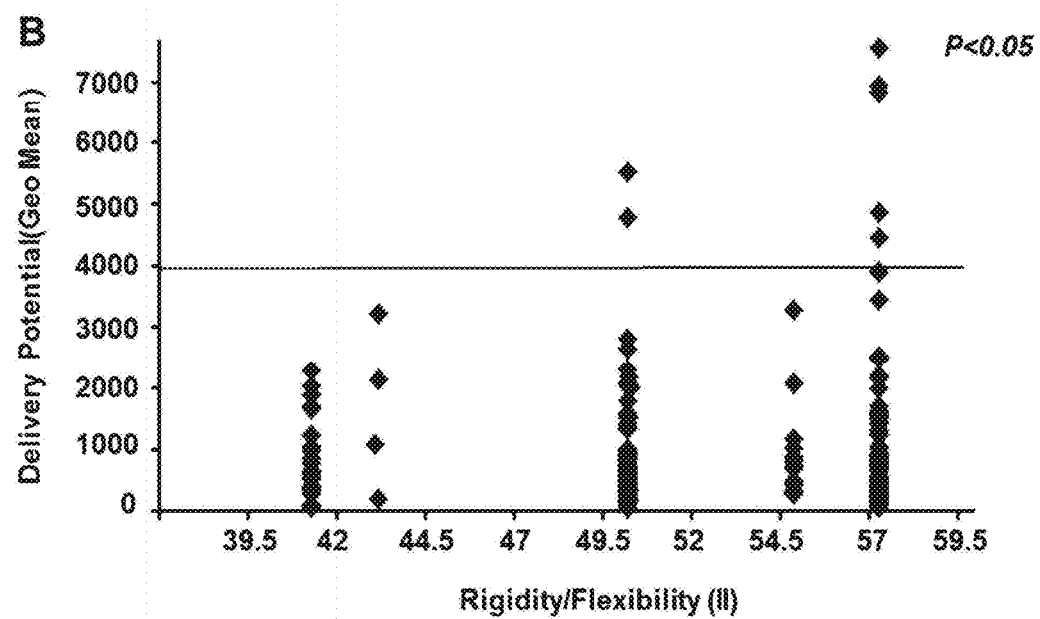

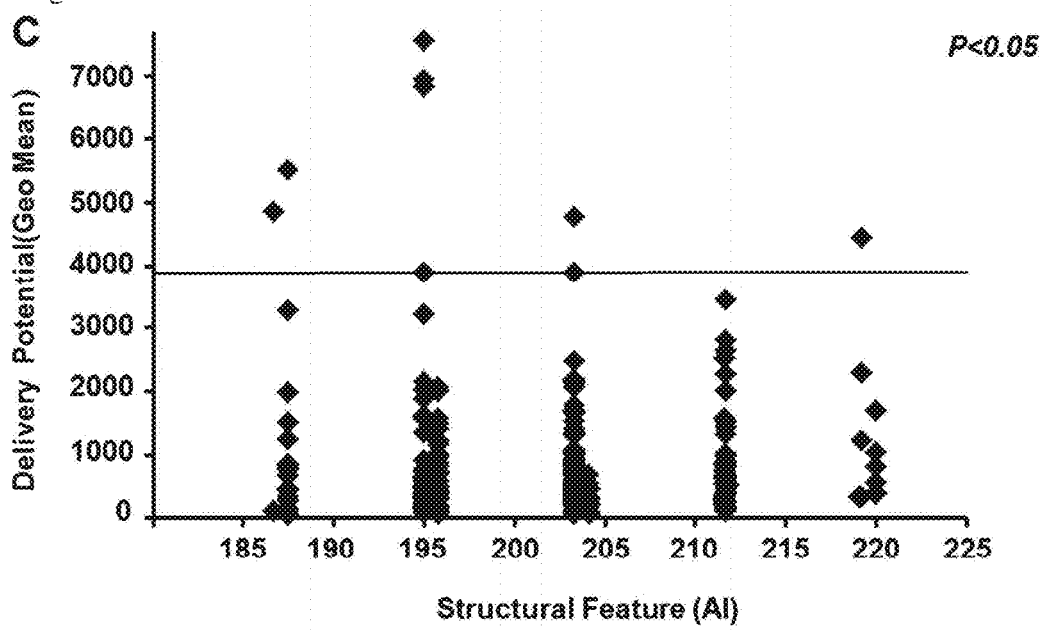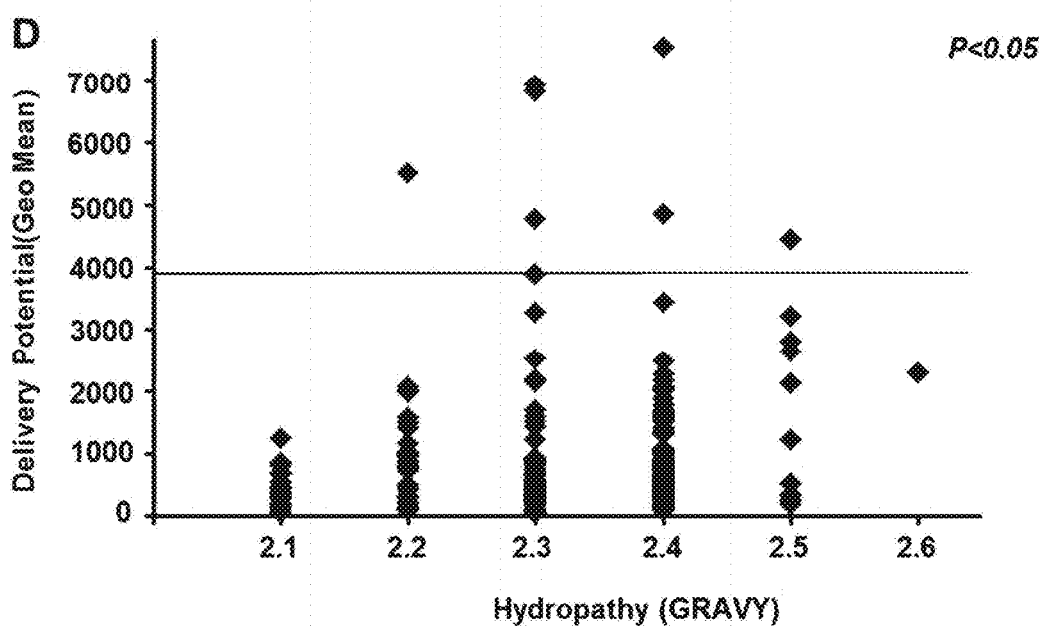

[Figure 15a]
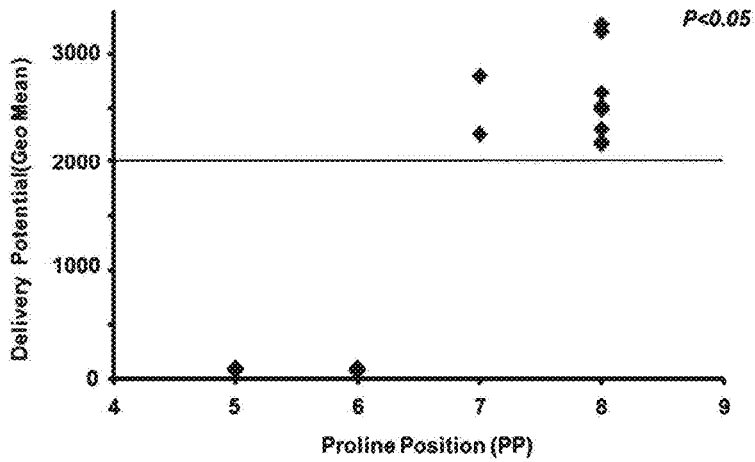
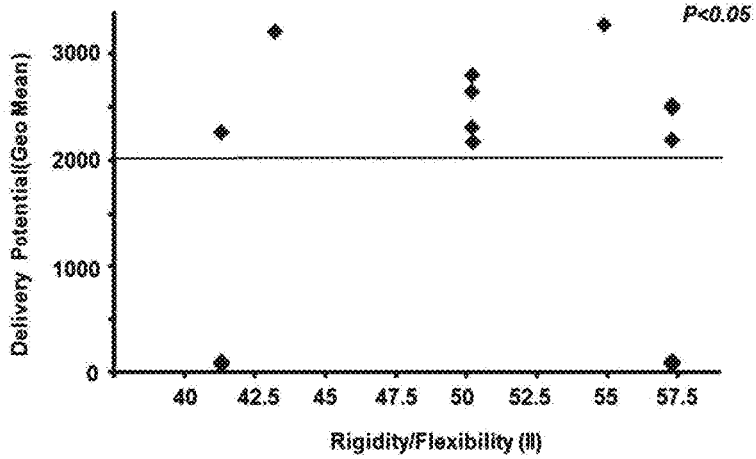

[Figure 15b]
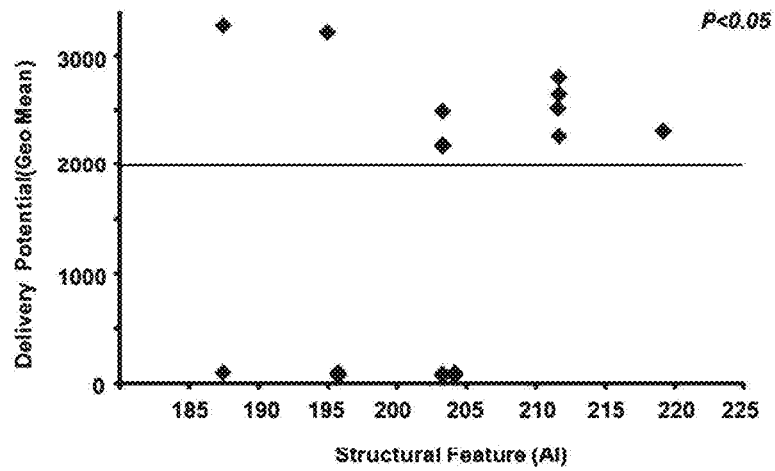
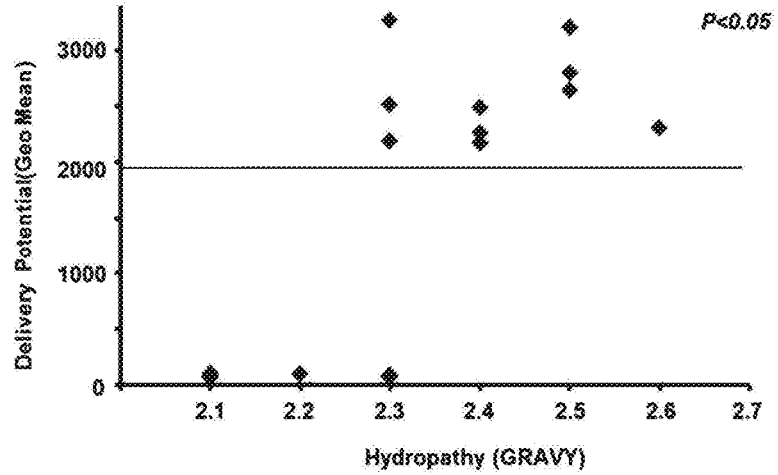

[Figure 16]
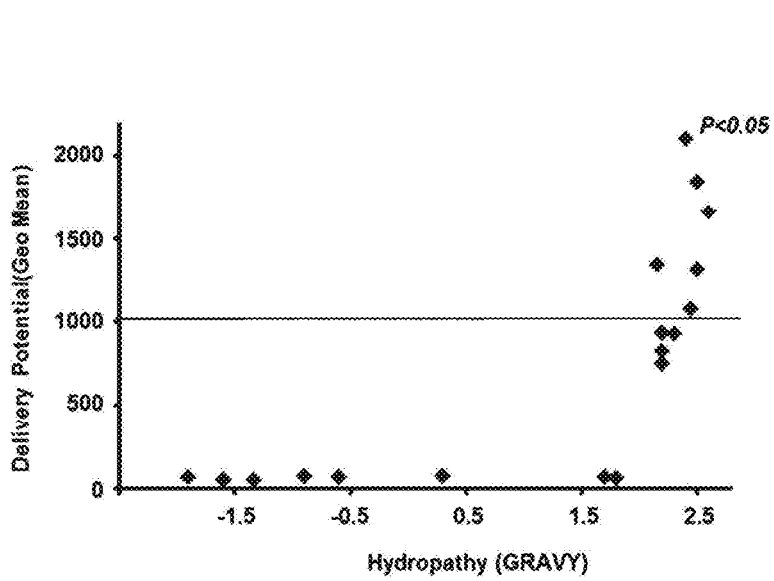
| ID | Hydropathy (GRAVY) | Delivery Potential (DP) |
|---|---|---|
| 33 | 2.4 | 2100 |
| 931 | 2.5 | 1843 |
| 436 | 2.6 | 1661 |
| 138 | 2.2 | 1339 |
| 77 | 2.5 | 1311 |
| 936 | 2.4 | 1077 |
| 226 | 2.2 | 935 |
| 30 | 2.3 | 931 |
| 6 | 2.2 | 824 |
| 750 | 2.2 | 750 |
| 67 | 0.3 | 71 |
| 20 | -0.9 | 70 |
| 635 | -1.9 | 67 |
| 29 | 1.7 | 63 |
| 40 | -0.6 | 63 |
| 190 | 1.8 | 59 |
| 57 | -1.6 | 51 |
| 159 | -1.3 | 51 |
| 700 | -1.6 | 47 |
[Figure 17]
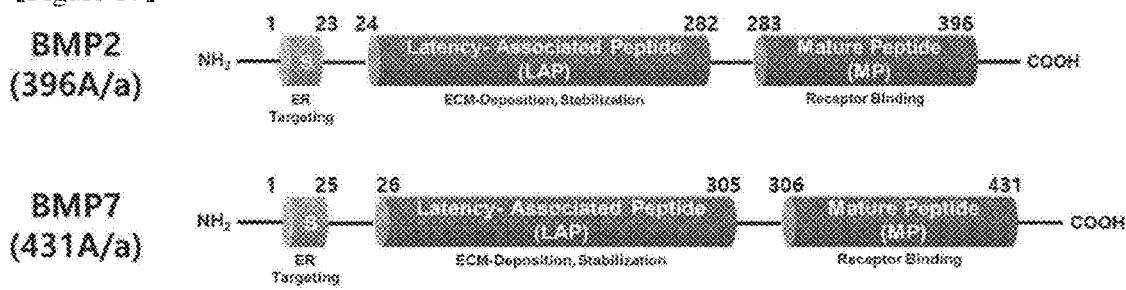

[Figure 18a]

| Clone ID | Structure | Full Name | Abbreviation (MW) |
|---|---|---|---|
| 2M-1 | [His-tag][B2 MP] | His-BMP2 MP | HB2M (15kDa) |
| 2 | [aMTD][B2 MP] | His-aMTD₂₄-BMP2 MP | HM₂₄B2M (16kDa) |
| 3 | [aMTD][B2 MP][SDA] | His-aMTD₂₄-BMP2 MP-SDA | HM₂₄B2MSA (36kDa) |
| 3C | [His-tag][B2 MP][SDA] | His-BMP2 MP-SDA | HB2MSA (35kDa) |
| 4 | [aMTD][B2 MP][SDB] | His-aMTD₂₄-BMP2 MP-SDB | HM₂₄B2MSB (27kDa) |
| 4C | [His-tag][B2 MP][SDB] | His-BMP2 MP-SDB | HB2MSB (26kDa) |

Legend: His-tag (19 A/a), aMTD (12 A/a), BMP2 Mature Peptide (114 A/a), SDA (184 A/a), SDB (99 A/a)

| Clone ID | Structure | Full Name | Abbreviation (MW) |
|---|---|---|---|
| 7M-1 | [His-tag][B7 MP] | His-BMP7 MP | HB7M (17kDa) |
| 2 | [aMTD][B7 MP] | His-aMTD₂₄-BMP7 MP | HM₂₄B7M (18kDa) |
| 3 | [aMTD][B7 MP][SDA] | His-aMTD₂₄-BMP7 MP-SDA | HM₂₄B7MSA (39kDa) |
| 3C | [His-tag][B7 MP][SDA] | His-BMP7 MP-SDA | HB7MSA (37kDa) |
| 4 | [aMTD][B7 MP][SDB] | His-aMTD₂₄-BMP7 MP-SDB | HM₂₄B7MSB (29kDa) |
| 4C | [His-tag][B7 MP][SDB] | His-BMP7 MP-SDB | HB7MSB (27kDa) |

Legend: His-tag (19 A/a), aMTD (12 A/a), BMP7 Mature Peptide (126 A/a), SDA (184 A/a), SDB (99 A/a)

[Figure 18b]

| Clone ID | Structure | Full Name | Abbreviation (MW) |
|---|---|---|---|
| 2L-1 | [His-tag][B2 LAP][B2 MP] | His-BMP2 LAP/MP | HB2L (44kDa) |
| 2 | [aMTD][B2 LAP][B2 MP] | His-aMTD₂₄-BMP2 LAP/MP | HM₂₄B2L (45kDa) |
| 3 | [aMTD][B2 LAP][B2 MP][SDA] | His-aMTD₂₄-BMP2 LAP/MP-SDA | HM₂₄B2LSA (65kDa) |
| 4 | [aMTD][B2 LAP][B2 MP][SDB] | His-aMTD₂₄-BMP2 LAP/MP-SDB | HM₂₄B2LSB (56kDa) |

Legend: His-tag (19 A/a), aMTD (12 A/a), BMP2 Mature Peptide (114 A/a), BMP2 Latency Associated Peptide (259 A/a), SDA (184 A/a), SDB (99 A/a)

| Clone ID | Structure | Full Name | Abbreviation (MW) |
|---|---|---|---|
| 7L-1 | [His-tag][B7 LAP][B7 MP] | His-BMP7 LAP/MP | HB7L (48kDa) |
| 2 | [aMTD][B7 LAP][B7 MP] | His-aMTD₂₄-BMP7 LAP/MP | HM₂₄B7L (49kDa) |
| 3 | [aMTD][B7 LAP][B7 MP][SDA] | His-aMTD₂₄-BMP7 LAP/MP-SDA | HM₂₄B7LSA (69kDa) |
| 4 | [aMTD][B7 LAP][B7 LAP][SDB] | His-aMTD₂₄-BMP7 LAP/MP-SDB | HM₂₄B7LSB (60kDa) |

Legend: His-tag (19 A/a), aMTD (12 A/a), BMP7 Mature Peptide (126 A/a), BMP7 Latency Associated Peptide (279 A/a), SDA (184 A/a), SDB (99 A/a)

[Figure 19a]
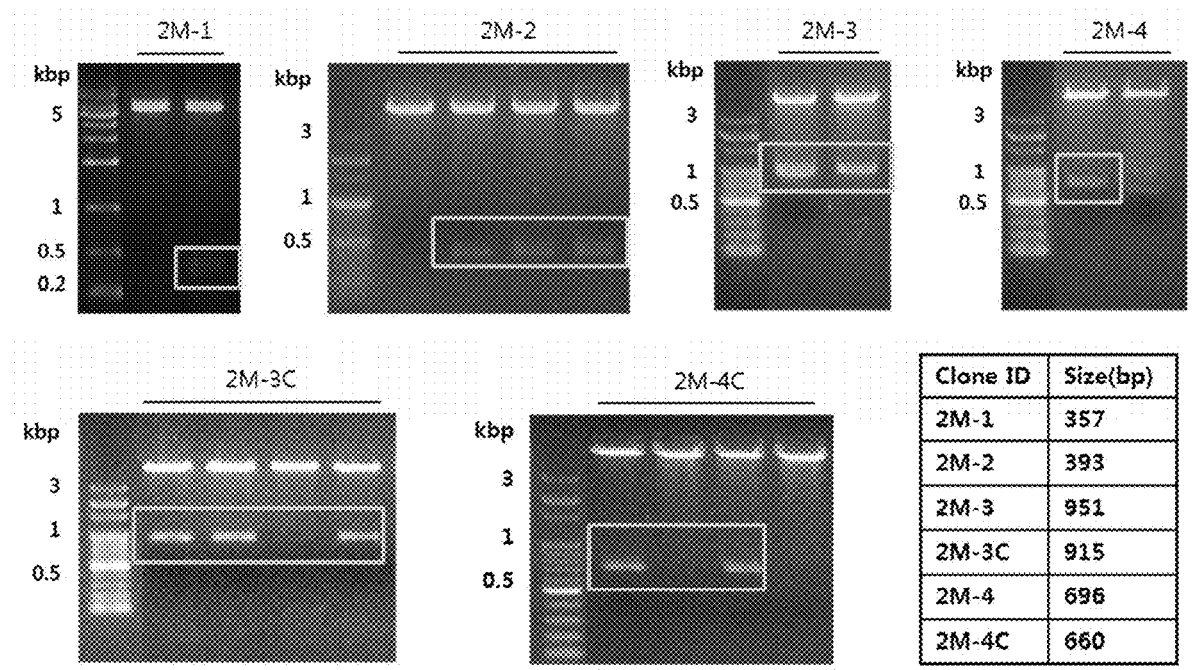

[Figure 19b]
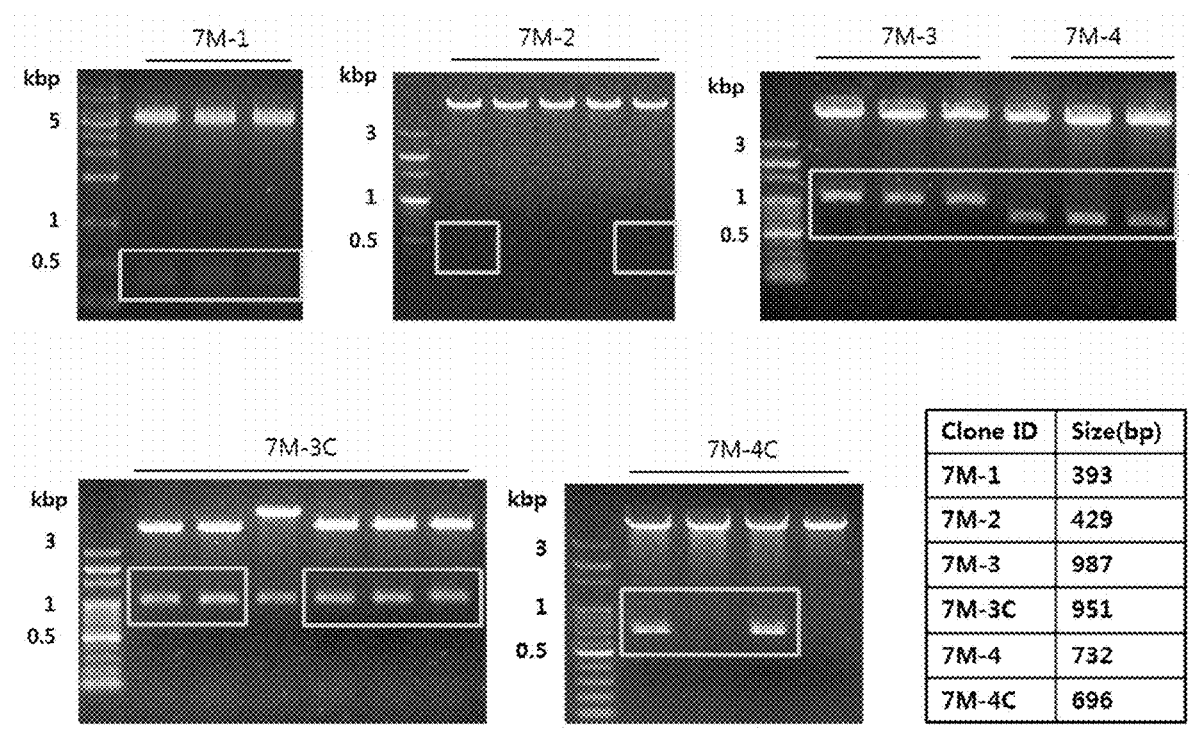

[Figure 19c]
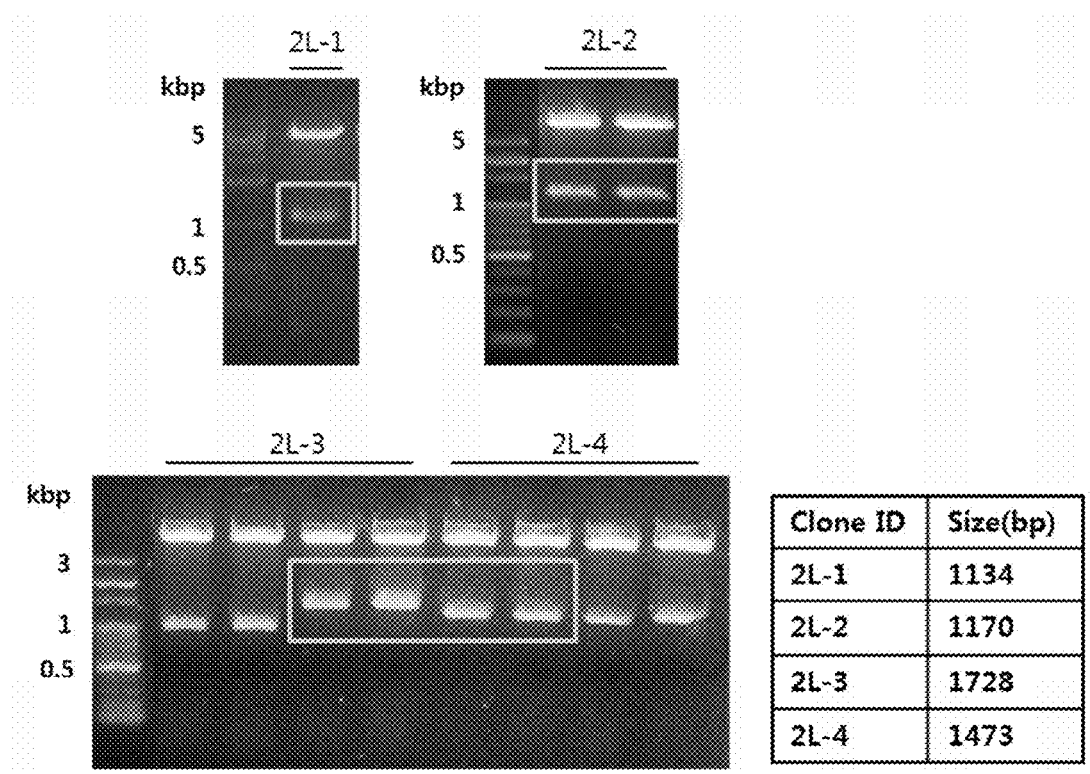

[Figure 19d]
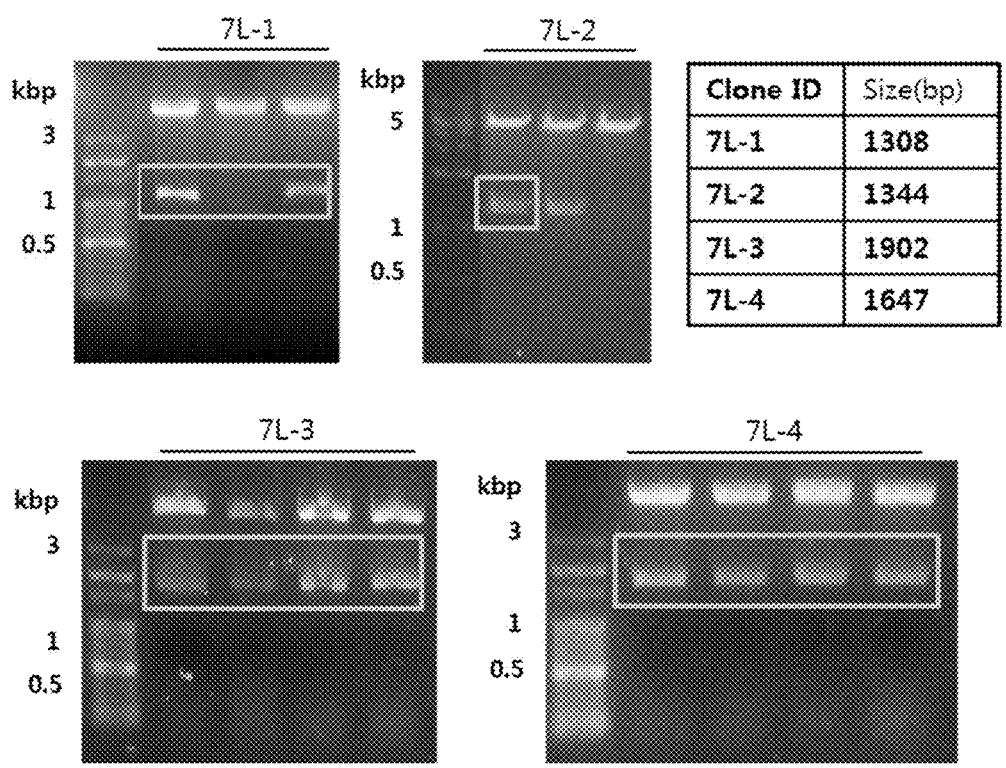

[Figure 20a]
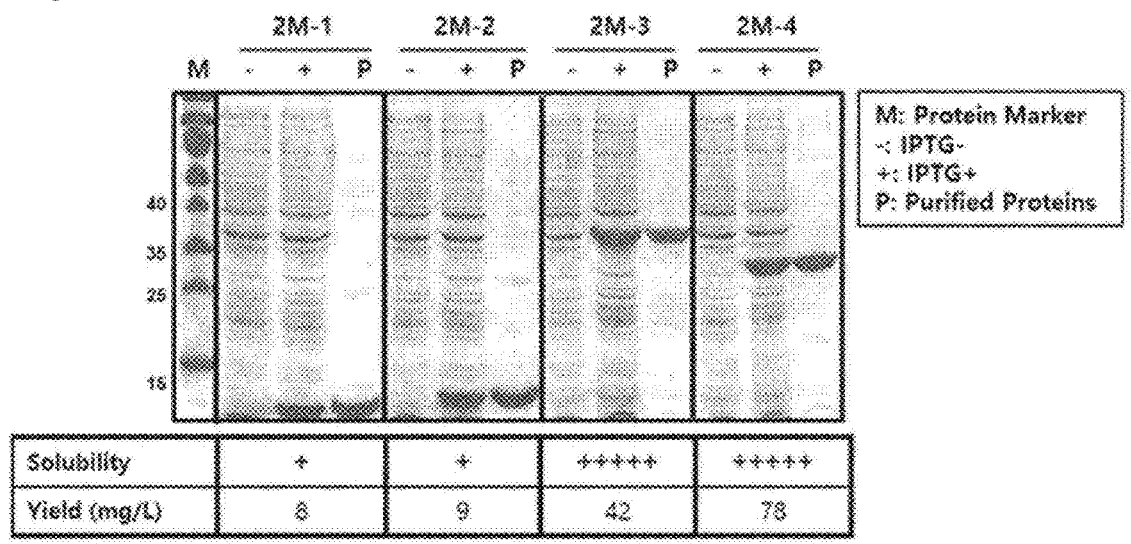
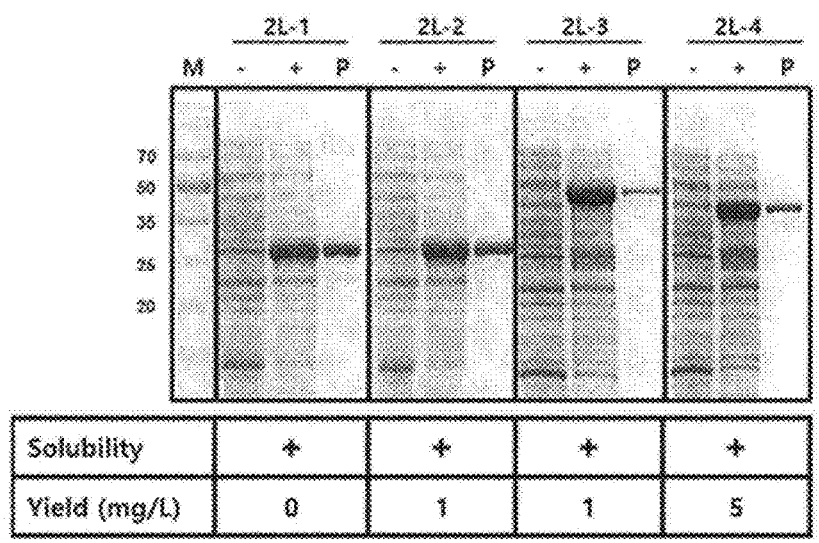

[Figure 20b]
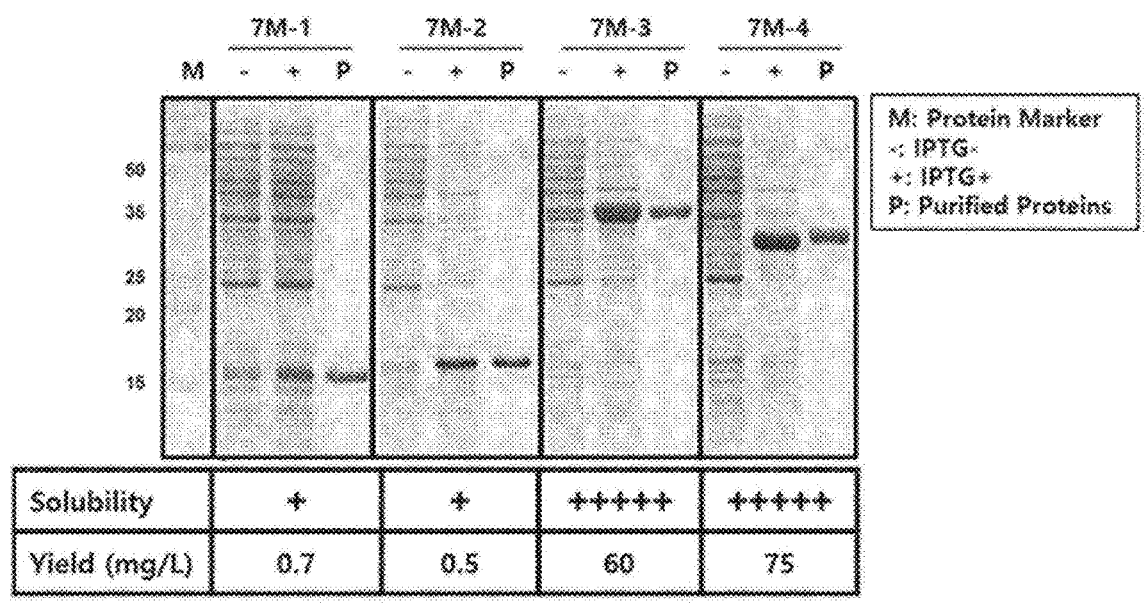
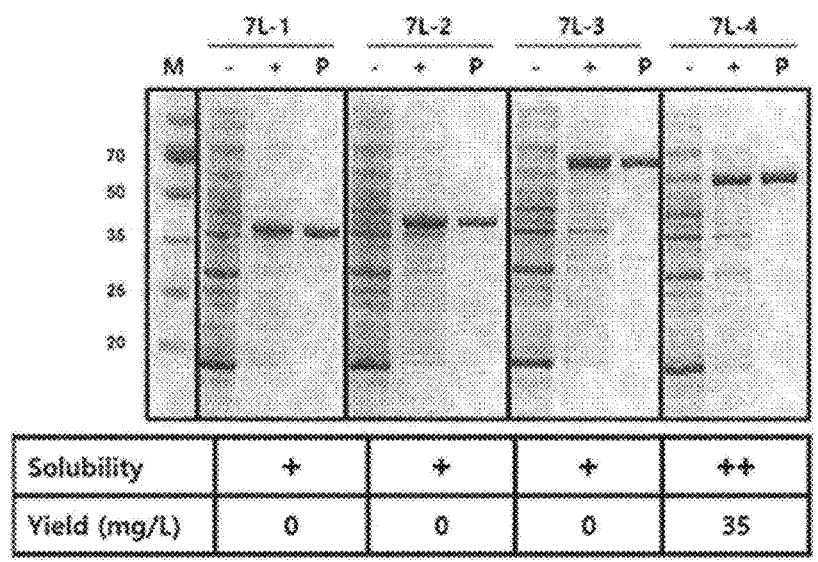

[Figure 21]

[Figure 22]
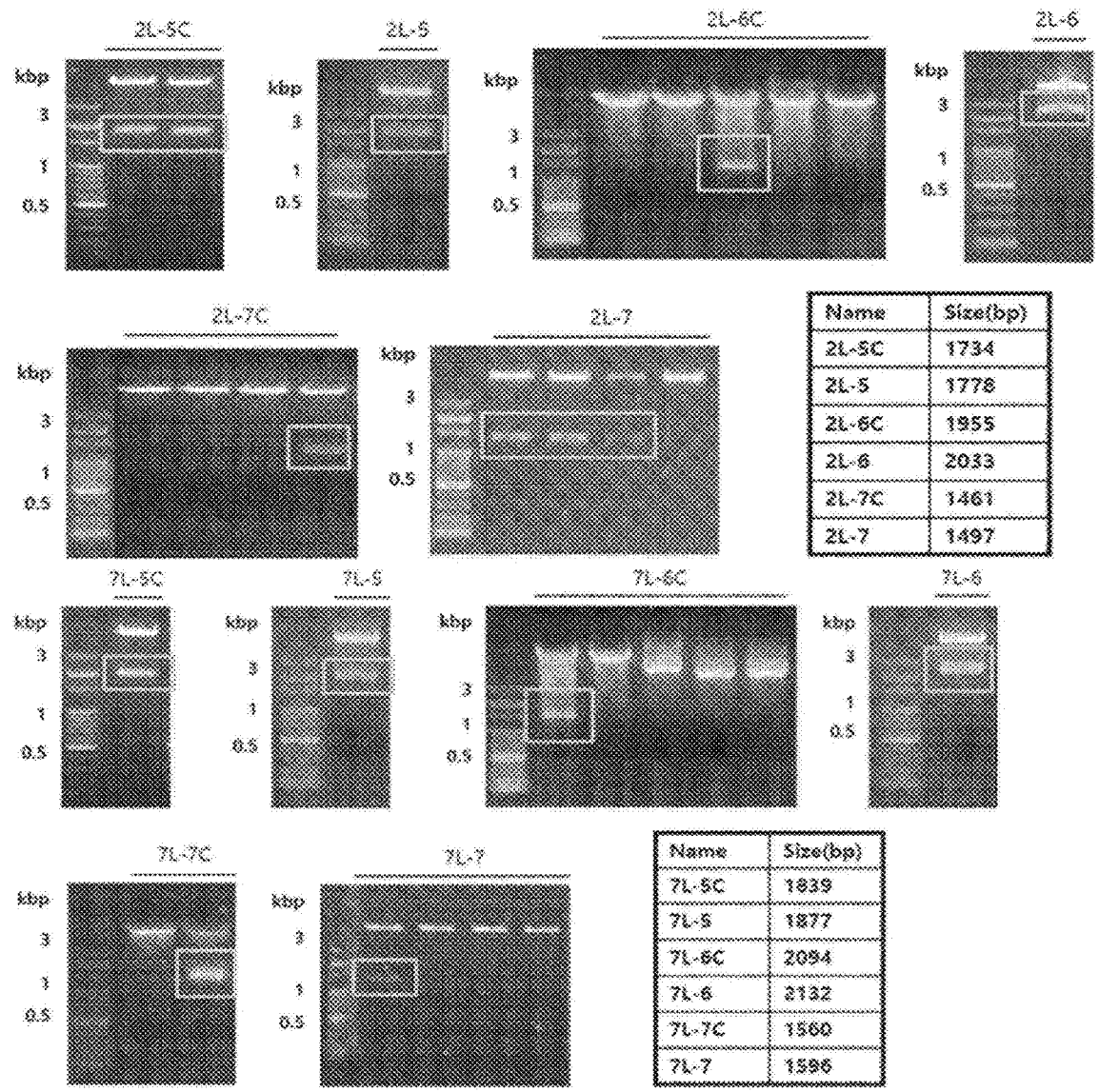

[Figure 23a]
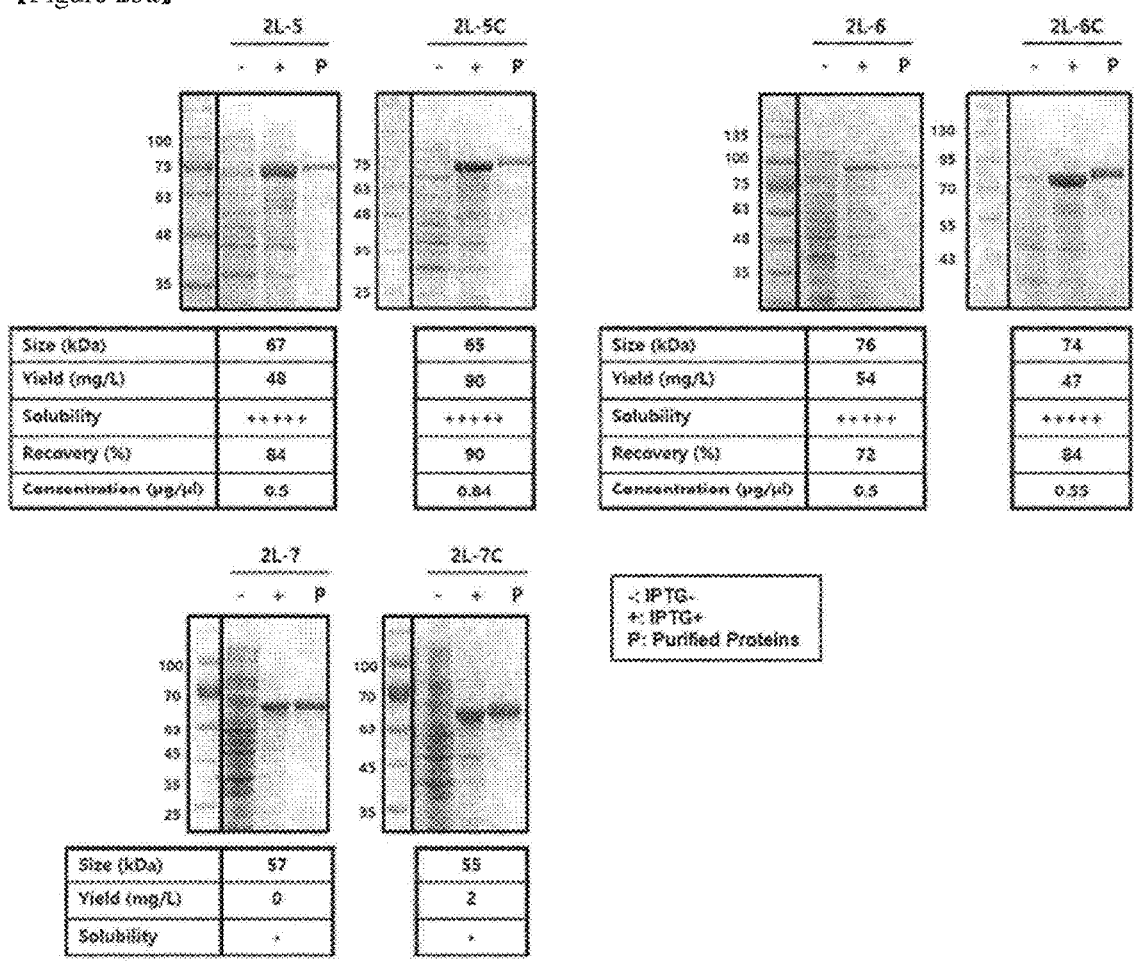

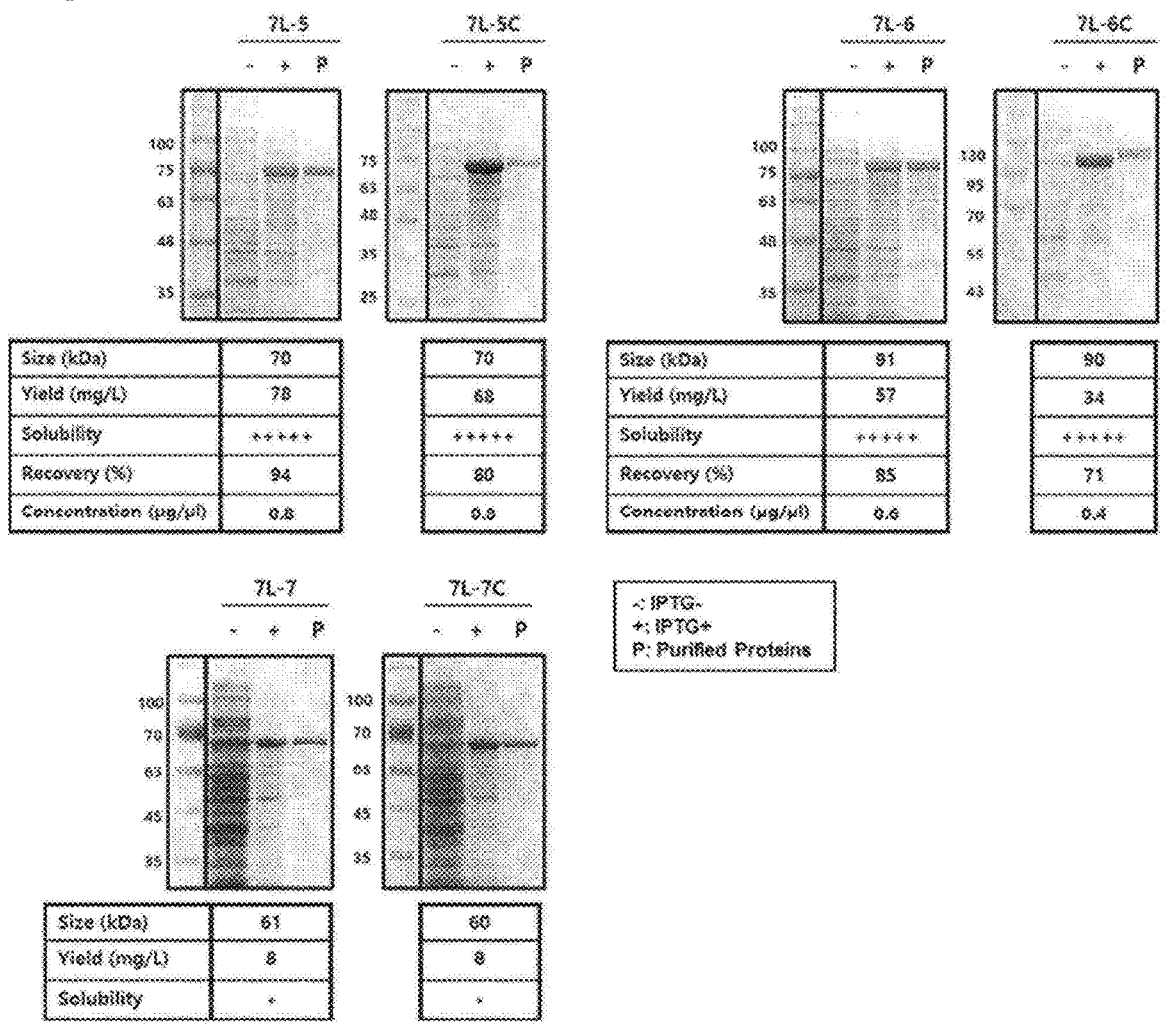
[Figure 23b]

[Figure 24]
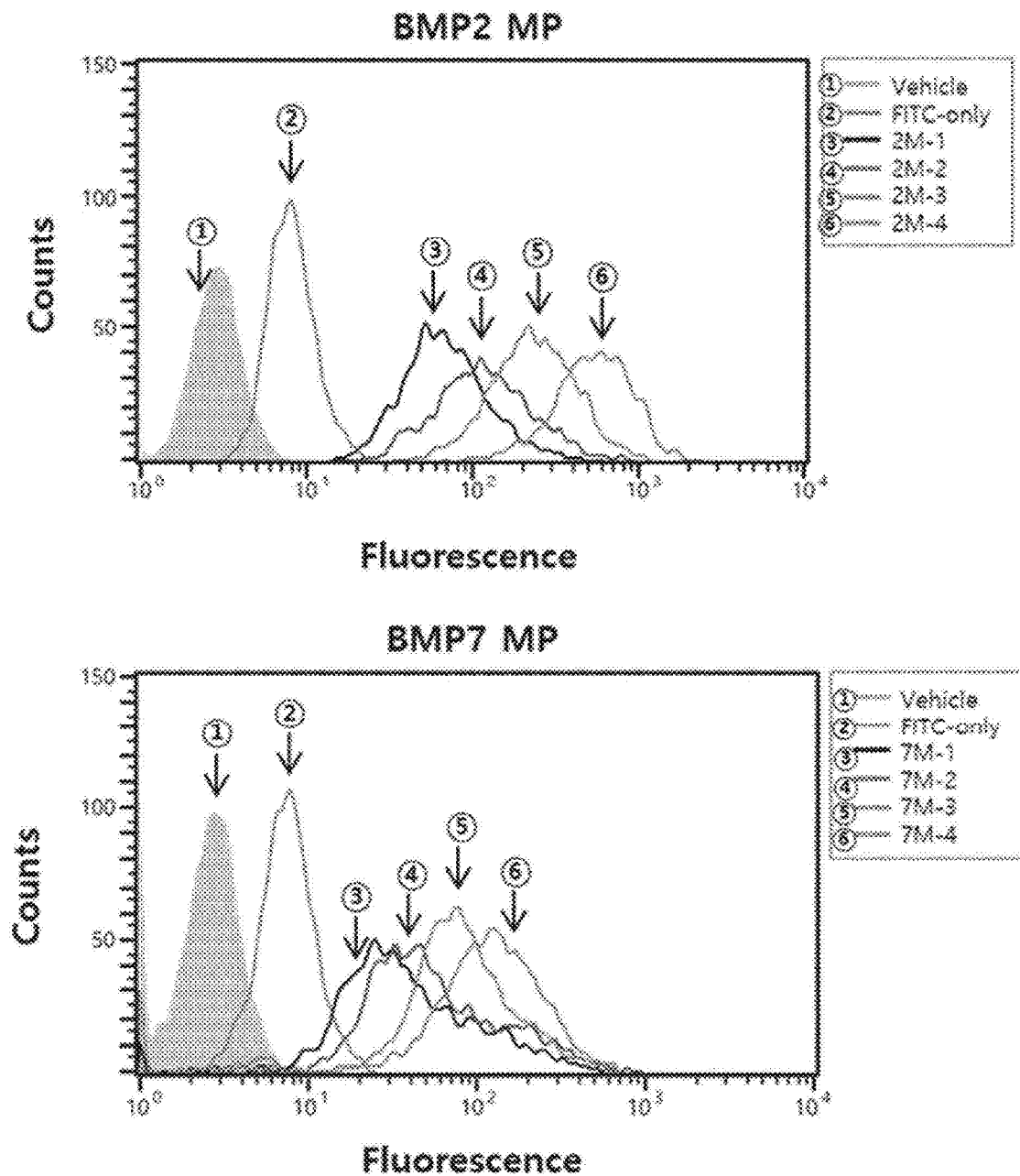

[Figure 25]
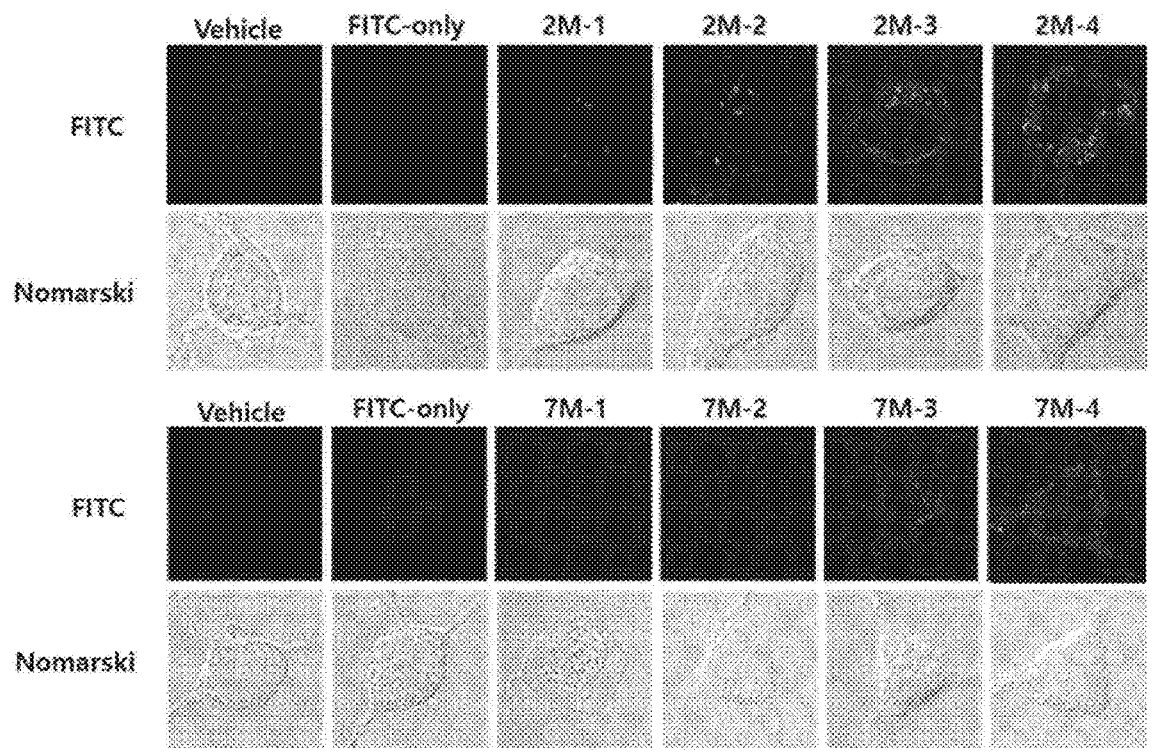
[Figure 26]
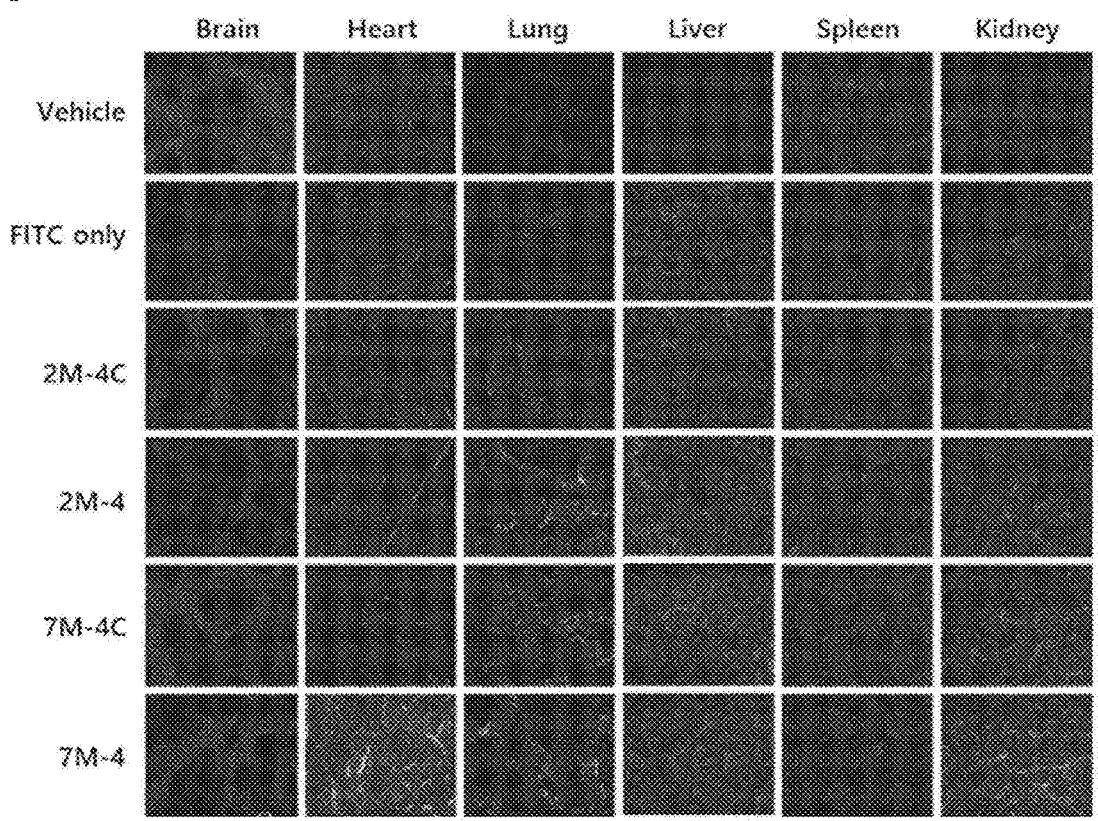

[Figure 27]
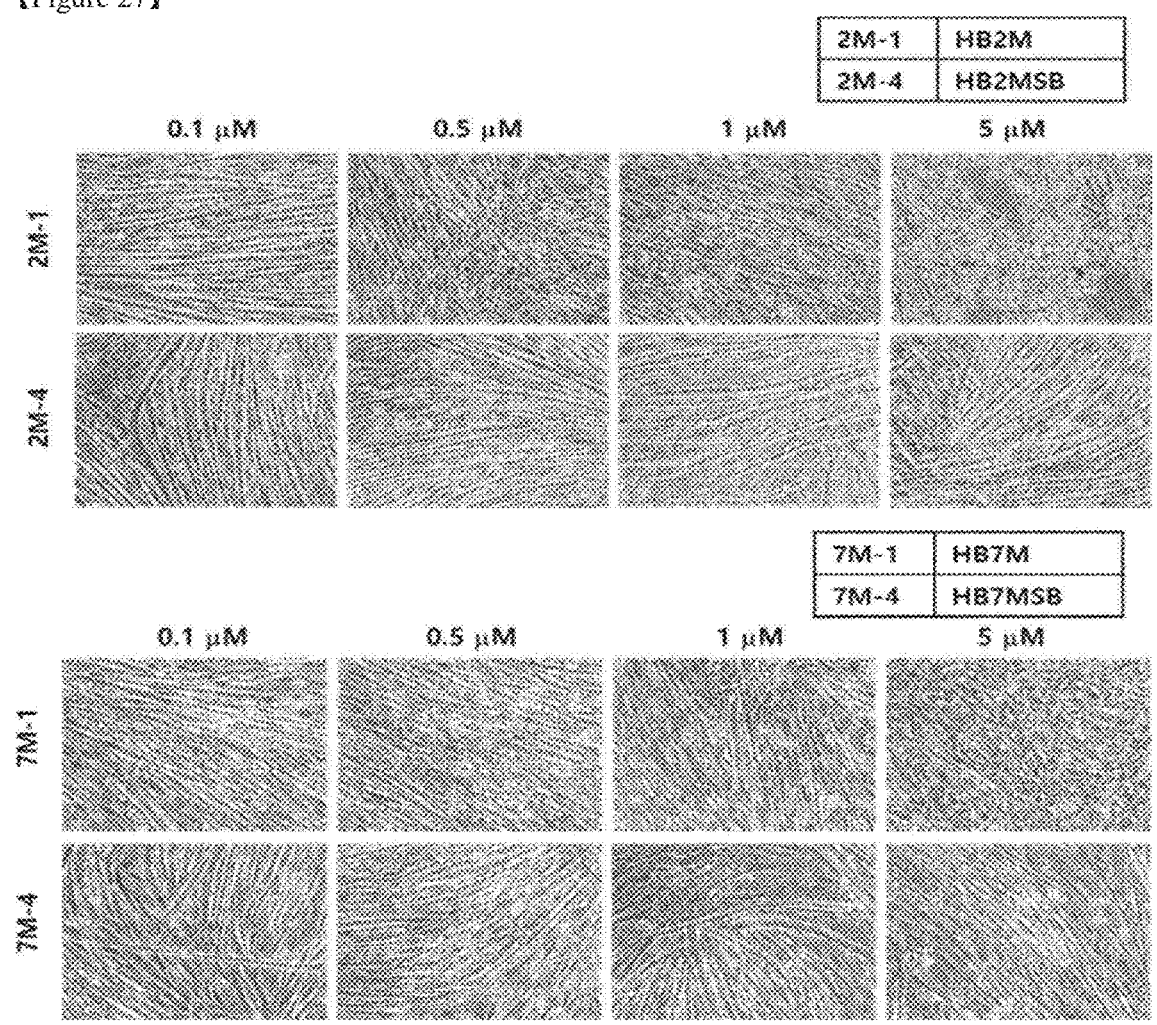

[Figure 28]
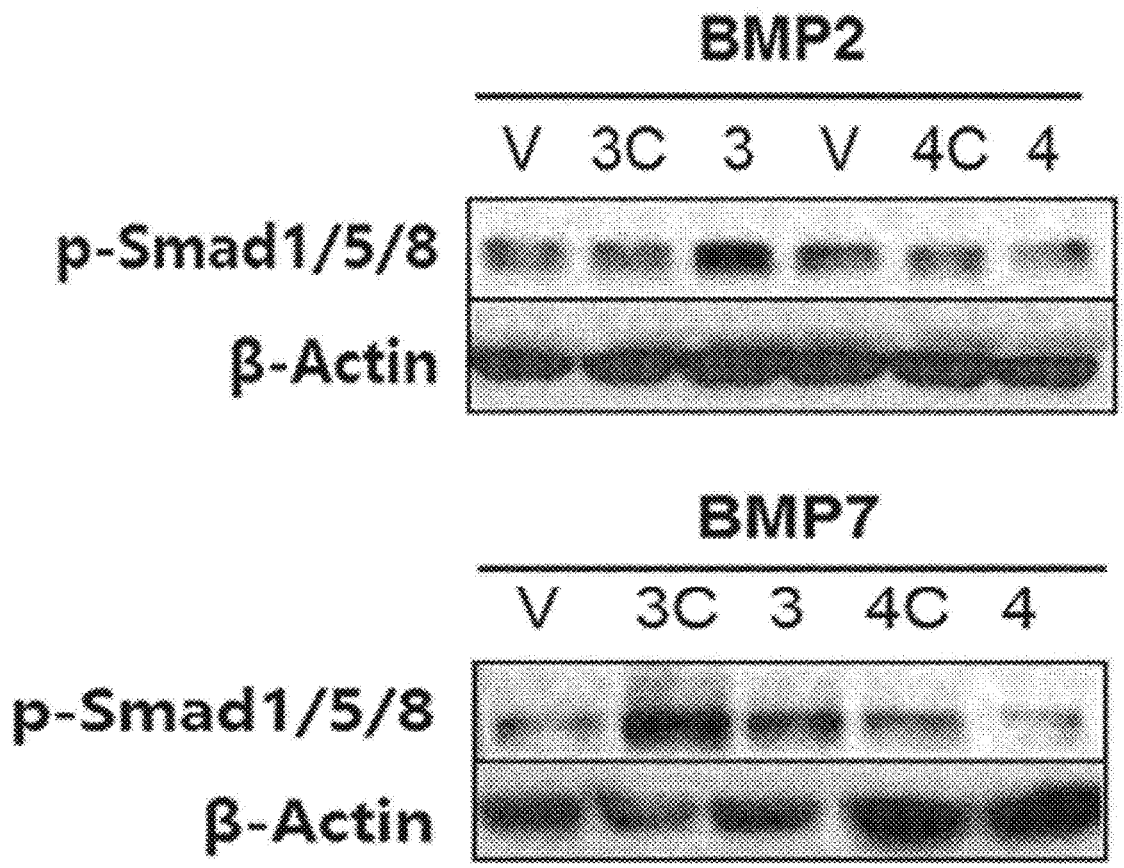

[Figure 29]
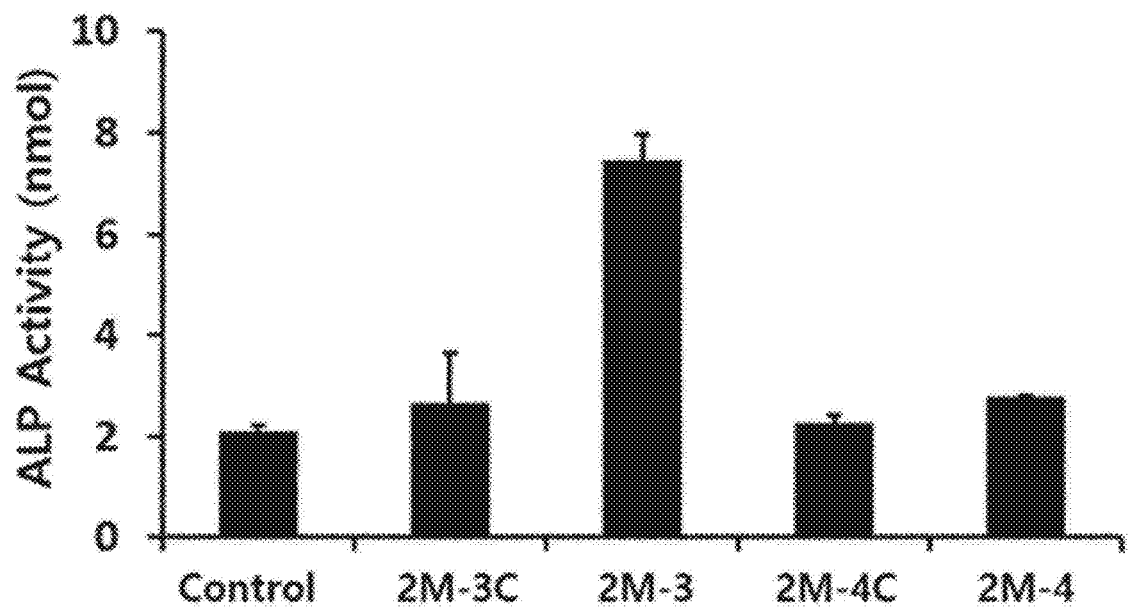
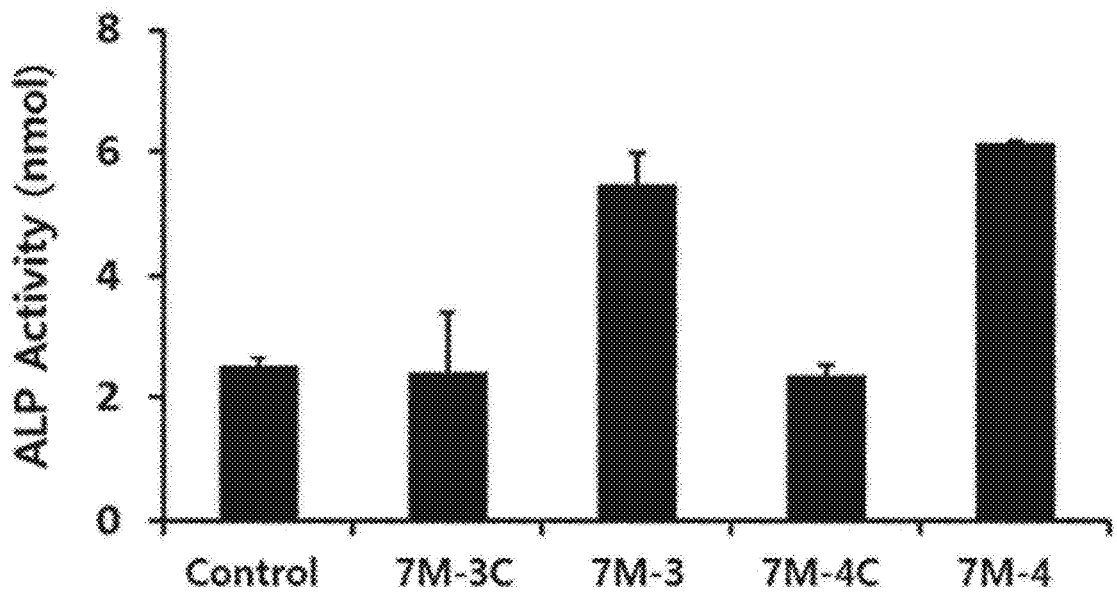

[Figure 30]
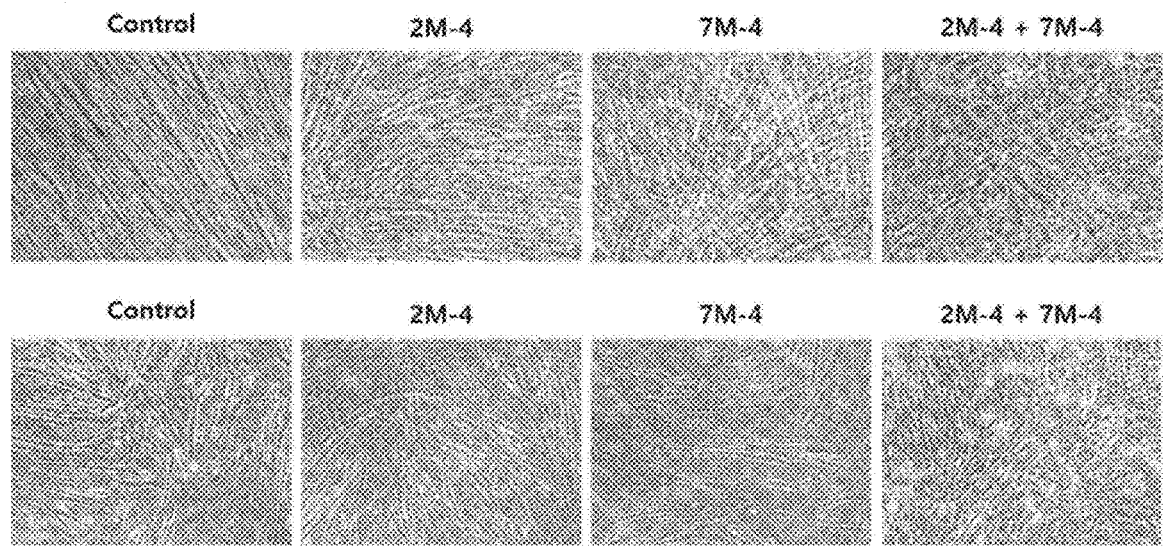
[Figure 31]
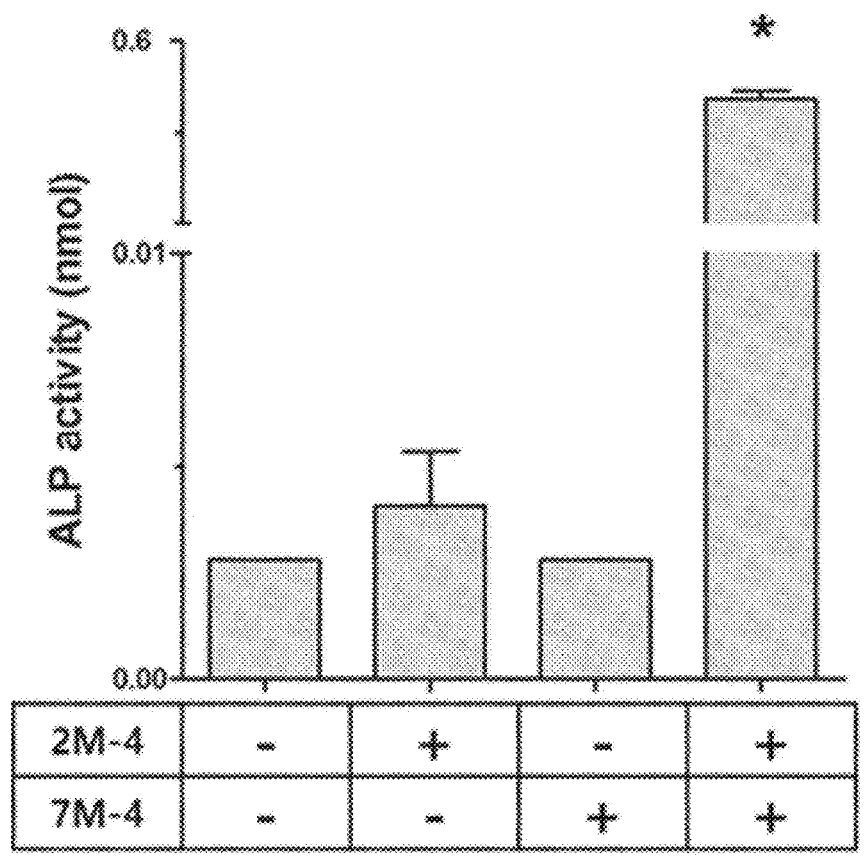

[Figure 32]
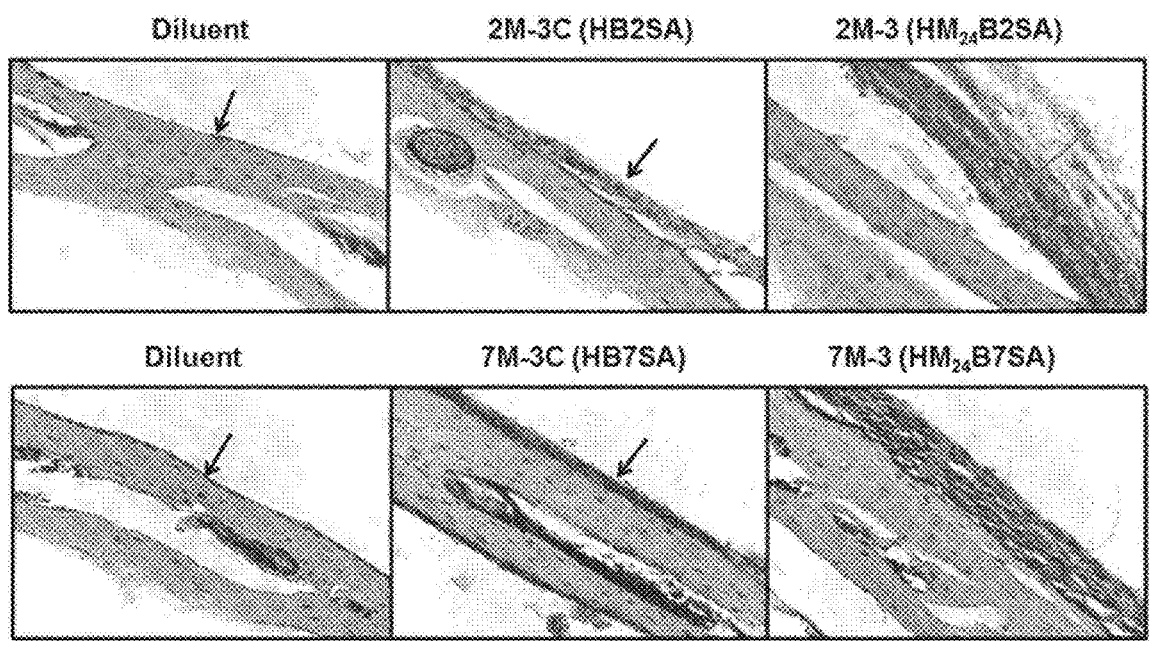
[Figure 33]
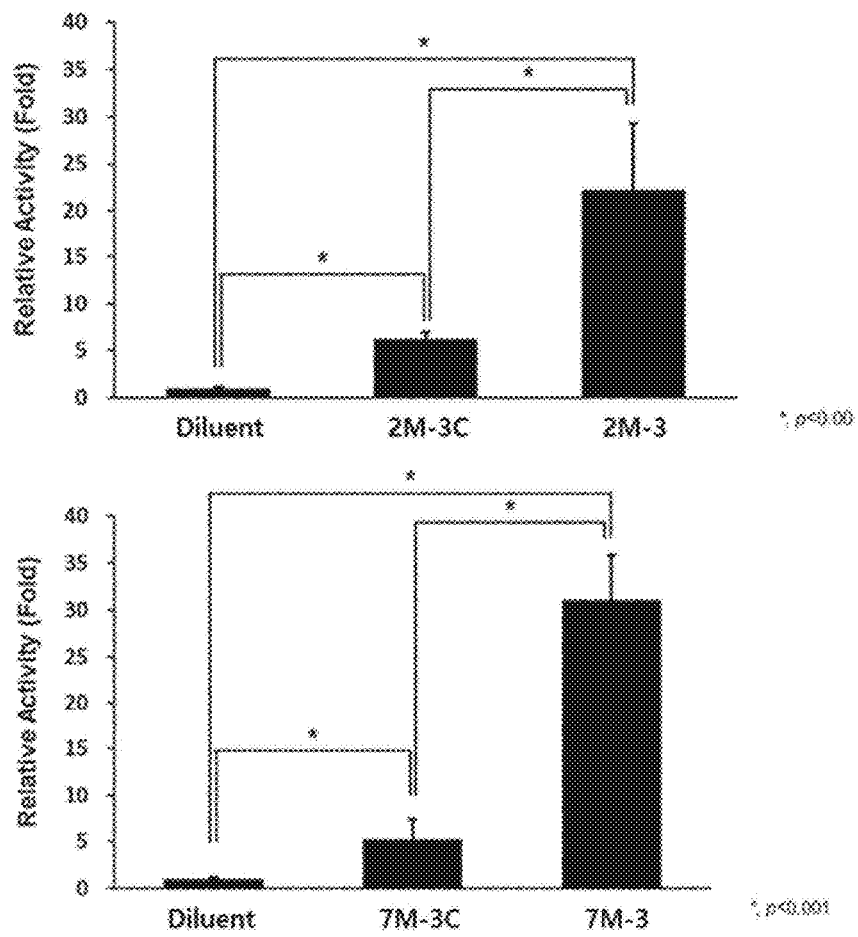

[Figure 34]

aMTD/SDA-Fused BMP2 (MP) Recombinant Protein

HMB2MSA [ BMP2 (MP) ]

10 + α aMTDs

| aMTD ID | Sequences | Rigidity/ Flexibility (II) | Structural Feature (AI) | Hydropathy (GRAVY) |
|---|---|---|---|---|
| 1 | AAALAPVVLALP | 57.3 | 187.5 | 2.1 |
| 3 | AALLVPAAVLAP | 57.3 | 187.5 | 2.1 |
| 61 | VAALPVLLAALP | 57.3 | 211.7 | 2.3 |
| 124 | IAVALPALIAAP | 50.3 | 195.8 | 2.2 |
| 241 | AAAVVPVLLVAP | 57.3 | 195.0 | 2.4 |
| 321 | IVAVALPALAVP | 50.2 | 203.3 | 2.3 |
| 385 | IVAIAVPALVAP | 50.2 | 203.3 | 2.4 |
| 403 | AAALVPAAILP | 54.9 | 195.8 | 2.3 |
| 442 | ALAALVPAVLVP | 57.3 | 203.3 | 2.3 |
| 603 | VLVALAAPVIAP | 57.3 | 203.3 | 2.4 |
| 563 | ALAVIVVPALAP | 50.2 | 203.3 | 2.4 |
| 481 | AIAIAIVPVALP | 50.2 | 211.6 | 2.4 |
| 585 | ALIVAIAPALVP | 50.2 | 211.6 | 2.4 |
| 623 | VAAAIALPAIVP | 50.2 | 187.5 | 2.3 |
| 847 | LVAIVVLPAVAP | 50.2 | 219.2 | 2.6 |
| 897 | AVIVPVAIIAAP | 50.2 | 203.3 | 2.5 |
| 889 | AVVIALPAVVAP | 57.3 | 195.0 | 2.4 |

[Figure 35a]
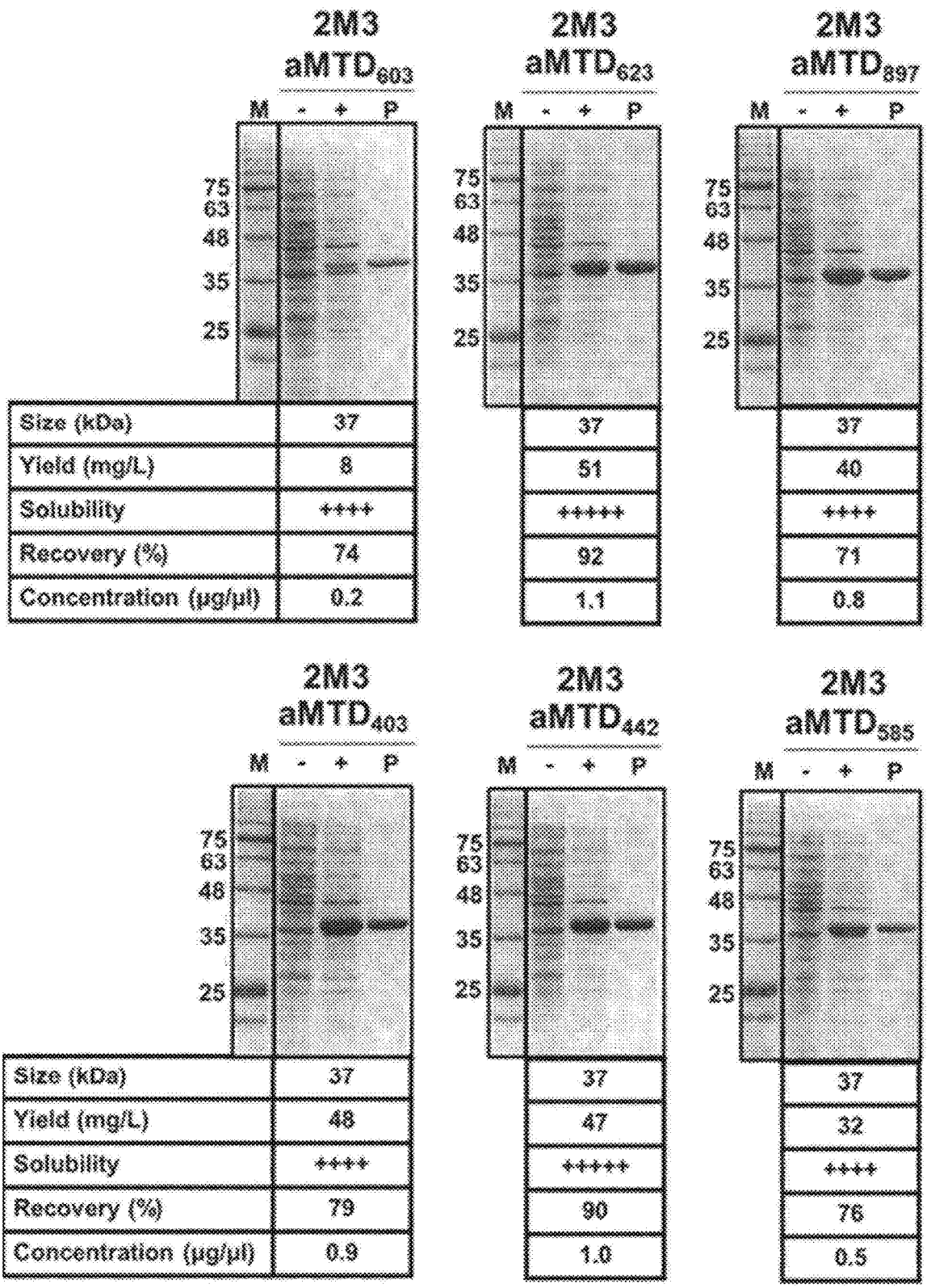

[Figure 35b]
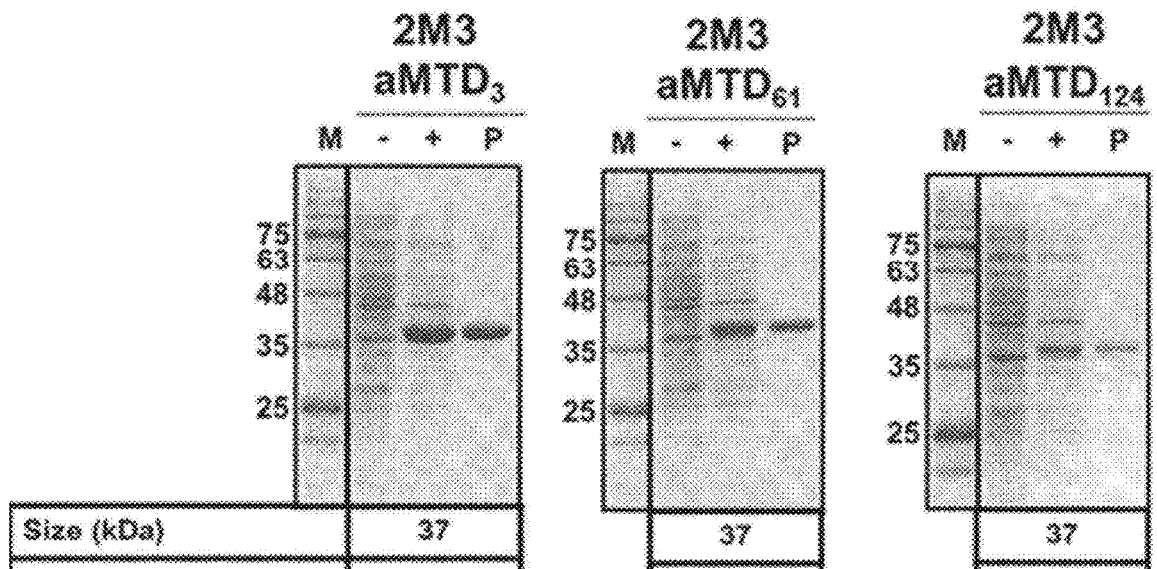
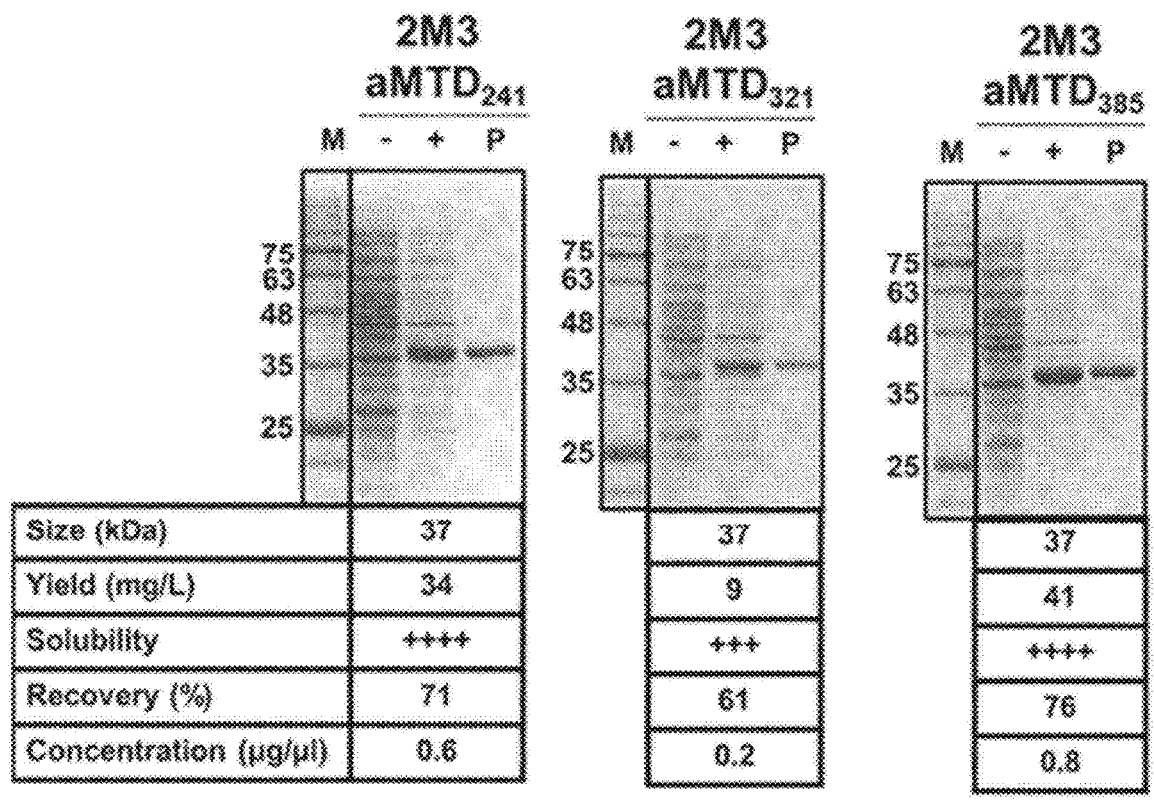

[Figure 36a]
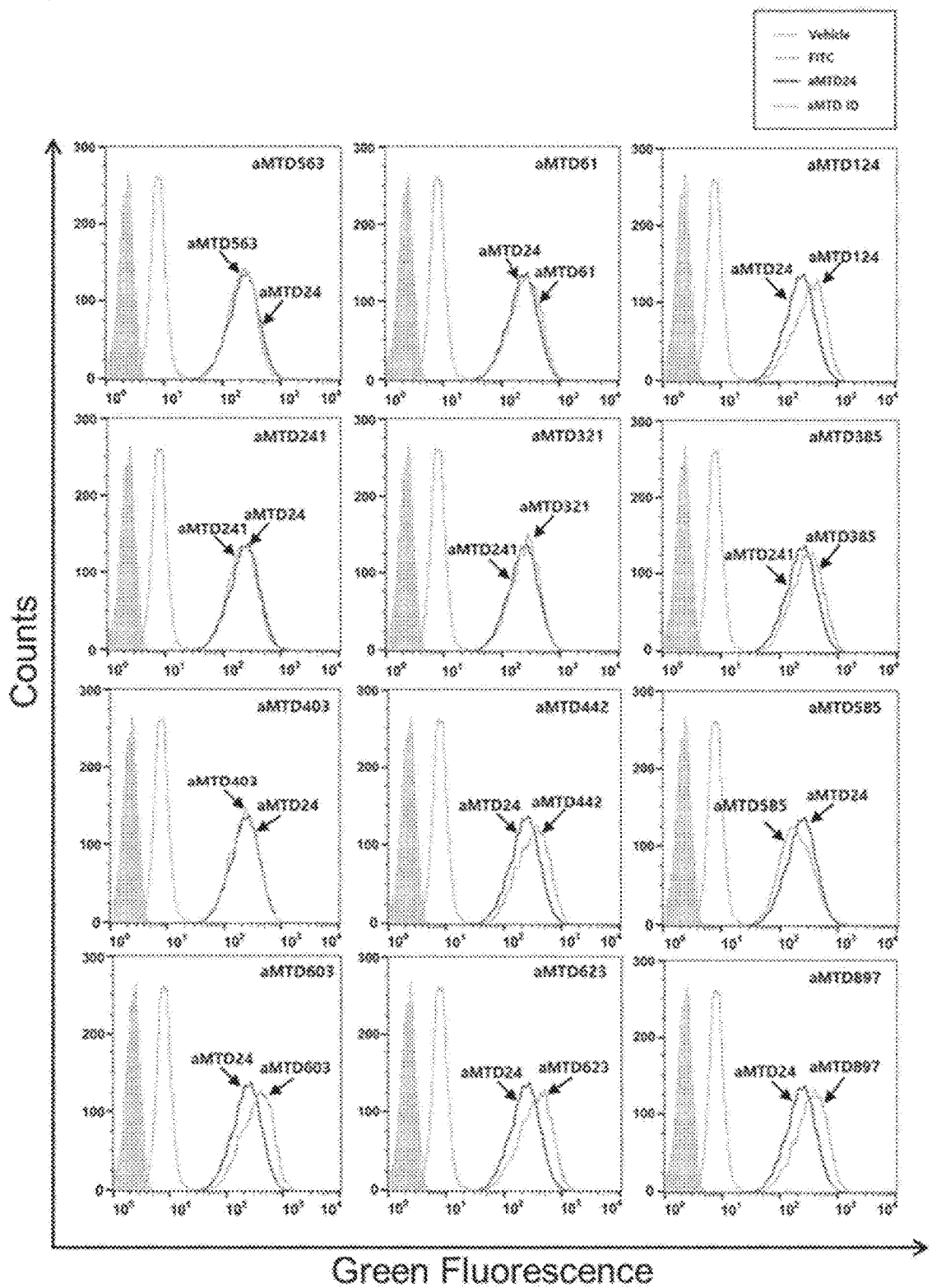

[Figure 36b]
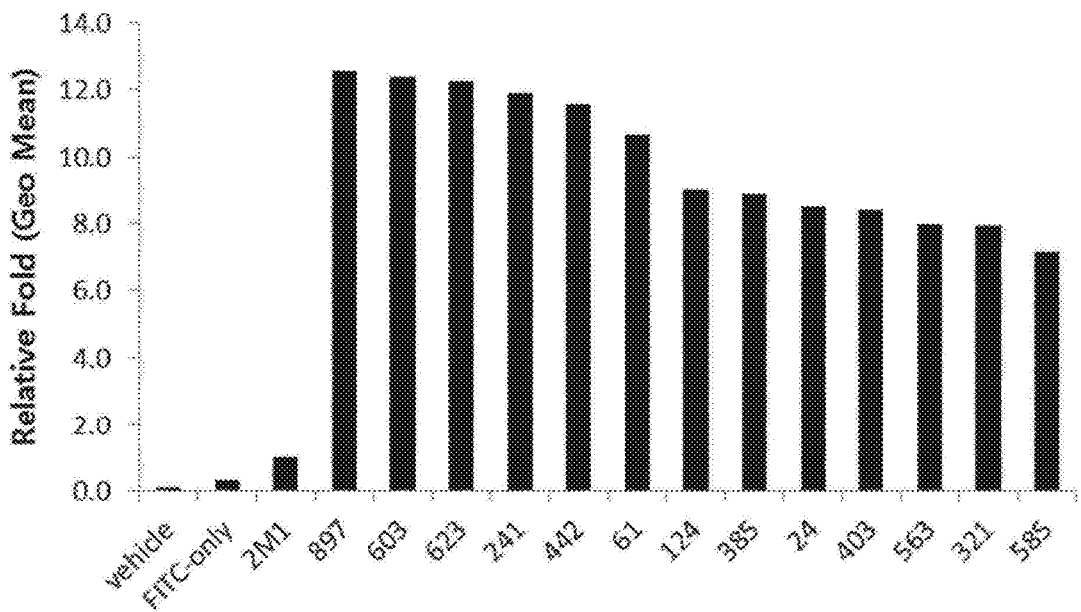
[Figure 37]
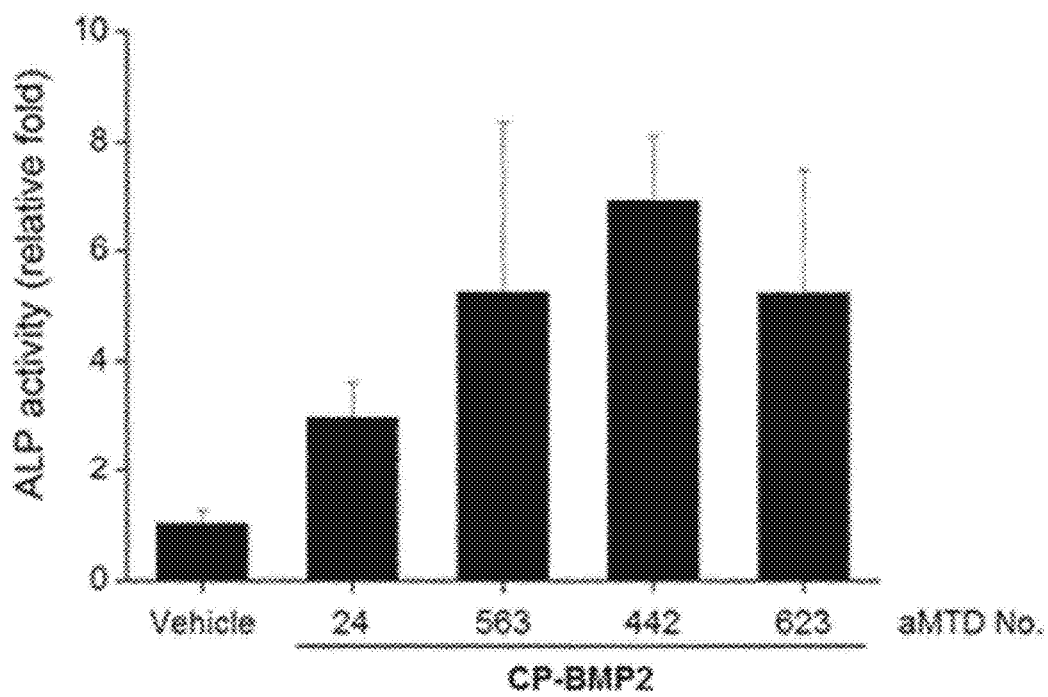

[Figure 38]
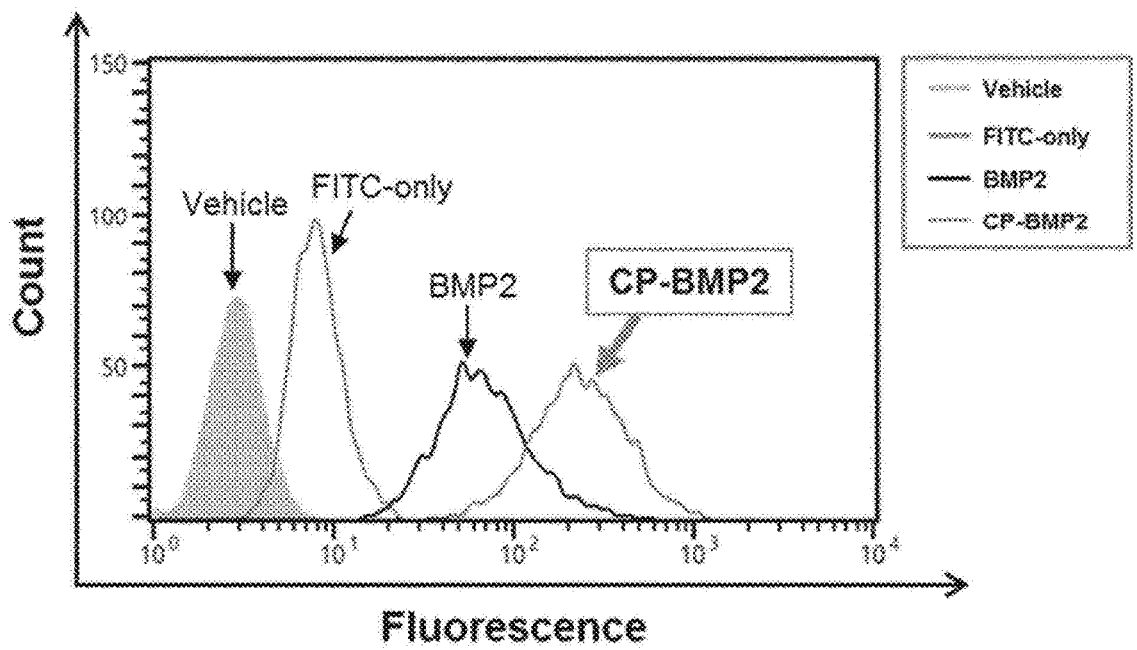
[Figure 39]
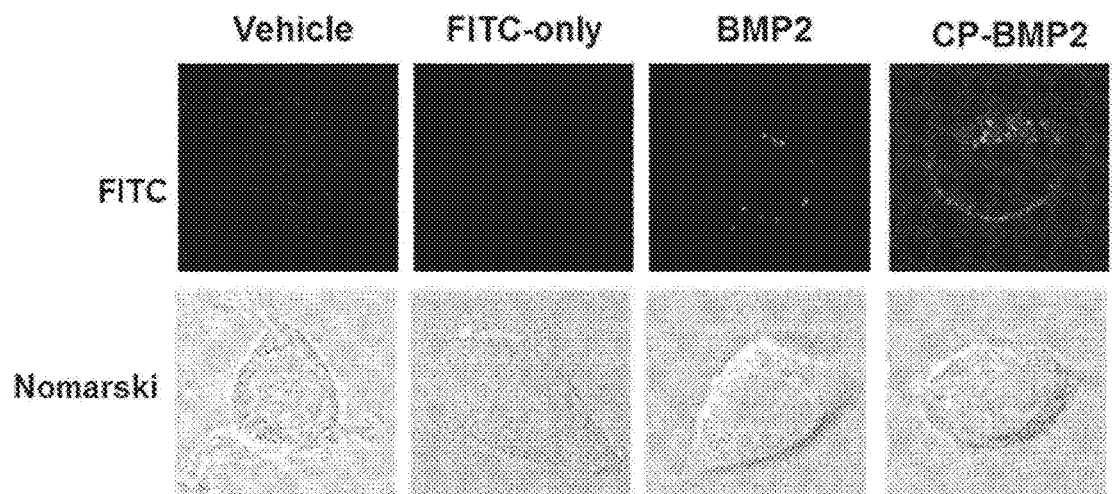

[Figure 40a]
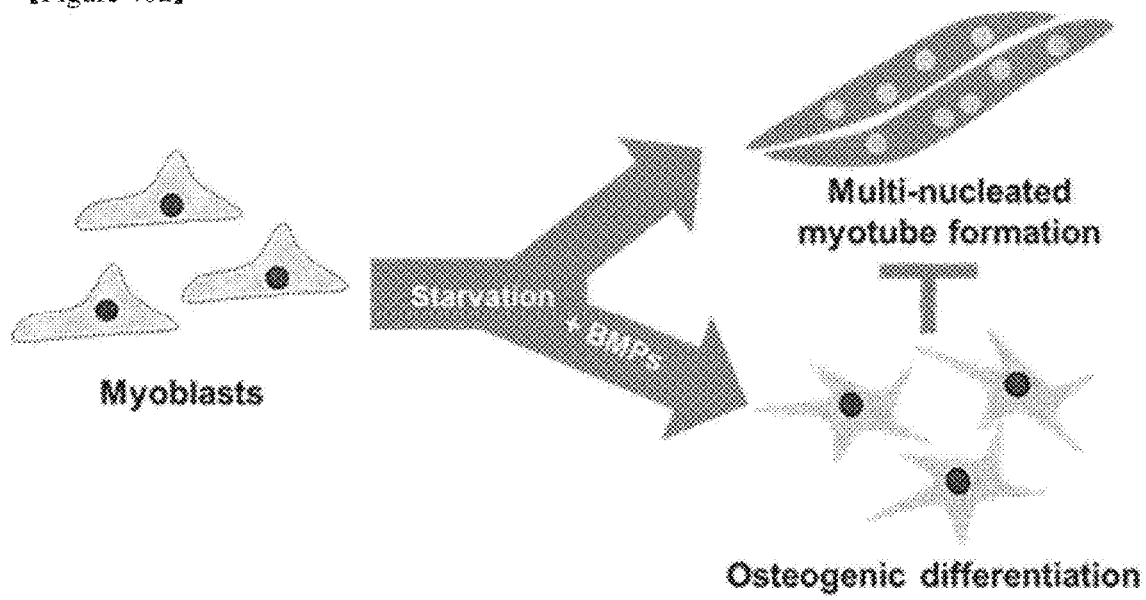
[Figure 40b]
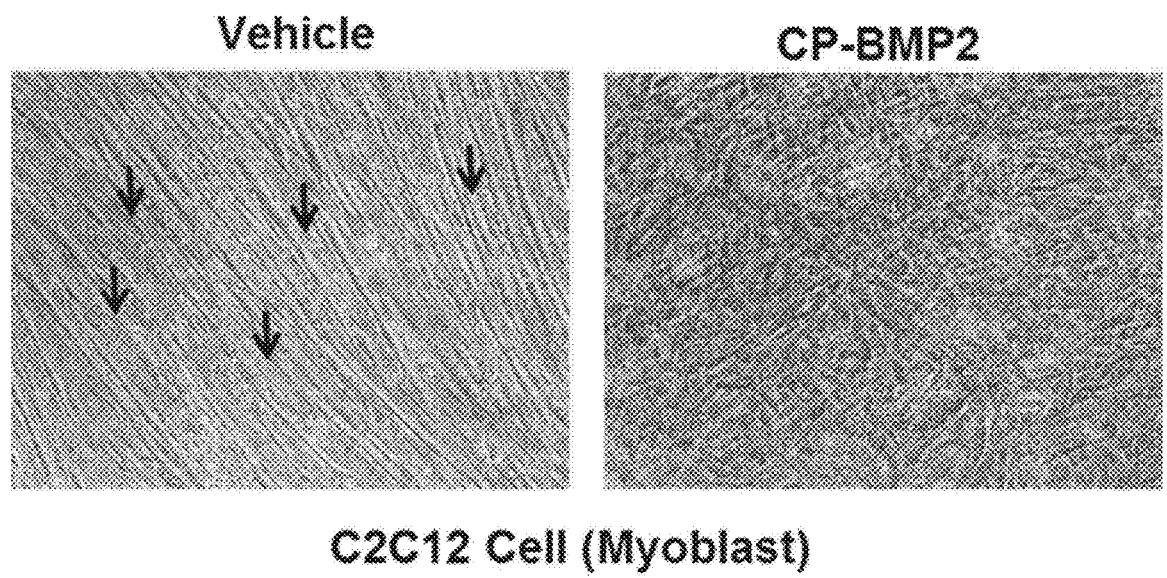
C2C12 Cell (Myoblast)

[Figure 41]
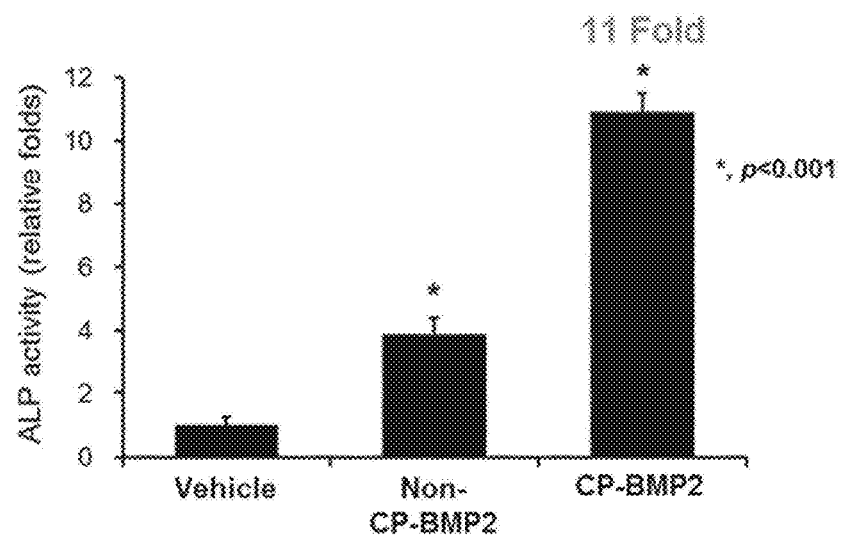
[Figure 42]
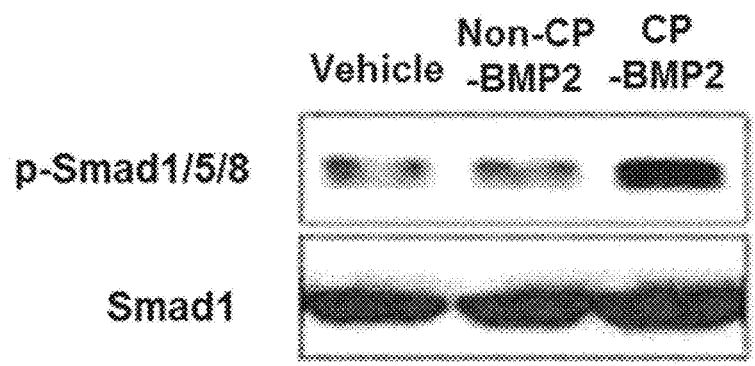

[Figure 43]
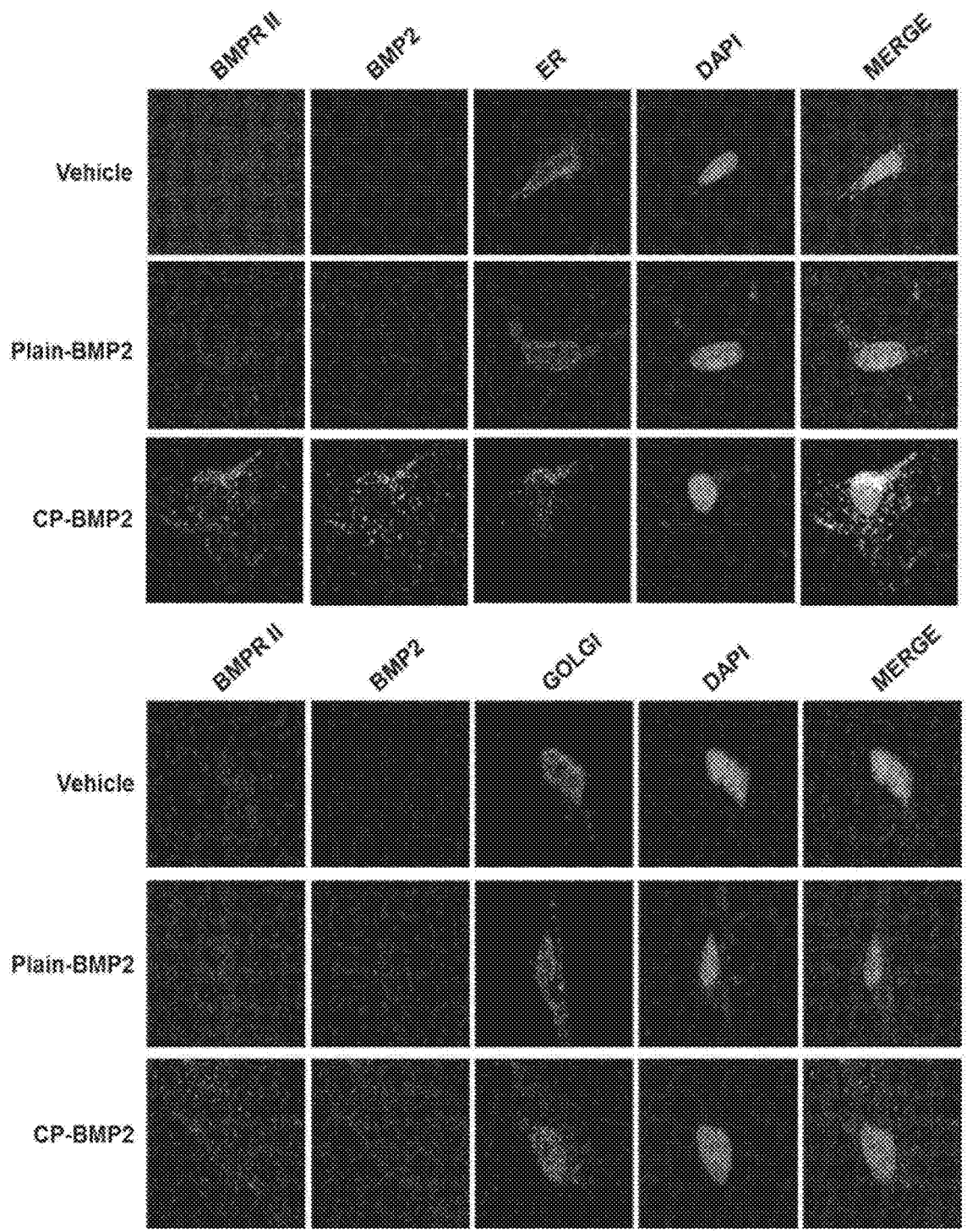

[Figure 44a]
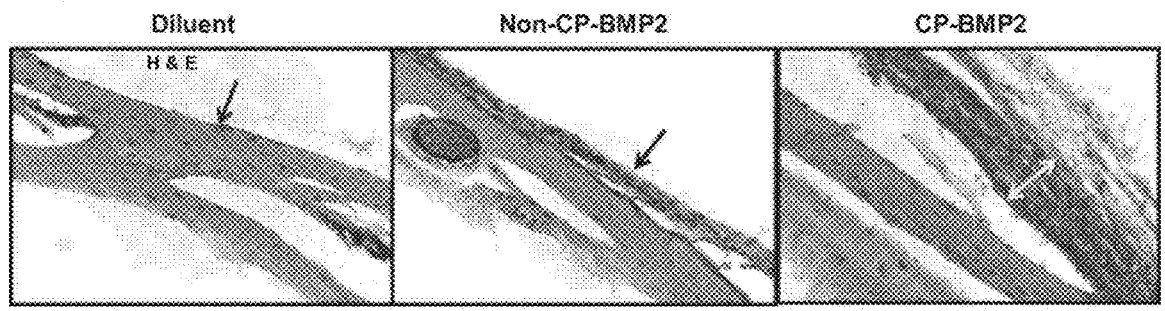
[Figure 44b]
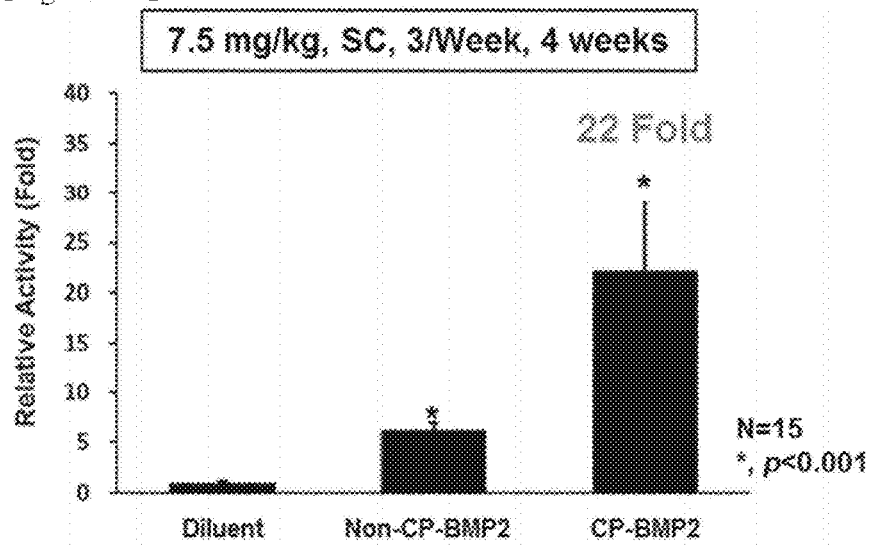
[Figure 45a]
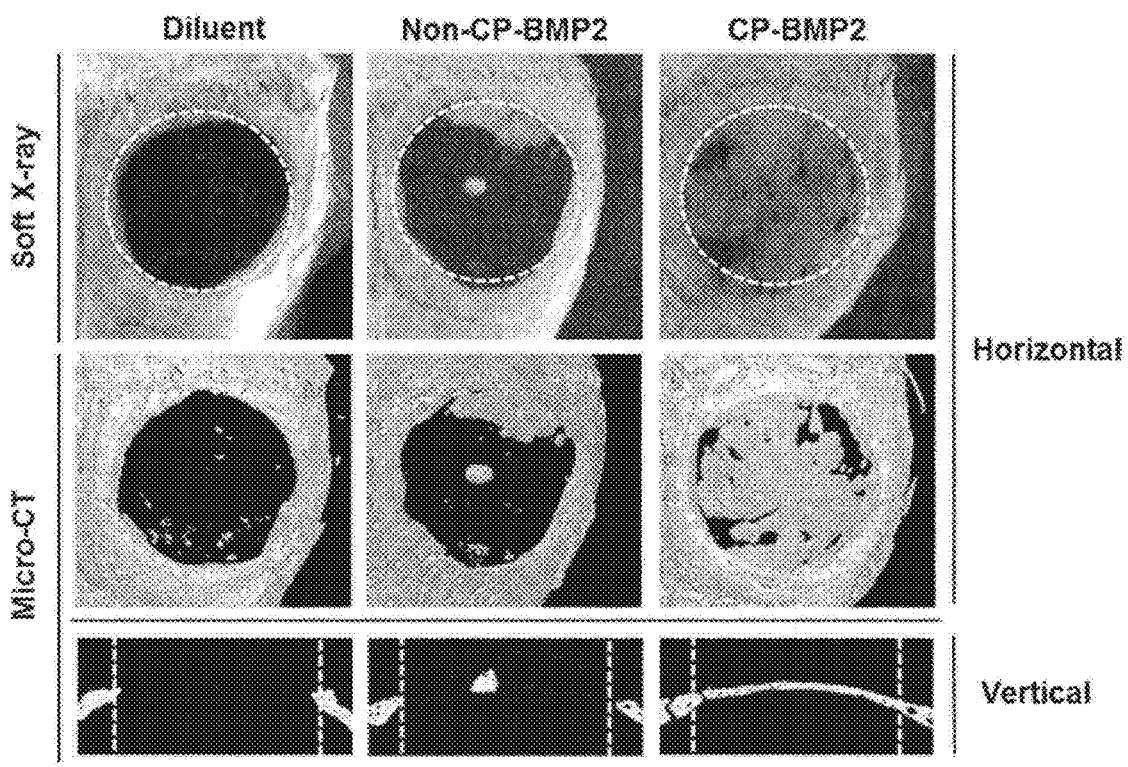

[Figure 45b]
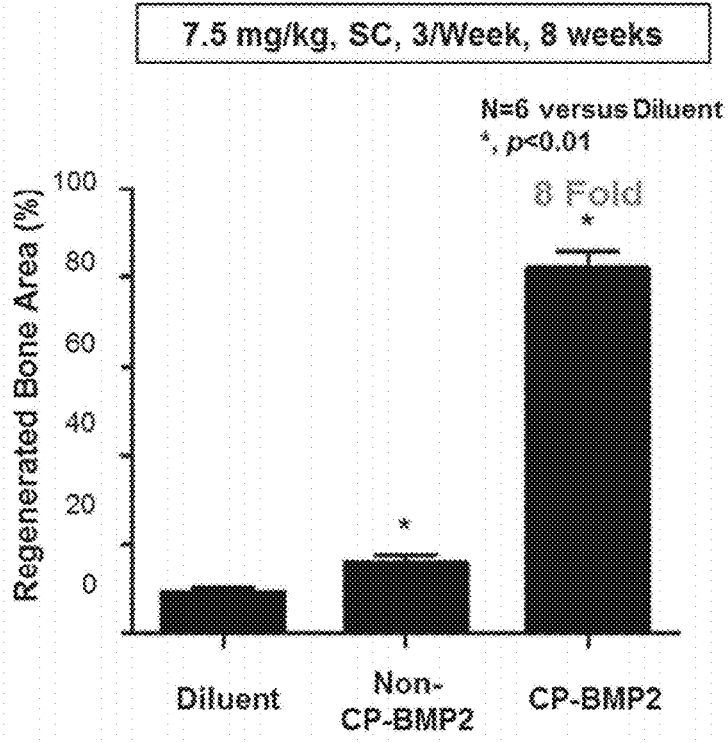
[Figure 46a]
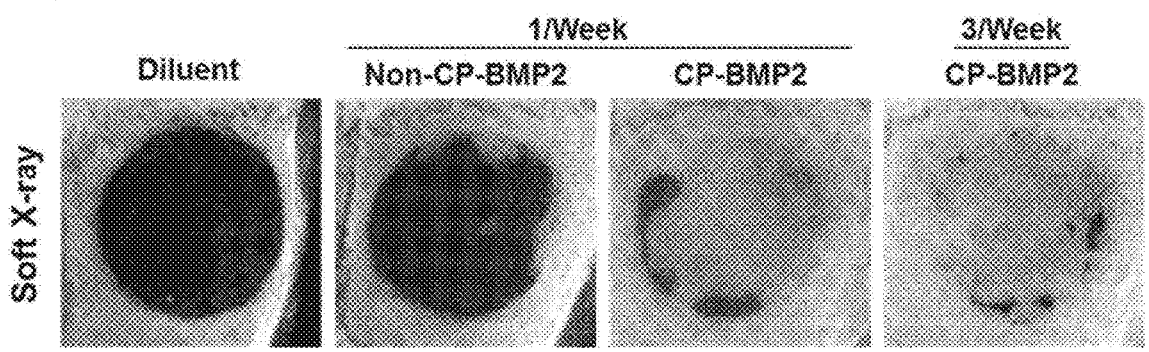

[Figure 46b]
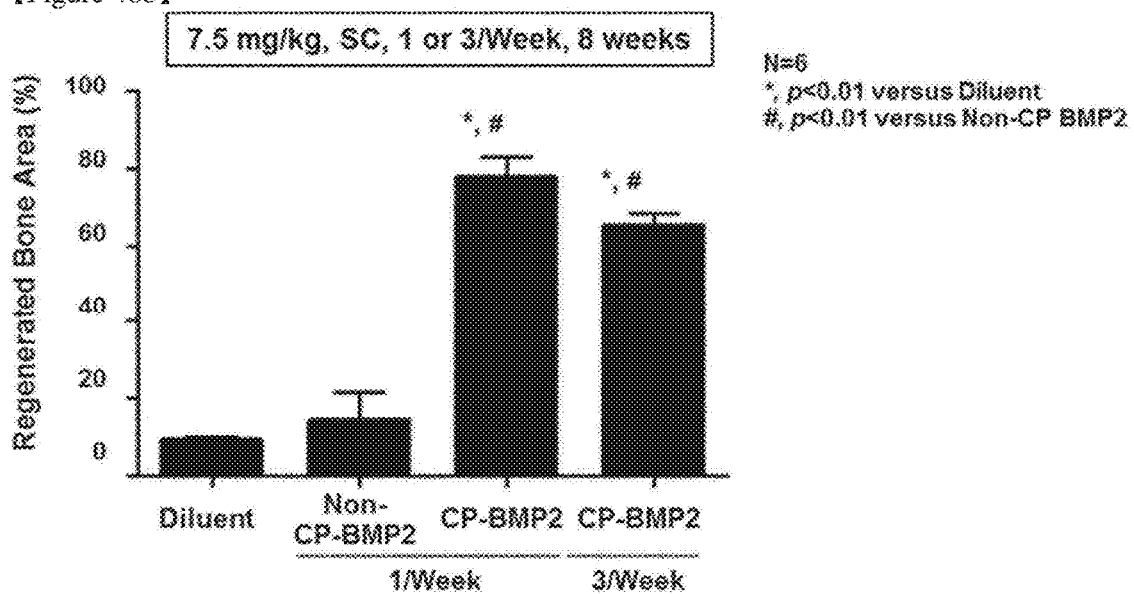
[Figure 47a]
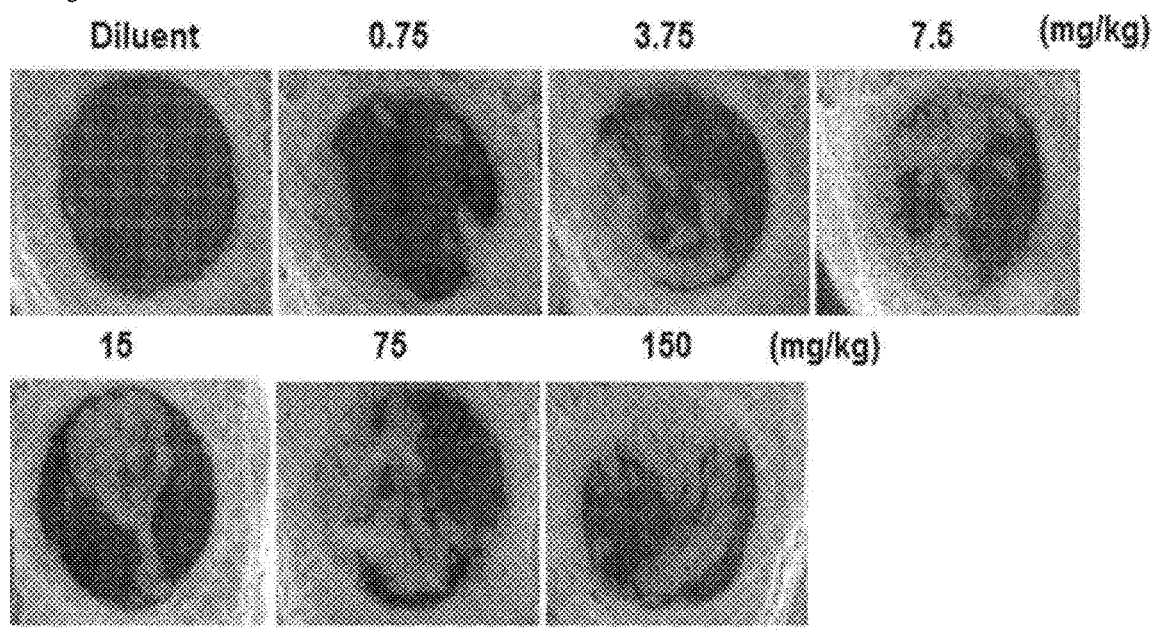

[Figure 47b]
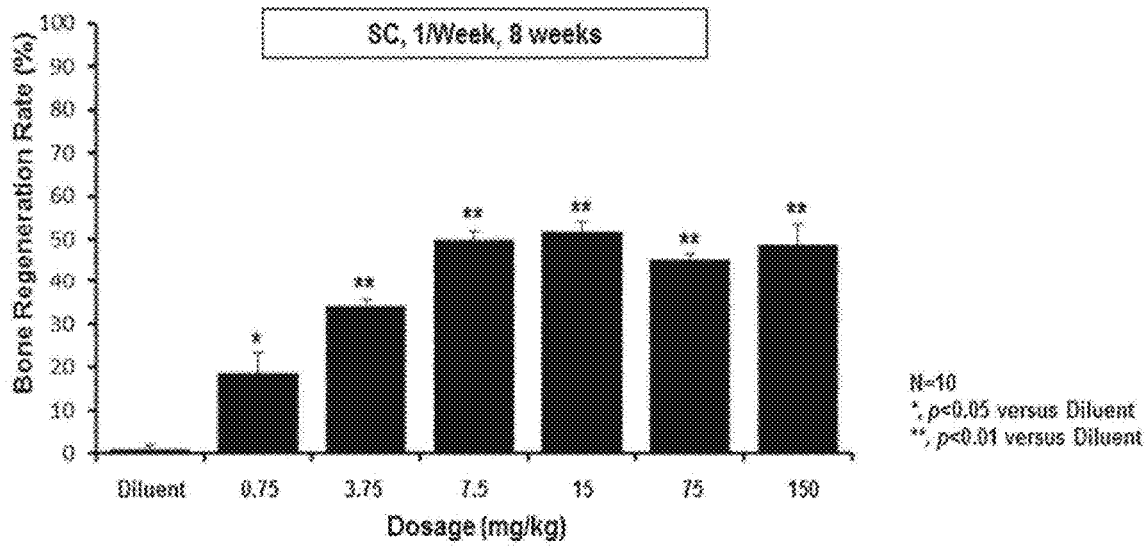
[Figure 48]
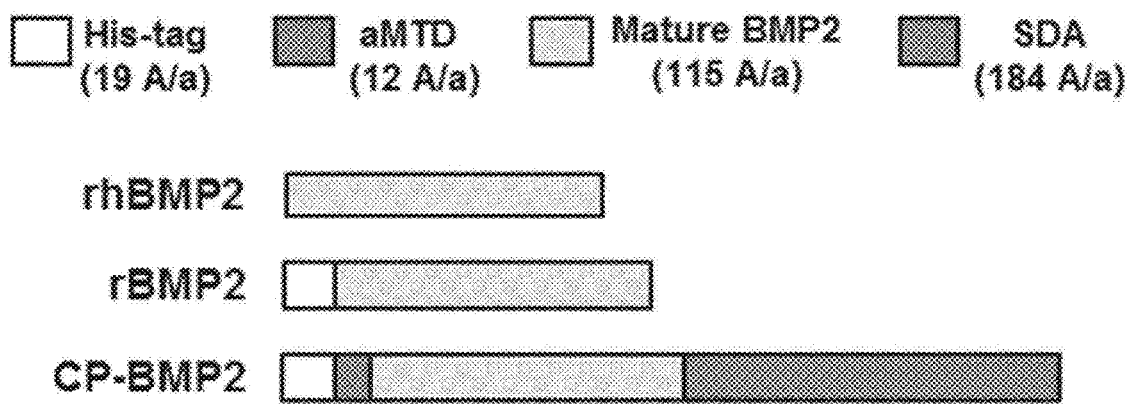
[Figure 49a]
| | Horses = 6 | |
|---|---|---|
| Age (Interquartile range) | 5 (5-7.5) | |
| Sex | F | 2 |
| | M | 4 |
| Weight | 469 ± 48.9 kg | |

[Figure 49b]
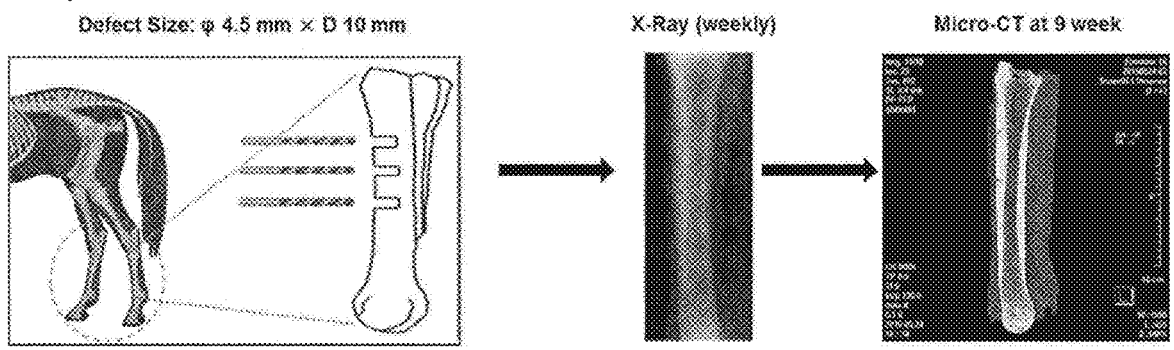
[Figure 50]
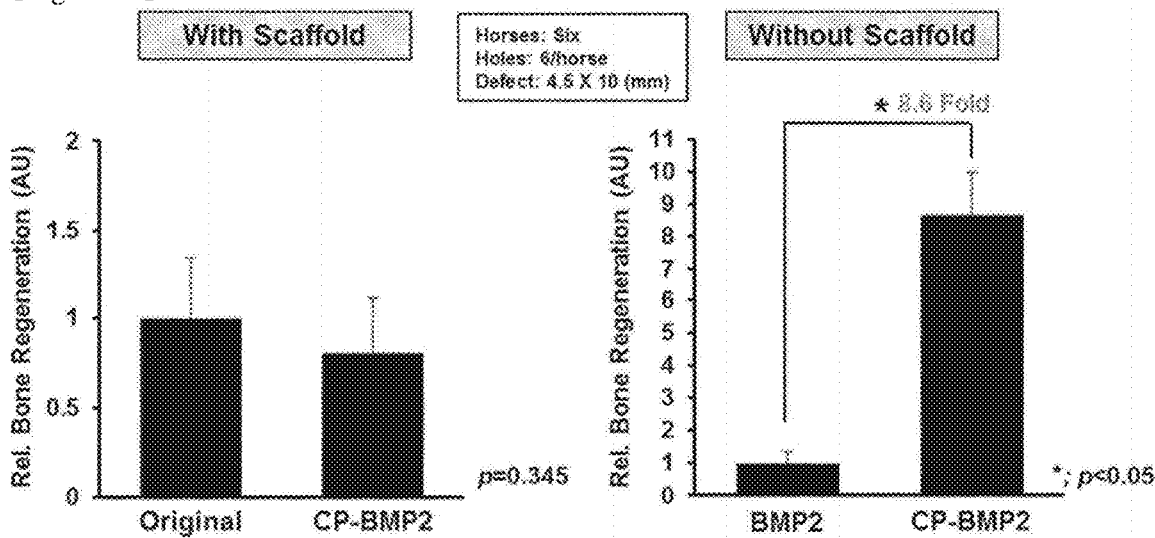

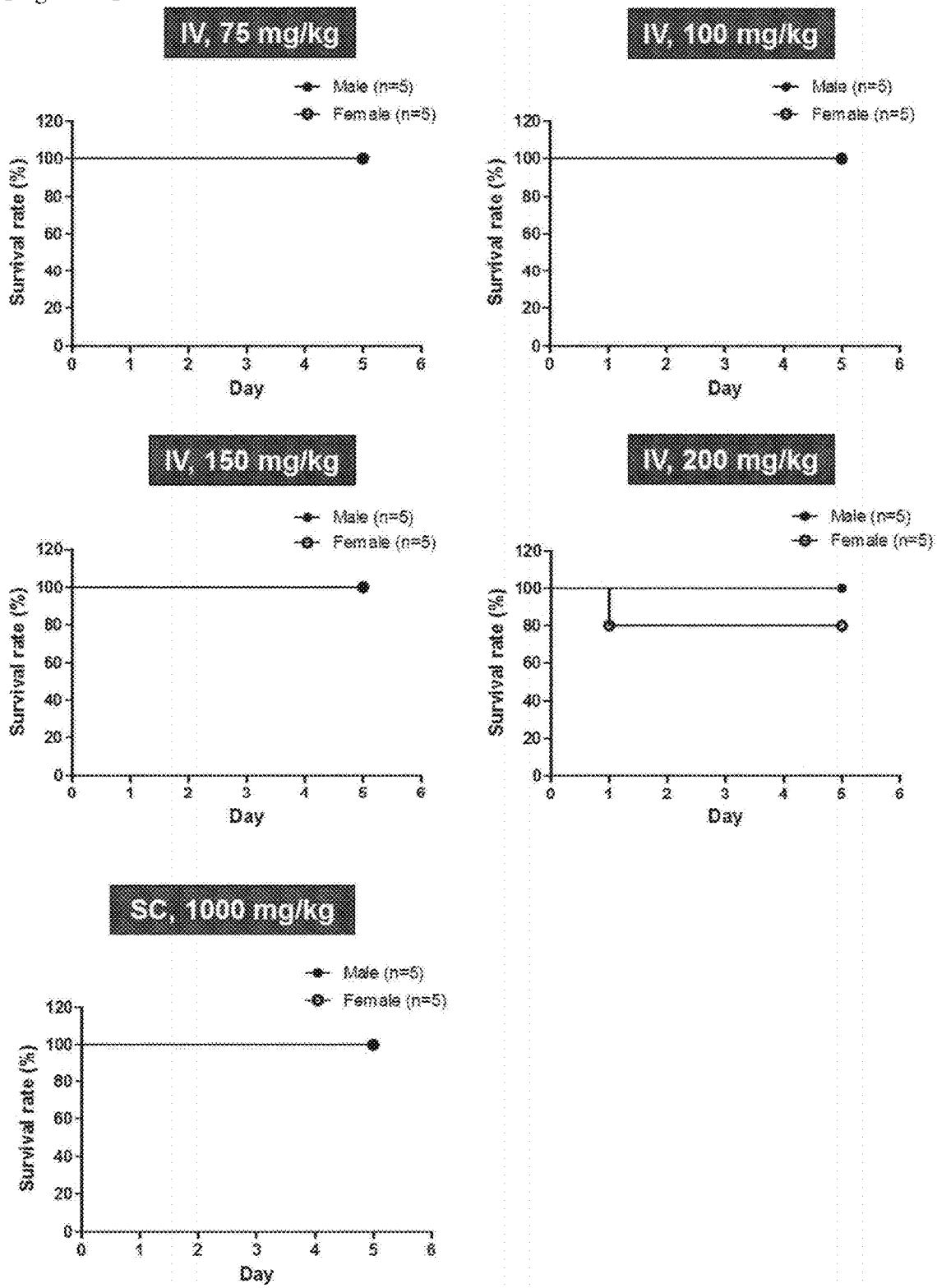
[Figure 51]

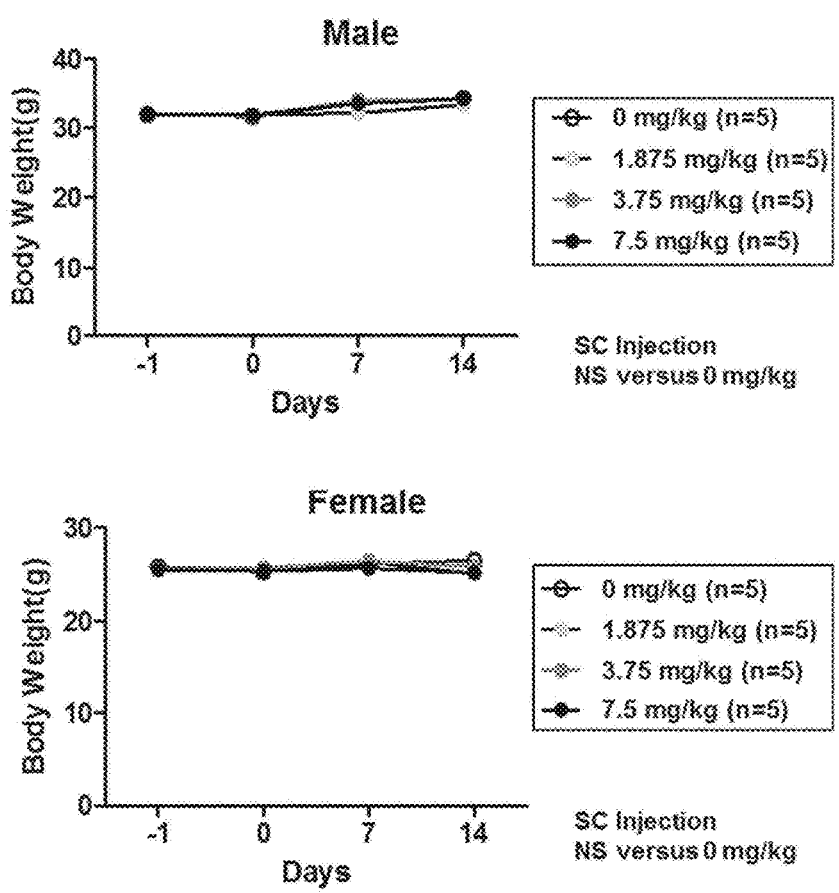
[Figure 52a]

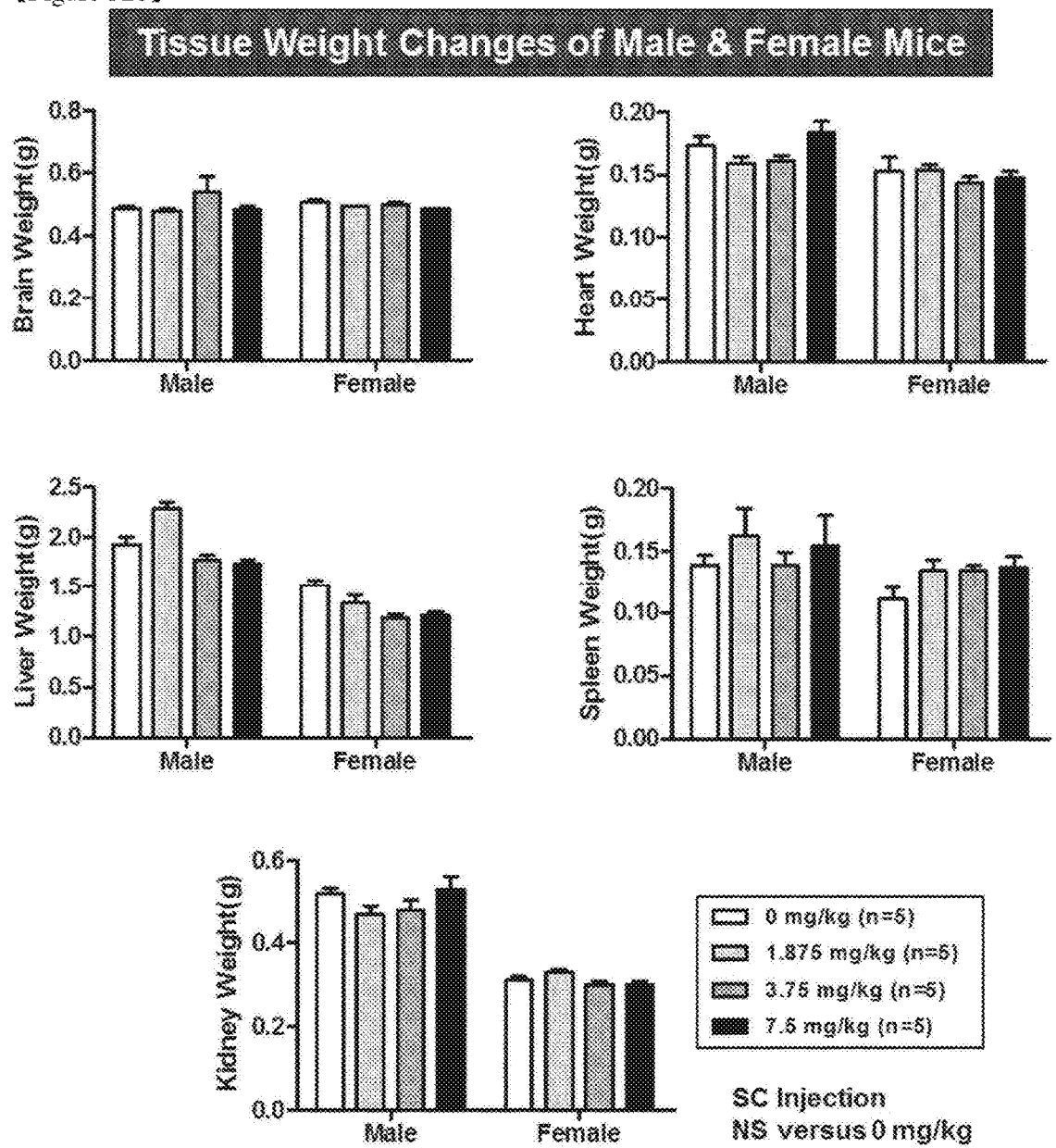
[Figure 52b]

[Figure 53]
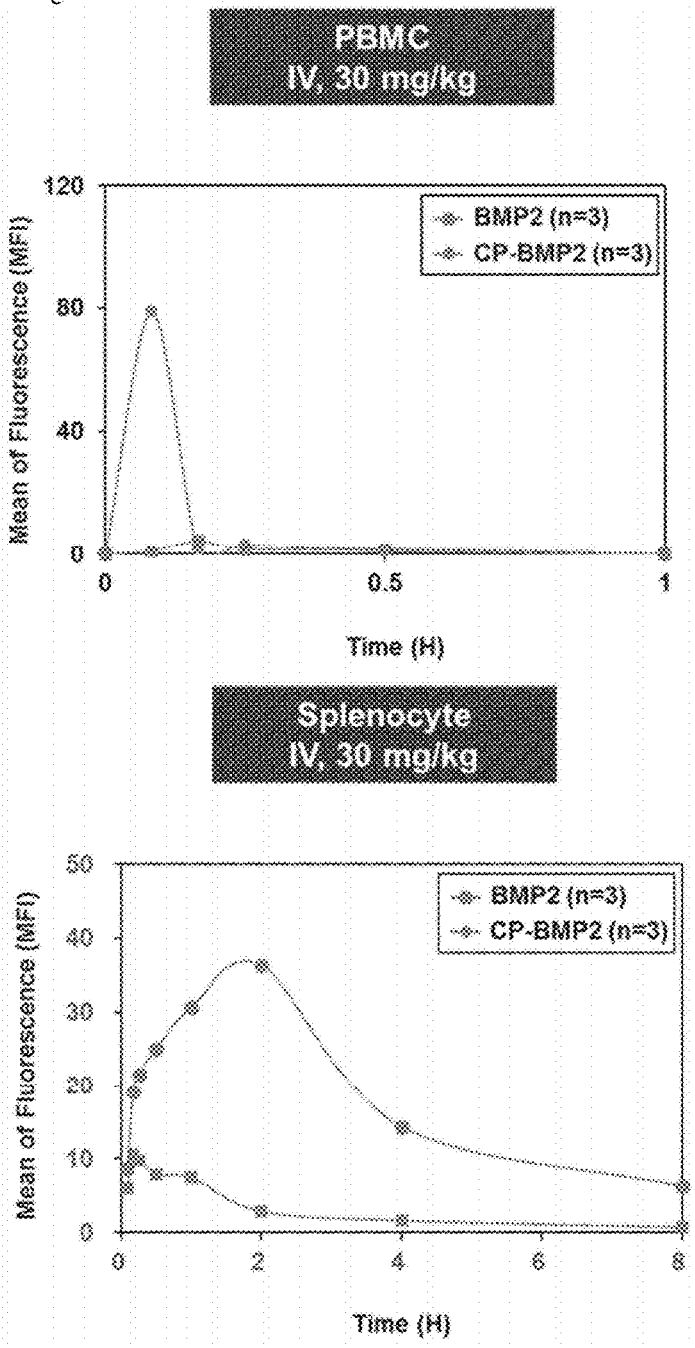

[Figure 54]
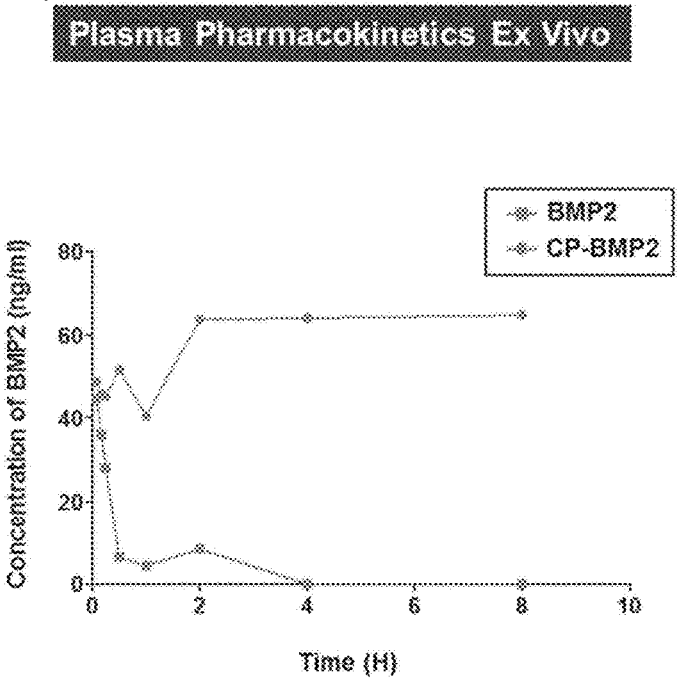
[Figure 55]
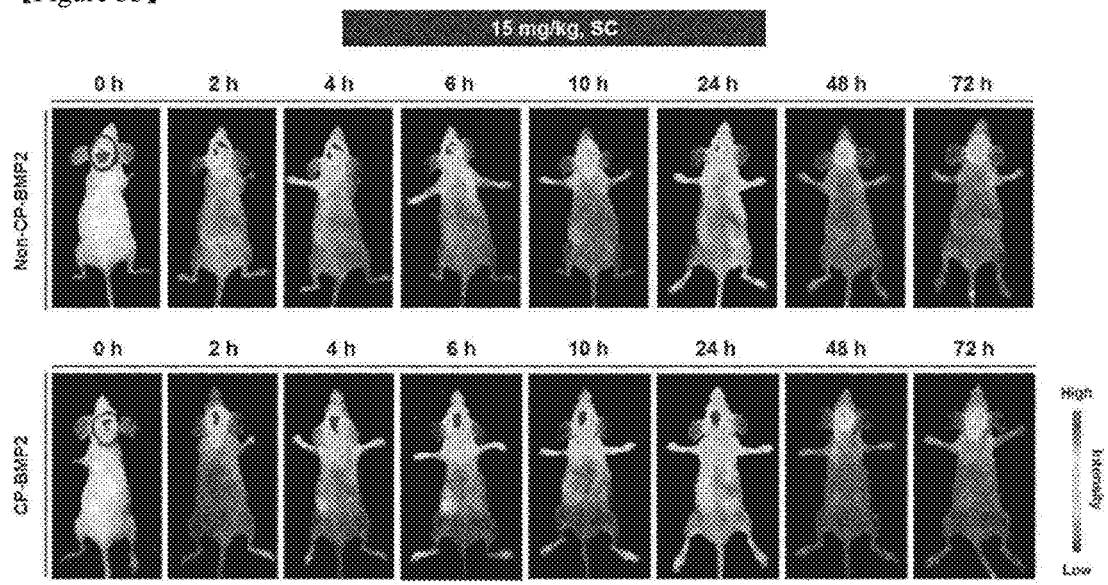

SEQUENCE LISTING

```
<160> NUMBER OF SEQ ID NOS: 832

<210> SEQ ID NO 1
<211> LENGTH: 12
<212> TYPE: PRT
<213> ORGANISM: Artificial Sequence
<220> FEATURE:
<223> OTHER INFORMATION: Amino acid Sequence of aMTD1

<400> SEQUENCE: 1

Ala Ala Ala Leu Ala Pro Val Val Leu Ala Leu Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Amino acid Sequence of aMTD2

<400> SEQUENCE: 2

Ala Ala Ala Val Pro Leu Leu Ala Val Val Val Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Amino acid Sequence of aMTD3

<400> SEQUENCE: 3

Ala Ala Leu Leu Val Pro Ala Ala Val Leu Ala Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Amino acid Sequence of aMTD4

<400> SEQUENCE: 4

Ala Leu Ala Leu Leu Pro Val Ala Ala Leu Ala Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Amino acid Sequence of aMTD5

<400> SEQUENCE: 5

Ala Ala Ala Leu Leu Pro Val Ala Leu Val Ala Pro
1               5                   10

<210> SEQ ID NO 6
<211> LENGTH: 12
```

```
<212> TYPE: PRT
<213> ORGANISM: Artificial Sequence
<220> FEATURE:
<223> OTHER INFORMATION: Amino acid Sequence of aMTD11

<400> SEQUENCE: 6

Val Val Ala Leu Ala Pro Ala Leu Ala Ala Leu Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Amino acid Sequence of aMTD12

<400> SEQUENCE: 7

Leu Leu Ala Ala Val Pro Ala Val Leu Leu Ala Pro
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Amino acid Sequence of aMTD13

<400> SEQUENCE: 8

Ala Ala Ala Leu Val Pro Val Val Ala Leu Leu Pro
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Amino acid Sequence of aMTD21

<400> SEQUENCE: 9

Ala Val Ala Leu Leu Pro Ala Leu Leu Ala Val Pro
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Amino acid Sequence of aMTD22

<400> SEQUENCE: 10

Ala Val Val Leu Val Pro Val Leu Ala Ala Ala Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Amino acid Sequence of aMTD23

<400> SEQUENCE: 11

Val Val Leu Val Leu Pro Ala Ala Ala Ala Val Pro
1               5                   10

<210> SEQ ID NO 12
<211> LENGTH: 12
<212> TYPE: PRT
```

```
<213> ORGANISM: Artificial Sequence
<220> FEATURE:
<223> OTHER INFORMATION: Amino acid Sequence of aMTD24

<400> SEQUENCE: 12

Ile Ala Leu Ala Ala Pro Ala Leu Ile Val Ala Pro
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Amino acid Sequence of aMTD25

<400> SEQUENCE: 13

Ile Val Ala Val Ala Pro Ala Leu Val Ala Leu Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Amino acid Sequence of aMTD42

<400> SEQUENCE: 14

Val Ala Ala Leu Pro Val Val Ala Val Val Ala Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Amino acid Sequence of aMTD43

<400> SEQUENCE: 15

Leu Leu Ala Ala Pro Leu Val Val Ala Ala Val Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Amino acid Sequence of aMTD44

<400> SEQUENCE: 16

Ala Leu Ala Val Pro Val Ala Leu Leu Val Ala Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Amino acid Sequence of aMTD61

<400> SEQUENCE: 17

Val Ala Ala Leu Pro Val Leu Leu Ala Ala Leu Pro
1               5                   10

<210> SEQ ID NO 18
<211> LENGTH: 12
<212> TYPE: PRT
<213> ORGANISM: Artificial Sequence
```

```
<220> FEATURE:
<223> OTHER INFORMATION: Amino acid Sequence of aMTD62

<400> SEQUENCE: 18

Val Ala Leu Leu Ala Pro Val Ala Leu Ala Val Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Amino acid Sequence of aMTD63

<400> SEQUENCE: 19

Ala Ala Leu Leu Val Pro Ala Leu Val Ala Val Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Amino acid Sequence of aMTD64

<400> SEQUENCE: 20

Ala Ile Val Ala Leu Pro Val Ala Val Leu Ala Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Amino acid Sequence of aMTD65

<400> SEQUENCE: 21

Ile Ala Ile Val Ala Pro Val Val Ala Leu Ala Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Amino acid Sequence of aMTD81

<400> SEQUENCE: 22

Ala Ala Leu Leu Pro Ala Leu Ala Ala Leu Leu Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Amino acid Sequence of aMTD82

<400> SEQUENCE: 23

Ala Val Val Leu Ala Pro Val Ala Ala Val Leu Pro
1               5                   10

<210> SEQ ID NO 24
<211> LENGTH: 12
<212> TYPE: PRT
<213> ORGANISM: Artificial Sequence
<220> FEATURE:
```

```
<223> OTHER INFORMATION: Amino acid Sequence of aMTD83

<400> SEQUENCE: 24

Leu Ala Val Ala Ala Pro Leu Ala Leu Ala Leu Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Amino acid Sequence of aMTD84

<400> SEQUENCE: 25

Ala Ala Val Ala Ala Pro Leu Leu Leu Ala Leu Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Amino acid Sequence of aMTD85

<400> SEQUENCE: 26

Leu Leu Val Leu Pro Ala Ala Ala Leu Ala Ala Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Amino acid Sequence of aMTD101

<400> SEQUENCE: 27

Leu Val Ala Leu Ala Pro Val Ala Ala Val Leu Pro
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Amino acid Sequence of aMTD102

<400> SEQUENCE: 28

Leu Ala Leu Ala Pro Ala Ala Leu Ala Leu Leu Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Amino acid Sequence of aMTD103

<400> SEQUENCE: 29

Ala Leu Ile Ala Ala Pro Ile Leu Ala Leu Ala Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Amino acid Sequence of aMTD104
```

```
<400> SEQUENCE: 30

Ala Val Val Ala Ala Pro Leu Val Leu Ala Leu Pro
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Amino acid Sequence of aMTD105

<400> SEQUENCE: 31

Leu Leu Ala Leu Ala Pro Ala Ala Leu Leu Ala Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Amino acid Sequence of aMTD121

<400> SEQUENCE: 32

Ala Ile Val Ala Leu Pro Ala Leu Ala Leu Ala Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Amino acid Sequence of aMTD123

<400> SEQUENCE: 33

Ala Ala Ile Ile Val Pro Ala Ala Leu Leu Ala Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Amino acid Sequence of aMTD124

<400> SEQUENCE: 34

Ile Ala Val Ala Leu Pro Ala Leu Ile Ala Ala Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Amino acid Sequence of aMTD141

<400> SEQUENCE: 35

Ala Val Ile Val Leu Pro Ala Leu Ala Val Ala Pro
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Amino acid Sequence of aMTD143
```

```
<400> SEQUENCE: 36

Ala Val Leu Ala Val Pro Ala Val Leu Val Ala Pro
1               5                  10

<210> SEQ ID NO 37
<211> LENGTH: 12
<212> TYPE: PRT
<213> ORGANISM: Artificial Sequence
<220> FEATURE:
<223> OTHER INFORMATION: Amino acid Sequence of aMTD144

<400> SEQUENCE: 37

Val Leu Ala Ile Val Pro Ala Val Ala Leu Ala Pro
1               5                  10

<210> SEQ ID NO 38
<211> LENGTH: 12
<212> TYPE: PRT
<213> ORGANISM: Artificial Sequence
<220> FEATURE:
<223> OTHER INFORMATION: Amino acid Sequence of aMTD145

<400> SEQUENCE: 38

Leu Leu Ala Val Val Pro Ala Val Ala Leu Ala Pro
1               5                  10

<210> SEQ ID NO 39
<211> LENGTH: 12
<212> TYPE: PRT
<213> ORGANISM: Artificial Sequence
<220> FEATURE:
<223> OTHER INFORMATION: Amino acid Sequence of aMTD161

<400> SEQUENCE: 39

Ala Val Ile Ala Leu Pro Ala Leu Ile Ala Ala Pro
1               5                  10

<210> SEQ ID NO 40
<211> LENGTH: 12
<212> TYPE: PRT
<213> ORGANISM: Artificial Sequence
<220> FEATURE:
<223> OTHER INFORMATION: Amino acid Sequence of aMTD162

<400> SEQUENCE: 40

Ala Val Val Ala Leu Pro Ala Ala Leu Ile Val Pro
1               5                  10

<210> SEQ ID NO 41
<211> LENGTH: 12
<212> TYPE: PRT
<213> ORGANISM: Artificial Sequence
<220> FEATURE:
<223> OTHER INFORMATION: Amino acid Sequence of aMTD163

<400> SEQUENCE: 41

Leu Ala Leu Val Leu Pro Ala Ala Leu Ala Ala Pro
1               5                  10

<210> SEQ ID NO 42
<211> LENGTH: 12
<212> TYPE: PRT
<213> ORGANISM: Artificial Sequence
<220> FEATURE:
<223> OTHER INFORMATION: Amino acid Sequence of aMTD164

<400> SEQUENCE: 42
```

```
Leu Ala Ala Val Leu Pro Ala Leu Leu Ala Ala Pro
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Amino acid Sequence of aMTD165

<400> SEQUENCE: 43

Ala Leu Ala Val Pro Val Ala Leu Ala Ile Val Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Amino acid Sequence of aMTD182

<400> SEQUENCE: 44

Ala Leu Ile Ala Pro Val Val Ala Leu Val Ala Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Amino acid Sequence of aMTD183

<400> SEQUENCE: 45

Leu Leu Ala Ala Pro Val Val Ile Ala Leu Ala Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Amino acid Sequence of aMTD184

<400> SEQUENCE: 46

Leu Ala Ala Ile Val Pro Ala Ile Ile Ala Val Pro
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Amino acid Sequence of aMTD185

<400> SEQUENCE: 47

Ala Ala Leu Val Leu Pro Leu Ile Ile Ala Ala Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Amino acid Sequence of aMTD201

<400> SEQUENCE: 48
```

```
Leu Ala Leu Ala Val Pro Ala Leu Ala Ala Leu Pro
1               5                  10
```

<210> SEQ ID NO 49
<211> LENGTH: 12
<212> TYPE: PRT
<213> ORGANISM: Artificial Sequence
<220> FEATURE:
<223> OTHER INFORMATION: Amino acid Sequence of aMTD204

<400> SEQUENCE: 49

```
Leu Ile Ala Ala Leu Pro Ala Val Ala Ala Leu Pro
1               5                  10
```

<210> SEQ ID NO 50
<211> LENGTH: 12
<212> TYPE: PRT
<213> ORGANISM: Artificial Sequence
<220> FEATURE:
<223> OTHER INFORMATION: Amino acid Sequence of aMTD205

<400> SEQUENCE: 50

```
Ala Leu Ala Leu Val Pro Ala Ile Ala Ala Leu Pro
1               5                  10
```

<210> SEQ ID NO 51
<211> LENGTH: 12
<212> TYPE: PRT
<213> ORGANISM: Artificial Sequence
<220> FEATURE:
<223> OTHER INFORMATION: Amino acid Sequence of aMTD221

<400> SEQUENCE: 51

```
Ala Ala Ile Leu Ala Pro Ile Val Ala Leu Ala Pro
1               5                  10
```

<210> SEQ ID NO 52
<211> LENGTH: 12
<212> TYPE: PRT
<213> ORGANISM: Artificial Sequence
<220> FEATURE:
<223> OTHER INFORMATION: Amino acid Sequence of aMTD222

<400> SEQUENCE: 52

```
Ala Leu Leu Ile Ala Pro Ala Ala Val Ile Ala Pro
1               5                  10
```

<210> SEQ ID NO 53
<211> LENGTH: 12
<212> TYPE: PRT
<213> ORGANISM: Artificial Sequence
<220> FEATURE:
<223> OTHER INFORMATION: Amino acid Sequence of aMTD223

<400> SEQUENCE: 53

```
Ala Ile Leu Ala Val Pro Ile Ala Val Val Ala Pro
1               5                  10
```

<210> SEQ ID NO 54
<211> LENGTH: 12
<212> TYPE: PRT
<213> ORGANISM: Artificial Sequence
<220> FEATURE:
<223> OTHER INFORMATION: Amino acid Sequence of aMTD224

<400> SEQUENCE: 54

```
Ile Leu Ala Ala Val Pro Ile Ala Leu Ala Ala Pro
```

<210> SEQ ID NO 55
<211> LENGTH: 12
<212> TYPE: PRT
<213> ORGANISM: Artificial Sequence
<220> FEATURE:
<223> OTHER INFORMATION: Amino acid Sequence of aMTD225

<400> SEQUENCE: 55

Val Ala Ala Leu Leu Pro Ala Ala Ala Val Leu Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Amino acid Sequence of aMTD241

<400> SEQUENCE: 56

Ala Ala Ala Val Val Pro Val Leu Leu Val Ala Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Amino acid Sequence of aMTD242

<400> SEQUENCE: 57

Ala Ala Leu Leu Val Pro Ala Leu Val Ala Ala Pro
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Amino acid Sequence of aMTD243

<400> SEQUENCE: 58

Ala Ala Val Leu Leu Pro Val Ala Leu Ala Ala Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Amino acid Sequence of aMTD245

<400> SEQUENCE: 59

Ala Ala Ala Leu Ala Pro Val Leu Ala Leu Val Pro
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Amino acid Sequence of aMTD261

<400> SEQUENCE: 60

Leu Val Leu Val Pro Leu Leu Ala Ala Ala Ala Pro
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Amino acid Sequence of aMTD262

<400> SEQUENCE: 61

Ala Leu Ile Ala Val Pro Ala Ile Ile Val Ala Pro
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Amino acid Sequence of aMTD263

<400> SEQUENCE: 62

Ala Leu Ala Val Ile Pro Ala Ala Ala Ile Leu Pro
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Amino acid Sequence of aMTD264

<400> SEQUENCE: 63

Leu Ala Ala Ala Pro Val Val Ile Val Ile Ala Pro
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Amino acid Sequence of aMTD265

<400> SEQUENCE: 64

Val Leu Ala Ile Ala Pro Leu Leu Ala Ala Val Pro
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Amino acid Sequence of aMTD281

<400> SEQUENCE: 65

Ala Leu Ile Val Leu Pro Ala Ala Val Ala Val Pro
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Amino acid Sequence of aMTD282

<400> SEQUENCE: 66

Val Leu Ala Val Ala Pro Ala Leu Ile Val Ala Pro
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Amino acid Sequence of aMTD283

<400> SEQUENCE: 67

Ala Ala Leu Leu Ala Pro Ala Leu Ile Val Ala Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Amino acid Sequence of aMTD284

<400> SEQUENCE: 68

Ala Leu Ile Ala Pro Ala Val Ala Leu Ile Val Pro
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Amino acid Sequence of aMTD285

<400> SEQUENCE: 69

Ala Ile Val Leu Leu Pro Ala Ala Val Val Ala Pro
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Amino acid Sequence of aMTD301

<400> SEQUENCE: 70

Val Ile Ala Ala Pro Val Leu Ala Val Leu Ala Pro
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Amino acid Sequence of aMTD302

<400> SEQUENCE: 71

Leu Ala Leu Ala Pro Ala Leu Ala Leu Leu Ala Pro
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Amino acid Sequence of aMTD304

<400> SEQUENCE: 72

Ala Ile Ile Leu Ala Pro Ile Ala Ala Ile Ala Pro
1               5                   10

```
<210> SEQ ID NO 73
<211> LENGTH: 12
<212> TYPE: PRT
<213> ORGANISM: Artificial Sequence
<220> FEATURE:
<223> OTHER INFORMATION: Amino acid Sequence of aMTD305

<400> SEQUENCE: 73

Ile Ala Leu Ala Ala Pro Ile Leu Leu Ala Ala Pro
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Amino acid Sequence of aMTD321

<400> SEQUENCE: 74

Ile Val Ala Val Ala Leu Pro Ala Leu Ala Val Pro
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Amino acid Sequence of aMTD322

<400> SEQUENCE: 75

Val Val Ala Ile Val Leu Pro Ala Leu Ala Ala Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Amino acid Sequence of aMTD323

<400> SEQUENCE: 76

Ile Val Ala Val Ala Leu Pro Val Ala Leu Ala Pro
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Amino acid Sequence of aMTD324

<400> SEQUENCE: 77

Ile Val Ala Val Ala Leu Pro Ala Ala Leu Val Pro
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Amino acid Sequence of aMTD325

<400> SEQUENCE: 78

Ile Val Ala Val Ala Leu Pro Ala Val Ala Leu Pro
1               5                   10

<210> SEQ ID NO 79
```

```
<211> LENGTH: 12
<212> TYPE: PRT
<213> ORGANISM: Artificial Sequence
<220> FEATURE:
<223> OTHER INFORMATION: Amino acid Sequence of aMTD341

<400> SEQUENCE: 79

Ile Val Ala Val Ala Leu Pro Ala Val Leu Ala Pro
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Amino acid Sequence of aMTD342

<400> SEQUENCE: 80

Val Ile Val Ala Leu Ala Pro Ala Val Leu Ala Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Amino acid Sequence of aMTD343

<400> SEQUENCE: 81

Ile Val Ala Val Ala Leu Pro Ala Leu Val Ala Pro
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Amino acid Sequence of aMTD345

<400> SEQUENCE: 82

Ala Leu Leu Ile Val Ala Pro Val Ala Val Ala Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Amino acid Sequence of aMTD361

<400> SEQUENCE: 83

Ala Val Val Ile Val Ala Pro Ala Val Ile Ala Pro
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Amino acid Sequence of aMTD363

<400> SEQUENCE: 84

Ala Val Leu Ala Val Ala Pro Ala Leu Ile Val Pro
1               5                   10

<210> SEQ ID NO 85
<211> LENGTH: 12
```

```
<212> TYPE: PRT
<213> ORGANISM: Artificial Sequence
<220> FEATURE:
<223> OTHER INFORMATION: Amino acid Sequence of aMTD364

<400> SEQUENCE: 85

Leu Val Ala Ala Val Ala Pro Ala Leu Ile Val Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Amino acid Sequence of aMTD365

<400> SEQUENCE: 86

Ala Val Ile Val Val Ala Pro Ala Leu Leu Ala Pro
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Amino acid Sequence of aMTD381

<400> SEQUENCE: 87

Val Val Ala Ile Val Leu Pro Ala Val Ala Ala Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Amino acid Sequence of aMTD382

<400> SEQUENCE: 88

Ala Ala Ala Leu Val Ile Pro Ala Ile Leu Ala Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Amino acid Sequence of aMTD383

<400> SEQUENCE: 89

Val Ile Val Ala Leu Ala Pro Ala Leu Leu Ala Pro
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Amino acid Sequence of aMTD384

<400> SEQUENCE: 90

Val Ile Val Ala Ile Ala Pro Ala Leu Leu Ala Pro
1               5                   10

<210> SEQ ID NO 91
<211> LENGTH: 12
<212> TYPE: PRT
```

<213> ORGANISM: Artificial Sequence
<220> FEATURE:
<223> OTHER INFORMATION: Amino acid Sequence of aMTD385

<400> SEQUENCE: 91

Ile Val Ala Ile Ala Val Pro Ala Leu Val Ala Pro
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Amino acid Sequence of aMTD401

<400> SEQUENCE: 92

Ala Ala Leu Ala Val Ile Pro Ala Ala Ile Leu Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Amino acid Sequence of aMTD402

<400> SEQUENCE: 93

Ala Leu Ala Ala Val Ile Pro Ala Ala Ile Leu Pro
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Amino acid Sequence of aMTD403

<400> SEQUENCE: 94

Ala Ala Ala Leu Val Ile Pro Ala Ala Ile Leu Pro
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Amino acid Sequence of aMTD404

<400> SEQUENCE: 95

Leu Ala Ala Ala Val Ile Pro Ala Ala Ile Leu Pro
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Amino acid Sequence of aMTD405

<400> SEQUENCE: 96

Leu Ala Ala Ala Val Ile Pro Val Ala Ile Leu Pro
1               5                   10

<210> SEQ ID NO 97
<211> LENGTH: 12
<212> TYPE: PRT
<213> ORGANISM: Artificial Sequence

```
<220> FEATURE:
<223> OTHER INFORMATION: Amino acid Sequence of aMTD421

<400> SEQUENCE: 97

Ala Ala Ile Leu Ala Ala Pro Leu Ile Ala Val Pro
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Amino acid Sequence of aMTD422

<400> SEQUENCE: 98

Val Val Ala Ile Leu Ala Pro Leu Leu Ala Ala Pro
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Amino acid Sequence of aMTD424

<400> SEQUENCE: 99

Ala Val Val Val Ala Ala Pro Val Leu Ala Leu Pro
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Amino acid Sequence of aMTD425

<400> SEQUENCE: 100

Ala Val Val Ala Ile Ala Pro Val Leu Ala Leu Pro
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Amino acid Sequence of aMTD442

<400> SEQUENCE: 101

Ala Leu Ala Ala Leu Val Pro Ala Val Leu Val Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Amino acid Sequence of aMTD443

<400> SEQUENCE: 102

Ala Leu Ala Ala Leu Val Pro Val Ala Leu Val Pro
1               5                   10

<210> SEQ ID NO 103
<211> LENGTH: 12
<212> TYPE: PRT
<213> ORGANISM: Artificial Sequence
<220> FEATURE:
```

<223> OTHER INFORMATION: Amino acid Sequence of aMTD444

<400> SEQUENCE: 103

Leu Ala Ala Ala Leu Val Pro Val Ala Leu Val Pro
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Amino acid Sequence of aMTD445

<400> SEQUENCE: 104

Ala Leu Ala Ala Leu Val Pro Ala Leu Val Val Pro
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Amino acid Sequence of aMTD461

<400> SEQUENCE: 105

Ile Ala Ala Val Ile Val Pro Ala Val Ala Leu Pro
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Amino acid Sequence of aMTD462

<400> SEQUENCE: 106

Ile Ala Ala Val Leu Val Pro Ala Val Ala Leu Pro
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Amino acid Sequence of aMTD463

<400> SEQUENCE: 107

Ala Val Ala Ile Leu Val Pro Leu Leu Ala Ala Pro
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Amino acid Sequence of aMTD464

<400> SEQUENCE: 108

Ala Val Val Ile Leu Val Pro Leu Ala Ala Ala Pro
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Amino acid Sequence of aMTD465

```
<400> SEQUENCE: 109

Ile Ala Ala Val Ile Val Pro Val Ala Ala Leu Pro
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Amino acid Sequence of aMTD481

<400> SEQUENCE: 110

Ala Ile Ala Ile Ala Ile Val Pro Val Ala Leu Pro
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Amino acid Sequence of aMTD482

<400> SEQUENCE: 111

Ile Leu Ala Val Ala Ala Ile Pro Val Ala Val Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Amino acid Sequence of aMTD483

<400> SEQUENCE: 112

Ile Leu Ala Ala Ala Ile Ile Pro Ala Ala Leu Pro
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Amino acid Sequence of aMTD484

<400> SEQUENCE: 113

Leu Ala Val Val Leu Ala Ala Pro Ala Ile Val Pro
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Amino acid Sequence of aMTD485

<400> SEQUENCE: 114

Ala Ile Leu Ala Ala Ile Val Pro Leu Ala Val Pro
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Amino acid Sequence of aMTD501
```

<400> SEQUENCE: 115

Val Ile Val Ala Leu Ala Val Pro Ala Leu Ala Pro
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Amino acid Sequence of aMTD502

<400> SEQUENCE: 116

Ala Ile Val Ala Leu Ala Val Pro Val Leu Ala Pro
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Amino acid Sequence of aMTD503

<400> SEQUENCE: 117

Ala Ala Ile Ile Ile Val Leu Pro Ala Ala Leu Pro
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Amino acid Sequence of aMTD504

<400> SEQUENCE: 118

Leu Ile Val Ala Leu Ala Val Pro Ala Leu Ala Pro
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Amino acid Sequence of aMTD505

<400> SEQUENCE: 119

Ala Ile Ile Ile Val Ile Ala Pro Ala Ala Ala Pro
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Amino acid Sequence of aMTD521

<400> SEQUENCE: 120

Leu Ala Ala Leu Ile Val Val Pro Ala Val Ala Pro
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Amino acid Sequence of aMTD522

<400> SEQUENCE: 121

Ala Leu Leu Val Ile Ala Val Pro Ala Val Ala Pro
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Amino acid Sequence of aMTD524

<400> SEQUENCE: 122

Ala Val Ala Leu Ile Val Val Pro Ala Leu Ala Pro
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Amino acid Sequence of aMTD525

<400> SEQUENCE: 123

Ala Leu Ala Ile Val Val Ala Pro Val Ala Val Pro
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Amino acid Sequence of aMTD541

<400> SEQUENCE: 124

Leu Leu Ala Leu Ile Ile Ala Pro Ala Ala Ala Pro
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Amino acid Sequence of aMTD542

<400> SEQUENCE: 125

Ala Leu Ala Leu Ile Ile Val Pro Ala Val Ala Pro
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Amino acid Sequence of aMTD543

<400> SEQUENCE: 126

Leu Leu Ala Ala Leu Ile Ala Pro Ala Ala Leu Pro
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Amino acid Sequence of aMTD544

<400> SEQUENCE: 127

Ile Val Ala Leu Ile Val Ala Pro Ala Ala Val Pro
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Amino acid Sequence of aMTD545

<400> SEQUENCE: 128

Val Val Leu Val Leu Ala Ala Pro Ala Ala Val Pro
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Amino acid Sequence of aMTD561

<400> SEQUENCE: 129

Ala Ala Val Ala Ile Val Leu Pro Ala Val Val Pro
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Amino acid Sequence of aMTD562

<400> SEQUENCE: 130

Ala Leu Ile Ala Ala Ile Val Pro Ala Leu Val Pro
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Amino acid Sequence of aMTD563

<400> SEQUENCE: 131

Ala Leu Ala Val Ile Val Val Pro Ala Leu Ala Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Amino acid Sequence of aMTD564

<400> SEQUENCE: 132

Val Ala Ile Ala Leu Ile Val Pro Ala Leu Ala Pro
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Amino acid Sequence of aMTD565

<400> SEQUENCE: 133

Val Ala Ile Val Leu Val Ala Pro Ala Val Ala Pro

```
<210> SEQ ID NO 134
<211> LENGTH: 12
<212> TYPE: PRT
<213> ORGANISM: Artificial Sequence
<220> FEATURE:
<223> OTHER INFORMATION: Amino acid Sequence of aMTD582

<400> SEQUENCE: 134

Val Ala Val Ala Leu Ile Val Pro Ala Leu Ala Pro
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Amino acid Sequence of aMTD583

<400> SEQUENCE: 135

Ala Val Ile Leu Ala Leu Ala Pro Ile Val Ala Pro
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Amino acid Sequence of aMTD585

<400> SEQUENCE: 136

Ala Leu Ile Val Ala Ile Ala Pro Ala Leu Val Pro
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Amino acid Sequence of aMTD601

<400> SEQUENCE: 137

Ala Ala Ile Leu Ile Ala Val Pro Ile Ala Ala Pro
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Amino acid Sequence of aMTD602

<400> SEQUENCE: 138

Val Ile Val Ala Leu Ala Ala Pro Val Leu Ala Pro
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Amino acid Sequence of aMTD603

<400> SEQUENCE: 139

Val Leu Val Ala Leu Ala Ala Pro Val Ile Ala Pro
1               5                   10
```

<210> SEQ ID NO 140
<211> LENGTH: 12
<212> TYPE: PRT
<213> ORGANISM: Artificial Sequence
<220> FEATURE:
<223> OTHER INFORMATION: Amino acid Sequence of aMTD604

<400> SEQUENCE: 140

Val Ala Leu Ile Ala Val Ala Pro Ala Val Val Pro
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Amino acid Sequence of aMTD605

<400> SEQUENCE: 141

Val Ile Ala Ala Val Leu Ala Pro Val Ala Val Pro
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Amino acid Sequence of aMTD622

<400> SEQUENCE: 142

Ala Leu Ile Val Leu Ala Ala Pro Val Ala Val Pro
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Amino acid Sequence of aMTD623

<400> SEQUENCE: 143

Val Ala Ala Ala Ile Ala Leu Pro Ala Ile Val Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Amino acid Sequence of aMTD625

<400> SEQUENCE: 144

Ile Leu Ala Ala Ala Ala Ala Pro Leu Ile Val Pro
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Amino acid Sequence of aMTD643

<400> SEQUENCE: 145

Leu Ala Leu Val Leu Ala Ala Pro Ala Ile Val Pro
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Amino acid Sequence of aMTD645

<400> SEQUENCE: 146

Ala Leu Ala Val Val Ala Leu Pro Ala Ile Val Pro
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Amino acid Sequence of aMTD661

<400> SEQUENCE: 147

Ala Ala Ile Leu Ala Pro Ile Val Ala Ala Leu Pro
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Amino acid Sequence of aMTD664

<400> SEQUENCE: 148

Ile Leu Ile Ala Ile Ala Ile Pro Ala Ala Ala Pro
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Amino acid Sequence of aMTD665

<400> SEQUENCE: 149

Leu Ala Ile Val Leu Ala Ala Pro Val Ala Val Pro
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Amino acid Sequence of aMTD666

<400> SEQUENCE: 150

Ala Ala Ile Ala Ile Ile Ala Pro Ala Ile Val Pro
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Amino acid Sequence of aMTD667

<400> SEQUENCE: 151

Leu Ala Val Ala Ile Val Ala Pro Ala Leu Val Pro
1               5                   10

```
<210> SEQ ID NO 152
<211> LENGTH: 12
<212> TYPE: PRT
<213> ORGANISM: Artificial Sequence
<220> FEATURE:
<223> OTHER INFORMATION: Amino acid Sequence of aMTD683

<400> SEQUENCE: 152

Leu Ala Ile Val Leu Ala Ala Pro Ala Val Leu Pro
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Amino acid Sequence of aMTD684

<400> SEQUENCE: 153

Ala Ala Ile Val Leu Ala Leu Pro Ala Val Leu Pro
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Amino acid Sequence of aMTD685

<400> SEQUENCE: 154

Ala Leu Leu Val Ala Val Leu Pro Ala Ala Leu Pro
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Amino acid Sequence of aMTD686

<400> SEQUENCE: 155

Ala Ala Leu Val Ala Val Leu Pro Val Ala Leu Pro
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Amino acid Sequence of aMTD687

<400> SEQUENCE: 156

Ala Ile Leu Ala Val Ala Leu Pro Leu Leu Ala Pro
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Amino acid Sequence of aMTD703

<400> SEQUENCE: 157

Ile Val Ala Val Ala Leu Val Pro Ala Leu Ala Pro
1               5                   10

<210> SEQ ID NO 158
```

```
<211> LENGTH: 12
<212> TYPE: PRT
<213> ORGANISM: Artificial Sequence
<220> FEATURE:
<223> OTHER INFORMATION: Amino acid Sequence of aMTD705

<400> SEQUENCE: 158

Ile Val Ala Val Ala Leu Leu Pro Ala Leu Ala Pro
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Amino acid Sequence of aMTD706

<400> SEQUENCE: 159

Ile Val Ala Val Ala Leu Leu Pro Ala Val Ala Pro
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Amino acid Sequence of aMTD707

<400> SEQUENCE: 160

Ile Val Ala Leu Ala Val Leu Pro Ala Val Ala Pro
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Amino acid Sequence of aMTD724

<400> SEQUENCE: 161

Val Ala Val Leu Ala Val Leu Pro Ala Leu Ala Pro
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Amino acid Sequence of aMTD725

<400> SEQUENCE: 162

Ile Ala Val Leu Ala Val Ala Pro Ala Val Leu Pro
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Amino acid Sequence of aMTD726

<400> SEQUENCE: 163

Leu Ala Val Ala Ile Ile Ala Pro Ala Val Ala Pro
1               5                   10

<210> SEQ ID NO 164
<211> LENGTH: 12
```

```
<212> TYPE: PRT
<213> ORGANISM: Artificial Sequence
<220> FEATURE:
<223> OTHER INFORMATION: Amino acid Sequence of aMTD727

<400> SEQUENCE: 164

Val Ala Leu Ala Ile Ala Leu Pro Ala Val Leu Pro
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Amino acid Sequence of aMTD743

<400> SEQUENCE: 165

Ala Ile Ala Ile Ala Leu Val Pro Val Ala Leu Pro
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Amino acid Sequence of aMTD744

<400> SEQUENCE: 166

Ala Ala Val Val Ile Val Ala Pro Val Ala Leu Pro
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Amino acid Sequence of aMTD746

<400> SEQUENCE: 167

Val Ala Ile Ile Val Val Ala Pro Ala Leu Ala Pro
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Amino acid Sequence of aMTD747

<400> SEQUENCE: 168

Val Ala Leu Leu Ala Ile Ala Pro Ala Leu Ala Pro
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Amino acid Sequence of aMTD763

<400> SEQUENCE: 169

Val Ala Val Leu Ile Ala Val Pro Ala Leu Ala Pro
1               5                   10

<210> SEQ ID NO 170
<211> LENGTH: 12
<212> TYPE: PRT
```

```
<213> ORGANISM: Artificial Sequence
<220> FEATURE:
<223> OTHER INFORMATION: Amino acid Sequence of aMTD764

<400> SEQUENCE: 170

Ala Val Ala Leu Ala Val Leu Pro Ala Val Val Pro
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Amino acid Sequence of aMTD765

<400> SEQUENCE: 171

Ala Val Ala Leu Ala Val Val Pro Ala Val Leu Pro
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Amino acid Sequence of aMTD766

<400> SEQUENCE: 172

Ile Val Val Ile Ala Val Ala Pro Ala Val Ala Pro
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Amino acid Sequence of aMTD767

<400> SEQUENCE: 173

Ile Val Val Ala Ala Val Val Pro Ala Leu Ala Pro
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Amino acid Sequence of aMTD783

<400> SEQUENCE: 174

Ile Val Ala Leu Val Pro Ala Val Ala Ile Ala Pro
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Amino acid Sequence of aMTD784

<400> SEQUENCE: 175

Val Ala Ala Leu Pro Ala Val Ala Leu Val Val Pro
1               5                   10

<210> SEQ ID NO 176
<211> LENGTH: 12
<212> TYPE: PRT
<213> ORGANISM: Artificial Sequence
```

```
<220> FEATURE:
<223> OTHER INFORMATION: Amino acid Sequence of aMTD786

<400> SEQUENCE: 176

Leu Val Ala Ile Ala Pro Leu Ala Val Leu Ala Pro
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Amino acid Sequence of aMTD787

<400> SEQUENCE: 177

Ala Val Ala Leu Val Pro Val Ile Val Ala Ala Pro
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Amino acid Sequence of aMTD788

<400> SEQUENCE: 178

Ala Ile Ala Val Ala Ile Ala Pro Val Ala Leu Pro
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Amino acid Sequence of aMTD803

<400> SEQUENCE: 179

Ala Ile Ala Leu Ala Val Pro Val Leu Ala Leu Pro
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Amino acid Sequence of aMTD805

<400> SEQUENCE: 180

Leu Val Leu Ile Ala Ala Ala Pro Ile Ala Leu Pro
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Amino acid Sequence of aMTD806

<400> SEQUENCE: 181

Leu Val Ala Leu Ala Val Pro Ala Ala Val Leu Pro
1               5                   10

<210> SEQ ID NO 182
<211> LENGTH: 12
<212> TYPE: PRT
<213> ORGANISM: Artificial Sequence
<220> FEATURE:
```

<223> OTHER INFORMATION: Amino acid Sequence of aMTD807

<400> SEQUENCE: 182

Ala Val Ala Leu Ala Val Pro Ala Leu Val Leu Pro
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Amino acid Sequence of aMTD808

<400> SEQUENCE: 183

Leu Val Val Leu Ala Ala Ala Pro Leu Ala Val Pro
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Amino acid Sequence of aMTD809

<400> SEQUENCE: 184

Leu Ile Val Leu Ala Ala Pro Ala Leu Ala Ala Pro
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Amino acid Sequence of aMTD810

<400> SEQUENCE: 185

Val Ile Val Leu Ala Ala Pro Ala Leu Ala Ala Pro
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Amino acid Sequence of aMTD811

<400> SEQUENCE: 186

Ala Val Val Leu Ala Val Pro Ala Leu Ala Val Pro
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Amino acid Sequence of aMTD824

<400> SEQUENCE: 187

Leu Ile Ile Val Ala Ala Ala Pro Ala Val Ala Pro
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Amino acid Sequence of aMTD825

```
<400> SEQUENCE: 188

Ile Val Ala Val Ile Val Ala Pro Ala Val Ala Pro
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Amino acid Sequence of aMTD826

<400> SEQUENCE: 189

Leu Val Ala Leu Ala Ala Pro Ile Ile Ala Val Pro
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Amino acid Sequence of aMTD827

<400> SEQUENCE: 190

Ile Ala Ala Val Leu Ala Ala Pro Ala Leu Val Pro
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Amino acid Sequence of aMTD828

<400> SEQUENCE: 191

Ile Ala Leu Leu Ala Ala Pro Ile Ile Ala Val Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Amino acid Sequence of aMTD829

<400> SEQUENCE: 192

Ala Ala Leu Ala Leu Val Ala Pro Val Ile Val Pro
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Amino acid Sequence of aMTD830

<400> SEQUENCE: 193

Ile Ala Leu Val Ala Ala Pro Val Ala Leu Val Pro
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Amino acid Sequence of aMTD831
```

<400> SEQUENCE: 194

Ile Ile Val Ala Val Ala Pro Ala Ala Ile Val Pro
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Amino acid Sequence of aMTD832

<400> SEQUENCE: 195

Ala Val Ala Ala Ile Val Pro Val Ile Val Ala Pro
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Amino acid Sequence of aMTD843

<400> SEQUENCE: 196

Ala Val Leu Val Leu Val Ala Pro Ala Ala Ala Pro
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Amino acid Sequence of aMTD844

<400> SEQUENCE: 197

Val Val Ala Leu Leu Ala Pro Leu Ile Ala Ala Pro
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Amino acid Sequence of aMTD845

<400> SEQUENCE: 198

Ala Ala Val Val Ile Ala Pro Leu Leu Ala Val Pro
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Amino acid Sequence of aMTD846

<400> SEQUENCE: 199

Ile Ala Val Ala Val Ala Ala Pro Leu Leu Val Pro
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Amino acid Sequence of aMTD847

<400> SEQUENCE: 200

```
Leu Val Ala Ile Val Val Leu Pro Ala Val Ala Pro
1               5                   10
```

<210> SEQ ID NO 201
<211> LENGTH: 12
<212> TYPE: PRT
<213> ORGANISM: Artificial Sequence
<220> FEATURE:
<223> OTHER INFORMATION: Amino acid Sequence of aMTD848

<400> SEQUENCE: 201

```
Ala Val Ala Ile Val Val Leu Pro Ala Val Ala Pro
1               5                   10
```

<210> SEQ ID NO 202
<211> LENGTH: 12
<212> TYPE: PRT
<213> ORGANISM: Artificial Sequence
<220> FEATURE:
<223> OTHER INFORMATION: Amino acid Sequence of aMTD849

<400> SEQUENCE: 202

```
Ala Val Ile Leu Leu Ala Pro Leu Ile Ala Ala Pro
1               5                   10
```

<210> SEQ ID NO 203
<211> LENGTH: 12
<212> TYPE: PRT
<213> ORGANISM: Artificial Sequence
<220> FEATURE:
<223> OTHER INFORMATION: Amino acid Sequence of aMTD850

<400> SEQUENCE: 203

```
Leu Val Ile Ala Leu Ala Ala Pro Val Ala Leu Pro
1               5                   10
```

<210> SEQ ID NO 204
<211> LENGTH: 12
<212> TYPE: PRT
<213> ORGANISM: Artificial Sequence
<220> FEATURE:
<223> OTHER INFORMATION: Amino acid Sequence of aMTD851

<400> SEQUENCE: 204

```
Val Leu Ala Val Val Leu Pro Ala Val Ala Leu Pro
1               5                   10
```

<210> SEQ ID NO 205
<211> LENGTH: 12
<212> TYPE: PRT
<213> ORGANISM: Artificial Sequence
<220> FEATURE:
<223> OTHER INFORMATION: Amino acid Sequence of aMTD852

<400> SEQUENCE: 205

```
Val Leu Ala Val Ala Ala Pro Ala Val Leu Leu Pro
1               5                   10
```

<210> SEQ ID NO 206
<211> LENGTH: 12
<212> TYPE: PRT
<213> ORGANISM: Artificial Sequence
<220> FEATURE:
<223> OTHER INFORMATION: Amino acid Sequence of aMTD863

<400> SEQUENCE: 206

```
Ala Ala Val Val Leu Leu Pro Ile Ile Ala Ala Pro
1               5                   10
```

<210> SEQ ID NO 207
<211> LENGTH: 12
<212> TYPE: PRT
<213> ORGANISM: Artificial Sequence
<220> FEATURE:
<223> OTHER INFORMATION: Amino acid Sequence of aMTD864

<400> SEQUENCE: 207

```
Ala Leu Leu Val Ile Ala Pro Ala Ile Ala Val Pro
1               5                   10
```

<210> SEQ ID NO 208
<211> LENGTH: 12
<212> TYPE: PRT
<213> ORGANISM: Artificial Sequence
<220> FEATURE:
<223> OTHER INFORMATION: Amino acid Sequence of aMTD865

<400> SEQUENCE: 208

```
Ala Val Leu Val Ile Ala Val Pro Ala Ile Ala Pro
1               5                   10
```

<210> SEQ ID NO 209
<211> LENGTH: 12
<212> TYPE: PRT
<213> ORGANISM: Artificial Sequence
<220> FEATURE:
<223> OTHER INFORMATION: Amino acid Sequence of aMTD867

<400> SEQUENCE: 209

```
Ala Leu Leu Val Val Ile Ala Pro Leu Ala Ala Pro
1               5                   10
```

<210> SEQ ID NO 210
<211> LENGTH: 12
<212> TYPE: PRT
<213> ORGANISM: Artificial Sequence
<220> FEATURE:
<223> OTHER INFORMATION: Amino acid Sequence of aMTD868

<400> SEQUENCE: 210

```
Val Leu Val Ala Ala Ile Leu Pro Ala Ala Ile Pro
1               5                   10
```

<210> SEQ ID NO 211
<211> LENGTH: 12
<212> TYPE: PRT
<213> ORGANISM: Artificial Sequence
<220> FEATURE:
<223> OTHER INFORMATION: Amino acid Sequence of aMTD870

<400> SEQUENCE: 211

```
Val Leu Val Ala Ala Val Leu Pro Ile Ala Ala Pro
1               5                   10
```

<210> SEQ ID NO 212
<211> LENGTH: 12
<212> TYPE: PRT
<213> ORGANISM: Artificial Sequence
<220> FEATURE:
<223> OTHER INFORMATION: Amino acid Sequence of aMTD872

<400> SEQUENCE: 212

Val Leu Ala Ala Ala Val Leu Pro Leu Val Val Pro

```
1               5                  10
```

<210> SEQ ID NO 213
<211> LENGTH: 12
<212> TYPE: PRT
<213> ORGANISM: Artificial Sequence
<220> FEATURE:
<223> OTHER INFORMATION: Amino acid Sequence of aMTD875

<400> SEQUENCE: 213

```
Ala Ile Ala Ile Val Val Pro Ala Val Ala Val Pro
1               5                  10
```

<210> SEQ ID NO 214
<211> LENGTH: 12
<212> TYPE: PRT
<213> ORGANISM: Artificial Sequence
<220> FEATURE:
<223> OTHER INFORMATION: Amino acid Sequence of aMTD877

<400> SEQUENCE: 214

```
Val Ala Ile Ile Ala Val Pro Ala Val Val Ala Pro
1               5                  10
```

<210> SEQ ID NO 215
<211> LENGTH: 12
<212> TYPE: PRT
<213> ORGANISM: Artificial Sequence
<220> FEATURE:
<223> OTHER INFORMATION: Amino acid Sequence of aMTD878

<400> SEQUENCE: 215

```
Ile Val Ala Leu Val Ala Pro Ala Ala Val Val Pro
1               5                  10
```

<210> SEQ ID NO 216
<211> LENGTH: 12
<212> TYPE: PRT
<213> ORGANISM: Artificial Sequence
<220> FEATURE:
<223> OTHER INFORMATION: Amino acid Sequence of aMTD879

<400> SEQUENCE: 216

```
Ala Ala Ile Val Leu Leu Pro Ala Val Val Val Pro
1               5                  10
```

<210> SEQ ID NO 217
<211> LENGTH: 12
<212> TYPE: PRT
<213> ORGANISM: Artificial Sequence
<220> FEATURE:
<223> OTHER INFORMATION: Amino acid Sequence of aMTD881

<400> SEQUENCE: 217

```
Ala Ala Leu Ile Val Val Pro Ala Val Ala Val Pro
1               5                  10
```

<210> SEQ ID NO 218
<211> LENGTH: 12
<212> TYPE: PRT
<213> ORGANISM: Artificial Sequence
<220> FEATURE:
<223> OTHER INFORMATION: Amino acid Sequence of aMTD882

<400> SEQUENCE: 218

```
Ala Ile Ala Leu Val Val Pro Ala Val Ala Val Pro
1               5                  10
```

<210> SEQ ID NO 219
<211> LENGTH: 12
<212> TYPE: PRT
<213> ORGANISM: Artificial Sequence
<220> FEATURE:
<223> OTHER INFORMATION: Amino acid Sequence of aMTD883

<400> SEQUENCE: 219

Leu Ala Ile Val Pro Ala Ala Ile Ala Ala Leu Pro
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Amino acid Sequence of aMTD885

<400> SEQUENCE: 220

Leu Val Ala Ile Ala Pro Ala Val Ala Val Leu Pro
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Amino acid Sequence of aMTD887

<400> SEQUENCE: 221

Val Leu Ala Val Ala Pro Ala Val Ala Val Leu Pro
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Amino acid Sequence of aMTD888

<400> SEQUENCE: 222

Ile Leu Ala Val Val Ala Ile Pro Ala Ala Ala Pro
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Amino acid Sequence of aMTD889

<400> SEQUENCE: 223

Ile Leu Val Ala Ala Ala Pro Ile Ala Ala Leu Pro
1               5                   10

<210> SEQ ID NO 224
<211> LENGTH: 12
<212> TYPE: PRT
<213> ORGANISM: Artificial Sequence
<220> FEATURE:
<223> OTHER INFORMATION: Amino acid Sequence of aMTD891

<400> SEQUENCE: 224

Ile Leu Ala Val Ala Ala Ile Pro Ala Ala Leu Pro
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Amino acid Sequence of aMTD893

<400> SEQUENCE: 225

Val Ile Ala Ile Pro Ala Ile Leu Ala Ala Ala Pro
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Amino acid Sequence of aMTD895

<400> SEQUENCE: 226

Ala Ile Ile Ile Val Val Pro Ala Ile Ala Ala Pro
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Amino acid Sequence of aMTD896

<400> SEQUENCE: 227

Ala Ile Leu Ile Val Val Ala Pro Ile Ala Ala Pro
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Amino acid Sequence of aMTD897

<400> SEQUENCE: 228

Ala Val Ile Val Pro Val Ala Ile Ile Ala Ala Pro
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Amino acid Sequence of aMTD899

<400> SEQUENCE: 229

Ala Val Val Ile Ala Leu Pro Ala Val Val Ala Pro
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Amino acid Sequence of aMTD900

<400> SEQUENCE: 230

Ala Leu Val Ala Val Ile Ala Pro Val Val Ala Pro
1               5                   10

```
<210> SEQ ID NO 231
<211> LENGTH: 12
<212> TYPE: PRT
<213> ORGANISM: Artificial Sequence
<220> FEATURE:
<223> OTHER INFORMATION: Amino acid Sequence of aMTD901

<400> SEQUENCE: 231

Ala Leu Val Ala Val Leu Pro Ala Val Ala Val Pro
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Amino acid Sequence of aMTD902

<400> SEQUENCE: 232

Ala Leu Val Ala Pro Leu Leu Ala Val Ala Val Pro
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Amino acid Sequence of aMTD904

<400> SEQUENCE: 233

Ala Val Leu Ala Val Val Ala Pro Val Val Ala Pro
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Amino acid Sequence of aMTD905

<400> SEQUENCE: 234

Ala Val Ile Ala Val Ala Pro Leu Val Val Ala Pro
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Amino acid Sequence of aMTD906

<400> SEQUENCE: 235

Ala Val Ile Ala Leu Ala Pro Val Val Val Ala Pro
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Amino acid Sequence of aMTD907

<400> SEQUENCE: 236

Val Ala Ile Ala Leu Ala Pro Val Val Val Ala Pro
1               5                   10

<210> SEQ ID NO 237
```

```
<211> LENGTH: 12
<212> TYPE: PRT
<213> ORGANISM: Artificial Sequence
<220> FEATURE:
<223> OTHER INFORMATION: Amino acid Sequence of aMTD908

<400> SEQUENCE: 237

Val Ala Leu Ala Leu Ala Pro Val Val Val Ala Pro
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Amino acid Sequence of aMTD910

<400> SEQUENCE: 238

Val Ala Ala Leu Leu Pro Ala Val Val Val Ala Pro
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Amino acid Sequence of aMTD911

<400> SEQUENCE: 239

Val Ala Leu Ala Leu Pro Ala Val Val Val Ala Pro
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Amino acid Sequence of aMTD912

<400> SEQUENCE: 240

Val Ala Leu Leu Ala Pro Ala Val Val Val Ala Pro
1               5                   10

<210> SEQ ID NO 241
<211> LENGTH: 36
<212> TYPE: DNA
<213> ORGANISM: Artificial Sequence
<220> FEATURE:
<223> OTHER INFORMATION: cDNA Sequence of aMTD1

<400> SEQUENCE: 241
gcggcggcgc tggcgccggt ggtgctggcg ctgccg                              36

<210> SEQ ID NO 242
<211> LENGTH: 36
<212> TYPE: DNA
<213> ORGANISM: Artificial Sequence
<220> FEATURE:
<223> OTHER INFORMATION: cDNA Sequence of aMTD2

<400> SEQUENCE: 242
gcggcggcgg tgccgctgct ggcggtggtg gtgccg                              36

<210> SEQ ID NO 243
<211> LENGTH: 36
<212> TYPE: DNA
<213> ORGANISM: Artificial Sequence
```

```
<220> FEATURE:
<223> OTHER INFORMATION: cDNA Sequence of aMTD3

<400> SEQUENCE: 243
gcggcgctgc tggtgccggc ggcggtgctg gcgccg                                    36

<210> SEQ ID NO 244
<211> LENGTH: 36
<212> TYPE: DNA
<213> ORGANISM: Artificial Sequence
<220> FEATURE:
<223> OTHER INFORMATION: cDNA Sequence of aMTD4

<400> SEQUENCE: 244
gcgctggcgc tgctgccggt ggcggcgctg gcgccg                                    36

<210> SEQ ID NO 245
<211> LENGTH: 36
<212> TYPE: DNA
<213> ORGANISM: Artificial Sequence
<220> FEATURE:
<223> OTHER INFORMATION: cDNA Sequence of aMTD5

<400> SEQUENCE: 245
gcggcggcgc tgctgccggt ggcgctggtg gcgccg                                    36

<210> SEQ ID NO 246
<211> LENGTH: 36
<212> TYPE: DNA
<213> ORGANISM: Artificial Sequence
<220> FEATURE:
<223> OTHER INFORMATION: cDNA Sequence of aMTD11

<400> SEQUENCE: 246
gtggtggcgc tggcgccggc gctggcggcg ctgccg                                    36

<210> SEQ ID NO 247
<211> LENGTH: 36
<212> TYPE: DNA
<213> ORGANISM: Artificial Sequence
<220> FEATURE:
<223> OTHER INFORMATION: cDNA Sequence of aMTD12

<400> SEQUENCE: 247
ctgctggcgg cggtgccggc ggtgctgctg gcgccg                                    36

<210> SEQ ID NO 248
<211> LENGTH: 36
<212> TYPE: DNA
<213> ORGANISM: Artificial Sequence
<220> FEATURE:
<223> OTHER INFORMATION: cDNA Sequence of aMTD13

<400> SEQUENCE: 248
gcggcggcgc tggtgccggt ggtggcgctg ctgccg                                    36

<210> SEQ ID NO 249
<211> LENGTH: 36
<212> TYPE: DNA
<213> ORGANISM: Artificial Sequence
<220> FEATURE:
<223> OTHER INFORMATION: cDNA Sequence of aMTD21

<400> SEQUENCE: 249
gcggtggcgc tgctgccggc gctgctggcg gtgccg                                    36
```

```
<210> SEQ ID NO 250
<211> LENGTH: 36
<212> TYPE: DNA
<213> ORGANISM: Artificial Sequence
<220> FEATURE:
<223> OTHER INFORMATION: cDNA Sequence of aMTD22

<400> SEQUENCE: 250
gcggtggtgc tggtgccggt gctggcggcg gcgccg                                 36

<210> SEQ ID NO 251
<211> LENGTH: 36
<212> TYPE: DNA
<213> ORGANISM: Artificial Sequence
<220> FEATURE:
<223> OTHER INFORMATION: cDNA Sequence of aMTD23

<400> SEQUENCE: 251
gtggtgctgg tgctgccggc ggcggcggcg gtgccg                                 36

<210> SEQ ID NO 252
<211> LENGTH: 36
<212> TYPE: DNA
<213> ORGANISM: Artificial Sequence
<220> FEATURE:
<223> OTHER INFORMATION: cDNA Sequence of aMTD24

<400> SEQUENCE: 252
attgcgctgg cggcgccggc gctgattgtg gcgccg                                 36

<210> SEQ ID NO 253
<211> LENGTH: 36
<212> TYPE: DNA
<213> ORGANISM: Artificial Sequence
<220> FEATURE:
<223> OTHER INFORMATION: cDNA Sequence of aMTD25

<400> SEQUENCE: 253
attgtggcgg tggcgccggc gctggtggcg ctgccg                                 36

<210> SEQ ID NO 254
<211> LENGTH: 36
<212> TYPE: DNA
<213> ORGANISM: Artificial Sequence
<220> FEATURE:
<223> OTHER INFORMATION: cDNA Sequence of aMTD42

<400> SEQUENCE: 254
gtggcggcgc tgccggtggt ggcggtggtg gcgccg                                 36

<210> SEQ ID NO 255
<211> LENGTH: 36
<212> TYPE: DNA
<213> ORGANISM: Artificial Sequence
<220> FEATURE:
<223> OTHER INFORMATION: cDNA Sequence of aMTD43

<400> SEQUENCE: 255
ctgctggcgg cgccgctggt ggtggcggcg gtgccg                                 36

<210> SEQ ID NO 256
<211> LENGTH: 36
<212> TYPE: DNA
<213> ORGANISM: Artificial Sequence
<220> FEATURE:
<223> OTHER INFORMATION: cDNA Sequence of aMTD44
```

```
<400> SEQUENCE: 256
gcgctggcgg tgccggtggc gctgctggtg gcgccg                     36

<210> SEQ ID NO 257
<211> LENGTH: 36
<212> TYPE: DNA
<213> ORGANISM: Artificial Sequence
<220> FEATURE:
<223> OTHER INFORMATION: cDNA Sequence of aMTD61

<400> SEQUENCE: 257
gtggcggcgc tgccggtgct gctggcggcg ctgccg                     36

<210> SEQ ID NO 258
<211> LENGTH: 36
<212> TYPE: DNA
<213> ORGANISM: Artificial Sequence
<220> FEATURE:
<223> OTHER INFORMATION: cDNA Sequence of aMTD62

<400> SEQUENCE: 258
gtggcgctgc tggcgccggt ggcgctggcg gtgccg                     36

<210> SEQ ID NO 259
<211> LENGTH: 36
<212> TYPE: DNA
<213> ORGANISM: Artificial Sequence
<220> FEATURE:
<223> OTHER INFORMATION: cDNA Sequence of aMTD63

<400> SEQUENCE: 259
gcggcgctgc tggtgccggc gctggtggcg gtgccg                     36

<210> SEQ ID NO 260
<211> LENGTH: 36
<212> TYPE: DNA
<213> ORGANISM: Artificial Sequence
<220> FEATURE:
<223> OTHER INFORMATION: cDNA Sequence of aMTD64

<400> SEQUENCE: 260
gcgattgtgg cgctgccggt ggcggtgctg gcgccg                     36

<210> SEQ ID NO 261
<211> LENGTH: 36
<212> TYPE: DNA
<213> ORGANISM: Artificial Sequence
<220> FEATURE:
<223> OTHER INFORMATION: cDNA Sequence of aMTD65

<400> SEQUENCE: 261
attgcgattg tggcgccggt ggtggcgctg gcgccg                     36

<210> SEQ ID NO 262
<211> LENGTH: 36
<212> TYPE: DNA
<213> ORGANISM: Artificial Sequence
<220> FEATURE:
<223> OTHER INFORMATION: cDNA Sequence of aMTD81

<400> SEQUENCE: 262
gcggcgctgc tgccggcgct ggcggcgctg ctgccg                     36

<210> SEQ ID NO 263
```

```
<211> LENGTH: 36
<212> TYPE: DNA
<213> ORGANISM: Artificial Sequence
<220> FEATURE:
<223> OTHER INFORMATION: cDNA Sequence of aMTD82

<400> SEQUENCE: 263
gcggtggtgc tggcgccggt ggcggcggtg ctgccg                          36

<210> SEQ ID NO 264
<211> LENGTH: 36
<212> TYPE: DNA
<213> ORGANISM: Artificial Sequence
<220> FEATURE:
<223> OTHER INFORMATION: cDNA Sequence of aMTD83

<400> SEQUENCE: 264
ctggcggtgg cggcgccgct ggcgctggcg ctgccg                          36

<210> SEQ ID NO 265
<211> LENGTH: 36
<212> TYPE: DNA
<213> ORGANISM: Artificial Sequence
<220> FEATURE:
<223> OTHER INFORMATION: cDNA Sequence of aMTD84

<400> SEQUENCE: 265
gcggcggtgg cggcgccgct gctgctggcg ctgccg                          36

<210> SEQ ID NO 266
<211> LENGTH: 36
<212> TYPE: DNA
<213> ORGANISM: Artificial Sequence
<220> FEATURE:
<223> OTHER INFORMATION: cDNA Sequence of aMTD85

<400> SEQUENCE: 266
ctgctggtgc tgccggcggc ggcgctggcg gcgccg                          36

<210> SEQ ID NO 267
<211> LENGTH: 36
<212> TYPE: DNA
<213> ORGANISM: Artificial Sequence
<220> FEATURE:
<223> OTHER INFORMATION: cDNA Sequence of aMTD101

<400> SEQUENCE: 267
ctggtggcgg tggcgccggt ggcggcggtg ctgccg                          36

<210> SEQ ID NO 268
<211> LENGTH: 36
<212> TYPE: DNA
<213> ORGANISM: Artificial Sequence
<220> FEATURE:
<223> OTHER INFORMATION: cDNA Sequence of aMTD102

<400> SEQUENCE: 268
ctggcgctgg cgccggcggc gctggcgctg ctgccg                          36

<210> SEQ ID NO 269
<211> LENGTH: 36
<212> TYPE: DNA
<213> ORGANISM: Artificial Sequence
<220> FEATURE:
<223> OTHER INFORMATION: cDNA Sequence of aMTD103

<400> SEQUENCE: 269
```
gcgctgattg cggcgccgat tctggcgctg gcgccg                                    36

<210> SEQ ID NO 270
<211> LENGTH: 36
<212> TYPE: DNA
<213> ORGANISM: Artificial Sequence
<220> FEATURE:
<223> OTHER INFORMATION: cDNA Sequence of aMTD104

<400> SEQUENCE: 270
gcggtggtgg cggcgccgct ggtgctggcg ctgccg                                    36

<210> SEQ ID NO 271
<211> LENGTH: 36
<212> TYPE: DNA
<213> ORGANISM: Artificial Sequence
<220> FEATURE:
<223> OTHER INFORMATION: cDNA Sequence of aMTD105

<400> SEQUENCE: 271
ctgctggcgc tggcgccggc ggcgctgctg gcgccg                                    36

<210> SEQ ID NO 272
<211> LENGTH: 36
<212> TYPE: DNA
<213> ORGANISM: Artificial Sequence
<220> FEATURE:
<223> OTHER INFORMATION: cDNA Sequence of aMTD121

<400> SEQUENCE: 272
gcgattgtgg cgctgccggc gctggcgctg gcgccg                                    36

<210> SEQ ID NO 273
<211> LENGTH: 36
<212> TYPE: DNA
<213> ORGANISM: Artificial Sequence
<220> FEATURE:
<223> OTHER INFORMATION: cDNA Sequence of aMTD123

<400> SEQUENCE: 273
gcggcgatta ttgtgccggc ggcgctgctg gcgccg                                    36

<210> SEQ ID NO 274
<211> LENGTH: 36
<212> TYPE: DNA
<213> ORGANISM: Artificial Sequence
<220> FEATURE:
<223> OTHER INFORMATION: cDNA Sequence of aMTD124

<400> SEQUENCE: 274
attgcggtgg cgctgccggc gctgattgcg gcgccg                                    36

<210> SEQ ID NO 275
<211> LENGTH: 36
<212> TYPE: DNA
<213> ORGANISM: Artificial Sequence
<220> FEATURE:
<223> OTHER INFORMATION: cDNA Sequence of aMTD141

<400> SEQUENCE: 275
gcggtgattg tgctgccggc gctggcggtg gcgccg                                    36

<210> SEQ ID NO 276
<211> LENGTH: 36
<212> TYPE: DNA

```
<213> ORGANISM: Artificial Sequence
<220> FEATURE:
<223> OTHER INFORMATION: cDNA Sequence of aMTD143

<400> SEQUENCE: 276
gcggtgctgg cggtgccggc ggtgctggtg gcgccg                                  36

<210> SEQ ID NO 277
<211> LENGTH: 36
<212> TYPE: DNA
<213> ORGANISM: Artificial Sequence
<220> FEATURE:
<223> OTHER INFORMATION: cDNA Sequence of aMTD144

<400> SEQUENCE: 277
gtgctggcga ttgtgccggc ggtggcgctg gcgccg                                  36

<210> SEQ ID NO 278
<211> LENGTH: 36
<212> TYPE: DNA
<213> ORGANISM: Artificial Sequence
<220> FEATURE:
<223> OTHER INFORMATION: cDNA Sequence of aMTD145

<400> SEQUENCE: 278
ctgctggcgg tggtgccggc ggtggcgctg gcgccg                                  36

<210> SEQ ID NO 279
<211> LENGTH: 36
<212> TYPE: DNA
<213> ORGANISM: Artificial Sequence
<220> FEATURE:
<223> OTHER INFORMATION: cDNA Sequence of aMTD161

<400> SEQUENCE: 279
gcggtgattg cgctgccggc gctgattgcg gcgccg                                  36

<210> SEQ ID NO 280
<211> LENGTH: 36
<212> TYPE: DNA
<213> ORGANISM: Artificial Sequence
<220> FEATURE:
<223> OTHER INFORMATION: cDNA Sequence of aMTD162

<400> SEQUENCE: 280
gcggtggtgg cgctgccggc ggcgctgatt gtgccg                                  36

<210> SEQ ID NO 281
<211> LENGTH: 36
<212> TYPE: DNA
<213> ORGANISM: Artificial Sequence
<220> FEATURE:
<223> OTHER INFORMATION: cDNA Sequence of aMTD163

<400> SEQUENCE: 281
ctggcgctgg tgctgccggc ggcgctggcg gcgccg                                  36

<210> SEQ ID NO 282
<211> LENGTH: 36
<212> TYPE: DNA
<213> ORGANISM: Artificial Sequence
<220> FEATURE:
<223> OTHER INFORMATION: cDNA Sequence of aMTD164

<400> SEQUENCE: 282
ctggcggcgg tgctgccggc gctgctggcg gcgccg                                  36
```

<210> SEQ ID NO 283
<211> LENGTH: 36
<212> TYPE: DNA
<213> ORGANISM: Artificial Sequence
<220> FEATURE:
<223> OTHER INFORMATION: cDNA Sequence of aMTD165

<400> SEQUENCE: 283
gcgctggcgg tgccggtggc gctggcgatt gtgccg                          36

<210> SEQ ID NO 284
<211> LENGTH: 36
<212> TYPE: DNA
<213> ORGANISM: Artificial Sequence
<220> FEATURE:
<223> OTHER INFORMATION: cDNA Sequence of aMTD182

<400> SEQUENCE: 284
gcgctgattg cgccggtggt ggcgctggtg gcgccg                          36

<210> SEQ ID NO 285
<211> LENGTH: 36
<212> TYPE: DNA
<213> ORGANISM: Artificial Sequence
<220> FEATURE:
<223> OTHER INFORMATION: cDNA Sequence of aMTD183

<400> SEQUENCE: 285
ctgctggcgg cgccggtggt gattgcgctg gcgccg                          36

<210> SEQ ID NO 286
<211> LENGTH: 36
<212> TYPE: DNA
<213> ORGANISM: Artificial Sequence
<220> FEATURE:
<223> OTHER INFORMATION: cDNA Sequence of aMTD184

<400> SEQUENCE: 286
ctggcggcga ttgtgccggc gattattgcg gtgccg                          36

<210> SEQ ID NO 287
<211> LENGTH: 36
<212> TYPE: DNA
<213> ORGANISM: Artificial Sequence
<220> FEATURE:
<223> OTHER INFORMATION: cDNA Sequence of aMTD185

<400> SEQUENCE: 287
gcggcgctgg tgctgccgct gattattgcg gcgccg                          36

<210> SEQ ID NO 288
<211> LENGTH: 36
<212> TYPE: DNA
<213> ORGANISM: Artificial Sequence
<220> FEATURE:
<223> OTHER INFORMATION: cDNA Sequence of aMTD201

<400> SEQUENCE: 288
ctggcgctgg cggtgccggc gctggcggcg ctgccg                          36

<210> SEQ ID NO 289
<211> LENGTH: 36
<212> TYPE: DNA
<213> ORGANISM: Artificial Sequence
<220> FEATURE:

<223> OTHER INFORMATION: cDNA Sequence of aMTD204

<400> SEQUENCE: 289
ctgattgcgg cgctgccggc ggtggcggcg ctgccg                              36

<210> SEQ ID NO 290
<211> LENGTH: 36
<212> TYPE: DNA
<213> ORGANISM: Artificial Sequence
<220> FEATURE:
<223> OTHER INFORMATION: cDNA Sequence of aMTD205

<400> SEQUENCE: 290
gcgctggcgc tggtgccggc gattgcggcg ctgccg                              36

<210> SEQ ID NO 291
<211> LENGTH: 36
<212> TYPE: DNA
<213> ORGANISM: Artificial Sequence
<220> FEATURE:
<223> OTHER INFORMATION: cDNA Sequence of aMTD221

<400> SEQUENCE: 291
gcggcgattc tggcgccgat tgtggcgctg gcgccg                              36

<210> SEQ ID NO 292
<211> LENGTH: 36
<212> TYPE: DNA
<213> ORGANISM: Artificial Sequence
<220> FEATURE:
<223> OTHER INFORMATION: cDNA Sequence of aMTD222

<400> SEQUENCE: 292
gcgctgctga ttgcgccggc ggcggtgatt gcgccg                              36

<210> SEQ ID NO 293
<211> LENGTH: 36
<212> TYPE: DNA
<213> ORGANISM: Artificial Sequence
<220> FEATURE:
<223> OTHER INFORMATION: cDNA Sequence of aMTD223

<400> SEQUENCE: 293
gcgattctgg cggtgccgat tgcggtggtg gcgccg                              36

<210> SEQ ID NO 294
<211> LENGTH: 36
<212> TYPE: DNA
<213> ORGANISM: Artificial Sequence
<220> FEATURE:
<223> OTHER INFORMATION: cDNA Sequence of aMTD224

<400> SEQUENCE: 294
attctggcgg cggtgccgat tgcgctggcg gcgccg                              36

<210> SEQ ID NO 295
<211> LENGTH: 36
<212> TYPE: DNA
<213> ORGANISM: Artificial Sequence
<220> FEATURE:
<223> OTHER INFORMATION: cDNA Sequence of aMTD225

<400> SEQUENCE: 295
gtggcggcgc tgctgccggc ggcggcggtg ctgccg                              36

```
<210> SEQ ID NO 296
<211> LENGTH: 36
<212> TYPE: DNA
<213> ORGANISM: Artificial Sequence
<220> FEATURE:
<223> OTHER INFORMATION: cDNA Sequence of aMTD241

<400> SEQUENCE: 296
gcggcggcgg tggtgccggt gctgctggtg gcgccg                              36

<210> SEQ ID NO 297
<211> LENGTH: 36
<212> TYPE: DNA
<213> ORGANISM: Artificial Sequence
<220> FEATURE:
<223> OTHER INFORMATION: cDNA Sequence of aMTD242

<400> SEQUENCE: 297
gcggcgctgc tggtgccggc gctggtggcg gcgccg                              36

<210> SEQ ID NO 298
<211> LENGTH: 36
<212> TYPE: DNA
<213> ORGANISM: Artificial Sequence
<220> FEATURE:
<223> OTHER INFORMATION: cDNA Sequence of aMTD243

<400> SEQUENCE: 298
gcggcggtgc tgctgccggt ggcgctggcg gcgccg                              36

<210> SEQ ID NO 299
<211> LENGTH: 36
<212> TYPE: DNA
<213> ORGANISM: Artificial Sequence
<220> FEATURE:
<223> OTHER INFORMATION: cDNA Sequence of aMTD245

<400> SEQUENCE: 299
gcggcggcgc tggcgccggt gctggcgctg gtgccg                              36

<210> SEQ ID NO 300
<211> LENGTH: 36
<212> TYPE: DNA
<213> ORGANISM: Artificial Sequence
<220> FEATURE:
<223> OTHER INFORMATION: cDNA Sequence of aMTD261

<400> SEQUENCE: 300
ctggtgctgg tgccgctgct ggcggcggcg gcgccg                              36

<210> SEQ ID NO 301
<211> LENGTH: 36
<212> TYPE: DNA
<213> ORGANISM: Artificial Sequence
<220> FEATURE:
<223> OTHER INFORMATION: cDNA Sequence of aMTD262

<400> SEQUENCE: 301
gcgctgattg cggtgccggc gattattgtg gcgccg                              36

<210> SEQ ID NO 302
<211> LENGTH: 36
<212> TYPE: DNA
<213> ORGANISM: Artificial Sequence
<220> FEATURE:
<223> OTHER INFORMATION: cDNA Sequence of aMTD263
```

```
<400> SEQUENCE: 302
gcgctggcgg tgattccggc ggcggcgatt ctgccg                                  36

<210> SEQ ID NO 303
<211> LENGTH: 36
<212> TYPE: DNA
<213> ORGANISM: Artificial Sequence
<220> FEATURE:
<223> OTHER INFORMATION: cDNA Sequence of aMTD264

<400> SEQUENCE: 303
ctggcggcgg cgccggtggt gattgtgatt gcgccg                                  36

<210> SEQ ID NO 304
<211> LENGTH: 36
<212> TYPE: DNA
<213> ORGANISM: Artificial Sequence
<220> FEATURE:
<223> OTHER INFORMATION: cDNA Sequence of aMTD265

<400> SEQUENCE: 304
gtgctggcga ttgcgccgct gctggcggcg gtgccg                                  36

<210> SEQ ID NO 305
<211> LENGTH: 36
<212> TYPE: DNA
<213> ORGANISM: Artificial Sequence
<220> FEATURE:
<223> OTHER INFORMATION: cDNA Sequence of aMTD281

<400> SEQUENCE: 305
gcgctgattg tgctgccggc ggcggtggcg gtgccg                                  36

<210> SEQ ID NO 306
<211> LENGTH: 36
<212> TYPE: DNA
<213> ORGANISM: Artificial Sequence
<220> FEATURE:
<223> OTHER INFORMATION: cDNA Sequence of aMTD282

<400> SEQUENCE: 306
gtgctggcgg tggcgccggc gctgattgtg gcgccg                                  36

<210> SEQ ID NO 307
<211> LENGTH: 36
<212> TYPE: DNA
<213> ORGANISM: Artificial Sequence
<220> FEATURE:
<223> OTHER INFORMATION: cDNA Sequence of aMTD283

<400> SEQUENCE: 307
gcggcgctgc tggcgccggc gctgattgtg gcgccg                                  36

<210> SEQ ID NO 308
<211> LENGTH: 36
<212> TYPE: DNA
<213> ORGANISM: Artificial Sequence
<220> FEATURE:
<223> OTHER INFORMATION: cDNA Sequence of aMTD284

<400> SEQUENCE: 308
gcgctgattg cgccggcggt ggcgctgatt gtgccg                                  36

<210> SEQ ID NO 309
<211> LENGTH: 36
```

```
<212> TYPE: DNA
<213> ORGANISM: Artificial Sequence
<220> FEATURE:
<223> OTHER INFORMATION: cDNA Sequence of aMTD285

<400> SEQUENCE: 309
gcgattgtgc tgctgccggc ggcggtggtg gcgccg                     36

<210> SEQ ID NO 310
<211> LENGTH: 36
<212> TYPE: DNA
<213> ORGANISM: Artificial Sequence
<220> FEATURE:
<223> OTHER INFORMATION: cDNA Sequence of aMTD301

<400> SEQUENCE: 310
gtgattgcgg cgccggtgct ggcggtgctg gcgccg                     36

<210> SEQ ID NO 311
<211> LENGTH: 36
<212> TYPE: DNA
<213> ORGANISM: Artificial Sequence
<220> FEATURE:
<223> OTHER INFORMATION: cDNA Sequence of aMTD302

<400> SEQUENCE: 311
ctggcgctgg cgccggcgct ggcgctgctg gcgccg                     36

<210> SEQ ID NO 312
<211> LENGTH: 36
<212> TYPE: DNA
<213> ORGANISM: Artificial Sequence
<220> FEATURE:
<223> OTHER INFORMATION: cDNA Sequence of aMTD304

<400> SEQUENCE: 312
gcgattattc tggcgccgat tgcggcgatt gcgccg                     36

<210> SEQ ID NO 313
<211> LENGTH: 36
<212> TYPE: DNA
<213> ORGANISM: Artificial Sequence
<220> FEATURE:
<223> OTHER INFORMATION: cDNA Sequence of aMTD305

<400> SEQUENCE: 313
attgcgctgg cggcgccgat tctgctggcg gcgccg                     36

<210> SEQ ID NO 314
<211> LENGTH: 36
<212> TYPE: DNA
<213> ORGANISM: Artificial Sequence
<220> FEATURE:
<223> OTHER INFORMATION: cDNA Sequence of aMTD321

<400> SEQUENCE: 314
attgtggcgg tggcgctgcc ggcgctggcg gtgccg                     36

<210> SEQ ID NO 315
<211> LENGTH: 36
<212> TYPE: DNA
<213> ORGANISM: Artificial Sequence
<220> FEATURE:
<223> OTHER INFORMATION: cDNA Sequence of aMTD322

<400> SEQUENCE: 315
```
gtggtggcga ttgtgctgcc ggcgctggcg gcgccg    36

<210> SEQ ID NO 316
<211> LENGTH: 36
<212> TYPE: DNA
<213> ORGANISM: Artificial Sequence
<220> FEATURE:
<223> OTHER INFORMATION: cDNA Sequence of aMTD323

<400> SEQUENCE: 316
attgtggcgg tggcgctgcc ggtggcgctg gcgccg    36

<210> SEQ ID NO 317
<211> LENGTH: 36
<212> TYPE: DNA
<213> ORGANISM: Artificial Sequence
<220> FEATURE:
<223> OTHER INFORMATION: cDNA Sequence of aMTD324

<400> SEQUENCE: 317
attgtggcgg tggcgctgcc ggcggcgctg gtgccg    36

<210> SEQ ID NO 318
<211> LENGTH: 36
<212> TYPE: DNA
<213> ORGANISM: Artificial Sequence
<220> FEATURE:
<223> OTHER INFORMATION: cDNA Sequence of aMTD325

<400> SEQUENCE: 318
attgtggcgg tggcgctgcc ggcggtggcg ctgccg    36

<210> SEQ ID NO 319
<211> LENGTH: 36
<212> TYPE: DNA
<213> ORGANISM: Artificial Sequence
<220> FEATURE:
<223> OTHER INFORMATION: cDNA Sequence of aMTD341

<400> SEQUENCE: 319
attgtggcgg tggcgctgcc ggcggtgctg gcgccg    36

<210> SEQ ID NO 320
<211> LENGTH: 36
<212> TYPE: DNA
<213> ORGANISM: Artificial Sequence
<220> FEATURE:
<223> OTHER INFORMATION: cDNA Sequence of aMTD342

<400> SEQUENCE: 320
gtgattgtgg cgctggcgcc ggcggtgctg gcgccg    36

<210> SEQ ID NO 321
<211> LENGTH: 36
<212> TYPE: DNA
<213> ORGANISM: Artificial Sequence
<220> FEATURE:
<223> OTHER INFORMATION: cDNA Sequence of aMTD343

<400> SEQUENCE: 321
attgtggcgg tggcgctgcc ggcgctggtg gcgccg    36

<210> SEQ ID NO 322
<211> LENGTH: 36
<212> TYPE: DNA
<213> ORGANISM: Artificial Sequence

```
<220> FEATURE:
<223> OTHER INFORMATION: cDNA Sequence of aMTD345

<400> SEQUENCE: 322
gcgctgctga ttgtggcgcc ggtggcggtg gcgccg                              36

<210> SEQ ID NO 323
<211> LENGTH: 36
<212> TYPE: DNA
<213> ORGANISM: Artificial Sequence
<220> FEATURE:
<223> OTHER INFORMATION: cDNA Sequence of aMTD361

<400> SEQUENCE: 323
gcggtggtga ttgtggcgcc ggcggtgatt gcgccg                              36

<210> SEQ ID NO 324
<211> LENGTH: 36
<212> TYPE: DNA
<213> ORGANISM: Artificial Sequence
<220> FEATURE:
<223> OTHER INFORMATION: cDNA Sequence of aMTD363

<400> SEQUENCE: 324
gcggtgctgg cggtggcgcc ggcgctgatt gtgccg                              36

<210> SEQ ID NO 325
<211> LENGTH: 36
<212> TYPE: DNA
<213> ORGANISM: Artificial Sequence
<220> FEATURE:
<223> OTHER INFORMATION: cDNA Sequence of aMTD364

<400> SEQUENCE: 325
ctggtggcgg cggtggcgcc ggcgctgatt gtgccg                              36

<210> SEQ ID NO 326
<211> LENGTH: 36
<212> TYPE: DNA
<213> ORGANISM: Artificial Sequence
<220> FEATURE:
<223> OTHER INFORMATION: cDNA Sequence of aMTD365

<400> SEQUENCE: 326
gcggtgattg tggtggcgcc ggcgctgctg gcgccg                              36

<210> SEQ ID NO 327
<211> LENGTH: 36
<212> TYPE: DNA
<213> ORGANISM: Artificial Sequence
<220> FEATURE:
<223> OTHER INFORMATION: cDNA Sequence of aMTD381

<400> SEQUENCE: 327
gtggtggcga ttgtgctgcc ggcggtggcg gcgccg                              36

<210> SEQ ID NO 328
<211> LENGTH: 36
<212> TYPE: DNA
<213> ORGANISM: Artificial Sequence
<220> FEATURE:
<223> OTHER INFORMATION: cDNA Sequence of aMTD382

<400> SEQUENCE: 328
gcggcggcgc tggtgattcc ggcgattctg gcgccg                              36
```

<210> SEQ ID NO 329
<211> LENGTH: 36
<212> TYPE: DNA
<213> ORGANISM: Artificial Sequence
<220> FEATURE:
<223> OTHER INFORMATION: cDNA Sequence of aMTD383

<400> SEQUENCE: 329
gtgattgtgg cgctggcgcc ggcgctgctg gcgccg                                    36

<210> SEQ ID NO 330
<211> LENGTH: 36
<212> TYPE: DNA
<213> ORGANISM: Artificial Sequence
<220> FEATURE:
<223> OTHER INFORMATION: cDNA Sequence of aMTD384

<400> SEQUENCE: 330
gtgattgtgg cgattgcgcc ggcgctgctg gcgccg                                    36

<210> SEQ ID NO 331
<211> LENGTH: 36
<212> TYPE: DNA
<213> ORGANISM: Artificial Sequence
<220> FEATURE:
<223> OTHER INFORMATION: cDNA Sequence of aMTD385

<400> SEQUENCE: 331
attgtggcga ttgcggtgcc ggcgctggtg gcgccg                                    36

<210> SEQ ID NO 332
<211> LENGTH: 36
<212> TYPE: DNA
<213> ORGANISM: Artificial Sequence
<220> FEATURE:
<223> OTHER INFORMATION: cDNA Sequence of aMTD401

<400> SEQUENCE: 332
gcggcgctgg cggtgattcc ggcggcgatt ctgccg                                    36

<210> SEQ ID NO 333
<211> LENGTH: 36
<212> TYPE: DNA
<213> ORGANISM: Artificial Sequence
<220> FEATURE:
<223> OTHER INFORMATION: cDNA Sequence of aMTD402

<400> SEQUENCE: 333
gcgctggcgg cggtgattcc ggcggcgatt ctgccg                                    36

<210> SEQ ID NO 334
<211> LENGTH: 36
<212> TYPE: DNA
<213> ORGANISM: Artificial Sequence
<220> FEATURE:
<223> OTHER INFORMATION: cDNA Sequence of aMTD403

<400> SEQUENCE: 334
gcggcggcgc tggtgattcc ggcggcgatt ctgccg                                    36

<210> SEQ ID NO 335
<211> LENGTH: 36
<212> TYPE: DNA
<213> ORGANISM: Artificial Sequence
<220> FEATURE:
<223> OTHER INFORMATION: cDNA Sequence of aMTD404

```
<400> SEQUENCE: 335
ctggcggcgg cggtgattcc ggcggcgatt ctgccg                                  36

<210> SEQ ID NO 336
<211> LENGTH: 36
<212> TYPE: DNA
<213> ORGANISM: Artificial Sequence
<220> FEATURE:
<223> OTHER INFORMATION: cDNA Sequence of aMTD405

<400> SEQUENCE: 336
ctggcggcgg cggtgattcc ggtggcgatt ctgccg                                  36

<210> SEQ ID NO 337
<211> LENGTH: 36
<212> TYPE: DNA
<213> ORGANISM: Artificial Sequence
<220> FEATURE:
<223> OTHER INFORMATION: cDNA Sequence of aMTD421

<400> SEQUENCE: 337
gcggcgattc tggcggcgcc gctgattgcg gtgccg                                  36

<210> SEQ ID NO 338
<211> LENGTH: 36
<212> TYPE: DNA
<213> ORGANISM: Artificial Sequence
<220> FEATURE:
<223> OTHER INFORMATION: cDNA Sequence of aMTD422

<400> SEQUENCE: 338
gtggtggcga ttctggcgcc gctgctggcg gcgccg                                  36

<210> SEQ ID NO 339
<211> LENGTH: 36
<212> TYPE: DNA
<213> ORGANISM: Artificial Sequence
<220> FEATURE:
<223> OTHER INFORMATION: cDNA Sequence of aMTD424

<400> SEQUENCE: 339
gcggtggtgg tggcggcgcc ggtgctggcg ctgccg                                  36

<210> SEQ ID NO 340
<211> LENGTH: 36
<212> TYPE: DNA
<213> ORGANISM: Artificial Sequence
<220> FEATURE:
<223> OTHER INFORMATION: cDNA Sequence of aMTD425

<400> SEQUENCE: 340
gcggtggtgg cgattgcgcc ggtgctggcg ctgccg                                  36

<210> SEQ ID NO 341
<211> LENGTH: 36
<212> TYPE: DNA
<213> ORGANISM: Artificial Sequence
<220> FEATURE:
<223> OTHER INFORMATION: cDNA Sequence of aMTD442

<400> SEQUENCE: 341
gcgctggcgg cgctggtgcc ggcggtgctg gtgccg                                  36

<210> SEQ ID NO 342
```

```
<211> LENGTH: 36
<212> TYPE: DNA
<213> ORGANISM: Artificial Sequence
<220> FEATURE:
<223> OTHER INFORMATION: cDNA Sequence of aMTD443

<400> SEQUENCE: 342
gcgctggcgg cgctggtgcc ggtggcgctg gtgccg                                    36

<210> SEQ ID NO 343
<211> LENGTH: 36
<212> TYPE: DNA
<213> ORGANISM: Artificial Sequence
<220> FEATURE:
<223> OTHER INFORMATION: cDNA Sequence of aMTD444

<400> SEQUENCE: 343
ctggcggcgg cgctggtgcc ggtggcgctg gtgccg                                    36

<210> SEQ ID NO 344
<211> LENGTH: 36
<212> TYPE: DNA
<213> ORGANISM: Artificial Sequence
<220> FEATURE:
<223> OTHER INFORMATION: cDNA Sequence of aMTD445

<400> SEQUENCE: 344
gcgctggcgg cgctggtgcc ggcgctggtg gtgccg                                    36

<210> SEQ ID NO 345
<211> LENGTH: 36
<212> TYPE: DNA
<213> ORGANISM: Artificial Sequence
<220> FEATURE:
<223> OTHER INFORMATION: cDNA Sequence of aMTD461

<400> SEQUENCE: 345
attgcggcgg tgattgtgcc ggcggtggcg ctgccg                                    36

<210> SEQ ID NO 346
<211> LENGTH: 36
<212> TYPE: DNA
<213> ORGANISM: Artificial Sequence
<220> FEATURE:
<223> OTHER INFORMATION: cDNA Sequence of aMTD462

<400> SEQUENCE: 346
attgcggcgg tgctggtgcc ggcggtggcg ctgccg                                    36

<210> SEQ ID NO 347
<211> LENGTH: 36
<212> TYPE: DNA
<213> ORGANISM: Artificial Sequence
<220> FEATURE:
<223> OTHER INFORMATION: cDNA Sequence of aMTD463

<400> SEQUENCE: 347
gcggtggcga ttctggtgcc gctgctggcg gcgccg                                    36

<210> SEQ ID NO 348
<211> LENGTH: 36
<212> TYPE: DNA
<213> ORGANISM: Artificial Sequence
<220> FEATURE:
<223> OTHER INFORMATION: cDNA Sequence of aMTD464

<400> SEQUENCE: 348
```
gcggtggtga ttctggtgcc gctggcggcg gcgccg        36

<210> SEQ ID NO 349
<211> LENGTH: 36
<212> TYPE: DNA
<213> ORGANISM: Artificial Sequence
<220> FEATURE:
<223> OTHER INFORMATION: cDNA Sequence of aMTD465

<400> SEQUENCE: 349
attgcggcgg tgattgtgcc ggtggcggcg ctgccg        36

<210> SEQ ID NO 350
<211> LENGTH: 36
<212> TYPE: DNA
<213> ORGANISM: Artificial Sequence
<220> FEATURE:
<223> OTHER INFORMATION: cDNA Sequence of aMTD481

<400> SEQUENCE: 350
gcgattgcga ttgcgattgt gccggtggcg ctgccg        36

<210> SEQ ID NO 351
<211> LENGTH: 36
<212> TYPE: DNA
<213> ORGANISM: Artificial Sequence
<220> FEATURE:
<223> OTHER INFORMATION: cDNA Sequence of aMTD482

<400> SEQUENCE: 351
attctggcgg tggcggcgat tccggtggcg gtgccg        36

<210> SEQ ID NO 352
<211> LENGTH: 36
<212> TYPE: DNA
<213> ORGANISM: Artificial Sequence
<220> FEATURE:
<223> OTHER INFORMATION: cDNA Sequence of aMTD483

<400> SEQUENCE: 352
attctggcgg cggcgattat tccggcggcg ctgccg        36

<210> SEQ ID NO 353
<211> LENGTH: 36
<212> TYPE: DNA
<213> ORGANISM: Artificial Sequence
<220> FEATURE:
<223> OTHER INFORMATION: cDNA Sequence of aMTD484

<400> SEQUENCE: 353
ctggcggtgg tgctggcggc gccggcgatt gtgccg        36

<210> SEQ ID NO 354
<211> LENGTH: 36
<212> TYPE: DNA
<213> ORGANISM: Artificial Sequence
<220> FEATURE:
<223> OTHER INFORMATION: cDNA Sequence of aMTD485

<400> SEQUENCE: 354
gcgattctgg cggcgattgt gccgctggcg gtgccg        36

<210> SEQ ID NO 355
<211> LENGTH: 36
<212> TYPE: DNA

```
<213> ORGANISM: Artificial Sequence
<220> FEATURE:
<223> OTHER INFORMATION: cDNA Sequence of aMTD501

<400> SEQUENCE: 355
gtgattgtgg cgctggcggt gccggcgctg gcgccg                                36

<210> SEQ ID NO 356
<211> LENGTH: 36
<212> TYPE: DNA
<213> ORGANISM: Artificial Sequence
<220> FEATURE:
<223> OTHER INFORMATION: cDNA Sequence of aMTD502

<400> SEQUENCE: 356
gcgattgtgg cgctggcggt gccggtgctg gcgccg                                36

<210> SEQ ID NO 357
<211> LENGTH: 36
<212> TYPE: DNA
<213> ORGANISM: Artificial Sequence
<220> FEATURE:
<223> OTHER INFORMATION: cDNA Sequence of aMTD503

<400> SEQUENCE: 357
gcggcgatta ttattgtgct gccggcggcg ctgccg                                36

<210> SEQ ID NO 358
<211> LENGTH: 36
<212> TYPE: DNA
<213> ORGANISM: Artificial Sequence
<220> FEATURE:
<223> OTHER INFORMATION: cDNA Sequence of aMTD504

<400> SEQUENCE: 358
ctgattgtgg cgctggcggt gccggcgctg gcgccg                                36

<210> SEQ ID NO 359
<211> LENGTH: 36
<212> TYPE: DNA
<213> ORGANISM: Artificial Sequence
<220> FEATURE:
<223> OTHER INFORMATION: cDNA Sequence of aMTD505

<400> SEQUENCE: 359
gcgattatta ttgtgattgc gccggcggcg gcgccg                                36

<210> SEQ ID NO 360
<211> LENGTH: 36
<212> TYPE: DNA
<213> ORGANISM: Artificial Sequence
<220> FEATURE:
<223> OTHER INFORMATION: cDNA Sequence of aMTD521

<400> SEQUENCE: 360
ctggcggcgc tgattgtggt gccggcggtg gcgccg                                36

<210> SEQ ID NO 361
<211> LENGTH: 36
<212> TYPE: DNA
<213> ORGANISM: Artificial Sequence
<220> FEATURE:
<223> OTHER INFORMATION: cDNA Sequence of aMTD522

<400> SEQUENCE: 361
gcgctgctgg tgattgcggt gccggcggtg gcgccg                                36
```

<210> SEQ ID NO 362
<211> LENGTH: 36
<212> TYPE: DNA
<213> ORGANISM: Artificial Sequence
<220> FEATURE:
<223> OTHER INFORMATION: cDNA Sequence of aMTD524

<400> SEQUENCE: 362
gcggtggcgc tgattgtggt gccggcgctg gcgccg      36

<210> SEQ ID NO 363
<211> LENGTH: 36
<212> TYPE: DNA
<213> ORGANISM: Artificial Sequence
<220> FEATURE:
<223> OTHER INFORMATION: cDNA Sequence of aMTD525

<400> SEQUENCE: 363
gcgctggcga ttgtggtggc gccggtggcg gtgccg      36

<210> SEQ ID NO 364
<211> LENGTH: 36
<212> TYPE: DNA
<213> ORGANISM: Artificial Sequence
<220> FEATURE:
<223> OTHER INFORMATION: cDNA Sequence of aMTD541

<400> SEQUENCE: 364
ctgctggcgc tgattattgc gccggcggcg gcgccg      36

<210> SEQ ID NO 365
<211> LENGTH: 36
<212> TYPE: DNA
<213> ORGANISM: Artificial Sequence
<220> FEATURE:
<223> OTHER INFORMATION: cDNA Sequence of aMTD542

<400> SEQUENCE: 365
gcgctggcgc tgattattgt gccggcggtg gcgccg      36

<210> SEQ ID NO 366
<211> LENGTH: 36
<212> TYPE: DNA
<213> ORGANISM: Artificial Sequence
<220> FEATURE:
<223> OTHER INFORMATION: cDNA Sequence of aMTD543

<400> SEQUENCE: 366
ctgctggcgg cgctgattgc gccggcggcg ctgccg      36

<210> SEQ ID NO 367
<211> LENGTH: 36
<212> TYPE: DNA
<213> ORGANISM: Artificial Sequence
<220> FEATURE:
<223> OTHER INFORMATION: cDNA Sequence of aMTD544

<400> SEQUENCE: 367
attgtggcgc tgattgtggc gccggcggcg gtgccg      36

<210> SEQ ID NO 368
<211> LENGTH: 36
<212> TYPE: DNA
<213> ORGANISM: Artificial Sequence
<220> FEATURE:

<223> OTHER INFORMATION: cDNA Sequence of aMTD545

<400> SEQUENCE: 368
gtggtgctgg tgctggcggc gccggcggcg gtgccg            36

<210> SEQ ID NO 369
<211> LENGTH: 36
<212> TYPE: DNA
<213> ORGANISM: Artificial Sequence
<220> FEATURE:
<223> OTHER INFORMATION: cDNA Sequence of aMTD561

<400> SEQUENCE: 369
gcggcggtgg cgattgtgct gccggcggtg gtgccg            36

<210> SEQ ID NO 370
<211> LENGTH: 36
<212> TYPE: DNA
<213> ORGANISM: Artificial Sequence
<220> FEATURE:
<223> OTHER INFORMATION: cDNA Sequence of aMTD562

<400> SEQUENCE: 370
gcgctgattg cggcgattgt gccggcgctg gtgccg            36

<210> SEQ ID NO 371
<211> LENGTH: 36
<212> TYPE: DNA
<213> ORGANISM: Artificial Sequence
<220> FEATURE:
<223> OTHER INFORMATION: cDNA Sequence of aMTD563

<400> SEQUENCE: 371
gcgctggcgg tgattgtggt gccggcgctg gcgccg            36

<210> SEQ ID NO 372
<211> LENGTH: 36
<212> TYPE: DNA
<213> ORGANISM: Artificial Sequence
<220> FEATURE:
<223> OTHER INFORMATION: cDNA Sequence of aMTD564

<400> SEQUENCE: 372
gtggcgattg cgctgattgt gccggcgctg gcgccg            36

<210> SEQ ID NO 373
<211> LENGTH: 36
<212> TYPE: DNA
<213> ORGANISM: Artificial Sequence
<220> FEATURE:
<223> OTHER INFORMATION: cDNA Sequence of aMTD565

<400> SEQUENCE: 373
gtggcgattg tgctggtggc gccggcggtg gcgccg            36

<210> SEQ ID NO 374
<211> LENGTH: 36
<212> TYPE: DNA
<213> ORGANISM: Artificial Sequence
<220> FEATURE:
<223> OTHER INFORMATION: cDNA Sequence of aMTD582

<400> SEQUENCE: 374
gtggcggtgg cgctgattgt gccggcgctg gcgccg            36

```
<210> SEQ ID NO 375
<211> LENGTH: 36
<212> TYPE: DNA
<213> ORGANISM: Artificial Sequence
<220> FEATURE:
<223> OTHER INFORMATION: cDNA Sequence of aMTD583

<400> SEQUENCE: 375
gcggtgattc tggcgctggc gccgattgtg gcgccg                    36

<210> SEQ ID NO 376
<211> LENGTH: 36
<212> TYPE: DNA
<213> ORGANISM: Artificial Sequence
<220> FEATURE:
<223> OTHER INFORMATION: cDNA Sequence of aMTD585

<400> SEQUENCE: 376
gcgctgattg tggcgattgc gccggcgctg gtgccg                    36

<210> SEQ ID NO 377
<211> LENGTH: 36
<212> TYPE: DNA
<213> ORGANISM: Artificial Sequence
<220> FEATURE:
<223> OTHER INFORMATION: cDNA Sequence of aMTD601

<400> SEQUENCE: 377
gcggcgattc tgattgcggt gccgattgcg gcgccg                    36

<210> SEQ ID NO 378
<211> LENGTH: 36
<212> TYPE: DNA
<213> ORGANISM: Artificial Sequence
<220> FEATURE:
<223> OTHER INFORMATION: cDNA Sequence of aMTD602

<400> SEQUENCE: 378
gtgattgtgg cgctggcggc gccggtgctg gcgccg                    36

<210> SEQ ID NO 379
<211> LENGTH: 36
<212> TYPE: DNA
<213> ORGANISM: Artificial Sequence
<220> FEATURE:
<223> OTHER INFORMATION: cDNA Sequence of aMTD603

<400> SEQUENCE: 379
gtgctggtgg cgctggcggc gccggtgatt gcgccg                    36

<210> SEQ ID NO 380
<211> LENGTH: 36
<212> TYPE: DNA
<213> ORGANISM: Artificial Sequence
<220> FEATURE:
<223> OTHER INFORMATION: cDNA Sequence of aMTD604

<400> SEQUENCE: 380
gtggcgctga ttgcggtggc gccggcggtg gtgccg                    36

<210> SEQ ID NO 381
<211> LENGTH: 36
<212> TYPE: DNA
<213> ORGANISM: Artificial Sequence
<220> FEATURE:
<223> OTHER INFORMATION: cDNA Sequence of aMTD605
```

```
<400> SEQUENCE: 381
gtgattgcgg cggtgctggc gccggtggcg gtgccg                                   36

<210> SEQ ID NO 382
<211> LENGTH: 36
<212> TYPE: DNA
<213> ORGANISM: Artificial Sequence
<220> FEATURE:
<223> OTHER INFORMATION: cDNA Sequence of aMTD622

<400> SEQUENCE: 382
gcgctgattg tgctggcggc gccggtggcg gtgccg                                   36

<210> SEQ ID NO 383
<211> LENGTH: 36
<212> TYPE: DNA
<213> ORGANISM: Artificial Sequence
<220> FEATURE:
<223> OTHER INFORMATION: cDNA Sequence of aMTD623

<400> SEQUENCE: 383
gtggcggcgg cgattgcgct gccggcgatt gtgccg                                   36

<210> SEQ ID NO 384
<211> LENGTH: 36
<212> TYPE: DNA
<213> ORGANISM: Artificial Sequence
<220> FEATURE:
<223> OTHER INFORMATION: cDNA Sequence of aMTD625

<400> SEQUENCE: 384
attctggcgg cggcggcggc gccgctgatt gtgccg                                   36

<210> SEQ ID NO 385
<211> LENGTH: 36
<212> TYPE: DNA
<213> ORGANISM: Artificial Sequence
<220> FEATURE:
<223> OTHER INFORMATION: cDNA Sequence of aMTD643

<400> SEQUENCE: 385
ctggcgctgg tgctggcggc gccggcgatt gtgccg                                   36

<210> SEQ ID NO 386
<211> LENGTH: 36
<212> TYPE: DNA
<213> ORGANISM: Artificial Sequence
<220> FEATURE:
<223> OTHER INFORMATION: cDNA Sequence of aMTD645

<400> SEQUENCE: 386
gcgctggcgg tggtggcgct gccggcgatt gtgccg                                   36

<210> SEQ ID NO 387
<211> LENGTH: 36
<212> TYPE: DNA
<213> ORGANISM: Artificial Sequence
<220> FEATURE:
<223> OTHER INFORMATION: cDNA Sequence of aMTD661

<400> SEQUENCE: 387
gcggcgattc tggcgccgat tgtggcggcg ctgccg                                   36

<210> SEQ ID NO 388
<211> LENGTH: 36
```

```
<212> TYPE: DNA
<213> ORGANISM: Artificial Sequence
<220> FEATURE:
<223> OTHER INFORMATION: cDNA Sequence of aMTD664

<400> SEQUENCE: 388
attctgattg cgattgcgat tccggcggcg gcgccg                              36

<210> SEQ ID NO 389
<211> LENGTH: 36
<212> TYPE: DNA
<213> ORGANISM: Artificial Sequence
<220> FEATURE:
<223> OTHER INFORMATION: cDNA Sequence of aMTD665

<400> SEQUENCE: 389
ctggcgattg tgctggcggc gccggtggcg gtgccg                              36

<210> SEQ ID NO 390
<211> LENGTH: 36
<212> TYPE: DNA
<213> ORGANISM: Artificial Sequence
<220> FEATURE:
<223> OTHER INFORMATION: cDNA Sequence of aMTD666

<400> SEQUENCE: 390
gcggcgattg cgattattgc gccggcgatt gtgccg                              36

<210> SEQ ID NO 391
<211> LENGTH: 36
<212> TYPE: DNA
<213> ORGANISM: Artificial Sequence
<220> FEATURE:
<223> OTHER INFORMATION: cDNA Sequence of aMTD667

<400> SEQUENCE: 391
ctggcggtgg cgattgtggc gccggcgctg gtgccg                              36

<210> SEQ ID NO 392
<211> LENGTH: 36
<212> TYPE: DNA
<213> ORGANISM: Artificial Sequence
<220> FEATURE:
<223> OTHER INFORMATION: cDNA Sequence of aMTD683

<400> SEQUENCE: 392
ctggcgattg tgctggcggc gccggcggtg ctgccg                              36

<210> SEQ ID NO 393
<211> LENGTH: 36
<212> TYPE: DNA
<213> ORGANISM: Artificial Sequence
<220> FEATURE:
<223> OTHER INFORMATION: cDNA Sequence of aMTD684

<400> SEQUENCE: 393
gcggcgattg tgctggcgct gccggcggtg ctgccg                              36

<210> SEQ ID NO 394
<211> LENGTH: 36
<212> TYPE: DNA
<213> ORGANISM: Artificial Sequence
<220> FEATURE:
<223> OTHER INFORMATION: cDNA Sequence of aMTD685

<400> SEQUENCE: 394
```
gcgctgctgg tggcggtgct gccggcggcg ctgccg        36

<210> SEQ ID NO 395
<211> LENGTH: 36
<212> TYPE: DNA
<213> ORGANISM: Artificial Sequence
<220> FEATURE:
<223> OTHER INFORMATION: cDNA Sequence of aMTD686

<400> SEQUENCE: 395
gcggcgctgg tggcggtgct gccggtggcg ctgccg        36

<210> SEQ ID NO 396
<211> LENGTH: 36
<212> TYPE: DNA
<213> ORGANISM: Artificial Sequence
<220> FEATURE:
<223> OTHER INFORMATION: cDNA Sequence of aMTD687

<400> SEQUENCE: 396
attgtggcgg tggcgctggt gccggcgctg gcgccg        36

<210> SEQ ID NO 397
<211> LENGTH: 36
<212> TYPE: DNA
<213> ORGANISM: Artificial Sequence
<220> FEATURE:
<223> OTHER INFORMATION: cDNA Sequence of aMTD703

<400> SEQUENCE: 397
attgtggcgg tggcgctggt gccggcgctg gcgccg        36

<210> SEQ ID NO 398
<211> LENGTH: 36
<212> TYPE: DNA
<213> ORGANISM: Artificial Sequence
<220> FEATURE:
<223> OTHER INFORMATION: cDNA Sequence of aMTD705

<400> SEQUENCE: 398
attgtggcgg tggcgctgct gccggcgctg gcgccg        36

<210> SEQ ID NO 399
<211> LENGTH: 36
<212> TYPE: DNA
<213> ORGANISM: Artificial Sequence
<220> FEATURE:
<223> OTHER INFORMATION: cDNA Sequence of aMTD706

<400> SEQUENCE: 399
attgtggcgg tggcgctgct gccggcggtg gcgccg        36

<210> SEQ ID NO 400
<211> LENGTH: 36
<212> TYPE: DNA
<213> ORGANISM: Artificial Sequence
<220> FEATURE:
<223> OTHER INFORMATION: cDNA Sequence of aMTD707

<400> SEQUENCE: 400
attgtggcgc tggcggtgct gccggcggtg gcgccg        36

<210> SEQ ID NO 401
<211> LENGTH: 36
<212> TYPE: DNA
<213> ORGANISM: Artificial Sequence
<220> FEATURE:
<223> OTHER INFORMATION: cDNA Sequence of aMTD724

<400> SEQUENCE: 401
gtggcggtgc tggcggtgct gccggcgctg gcgccg                              36

<210> SEQ ID NO 402
<211> LENGTH: 36
<212> TYPE: DNA
<213> ORGANISM: Artificial Sequence
<220> FEATURE:
<223> OTHER INFORMATION: cDNA Sequence of aMTD725

<400> SEQUENCE: 402
attgcggtgc tggcggtggc gccggcggtg ctgccg                              36

<210> SEQ ID NO 403
<211> LENGTH: 36
<212> TYPE: DNA
<213> ORGANISM: Artificial Sequence
<220> FEATURE:
<223> OTHER INFORMATION: cDNA Sequence of aMTD726

<400> SEQUENCE: 403
ctggcggtgg cgattattgc gccggcggtg gcgccg                              36

<210> SEQ ID NO 404
<211> LENGTH: 36
<212> TYPE: DNA
<213> ORGANISM: Artificial Sequence
<220> FEATURE:
<223> OTHER INFORMATION: cDNA Sequence of aMTD727

<400> SEQUENCE: 404
gtggcgctgg cgattgcgct gccggcggtg ctgccg                              36

<210> SEQ ID NO 405
<211> LENGTH: 36
<212> TYPE: DNA
<213> ORGANISM: Artificial Sequence
<220> FEATURE:
<223> OTHER INFORMATION: cDNA Sequence of aMTD743

<400> SEQUENCE: 405
gcgattgcga ttgcgctggt gccggtggcg ctgccg                              36

<210> SEQ ID NO 406
<211> LENGTH: 36
<212> TYPE: DNA
<213> ORGANISM: Artificial Sequence
<220> FEATURE:
<223> OTHER INFORMATION: cDNA Sequence of aMTD744

<400> SEQUENCE: 406
gcggcggtgg tgattgtggc gccggtggcg ctgccg                              36

<210> SEQ ID NO 407
<211> LENGTH: 36
<212> TYPE: DNA
<213> ORGANISM: Artificial Sequence
<220> FEATURE:
<223> OTHER INFORMATION: cDNA Sequence of aMTD746

<400> SEQUENCE: 407
gcggcgattc tggcgattgt ggcgccgctg gcgccg                              36

<210> SEQ ID NO 408
<211> LENGTH: 36
<212> TYPE: DNA
<213> ORGANISM: Artificial Sequence
<220> FEATURE:
<223> OTHER INFORMATION: cDNA Sequence of aMTD747

<400> SEQUENCE: 408
gtggcgctgc tggcgattgc gccggcgctg gcgccg        36

<210> SEQ ID NO 409
<211> LENGTH: 36
<212> TYPE: DNA
<213> ORGANISM: Artificial Sequence
<220> FEATURE:
<223> OTHER INFORMATION: cDNA Sequence of aMTD763

<400> SEQUENCE: 409
gtggcggtgc tgattgcggt gccggcgctg gcgccg        36

<210> SEQ ID NO 410
<211> LENGTH: 36
<212> TYPE: DNA
<213> ORGANISM: Artificial Sequence
<220> FEATURE:
<223> OTHER INFORMATION: cDNA Sequence of aMTD764

<400> SEQUENCE: 410
gcggtggcgc tggcggtgct gccggcggtg gtgccg        36

<210> SEQ ID NO 411
<211> LENGTH: 36
<212> TYPE: DNA
<213> ORGANISM: Artificial Sequence
<220> FEATURE:
<223> OTHER INFORMATION: cDNA Sequence of aMTD765

<400> SEQUENCE: 411
gcggtggcgc tggcggtggt gccggcggtg ctgccg        36

<210> SEQ ID NO 412
<211> LENGTH: 36
<212> TYPE: DNA
<213> ORGANISM: Artificial Sequence
<220> FEATURE:
<223> OTHER INFORMATION: cDNA Sequence of aMTD766

<400> SEQUENCE: 412
attgtggtga ttgcggtggc gccggcggtg gcgccg        36

<210> SEQ ID NO 413
<211> LENGTH: 36
<212> TYPE: DNA
<213> ORGANISM: Artificial Sequence
<220> FEATURE:
<223> OTHER INFORMATION: cDNA Sequence of aMTD767

<400> SEQUENCE: 413
attgtggtgg cggcggtggt gccggcgctg gcgccg        36

<210> SEQ ID NO 414
<211> LENGTH: 36
<212> TYPE: DNA
<213> ORGANISM: Artificial Sequence
<220> FEATURE:
<223> OTHER INFORMATION: cDNA Sequence of aMTD783

<400> SEQUENCE: 414
attgtggcgc tggtgccggc ggtggcgatt gcgccg                                36

<210> SEQ ID NO 415
<211> LENGTH: 36
<212> TYPE: DNA
<213> ORGANISM: Artificial Sequence
<220> FEATURE:
<223> OTHER INFORMATION: cDNA Sequence of aMTD784

<400> SEQUENCE: 415
gtggcggcgc tgccggcggt ggcgctggtg gtgccg                                36

<210> SEQ ID NO 416
<211> LENGTH: 36
<212> TYPE: DNA
<213> ORGANISM: Artificial Sequence
<220> FEATURE:
<223> OTHER INFORMATION: cDNA Sequence of aMTD786

<400> SEQUENCE: 416
ctggtggcga ttgcgccgct ggcggtgctg gcgccg                                36

<210> SEQ ID NO 417
<211> LENGTH: 36
<212> TYPE: DNA
<213> ORGANISM: Artificial Sequence
<220> FEATURE:
<223> OTHER INFORMATION: cDNA Sequence of aMTD787

<400> SEQUENCE: 417
gcggtggcgc tggtgccggt gattgtggcg gcgccg                                36

<210> SEQ ID NO 418
<211> LENGTH: 36
<212> TYPE: DNA
<213> ORGANISM: Artificial Sequence
<220> FEATURE:
<223> OTHER INFORMATION: cDNA Sequence of aMTD788

<400> SEQUENCE: 418
gcgattgcgg tggcgattgc gccggtggcg ctgccg                                36

<210> SEQ ID NO 419
<211> LENGTH: 36
<212> TYPE: DNA
<213> ORGANISM: Artificial Sequence
<220> FEATURE:
<223> OTHER INFORMATION: cDNA Sequence of aMTD803

<400> SEQUENCE: 419
gcgattgcgc tggcggtgcc ggtgctggcg ctgccg                                36

<210> SEQ ID NO 420
<211> LENGTH: 36
<212> TYPE: DNA
<213> ORGANISM: Artificial Sequence
<220> FEATURE:
<223> OTHER INFORMATION: cDNA Sequence of aMTD805

<400> SEQUENCE: 420
ctggtgctga ttgcggcggc gccgattgcg ctgccg                                36

<210> SEQ ID NO 421

```
<211> LENGTH: 36
<212> TYPE: DNA
<213> ORGANISM: Artificial Sequence
<220> FEATURE:
<223> OTHER INFORMATION: cDNA Sequence of aMTD806

<400> SEQUENCE: 421
ctggtggcgc tggcggtgcc ggcggcggtg ctgccg                                36

<210> SEQ ID NO 422
<211> LENGTH: 36
<212> TYPE: DNA
<213> ORGANISM: Artificial Sequence
<220> FEATURE:
<223> OTHER INFORMATION: cDNA Sequence of aMTD807

<400> SEQUENCE: 422
gcggtggcgc tggcggtgcc ggcgctggtg ctgccg                                36

<210> SEQ ID NO 423
<211> LENGTH: 36
<212> TYPE: DNA
<213> ORGANISM: Artificial Sequence
<220> FEATURE:
<223> OTHER INFORMATION: cDNA Sequence of aMTD808

<400> SEQUENCE: 423
ctggtggtgc tggcggcggc gccgctggcg gtgccg                                36

<210> SEQ ID NO 424
<211> LENGTH: 36
<212> TYPE: DNA
<213> ORGANISM: Artificial Sequence
<220> FEATURE:
<223> OTHER INFORMATION: cDNA Sequence of aMTD809

<400> SEQUENCE: 424
ctgattgtgc tggcggcgcc ggcgctggcg gcgccg                                36

<210> SEQ ID NO 425
<211> LENGTH: 36
<212> TYPE: DNA
<213> ORGANISM: Artificial Sequence
<220> FEATURE:
<223> OTHER INFORMATION: cDNA Sequence of aMTD810

<400> SEQUENCE: 425
gtgattgtgc tggcggcgcc ggcgctggcg gcgccg                                36

<210> SEQ ID NO 426
<211> LENGTH: 36
<212> TYPE: DNA
<213> ORGANISM: Artificial Sequence
<220> FEATURE:
<223> OTHER INFORMATION: cDNA Sequence of aMTD811

<400> SEQUENCE: 426
gcggtggtgc tggcggtgcc ggcgctggcg gtgccg                                36

<210> SEQ ID NO 427
<211> LENGTH: 36
<212> TYPE: DNA
<213> ORGANISM: Artificial Sequence
<220> FEATURE:
<223> OTHER INFORMATION: cDNA Sequence of aMTD824

<400> SEQUENCE: 427
```
ctgattattg tggcggcggc gccggcggtg gcgccg          36

<210> SEQ ID NO 428
<211> LENGTH: 36
<212> TYPE: DNA
<213> ORGANISM: Artificial Sequence
<220> FEATURE:
<223> OTHER INFORMATION: cDNA Sequence of aMTD825

<400> SEQUENCE: 428
attgtggcgg tgattgtggc gccggcggtg gcgccg          36

<210> SEQ ID NO 429
<211> LENGTH: 36
<212> TYPE: DNA
<213> ORGANISM: Artificial Sequence
<220> FEATURE:
<223> OTHER INFORMATION: cDNA Sequence of aMTD826

<400> SEQUENCE: 429
ctggtggcgc tggcggcgcc gattattgcg gtgccg          36

<210> SEQ ID NO 430
<211> LENGTH: 36
<212> TYPE: DNA
<213> ORGANISM: Artificial Sequence
<220> FEATURE:
<223> OTHER INFORMATION: cDNA Sequence of aMTD827

<400> SEQUENCE: 430
attgcggcgg tgctggcggc gccggcgctg gtgccg          36

<210> SEQ ID NO 431
<211> LENGTH: 36
<212> TYPE: DNA
<213> ORGANISM: Artificial Sequence
<220> FEATURE:
<223> OTHER INFORMATION: cDNA Sequence of aMTD828

<400> SEQUENCE: 431
attgcgctgc tggcggcgcc gattattgcg gtgccg          36

<210> SEQ ID NO 432
<211> LENGTH: 36
<212> TYPE: DNA
<213> ORGANISM: Artificial Sequence
<220> FEATURE:
<223> OTHER INFORMATION: cDNA Sequence of aMTD829

<400> SEQUENCE: 432
gcggcgctgg cgctggtggc gccggtgatt gtgccg          36

<210> SEQ ID NO 433
<211> LENGTH: 36
<212> TYPE: DNA
<213> ORGANISM: Artificial Sequence
<220> FEATURE:
<223> OTHER INFORMATION: cDNA Sequence of aMTD830

<400> SEQUENCE: 433
attgcgctgg tggcggcgcc ggtggcgctg gtgccg          36

<210> SEQ ID NO 434
<211> LENGTH: 36
<212> TYPE: DNA

```
<213> ORGANISM: Artificial Sequence
<220> FEATURE:
<223> OTHER INFORMATION: cDNA Sequence of aMTD831

<400> SEQUENCE: 434
attattgtgg cggtggcgcc ggcggcgatt gtgccg                                36

<210> SEQ ID NO 435
<211> LENGTH: 36
<212> TYPE: DNA
<213> ORGANISM: Artificial Sequence
<220> FEATURE:
<223> OTHER INFORMATION: cDNA Sequence of aMTD832

<400> SEQUENCE: 435
gcggtggcgg cgattgtgcc ggtgattgtg gcgccg                                36

<210> SEQ ID NO 436
<211> LENGTH: 36
<212> TYPE: DNA
<213> ORGANISM: Artificial Sequence
<220> FEATURE:
<223> OTHER INFORMATION: cDNA Sequence of aMTD843

<400> SEQUENCE: 436
gcggtgctgg tgctggtggc gccggcggcg gcgccg                                36

<210> SEQ ID NO 437
<211> LENGTH: 36
<212> TYPE: DNA
<213> ORGANISM: Artificial Sequence
<220> FEATURE:
<223> OTHER INFORMATION: cDNA Sequence of aMTD844

<400> SEQUENCE: 437
gtggtggcgc tgctggcgcc gctgattgcg gcgccg                                36

<210> SEQ ID NO 438
<211> LENGTH: 36
<212> TYPE: DNA
<213> ORGANISM: Artificial Sequence
<220> FEATURE:
<223> OTHER INFORMATION: cDNA Sequence of aMTD845

<400> SEQUENCE: 438
gcggcggtgg tgattgcgcc gctgctggcg gtgccg                                36

<210> SEQ ID NO 439
<211> LENGTH: 36
<212> TYPE: DNA
<213> ORGANISM: Artificial Sequence
<220> FEATURE:
<223> OTHER INFORMATION: cDNA Sequence of aMTD846

<400> SEQUENCE: 439
attgcggtgg cggtggcggc gccgctgctg gtgccg                                36

<210> SEQ ID NO 440
<211> LENGTH: 36
<212> TYPE: DNA
<213> ORGANISM: Artificial Sequence
<220> FEATURE:
<223> OTHER INFORMATION: cDNA Sequence of aMTD847

<400> SEQUENCE: 440
ctggtggcga ttgtggtgct gccggcggtg gcgccg                                36
```

<210> SEQ ID NO 441
<211> LENGTH: 36
<212> TYPE: DNA
<213> ORGANISM: Artificial Sequence
<220> FEATURE:
<223> OTHER INFORMATION: cDNA Sequence of aMTD848

<400> SEQUENCE: 441
gcggtggcga ttgtggtgct gccggcggtg gcgccg                                    36

<210> SEQ ID NO 442
<211> LENGTH: 36
<212> TYPE: DNA
<213> ORGANISM: Artificial Sequence
<220> FEATURE:
<223> OTHER INFORMATION: cDNA Sequence of aMTD849

<400> SEQUENCE: 442
gcggtgattc tgctggcgcc gctgattgcg gcgccg                                    36

<210> SEQ ID NO 443
<211> LENGTH: 36
<212> TYPE: DNA
<213> ORGANISM: Artificial Sequence
<220> FEATURE:
<223> OTHER INFORMATION: cDNA Sequence of aMTD850

<400> SEQUENCE: 443
ctggtgattg cgctggcggc gccggtggcg ctgccg                                    36

<210> SEQ ID NO 444
<211> LENGTH: 36
<212> TYPE: DNA
<213> ORGANISM: Artificial Sequence
<220> FEATURE:
<223> OTHER INFORMATION: cDNA Sequence of aMTD851

<400> SEQUENCE: 444
gtgctggcgg tggtgctgcc ggcggtggcg ctgccg                                    36

<210> SEQ ID NO 445
<211> LENGTH: 36
<212> TYPE: DNA
<213> ORGANISM: Artificial Sequence
<220> FEATURE:
<223> OTHER INFORMATION: cDNA Sequence of aMTD852

<400> SEQUENCE: 445
gtgctggcgg tggcggcgcc ggcggtgctg ctgccg                                    36

<210> SEQ ID NO 446
<211> LENGTH: 36
<212> TYPE: DNA
<213> ORGANISM: Artificial Sequence
<220> FEATURE:
<223> OTHER INFORMATION: cDNA Sequence of aMTD863

<400> SEQUENCE: 446
gcggcggtgg tgctgctgcc gattattgcg gcgccg                                    36

<210> SEQ ID NO 447
<211> LENGTH: 36
<212> TYPE: DNA
<213> ORGANISM: Artificial Sequence
<220> FEATURE:

<223> OTHER INFORMATION: cDNA Sequence of aMTD864

<400> SEQUENCE: 447
gcgctgctgg tgattgcgcc ggcgattgcg gtgccg  36

<210> SEQ ID NO 448
<211> LENGTH: 36
<212> TYPE: DNA
<213> ORGANISM: Artificial Sequence
<220> FEATURE:
<223> OTHER INFORMATION: cDNA Sequence of aMTD865

<400> SEQUENCE: 448
gcggtgctgg tgattgcggt gccggcgatt gcgccg  36

<210> SEQ ID NO 449
<211> LENGTH: 36
<212> TYPE: DNA
<213> ORGANISM: Artificial Sequence
<220> FEATURE:
<223> OTHER INFORMATION: cDNA Sequence of aMTD867

<400> SEQUENCE: 449
gcgctgctgg tggtgattgc gccgctggcg gcgccg  36

<210> SEQ ID NO 450
<211> LENGTH: 36
<212> TYPE: DNA
<213> ORGANISM: Artificial Sequence
<220> FEATURE:
<223> OTHER INFORMATION: cDNA Sequence of aMTD868

<400> SEQUENCE: 450
gtgctggtgg cggcgattct gccggcggcg attccg  36

<210> SEQ ID NO 451
<211> LENGTH: 36
<212> TYPE: DNA
<213> ORGANISM: Artificial Sequence
<220> FEATURE:
<223> OTHER INFORMATION: cDNA Sequence of aMTD870

<400> SEQUENCE: 451
gtgctggtgg cggcggtgct gccgattgcg gcgccg  36

<210> SEQ ID NO 452
<211> LENGTH: 36
<212> TYPE: DNA
<213> ORGANISM: Artificial Sequence
<220> FEATURE:
<223> OTHER INFORMATION: cDNA Sequence of aMTD872

<400> SEQUENCE: 452
gtgctggcgg cggcggtgct gccgctggtg gtgccg  36

<210> SEQ ID NO 453
<211> LENGTH: 36
<212> TYPE: DNA
<213> ORGANISM: Artificial Sequence
<220> FEATURE:
<223> OTHER INFORMATION: cDNA Sequence of aMTD875

<400> SEQUENCE: 453
gcgattgcga ttgtggtgcc ggcggtggcg gtgccg  36

```
<210> SEQ ID NO 454
<211> LENGTH: 36
<212> TYPE: DNA
<213> ORGANISM: Artificial Sequence
<220> FEATURE:
<223> OTHER INFORMATION: cDNA Sequence of aMTD877

<400> SEQUENCE: 454
gtggcgatta ttgcggtgcc ggcggtggtg gcgccg                              36

<210> SEQ ID NO 455
<211> LENGTH: 36
<212> TYPE: DNA
<213> ORGANISM: Artificial Sequence
<220> FEATURE:
<223> OTHER INFORMATION: cDNA Sequence of aMTD878

<400> SEQUENCE: 455
attgtggcgc tggtggcgcc ggcggcggtg gtgccg                              36

<210> SEQ ID NO 456
<211> LENGTH: 36
<212> TYPE: DNA
<213> ORGANISM: Artificial Sequence
<220> FEATURE:
<223> OTHER INFORMATION: cDNA Sequence of aMTD879

<400> SEQUENCE: 456
gcggcgattg tgctgctgcc ggcggtggtg gtgccg                              36

<210> SEQ ID NO 457
<211> LENGTH: 36
<212> TYPE: DNA
<213> ORGANISM: Artificial Sequence
<220> FEATURE:
<223> OTHER INFORMATION: cDNA Sequence of aMTD881

<400> SEQUENCE: 457
gcggcgctga ttgtggtgcc ggcggtggcg gtgccg                              36

<210> SEQ ID NO 458
<211> LENGTH: 36
<212> TYPE: DNA
<213> ORGANISM: Artificial Sequence
<220> FEATURE:
<223> OTHER INFORMATION: cDNA Sequence of aMTD882

<400> SEQUENCE: 458
gcgattgcgc tggtggtgcc ggcggtggcg gtgccg                              36

<210> SEQ ID NO 459
<211> LENGTH: 36
<212> TYPE: DNA
<213> ORGANISM: Artificial Sequence
<220> FEATURE:
<223> OTHER INFORMATION: cDNA Sequence of aMTD883

<400> SEQUENCE: 459
ctggcgattg tgccggcggc gattgcggcg ctgccg                              36

<210> SEQ ID NO 460
<211> LENGTH: 36
<212> TYPE: DNA
<213> ORGANISM: Artificial Sequence
<220> FEATURE:
<223> OTHER INFORMATION: cDNA Sequence of aMTD885
```

```
<400> SEQUENCE: 460
ctggtggcga ttgcgccggc ggtggcggtg ctgccg                            36

<210> SEQ ID NO 461
<211> LENGTH: 36
<212> TYPE: DNA
<213> ORGANISM: Artificial Sequence
<220> FEATURE:
<223> OTHER INFORMATION: cDNA Sequence of aMTD887

<400> SEQUENCE: 461
gtgctggcgg tggcgccggc ggtggcggtg ctgccg                            36

<210> SEQ ID NO 462
<211> LENGTH: 36
<212> TYPE: DNA
<213> ORGANISM: Artificial Sequence
<220> FEATURE:
<223> OTHER INFORMATION: cDNA Sequence of aMTD888

<400> SEQUENCE: 462
attctggcgg tggtggcgat tccggcggcg gcgccg                            36

<210> SEQ ID NO 463
<211> LENGTH: 36
<212> TYPE: DNA
<213> ORGANISM: Artificial Sequence
<220> FEATURE:
<223> OTHER INFORMATION: cDNA Sequence of aMTD889

<400> SEQUENCE: 463
attctggtgg cggcggcgcc gattgcggcg ctgccg                            36

<210> SEQ ID NO 464
<211> LENGTH: 36
<212> TYPE: DNA
<213> ORGANISM: Artificial Sequence
<220> FEATURE:
<223> OTHER INFORMATION: cDNA Sequence of aMTD891

<400> SEQUENCE: 464
attctggcgg tggcggcgat tccggcggcg ctgccg                            36

<210> SEQ ID NO 465
<211> LENGTH: 36
<212> TYPE: DNA
<213> ORGANISM: Artificial Sequence
<220> FEATURE:
<223> OTHER INFORMATION: cDNA Sequence of aMTD893

<400> SEQUENCE: 465
gtgattgcga ttccggcgat tctggcggcg gcgccg                            36

<210> SEQ ID NO 466
<211> LENGTH: 36
<212> TYPE: DNA
<213> ORGANISM: Artificial Sequence
<220> FEATURE:
<223> OTHER INFORMATION: cDNA Sequence of aMTD895

<400> SEQUENCE: 466
gcgattatta ttgtggtgcc ggcgattgcg gcgccg                            36

<210> SEQ ID NO 467
<211> LENGTH: 36
```

```
<212> TYPE: DNA
<213> ORGANISM: Artificial Sequence
<220> FEATURE:
<223> OTHER INFORMATION: cDNA Sequence of aMTD896

<400> SEQUENCE: 467
gcgattctga ttgtggtggc gccgattgcg gcgccg                               36

<210> SEQ ID NO 468
<211> LENGTH: 36
<212> TYPE: DNA
<213> ORGANISM: Artificial Sequence
<220> FEATURE:
<223> OTHER INFORMATION: cDNA Sequence of aMTD897

<400> SEQUENCE: 468
gcggtgattg tgccggtggc gattattgcg gcgccg                               36

<210> SEQ ID NO 469
<211> LENGTH: 36
<212> TYPE: DNA
<213> ORGANISM: Artificial Sequence
<220> FEATURE:
<223> OTHER INFORMATION: cDNA Sequence of aMTD899

<400> SEQUENCE: 469
gcggtggtga ttgcgctgcc ggcggtggtg gcgccg                               36

<210> SEQ ID NO 470
<211> LENGTH: 36
<212> TYPE: DNA
<213> ORGANISM: Artificial Sequence
<220> FEATURE:
<223> OTHER INFORMATION: cDNA Sequence of aMTD900

<400> SEQUENCE: 470
gcgctggtgg cggtgattgc gccggtggtg gcgccg                               36

<210> SEQ ID NO 471
<211> LENGTH: 36
<212> TYPE: DNA
<213> ORGANISM: Artificial Sequence
<220> FEATURE:
<223> OTHER INFORMATION: cDNA Sequence of aMTD901

<400> SEQUENCE: 471
gcgctggtgg cggtgctgcc ggcggtggcg gtgccg                               36

<210> SEQ ID NO 472
<211> LENGTH: 36
<212> TYPE: DNA
<213> ORGANISM: Artificial Sequence
<220> FEATURE:
<223> OTHER INFORMATION: cDNA Sequence of aMTD902

<400> SEQUENCE: 472
gcgctggtgg cgccgctgct ggcggtggcg gtgccg                               36

<210> SEQ ID NO 473
<211> LENGTH: 36
<212> TYPE: DNA
<213> ORGANISM: Artificial Sequence
<220> FEATURE:
<223> OTHER INFORMATION: cDNA Sequence of aMTD904

<400> SEQUENCE: 473
```

```
gcggtgctgg cggtggtggc gccggtggtg gcgccg                                36

<210> SEQ ID NO 474
<211> LENGTH: 36
<212> TYPE: DNA
<213> ORGANISM: Artificial Sequence
<220> FEATURE:
<223> OTHER INFORMATION: cDNA Sequence of aMTD905

<400> SEQUENCE: 474
gcggtgattg cggtggcgcc gctggtggtg gcgccg                                36

<210> SEQ ID NO 475
<211> LENGTH: 36
<212> TYPE: DNA
<213> ORGANISM: Artificial Sequence
<220> FEATURE:
<223> OTHER INFORMATION: cDNA Sequence of aMTD906

<400> SEQUENCE: 475
gcggtgattg cgctggcgcc ggtggtggtg gcgccg                                36

<210> SEQ ID NO 476
<211> LENGTH: 36
<212> TYPE: DNA
<213> ORGANISM: Artificial Sequence
<220> FEATURE:
<223> OTHER INFORMATION: cDNA Sequence of aMTD907

<400> SEQUENCE: 476
gtggcgattg cgctggcgcc ggtggtggtg gcgccg                                36

<210> SEQ ID NO 477
<211> LENGTH: 36
<212> TYPE: DNA
<213> ORGANISM: Artificial Sequence
<220> FEATURE:
<223> OTHER INFORMATION: cDNA Sequence of aMTD908

<400> SEQUENCE: 477
gtggcgctgg cgctggcgcc ggtggtggtg gcgccg                                36

<210> SEQ ID NO 478
<211> LENGTH: 36
<212> TYPE: DNA
<213> ORGANISM: Artificial Sequence
<220> FEATURE:
<223> OTHER INFORMATION: cDNA Sequence of aMTD910

<400> SEQUENCE: 478
gtggcggcgc tgctgccggc ggtggtggtg gcgccg                                36

<210> SEQ ID NO 479
<211> LENGTH: 36
<212> TYPE: DNA
<213> ORGANISM: Artificial Sequence
<220> FEATURE:
<223> OTHER INFORMATION: cDNA Sequence of aMTD911

<400> SEQUENCE: 479
gtggcgctgg cgctgccggc ggtggtggtg gcgccg                                36

<210> SEQ ID NO 480
<211> LENGTH: 36
<212> TYPE: DNA
<213> ORGANISM: Artificial Sequence
```

```
-continued

<220> FEATURE:
<223> OTHER INFORMATION: cDNA Sequence of aMTD912

<400> SEQUENCE: 480
gtggcgctgc tggcgccggc ggtggtggtg gcgccg                                      36

<210> SEQ ID NO 481
<211> LENGTH: 36
<212> TYPE: DNA
<213> ORGANISM: Artificial Sequence
<220> FEATURE:
<223> OTHER INFORMATION: cDNA Sequence of aMTD442 for Codon-optimization

<400> SEQUENCE: 481
gcgctggcgg cgctggttcc ggcggttctg gttccg                                      36

<210> SEQ ID NO 482
<211> LENGTH: 69
<212> TYPE: DNA
<213> ORGANISM: Artificial Sequence
<220> FEATURE:
<223> OTHER INFORMATION: cDNA Sequence of aMTD1 5'-primer

<400> SEQUENCE: 482
gggtttcata tggcggcggc gctggcgccg gtggtgctgg cgctgccggc aaatattacc           60
gttttctat                                                                   69

<210> SEQ ID NO 483
<211> LENGTH: 69
<212> TYPE: DNA
<213> ORGANISM: Artificial Sequence
<220> FEATURE:
<223> OTHER INFORMATION: cDNA Sequence of aMTD2 5'-primer

<400> SEQUENCE: 483
gggtttcata tggcggcggc ggtgccgctg ctggcggtgg tggtgccggc aaatattacc           60
gttttctat                                                                   69

<210> SEQ ID NO 484
<211> LENGTH: 69
<212> TYPE: DNA
<213> ORGANISM: Artificial Sequence
<220> FEATURE:
<223> OTHER INFORMATION: cDNA Sequence of aMTD3 5'-primer

<400> SEQUENCE: 484
gggtttcata tggcggcgct gctggtgccg gcggcggtgc tggcgccggc aaatattacc           60
gttttctat                                                                   69

<210> SEQ ID NO 485
<211> LENGTH: 69
<212> TYPE: DNA
<213> ORGANISM: Artificial Sequence
<220> FEATURE:
<223> OTHER INFORMATION: cDNA Sequence of aMTD4 5'-primer

<400> SEQUENCE: 485
gggtttcata tggcgctggc gctgctgccg gtggcggcgc tggcgccggc aaatattacc           60
gttttctat                                                                   69

<210> SEQ ID NO 486
<211> LENGTH: 69
<212> TYPE: DNA
```

<213> ORGANISM: Artificial Sequence
<220> FEATURE:
<223> OTHER INFORMATION: cDNA Sequence of aMTD5 5'-primer

<400> SEQUENCE: 486
gggtttcata tggcggcggc gctgctgccg gtggcgctgg tggcgccggc aaatattacc    60
gttttctat                                                             69

<210> SEQ ID NO 487
<211> LENGTH: 69
<212> TYPE: DNA
<213> ORGANISM: Artificial Sequence
<220> FEATURE:
<223> OTHER INFORMATION: cDNA Sequence of aMTD6 5'-primer

<400> SEQUENCE: 487
gggtttcata tggtgattgc gatgattccg gcggcgtttt gggtggcggc aaatattacc    60
gttttctat                                                             69

<210> SEQ ID NO 488
<211> LENGTH: 69
<212> TYPE: DNA
<213> ORGANISM: Artificial Sequence
<220> FEATURE:
<223> OTHER INFORMATION: cDNA Sequence of aMTD9 5'-primer

<400> SEQUENCE: 488
gggtttcata tggtggcgct ggtgccggcg gcgctgattc tgccgccggc aaatattacc    60
gttttctat                                                             69

<210> SEQ ID NO 489
<211> LENGTH: 69
<212> TYPE: DNA
<213> ORGANISM: Artificial Sequence
<220> FEATURE:
<223> OTHER INFORMATION: cDNA Sequence of aMTD11 5'-primer

<400> SEQUENCE: 489
gggtttcata tggtggtggc gctggcgccg gcgctggcgg cgctgccggc aaatattacc    60
gttttctat                                                             69

<210> SEQ ID NO 490
<211> LENGTH: 69
<212> TYPE: DNA
<213> ORGANISM: Artificial Sequence
<220> FEATURE:
<223> OTHER INFORMATION: cDNA Sequence of aMTD12 5'-primer

<400> SEQUENCE: 490
gggtttcata tgctgctggc ggcggtgccg gcggtgctgc tggcgccggc aaatattacc    60
gttttctat                                                             69

<210> SEQ ID NO 491
<211> LENGTH: 69
<212> TYPE: DNA
<213> ORGANISM: Artificial Sequence
<220> FEATURE:
<223> OTHER INFORMATION: cDNA Sequence of aMTD13 5'-primer

<400> SEQUENCE: 491
gggtttcata tggcggcggc gctggtgccg gtggtggcgc tgctgccggc aaatattacc    60
gttttctat                                                             69

<210> SEQ ID NO 492
<211> LENGTH: 69
<212> TYPE: DNA
<213> ORGANISM: Artificial Sequence
<220> FEATURE:
<223> OTHER INFORMATION: cDNA Sequence of aMTD16 5'-primer

<400> SEQUENCE: 492
gggtttcata tgaacaacag ctgcaccacc tataccaacg gcagccaggc aaatattacc     60
gttttctat                                                            69

<210> SEQ ID NO 493
<211> LENGTH: 69
<212> TYPE: DNA
<213> ORGANISM: Artificial Sequence
<220> FEATURE:
<223> OTHER INFORMATION: cDNA Sequence of aMTD17 5'-primer

<400> SEQUENCE: 493
gggtttcata tgggcggctg cagcgcgccg cagaccacct gcagcaacgc aaatattacc     60
gttttctat                                                            69

<210> SEQ ID NO 494
<211> LENGTH: 69
<212> TYPE: DNA
<213> ORGANISM: Artificial Sequence
<220> FEATURE:
<223> OTHER INFORMATION: cDNA Sequence of aMTD18 5'-primer

<400> SEQUENCE: 494
gggtttcata tgaactattg ctgcaccccg accaccaacg gccagagcgc aaatattacc     60
gttttctat                                                            69

<210> SEQ ID NO 495
<211> LENGTH: 69
<212> TYPE: DNA
<213> ORGANISM: Artificial Sequence
<220> FEATURE:
<223> OTHER INFORMATION: cDNA Sequence of aMTD19 5'-primer

<400> SEQUENCE: 495
gggtttcata tgtatgtgag ctgctgcacc tataccaacg gcagccaggc aaatattacc     60
gttttctat                                                            69

<210> SEQ ID NO 496
<211> LENGTH: 69
<212> TYPE: DNA
<213> ORGANISM: Artificial Sequence
<220> FEATURE:
<223> OTHER INFORMATION: cDNA Sequence of aMTD20 5'-primer

<400> SEQUENCE: 496
gggtttcata tgaactattg caacacctgc ccgacctatg gccagagcgc aaatattacc     60
gttttctat                                                            69

<210> SEQ ID NO 497
<211> LENGTH: 69
<212> TYPE: DNA
<213> ORGANISM: Artificial Sequence
<220> FEATURE:
<223> OTHER INFORMATION: cDNA Sequence of aMTD21 5'-primer

<400> SEQUENCE: 497
gggtttcata tggcggtggc gctgctgccg gcgctgctgg cggtgccggc aaatattacc      60
gttttctat                                                              69

<210> SEQ ID NO 498
<211> LENGTH: 69
<212> TYPE: DNA
<213> ORGANISM: Artificial Sequence
<220> FEATURE:
<223> OTHER INFORMATION: cDNA Sequence of aMTD22 5'-primer

<400> SEQUENCE: 498
gggtttcata tggcggtggt gctggtgccg gtgctggcgg cggcgccggc aaatattacc      60
gttttctat                                                              69

<210> SEQ ID NO 499
<211> LENGTH: 69
<212> TYPE: DNA
<213> ORGANISM: Artificial Sequence
<220> FEATURE:
<223> OTHER INFORMATION: cDNA Sequence of aMTD23 5'-primer

<400> SEQUENCE: 499
gggtttcata tggtggtgct ggtgctgccg gcggcggcgg cggtgccggc aaatattacc      60
gttttctat                                                              69

<210> SEQ ID NO 500
<211> LENGTH: 69
<212> TYPE: DNA
<213> ORGANISM: Artificial Sequence
<220> FEATURE:
<223> OTHER INFORMATION: cDNA Sequence of aMTD24 5'-primer

<400> SEQUENCE: 500
gggtttcata tgattgcgct ggcggcgccg gcgctgattg tggcgccggc aaatattacc      60
gttttctat                                                              69

<210> SEQ ID NO 501
<211> LENGTH: 69
<212> TYPE: DNA
<213> ORGANISM: Artificial Sequence
<220> FEATURE:
<223> OTHER INFORMATION: cDNA Sequence of aMTD25 5'-primer

<400> SEQUENCE: 501
gggtttcata tgattgtggc ggtggcgccg gcgctggtgg cgctgccggc aaatattacc      60
gttttctat                                                              69

<210> SEQ ID NO 502
<211> LENGTH: 69
<212> TYPE: DNA
<213> ORGANISM: Artificial Sequence
<220> FEATURE:
<223> OTHER INFORMATION: cDNA Sequence of aMTD26 5'-primer

<400> SEQUENCE: 502
gggtttcata tggcggcgat tgcgctggcg gcgccgctgg cgattgtggc aaatattacc      60
gttttctat                                                              69

<210> SEQ ID NO 503
<211> LENGTH: 69

```
<212> TYPE: DNA
<213> ORGANISM: Artificial Sequence
<220> FEATURE:
<223> OTHER INFORMATION: cDNA Sequence of aMTD27 5'-primer

<400> SEQUENCE: 503
gggtttcata tgctggcgat tgtggcggcg gcggcggcgc tggtggcggc aaatattacc    60
gttttctat                                                            69

<210> SEQ ID NO 504
<211> LENGTH: 69
<212> TYPE: DNA
<213> ORGANISM: Artificial Sequence
<220> FEATURE:
<223> OTHER INFORMATION: cDNA Sequence of aMTD28 5'-primer

<400> SEQUENCE: 504
gggtttcata tggcggtgcc gctgctgccg ctggtgccgg cggtgccggc aaatattacc    60
gttttctat                                                            69

<210> SEQ ID NO 505
<211> LENGTH: 69
<212> TYPE: DNA
<213> ORGANISM: Artificial Sequence
<220> FEATURE:
<223> OTHER INFORMATION: cDNA Sequence of aMTD29 5'-primer

<400> SEQUENCE: 505
gggtttcata tggtgctgcc gccgctgccg gtgctgccgg tgctgccggc aaatattacc    60
gttttctat                                                            69

<210> SEQ ID NO 506
<211> LENGTH: 69
<212> TYPE: DNA
<213> ORGANISM: Artificial Sequence
<220> FEATURE:
<223> OTHER INFORMATION: cDNA Sequence of aMTD30 5'-primer

<400> SEQUENCE: 506
gggtttcata tggcgatggc gctgctgccg gcggcggtgg cggtggcggc aaatattacc    60
gttttctat                                                            69

<210> SEQ ID NO 507
<211> LENGTH: 69
<212> TYPE: DNA
<213> ORGANISM: Artificial Sequence
<220> FEATURE:
<223> OTHER INFORMATION: cDNA Sequence of aMTD33 5'-primer

<400> SEQUENCE: 507
gggtttcata tggcggcggc gattctggcg ccggcgtttc tggcggtggc aaatattacc    60
gttttctat                                                            69

<210> SEQ ID NO 508
<211> LENGTH: 69
<212> TYPE: DNA
<213> ORGANISM: Artificial Sequence
<220> FEATURE:
<223> OTHER INFORMATION: cDNA Sequence of aMTD37 5'-primer

<400> SEQUENCE: 508
gggtttcata tgtattataa ccagagcacc tgcggcggcc agtgctatgc aaatattacc    60
``` gttttctat 69

<210> SEQ ID NO 509
<211> LENGTH: 69
<212> TYPE: DNA
<213> ORGANISM: Artificial Sequence
<220> FEATURE:
<223> OTHER INFORMATION: cDNA Sequence of aMTD38 5'-primer

<400> SEQUENCE: 509
gggtttcata tgaccacctg cagccagcag cagtattgca ccaacggcgc aaatattacc    60
gttttctat                                                            69

<210> SEQ ID NO 510
<211> LENGTH: 69
<212> TYPE: DNA
<213> ORGANISM: Artificial Sequence
<220> FEATURE:
<223> OTHER INFORMATION: cDNA Sequence of aMTD39 5'-primer

<400> SEQUENCE: 510
gggtttcata tgtgctataa caccagcccg tgcaccggct gctgctatgc aaatattacc    60
gttttctat                                                            69

<210> SEQ ID NO 511
<211> LENGTH: 69
<212> TYPE: DNA
<213> ORGANISM: Artificial Sequence
<220> FEATURE:
<223> OTHER INFORMATION: cDNA Sequence of aMTD40 5'-primer

<400> SEQUENCE: 511
gggtttcata tgacctataa caccagctgc accccgggca cctgctatgc aaatattacc    60
gttttctat                                                            69

<210> SEQ ID NO 512
<211> LENGTH: 69
<212> TYPE: DNA
<213> ORGANISM: Artificial Sequence
<220> FEATURE:
<223> OTHER INFORMATION: cDNA Sequence of aMTD42 5'-primer

<400> SEQUENCE: 512
gggtttcata tggtggcggc gctgccggtg gtggcggtgg tggcgccggc aaatattacc    60
gttttctat                                                            69

<210> SEQ ID NO 513
<211> LENGTH: 69
<212> TYPE: DNA
<213> ORGANISM: Artificial Sequence
<220> FEATURE:
<223> OTHER INFORMATION: cDNA Sequence of aMTD43 5'-primer

<400> SEQUENCE: 513
gggtttcata tgctgctggc ggcgccgctg gtggtggcgg cggtgccggc aaatattacc    60
gttttctat                                                            69

<210> SEQ ID NO 514
<211> LENGTH: 69
<212> TYPE: DNA
<213> ORGANISM: Artificial Sequence
<220> FEATURE:
<223> OTHER INFORMATION: cDNA Sequence of aMTD44 5'-primer

<400> SEQUENCE: 514
gggtttcata tggcgctggc ggtgccggtg gcgctgctgg tggcgccggc aaatattacc    60
gttttctat                                                            69

<210> SEQ ID NO 515
<211> LENGTH: 69
<212> TYPE: DNA
<213> ORGANISM: Artificial Sequence
<220> FEATURE:
<223> OTHER INFORMATION: cDNA Sequence of aMTD49 5'-primer

<400> SEQUENCE: 515
gggtttcata tggtggtgcc ggcggcgccg gcggtgccgg tggtgccggc aaatattacc    60
gttttctat                                                            69

<210> SEQ ID NO 516
<211> LENGTH: 69
<212> TYPE: DNA
<213> ORGANISM: Artificial Sequence
<220> FEATURE:
<223> OTHER INFORMATION: cDNA Sequence of aMTD54 5'-primer

<400> SEQUENCE: 516
gggtttcata tgctggcggt ggcggcgccg ccggtggtgg cgctgctggc aaatattacc    60
gttttctat                                                            69

<210> SEQ ID NO 517
<211> LENGTH: 69
<212> TYPE: DNA
<213> ORGANISM: Artificial Sequence
<220> FEATURE:
<223> OTHER INFORMATION: cDNA Sequence of aMTD57 5'-primer

<400> SEQUENCE: 517
gggtttcata tgcagaacaa ctgcaacacc agcagccagg gcggcggcgc aaatattacc    60
gttttctat                                                            69

<210> SEQ ID NO 518
<211> LENGTH: 69
<212> TYPE: DNA
<213> ORGANISM: Artificial Sequence
<220> FEATURE:
<223> OTHER INFORMATION: cDNA Sequence of aMTD59 5'-primer

<400> SEQUENCE: 518
gggtttcata tggcggtgct ggcggcgccg gtggtggcgg cgctggcggc aaatattacc    60
gttttctat                                                            69

<210> SEQ ID NO 519
<211> LENGTH: 69
<212> TYPE: DNA
<213> ORGANISM: Artificial Sequence
<220> FEATURE:
<223> OTHER INFORMATION: cDNA Sequence of aMTD61 5'-primer

<400> SEQUENCE: 519
gggtttcata tggtggcggc gctgccggtg ctgctggcgg cgctgccggc aaatattacc    60
gttttctat                                                            69

<210> SEQ ID NO 520

```
<211> LENGTH: 69
<212> TYPE: DNA
<213> ORGANISM: Artificial Sequence
<220> FEATURE:
<223> OTHER INFORMATION: cDNA Sequence of aMTD62 5'-primer

<400> SEQUENCE: 520
gggtttcata tggtggcgct gctggcgccg gtggcgctgg cggtgccggc aaatattacc      60
gttttctat                                                              69

<210> SEQ ID NO 521
<211> LENGTH: 69
<212> TYPE: DNA
<213> ORGANISM: Artificial Sequence
<220> FEATURE:
<223> OTHER INFORMATION: cDNA Sequence of aMTD63 5'-primer

<400> SEQUENCE: 521
gggtttcata tggcggcgct gctggtgccg gcgctggtgg cggtgccggc aaatattacc      60
gttttctat                                                              69

<210> SEQ ID NO 522
<211> LENGTH: 69
<212> TYPE: DNA
<213> ORGANISM: Artificial Sequence
<220> FEATURE:
<223> OTHER INFORMATION: cDNA Sequence of aMTD64 5'-primer

<400> SEQUENCE: 522
gggtttcata tggcgattgt ggcgctgccg gtggcggtgc tggcgccggc aaatattacc      60
gttttctat                                                              69

<210> SEQ ID NO 523
<211> LENGTH: 69
<212> TYPE: DNA
<213> ORGANISM: Artificial Sequence
<220> FEATURE:
<223> OTHER INFORMATION: cDNA Sequence of aMTD65 5'-primer

<400> SEQUENCE: 523
gggtttcata tgattgcgat tgtggcgccg gtggtggcgc tggcgccggc aaatattacc      60
gttttctat                                                              69

<210> SEQ ID NO 524
<211> LENGTH: 69
<212> TYPE: DNA
<213> ORGANISM: Artificial Sequence
<220> FEATURE:
<223> OTHER INFORMATION: cDNA Sequence of aMTD66 5'-primer

<400> SEQUENCE: 524
gggtttcata tggcgggcgt gctgggcggc ccgattatgg gcgtgccggc aaatattacc      60
gttttctat                                                              69

<210> SEQ ID NO 525
<211> LENGTH: 69
<212> TYPE: DNA
<213> ORGANISM: Artificial Sequence
<220> FEATURE:
<223> OTHER INFORMATION: cDNA Sequence of aMTD67 5'-primer

<400> SEQUENCE: 525
gggtttcata tgctggatgc ggaagtgccg ctggcggatg atgtgccggc aaatattacc      60
``` gttttctat 69

<210> SEQ ID NO 526
<211> LENGTH: 69
<212> TYPE: DNA
<213> ORGANISM: Artificial Sequence
<220> FEATURE:
<223> OTHER INFORMATION: cDNA Sequence of aMTD68 5'-primer

<400> SEQUENCE: 526
gggtttcata tggtggcgcc ggtgctgccg gcggcgccgc tggtgccggc aaatattacc    60
gttttctat                                                           69

<210> SEQ ID NO 527
<211> LENGTH: 69
<212> TYPE: DNA
<213> ORGANISM: Artificial Sequence
<220> FEATURE:
<223> OTHER INFORMATION: cDNA Sequence of aMTD69 5'-primer

<400> SEQUENCE: 527
gggtttcata tgccggtggc ggtgctgccg ccggcggcgc tggtgccggc aaatattacc    60
gttttctat                                                           69

<210> SEQ ID NO 528
<211> LENGTH: 69
<212> TYPE: DNA
<213> ORGANISM: Artificial Sequence
<220> FEATURE:
<223> OTHER INFORMATION: cDNA Sequence of aMTD71 5'-primer

<400> SEQUENCE: 528
gggtttcata tgtttatgtg gatgtggttt ccgtttatgt ggtatccggc aaatattacc    60
gttttctat                                                           69

<210> SEQ ID NO 529
<211> LENGTH: 69
<212> TYPE: DNA
<213> ORGANISM: Artificial Sequence
<220> FEATURE:
<223> OTHER INFORMATION: cDNA Sequence of aMTD77 5'-primer

<400> SEQUENCE: 529
gggtttcata tggcgatgct gctgatgccg attgtgctga ttgcgccggc aaatattacc    60
gttttctat                                                           69

<210> SEQ ID NO 530
<211> LENGTH: 69
<212> TYPE: DNA
<213> ORGANISM: Artificial Sequence
<220> FEATURE:
<223> OTHER INFORMATION: cDNA Sequence of aMTD81 5'-primer

<400> SEQUENCE: 530
gggtttcata tggcggcgct gctgccggcg ctggcggcgc tgctgccggc aaatattacc    60
gttttctat                                                           69

<210> SEQ ID NO 531
<211> LENGTH: 69
<212> TYPE: DNA
<213> ORGANISM: Artificial Sequence
<220> FEATURE:

```
<223> OTHER INFORMATION: cDNA Sequence of aMTD82 5'-primer

<400> SEQUENCE: 531
gggtttcata tggcggtggt gctggcgccg gtggcggcgg tgctgccggc aaatattacc      60
gttttctat                                                              69

<210> SEQ ID NO 532
<211> LENGTH: 69
<212> TYPE: DNA
<213> ORGANISM: Artificial Sequence
<220> FEATURE:
<223> OTHER INFORMATION: cDNA Sequence of aMTD83 5'-primer

<400> SEQUENCE: 532
gggtttcata tgctggcggt ggcggcgccg ctggcgctgg cgctgccggc aaatattacc      60
gttttctat                                                              69

<210> SEQ ID NO 533
<211> LENGTH: 69
<212> TYPE: DNA
<213> ORGANISM: Artificial Sequence
<220> FEATURE:
<223> OTHER INFORMATION: cDNA Sequence of aMTD84 5'-primer

<400> SEQUENCE: 533
gggtttcata tggcggcggt ggcggcgccg ctgctgctgg cgctgccggc aaatattacc      60
gttttctat                                                              69

<210> SEQ ID NO 534
<211> LENGTH: 69
<212> TYPE: DNA
<213> ORGANISM: Artificial Sequence
<220> FEATURE:
<223> OTHER INFORMATION: cDNA Sequence of aMTD85 5'-primer

<400> SEQUENCE: 534
gggtttcata tgctgctggt gctgccggcg gcggcgctgg cggcgccggc aaatattacc      60
gttttctat                                                              69

<210> SEQ ID NO 535
<211> LENGTH: 69
<212> TYPE: DNA
<213> ORGANISM: Artificial Sequence
<220> FEATURE:
<223> OTHER INFORMATION: cDNA Sequence of aMTD97 5'-primer

<400> SEQUENCE: 535
gggtttcata tggcgctgct ggcggcgccg ccggcgctgc tggcgctggc aaatattacc      60
gttttctat                                                              69

<210> SEQ ID NO 536
<211> LENGTH: 69
<212> TYPE: DNA
<213> ORGANISM: Artificial Sequence
<220> FEATURE:
<223> OTHER INFORMATION: cDNA Sequence of aMTD101 5'-primer

<400> SEQUENCE: 536
gggtttcata tgctggtggc ggtggcgccg gtggcggcgg tgctgccggc aaatattacc      60
gttttctat                                                              69
```

```
<210> SEQ ID NO 537
<211> LENGTH: 69
<212> TYPE: DNA
<213> ORGANISM: Artificial Sequence
<220> FEATURE:
<223> OTHER INFORMATION: cDNA Sequence of aMTD102 5'-primer

<400> SEQUENCE: 537
gggtttcata tgctggcgct ggcgccggcg gcgctggcgc tgctgccggc aaatattacc    60
gttttctat                                                            69

<210> SEQ ID NO 538
<211> LENGTH: 69
<212> TYPE: DNA
<213> ORGANISM: Artificial Sequence
<220> FEATURE:
<223> OTHER INFORMATION: cDNA Sequence of aMTD103 5'-primer

<400> SEQUENCE: 538
gggtttcata tggcgctgat tgcggcgccg attctggcgc tggcgccggc aaatattacc    60
gttttctat                                                            69

<210> SEQ ID NO 539
<211> LENGTH: 69
<212> TYPE: DNA
<213> ORGANISM: Artificial Sequence
<220> FEATURE:
<223> OTHER INFORMATION: cDNA Sequence of aMTD104 5'-primer

<400> SEQUENCE: 539
gggtttcata tggcggtggt ggcggcgccg ctggtgctgg cgctgccggc aaatattacc    60
gttttctat                                                            69

<210> SEQ ID NO 540
<211> LENGTH: 69
<212> TYPE: DNA
<213> ORGANISM: Artificial Sequence
<220> FEATURE:
<223> OTHER INFORMATION: cDNA Sequence of aMTD105 5'-primer

<400> SEQUENCE: 540
gggtttcata tgctgctggc gctggcgccg gcggcgctgc tggcgccggc aaatattacc    60
gttttctat                                                            69

<210> SEQ ID NO 541
<211> LENGTH: 69
<212> TYPE: DNA
<213> ORGANISM: Artificial Sequence
<220> FEATURE:
<223> OTHER INFORMATION: cDNA Sequence of aMTD113 5'-primer

<400> SEQUENCE: 541
gggtttcata tgccggtggc ggtggcgctg ctgattgcgg tgccgccggc aaatattacc    60
gttttctat                                                            69

<210> SEQ ID NO 542
<211> LENGTH: 69
<212> TYPE: DNA
<213> ORGANISM: Artificial Sequence
<220> FEATURE:
<223> OTHER INFORMATION: cDNA Sequence of aMTD121 5'-primer

<400> SEQUENCE: 542
```

```
gggtttcata tggcgattgt ggcgctgccg gcgctggcgc tggcgccggc aaatattacc    60
gttttctat                                                           69

<210> SEQ ID NO 543
<211> LENGTH: 69
<212> TYPE: DNA
<213> ORGANISM: Artificial Sequence
<220> FEATURE:
<223> OTHER INFORMATION: cDNA Sequence of aMTD123 5'-primer

<400> SEQUENCE: 543
gggtttcata tggcggcgat tattgtgccg gcggcgctgc tggcgccggc aaatattacc    60
gttttctat                                                           69

<210> SEQ ID NO 544
<211> LENGTH: 69
<212> TYPE: DNA
<213> ORGANISM: Artificial Sequence
<220> FEATURE:
<223> OTHER INFORMATION: cDNA Sequence of aMTD124 5'-primer

<400> SEQUENCE: 544
gggtttcata tgattgcggt ggcgctgccg gcgctgattg cggcgccggc aaatattacc    60
gttttctat                                                           69

<210> SEQ ID NO 545
<211> LENGTH: 69
<212> TYPE: DNA
<213> ORGANISM: Artificial Sequence
<220> FEATURE:
<223> OTHER INFORMATION: cDNA Sequence of aMTD131 5'-primer

<400> SEQUENCE: 545
gggtttcata tgtggattat tgcgccggtg tggctggcgt ggattgcggc aaatattacc    60
gttttctat                                                           69

<210> SEQ ID NO 546
<211> LENGTH: 69
<212> TYPE: DNA
<213> ORGANISM: Artificial Sequence
<220> FEATURE:
<223> OTHER INFORMATION: cDNA Sequence of aMTD138 5'-primer

<400> SEQUENCE: 546
gggtttcata tgccgccggc ggcgctgctg gcgattctgg cggtggcggc aaatattacc    60
gttttctat                                                           69

<210> SEQ ID NO 547
<211> LENGTH: 69
<212> TYPE: DNA
<213> ORGANISM: Artificial Sequence
<220> FEATURE:
<223> OTHER INFORMATION: cDNA Sequence of aMTD139 5'-primer

<400> SEQUENCE: 547
gggtttcata tgaccggcag caccaacagc ccgacctgca ccagcaccgc aaatattacc    60
gttttctat                                                           69

<210> SEQ ID NO 548
<211> LENGTH: 69
<212> TYPE: DNA
<213> ORGANISM: Artificial Sequence
```

```
<220> FEATURE:
<223> OTHER INFORMATION: cDNA Sequence of aMTD141 5'-primer

<400> SEQUENCE: 548
gggtttcata tggcggtgat tgtgctgccg gcgctggcgg tggcgccggc aaatattacc    60
gttttctat                                                            69

<210> SEQ ID NO 549
<211> LENGTH: 69
<212> TYPE: DNA
<213> ORGANISM: Artificial Sequence
<220> FEATURE:
<223> OTHER INFORMATION: cDNA Sequence of aMTD142 5'-primer

<400> SEQUENCE: 549
gggtttcata tgctgctggc ggcggtgccg gtggcgctgg tggcgccggc aaatattacc    60
gttttctat                                                            69

<210> SEQ ID NO 550
<211> LENGTH: 69
<212> TYPE: DNA
<213> ORGANISM: Artificial Sequence
<220> FEATURE:
<223> OTHER INFORMATION: cDNA Sequence of aMTD143 5'-primer

<400> SEQUENCE: 550
gggtttcata tggcggtgct ggcggtgccg gcggtgctgg tggcgccggc aaatattacc    60
gttttctat                                                            69

<210> SEQ ID NO 551
<211> LENGTH: 69
<212> TYPE: DNA
<213> ORGANISM: Artificial Sequence
<220> FEATURE:
<223> OTHER INFORMATION: cDNA Sequence of aMTD144 5'-primer

<400> SEQUENCE: 551
gggtttcata tggcggtgct ggcggtgccg gcggtgctgg tggcgccggc aaatattacc    60
gttttctat                                                            69

<210> SEQ ID NO 552
<211> LENGTH: 69
<212> TYPE: DNA
<213> ORGANISM: Artificial Sequence
<220> FEATURE:
<223> OTHER INFORMATION: cDNA Sequence of aMTD145 5'-primer

<400> SEQUENCE: 552
gggtttcata tgctgctggc ggtggtgccg gcggtggcgc tggcgccggc aaatattacc    60
gttttctat                                                            69

<210> SEQ ID NO 553
<211> LENGTH: 69
<212> TYPE: DNA
<213> ORGANISM: Artificial Sequence
<220> FEATURE:
<223> OTHER INFORMATION: cDNA Sequence of aMTD152 5'-primer

<400> SEQUENCE: 553
gggtttcata tgctggcggc ggcggtggcg cggtggcgg cgctgctggc aaatattacc     60
gttttctat                                                            69
```

<210> SEQ ID NO 554
<211> LENGTH: 69
<212> TYPE: DNA
<213> ORGANISM: Artificial Sequence
<220> FEATURE:
<223> OTHER INFORMATION: cDNA Sequence of aMTD159 5'-primer

<400> SEQUENCE: 554
gggtttcata tgtgctatag cggcagcacc agccagaacc agccgccggc aaatattacc    60
gttttctat                                                            69

<210> SEQ ID NO 555
<211> LENGTH: 69
<212> TYPE: DNA
<213> ORGANISM: Artificial Sequence
<220> FEATURE:
<223> OTHER INFORMATION: cDNA Sequence of aMTD161 5'-primer

<400> SEQUENCE: 555
gggtttcata tggcggtgat tgcgctgccg gcgctgattg cggcgccggc aaatattacc    60
gttttctat                                                            69

<210> SEQ ID NO 556
<211> LENGTH: 69
<212> TYPE: DNA
<213> ORGANISM: Artificial Sequence
<220> FEATURE:
<223> OTHER INFORMATION: cDNA Sequence of aMTD162 5'-primer

<400> SEQUENCE: 556
gggtttcata tggcggtggt ggcgctgccg gcggcgctga ttgtgccggc aaatattacc    60
gttttctat                                                            69

<210> SEQ ID NO 557
<211> LENGTH: 69
<212> TYPE: DNA
<213> ORGANISM: Artificial Sequence
<220> FEATURE:
<223> OTHER INFORMATION: cDNA Sequence of aMTD163 5'-primer

<400> SEQUENCE: 557
gggtttcata tgctggcgct ggtgctgccg gcggcgctgg cggcgccggc aaatattacc    60
gttttctat                                                            69

<210> SEQ ID NO 558
<211> LENGTH: 69
<212> TYPE: DNA
<213> ORGANISM: Artificial Sequence
<220> FEATURE:
<223> OTHER INFORMATION: cDNA Sequence of aMTD164 5'-primer

<400> SEQUENCE: 558
gggtttcata tgctggcggc ggtgctgccg gcgctgctgg cggcgccggc aaatattacc    60
gttttctat                                                            69

<210> SEQ ID NO 559
<211> LENGTH: 69
<212> TYPE: DNA
<213> ORGANISM: Artificial Sequence
<220> FEATURE:
<223> OTHER INFORMATION: cDNA Sequence of aMTD165 5'-primer

<400> SEQUENCE: 559

-continued

```
gggtttcata tggcgctggc ggtgccggtg gcgctggcga ttgtgccggc aaatattacc    60
gttttctat                                                           69

<210> SEQ ID NO 560
<211> LENGTH: 69
<212> TYPE: DNA
<213> ORGANISM: Artificial Sequence
<220> FEATURE:
<223> OTHER INFORMATION: cDNA Sequence of aMTD167 5'-primer

<400> SEQUENCE: 560
gggtttcata tggtggcgat tgcgattccg gcggcgctgg cgattccggc aaatattacc    60
gttttctat                                                           69

<210> SEQ ID NO 561
<211> LENGTH: 69
<212> TYPE: DNA
<213> ORGANISM: Artificial Sequence
<220> FEATURE:
<223> OTHER INFORMATION: cDNA Sequence of aMTD169 5'-primer

<400> SEQUENCE: 561
gggtttcata tggtggcgct ggtggcgccg gcgctgattc tggcgccggc aaatattacc    60
gttttctat                                                           69

<210> SEQ ID NO 562
<211> LENGTH: 69
<212> TYPE: DNA
<213> ORGANISM: Artificial Sequence
<220> FEATURE:
<223> OTHER INFORMATION: cDNA Sequence of aMTD182 5'-primer

<400> SEQUENCE: 562
gggtttcata tggcgctgat tgcgccggtg gtggcgctgg tggcgccggc aaatattacc    60
gttttctat                                                           69

<210> SEQ ID NO 563
<211> LENGTH: 69
<212> TYPE: DNA
<213> ORGANISM: Artificial Sequence
<220> FEATURE:
<223> OTHER INFORMATION: cDNA Sequence of aMTD183 5'-primer

<400> SEQUENCE: 563
gggtttcata tgctgctggc ggcgccggtg gtgattgcgc tggcgccggc aaatattacc    60
gttttctat                                                           69

<210> SEQ ID NO 564
<211> LENGTH: 69
<212> TYPE: DNA
<213> ORGANISM: Artificial Sequence
<220> FEATURE:
<223> OTHER INFORMATION: cDNA Sequence of aMTD184 5'-primer

<400> SEQUENCE: 564
gggtttcata tgctggcggc gattgtgccg gcgattattg cggtgccggc aaatattacc    60
gttttctat                                                           69

<210> SEQ ID NO 565
<211> LENGTH: 69
<212> TYPE: DNA
```

<213> ORGANISM: Artificial Sequence
<220> FEATURE:
<223> OTHER INFORMATION: cDNA Sequence of aMTD185 5'-primer

<400> SEQUENCE: 565
gggtttcata tggcggcgct ggtgctgccg ctgattattg cggcgccggc aaatattacc    60
gttttctat                                                            69

<210> SEQ ID NO 566
<211> LENGTH: 69
<212> TYPE: DNA
<213> ORGANISM: Artificial Sequence
<220> FEATURE:
<223> OTHER INFORMATION: cDNA Sequence of aMTD189 5'-primer

<400> SEQUENCE: 566
gggtttcata tggtgattct ggtggcgccg gcggtgattg cgccgccggc aaatattacc    60
gttttctat                                                            69

<210> SEQ ID NO 567
<211> LENGTH: 69
<212> TYPE: DNA
<213> ORGANISM: Artificial Sequence
<220> FEATURE:
<223> OTHER INFORMATION: cDNA Sequence of aMTD190 5'-primer

<400> SEQUENCE: 567
gggtttcata tggcggcgat tctggcgccg gcggtgattg cgccgccggc aaatattacc    60
gttttctat                                                            69

<210> SEQ ID NO 568
<211> LENGTH: 69
<212> TYPE: DNA
<213> ORGANISM: Artificial Sequence
<220> FEATURE:
<223> OTHER INFORMATION: cDNA Sequence of aMTD201 5'-primer

<400> SEQUENCE: 568
gggtttcata tgctggcgct ggcggtgccg gcgctggcgg cgctgccggc aaatattacc    60
gttttctat                                                            69

<210> SEQ ID NO 569
<211> LENGTH: 69
<212> TYPE: DNA
<213> ORGANISM: Artificial Sequence
<220> FEATURE:
<223> OTHER INFORMATION: cDNA Sequence of aMTD204 5'-primer

<400> SEQUENCE: 569
gggtttcata tgctgattgc ggcgctgccg gcggtggcgg cgctgccggc aaatattacc    60
gttttctat                                                            69

<210> SEQ ID NO 570
<211> LENGTH: 69
<212> TYPE: DNA
<213> ORGANISM: Artificial Sequence
<220> FEATURE:
<223> OTHER INFORMATION: cDNA Sequence of aMTD205 5'-primer

<400> SEQUENCE: 570
gggtttcata tggcgctggc gctggtgccg gcgattgcgg cgctgccggc aaatattacc    60
gttttctat                                                            69

<210> SEQ ID NO 571
<211> LENGTH: 69
<212> TYPE: DNA
<213> ORGANISM: Artificial Sequence
<220> FEATURE:
<223> OTHER INFORMATION: cDNA Sequence of aMTD210 5'-primer

<400> SEQUENCE: 571
gggtttcata tggcgctgat tgcgctgccg gcgctgccgg cgctgccggc aaatattacc    60
gttttctat                                                            69

<210> SEQ ID NO 572
<211> LENGTH: 69
<212> TYPE: DNA
<213> ORGANISM: Artificial Sequence
<220> FEATURE:
<223> OTHER INFORMATION: cDNA Sequence of aMTD214 5'-primer

<400> SEQUENCE: 572
gggtttcata tggcgctgat tgtggcgccg gcgctgatgg cgctgccggc aaatattacc    60
gttttctat                                                            69

<210> SEQ ID NO 573
<211> LENGTH: 69
<212> TYPE: DNA
<213> ORGANISM: Artificial Sequence
<220> FEATURE:
<223> OTHER INFORMATION: cDNA Sequence of aMTD221 5'-primer

<400> SEQUENCE: 573
gggtttcata tggcggcgat tctggcgccg attgtggcgc tggcgccggc aaatattacc    60
gttttctat                                                            69

<210> SEQ ID NO 574
<211> LENGTH: 69
<212> TYPE: DNA
<213> ORGANISM: Artificial Sequence
<220> FEATURE:
<223> OTHER INFORMATION: cDNA Sequence of aMTD222 5'-primer

<400> SEQUENCE: 574
gggtttcata tggcgctgct gattgcgccg gcggcggtga ttgcgccggc aaatattacc    60
gttttctat                                                            69

<210> SEQ ID NO 575
<211> LENGTH: 69
<212> TYPE: DNA
<213> ORGANISM: Artificial Sequence
<220> FEATURE:
<223> OTHER INFORMATION: cDNA Sequence of aMTD223 5'-primer

<400> SEQUENCE: 575
gggtttcata tggcgattct ggcggtgccg attgcggtgg tggcgccggc aaatattacc    60
gttttctat                                                            69

<210> SEQ ID NO 576
<211> LENGTH: 69
<212> TYPE: DNA
<213> ORGANISM: Artificial Sequence
<220> FEATURE:
<223> OTHER INFORMATION: cDNA Sequence of aMTD224 5'-primer -continued

<400> SEQUENCE: 576
gggtttcata tgattctggc ggcggtgccg attgcgctgg cggcgccggc aaatattacc    60
gttttctat                                                            69

<210> SEQ ID NO 577
<211> LENGTH: 69
<212> TYPE: DNA
<213> ORGANISM: Artificial Sequence
<220> FEATURE:
<223> OTHER INFORMATION: cDNA Sequence of aMTD225 5'-primer

<400> SEQUENCE: 577
gggtttcata tggtggcggc gctgctgccg gcggcggcgg tgctgccggc aaatattacc    60
gttttctat                                                            69

<210> SEQ ID NO 578
<211> LENGTH: 69
<212> TYPE: DNA
<213> ORGANISM: Artificial Sequence
<220> FEATURE:
<223> OTHER INFORMATION: cDNA Sequence of aMTD226 5'-primer

<400> SEQUENCE: 578
gggtttcata tggcgctggt ggcggcgatt ccggcgctgg cgattccggc aaatattacc    60
gttttctat                                                            69

<210> SEQ ID NO 579
<211> LENGTH: 69
<212> TYPE: DNA
<213> ORGANISM: Artificial Sequence
<220> FEATURE:
<223> OTHER INFORMATION: cDNA Sequence of aMTD227 5'-primer

<400> SEQUENCE: 579
gggtttcata tgctggcggc gattgtgccg attgcggcgg cggtgccggc aaatattacc    60
gttttctat                                                            69

<210> SEQ ID NO 580
<211> LENGTH: 69
<212> TYPE: DNA
<213> ORGANISM: Artificial Sequence
<220> FEATURE:
<223> OTHER INFORMATION: cDNA Sequence of aMTD241 5'-primer

<400> SEQUENCE: 580
gggtttcata tggcggcggc ggtggtgccg gtgctgctgg tggcgccggc aaatattacc    60
gttttctat                                                            69

<210> SEQ ID NO 581
<211> LENGTH: 69
<212> TYPE: DNA
<213> ORGANISM: Artificial Sequence
<220> FEATURE:
<223> OTHER INFORMATION: cDNA Sequence of aMTD242 5'-primer

<400> SEQUENCE: 581
gggtttcata tggcggcgct gctggtgccg gcgctggtgg cggcgccggc aaatattacc    60
gttttctat                                                            69

<210> SEQ ID NO 582
<211> LENGTH: 69

```
<212> TYPE: DNA
<213> ORGANISM: Artificial Sequence
<220> FEATURE:
<223> OTHER INFORMATION: cDNA Sequence of aMTD243 5'-primer

<400> SEQUENCE: 582
gggtttcata tggcggcggt gctgctgccg gtggcgctgg cggcgccggc aaatattacc      60
gttttctat                                                             69

<210> SEQ ID NO 583
<211> LENGTH: 69
<212> TYPE: DNA
<213> ORGANISM: Artificial Sequence
<220> FEATURE:
<223> OTHER INFORMATION: cDNA Sequence of aMTD245 5'-primer

<400> SEQUENCE: 583
gggtttcata tggcggcggc gctggcgccg gtgctggcgc tggtgccggc aaatattacc      60
gttttctat                                                             69

<210> SEQ ID NO 584
<211> LENGTH: 69
<212> TYPE: DNA
<213> ORGANISM: Artificial Sequence
<220> FEATURE:
<223> OTHER INFORMATION: cDNA Sequence of aMTD246 5'-primer

<400> SEQUENCE: 584
gggtttcata tggtggtggc ggtgccgctg ctggtggcgt ttgcggcggc aaatattacc      60
gttttctat                                                             69

<210> SEQ ID NO 585
<211> LENGTH: 69
<212> TYPE: DNA
<213> ORGANISM: Artificial Sequence
<220> FEATURE:
<223> OTHER INFORMATION: cDNA Sequence of aMTD248 5'-primer

<400> SEQUENCE: 585
gggtttcata tggtggcggc gattgtgccg attgcggcgc tggtgccggc aaatattacc      60
gttttctat                                                             69

<210> SEQ ID NO 586
<211> LENGTH: 69
<212> TYPE: DNA
<213> ORGANISM: Artificial Sequence
<220> FEATURE:
<223> OTHER INFORMATION: cDNA Sequence of aMTD261 5'-primer

<400> SEQUENCE: 586
gggtttcata tgctggtgct ggtgccgctg ctggcggcgg cggcgccggc aaatattacc      60
gttttctat                                                             69

<210> SEQ ID NO 587
<211> LENGTH: 69
<212> TYPE: DNA
<213> ORGANISM: Artificial Sequence
<220> FEATURE:
<223> OTHER INFORMATION: cDNA Sequence of aMTD262 5'-primer

<400> SEQUENCE: 587
gggtttcata tggcgctgat tgcggtgccg gcgattattg tggcgccggc aaatattacc      60
``` gttttctat                                                                 69

<210> SEQ ID NO 588
<211> LENGTH: 69
<212> TYPE: DNA
<213> ORGANISM: Artificial Sequence
<220> FEATURE:
<223> OTHER INFORMATION: cDNA Sequence of aMTD263 5'-primer

<400> SEQUENCE: 588
gggtttcata tggcgctggc ggtgattccg gcggcggcga ttctgccggc aaatattacc    60
gttttctat                                                                 69

<210> SEQ ID NO 589
<211> LENGTH: 69
<212> TYPE: DNA
<213> ORGANISM: Artificial Sequence
<220> FEATURE:
<223> OTHER INFORMATION: cDNA Sequence of aMTD264 5'-primer

<400> SEQUENCE: 589
gggtttcata tgctggcggc ggcgccggtg gtgattgtga ttgcgccggc aaatattacc    60
gttttctat                                                                 69

<210> SEQ ID NO 590
<211> LENGTH: 69
<212> TYPE: DNA
<213> ORGANISM: Artificial Sequence
<220> FEATURE:
<223> OTHER INFORMATION: cDNA Sequence of aMTD265 5'-primer

<400> SEQUENCE: 590
gggtttcata tggtgctggc gattgcgccg ctgctggcgg cggtgccggc aaatattacc    60
gttttctat                                                                 69

<210> SEQ ID NO 591
<211> LENGTH: 69
<212> TYPE: DNA
<213> ORGANISM: Artificial Sequence
<220> FEATURE:
<223> OTHER INFORMATION: cDNA Sequence of aMTD281 5'-primer

<400> SEQUENCE: 591
gggtttcata tggcgctgat tgtgctgccg gcggcggtgg cggtgccggc aaatattacc    60
gttttctat                                                                 69

<210> SEQ ID NO 592
<211> LENGTH: 69
<212> TYPE: DNA
<213> ORGANISM: Artificial Sequence
<220> FEATURE:
<223> OTHER INFORMATION: cDNA Sequence of aMTD282 5'-primer

<400> SEQUENCE: 592
gggtttcata tggtgctggc ggtggcgccg gcgctgattg tggcgccggc aaatattacc    60
gttttctat                                                                 69

<210> SEQ ID NO 593
<211> LENGTH: 69
<212> TYPE: DNA
<213> ORGANISM: Artificial Sequence
<220> FEATURE:
<223> OTHER INFORMATION: cDNA Sequence of aMTD283 5'-primer

<400> SEQUENCE: 593
gggtttcata tggcggcgct gctggcgccg gcgctgattg tggcgccggc aaatattacc    60
gttttctat                                                           69

<210> SEQ ID NO 594
<211> LENGTH: 69
<212> TYPE: DNA
<213> ORGANISM: Artificial Sequence
<220> FEATURE:
<223> OTHER INFORMATION: cDNA Sequence of aMTD284 5'-primer

<400> SEQUENCE: 594
gggtttcata tggcgctgat tgcgccggcg gtggcgctga ttgtgccggc aaatattacc    60
gttttctat                                                           69

<210> SEQ ID NO 595
<211> LENGTH: 69
<212> TYPE: DNA
<213> ORGANISM: Artificial Sequence
<220> FEATURE:
<223> OTHER INFORMATION: cDNA Sequence of aMTD285 5'-primer

<400> SEQUENCE: 595
gggtttcata tggcgattgt gctgctgccg gcggcggtgg tggcgccggc aaatattacc    60
gttttctat                                                           69

<210> SEQ ID NO 596
<211> LENGTH: 69
<212> TYPE: DNA
<213> ORGANISM: Artificial Sequence
<220> FEATURE:
<223> OTHER INFORMATION: cDNA Sequence of aMTD301 5'-primer

<400> SEQUENCE: 596
gggtttcata tggtgattgc ggcgccggtg ctggcggtgc tggcgccggc aaatattacc    60
gttttctat                                                           69

<210> SEQ ID NO 597
<211> LENGTH: 69
<212> TYPE: DNA
<213> ORGANISM: Artificial Sequence
<220> FEATURE:
<223> OTHER INFORMATION: cDNA Sequence of aMTD302 5'-primer

<400> SEQUENCE: 597
gggtttcata tgctggcgct ggcgccggcg ctggcgctgc tggcgccggc aaatattacc    60
gttttctat                                                           69

<210> SEQ ID NO 598
<211> LENGTH: 69
<212> TYPE: DNA
<213> ORGANISM: Artificial Sequence
<220> FEATURE:
<223> OTHER INFORMATION: cDNA Sequence of aMTD304 5'-primer

<400> SEQUENCE: 598
gggtttcata tggcgattat tctggcgccg attgcggcga ttgcgccggc aaatattacc    60
gttttctat                                                           69

<210> SEQ ID NO 599

```
<211> LENGTH: 69
<212> TYPE: DNA
<213> ORGANISM: Artificial Sequence
<220> FEATURE:
<223> OTHER INFORMATION: cDNA Sequence of aMTD305 5'-primer

<400> SEQUENCE: 599
gggtttcata tgattgcgct ggcggcgccg attctgctgg cggcgccggc aaatattacc    60
gttttctat                                                           69

<210> SEQ ID NO 600
<211> LENGTH: 69
<212> TYPE: DNA
<213> ORGANISM: Artificial Sequence
<220> FEATURE:
<223> OTHER INFORMATION: cDNA Sequence of aMTD321 5'-primer

<400> SEQUENCE: 600
gggtttcata tgattgtggc ggtggcgctg ccggcgctgg cggtgccggc aaatattacc    60
gttttctat                                                           69

<210> SEQ ID NO 601
<211> LENGTH: 69
<212> TYPE: DNA
<213> ORGANISM: Artificial Sequence
<220> FEATURE:
<223> OTHER INFORMATION: cDNA Sequence of aMTD322 5'-primer

<400> SEQUENCE: 601
gggtttcata tggtggtggc gattgtgctg ccggcgctgg cggcgccggc aaatattacc    60
gttttctat                                                           69

<210> SEQ ID NO 602
<211> LENGTH: 69
<212> TYPE: DNA
<213> ORGANISM: Artificial Sequence
<220> FEATURE:
<223> OTHER INFORMATION: cDNA Sequence of aMTD323 5'-primer

<400> SEQUENCE: 602
gggtttcata tgattgtggc ggtggcgctg ccggtggcgc tggcgccggc aaatattacc    60
gttttctat                                                           69

<210> SEQ ID NO 603
<211> LENGTH: 69
<212> TYPE: DNA
<213> ORGANISM: Artificial Sequence
<220> FEATURE:
<223> OTHER INFORMATION: cDNA Sequence of aMTD324 5'-primer

<400> SEQUENCE: 603
gggtttcata tgattgtggc ggtggcgctg ccggcggcgc tggtgccggc aaatattacc    60
gttttctat                                                           69

<210> SEQ ID NO 604
<211> LENGTH: 69
<212> TYPE: DNA
<213> ORGANISM: Artificial Sequence
<220> FEATURE:
<223> OTHER INFORMATION: cDNA Sequence of aMTD325 5'-primer

<400> SEQUENCE: 604
gggtttcata tgattgtggc ggtggcgctg ccggcggtgg cgctgccggc aaatattacc    60
``` gttttctat 69

<210> SEQ ID NO 605
<211> LENGTH: 69
<212> TYPE: DNA
<213> ORGANISM: Artificial Sequence
<220> FEATURE:
<223> OTHER INFORMATION: cDNA Sequence of aMTD329 5'-primer

<400> SEQUENCE: 605
gggtttcata tgctgccggt gctggtgccg gtggtgccgg tggtgccggc aaatattacc    60
gttttctat                                                            69

<210> SEQ ID NO 606
<211> LENGTH: 69
<212> TYPE: DNA
<213> ORGANISM: Artificial Sequence
<220> FEATURE:
<223> OTHER INFORMATION: cDNA Sequence of aMTD331 5'-primer

<400> SEQUENCE: 606
gggtttcata tggtgccggt gctggtgccg ctggtgccgg tggtgccggc aaatattacc    60
gttttctat                                                            69

<210> SEQ ID NO 607
<211> LENGTH: 69
<212> TYPE: DNA
<213> ORGANISM: Artificial Sequence
<220> FEATURE:
<223> OTHER INFORMATION: cDNA Sequence of aMTD341 5'-primer

<400> SEQUENCE: 607
gggtttcata tgattgtggc ggtggcgctg ccggcggtgc tggcgccggc aaatattacc    60
gttttctat                                                            69

<210> SEQ ID NO 608
<211> LENGTH: 69
<212> TYPE: DNA
<213> ORGANISM: Artificial Sequence
<220> FEATURE:
<223> OTHER INFORMATION: cDNA Sequence of aMTD342 5'-primer

<400> SEQUENCE: 608
gggtttcata tggtgattgt ggcgctggcg ccggcggtgc tggcgccggc aaatattacc    60
gttttctat                                                            69

<210> SEQ ID NO 609
<211> LENGTH: 69
<212> TYPE: DNA
<213> ORGANISM: Artificial Sequence
<220> FEATURE:
<223> OTHER INFORMATION: cDNA Sequence of aMTD343 5'-primer

<400> SEQUENCE: 609
gggtttcata tgattgtggc ggtggcgctg ccggcgctgg tggcgccggc aaatattacc    60
gttttctat                                                            69

<210> SEQ ID NO 610
<211> LENGTH: 69
<212> TYPE: DNA
<213> ORGANISM: Artificial Sequence
<220> FEATURE:

<223> OTHER INFORMATION: cDNA Sequence of aMTD345 5'-primer

<400> SEQUENCE: 610
gggtttcata tggcgctgct gattgtggcg ccggtggcgg tggcgccggc aaatattacc    60
gttttctat                                                           69

<210> SEQ ID NO 611
<211> LENGTH: 69
<212> TYPE: DNA
<213> ORGANISM: Artificial Sequence
<220> FEATURE:
<223> OTHER INFORMATION: cDNA Sequence of aMTD349 5'-primer

<400> SEQUENCE: 611
gggtttcata tggtgccggt gctggtgccg gtggtgccgg tggtgccggc aaatattacc    60
gttttctat                                                           69

<210> SEQ ID NO 612
<211> LENGTH: 69
<212> TYPE: DNA
<213> ORGANISM: Artificial Sequence
<220> FEATURE:
<223> OTHER INFORMATION: cDNA Sequence of aMTD350 5'-primer

<400> SEQUENCE: 612
gggtttcata tggtgccgat tctggtgccg gtggtgccgg tggtgccggc aaatattacc    60
gttttctat                                                           69

<210> SEQ ID NO 613
<211> LENGTH: 69
<212> TYPE: DNA
<213> ORGANISM: Artificial Sequence
<220> FEATURE:
<223> OTHER INFORMATION: cDNA Sequence of aMTD361 5'-primer

<400> SEQUENCE: 613
gggtttcata tggcggtggt gattgtggcg ccggcggtga ttgcgccggc aaatattacc    60
gttttctat                                                           69

<210> SEQ ID NO 614
<211> LENGTH: 69
<212> TYPE: DNA
<213> ORGANISM: Artificial Sequence
<220> FEATURE:
<223> OTHER INFORMATION: cDNA Sequence of aMTD363 5'-primer

<400> SEQUENCE: 614
gggtttcata tggcggtgct ggcggtggcg ccggcgctga ttgtgccggc aaatattacc    60
gttttctat                                                           69

<210> SEQ ID NO 615
<211> LENGTH: 69
<212> TYPE: DNA
<213> ORGANISM: Artificial Sequence
<220> FEATURE:
<223> OTHER INFORMATION: cDNA Sequence of aMTD364 5'-primer

<400> SEQUENCE: 615
gggtttcata tgctggtggc ggcggtggcg ccggcgctga ttgtgccggc aaatattacc    60
gttttctat                                                           69

```
<210> SEQ ID NO 616
<211> LENGTH: 69
<212> TYPE: DNA
<213> ORGANISM: Artificial Sequence
<220> FEATURE:
<223> OTHER INFORMATION: cDNA Sequence of aMTD365 5'-primer

<400> SEQUENCE: 616
gggtttcata tggcggtgat tgtggtggcg ccggcgctgc tggcgccggc aaatattacc      60
gttttctat                                                             69

<210> SEQ ID NO 617
<211> LENGTH: 69
<212> TYPE: DNA
<213> ORGANISM: Artificial Sequence
<220> FEATURE:
<223> OTHER INFORMATION: cDNA Sequence of aMTD381 5'-primer

<400> SEQUENCE: 617
gggtttcata tggtggtggc gattgtgctg ccggcggtgg cggcgccggc aaatattacc      60
gttttctat                                                             69

<210> SEQ ID NO 618
<211> LENGTH: 69
<212> TYPE: DNA
<213> ORGANISM: Artificial Sequence
<220> FEATURE:
<223> OTHER INFORMATION: cDNA Sequence of aMTD382 5'-primer

<400> SEQUENCE: 618
gggtttcata tggcggcggc gctggtgatt ccggcgattc tggcgccggc aaatattacc      60
gttttctat                                                             69

<210> SEQ ID NO 619
<211> LENGTH: 69
<212> TYPE: DNA
<213> ORGANISM: Artificial Sequence
<220> FEATURE:
<223> OTHER INFORMATION: cDNA Sequence of aMTD383 5'-primer

<400> SEQUENCE: 619
gggtttcata tggtgattgt ggcgctggcg ccggcgctgc tggcgccggc aaatattacc      60
gttttctat                                                             69

<210> SEQ ID NO 620
<211> LENGTH: 69
<212> TYPE: DNA
<213> ORGANISM: Artificial Sequence
<220> FEATURE:
<223> OTHER INFORMATION: cDNA Sequence of aMTD384 5'-primer

<400> SEQUENCE: 620
gggtttcata tggtgattgt ggcgattgcg ccggcgctgc tggcgccggc aaatattacc      60
gttttctat                                                             69

<210> SEQ ID NO 621
<211> LENGTH: 69
<212> TYPE: DNA
<213> ORGANISM: Artificial Sequence
<220> FEATURE:
<223> OTHER INFORMATION: cDNA Sequence of aMTD385 5'-primer

<400> SEQUENCE: 621
```

```
gggtttcata tgattgtggc gattgcggtg ccggcgctgg tggcgccggc aaatattacc       60
gttttctat                                                              69
```

<210> SEQ ID NO 622
<211> LENGTH: 69
<212> TYPE: DNA
<213> ORGANISM: Artificial Sequence
<220> FEATURE:
<223> OTHER INFORMATION: cDNA Sequence of aMTD390 5'-primer

<400> SEQUENCE: 622

```
gggtttcata tggtgccgct gctggtgccg gtggtgccgg tggtgccggc aaatattacc       60
gttttctat                                                              69
```

<210> SEQ ID NO 623
<211> LENGTH: 69
<212> TYPE: DNA
<213> ORGANISM: Artificial Sequence
<220> FEATURE:
<223> OTHER INFORMATION: cDNA Sequence of aMTD401 5'-primer

<400> SEQUENCE: 623

```
gggtttcata tggcggcgct ggcggtgatt ccggcggcga ttctgccggc aaatattacc       60
gttttctat                                                              69
```

<210> SEQ ID NO 624
<211> LENGTH: 69
<212> TYPE: DNA
<213> ORGANISM: Artificial Sequence
<220> FEATURE:
<223> OTHER INFORMATION: cDNA Sequence of aMTD402 5'-primer

<400> SEQUENCE: 624

```
gggtttcata tggcgctggc ggcggtgatt ccggcggcga ttctgccggc aaatattacc       60
gttttctat                                                              69
```

<210> SEQ ID NO 625
<211> LENGTH: 69
<212> TYPE: DNA
<213> ORGANISM: Artificial Sequence
<220> FEATURE:
<223> OTHER INFORMATION: cDNA Sequence of aMTD403 5'-primer

<400> SEQUENCE: 625

```
gggtttcata tggcggcggc gctggtgatt ccggcggcga ttctgccggc aaatattacc       60
gttttctat                                                              69
```

<210> SEQ ID NO 626
<211> LENGTH: 69
<212> TYPE: DNA
<213> ORGANISM: Artificial Sequence
<220> FEATURE:
<223> OTHER INFORMATION: cDNA Sequence of aMTD404 5'-primer

<400> SEQUENCE: 626

```
gggtttcata tgctggcggc ggcggtgatt ccggcggcga ttctgccggc aaatattacc       60
gttttctat                                                              69
```

<210> SEQ ID NO 627
<211> LENGTH: 69
<212> TYPE: DNA
<213> ORGANISM: Artificial Sequence

```
<220> FEATURE:
<223> OTHER INFORMATION: cDNA Sequence of aMTD405 5'-primer

<400> SEQUENCE: 627
gggtttcata tgctggcggc ggcggtgatt ccggtggcga ttctgccggc aaatattacc    60
gttttctat                                                            69

<210> SEQ ID NO 628
<211> LENGTH: 69
<212> TYPE: DNA
<213> ORGANISM: Artificial Sequence
<220> FEATURE:
<223> OTHER INFORMATION: cDNA Sequence of aMTD421 5'-primer

<400> SEQUENCE: 628
gggtttcata tggcggcgat tctggcggcg ccgctgattg cggtgccggc aaatattacc    60
gttttctat                                                            69

<210> SEQ ID NO 629
<211> LENGTH: 69
<212> TYPE: DNA
<213> ORGANISM: Artificial Sequence
<220> FEATURE:
<223> OTHER INFORMATION: cDNA Sequence of aMTD422 5'-primer

<400> SEQUENCE: 629
gggtttcata tggtggtggc gattctggcg ccgctgctgg cggcgccggc aaatattacc    60
gttttctat                                                            69

<210> SEQ ID NO 630
<211> LENGTH: 69
<212> TYPE: DNA
<213> ORGANISM: Artificial Sequence
<220> FEATURE:
<223> OTHER INFORMATION: cDNA Sequence of aMTD424 5'-primer

<400> SEQUENCE: 630
gggtttcata tggcggtggt ggtggcggcg ccggtgctgg cgctgccggc aaatattacc    60
gttttctat                                                            69

<210> SEQ ID NO 631
<211> LENGTH: 69
<212> TYPE: DNA
<213> ORGANISM: Artificial Sequence
<220> FEATURE:
<223> OTHER INFORMATION: cDNA Sequence of aMTD425 5'-primer

<400> SEQUENCE: 631
gggtttcata tggcggtggt ggcgattgcg ccggtgctgg cgctgccggc aaatattacc    60
gttttctat                                                            69

<210> SEQ ID NO 632
<211> LENGTH: 69
<212> TYPE: DNA
<213> ORGANISM: Artificial Sequence
<220> FEATURE:
<223> OTHER INFORMATION: cDNA Sequence of aMTD426 5'-primer

<400> SEQUENCE: 632
gggtttcata tggcggcggc gctggcgatt ccgctggcga ttattccggc aaatattacc    60
gttttctat                                                            69
```

<210> SEQ ID NO 633
<211> LENGTH: 69
<212> TYPE: DNA
<213> ORGANISM: Artificial Sequence
<220> FEATURE:
<223> OTHER INFORMATION: cDNA Sequence of aMTD436 5'-primer

<400> SEQUENCE: 633
gggtttcata tggcggtggt gctggtgatt atgccggcgg cgattccggc aaatattacc    60
gttttctat                                                           69

<210> SEQ ID NO 634
<211> LENGTH: 69
<212> TYPE: DNA
<213> ORGANISM: Artificial Sequence
<220> FEATURE:
<223> OTHER INFORMATION: cDNA Sequence of aMTD442 5'-primer

<400> SEQUENCE: 634
gggtttcata tggcgctggc ggcgctggtg ccggcggtgc tggtgccggc aaatattacc    60
gttttctat                                                           69

<210> SEQ ID NO 635
<211> LENGTH: 69
<212> TYPE: DNA
<213> ORGANISM: Artificial Sequence
<220> FEATURE:
<223> OTHER INFORMATION: cDNA Sequence of aMTD443 5'-primer

<400> SEQUENCE: 635
gggtttcata tggcgctggc ggcgctggtg ccggtggcgc tggtgccggc aaatattacc    60
gttttctat                                                           69

<210> SEQ ID NO 636
<211> LENGTH: 69
<212> TYPE: DNA
<213> ORGANISM: Artificial Sequence
<220> FEATURE:
<223> OTHER INFORMATION: cDNA Sequence of aMTD444 5'-primer

<400> SEQUENCE: 636
gggtttcata tgctggcggc ggcgctggtg ccggtggcgc tggtgccggc aaatattacc    60
gttttctat                                                           69

<210> SEQ ID NO 637
<211> LENGTH: 69
<212> TYPE: DNA
<213> ORGANISM: Artificial Sequence
<220> FEATURE:
<223> OTHER INFORMATION: cDNA Sequence of aMTD445 5'-primer

<400> SEQUENCE: 637
gggtttcata tggcgctggc ggcgctggtg ccggcgctgg tggtgccggc aaatattacc    60
gttttctat                                                           69

<210> SEQ ID NO 638
<211> LENGTH: 69
<212> TYPE: DNA
<213> ORGANISM: Artificial Sequence
<220> FEATURE:
<223> OTHER INFORMATION: cDNA Sequence of aMTD461 5'-primer

<400> SEQUENCE: 638

```
gggtttcata tgattgcggc ggtgattgtg ccggcggtgg cgctgccggc aaatattacc    60
gttttctat                                                            69

<210> SEQ ID NO 639
<211> LENGTH: 69
<212> TYPE: DNA
<213> ORGANISM: Artificial Sequence
<220> FEATURE:
<223> OTHER INFORMATION: cDNA Sequence of aMTD462 5'-primer

<400> SEQUENCE: 639
gggtttcata tgattgcggc ggtgctggtg ccggcggtgg cgctgccggc aaatattacc    60
gttttctat                                                            69

<210> SEQ ID NO 640
<211> LENGTH: 69
<212> TYPE: DNA
<213> ORGANISM: Artificial Sequence
<220> FEATURE:
<223> OTHER INFORMATION: cDNA Sequence of aMTD463 5'-primer

<400> SEQUENCE: 640
gggtttcata tggcggtggc gattctggtg ccgctgctgg cggcgccggc aaatattacc    60
gttttctat                                                            69

<210> SEQ ID NO 641
<211> LENGTH: 69
<212> TYPE: DNA
<213> ORGANISM: Artificial Sequence
<220> FEATURE:
<223> OTHER INFORMATION: cDNA Sequence of aMTD464 5'-primer

<400> SEQUENCE: 641
gggtttcata tggcggtggt gattctggtg ccgctggcgg cggcgccggc aaatattacc    60
gttttctat                                                            69

<210> SEQ ID NO 642
<211> LENGTH: 69
<212> TYPE: DNA
<213> ORGANISM: Artificial Sequence
<220> FEATURE:
<223> OTHER INFORMATION: cDNA Sequence of aMTD465 5'-primer

<400> SEQUENCE: 642
gggtttcata tgattgcggc ggtgattgtg ccggtggcgg cgctgccggc aaatattacc    60
gttttctat                                                            69

<210> SEQ ID NO 643
<211> LENGTH: 69
<212> TYPE: DNA
<213> ORGANISM: Artificial Sequence
<220> FEATURE:
<223> OTHER INFORMATION: cDNA Sequence of aMTD466 5'-primer

<400> SEQUENCE: 643
gggtttcata tgattattgc ggcggcggcg ccgctggcga ttattccggc aaatattacc    60
gttttctat                                                            69

<210> SEQ ID NO 644
<211> LENGTH: 69
<212> TYPE: DNA
```

<213> ORGANISM: Artificial Sequence
<220> FEATURE:
<223> OTHER INFORMATION: cDNA Sequence of aMTD481 5'-primer

<400> SEQUENCE: 644
gggtttcata tggcgattgc gattgcgatt gtgccggtgg cgctgccggc aaatattacc    60
gttttctat    69

<210> SEQ ID NO 645
<211> LENGTH: 69
<212> TYPE: DNA
<213> ORGANISM: Artificial Sequence
<220> FEATURE:
<223> OTHER INFORMATION: cDNA Sequence of aMTD482 5'-primer

<400> SEQUENCE: 645
gggtttcata tgattctggc ggtggcggcg attccggtgg cggtgccggc aaatattacc    60
gttttctat    69

<210> SEQ ID NO 646
<211> LENGTH: 69
<212> TYPE: DNA
<213> ORGANISM: Artificial Sequence
<220> FEATURE:
<223> OTHER INFORMATION: cDNA Sequence of aMTD483 5'-primer

<400> SEQUENCE: 646
gggtttcata tgattctggc ggcggcgatt attccggcgg cgctgccggc aaatattacc    60
gttttctat    69

<210> SEQ ID NO 647
<211> LENGTH: 69
<212> TYPE: DNA
<213> ORGANISM: Artificial Sequence
<220> FEATURE:
<223> OTHER INFORMATION: cDNA Sequence of aMTD484 5'-primer

<400> SEQUENCE: 647
gggtttcata tgctggcggt ggtgctggcg gcgccggcga ttgtgccggc aaatattacc    60
gttttctat    69

<210> SEQ ID NO 648
<211> LENGTH: 69
<212> TYPE: DNA
<213> ORGANISM: Artificial Sequence
<220> FEATURE:
<223> OTHER INFORMATION: cDNA Sequence of aMTD485 5'-primer

<400> SEQUENCE: 648
gggtttcata tggcgattct ggcggcgatt gtgccgctgg cggtgccggc aaatattacc    60
gttttctat    69

<210> SEQ ID NO 649
<211> LENGTH: 69
<212> TYPE: DNA
<213> ORGANISM: Artificial Sequence
<220> FEATURE:
<223> OTHER INFORMATION: cDNA Sequence of aMTD501 5'-primer

<400> SEQUENCE: 649
gggtttcata tggtgattgt ggcgctggcg gtgccggcgc tggcgccggc aaatattacc    60
gttttctat    69

<210> SEQ ID NO 650
<211> LENGTH: 69
<212> TYPE: DNA
<213> ORGANISM: Artificial Sequence
<220> FEATURE:
<223> OTHER INFORMATION: cDNA Sequence of aMTD502 5'-primer

<400> SEQUENCE: 650
gggtttcata tggcgattgt ggcgctggcg gtgccggtgc tggcgccggc aaatattacc    60
gttttctat                                                           69

<210> SEQ ID NO 651
<211> LENGTH: 69
<212> TYPE: DNA
<213> ORGANISM: Artificial Sequence
<220> FEATURE:
<223> OTHER INFORMATION: cDNA Sequence of aMTD503 5'-primer

<400> SEQUENCE: 651
gggtttcata tggcggcgat tattattgtg ctgccggcgg cgctgccggc aaatattacc    60
gttttctat                                                           69

<210> SEQ ID NO 652
<211> LENGTH: 69
<212> TYPE: DNA
<213> ORGANISM: Artificial Sequence
<220> FEATURE:
<223> OTHER INFORMATION: cDNA Sequence of aMTD504 5'-primer

<400> SEQUENCE: 652
gggtttcata tgctgattgt ggcgctggcg gtgccggcgc tggcgccggc aaatattacc    60
gttttctat                                                           69

<210> SEQ ID NO 653
<211> LENGTH: 69
<212> TYPE: DNA
<213> ORGANISM: Artificial Sequence
<220> FEATURE:
<223> OTHER INFORMATION: cDNA Sequence of aMTD505 5'-primer

<400> SEQUENCE: 653
gggtttcata tggcgattat tattgtgatt gcgccggcgg cggcgccggc aaatattacc    60
gttttctat                                                           69

<210> SEQ ID NO 654
<211> LENGTH: 69
<212> TYPE: DNA
<213> ORGANISM: Artificial Sequence
<220> FEATURE:
<223> OTHER INFORMATION: cDNA Sequence of aMTD521 5'-primer

<400> SEQUENCE: 654
gggtttcata tgctggcggc gctgattgtg gtgccggcgg tggcgccggc aaatattacc    60
gttttctat                                                           69

<210> SEQ ID NO 655
<211> LENGTH: 69
<212> TYPE: DNA
<213> ORGANISM: Artificial Sequence
<220> FEATURE:
<223> OTHER INFORMATION: cDNA Sequence of aMTD522 5'-primer

<400> SEQUENCE: 655
gggtttcata tggcgctgct ggtgattgcg gtgccggcgg tggcgccggc aaatattacc    60
gttttctat                                                            69

<210> SEQ ID NO 656
<211> LENGTH: 69
<212> TYPE: DNA
<213> ORGANISM: Artificial Sequence
<220> FEATURE:
<223> OTHER INFORMATION: cDNA Sequence of aMTD524 5'-primer

<400> SEQUENCE: 656
gggtttcata tggcggtggc gctgattgtg gtgccggcgc tggcgccggc aaatattacc    60
gttttctat                                                            69

<210> SEQ ID NO 657
<211> LENGTH: 69
<212> TYPE: DNA
<213> ORGANISM: Artificial Sequence
<220> FEATURE:
<223> OTHER INFORMATION: cDNA Sequence of aMTD525 5'-primer

<400> SEQUENCE: 657
gggtttcata tggcgctggc gattgtggtg gcgccggtgg cggtgccggc aaatattacc    60
gttttctat                                                            69

<210> SEQ ID NO 658
<211> LENGTH: 69
<212> TYPE: DNA
<213> ORGANISM: Artificial Sequence
<220> FEATURE:
<223> OTHER INFORMATION: cDNA Sequence of aMTD527 5'-primer

<400> SEQUENCE: 658
gggtttcata tgctggtgct ggcggcggtg gcgccgattg cgattccggc aaatattacc    60
gttttctat                                                            69

<210> SEQ ID NO 659
<211> LENGTH: 69
<212> TYPE: DNA
<213> ORGANISM: Artificial Sequence
<220> FEATURE:
<223> OTHER INFORMATION: cDNA Sequence of aMTD541 5'-primer

<400> SEQUENCE: 659
gggtttcata tgctgctggc gctgattatt gcgccggcgg cggcgccggc aaatattacc    60
gttttctat                                                            69

<210> SEQ ID NO 660
<211> LENGTH: 69
<212> TYPE: DNA
<213> ORGANISM: Artificial Sequence
<220> FEATURE:
<223> OTHER INFORMATION: cDNA Sequence of aMTD542 5'-primer

<400> SEQUENCE: 660
gggtttcata tggcgctggc gctgattatt gtgccggcgg tggcgccggc aaatattacc    60
gttttctat                                                            69

<210> SEQ ID NO 661
<211> LENGTH: 69

```
<212> TYPE: DNA
<213> ORGANISM: Artificial Sequence
<220> FEATURE:
<223> OTHER INFORMATION: cDNA Sequence of aMTD543 5'-primer

<400> SEQUENCE: 661
gggtttcata tgctgctggc ggcgctgatt gcgccggcgg cgctgccggc aaatattacc    60
gttttctat                                                            69

<210> SEQ ID NO 662
<211> LENGTH: 69
<212> TYPE: DNA
<213> ORGANISM: Artificial Sequence
<220> FEATURE:
<223> OTHER INFORMATION: cDNA Sequence of aMTD544 5'-primer

<400> SEQUENCE: 662
gggtttcata tgattgtggc gctgattgtg gcgccggcgg cggtgccggc aaatattacc    60
gttttctat                                                            69

<210> SEQ ID NO 663
<211> LENGTH: 69
<212> TYPE: DNA
<213> ORGANISM: Artificial Sequence
<220> FEATURE:
<223> OTHER INFORMATION: cDNA Sequence of aMTD545 5'-primer

<400> SEQUENCE: 663
gggtttcata tggtggtgct ggtgctggcg gcgccggcgg cggtgccggc aaatattacc    60
gttttctat                                                            69

<210> SEQ ID NO 664
<211> LENGTH: 69
<212> TYPE: DNA
<213> ORGANISM: Artificial Sequence
<220> FEATURE:
<223> OTHER INFORMATION: cDNA Sequence of aMTD561 5'-primer

<400> SEQUENCE: 664
gggtttcata tggcggcggt ggcgattgtg ctgccggcgg tggtgccggc aaatattacc    60
gttttctat                                                            69

<210> SEQ ID NO 665
<211> LENGTH: 69
<212> TYPE: DNA
<213> ORGANISM: Artificial Sequence
<220> FEATURE:
<223> OTHER INFORMATION: cDNA Sequence of aMTD562 5'-primer

<400> SEQUENCE: 665
gggtttcata tggcgctgat tgcggcgatt gtgccggcgc tggtgccggc aaatattacc    60
gttttctat                                                            69

<210> SEQ ID NO 666
<211> LENGTH: 69
<212> TYPE: DNA
<213> ORGANISM: Artificial Sequence
<220> FEATURE:
<223> OTHER INFORMATION: cDNA Sequence of aMTD563 5'-primer

<400> SEQUENCE: 666
gggtttcata tggcgctggc ggtgattgtg gtgccggcgc tggcgccggc aaatattacc    60
```

```
gttttctat                                                              69

<210> SEQ ID NO 667
<211> LENGTH: 69
<212> TYPE: DNA
<213> ORGANISM: Artificial Sequence
<220> FEATURE:
<223> OTHER INFORMATION: cDNA Sequence of aMTD564 5'-primer

<400> SEQUENCE: 667
gggtttcata tggtggcgat tgcgctgatt gtgccggcgc tggcgccggc aaatattacc      60
gttttctat                                                              69

<210> SEQ ID NO 668
<211> LENGTH: 69
<212> TYPE: DNA
<213> ORGANISM: Artificial Sequence
<220> FEATURE:
<223> OTHER INFORMATION: cDNA Sequence of aMTD565 5'-primer

<400> SEQUENCE: 668
gggtttcata tggtggcgat tgtgctggtg gcgccggcgg tggcgccggc aaatattacc      60
gttttctat                                                              69

<210> SEQ ID NO 669
<211> LENGTH: 69
<212> TYPE: DNA
<213> ORGANISM: Artificial Sequence
<220> FEATURE:
<223> OTHER INFORMATION: cDNA Sequence of aMTD577 5'-primer

<400> SEQUENCE: 669
gggtttcata tggcggcggt gctgattgtg ccgattatgg tgatgccggc aaatattacc      60
gttttctat                                                              69

<210> SEQ ID NO 670
<211> LENGTH: 69
<212> TYPE: DNA
<213> ORGANISM: Artificial Sequence
<220> FEATURE:
<223> OTHER INFORMATION: cDNA Sequence of aMTD582 5'-primer

<400> SEQUENCE: 670
gggtttcata tggtggcggt ggcgctgatt gtgccggcgc tggcgccggc aaatattacc      60
gttttctat                                                              69

<210> SEQ ID NO 671
<211> LENGTH: 69
<212> TYPE: DNA
<213> ORGANISM: Artificial Sequence
<220> FEATURE:
<223> OTHER INFORMATION: cDNA Sequence of aMTD583 5'-primer

<400> SEQUENCE: 671
gggtttcata tggcggtgat tctggcgctg gcgccgattg tggcgccggc aaatattacc      60
gttttctat                                                              69

<210> SEQ ID NO 672
<211> LENGTH: 69
<212> TYPE: DNA
<213> ORGANISM: Artificial Sequence
<220> FEATURE:
<223> OTHER INFORMATION: cDNA Sequence of aMTD585 5'-primer
```

<400> SEQUENCE: 672
gggtttcata tggcgctgat tgtggcgatt gcgccggcgc tggtgccggc aaatattacc    60
gttttctat                                                            69

<210> SEQ ID NO 673
<211> LENGTH: 69
<212> TYPE: DNA
<213> ORGANISM: Artificial Sequence
<220> FEATURE:
<223> OTHER INFORMATION: cDNA Sequence of aMTD601 5'-primer

<400> SEQUENCE: 673
gggtttcata tggcggcgat tctgattgcg gtgccgattg cggcgccggc aaatattacc    60
gttttctat                                                            69

<210> SEQ ID NO 674
<211> LENGTH: 69
<212> TYPE: DNA
<213> ORGANISM: Artificial Sequence
<220> FEATURE:
<223> OTHER INFORMATION: cDNA Sequence of aMTD602 5'-primer

<400> SEQUENCE: 674
gggtttcata tggtgattgt ggcgctggcg gcgccggtgc tggcgccggc aaatattacc    60
gttttctat                                                            69

<210> SEQ ID NO 675
<211> LENGTH: 69
<212> TYPE: DNA
<213> ORGANISM: Artificial Sequence
<220> FEATURE:
<223> OTHER INFORMATION: cDNA Sequence of aMTD603 5'-primer

<400> SEQUENCE: 675
gggtttcata tggtgctggt ggcgctggcg gcgccggtga ttgcgccggc aaatattacc    60
gttttctat                                                            69

<210> SEQ ID NO 676
<211> LENGTH: 69
<212> TYPE: DNA
<213> ORGANISM: Artificial Sequence
<220> FEATURE:
<223> OTHER INFORMATION: cDNA Sequence of aMTD604 5'-primer

<400> SEQUENCE: 676
gggtttcata tggtggcgct gattgcggtg gcgccggcgg tggtgccggc aaatattacc    60
gttttctat                                                            69

<210> SEQ ID NO 677
<211> LENGTH: 69
<212> TYPE: DNA
<213> ORGANISM: Artificial Sequence
<220> FEATURE:
<223> OTHER INFORMATION: cDNA Sequence of aMTD605 5'-primer

<400> SEQUENCE: 677
gggtttcata tggtgattgc ggcggtgctg gcgccggtgg cggtgccggc aaatattacc    60
gttttctat                                                            69

<210> SEQ ID NO 678

```
<211> LENGTH: 69
<212> TYPE: DNA
<213> ORGANISM: Artificial Sequence
<220> FEATURE:
<223> OTHER INFORMATION: cDNA Sequence of aMTD606 5'-primer

<400> SEQUENCE: 678
gggtttcata tggcggcggc gattgcggcg attccgatta ttattccggc aaatattacc    60
gttttctat                                                           69

<210> SEQ ID NO 679
<211> LENGTH: 69
<212> TYPE: DNA
<213> ORGANISM: Artificial Sequence
<220> FEATURE:
<223> OTHER INFORMATION: cDNA Sequence of aMTD622 5'-primer

<400> SEQUENCE: 679
gggtttcata tggcggcggc gattgcggcg attccgatta ttattccggc aaatattacc    60
gttttctat                                                           69

<210> SEQ ID NO 680
<211> LENGTH: 69
<212> TYPE: DNA
<213> ORGANISM: Artificial Sequence
<220> FEATURE:
<223> OTHER INFORMATION: cDNA Sequence of aMTD623 5'-primer

<400> SEQUENCE: 680
gggtttcata tggtggcggc ggcgattgcg ctgccggcga ttgtgccggc aaatattacc    60
gttttctat                                                           69

<210> SEQ ID NO 681
<211> LENGTH: 69
<212> TYPE: DNA
<213> ORGANISM: Artificial Sequence
<220> FEATURE:
<223> OTHER INFORMATION: cDNA Sequence of aMTD625 5'-primer

<400> SEQUENCE: 681
gggtttcata tgattctggc ggcggcggcg gcgccgctga ttgtgccggc aaatattacc    60
gttttctat                                                           69

<210> SEQ ID NO 682
<211> LENGTH: 69
<212> TYPE: DNA
<213> ORGANISM: Artificial Sequence
<220> FEATURE:
<223> OTHER INFORMATION: cDNA Sequence of aMTD635 5'-primer

<400> SEQUENCE: 682
gggtttcata tgggcagcac cggcggcagc cagcagaaca accagtatgc aaatattacc    60
gttttctat                                                           69

<210> SEQ ID NO 683
<211> LENGTH: 69
<212> TYPE: DNA
<213> ORGANISM: Artificial Sequence
<220> FEATURE:
<223> OTHER INFORMATION: cDNA Sequence of aMTD643 5'-primer

<400> SEQUENCE: 683
gggtttcata tgctggcgct ggtgctggcg gcgccggcga ttgtgccggc aaatattacc    60
``` gttttctat 69

<210> SEQ ID NO 684
<211> LENGTH: 69
<212> TYPE: DNA
<213> ORGANISM: Artificial Sequence
<220> FEATURE:
<223> OTHER INFORMATION: cDNA Sequence of aMTD645 5'-primer

<400> SEQUENCE: 684
gggtttcata tggcgctggc ggtggtggcg ctgccggcga ttgtgccggc aaatattacc    60
gttttctat                                                            69

<210> SEQ ID NO 685
<211> LENGTH: 69
<212> TYPE: DNA
<213> ORGANISM: Artificial Sequence
<220> FEATURE:
<223> OTHER INFORMATION: cDNA Sequence of aMTD661 5'-primer

<400> SEQUENCE: 685
gggtttcata tggcggcgat tctggcgccg attgtggcgg cgctgccggc aaatattacc    60
gttttctat                                                            69

<210> SEQ ID NO 686
<211> LENGTH: 69
<212> TYPE: DNA
<213> ORGANISM: Artificial Sequence
<220> FEATURE:
<223> OTHER INFORMATION: cDNA Sequence of aMTD664 5'-primer

<400> SEQUENCE: 686
gggtttcata tgattctgat tgcgattgcg attccggcgg cggcgccggc aaatattacc    60
gttttctat                                                            69

<210> SEQ ID NO 687
<211> LENGTH: 69
<212> TYPE: DNA
<213> ORGANISM: Artificial Sequence
<220> FEATURE:
<223> OTHER INFORMATION: cDNA Sequence of aMTD665 5'-primer

<400> SEQUENCE: 687
gggtttcata tgctggcgat tgtgctggcg gcgccggtgg cggtgccggc aaatattacc    60
gttttctat                                                            69

<210> SEQ ID NO 688
<211> LENGTH: 69
<212> TYPE: DNA
<213> ORGANISM: Artificial Sequence
<220> FEATURE:
<223> OTHER INFORMATION: cDNA Sequence of aMTD666 5'-primer

<400> SEQUENCE: 688
gggtttcata tggcggcgat tgcgattatt gcgccggcga ttgtgccggc aaatattacc    60
gttttctat                                                            69

<210> SEQ ID NO 689
<211> LENGTH: 69
<212> TYPE: DNA
<213> ORGANISM: Artificial Sequence
<220> FEATURE:

<223> OTHER INFORMATION: cDNA Sequence of aMTD667 5'-primer

<400> SEQUENCE: 689
gggtttcata tgctggcggt ggcgattgtg gcgccggcgc tggtgccggc aaatattacc    60
gttttctat                                                            69

<210> SEQ ID NO 690
<211> LENGTH: 69
<212> TYPE: DNA
<213> ORGANISM: Artificial Sequence
<220> FEATURE:
<223> OTHER INFORMATION: cDNA Sequence of aMTD676 5'-primer

<400> SEQUENCE: 690
gggtttcata tggtgccgct gctggtgccg gtgccggtgg tggtgccggc aaatattacc    60
gttttctat                                                            69

<210> SEQ ID NO 691
<211> LENGTH: 69
<212> TYPE: DNA
<213> ORGANISM: Artificial Sequence
<220> FEATURE:
<223> OTHER INFORMATION: cDNA Sequence of aMTD683 5'-primer

<400> SEQUENCE: 691
gggtttcata tgctggcgat tgtgctggcg gcgccggcgg tgctgccggc aaatattacc    60
gttttctat                                                            69

<210> SEQ ID NO 692
<211> LENGTH: 69
<212> TYPE: DNA
<213> ORGANISM: Artificial Sequence
<220> FEATURE:
<223> OTHER INFORMATION: cDNA Sequence of aMTD684 5'-primer

<400> SEQUENCE: 692
gggtttcata tggcggcgat tgtgctggcg ctgccggcgg tgctgccggc aaatattacc    60
gttttctat                                                            69

<210> SEQ ID NO 693
<211> LENGTH: 69
<212> TYPE: DNA
<213> ORGANISM: Artificial Sequence
<220> FEATURE:
<223> OTHER INFORMATION: cDNA Sequence of aMTD685 5'-primer

<400> SEQUENCE: 693
gggtttcata tggcgctgct ggtggcggtg ctgccggcgg cgctgccggc aaatattacc    60
gttttctat                                                            69

<210> SEQ ID NO 694
<211> LENGTH: 69
<212> TYPE: DNA
<213> ORGANISM: Artificial Sequence
<220> FEATURE:
<223> OTHER INFORMATION: cDNA Sequence of aMTD686 5'-primer

<400> SEQUENCE: 694
gggtttcata tggcggcgct ggtggcggtg ctgccggtgg cgctgccggc aaatattacc    60
gttttctat                                                            69

```
<210> SEQ ID NO 695
<211> LENGTH: 69
<212> TYPE: DNA
<213> ORGANISM: Artificial Sequence
<220> FEATURE:
<223> OTHER INFORMATION: cDNA Sequence of aMTD687 5'-primer

<400> SEQUENCE: 695
gggtttcata tggcgattct ggcggtggcg ctgccgctgc tggcgccggc aaatattacc    60
gttttctat                                                           69

<210> SEQ ID NO 696
<211> LENGTH: 69
<212> TYPE: DNA
<213> ORGANISM: Artificial Sequence
<220> FEATURE:
<223> OTHER INFORMATION: cDNA Sequence of aMTD692 5'-primer

<400> SEQUENCE: 696
gggtttcata tgccggcgcc gctgccgccg gtggtgattc tggcggtggc aaatattacc    60
gttttctat                                                           69

<210> SEQ ID NO 697
<211> LENGTH: 69
<212> TYPE: DNA
<213> ORGANISM: Artificial Sequence
<220> FEATURE:
<223> OTHER INFORMATION: cDNA Sequence of aMTD693 5'-primer

<400> SEQUENCE: 697
gggtttcata tggcggcgcc ggtgctgccg gtggcggtgc cgattgtggc aaatattacc    60
gttttctat                                                           69

<210> SEQ ID NO 698
<211> LENGTH: 69
<212> TYPE: DNA
<213> ORGANISM: Artificial Sequence
<220> FEATURE:
<223> OTHER INFORMATION: cDNA Sequence of aMTD700 5'-primer

<400> SEQUENCE: 698
gggtttcata tgggcaccag caacacctgc cagagcaacc agaacagcgc aaatattacc    60
gttttctat                                                           69

<210> SEQ ID NO 699
<211> LENGTH: 69
<212> TYPE: DNA
<213> ORGANISM: Artificial Sequence
<220> FEATURE:
<223> OTHER INFORMATION: cDNA Sequence of aMTD703 5'-primer

<400> SEQUENCE: 699
gggtttcata tgattgtggc ggtggcgctg gtgccggcgc tggcgccggc aaatattacc    60
gttttctat                                                           69

<210> SEQ ID NO 700
<211> LENGTH: 68
<212> TYPE: DNA
<213> ORGANISM: Artificial Sequence
<220> FEATURE:
<223> OTHER INFORMATION: cDNA Sequence of aMTD705 5'-primer

<400> SEQUENCE: 700
```

```
gggtttcata tattgtggcg gtggcgctgc tgccggcgct ggcgccggca aatattaccg    60
ttttctat                                                              68
```

<210> SEQ ID NO 701
<211> LENGTH: 69
<212> TYPE: DNA
<213> ORGANISM: Artificial Sequence
<220> FEATURE:
<223> OTHER INFORMATION: cDNA Sequence of aMTD706 5'-primer

<400> SEQUENCE: 701

```
gggtttcata tgattgtggc ggtggcgctg ctgccggcgg tggcgccggc aaatattacc    60
gttttctat                                                             69
```

<210> SEQ ID NO 702
<211> LENGTH: 69
<212> TYPE: DNA
<213> ORGANISM: Artificial Sequence
<220> FEATURE:
<223> OTHER INFORMATION: cDNA Sequence of aMTD707 5'-primer

<400> SEQUENCE: 702

```
gggtttcata tgattgtggc gctggcggtg ctgccggcgg tggcgccggc aaatattacc    60
gttttctat                                                             69
```

<210> SEQ ID NO 703
<211> LENGTH: 69
<212> TYPE: DNA
<213> ORGANISM: Artificial Sequence
<220> FEATURE:
<223> OTHER INFORMATION: cDNA Sequence of aMTD724 5'-primer

<400> SEQUENCE: 703

```
gggtttcata tggtggcggt gctggcggtg ctgccggcgc tggcgccggc aaatattacc    60
gttttctat                                                             69
```

<210> SEQ ID NO 704
<211> LENGTH: 69
<212> TYPE: DNA
<213> ORGANISM: Artificial Sequence
<220> FEATURE:
<223> OTHER INFORMATION: cDNA Sequence of aMTD725 5'-primer

<400> SEQUENCE: 704

```
gggtttcata tgattgcggt gctggcggtg gcgccggcgg tgctgccggc aaatattacc    60
gttttctat                                                             69
```

<210> SEQ ID NO 705
<211> LENGTH: 69
<212> TYPE: DNA
<213> ORGANISM: Artificial Sequence
<220> FEATURE:
<223> OTHER INFORMATION: cDNA Sequence of aMTD726 5'-primer

<400> SEQUENCE: 705

```
gggtttcata tgctggcggt ggcgattatt gcgccggcgg tggcgccggc aaatattacc    60
gttttctat                                                             69
```

<210> SEQ ID NO 706
<211> LENGTH: 69
<212> TYPE: DNA
<213> ORGANISM: Artificial Sequence

```
<220> FEATURE:
<223> OTHER INFORMATION: cDNA Sequence of aMTD727 5'-primer

<400> SEQUENCE: 706
gggtttcata tggtggcgct ggcgattgcg ctgccggcgg tgctgccggc aaatattacc      60
gttttctat                                                              69

<210> SEQ ID NO 707
<211> LENGTH: 69
<212> TYPE: DNA
<213> ORGANISM: Artificial Sequence
<220> FEATURE:
<223> OTHER INFORMATION: cDNA Sequence of aMTD743 5'-primer

<400> SEQUENCE: 707
gggtttcata tggcgattgc gattgcgctg gtgccggtgg cgctgccggc aaatattacc      60
gttttctat                                                              69

<210> SEQ ID NO 708
<211> LENGTH: 69
<212> TYPE: DNA
<213> ORGANISM: Artificial Sequence
<220> FEATURE:
<223> OTHER INFORMATION: cDNA Sequence of aMTD744 5'-primer

<400> SEQUENCE: 708
gggtttcata tggcggcggt ggtgattgtg gcgccggtgg cgctgccggc aaatattacc      60
gttttctat                                                              69

<210> SEQ ID NO 709
<211> LENGTH: 69
<212> TYPE: DNA
<213> ORGANISM: Artificial Sequence
<220> FEATURE:
<223> OTHER INFORMATION: cDNA Sequence of aMTD745 5'-primer

<400> SEQUENCE: 709
gggtttcata tggcggcgat tctggcgatt gtggcgccgc tggcgccggc aaatattacc      60
gttttctat                                                              69

<210> SEQ ID NO 710
<211> LENGTH: 69
<212> TYPE: DNA
<213> ORGANISM: Artificial Sequence
<220> FEATURE:
<223> OTHER INFORMATION: cDNA Sequence of aMTD746 5'-primer

<400> SEQUENCE: 710
gggtttcata tggtggcgat tattgtggtg gcgccggcgc tggcgccggc aaatattacc      60
gttttctat                                                              69

<210> SEQ ID NO 711
<211> LENGTH: 69
<212> TYPE: DNA
<213> ORGANISM: Artificial Sequence
<220> FEATURE:
<223> OTHER INFORMATION: cDNA Sequence of aMTD747 5'-primer

<400> SEQUENCE: 711
gggtttcata tggtggcgct gctggcgatt gcgccggcgc tggcgccggc aaatattacc      60
gttttctat                                                              69
```

```
<210> SEQ ID NO 712
<211> LENGTH: 69
<212> TYPE: DNA
<213> ORGANISM: Artificial Sequence
<220> FEATURE:
<223> OTHER INFORMATION: cDNA Sequence of aMTD750 5'-primer

<400> SEQUENCE: 712
gggtttcata tgctggcgat tgcggcgatt gcgccgctgg cgattccggc aaatattacc    60
gttttctat                                                            69

<210> SEQ ID NO 713
<211> LENGTH: 69
<212> TYPE: DNA
<213> ORGANISM: Artificial Sequence
<220> FEATURE:
<223> OTHER INFORMATION: cDNA Sequence of aMTD763 5'-primer

<400> SEQUENCE: 713
gggtttcata tggtggcggt gctgattgcg gtgccggcgc tggcgccggc aaatattacc    60
gttttctat                                                            69

<210> SEQ ID NO 714
<211> LENGTH: 69
<212> TYPE: DNA
<213> ORGANISM: Artificial Sequence
<220> FEATURE:
<223> OTHER INFORMATION: cDNA Sequence of aMTD764 5'-primer

<400> SEQUENCE: 714
gggtttcata tggcggtggc gctggcggtg ctgccggcgg tggtgccggc aaatattacc    60
gttttctat                                                            69

<210> SEQ ID NO 715
<211> LENGTH: 69
<212> TYPE: DNA
<213> ORGANISM: Artificial Sequence
<220> FEATURE:
<223> OTHER INFORMATION: cDNA Sequence of aMTD765 5'-primer

<400> SEQUENCE: 715
gggtttcata tggcggtggc gctggcggtg gtgccggcgg tgctgccggc aaatattacc    60
gttttctat                                                            69

<210> SEQ ID NO 716
<211> LENGTH: 69
<212> TYPE: DNA
<213> ORGANISM: Artificial Sequence
<220> FEATURE:
<223> OTHER INFORMATION: cDNA Sequence of aMTD766 5'-primer

<400> SEQUENCE: 716
gggtttcata tgattgtggt gattgcggtg gcgccggcgg tggcgccggc aaatattacc    60
gttttctat                                                            69

<210> SEQ ID NO 717
<211> LENGTH: 69
<212> TYPE: DNA
<213> ORGANISM: Artificial Sequence
<220> FEATURE:
<223> OTHER INFORMATION: cDNA Sequence of aMTD767 5'-primer

<400> SEQUENCE: 717
```

```
<210> SEQ ID NO 718
<211> LENGTH: 69
<212> TYPE: DNA
<213> ORGANISM: Artificial Sequence
<220> FEATURE:
<223> OTHER INFORMATION: cDNA Sequence of aMTD772 5'-primer

<400> SEQUENCE: 718
gggtttcata tgctgccggt ggcgccggtg attccgatta ttgtgccggc aaatattacc      60
gttttctat                                                             69

<210> SEQ ID NO 719
<211> LENGTH: 69
<212> TYPE: DNA
<213> ORGANISM: Artificial Sequence
<220> FEATURE:
<223> OTHER INFORMATION: cDNA Sequence of aMTD783 5'-primer

<400> SEQUENCE: 719
gggtttcata tgattgtggc gctggtgccg gcggtggcga ttgcgccggc aaatattacc      60
gttttctat                                                             69

<210> SEQ ID NO 720
<211> LENGTH: 69
<212> TYPE: DNA
<213> ORGANISM: Artificial Sequence
<220> FEATURE:
<223> OTHER INFORMATION: cDNA Sequence of aMTD784 5'-primer

<400> SEQUENCE: 720
gggtttcata tggtggcggc gctgccggcg gtggcgctgg tggtgccggc aaatattacc      60
gttttctat                                                             69

<210> SEQ ID NO 721
<211> LENGTH: 69
<212> TYPE: DNA
<213> ORGANISM: Artificial Sequence
<220> FEATURE:
<223> OTHER INFORMATION: cDNA Sequence of aMTD786 5'-primer

<400> SEQUENCE: 721
gggtttcata tgctggtggc gattgcgccg ctggcggtgc tggcgccggc aaatattacc      60
gttttctat                                                             69

<210> SEQ ID NO 722
<211> LENGTH: 69
<212> TYPE: DNA
<213> ORGANISM: Artificial Sequence
<220> FEATURE:
<223> OTHER INFORMATION: cDNA Sequence of aMTD787 5'-primer

<400> SEQUENCE: 722
gggtttcata tggcggtggc gctggtgccg gtgattgtgg cggcgccggc aaatattacc      60
gttttctat                                                             69

<210> SEQ ID NO 723
<211> LENGTH: 69
<212> TYPE: DNA
```

<213> ORGANISM: Artificial Sequence
<220> FEATURE:
<223> OTHER INFORMATION: cDNA Sequence of aMTD788 5'-primer

<400> SEQUENCE: 723
gggtttcata tggcgattgc ggtggcgatt gcgccggtgg cgctgccggc aaatattacc    60
gttttctat                                                            69

<210> SEQ ID NO 724
<211> LENGTH: 69
<212> TYPE: DNA
<213> ORGANISM: Artificial Sequence
<220> FEATURE:
<223> OTHER INFORMATION: cDNA Sequence of aMTD803 5'-primer

<400> SEQUENCE: 724
gggtttcata tggcgattgc gctggcggtg ccggtgctgg cgctgccggc aaatattacc    60
gttttctat                                                            69

<210> SEQ ID NO 725
<211> LENGTH: 69
<212> TYPE: DNA
<213> ORGANISM: Artificial Sequence
<220> FEATURE:
<223> OTHER INFORMATION: cDNA Sequence of aMTD805 5'-primer

<400> SEQUENCE: 725
gggtttcata tgctggtgct gattgcggcg gcgccgattg cgctgccggc aaatattacc    60
gttttctat                                                            69

<210> SEQ ID NO 726
<211> LENGTH: 69
<212> TYPE: DNA
<213> ORGANISM: Artificial Sequence
<220> FEATURE:
<223> OTHER INFORMATION: cDNA Sequence of aMTD806 5'-primer

<400> SEQUENCE: 726
gggtttcata tgctggtggc gctggcggtg ccggcggcgg tgctgccggc aaatattacc    60
gttttctat                                                            69

<210> SEQ ID NO 727
<211> LENGTH: 69
<212> TYPE: DNA
<213> ORGANISM: Artificial Sequence
<220> FEATURE:
<223> OTHER INFORMATION: cDNA Sequence of aMTD807 5'-primer

<400> SEQUENCE: 727
gggtttcata tggcggtggc gctggcggtg ccggcgctgg tgctgccggc aaatattacc    60
gttttctat                                                            69

<210> SEQ ID NO 728
<211> LENGTH: 69
<212> TYPE: DNA
<213> ORGANISM: Artificial Sequence
<220> FEATURE:
<223> OTHER INFORMATION: cDNA Sequence of aMTD808 5'-primer

<400> SEQUENCE: 728
gggtttcata tgctggtggt gctggcggcg gcgccgctgg cggtgccggc aaatattacc    60
gttttctat                                                            69

<210> SEQ ID NO 729
<211> LENGTH: 69
<212> TYPE: DNA
<213> ORGANISM: Artificial Sequence
<220> FEATURE:
<223> OTHER INFORMATION: cDNA Sequence of aMTD809 5'-primer

<400> SEQUENCE: 729
gggtttcata tgctgattgt gctggcggcg ccggcgctgg cggcgccggc aaatattacc    60
gttttctat                                                           69

<210> SEQ ID NO 730
<211> LENGTH: 69
<212> TYPE: DNA
<213> ORGANISM: Artificial Sequence
<220> FEATURE:
<223> OTHER INFORMATION: cDNA Sequence of aMTD810 5'-primer

<400> SEQUENCE: 730
gggtttcata tggtgattgt gctggcggcg ccggcgctgg cggcgccggc aaatattacc    60
gttttctat                                                           69

<210> SEQ ID NO 731
<211> LENGTH: 69
<212> TYPE: DNA
<213> ORGANISM: Artificial Sequence
<220> FEATURE:
<223> OTHER INFORMATION: cDNA Sequence of aMTD811 5'-primer

<400> SEQUENCE: 731
gggtttcata tggcggtggt gctggcggtg ccggcgctgg cggtgccggc aaatattacc    60
gttttctat                                                           69

<210> SEQ ID NO 732
<211> LENGTH: 69
<212> TYPE: DNA
<213> ORGANISM: Artificial Sequence
<220> FEATURE:
<223> OTHER INFORMATION: cDNA Sequence of aMTD824 5'-primer

<400> SEQUENCE: 732
gggtttcata tgctgattat tgtggcggcg gcgccggcgg tggcgccggc aaatattacc    60
gttttctat                                                           69

<210> SEQ ID NO 733
<211> LENGTH: 69
<212> TYPE: DNA
<213> ORGANISM: Artificial Sequence
<220> FEATURE:
<223> OTHER INFORMATION: cDNA Sequence of aMTD825 5'-primer

<400> SEQUENCE: 733
gggtttcata tgattgtggc ggtgattgtg gcgccggcgg tggcgccggc aaatattacc    60
gttttctat                                                           69

<210> SEQ ID NO 734
<211> LENGTH: 69
<212> TYPE: DNA
<213> ORGANISM: Artificial Sequence
<220> FEATURE:
<223> OTHER INFORMATION: cDNA Sequence of aMTD826 5'-primer

<400> SEQUENCE: 734
gggtttcata tgctggtggc gctggcggcg ccgattattg cggtgccggc aaatattacc    60
gttttctat    69

<210> SEQ ID NO 735
<211> LENGTH: 69
<212> TYPE: DNA
<213> ORGANISM: Artificial Sequence
<220> FEATURE:
<223> OTHER INFORMATION: cDNA Sequence of aMTD827 5'-primer

<400> SEQUENCE: 735
gggtttcata tgattgcggc ggtgctggcg gcgccggcgc tggtgccggc aaatattacc    60
gttttctat    69

<210> SEQ ID NO 736
<211> LENGTH: 69
<212> TYPE: DNA
<213> ORGANISM: Artificial Sequence
<220> FEATURE:
<223> OTHER INFORMATION: cDNA Sequence of aMTD828 5'-primer

<400> SEQUENCE: 736
gggtttcata tgattgcgct gctggcggcg ccgattattg cggtgccggc aaatattacc    60
gttttctat    69

<210> SEQ ID NO 737
<211> LENGTH: 69
<212> TYPE: DNA
<213> ORGANISM: Artificial Sequence
<220> FEATURE:
<223> OTHER INFORMATION: cDNA Sequence of aMTD829 5'-primer

<400> SEQUENCE: 737
gggtttcata tggcggcgct ggcgctggtg gcgccggtga ttgtgccggc aaatattacc    60
gttttctat    69

<210> SEQ ID NO 738
<211> LENGTH: 69
<212> TYPE: DNA
<213> ORGANISM: Artificial Sequence
<220> FEATURE:
<223> OTHER INFORMATION: cDNA Sequence of aMTD830 5'-primer

<400> SEQUENCE: 738
gggtttcata tgattgcgct ggtggcggcg ccggtggcgc tggtgccggc aaatattacc    60
gttttctat    69

<210> SEQ ID NO 739
<211> LENGTH: 69
<212> TYPE: DNA
<213> ORGANISM: Artificial Sequence
<220> FEATURE:
<223> OTHER INFORMATION: cDNA Sequence of aMTD831 5'-primer

<400> SEQUENCE: 739
gggtttcata tgattattgt ggcggtggcg ccggcggcga ttgtgccggc aaatattacc    60
gttttctat    69

<210> SEQ ID NO 740
<211> LENGTH: 69

```
<212> TYPE: DNA
<213> ORGANISM: Artificial Sequence
<220> FEATURE:
<223> OTHER INFORMATION: cDNA Sequence of aMTD832 5'-primer

<400> SEQUENCE: 740
gggtttcata tggcggtggc ggcgattgtg ccggtgattg tggcgccggc aaatattacc       60
gttttctat                                                              69

<210> SEQ ID NO 741
<211> LENGTH: 69
<212> TYPE: DNA
<213> ORGANISM: Artificial Sequence
<220> FEATURE:
<223> OTHER INFORMATION: cDNA Sequence of aMTD843 5'-primer

<400> SEQUENCE: 741
gggtttcata tggcggtgct ggtgctggtg gcgccggcgg cggcgccggc aaatattacc       60
gttttctat                                                              69

<210> SEQ ID NO 742
<211> LENGTH: 69
<212> TYPE: DNA
<213> ORGANISM: Artificial Sequence
<220> FEATURE:
<223> OTHER INFORMATION: cDNA Sequence of aMTD844 5'-primer

<400> SEQUENCE: 742
gggtttcata tggtggtggc gctgctggcg ccgctgattg cggcgccggc aaatattacc       60
gttttctat                                                              69

<210> SEQ ID NO 743
<211> LENGTH: 69
<212> TYPE: DNA
<213> ORGANISM: Artificial Sequence
<220> FEATURE:
<223> OTHER INFORMATION: cDNA Sequence of aMTD845 5'-primer

<400> SEQUENCE: 743
gggtttcata tggcggcggt ggtgattgcg ccgctgctgg cggtgccggc aaatattacc       60
gttttctat                                                              69

<210> SEQ ID NO 744
<211> LENGTH: 69
<212> TYPE: DNA
<213> ORGANISM: Artificial Sequence
<220> FEATURE:
<223> OTHER INFORMATION: cDNA Sequence of aMTD846 5'-primer

<400> SEQUENCE: 744
gggtttcata tgattgcggt ggcggtggcg gcgccgctgc tggtgccggc aaatattacc       60
gttttctat                                                              69

<210> SEQ ID NO 745
<211> LENGTH: 69
<212> TYPE: DNA
<213> ORGANISM: Artificial Sequence
<220> FEATURE:
<223> OTHER INFORMATION: cDNA Sequence of aMTD847 5'-primer

<400> SEQUENCE: 745
gggtttcata tgctggtggc gattgtggtg ctgccggcgg tggcgccggc aaatattacc       60
``` gttttctat                                                                        69

<210> SEQ ID NO 746
<211> LENGTH: 69
<212> TYPE: DNA
<213> ORGANISM: Artificial Sequence
<220> FEATURE:
<223> OTHER INFORMATION: cDNA Sequence of aMTD848 5'-primer

<400> SEQUENCE: 746
gggtttcata tggcggtggc gattgtggtg ctgccggcgg tggcgccggc aaatattacc    60
gttttctat                                                                        69

<210> SEQ ID NO 747
<211> LENGTH: 69
<212> TYPE: DNA
<213> ORGANISM: Artificial Sequence
<220> FEATURE:
<223> OTHER INFORMATION: cDNA Sequence of aMTD849 5'-primer

<400> SEQUENCE: 747
gggtttcata tggcggtgat tctgctggcg ccgctgattg cggcgccggc aaatattacc    60
gttttctat                                                                        69

<210> SEQ ID NO 748
<211> LENGTH: 69
<212> TYPE: DNA
<213> ORGANISM: Artificial Sequence
<220> FEATURE:
<223> OTHER INFORMATION: cDNA Sequence of aMTD850 5'-primer

<400> SEQUENCE: 748
gggtttcata tgctggtgat tgcgctggcg gcgccggtgg cgctgccggc aaatattacc    60
gttttctat                                                                        69

<210> SEQ ID NO 749
<211> LENGTH: 69
<212> TYPE: DNA
<213> ORGANISM: Artificial Sequence
<220> FEATURE:
<223> OTHER INFORMATION: cDNA Sequence of aMTD851 5'-primer

<400> SEQUENCE: 749
gggtttcata tggtgctggc ggtggtgctg ccggcggtgg cgctgccggc aaatattacc    60
gttttctat                                                                        69

<210> SEQ ID NO 750
<211> LENGTH: 69
<212> TYPE: DNA
<213> ORGANISM: Artificial Sequence
<220> FEATURE:
<223> OTHER INFORMATION: cDNA Sequence of aMTD852 5'-primer

<400> SEQUENCE: 750
gggtttcata tggtgctggc ggtggcggcg ccggcggtgc tgctgccggc aaatattacc    60
gttttctat                                                                        69

<210> SEQ ID NO 751
<211> LENGTH: 69
<212> TYPE: DNA
<213> ORGANISM: Artificial Sequence
<220> FEATURE:
<223> OTHER INFORMATION: cDNA Sequence of aMTD863 5'-primer

<400> SEQUENCE: 751
gggtttcata tggcggcggt ggtgctgctg ccgattattg cggcgccggc aaatattacc    60
gttttctat                                                           69

<210> SEQ ID NO 752
<211> LENGTH: 69
<212> TYPE: DNA
<213> ORGANISM: Artificial Sequence
<220> FEATURE:
<223> OTHER INFORMATION: cDNA Sequence of aMTD864 5'-primer

<400> SEQUENCE: 752
gggtttcata tggcgctgct ggtgattgcg ccggcgattg cggtgccggc aaatattacc    60
gttttctat                                                           69

<210> SEQ ID NO 753
<211> LENGTH: 69
<212> TYPE: DNA
<213> ORGANISM: Artificial Sequence
<220> FEATURE:
<223> OTHER INFORMATION: cDNA Sequence of aMTD865 5'-primer

<400> SEQUENCE: 753
gggtttcata tggcggtgct ggtgattgcg gtgccggcga ttgcgccggc aaatattacc    60
gttttctat                                                           69

<210> SEQ ID NO 754
<211> LENGTH: 69
<212> TYPE: DNA
<213> ORGANISM: Artificial Sequence
<220> FEATURE:
<223> OTHER INFORMATION: cDNA Sequence of aMTD867 5'-primer

<400> SEQUENCE: 754
gggtttcata tggcgctgct ggtggtgatt gcgccgctgg cggcgccggc aaatattacc    60
gttttctat                                                           69

<210> SEQ ID NO 755
<211> LENGTH: 69
<212> TYPE: DNA
<213> ORGANISM: Artificial Sequence
<220> FEATURE:
<223> OTHER INFORMATION: cDNA Sequence of aMTD868 5'-primer

<400> SEQUENCE: 755
gggtttcata tggtgctggt ggcggcgatt ctgccggcgg cgattccggc aaatattacc    60
gttttctat                                                           69

<210> SEQ ID NO 756
<211> LENGTH: 69
<212> TYPE: DNA
<213> ORGANISM: Artificial Sequence
<220> FEATURE:
<223> OTHER INFORMATION: cDNA Sequence of aMTD870 5'-primer

<400> SEQUENCE: 756
gggtttcata tggtgctggt ggcggcggtg ctgccgattg cggcgccggc aaatattacc    60
gttttctat                                                           69

<210> SEQ ID NO 757

```
<211> LENGTH: 69
<212> TYPE: DNA
<213> ORGANISM: Artificial Sequence
<220> FEATURE:
<223> OTHER INFORMATION: cDNA Sequence of aMTD872 5'-primer

<400> SEQUENCE: 757
gggtttcata tggtgctggc ggcggcggtg ctgccgctgg tggtgccggc aaatattacc    60
gttttctat                                                            69

<210> SEQ ID NO 758
<211> LENGTH: 69
<212> TYPE: DNA
<213> ORGANISM: Artificial Sequence
<220> FEATURE:
<223> OTHER INFORMATION: cDNA Sequence of aMTD875 5'-primer

<400> SEQUENCE: 758
gggtttcata tggcgattgc gattgtggtg ccggcggtgg cggtgccggc aaatattacc    60
gttttctat                                                            69

<210> SEQ ID NO 759
<211> LENGTH: 69
<212> TYPE: DNA
<213> ORGANISM: Artificial Sequence
<220> FEATURE:
<223> OTHER INFORMATION: cDNA Sequence of aMTD877 5'-primer

<400> SEQUENCE: 759
gggtttcata tggtggcgat tattgcggtg ccggcggtgg tggcgccggc aaatattacc    60
gttttctat                                                            69

<210> SEQ ID NO 760
<211> LENGTH: 69
<212> TYPE: DNA
<213> ORGANISM: Artificial Sequence
<220> FEATURE:
<223> OTHER INFORMATION: cDNA Sequence of aMTD878 5'-primer

<400> SEQUENCE: 760
gggtttcata tgattgtggc gctggtggcg ccggcggcgg tggtgccggc aaatattacc    60
gttttctat                                                            69

<210> SEQ ID NO 761
<211> LENGTH: 69
<212> TYPE: DNA
<213> ORGANISM: Artificial Sequence
<220> FEATURE:
<223> OTHER INFORMATION: cDNA Sequence of aMTD879 5'-primer

<400> SEQUENCE: 761
gggtttcata tggcggcgat tgtgctgctg ccggcggtgg tggtgccggc aaatattacc    60
gttttctat                                                            69

<210> SEQ ID NO 762
<211> LENGTH: 69
<212> TYPE: DNA
<213> ORGANISM: Artificial Sequence
<220> FEATURE:
<223> OTHER INFORMATION: cDNA Sequence of aMTD881 5'-primer

<400> SEQUENCE: 762
gggtttcata tggcggcgct gattgtggtg ccggcggtgg cggtgccggc aaatattacc    60
```

```
gttttctat                                                              69

<210> SEQ ID NO 763
<211> LENGTH: 69
<212> TYPE: DNA
<213> ORGANISM: Artificial Sequence
<220> FEATURE:
<223> OTHER INFORMATION: cDNA Sequence of aMTD882 5'-primer

<400> SEQUENCE: 763
gggtttcata tggcgattgc gctggtggtg ccggcggtgg cggtgccggc aaatattacc       60
gttttctat                                                              69

<210> SEQ ID NO 764
<211> LENGTH: 69
<212> TYPE: DNA
<213> ORGANISM: Artificial Sequence
<220> FEATURE:
<223> OTHER INFORMATION: cDNA Sequence of aMTD883 5'-primer

<400> SEQUENCE: 764
gggtttcata tgctggcgat tgtgccggcg gcgattgcgg cgctgccggc aaatattacc       60
gttttctat                                                              69

<210> SEQ ID NO 765
<211> LENGTH: 69
<212> TYPE: DNA
<213> ORGANISM: Artificial Sequence
<220> FEATURE:
<223> OTHER INFORMATION: cDNA Sequence of aMTD884 5'-primer

<400> SEQUENCE: 765
gggtttcata tggtgctgat tgtgccggcg gcgattgcgg cgctgccggc aaatattacc       60
gttttctat                                                              69

<210> SEQ ID NO 766
<211> LENGTH: 69
<212> TYPE: DNA
<213> ORGANISM: Artificial Sequence
<220> FEATURE:
<223> OTHER INFORMATION: cDNA Sequence of aMTD885 5'-primer

<400> SEQUENCE: 766
gggtttcata tgctggtggc gattgcgccg gcggtggcgg tgctgccggc aaatattacc       60
gttttctat                                                              69

<210> SEQ ID NO 767
<211> LENGTH: 69
<212> TYPE: DNA
<213> ORGANISM: Artificial Sequence
<220> FEATURE:
<223> OTHER INFORMATION: cDNA Sequence of aMTD886 5'-primer

<400> SEQUENCE: 767
gggtttcata tggtgctggc ggtgccggcg gcgattgcgg cgctgccggc aaatattacc       60
gttttctat                                                              69

<210> SEQ ID NO 768
<211> LENGTH: 69
<212> TYPE: DNA
<213> ORGANISM: Artificial Sequence
<220> FEATURE:
```

<223> OTHER INFORMATION: cDNA Sequence of aMTD887 5'-primer

<400> SEQUENCE: 768
gggtttcata tggtgctggc ggtggcgccg gcggtggcgg tgctgccggc aaatattacc    60
gttttctat                                                            69

<210> SEQ ID NO 769
<211> LENGTH: 69
<212> TYPE: DNA
<213> ORGANISM: Artificial Sequence
<220> FEATURE:
<223> OTHER INFORMATION: cDNA Sequence of aMTD888 5'-primer

<400> SEQUENCE: 769
gggtttcata tgattctggc ggtggtggcg attccggcgg cggcgccggc aaatattacc    60
gttttctat                                                            69

<210> SEQ ID NO 770
<211> LENGTH: 69
<212> TYPE: DNA
<213> ORGANISM: Artificial Sequence
<220> FEATURE:
<223> OTHER INFORMATION: cDNA Sequence of aMTD889 5'-primer

<400> SEQUENCE: 770
gggtttcata tgattctggt ggcggcggcg ccgattgcgg cgctgccggc aaatattacc    60
gttttctat                                                            69

<210> SEQ ID NO 771
<211> LENGTH: 69
<212> TYPE: DNA
<213> ORGANISM: Artificial Sequence
<220> FEATURE:
<223> OTHER INFORMATION: cDNA Sequence of aMTD891 5'-primer

<400> SEQUENCE: 771
gggtttcata tgattctggc ggtggcggcg attccggcgg cgctgccggc aaatattacc    60
gttttctat                                                            69

<210> SEQ ID NO 772
<211> LENGTH: 69
<212> TYPE: DNA
<213> ORGANISM: Artificial Sequence
<220> FEATURE:
<223> OTHER INFORMATION: cDNA Sequence of aMTD893 5'-primer

<400> SEQUENCE: 772
gggtttcata tggtgattgc gattccggcg attctggcgg cggcgccggc aaatattacc    60
gttttctat                                                            69

<210> SEQ ID NO 773
<211> LENGTH: 69
<212> TYPE: DNA
<213> ORGANISM: Artificial Sequence
<220> FEATURE:
<223> OTHER INFORMATION: cDNA Sequence of aMTD895 5'-primer

<400> SEQUENCE: 773
gggtttcata tggcgattat tattgtggtg ccggcgattg cggcgccggc aaatattacc    60
gttttctat                                                            69

<210> SEQ ID NO 774
<211> LENGTH: 69
<212> TYPE: DNA
<213> ORGANISM: Artificial Sequence
<220> FEATURE:
<223> OTHER INFORMATION: cDNA Sequence of aMTD896 5'-primer

<400> SEQUENCE: 774
gggtttcata tggcgattct gattgtggtg gcgccgattg cggcgccggc aaatattacc    60
gttttctat                                                            69

<210> SEQ ID NO 775
<211> LENGTH: 69
<212> TYPE: DNA
<213> ORGANISM: Artificial Sequence
<220> FEATURE:
<223> OTHER INFORMATION: cDNA Sequence of aMTD897 5'-primer

<400> SEQUENCE: 775
gggtttcata tggcggtgat tgtgccggtg gcgattattg cggcgccggc aaatattacc    60
gttttctat                                                            69

<210> SEQ ID NO 776
<211> LENGTH: 69
<212> TYPE: DNA
<213> ORGANISM: Artificial Sequence
<220> FEATURE:
<223> OTHER INFORMATION: cDNA Sequence of aMTD899 5'-primer

<400> SEQUENCE: 776
gggtttcata tggcggtggt gattgcgctg ccggcggtgg tggcgccggc aaatattacc    60
gttttctat                                                            69

<210> SEQ ID NO 777
<211> LENGTH: 69
<212> TYPE: DNA
<213> ORGANISM: Artificial Sequence
<220> FEATURE:
<223> OTHER INFORMATION: cDNA Sequence of aMTD900 5'-primer

<400> SEQUENCE: 777
gggtttcata tggcgctggt ggcggtgatt gcgccggtgg tggcgccggc aaatattacc    60
gttttctat                                                            69

<210> SEQ ID NO 778
<211> LENGTH: 69
<212> TYPE: DNA
<213> ORGANISM: Artificial Sequence
<220> FEATURE:
<223> OTHER INFORMATION: cDNA Sequence of aMTD901 5'-primer

<400> SEQUENCE: 778
gggtttcata tggcgctggt ggcggtgctg ccggcggtgg cggtgccggc aaatattacc    60
gttttctat                                                            69

<210> SEQ ID NO 779
<211> LENGTH: 69
<212> TYPE: DNA
<213> ORGANISM: Artificial Sequence
<220> FEATURE:
<223> OTHER INFORMATION: cDNA Sequence of aMTD902 5'-primer

<400> SEQUENCE: 779
gggtttcata tggcgctggt ggcgccgctg ctggcggtgg cggtgccggc aaatattacc    60
gttttctat                                                             69

<210> SEQ ID NO 780
<211> LENGTH: 69
<212> TYPE: DNA
<213> ORGANISM: Artificial Sequence
<220> FEATURE:
<223> OTHER INFORMATION: cDNA Sequence of aMTD904 5'-primer

<400> SEQUENCE: 780
gggtttcata tggcggtgct ggcggtggtg gcgccggtgg tggcgccggc aaatattacc    60
gttttctat                                                             69

<210> SEQ ID NO 781
<211> LENGTH: 69
<212> TYPE: DNA
<213> ORGANISM: Artificial Sequence
<220> FEATURE:
<223> OTHER INFORMATION: cDNA Sequence of aMTD905 5'-primer

<400> SEQUENCE: 781
gggtttcata tggcggtgat tgcggtggcg ccgctggtgg tggcgccggc aaatattacc    60
gttttctat                                                             69

<210> SEQ ID NO 782
<211> LENGTH: 69
<212> TYPE: DNA
<213> ORGANISM: Artificial Sequence
<220> FEATURE:
<223> OTHER INFORMATION: cDNA Sequence of aMTD906 5'-primer

<400> SEQUENCE: 782
gggtttcata tggcggtgat tgcgctggcg ccggtggtgg tggcgccggc aaatattacc    60
gttttctat                                                             69

<210> SEQ ID NO 783
<211> LENGTH: 69
<212> TYPE: DNA
<213> ORGANISM: Artificial Sequence
<220> FEATURE:
<223> OTHER INFORMATION: cDNA Sequence of aMTD907 5'-primer

<400> SEQUENCE: 783
gggtttcata tggtggcgat tgcgctggcg ccggtggtgg tggcgccggc aaatattacc    60
gttttctat                                                             69

<210> SEQ ID NO 784
<211> LENGTH: 69
<212> TYPE: DNA
<213> ORGANISM: Artificial Sequence
<220> FEATURE:
<223> OTHER INFORMATION: cDNA Sequence of aMTD908 5'-primer

<400> SEQUENCE: 784
gggtttcata tggtggcgct ggcgctggcg ccggtggtgg tggcgccggc aaatattacc    60
gttttctat                                                             69

<210> SEQ ID NO 785
<211> LENGTH: 69
<212> TYPE: DNA
<213> ORGANISM: Artificial Sequence -continued
<220> FEATURE:
<223> OTHER INFORMATION: cDNA Sequence of aMTD910 5'-primer

<400> SEQUENCE: 785
gggtttcata tggtggcggc gctgctgccg gcggtggtgg tggcgccggc aaatattacc    60
gttttctat                                                            69

<210> SEQ ID NO 786
<211> LENGTH: 69
<212> TYPE: DNA
<213> ORGANISM: Artificial Sequence
<220> FEATURE:
<223> OTHER INFORMATION: cDNA Sequence of aMTD911 5'-primer

<400> SEQUENCE: 786
gggtttcata tggtggcgct ggcgctgccg gcggtggtgg tggcgccggc aaatattacc    60
gttttctat                                                            69

<210> SEQ ID NO 787
<211> LENGTH: 69
<212> TYPE: DNA
<213> ORGANISM: Artificial Sequence
<220> FEATURE:
<223> OTHER INFORMATION: cDNA Sequence of aMTD912 5'-primer

<400> SEQUENCE: 787
gggtttcata tggtggcgct gctggcgccg gcggtggtgg tggcgccggc aaatattacc    60
gttttctat                                                            69

<210> SEQ ID NO 788
<211> LENGTH: 69
<212> TYPE: DNA
<213> ORGANISM: Artificial Sequence
<220> FEATURE:
<223> OTHER INFORMATION: cDNA Sequence of aMTD921 5'-primer

<400> SEQUENCE: 788
gggtttcata tgatttggtg gtttgtggtg ctgccgctgg tggtgccggc aaatattacc    60
gttttctat                                                            69

<210> SEQ ID NO 789
<211> LENGTH: 69
<212> TYPE: DNA
<213> ORGANISM: Artificial Sequence
<220> FEATURE:
<223> OTHER INFORMATION: cDNA Sequence of aMTD922 5'-primer

<400> SEQUENCE: 789
gggtttcata tgtggtatgt gattttgtg ctgccgctgg tggtgccggc aaatattacc     60
gttttctat                                                            69

<210> SEQ ID NO 790
<211> LENGTH: 69
<212> TYPE: DNA
<213> ORGANISM: Artificial Sequence
<220> FEATURE:
<223> OTHER INFORMATION: cDNA Sequence of aMTD931 5'-primer

<400> SEQUENCE: 790
gggtttcata tggcggtgct gattgcgccg gcgattctgg cggcggcggc aaatattacc    60
gttttctat                                                            69

```
<210> SEQ ID NO 791
<211> LENGTH: 69
<212> TYPE: DNA
<213> ORGANISM: Artificial Sequence
<220> FEATURE:
<223> OTHER INFORMATION: cDNA Sequence of aMTD934 5'-primer

<400> SEQUENCE: 791
gggtttcata tgctgattct ggcgccggcg gcggtggtgg cggcggcggc aaatattacc     60
gttttctat                                                             69

<210> SEQ ID NO 792
<211> LENGTH: 69
<212> TYPE: DNA
<213> ORGANISM: Artificial Sequence
<220> FEATURE:
<223> OTHER INFORMATION: cDNA Sequence of aMTD935 5'-primer

<400> SEQUENCE: 792
gggtttcata tggcgctgct gattctgccg gcggcggcgg tggcggcggc aaatattacc     60
gttttctat                                                             69

<210> SEQ ID NO 793
<211> LENGTH: 69
<212> TYPE: DNA
<213> ORGANISM: Artificial Sequence
<220> FEATURE:
<223> OTHER INFORMATION: cDNA Sequence of aMTD936 5'-primer

<400> SEQUENCE: 793
gggtttcata tggcgctgct gattctggcg gcggcggtgg cggcgccggc aaatattacc     60
gttttctat                                                             69

<210> SEQ ID NO 794
<211> LENGTH: 69
<212> TYPE: DNA
<213> ORGANISM: Artificial Sequence
<220> FEATURE:
<223> OTHER INFORMATION: cDNA Sequence of aMTD937 5'-primer

<400> SEQUENCE: 794
gggtttcata tggtgccggt gctggtgccg ctgccggtgc cggtggtggc aaatattacc     60
gttttctat                                                             69

<210> SEQ ID NO 795
<211> LENGTH: 69
<212> TYPE: DNA
<213> ORGANISM: Artificial Sequence
<220> FEATURE:
<223> OTHER INFORMATION: cDNA Sequence of aMTD938 5'-primer

<400> SEQUENCE: 795
gggtttcata tggtgccggt gctgctgccg gtggtggtgc cggtgccggc aaatattacc     60
gttttctat                                                             69

<210> SEQ ID NO 796
<211> LENGTH: 69
<212> TYPE: DNA
<213> ORGANISM: Artificial Sequence
<220> FEATURE:
<223> OTHER INFORMATION: cDNA Sequence of aMTD947 5'-primer

<400> SEQUENCE: 796
```
gggtttcata tgtgctatta taatcagcag tccaataata ataatcaggc aaatattacc    60
gttttctat    69

<210> SEQ ID NO 797
<211> LENGTH: 69
<212> TYPE: DNA
<213> ORGANISM: Artificial Sequence
<220> FEATURE:
<223> OTHER INFORMATION: cDNA Sequence of aMTD949 5'-primer

<400> SEQUENCE: 797
gggtttcata tgtccggcaa ttcctgccag cagtgcggca attcctccgc aaatattacc    60
gttttctat    69

<210> SEQ ID NO 798
<211> LENGTH: 39
<212> TYPE: DNA
<213> ORGANISM: Artificial Sequence
<220> FEATURE:
<223> OTHER INFORMATION: cDNA Sequence of aMTD 3'-primer

<400> SEQUENCE: 798
cgcgtcgact tacctcggct gcaccggcac ggagatgac    39

<210> SEQ ID NO 799
<211> LENGTH: 184
<212> TYPE: PRT
<213> ORGANISM: Artificial Sequence
<220> FEATURE:
<223> OTHER INFORMATION: Amino acid Sequence of SDA

<400> SEQUENCE: 799

Met Ala Asn Ile Thr Val Phe Tyr Asn Glu Asp Phe Gln Gly Lys Gln
1               5                   10                  15

Val Asp Leu Pro Pro Gly Asn Tyr Thr Arg Ala Gln Leu Ala Ala Leu
            20                  25                  30

Gly Ile Glu Asn Asn Thr Ile Ser Ser Val Lys Val Pro Pro Gly Val
        35                  40                  45

Lys Ala Ile Leu Tyr Gln Asn Asp Gly Phe Ala Gly Asp Gln Ile Glu
    50                  55                  60

Val Val Ala Asn Ala Glu Glu Leu Gly Pro Leu Asn Asn Asn Val Ser
65                  70                  75                  80

Ser Ile Arg Val Ile Ser Val Pro Val Gln Pro Arg Met Ala Asn Ile
                85                  90                  95

Thr Val Phe Tyr Asn Glu Asp Phe Gln Gly Lys Gln Val Asp Leu Pro
            100                 105                 110

Pro Gly Asn Tyr Thr Arg Ala Gln Leu Ala Ala Leu Gly Ile Glu Asn
        115                 120                 125

Asn Thr Ile Ser Ser Val Lys Val Pro Pro Gly Val Lys Ala Ile Leu
    130                 135                 140

Tyr Gln Asn Asp Gly Phe Ala Gly Asp Gln Ile Glu Val Val Ala Asn
145                 150                 155                 160

Ala Glu Glu Leu Gly Pro Leu Asn Asn Asn Val Ser Ser Ile Arg Val
                165                 170                 175

Ile Ser Val Pro Val Gln Pro Arg
            180

<210> SEQ ID NO 800

```
<211> LENGTH: 99
<212> TYPE: PRT
<213> ORGANISM: Artificial Sequence
<220> FEATURE:
<223> OTHER INFORMATION: Amino acid Sequence of SDB

<400> SEQUENCE: 800

Met Ala Glu Gln Ser Asp Lys Asp Val Lys Tyr Tyr Thr Leu Glu Glu
1               5                   10                  15

Ile Gln Lys His Lys Asp Ser Lys Ser Thr Trp Val Ile Leu His His
            20                  25                  30

Lys Val Tyr Asp Leu Thr Lys Phe Leu Glu Glu His Pro Gly Gly Glu
        35                  40                  45

Glu Val Leu Gly Glu Gln Ala Gly Gly Asp Ala Thr Glu Asn Phe Glu
    50                  55                  60

Asp Val Gly His Ser Thr Asp Ala Arg Glu Leu Ser Lys Thr Tyr Ile
65                  70                  75                  80

Ile Gly Glu Leu His Pro Asp Asp Arg Ser Lys Ile Ala Lys Pro Ser
                85                  90                  95

Glu Thr Leu

<210> SEQ ID NO 801
<211> LENGTH: 109
<212> TYPE: PRT
<213> ORGANISM: Artificial Sequence
<220> FEATURE:
<223> OTHER INFORMATION: Amino acid Sequence of SDC

<400> SEQUENCE: 801

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 802
<211> LENGTH: 208
<212> TYPE: PRT
<213> ORGANISM: Artificial Sequence
<220> FEATURE:
<223> OTHER INFORMATION: Amino acid Sequence of SDD

<400> SEQUENCE: 802

Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
```

```
                50                  55                  60
Val Lys Lys Lys Leu Pro Glu Gly Val Lys Met Thr Lys Tyr His Val
 65                  70                  75                  80

Asn Phe Met Gly Gly Asp Leu Gly Lys Asp Leu Thr Gln Ala Trp Ala
                 85                  90                  95

Val Ala Met Ala Leu Gly Val Glu Asp Lys Val Thr Val Pro Leu Phe
                100                 105                 110

Glu Gly Val Gln Lys Thr Gln Thr Ile Arg Ser Ala Ser Asp Ile Arg
                115                 120                 125

Asp Val Phe Ile Asn Ala Gly Ile Lys Gly Glu Glu Tyr Asp Ala Ala
                130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
                180                 185                 190

Phe Val Gln Gln Tyr Ala Asp Thr Val Lys Tyr Leu Ser Glu Lys Lys
                195                 200                 205

<210> SEQ ID NO 803
<211> LENGTH: 100
<212> TYPE: PRT
<213> ORGANISM: Artificial Sequence
<220> FEATURE:
<223> OTHER INFORMATION: Amino acid Sequence of SDE

<400> SEQUENCE: 803

Gly Ser Leu Gln Asp Ser Glu Val Asn Gln Glu Ala Lys Pro Glu Val
  1               5                  10                  15

Lys Pro Glu Val Lys Pro Glu Thr His Ile Asn Leu Lys Val Ser Asp
                 20                  25                  30

Gly Ser Ser Glu Ile Phe Phe Lys Ile Lys Lys Thr Thr Pro Leu Arg
                 35                  40                  45

Arg Leu Met Glu Ala Phe Ala Lys Arg Gln Gly Lys Glu Met Asp Ser
 50                  55                  60

Leu Thr Phe Leu Tyr Asp Gly Ile Glu Ile Gln Ala Asp Gln Thr Pro
 65                  70                  75                  80

Glu Asp Leu Asp Met Glu Asp Asn Asp Ile Ile Glu Ala His Arg Glu
                 85                  90                  95

Gln Ile Gly Gly
                100

<210> SEQ ID NO 804
<211> LENGTH: 297
<212> TYPE: PRT
<213> ORGANISM: Artificial Sequence
<220> FEATURE:
<223> OTHER INFORMATION: Amino acid Sequence of SDF

<400> SEQUENCE: 804

Gly Ser Glu Ile Gly Thr Gly Phe Pro Phe Asp Pro His Tyr Val Glu
  1               5                  10                  15

Val Leu Gly Glu Arg Met His Tyr Val Asp Val Gly Pro Arg Asp Gly
                 20                  25                  30

Thr Pro Val Leu Phe Leu His Gly Asn Pro Thr Ser Ser Tyr Val Trp
                 35                  40                  45
```

Arg Asn Ile Ile Pro His Val Ala Pro Thr His Arg Cys Ile Ala Pro
 50                  55                  60

Asp Leu Ile Gly Met Gly Lys Ser Asp Lys Pro Asp Leu Gly Tyr Phe
 65                  70                  75                  80

Phe Asp Asp His Val Arg Phe Met Asp Ala Phe Ile Glu Ala Leu Gly
                 85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
290                 295

<210> SEQ ID NO 805
<211> LENGTH: 99
<212> TYPE: PRT
<213> ORGANISM: Artificial Sequence
<220> FEATURE:
<223> OTHER INFORMATION: Amino acid Sequence of SDB for deimmunization

<400> SEQUENCE: 805

Met Ala Glu Gln Ser Asp Lys Asp Val Lys Tyr Tyr Thr Leu Glu Glu
1               5                   10                  15

Ile Gln Lys His Lys Asp Ser Lys Ser Thr Trp Leu Ile Leu His His
            20                  25                  30

Lys Val Tyr Asp Leu Thr Lys Phe Leu Glu Glu His Pro Gly Gly Glu
        35                  40                  45

Glu Val Leu Gly Glu Gln Ala Gly Gly Asp Ala Thr Glu Asn Phe Glu
    50                  55                  60

Asp Val Gly His Ser Thr Asp Ala Arg Glu Leu Ser Lys Thr Tyr Ile
65                  70                  75                  80

Ile Gly Glu Leu His Pro Asp Asp Arg Ser Lys Ile Ala Lys Pro Ser
                85                  90                  95

Glu Thr Leu

-continued

<210> SEQ ID NO 806
<211> LENGTH: 552
<212> TYPE: DNA
<213> ORGANISM: Artificial Sequence
<220> FEATURE:
<223> OTHER INFORMATION: cDNA Sequence of SDA

<400> SEQUENCE: 806

| atggcaaata ttaccgtttt ctataacgaa gacttccagg gtaagcaggt cgatctgccg | 60 |
| cctggcaact atacccgcgc ccagttggcg gcgctgggca tcgagaataa taccatcagc | 120 |
| tcggtgaagg tgccgcctgg cgtgaaggct atcctgtacc agaacgatgg tttcgccggc | 180 |
| gaccagatcg aagtggtggc caatgccgag gagttgggcc cgctgaataa taacgtctcc | 240 |
| agcatccgcg tcatctccgt gcccgtgcag ccgcgcatgg caaatattac cgttttctat | 300 |
| aacgaagact tccagggtaa gcaggtcgat ctgccgcctg caactatac ccgcgcccag | 360 |
| ttggcggcgc tgggcatcga gaataatacc atcagctcgg tgaaggtgcc gcctggcgtg | 420 |
| aaggctatcc tctaccagaa cgatggtttc gccggcgacc agatcgaagt ggtggccaat | 480 |
| gccgaggagc tgggtccgct gaataataac gtctccagca tccgcgtcat ctccgtgccg | 540 |
| gtgcagccga gg | 552 |

<210> SEQ ID NO 807
<211> LENGTH: 297
<212> TYPE: DNA
<213> ORGANISM: Artificial Sequence
<220> FEATURE:
<223> OTHER INFORMATION: cDNA Sequence of SDB

<400> SEQUENCE: 807

| atggcagaac aaagcgacaa ggatgtgaag tactacactc tggaggagat tcagaagcac | 60 |
| aaagacagca agagcacctg ggtgatccta catcataagg tgtacgatct gaccaagttt | 120 |
| ctcgaagagc atcctggtgg ggaagaagtc ctgggcgagc aagctggggg tgatgctact | 180 |
| gagaactttg aggacgtcgg gcactctacg gatgcacgag aactgtccaa acatacatc | 240 |
| atcggggagc tccatccaga tgacagatca agatagcca agccttcgga aacccctt | 297 |

<210> SEQ ID NO 808
<211> LENGTH: 327
<212> TYPE: DNA
<213> ORGANISM: Artificial Sequence
<220> FEATURE:
<223> OTHER INFORMATION: cDNA Sequence of SDC

<400> SEQUENCE: 808

| atgagcgata aaattattca cctgactgac gacagttttg acacggatgt actcaaagcg | 60 |
| gacggggcga tcctcgtcga tttctgggca gagtggtgcg gtccgtgcaa aatgatcgcc | 120 |
| ccgattctgg atgaaatcgc tgacgaatat cagggcaaac tgaccgttgc aaaactgaac | 180 |
| atcgatcaaa accctggcac tgcgccgaaa tatggcatcc gtggtatccc gactctgctg | 240 |
| ctgttcaaaa acggtgaagt ggcggcaacc aaagtgggtg cactgtctaa aggtcagttg | 300 |
| aaagagttcc tcgacgctaa cctggcc | 327 |

<210> SEQ ID NO 809
<211> LENGTH: 624
<212> TYPE: DNA
<213> ORGANISM: Artificial Sequence
<220> FEATURE:
<223> OTHER INFORMATION: cDNA Sequence of SDD

<400> SEQUENCE: 809

```
atgaaaaaga tttggctggc gctggctggt ttagttttag cgtttagcgc atcggcggcg      60
cagtatgaag atggtaaaca gtacactacc ctggaaaaac cggtagctgg cgcgccgcaa     120
gtgctggagt ttttctcttt cttctgcccg cactgctatc agtttgaaga agttctgcat     180
atttctgata atgtgaagaa aaaactgccg gaaggcgtga agatgactaa ataccacgtc     240
aacttcatgg gtggtgacct gggcaaagat ctgactcagg catgggctgt ggcgatggcg     300
ctgggcgtgg aagacaaagt gactgttccg ctgtttgaag gcgtacagaa acccagacc      360
attcgttctg cttctgatat ccgcgatgta tttatcaacg caggtattaa aggtgaagag     420
tacgacgcgg cgtggaacag cttcgtggtg aaatctctgg tcgctcagca ggaaaaagct     480
gcagctgacg tgcaattgcg tggcgttccg gcgatgtttg ttaacggtaa atatcagctg     540
aatccgcagg gtatggatac cagcaatatg gatgttttg ttcagcagta tgctgataca     600
gtgaaatatc tgtccgagaa aaaa                                            624
```

<210> SEQ ID NO 810
<211> LENGTH: 300
<212> TYPE: DNA
<213> ORGANISM: Artificial Sequence
<220> FEATURE:
<223> OTHER INFORMATION: cDNA Sequence of SDE

<400> SEQUENCE: 810

```
gggtccctgc aggactcaga agtcaatcaa gaagctaagc cagaggtcaa gccagaagtc      60
aagcctgaga ctcacatcaa tttaaaggtg tccgatggat cttcagagat cttcttcaag     120
atcaaaaaga ccactccttt aagaaggctg atggaagcgt tcgctaaaag acagggtaag     180
gaaatggact ccttaacgtt cttgtacgac ggtattgaaa ttcaagctga tcagacccct     240
gaagatttgg acatggagga taacgatatt attgaggctc accgcgaaca gattggaggt     300
```

<210> SEQ ID NO 811
<211> LENGTH: 891
<212> TYPE: DNA
<213> ORGANISM: Artificial Sequence
<220> FEATURE:
<223> OTHER INFORMATION: cDNA Sequence of SDF

<400> SEQUENCE: 811

```
ggatccgaaa tcggtactgg ctttccattc gaccccatt atgtggaagt cctgggcgag      60
cgcatgcact acgtcgatgt tggtccgcgc gatggcaccc ctgtgctgtt cctgcacggt     120
aacccgacct cctcctacgt gtggcgcaac atcatcccgc atgttgcacc gacccatcgc     180
tgcattgctc cagacctgat cggtatgggc aaatccgaca aaccagacct gggttatttc     240
ttcgacgacc acgtccgctt catggatgcc ttcatcgaag ccctgggtct ggaagaggtc     300
gtcctggtca ttcacgactg gggctccgct ctgggtttcc actgggccaa gcgcaatcca     360
gagcgcgtca aaggtattgc atttatggag ttcatccgcc ctatcccgac ctgggacgaa     420
tggccagaat ttgcccgcga accttccag gccttccgca ccaccgacgt cggccgcaag     480
ctgatcatcg atcagaacgt ttttatcgag ggtacgctgc cgatgggtgt cgtccgcccg     540
ctgactgaag tcgagatgga ccattaccgc gagccgttcc tgaatcctgt tgaccgcgag     600
ccactgtggc gcttcccaaa cgagctgcca atcgccggtg agccagcgaa catcgtcgcg     660
ctggtcgaag aatacatgga ctggctgcac cagtcccctg tcccgaagct gctgttctgg     720
ggcacccag gcgttctgat cccaccggcc gaagccgctc gcctggccaa aagcctgcct     780
```

```
aactgcaagg ctgtggacat cggcccgggt ctgaatctgc tgcaagaaga caacccggac      840
ctgatcggca gcgagatcgc gcgctggctg tctactctgg agatttccgg t               891
```

<210> SEQ ID NO 812
<211> LENGTH: 297
<212> TYPE: DNA
<213> ORGANISM: Artificial Sequence
<220> FEATURE:
<223> OTHER INFORMATION: cDNA Sequence of SDB for deimmunization

<400> SEQUENCE: 812

```
atggcagaac aaagcgacaa ggatgtgaag tactacactc tggaggagat tcagaagcac      60
aaagacagca agagcacctg gctgatccta catcataagg tgtacgatct gaccaagttt     120
ctcgaagagc atcctggtgg ggaagaagtc ctgggcgagc aagctggggg tgatgctact     180
gagaactttg aggacgtcgg cactctacg gatgcacgag aactgtccaa acatacatc       240 atcggggagc tccatccaga tgacagatca aagatagcca agccttcgga aacccctt      297
```

<210> SEQ ID NO 813
<211> LENGTH: 19
<212> TYPE: PRT
<213> ORGANISM: Artificial Sequence
<220> FEATURE:
<223> OTHER INFORMATION: Amino acid Sequence of Histidine Tag

<400> SEQUENCE: 813

```
Met Gly Ser Ser His His His His His His Ser Ser Gly Leu Val Pro
1               5                   10                  15

Arg Gly Ser
```

<210> SEQ ID NO 814
<211> LENGTH: 57
<212> TYPE: DNA
<213> ORGANISM: Artificial Sequence
<220> FEATURE:
<223> OTHER INFORMATION: cDNA Sequence of Histidine Tag

<400> SEQUENCE: 814

```
atgggcagca gccatcatca tcatcatcac agcagcggcc tggtgccgcg cggcagc        57
```

<210> SEQ ID NO 815
<211> LENGTH: 115
<212> TYPE: PRT
<213> ORGANISM: Artificial Sequence
<220> FEATURE:
<223> OTHER INFORMATION: Amino acid Sequence of human BMP2 (M form)

<400> SEQUENCE: 815

```
Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Asn His Ala Ile Val Gln
        50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95
```

```
Lys Val Val Leu Lys Asn Tyr Gln Asp Met Val Val Glu Gly Cys Gly
                100                 105                 110

Cys Arg Tyr
        115

<210> SEQ ID NO 816
<211> LENGTH: 259
<212> TYPE: PRT
<213> ORGANISM: Artificial Sequence
<220> FEATURE:
<223> OTHER INFORMATION: Amino acid Sequence of human BMP2 (L form)

<400> SEQUENCE: 816

Leu Val Pro Glu Leu Gly Arg Arg Lys Phe Ala Ala Ala Ser Ser Gly
1               5                   10                  15

Arg Pro Ser Ser Gln Pro Ser Asp Glu Val Leu Ser Glu Phe Glu Leu
            20                  25                  30

Arg Leu Leu Ser Met Phe Gly Leu Lys Gln Arg Pro Thr Pro Ser Arg
        35                  40                  45

Asp Ala Val Val Pro Pro Tyr Met Leu Asp Leu Tyr Arg Arg His Ser
    50                  55                  60

Gly Gln Pro Gly Ser Pro Ala Pro Asp His Arg Leu Glu Arg Ala Ala
65                  70                  75                  80

Ser Arg Ala Asn Thr Val Arg Ser Phe His His Glu Glu Ser Leu Glu
                85                  90                  95

Glu Leu Pro Glu Thr Ser Gly Lys Thr Thr Arg Arg Phe Phe Phe Asn
            100                 105                 110

Leu Ser Ser Ile Pro Thr Glu Glu Phe Ile Thr Ser Ala Glu Leu Gln
        115                 120                 125

Val Phe Arg Glu Gln Met Gln Asp Ala Leu Gly Asn Asn Ser Ser Phe
    130                 135                 140

His His Arg Ile Asn Ile Tyr Glu Ile Ile Lys Pro Ala Thr Ala Asn
145                 150                 155                 160

Ser Lys Phe Pro Val Thr Ser Leu Leu Asp Thr Arg Leu Val Asn Gln
                165                 170                 175

Asn Ala Ser Arg Trp Glu Ser Phe Asp Val Thr Pro Ala Val Met Arg
            180                 185                 190

Trp Thr Ala Gln Gly His Ala Asn His Gly Phe Val Val Glu Val Ala
        195                 200                 205

His Leu Glu Glu Lys Gln Gly Val Ser Lys Arg His Val Arg Ile Ser
    210                 215                 220

Arg Ser Leu His Gln Asp Glu His Ser Trp Ser Gln Ile Arg Pro Leu
225                 230                 235                 240

Leu Val Thr Phe Gly His Asp Gly Lys Gly His Pro Leu His Lys Arg
                245                 250                 255

Glu Lys Arg

<210> SEQ ID NO 817
<211> LENGTH: 127
<212> TYPE: PRT
<213> ORGANISM: Artificial Sequence
<220> FEATURE:
<223> OTHER INFORMATION: Amino acid Sequence of human BMP7 (M form)

<400> SEQUENCE: 817

Thr Pro Lys Asn Gln Glu Ala Leu Arg Met Ala Asn Val Ala Glu Asn
1               5                   10                  15
```

```
Ser Ser Ser Asp Gln Arg Gln Ala Cys Lys Lys His Glu Leu Tyr Val
            20                  25                  30

Ser Phe Arg Asp Leu Gly Trp Gln Asp Trp Ile Ile Ala Pro Glu Gly
        35                  40                  45

Tyr Ala Ala Tyr Tyr Cys Glu Gly Glu Cys Ala Phe Pro Leu Asn Ser
    50                  55                  60

Tyr Met Asn Ala Thr Asn His Ala Ile Val Gln Thr Leu Val His Phe
65                  70                  75                  80

Ile Asn Pro Glu Thr Val Pro Lys Pro Cys Cys Ala Pro Thr Gln Leu
                85                  90                  95

Asn Ala Ile Ser Val Leu Tyr Phe Asp Asp Ser Ser Asn Val Ile Leu
            100                 105                 110

Lys Lys Tyr Arg Asn Met Val Val Arg Ala Cys Gly Cys His Tyr
        115                 120                 125
```

<210> SEQ ID NO 818
<211> LENGTH: 280
<212> TYPE: PRT
<213> ORGANISM: Artificial Sequence
<220> FEATURE:
<223> OTHER INFORMATION: Amino acid Sequence of human BMP7 (L form)

<400> SEQUENCE: 818

```
Ser Ala Leu Ala Asp Phe Ser Leu Asp Asn Glu Val His Ser Ser Phe
1               5                   10                  15

Ile His Arg Arg Leu Arg Ser Gln Glu Arg Arg Glu Met Gln Arg Glu
            20                  25                  30

Ile Leu Ser Ile Leu Gly Leu Pro His Arg Pro Arg Pro His Leu Gln
        35                  40                  45

Gly Lys His Asn Ser Ala Pro Met Phe Met Leu Asp Leu Tyr Asn Ala
    50                  55                  60

Met Ala Val Glu Glu Gly Gly Pro Gly Gly Gln Gly Phe Ser Tyr
65                  70                  75                  80

Pro Tyr Lys Ala Val Phe Ser Thr Gln Gly Pro Pro Leu Ala Ser Leu
                85                  90                  95

Gln Asp Ser His Phe Leu Thr Asp Ala Asp Met Val Met Ser Phe Val
            100                 105                 110

Asn Leu Val Glu His Asp Lys Glu Phe Phe His Pro Arg Tyr His His
        115                 120                 125

Arg Glu Phe Arg Phe Asp Leu Ser Lys Ile Pro Glu Gly Glu Ala Val
    130                 135                 140

Thr Ala Ala Glu Phe Arg Ile Tyr Lys Asp Tyr Ile Arg Glu Arg Phe
145                 150                 155                 160

Asp Asn Glu Thr Phe Arg Ile Ser Val Tyr Gln Val Leu Gln Glu His
                165                 170                 175

Leu Gly Arg Glu Ser Asp Leu Phe Leu Leu Asp Ser Arg Thr Leu Trp
            180                 185                 190

Ala Ser Glu Glu Gly Trp Leu Val Phe Asp Ile Thr Ala Thr Ser Asn
        195                 200                 205

His Trp Val Val Asn Pro Arg His Asn Leu Gly Leu Gln Leu Ser Val
    210                 215                 220

Glu Thr Leu Asp Gly Gln Ser Ile Asn Pro Lys Leu Ala Gly Leu Ile
225                 230                 235                 240

Gly Arg His Gly Pro Gln Asn Lys Gln Pro Phe Met Val Ala Phe Phe
                245                 250                 255
```

```
Lys Ala Thr Glu Val His Phe Arg Ser Ile Arg Ser Thr Gly Ser Lys
        260                 265                 270

Gln Arg Ser Gln Asn Arg Ser Lys
        275                 280
```

<210> SEQ ID NO 819
<211> LENGTH: 342
<212> TYPE: DNA
<213> ORGANISM: Artificial Sequence
<220> FEATURE:
<223> OTHER INFORMATION: cDNA Sequence of human BMP2 (M form)

<400> SEQUENCE: 819

```
caagccaaac acaaacagcg aaacgccctt aagtccagct gtaagagaca ccctttgtac      60
gtggacttca gtgacgtggg gtggaatgac tggattgtgg ctcccccggg gtatcacgcc     120
ttttactgcc acggagaatg ccctttcct ctggctgatc atctgaactc cactaatcat     180
gccattgttc agacgttggt caactctgtt aactctaaga ttcctaaggc atgctgtgtc     240
ccgacagaac tcagtgctat ctcgatgctg taccttgacg agaatgaaaa ggttgtatta     300
aagaactatc aggacatggt tgtggagggt tgtgggtgtc gc                       342
```

<210> SEQ ID NO 820
<211> LENGTH: 342
<212> TYPE: DNA
<213> ORGANISM: Artificial Sequence
<220> FEATURE:
<223> OTHER INFORMATION: cDNA Sequence of human BMP2 (M form) for Codon-
      optimization

<400> SEQUENCE: 820

```
caggcgaaac acaagcaacg caaacgtctg aaaagcagct gcaaacgtca tccgctgtat      60
gtggacttca gcgatgttgg ttggaacgac tggatcgttg cgccgccggg ttaccacgcg     120
ttctattgcc acggcgagtg cccgtttccg ctggcggatc acctgaacag caccaaccac     180
gcgatcgttc agaccctggt gaacagcgtt aacagcaaga ttccgaaagc gtgctgcgtg     240
ccgaccgaac tgagcgcgat tagcatgctg tacctggacg agaacgaaaa ggtggttctg     300
aaaaactatc aagatatggt ggttgagggt tgcggctgcc gt                       342
```

<210> SEQ ID NO 821
<211> LENGTH: 1119
<212> TYPE: DNA
<213> ORGANISM: Artificial Sequence
<220> FEATURE:
<223> OTHER INFORMATION: cDNA Sequence of human BMP2 (L form)

<400> SEQUENCE: 821

```
ctcgttccgg agctgggccg caggaagttc gcggcggcgt cgtcgggccg ccctcatcc       60
cagccctctg acgaggtcct gagcgagttc gagttgcggc tgctcagcat gttcggcctg     120
aaacagagac ccaccccag cagggacgcc gtggtgcccc cctacatgct agacctgtat     180
cgcaggcact cgggtcagcc gggctcaccc gccccagacc accggttgga gagggcagcc     240
agccgagcca acactgtgcg cagcttccac catgaagaat ctttggaaga actaccagaa     300
acgagtggga aaacaaccccg agattcttc ttaatttaa gttctatccc cacggaggag     360
tttatcacct cagcagagct tcaggttttc cgagaacaga tgcaagatgc tttaggaaac     420
aatagcagtt tccatcaccg aattaatatt tatgaaatca taaaacctgc aacagccaac     480
tcgaaattcc ccgtgaccag tctttggac accaggttgg tgaatcagaa tgcaagcagg     540
```

```
tgggaaagtt ttgatgtcac ccccgctgtg atgcggtgga ctgcacaggg acacgccaac      600
catggattcg tggtggaagt ggcccacttg gaggagaaac aaggtgtctc caagagacat      660
gttaggataa gcaggtcttt gcaccaagat gaacacagct ggtcacagat aaggccattg      720
ctagtaactt ttggccatga tggaaaaggg catcctctcc acaaaagaga aaacgtcaa       780 gccaaacaca aacagcggaa acgccttaag tccagctgta agagacaccc tttgtacgtg      840
gacttcagtg acgtggggtg gaatgactgg attgtggctc ccccggggta tcacgccttt      900
tactgccacg gagaatgccc ttttcctctg ctgatcatc tgaactccac taatcatgcc       960
attgttcaga cgttggtcaa ctctgttaac tctaagattc ctaaggcatg ctgtgtcccg     1020
acagaactca gtgctatctc gatgctgtac cttgacgaga atgaaaaggt tgtattaaag     1080
aactatcagg acatggttgt ggagggttgt gggtgtcgc                            1119

<210> SEQ ID NO 822
<211> LENGTH: 378
<212> TYPE: DNA
<213> ORGANISM: Artificial Sequence
<220> FEATURE:
<223> OTHER INFORMATION: cDNA Sequence of human BMP7 (M form)

<400> SEQUENCE: 822
acgcccaaga accaggaagc cctgcggatg gccaacgtgg cagagaacag cagcagcgac       60
cagaggcagg cctgtaagaa gcacgagctg tatgtcagct ccgagacct gggctggcag      120 gactggatca tcgcgcctga aggctacgcc gcctactact gtgaggggga gtgtgccttc      180
cctctgaact cctacatgaa cgccaccaac cacgccatcg tgcagacgct ggtccacttc      240
atcaacccgg aaacggtgcc caagccctgc tgtgcgccca gcagctcaa tgccatctcc      300 gtcctctact tcgatgacag ctccaacgtc atcctgaaga aatacagaaa catggtggtc      360
cgggcctgtg gctgccac                                                   378

<210> SEQ ID NO 823
<211> LENGTH: 1218
<212> TYPE: DNA
<213> ORGANISM: Artificial Sequence
<220> FEATURE:
<223> OTHER INFORMATION: cDNA Sequence of human BMP7 (L form)

<400> SEQUENCE: 823
tccgccctgg ccgacttcag cctggacaac gaggtgcact cgagcttcat ccaccggcgc       60
ctccgcagcc aggagcggcg ggagatgcag cgcgagatcc tctccatttt gggcttgccc      120
caccgcccgc gcccgcacct ccagggcaag cacaactcgg cacccatgtt catgctggac      180
ctgtacaacg ccatggcggt ggaggagggc ggcgggcccg gcggcagggg cttctcctac      240
ccctacaagg ccgtcttcag tacccagggc cccccctctgg ccagcctgca agatagccat      300
ttcctcaccg acgccgacat ggtcatgagc ttcgtcaacc tcgtggaaca tgacaaggaa      360
ttcttccacc cacgctacca ccatcgagag ttccggtttg atctttccaa gatcccagaa      420
ggggaagctg tcacggcagc cgaattccgg atctacaagg actacatccg gaacgcttc      480 gacaatgaga cgttccggat cagcgtttat caggtgctcc aggagcactt gggcagggaa      540
tcggatctct tcctgctcga cagccgtacc ctctgggcct cggaggaggg ctggctggtg      600
tttgacatca cagccaccag caaccactgg gtggtcaatc cgcggcacaa cctgggcctg      660
cagctctcgg tggagacgct ggatgggcag agcatcaacc ccaagttggc gggcctgatt      720
```

| | |
|---|---|
| gggcggcacg ggccccagaa caagcagccc ttcatggtgg ctttcttcaa ggccacggag | 780 |
| gtccacttcc gcagcatccg gtccacgggg agcaaacagc gcagccagaa ccgctccaag | 840 |
| acgcccaaga accaggaagc cctgcggatg ccaacgtgg cagagaacag cagcagcgac | 900 |
| cagaggcagg cctgtaagaa gcacgagctg tatgtcagct tccgagacct gggctggcag | 960 |
| gactggatca tcgcgcctga aggctacgcc gcctactact gtgaggggga gtgtgccttc | 1020 |
| cctctgaact cctacatgaa cgccaccaac cacgccatcg tgcagacgct ggtccacttc | 1080 |
| atcaacccgg aaacggtgcc caagccctgc tgtgcgccca cgcagctcaa tgccatctcc | 1140 |
| gtcctctact tcgatgacag ctccaacgtc atcctgaaga aatacagaaa catggtggtc | 1200 |
| cgggcctgtg gctgccac | 1218 |

<210> SEQ ID NO 824
<211> LENGTH: 381
<212> TYPE: DNA
<213> ORGANISM: Artificial Sequence
<220> FEATURE:
<223> OTHER INFORMATION: cDNA Sequence of M24B2M

<400> SEQUENCE: 824

| | |
|---|---|
| attgcgctgg cggcgccggc gctgattgtg gcgccgcaag ccaaacacaa acagcggaaa | 60 |
| cgccttaagt ccagctgtaa gagacaccct ttgtacgtgg acttcagtga cgtggggtgg | 120 |
| aatgactgga ttgtggctcc cccggggtat cacgcctttt actgccacgg agaatgccct | 180 |
| tttcctctgg ctgatcatct gaactccact aatcatgcca ttgttcagac gttggtcaac | 240 |
| tctgttaact ctaagattcc taaggcatgc tgtgtcccga cagaactcag tgctatctcg | 300 |
| atgctgtacc ttgacgagaa tgaaaaggtt gtattaaaga actatcagga catggttgtg | 360 |
| gagggttgtg ggtgtcgcta c | 381 |

<210> SEQ ID NO 825
<211> LENGTH: 381
<212> TYPE: DNA
<213> ORGANISM: Artificial Sequence
<220> FEATURE:
<223> OTHER INFORMATION: cDNA Sequence of M442B2M

<400> SEQUENCE: 825

| | |
|---|---|
| gcgctggcgg cgctggtgcc ggcggtgctg gtgccgcaag ccaaacacaa acagcggaaa | 60 |
| cgccttaagt ccagctgtaa gagacaccct ttgtacgtgg acttcagtga cgtggggtgg | 120 |
| aatgactgga ttgtggctcc cccggggtat cacgcctttt actgccacgg agaatgccct | 180 |
| tttcctctgg ctgatcatct gaactccact aatcatgcca ttgttcagac gttggtcaac | 240 |
| tctgttaact ctaagattcc taaggcatgc tgtgtcccga cagaactcag tgctatctcg | 300 |
| atgctgtacc ttgacgagaa tgaaaaggtt gtattaaaga actatcagga catggttgtg | 360 |
| gagggttgtg ggtgtcgcta c | 381 |

<210> SEQ ID NO 826
<211> LENGTH: 942
<212> TYPE: DNA
<213> ORGANISM: Artificial Sequence
<220> FEATURE:
<223> OTHER INFORMATION: cDNA Sequence of M24B2MSA

<400> SEQUENCE: 826

| | |
|---|---|
| attgcgctgg cggcgccggc gctgattgtg gcgccgcaag ccaaacacaa acagcggaaa | 60 |
| cgccttaagt ccagctgtaa gagacaccct ttgtacgtgg acttcagtga cgtggggtgg | 120 |

```
aatgactgga ttgtggctcc cccggggtat cacgcctttt actgccacgg agaatgccct      180
tttcctctgg ctgatcatct gaactccact aatcatgcca ttgttcagac gttggtcaac      240
tctgttaact ctaagattcc taaggcatgc tgtgtcccga cagaactcag tgctatctcg      300
atgctgtacc ttgacgagaa tgaaaaggtt gtattaaaga actatcagga catggttgtg      360
gagggttgtg ggtgtcgcta cggatccatg gcaaatatta ccgttttcta taacgaagac      420
ttccagggta agcaggtcga tctgccgcct ggcaactata cccgcgccca gttggcggcg      480
ctgggcatcg agaataatac catcagctcg gtgaaggtgc cgcctggcgt gaaggctatc      540
ctgtaccaga acgatggttt cgccggcgac cagatcgaag tggtggccaa tgccgaggag      600
ttgggcccgc tgaataataa cgtctccagc atccgcgtca tctccgtgcc cgtgcagccg      660
cgcatggcaa atattaccgt tttctataac gaagacttcc agggtaagca ggtcgatctg      720
ccgcctggca actataccccg cgcccagttg gcggcgctgg gcatcgagaa taataccatc      780
agctcggtga aggtgccgcc tggcgtgaag gctatcctct accagaacga tggtttcgcc      840
ggcgaccaga tcgaagtggt ggccaatgcc gaggagctgg gtccgctgaa taataacgtc      900
tccagcatcc gcgtcatctc cgtgccggtg cagccgaggt aa                        942
```

`<210>` SEQ ID NO 827
`<211>` LENGTH: 942
`<212>` TYPE: DNA
`<213>` ORGANISM: Artificial Sequence
`<220>` FEATURE:
`<223>` OTHER INFORMATION: cDNA Sequence of M442B2MSA

`<400>` SEQUENCE: 827

```
gcgctggcgg cgctggtgcc ggcggtgctg gtgccgcaag ccaaacacaa acagcggaaa       60
cgccttaagt ccagctgtaa gagacaccct ttgtacgtgg acttcagtga cgtggggtgg      120
aatgactgga ttgtggctcc cccggggtat cacgcctttt actgccacgg agaatgccct      180
tttcctctgg ctgatcatct gaactccact aatcatgcca ttgttcagac gttggtcaac      240
tctgttaact ctaagattcc taaggcatgc tgtgtcccga cagaactcag tgctatctcg      300
atgctgtacc ttgacgagaa tgaaaaggtt gtattaaaga actatcagga catggttgtg      360
gagggttgtg ggtgtcgcta cggatccatg gcaaatatta ccgttttcta taacgaagac      420
ttccagggta agcaggtcga tctgccgcct ggcaactata cccgcgccca gttggcggcg      480
ctgggcatcg agaataatac catcagctcg gtgaaggtgc cgcctggcgt gaaggctatc      540
ctgtaccaga acgatggttt cgccggcgac cagatcgaag tggtggccaa tgccgaggag      600
ttgggcccgc tgaataataa cgtctccagc atccgcgtca tctccgtgcc cgtgcagccg      660
cgcatggcaa atattaccgt tttctataac gaagacttcc agggtaagca ggtcgatctg      720
ccgcctggca actataccccg cgcccagttg gcggcgctgg gcatcgagaa taataccatc      780
agctcggtga aggtgccgcc tggcgtgaag gctatcctct accagaacga tggtttcgcc      840
ggcgaccaga tcgaagtggt ggccaatgcc gaggagctgg gtccgctgaa taataacgtc      900
tccagcatcc gcgtcatctc cgtgccggtg cagccgaggt aa                        942
```

`<210>` SEQ ID NO 828
`<211>` LENGTH: 1025
`<212>` TYPE: DNA
`<213>` ORGANISM: Artificial Sequence
`<220>` FEATURE:
`<223>` OTHER INFORMATION: cDNA Sequence of HM24B2MSA

<400> SEQUENCE: 828

```
gaaggagata taccatgggc agcagccatc atcatcatca tcacagcagc ggcctggtgc    60
cgcgcggcag ccatatgatt gcgctggcgg cgccggcgct gattgtggcg ccgcaagcca   120
aacacaaaca gcggaaacgc cttaagtcca gctgtaagag acacccttttg tacgtggact   180
tcagtgacgt ggggtggaat gactggattg tggctccccc ggggtatcac gccttttact   240
gccacggaga atgcccttttt cctctggctg atcatctgaa ctccactaat catgccattg   300
ttcagacgtt ggtcaactct gttaactcta agattcctaa ggcatgctgt gtcccgacag   360
aactcagtgc tatctcgatg ctgtaccttg acgagaatga aaaggttgta ttaaagaact   420
atcaggacat ggttgtggag ggttgtgggt gtcgctacgg atccatggca aatattaccg   480
ttttctataa cgaagacttc cagggtaagc aggtcgatct gccgcctggc aactataccc   540
gcgcccagtt ggcggcgctg ggcatcgaga ataataccat cagctcggtg aaggtgccgc   600
ctggcgtgaa ggctatcctg taccagaacg atggtttcgc cggcgaccag atcgaagtgg   660
tggccaatgc cgaggagttg ggcccgctga ataataacgt ctccagcatc cgcgtcatct   720
ccgtgcccgt gcagccgcgc atggcaaata ttaccgtttt ctataacgaa gacttccagg   780
gtaagcaggt cgatctgccg cctggcaact atacccgcgc ccagttggcg gcgctgggca   840
tcgagaataa taccatcagc tcggtgaagg tgccgcctgg cgtgaaggct atcctctacc   900
agaacgatgg tttcgccggc gaccagatcg aagtggtggc caatgccgag gagctgggtc   960
cgctgaataa taacgtctcc agcatccgcg tcatctccgt gccggtgcag ccgaggtaag  1020
tcgac                                                              1025
```

<210> SEQ ID NO 829
<211> LENGTH: 1025
<212> TYPE: DNA
<213> ORGANISM: Artificial Sequence
<220> FEATURE:
<223> OTHER INFORMATION: cDNA Sequence of HM442B2MSA

<400> SEQUENCE: 829

```
gaaggagata taccatgggc agcagccatc atcatcatca tcacagcagc ggcctggtgc    60
cgcgcggcag ccatatggcg ctggcggcgc tggtgccggc ggtgctggtg ccgcaagcca   120
aacacaaaca gcggaaacgc cttaagtcca gctgtaagag acacccttttg tacgtggact   180
tcagtgacgt ggggtggaat gactggattg tggctccccc ggggtatcac gccttttact   240
gccacggaga atgcccttttt cctctggctg atcatctgaa ctccactaat catgccattg   300
ttcagacgtt ggtcaactct gttaactcta agattcctaa ggcatgctgt gtcccgacag   360
aactcagtgc tatctcgatg ctgtaccttg acgagaatga aaaggttgta ttaaagaact   420
atcaggacat ggttgtggag ggttgtgggt gtcgctacgg atccatggca aatattaccg   480
ttttctataa cgaagacttc cagggtaagc aggtcgatct gccgcctggc aactatacccc  540
gcgcccagtt ggcggcgctg ggcatcgaga ataataccat cagctcggtg aaggtgccgc   600
ctggcgtgaa ggctatcctg taccagaacg atggtttcgc cggcgaccag atcgaagtgg   660
tggccaatgc cgaggagttg ggcccgctga ataataacgt ctccagcatc cgcgtcatct   720
ccgtgcccgt gcagccgcgc atggcaaata ttaccgtttt ctataacgaa gacttccagg   780
gtaagcaggt cgatctgccg cctggcaact atacccgcgc ccagttggcg gcgctgggca   840
tcgagaataa taccatcagc tcggtgaagg tgccgcctgg cgtgaaggct atcctctacc   900
agaacgatgg tttcgccggc gaccagatcg aagtggtggc caatgccgag gagctgggtc   960
```

```
cgctgaataa taacgtctcc agcatccgcg tcatctccgt gccggtgcag ccgaggtaag    1020
tcgac                                                                1025

<210> SEQ ID NO 830
<211> LENGTH: 770
<212> TYPE: DNA
<213> ORGANISM: Artificial Sequence
<220> FEATURE:
<223> OTHER INFORMATION: cDNA Sequence of HM24B2MSB

<400> SEQUENCE: 830
gaaggagata taccatgggc agcagccatc atcatcatca tcacagcagc ggcctggtgc      60
cgcgcggcag ccatatgatt gcgctggcgg cgccggcgct gattgtggcg ccgcaagcca    120
aacacaaaca gcgaaacgc cttaagtcca gctgtaagag acacccttg tacgtggact      180 tcagtgacgt ggggtggaat gactggattg tggctccccc ggggtatcac gccttttact    240
gccacggaga atgcccttt cctctggctg atcatctgaa ctccactaat catgccattg    300
ttcagacgtt ggtcaactct gttaactcta agattcctaa ggcatgctgt gtcccgacag    360
aactcagtgc tatctcgatg ctgtaccttg acgagaatga aaaggttgta ttaaagaact    420
atcaggacat ggttgtggag ggttgtgggt gtcgctacgg atccatggca gaacaaagcg    480
acaaggatgt gaagtactac actctggagg agattcagaa gcacaaagac agcaagagca    540
cctgggtgat cctacatcat aaggtgtacg atctgaccaa gtttctcgaa gagcatcctg    600
gtggggaaga agtcctgggc gagcaagctg ggggtgatgc tactgagaac tttgaggacg    660
tcgggcactc tacggatgca cgagaactgt ccaaaacata catcatcggg gagctccatc    720
cagatgacag atcaaagata gccaagcctt cggaaaccct ttaagtcgac                770

<210> SEQ ID NO 831
<211> LENGTH: 1061
<212> TYPE: DNA
<213> ORGANISM: Artificial Sequence
<220> FEATURE:
<223> OTHER INFORMATION: cDNA Sequence of HM24B7MSA

<400> SEQUENCE: 831
gaaggagata taccatgggc agcagccatc atcatcatca tcacagcagc ggcctggtgc     60
cgcgcggcag ccatatgatt gcgctggcgg cgccggcgct gattgtggcg ccgacgccca    120
agaaccagga agccctgcgg atggccaacg tggcagagaa cagcagcagc gaccagaggc    180
aggcctgtaa gaagcacgag ctgtatgtca gcttccgaga cctgggctgg caggactgga    240
tcatcgcgcc tgaaggctac gccgcctact actgtgaggg ggagtgtgcc ttccctctga    300
actcctacat gaacgccacc aaccacgcca tcgtgcagac gctggtccac ttcatcaacc    360
cggaaacggt gcccaagccc tgctgtgcgc ccacgcagct caatgccatc tccgtcctct    420
acttcgatga cagctccaac gtcatcctga agaaatacag aaacatggtg gtcccgggcct    480 gtggctgcca ctacggatcc atggcaaata ttaccgtttt ctataacgaa gacttccagg    540
gtaagcaggt cgatctgccg cctggcaact atacccgcgc ccagttggcg cgcctgggca    600
tcgagaataa taccatcagc tcggtgaagg tgccgcctgg cgtgaaggct atcctgtacc    660
agaacgatgg tttcgccggc gaccagatcg aagtggtggc caatgccgag gagttgggcc    720
cgctgaataa taacgtctcc agcatccgcg tcatctccgt gcccgtgcag ccgcgcatgg    780
caaatattac cgttttctat aacgaagact tccagggtaa gcaggtcgat ctgccgcctg    840
```

```
gcaactatac ccgcgcccag ttggcggcgc tgggcatcga gaataatacc atcagctcgg      900
tgaaggtgcc gcctggcgtg aaggctatcc tctaccagaa cgatggtttc gccggcgacc      960
agatcgaagt ggtggccaat gccgaggagc tgggtccgct gaataataac gtctccagca     1020
tccgcgtcat ctccgtgccg gtgcagccga ggtaagtcga c                         1061

<210> SEQ ID NO 832
<211> LENGTH: 806
<212> TYPE: DNA
<213> ORGANISM: Artificial Sequence
<220> FEATURE:
<223> OTHER INFORMATION: cDNA Sequence of HM24B7MSB

<400> SEQUENCE: 832
gaaggagata taccatgggc agcagccatc atcatcatca tcacagcagc ggcctggtgc       60
cgcgcggcag ccatatgatt gcgctggcgg cgccggcgct gattgtggcg ccgacgccca      120
agaaccagga agccctgcgg atggccaacg tggcagagaa cagcagcagc gaccagaggc      180
aggcctgtaa gaagcacgag ctgtatgtca gcttccgaga cctgggctgg caggactgga      240
tcatcgcgcc tgaaggctac gccgcctact actgtgaggg ggagtgtgcc ttccctctga      300
actcctacat gaacgccacc aaccacgcca tcgtgcagac gctggtccac ttcatcaacc      360
cggaaacggt gcccaagccc tgctgtgcgc ccacgcagct caatgccatc tccgtcctct      420
acttcgatga cagctccaac gtcatcctga agaaatacag aaacatggtg gtcccgggcct     480 gtggctgcca ctacggatcc atggcagaac aaagcgacaa ggatgtgaag tactacactc      540
tggaggagat tcagaagcac aaagacagca agagcacctg ggtgatccta catcataagg      600
tgtacgatct gaccaagttt ctcgaagagc atcctggtgg ggaagaagtc ctgggcgagc      660
aagctggggg tgatgctact gagaactttg aggacgtcgg gcactctacg gatgcacgag      720
aactgtccaa aacatacatc atcggggagc tccatccaga tgacagatca aagatagcca      780
agccttcgga aaccctttaa gtcgac                                          806
```

CELL-PERMEABLE BONE MORPHOGENETIC PROTEIN (CP-BMP) RECOMBINANT PROTEIN AND USE THEREOF

CROSS-REFERENCE TO RELATED APPLICATIONS

This application is a Bypass Continuation of PCT International Application No. PCT/KR2016/009405 filed on Aug. 25, 2016, which claims priority under 35 U.S.C § 119(a) to U.S. patent application Ser. No. 14/838,318 filed on Aug. 27, 2015. Each of the above application(s) is hereby expressly incorporated by reference, in its entirety, into the present application.

TECHNICAL FIELD

The present invention relates to cell-permeable bone morphogenetic protein (CP-BMP) recombinant protein and use thereof. The recombinant protein of the present invention has on improved cell-permeability and biological activity as an intracellular protein therapy for regenerating of defected bone caused by osteogenesis imperfecta, osteoporosis, fracture and osteotomy.

BACKGROUND ART

Bone is a unique tissue that undergoes continuous remodeling throughout life and retains the potential for regeneration even in adult. Bone regeneration is required for bone defects caused by fracture and osteoporosis. Bone morphogenetic proteins (BMPs) are multifunctional growth factors that belong to the transforming growth factor (TGF) super-family. About 30 BMP-related proteins have been identified and can be subdivided into several groups based on their structures and functions. Especially, BMP2, BMP4 and BMP7 could induce chondrocyte-derived osteoprogenitor (CDOP) cell differentiation, and are important in bone formation and regeneration.

BMPs are synthesized as pre-pro peptides consisting of a signal peptide (SP), latency associated peptide (LAP) and mature peptide (MP). After the synthesis, SP and LAP are processed by enzymatic cleavage, where the C-terminal mature domain is released and secreted. BMPs bind to two-types of BMP receptors and signals through Smad-dependent (canonical) and Smad-independent (non-canonical) pathways. In the canonical pathway, BMP type I receptors phosphorylate receptor-regulated Smads (R-Smads). Phosphorylated R-Smads form a complex compound with common-partner Smads (Co-Smads), translocate into the nucleus and regulate the transcription of osteogenic-related genes.

There are four phases in the process of bone fracture repair: i) inflammatory response, ii) endochondral formation (soft callus formation and osteoblast recruitment), iii) primary bone formation (hard callus formation and mineralization), and iv) secondary bone formation (remodeling). The bone healing process involves various associated factors including BMPs and TGF-β. The effect of BMPs in recombinant systems demonstrates their abilities to enhance fracture healing and skeletal defect repairs in a variety of animal models. Osteogenic potential of BMPs has allowed for their successful use as therapeutic agents for fracture healing, where enhancing bone regeneration has become general practice in spine fusion surgeries and fracture repair. The responsible genes and associated transcription factors for osteogenesis are also activated to express within a few hours of BMP treatment.

The FDA has approved the use of recombinant human BMPs (rhBMPs) including BMP2. However, rhBMPs have rapid systemic clearance and short biological half-life (7 to 16 minutes systemically and up to 8 days locally) and possible negative side-effects (ex. cancer risk) due to high dosage of BMP.

REFERENCES

1. Soltanoff C S, Yang S, Chen W, Li Y P. Signaling networks that control the lineage commitment and differentiation of bone cells. Crit Rev Eukaryot Gene Expr 2009; 19(1):1-46.
2. Kawabata M, Imamura T, Miyazono K. Signal transduction by bone morphogenetic proteins. Cytokine Growth Factor Rev 1998; 9(1):49-61.
3. Carreira A C, Alves G G, Zambuzzi W F, Sogayar M C, Granjeiro J M. Bone Morphogenetic Proteins: structure, biological function and therapeutic applications. Arch Biochem Biophys 2014; 561:64-73.
4. Ten Dijke P, Fu J, Schaap P, Roelen B A. Signal transduction of bone morphogenetic proteins in osteoblast differentiation. J Bone Joint Surg Am 2003; 85-A Suppl 3:34-8.
5. Canalis E, Economides A N, Gazzerro E. Bone morphogenetic proteins, their antagonists, and the skeleton. Endocr Rev 2003; 24(2):218-35.
6. Huang Z, Ren P G, Ma T, Smith R L, Goodman S B. Modulating osteogenesis of mesenchymal.
7. Noel D, Gazit D, Bouquet C, Apparailly F, Bony C, Plence P, et al. Short-term BMP-2 expression is sufficient for in vivo osteochondral differentiation of mesenchymal stem cells. Stem Cells 2004; 22(1):74-85.
8. Shen B, Wei A, Whittaker S, Williams L A, Tao H, Ma D D, et al. The role of BMP-7 in chondrogenic and osteogenic differentiation of human bone marrow multipotent mesenchymal stromal cells in vitro. J Cell Biochem 2010; 109(2):406-16.
9. Weiskirchen R, Meurer S K. BMP-7 counteracting TGF-beta1 activities in organ fibrosis. Front Biosci (Landmark Ed) 2013; 18:1407-34.
10. Kudo T A, Kanetaka H, Watanabe A, Okumoto A, Asano M, Zhang Y, et al.
    Investigating bone morphogenetic protein (BMP) signaling in a newly established human cell line expressing BMP receptor type II. Tohoku J Exp Med 2010; 222(2):121-9.
11. Liu H, Zhang R, Chen D, Oyajobi B O, Zhao M. Functional redundancy of type II BMP receptor and type IIB activin receptor in BMP2-induced osteoblast differentiation. J Cell Physiol 2012; 227(3):952-63.
12. Zhang X, Schwarz E M, Young D A, Puzas J E, Rosier R N, O'Keefe R J. Cyclooxygenase-2 regulates mesenchymal cell differentiation into the osteoblast lineage and is critically involved in bone repair. J Clin Invest 2002; 109(11):1405-15.
13. van der Kraan P M, de Vries B J, Vitters E L, van den Berg W B, van de Putte L B. The effect of low sulfate concentrations on the glycosaminoglycan synthesis in anatomically intact articular cartilage of the mouse. J Orthop Res 1989; 7(5):645-53.
14. Hunziker E B, Schenk R K, Cruz-Drive L M. Quantitation of chondrocyte performance in growth-plate cartilage during longitudinal bone growth. J Bone Joint Surg Am 1987; 69(2):162-73.

15. Urist M R. Bone: formation by autoinduction. Science 1965; 150(3698):893-9.
16. Khattab H M, Ono M, Sonoyama W, Oida Y, Shinkawa S, Yoshioka Y, et al. The BMP2 antagonist inhibitor L51P enhances the osteogenic potential of BMP2 by simultaneous and delayed synergism. Bone 2014; 69:165-73.
17. Shim J H, Greenblatt M B, Singh A, Brady N, Hu D, Drapp R, et al. Administration of BMP2/7 in utero partially reverses Rubinstein-Taybi syndrome-like skeletal defects induced by Pdk1 or Cbp mutations in mice. J Clin Invest 2012; 122(1):91-106.
18. Yasko A W, Lane J M, Fellinger E J, Rosen V, Wozney J M, Wang E A. The healing of segmental bone defects, induced by recombinant human bone morphogenetic protein (rhBMP-2). A radiographic, histological, and biomechanical study in rats. J Bone Joint Surg Am 1992; 74(5):659-70.
19. Einhorn T A, Majeska R J, Mohaideen A, Kagel E M, Bouxsein M L, Turek T J, et al. A single percutaneous injection of recombinant human bone morphogenetic protein-2 accelerates fracture repair. J Bone Joint Surg Am 2003; 85-A(8):1425-35.
20. Nakase T, Nomura S, Yoshikawa H, Hashimoto J, Hirota S, Kitamura Y, et al. Transient and localized expression of bone morphogenetic protein 4 messenger RNA during fracture healing. J Bone Miner Res 1994; 9(5):651-9.
21. Balint E, Lapointe D, Drissi H, van der Meijden C, Young D W, van Wijnen A J, et al. Phenotype discovery by gene expression profiling: mapping of biological processes linked to BMP-2-mediated osteoblast differentiation. J Cell Biochem 2003; 89(2):401-26.
22. Nakashima K, Thou X, Kunkel G, Zhang Z, Deng J M, Behringer R R, et al. The novel zinc finger-containing transcription factor osterix is required for osteoblast differentiation and bone formation. Cell 2002; 108(1):17-29.
23. Wegman F, Bijenhof A, Schuijff L, Oner F C, Dhert W J, Alblas J. Osteogenic differentiation as a result of BMP-2 plasmid DNA based gene therapy in vitro and in vivo. European cells & materials 2011; 21:230-42; discussion 42.
24. Fischer P M. Cellular uptake mechanisms and potential therapeutic utility of peptidic cell delivery vectors: progress 2001-2006. Med Res Rev 2007; 27:755-95.
25. Heitz F, Morris M C, Divita G. Twenty years of cell-penetrating peptides: from molecular mechanisms to therapeutics. Br J Pharmacol 2009; 157:195-206.
26. Lapenna S, Giordano A. Cell cycle kinases as therapeutic targets for cancer. Nat Rev Drug Discov 2009; 8:547-66.
27. Lim J, Kim J, Duong T, Lee G, Kim J, Yoon J. et al. Antitumor activity of cell-permeable p18(INK4c) with enhanced membrane and tissue penetration. Mol Ther 2012; 20:1540-9.
28. Jo D, Liu D, Yao S, Collins R D, Hawiger J. Intracellular protein therapy with SOCS3 inhibits inflammation and apoptosis. Nat Med 2005; 11:892-8.
29. Jo D, Nashabi A, Doxsee C, Lin Q, Unutmaz D, Chen J. et al. Epigenetic regulation of gene structure and function with a cell-permeable Cre recombinase. Nat Biotechnol 2001; 19:929-33.
30. Liu D, Li C, Chen Y, Burnett C, Liu X Y, Downs S. et al. Nuclear import of proinflammatory transcription factors is required for massive liver apoptosis induced by bacterial lipopolysaccharide J Biol Chem. 2004; 279: 48434-42.
31. Liu D, Liu X Y, Robinson D, Burnett C, Jackson C, Seele L. et al. Suppression of Staphylococcal Enterotoxin B-induced Toxicity by a Nuclear Import Inhibitor. J Biol Chem 2004; 279:19239-46.
32. Liu D, Zienkiewicz J, DiGiandomenico A, Hawiger J., Suppression of acute lung inflammation by intracellular peptide delivery of a nuclear import inhibitor. Mol Ther 2009; 17: 796-802.
33. Moore D J, Zienkiewicz J, Kendall P L, Liu D, Liu X, Veach R A. et al. In vivo islet protection by a nuclear import inhibitor in a mouse model of type 1 diabetes. PLoS One 2010; 5:e13235.
34. Lim J, Jang G, Kang S, Lee G, Nga do TT, Phuong do TL. et al. Cell-permeable NM23 blocks the maintenance and progression of established pulmonary metastasis. Cancer Res 2011; 71:7216-25.
35. Duong T, Kim J, Ruley H E, Jo D. Cell-permeable parkin proteins suppress Parkinson disease-associated phenotypes in cultured cells and animals. PLoS One 2014; 9:e102517.
36. Lim J, Duong T, Do N, Do P, Kim J, Kim H. et al. Antitumor activity of cell-permeable RUNX3 protein in gastric cancer cells. Clin Cancer Res 2013; 19:680-90.
37. Lim J, Duong T, Lee G, Seong B L, El-Rifai W, Ruley H E et al. The effect of intracellular protein delivery on the anti-tumor activity of recombinant human endostatin. Biomaterials 2013; 34:6261-71.
38. Lim J, Kim J, Kang J, Jo D. Partial somatic to stem cell transformations induced by cell-permeable reprogramming factors, Scientific Reports 2014; 4:4361.

DISCLOSURE

Technical Problem

Macromolecule, such as bone morphogenetic proteins (BMPs), cannot be translocated across the cell membrane. Therefore, there was a need to develop macromolecule intracellular transduction technology (MITT), which enables the translocation of macromolecules into the cell/tissues.

In the previous studies, MITT-based hydrophobic CPPs named membrane translocating sequence (MTS) and membrane translocating motif (MTM), derived from the hydrophobic signal peptide of fibroblast growth factor 4 (FGF4) have been reported and used to deliver biologically active peptides and proteins, such as BMP, systemically in animals.

However, they could not effectively deliver BMP in vivo and in vitro, and their delivery efficiency was in sufficient due to protein aggregation, low solubility/yield and poor cell-/tissue-permeability.

Technical Solution

To resolve these problems, newly designed advanced macromolecule transduction domain (aMTD)-enabled macromolecule intracellular transduction technology (MITT) has been adopted for the development of novel protein using BMP against bone formation and regeneration.

For MITT, six critical factors (length, bending potential, instability index, aliphatic index, GRAVY, amino acid composition) have been determined through analysis of baseline hydrophobic CPPs. Advanced macromolecule transduction domain (aMTD), newly designed based on these six critical factors, could optimize cell-/tissue-permeability of cargo proteins that have a therapeutic effects and develop them as protein-based drugs. Further, in order to increase solubility and yield of recombinant protein, solubilization domains (SDs) additionally fused to the aMTD-cargo recombinant protein, thereby notably increased the solubility and yield of the recombinant protein.

One embodiment of the present invention provides a cell-permeable bone morphogenetic protein (CP-BMP), which comprises a BMP being one of BMP2 and BMP7 and an advanced macromolecule transduction domain (aMTD) being composed of 9 to 13 amino acid sequences and having improved cell or tissue permeability, wherein the aMTD is fused to one end or both ends of the BMP and has the following features of:

(a) being composed of 3 or more amino acids selected from the group consisting of Ala, Val, Ile, Leu, and Pro;

(b) having proline as amino acids corresponding to any one or more of positions 5 to 8, and 12 of its amino acid sequence; and (c) having an instability index of 40 to 60; an aliphatic index of 180 to 220; and a grand average of hydropathy (GRAVY) of 2.1 to 2.6, as measured by Protparam.

According to one embodiment, one or more solubilization domain (SD)(s) are further fused to the end(s) of one or more of the BMP and the aMTD.

According to another embodiment, the aMTD may have α-Helix structure.

According to still another embodiment, the aMTD may be composed of 12 amino acid sequences and represented by the following general formula:

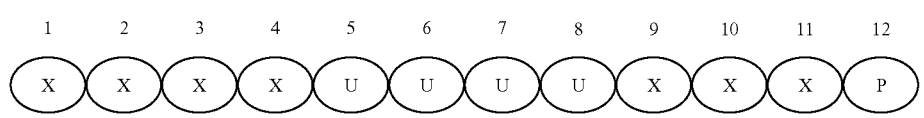

[General formula]

wherein X(s) refers to Alanine (A), Valine (V), Leucine (L) or Isoleucine (I); one of U refers to proline and the other U(s) refer to A, V, L or I; and P refers to proline.

Another embodiment of the present invention provides a CP-BMP recombinant protein which is represented by any one of the following structural formula:

A-B-C, A-C-B, B-A-C, B-C-A, C-A-B, C-B-A and A-C-B-C wherein A is an advanced macromolecule transduction domain (aMTD) having improved cell or tissue permeability, B is a BMP having one of BMP2 and BMP7, and C is a solubilization domain (SD); and the aMTD is composed of 9 to 13 amino acid sequences and has the following features of:

(a) being composed of 3 or more amino acids selected from the group consisting of Ala, Val, Ile, Leu, and Pro;

(b) having proline as amino acids corresponding to any one or more of positions 5 to 8, and 12 of its amino acid sequence;

(c) having an instability index of 40 to 60; an aliphatic index of 180 to 220; and a grand average of hydropathy (GRAVY) of 2.1 to 2.6, as measured by Protparam; and (d) having α-Helix structure.

According to one embodiment of the present invention, the BMP may have an amino acid sequence selected from the group consisting of SEQ ID NOs: 815 to 818.

According to another embodiment of the present invention, the BMP may be encoded by a polynucleotide sequence selected from the group consisting of SEQ ID NOs: 819 to 823.

According to still another embodiment of the present invention, the BMP may further include a ligand selectively binding to a receptor of a cell, a tissue, or an organ.

According to still another embodiment of the present invention, the aMTD may have an amino acid sequence selected from the group consisting of SEQ ID NOs: 1 to 240.

According to still another embodiment of the present invention, the aMTD may be encoded by a polynucleotide sequence selected from the group consisting of SEQ ID NOs: 241 to 481.

According to still another embodiment of the present invention, the SD(s), independently, may have an amino acid sequence selected from the group consisting of SEQ ID NOs: 799 to 805.

According to still another embodiment of the present invention, the SD(s), independently, may be encoded by a polynucleotide sequence selected from the group consisting of SEQ ID NOs: 806 to 812.

According to still another embodiment of the present invention, the BMP recombinant protein may have a histidine-tag affinity domain additionally fused to one end thereof.

According to still another embodiment of the present invention, the histidine-tag affinity domain may have an amino acid sequence of SEQ ID NO: 813.

According to still another embodiment of the present invention, the histidine-tag affinity domain may be encoded by a polynucleotide sequence of SEQ ID NO: 814.

According to still another embodiment of the present invention, the fusion may be formed via a peptide bond or a chemical bond.

According to still another embodiment of the present invention, the CP-BMP recombinant protein may be used for the regeneration of defected bone.

Still another embodiment of the present invention provides a polynucleotide sequence encoding the CP-BMP recombinant protein.

According to one embodiment of the present invention, the polynucleotide sequence may be selected from the group consisting of SEQ ID NOs: 824 and 825.

According to another embodiment of the present invention, the polynucleotide sequence may be selected from the group consisting of SEQ ID NOs: 826 and 827.

Still another embodiment of the present invention provides a recombinant expression vector including the polynucleotide sequence.

Still another embodiment of the present invention provides a transformant transformed with the recombinant expression vector.

Still another embodiment of the present invention provides a preparing method of the CP-BMP recombinant protein including preparing the recombinant expression vector; preparing the transformant using the recombinant expression vector; culturing the transformant; and recovering the recombinant protein expressed by the culturing.

Still another embodiment of the present invention provides a composition including the CP-BMP recombinant protein as an active ingredient.

Still another embodiment of the present invention provides a pharmaceutical composition for regenerating of defected bone including the CP-BMP recombinant protein as an active ingredient; and a pharmaceutically acceptable carrier.

Still another embodiment of the present invention provides use of the CP-BMP recombinant protein as a medicament for regenerating of defected bone.

Still another embodiment of the present invention provides a medicament including the CP-BMP recombinant protein.

Still another embodiment of the present invention provides use of the CP-BMP recombinant protein in the preparation of a medicament for regenerating of defected bone.

Still another embodiment of the present invention provides a method of regenerating of defected bone, the method including preparing defected bone; and treating the defected bone with an therapeutically effective amount of the CP-BMP recombinant protein.

According to one embodiment of the present invention, the subject may be a mammal.

Unless defined otherwise, all terms used herein have the same meaning as commonly understood by one of ordinary skill in the art to which the present invention belongs. Although a certain method and a material is described herein, it should not be construed as being limited thereto, any similar or equivalent method and material to those may also be used in the practice or testing of the present invention. All publications mentioned herein are incorporated herein by reference in their entirety to disclose and describe the methods and/or materials in connection with which the publications are cited. It must be noted that as used herein and in the appended claims, the singular forms "a," "an," and "the" include plural referents unless the context clearly dictates otherwise.

A "peptide" refers to a chain-type polymer formed by amino acid residues which are linked to each other via peptide bonds, and used interchangeably with "polypeptide." Further, a "polypeptide" includes a peptide and a protein.

Further, the term "peptide" includes amino acid sequences that are conservative variations of those peptides specifically exemplified herein. The term "conservative variation," as used herein, denotes the replacement of an amino acid residue by another, biologically similar residue. Examples of conservative variations include substitution of one hydrophobic residue, such as isoleucine, valine, leucine, alanine, cysteine, glycine, phenylalanine, proline, tryptophan, tyrosine, norleucine, or methionine for another, or substitution of one polar residue for another, for example, substitution of arginine for lysine, glutamic acid for aspartic acid, or glutamine for asparagine, and the like. Neutral hydrophilic amino acids which may be substituted for one another include asparagine, glutamine, serine, and threonine.

The term "conservative variation" also includes use of a substituted amino acid in place of an unsubstituted parent amino acid, provided that antibodies raised to the substituted polypeptide also immunoreacts with the unsubstituted polypeptide. Such conservative substitutions are within the definition of the classes of the peptides according to one embodiment of the present invention.

A person having ordinary skill in the art may make similar substitutions to obtain peptides having higher cell permeability and a broader host range. For example, one embodiment of the present invention provides peptides corresponding to amino acid sequences (e.g. SEQ ID NOs: 1 to 240) provided herein, as well as analogues, homologs, isomers, derivatives, amidated variations, and conservative variations thereof, as long as the cell permeability of the peptide remains.

Minor modifications to primary amino acid sequence of the peptides according to one embodiment of the present invention may result in peptides which have substantially equivalent or enhanced cell permeability, as compared to the specific peptides described herein. Such modifications may be deliberate, as by site-directed mutagenesis, or may be spontaneous.

All peptides may be synthesized using L-amino acids, but D forms of all of the peptides may be synthetically produced. In addition, C-terminal derivatives, such as C-terminal methyl esters and C-terminal amidates, may be produced in order to increase the cell permeability of the peptide according to one embodiment of the present invention.

All of the peptides produced by these modifications are included herein, as long as in the case of amidated versions of the peptide, the cell permeability of the original peptide is altered or enhanced such that the amidated peptide is therapeutically useful. It is envisioned that such modifications are useful for altering or enhancing cell permeability of a particular peptide.

Furthermore, deletion of one or more amino acids may also result in a modification to the structure of the resultant molecule without any significant change in its cell permeability. This may lead to the development of a smaller active molecule which may also have utility. For example, amino- or carboxyl-terminal amino acids which may not be required for the cell permeability of a particular peptide may be removed.

The term "gene" refers to an arbitrary nucleic acid sequence or a part thereof having a functional role in protein coding or transcription, or regulation of other gene expression. The gene may be composed of all nucleic acids encoding a functional protein or a part of the nucleic acid encoding or expressing the protein. The nucleic acid sequence may include a gene mutation in exon, intron, initiation or termination region, promoter sequence, other regulatory sequence, or a unique sequence adjacent to the gene.

The term "primer" refers to an oligonucleotide sequence that hybridizes to a complementary RNA or DNA target polynucleotide and serves as the starting points for the stepwise synthesis of a polynucleotide from mononucleotides by the action of a nucleotidyltransferase as occurs, for example, in a polymerase chain reaction.

The term "coding region" or "coding sequence" refers to a nucleic acid sequence, a complement thereof, or a part thereof which encodes a particular gene product or a fragment thereof for which expression is desired, according to the normal base pairing and codon usage relationships. Coding sequences include exons in genomic DNA or immature primary RNA transcripts, which are joined together by the cellular biochemical machinery to provide a mature mRNA. The anti-sense strand is the complement of the nucleic acid, and the coding sequence may be deduced therefrom.

One embodiment of the present invention provides a CP-BMP recombinant protein, which comprises a BMP being one of BMP2 and BMP7, and an advanced macromolecule transduction domain (aMTD) being composed of 9 to 13 amino acid sequences, preferably 10 to 12 amino acid sequences, and having improved cell or tissue permeability, wherein the aMTD is fused to one end or both ends of the BMP and has the following features of:

(a) being preferably composed of 3 or more amino acids selected from the group consisting of Ala, Val, Ile, Leu, and Pro;

(b) having proline as amino acid sequences corresponding to any one or more of positions 5 to 8, and 12 of its amino acids, and preferably one or more of positions 5 to 8 and position 12 of its amino acid sequence; and (c) having an instability index of preferably 40 to 60 and more preferably 41 to 58; an aliphatic index of preferably 180 to 220 and more preferably 185 to 225; and a grand average of hydropathy (GRAVY) of preferably 2.1 to 2.6 and more preferably 2.2 to 2.6 as measured by Protparam (see web.expasy.org/protparam/).

According to one embodiment, one or more solubilization domain (SD)(s) are further fused to one or more of the BMP and the aMTD, preferably one end or both ends of the BMP, and more preferably the C-terminus of the BMP.

According to another embodiment, the aMTD may have α-Helix structure.

According to still another embodiment, the aMTD may be preferably composed of 12 amino acid sequences and represented by the following general formula:

[General formula]

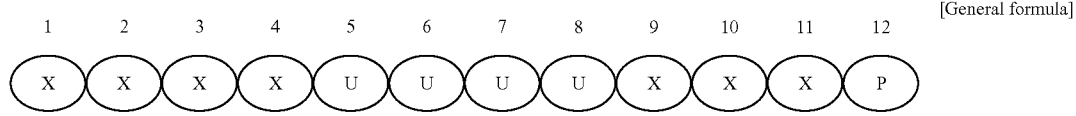

wherein X(s) refers to Alanine (A), Valine (V), Leucine (L) or Isoleucine (I); one of U refers to proline and the other U(s) refer to A, V, L or I; and P refers to proline.

Still another embodiment of the present invention provides a CP-BMP recombinant protein which is represented by any one of structural formula A-B-C, A-C-B, B-A-C, B-C-A, C-A-B, C-B-A and A-C-B-C, and preferably by A-B-C or A-C-B-C:

wherein A is an advanced macromolecule transduction domain (aMTD) having improved cell or tissue permeability, B is a BMP having one of BMP2 and BMP7, and C is a solubilization domain (SD); and the aMTD is composed of 9 to 13, preferably 10 to 12 amino acid sequences and has the following features of:

(a) being composed of 3 or more amino acids selected from the group consisting of Ala, Val, Ile, Leu, and Pro;

(b) having proline as amino acids corresponding to any one or more of positions 5 to 8, and 12 of its amino acid sequence, and preferably, one or more of positions 5 to 8 and position 12 of its amino acid sequence;

(c) having an instability index of preferably 40 to 60 and more preferably 41 to 58; an aliphatic index of preferably 180 to 220 and more preferably 185 to 225; and a grand average of hydropathy (GRAVY) of preferably 2.1 to 2.6 and more preferably 2.2 to 2.6, as measured by Protparam (see web.expasy.org/protparam/); and (d) preferably having α-Helix structure.

In one embodiment of the present invention, the BMP may have an amino acid sequence selected from the group consisting of SEQ ID NOs: 815 to 818. The BMP may have one selected from the group consisting of BMP2 (M form), BMP2 (L form), BMP7 (M form) and BMP7 (L form). The BMP may be preferably BMP2 (M form) of SEQ ID NO: 815 or a BMP7 (M form) of SEQ ID NO: 817.

In another embodiment of the present invention, the BMP may be encoded by a polynucleotide sequence selected from the group consisting of SEQ ID NOs: 819 to 823. The BMP may be preferably BMP2 (M form) encoded by a polynucleotide sequence of SEQ ID NO: 819, BMP2 (M form) for codon-optimization encoded by a polynucleotide sequence of SEQ ID NO: 820 or BMP7 (M form) encoded by a polynucleotide sequence of SEQ ID NO: 822. The BMP may be more preferably BMP2 (M form) encoded by a polynucleotide sequence of SEQ ID NO: 819 or BMP2 (M form) for codon-optimization encoded by a polynucleotide sequence of SEQ ID NO: 820.

When the CP-BMP recombinant protein is intended to be delivered to a particular cell, tissue, or organ, the BMP may form a fusion product, together with an extracellular domain of a ligand capable of selectively binding to a receptor which is specifically expressed on the particular cell, tissue, or organ, or monoclonal antibody (mAb) capable of specifically binding to the receptor or the ligand and a modified form thereof.

The binding of the peptide and a biologically active substance may be formed either by indirect linkage by a cloning technique using an expression vector at a nucleotide level or by direct linkage via chemical or physical covalent or non-covalent bond of the peptide and the biologically active substance.

In still another embodiment of the present invention, the BMP may preferably further include a ligand selectively binding to a receptor of a cell, a tissue, or an organ.

In one embodiment of the present invention, the aMTD may have an amino acid sequence selected from the group consisting of SEQ ID NOs: 1 to 240. The aMTD may be preferably aMTD$_1$ of SEQ ID NO: 1, aMTD$_3$ of SEQ ID NO: 3, aMTD$_{24}$ of SEQ ID NO: 12, aMTD$_{61}$ of SEQ ID NO: 17, aMTD$_{123}$ of SEQ ID NO: 33, aMTD$_{124}$ of SEQ ID NO: 34, aMTD$_{241}$ of SEQ ID NO: 56, aMTD$_{321}$ of SEQ ID NO: 74, aMTD$_{385}$ of SEQ ID NO: 91, aMTD$_{403}$ of SEQ ID NO: 94, aMTD$_{442}$ of SEQ ID NO: 101, aMTD$_{481}$ of SEQ ID NO: 110, aMTD$_{563}$ of SEQ ID NO: 131, aMTD$_{585}$ of SEQ ID NO: 136, aMTD$_{603}$ of SEQ ID NO: 139, aMTD$_{623}$ of SEQ ID NO: 143, aMTD$_{847}$ of SEQ ID NO: 200 and aMTD$_{897}$ of SEQ ID NO: 228 and aMTD$_{899}$ of SEQ ID NO: 229, and more preferably aMTD$_{24}$ of SEQ ID NO: 12 and aMTD$_{442}$ of SEQ ID NO: 101.

In still another embodiment of the present invention, the aMTD may be encoded by a polynucleotide sequence selected from the group consisting of SEQ ID NOs: 241 to 481. The aMTD may be preferably aMTD$_1$ encoded by a polynucleotide sequence of SEQ ID NO: 241, aMTD$_3$ encoded by a polynucleotide sequence of SEQ ID NO: 243, aMTD$_{24}$ encoded by a polynucleotide sequence of SEQ ID NO: 252, aMTD$_{61}$ encoded by a polynucleotide sequence of SEQ ID NO: 257, aMTD$_{123}$ encoded by a polynucleotide sequence of SEQ ID NO: 273, aMTD$_{124}$ encoded by a polynucleotide sequence of SEQ ID NO: 274, aMTD$_{241}$ encoded by a polynucleotide sequence of SEQ ID NO: 296, aMTD$_{321}$ encoded by a polynucleotide sequence of SEQ ID NO: 314, aMTD$_{385}$ encoded by a polynucleotide sequence of SEQ ID NO: 331, aMTD$_{403}$ encoded by a polynucleotide sequence of SEQ ID NO: 334, aMTD$_{442}$ encoded by a polynucleotide sequence of SEQ ID NO: 341, aMTD$_{442}$ for codon-optimization encoded by a polynucleotide sequence of SEQ ID NO: 481, aMTD$_{481}$ encoded by a polynucleotide sequence of SEQ ID NO: 350, aMTD$_{563}$ encoded by a polynucleotide sequence of SEQ ID NO: 371, aMTD$_{585}$ encoded by a polynucleotide sequence of SEQ ID NO: 376, aMTD$_{603}$ encoded by a polynucleotide sequence of SEQ ID NO: 379, aMTD$_{623}$ encoded by a polynucleotide sequence of SEQ ID NO: 383, aMTD$_{847}$ encoded by a polynucleotide sequence of SEQ ID NO: 440, aMTD$_{897}$ encoded by a polynucleotide sequence of SEQ ID NO: 468 and aMTD$_{899}$ encoded by a polynucleotide sequence of SEQ ID NO: 469, and more preferably aMTD$_{24}$ encoded by a polynucleotide sequence of SEQ ID NO: 252, aMTD$_{442}$ encoded by a polynucleotide sequence of SEQ ID NO: 341 and aMTD$_{442}$ for codon-optimization encoded by a polynucleotide sequence of SEQ ID NO: 481.

In still another embodiment of the present invention, the SD(s) may have an amino acid sequence independently selected from the group consisting of SEQ ID NOs: 799 to 805. The SD(s) may has one or more selected from the group consisting of SDA, SDB, SDB' (SDB for deimmunization), SDC, SDD, SDE and SDF. The SD may be preferably SDA of SEQ ID NO: 799, SDB of SEQ ID NO: 800, SDB' of SEQ ID NO: 805 or SDC of SEQ ID NO: 801, and more preferably, SDB of SEQ ID NO: 800 and SDB' of SEQ ID NO: 805 which have superior structural stability.

In still another embodiment of the present invention, the SDs may be encoded by a polynucleotide sequence independently selected from the group consisting of SEQ ID NOs: 806 to 812. The SD may be preferably SDA encoded by a polynucleotide sequence of SEQ ID NO: 806, SDB encoded by a polynucleotide sequence of SEQ ID NO: 807, SDB' encoded by a polynucleotide sequence of SEQ ID NO: 812, or SDC encoded by a polynucleotide sequence of SEQ ID NO: 808, and more preferably, SDB and SDB' having superior structural stability, which is encoded by a polynucleotide sequence of SEQ ID NO: 807 and SEQ ID NO: 812.

In still another embodiment of the present invention, the CP-BMP recombinant protein may be preferably selected from the group consisting of:

1) a recombinant protein, in which BMP protein having an amino acid sequence of SEQ ID NOs: 815 and 818 is fused to the N-terminus or the C-terminus of aMTD having any one amino acid sequence selected from the group consisting of SEQ ID NOs: 1 to 240, preferably SEQ ID NOs: 1, 3, 12, 17, 33, 34, 56, 74, 91, 94, 101, 110, 131, 136, 139, 143, 200, 228 and 229 and more preferably SEQ ID NO: 12 and 101;

2) a recombinant protein, in which SD having any one amino acid sequence selected from the group consisting of SEQ ID NOs: 799 to 805, preferably SEQ ID NOs: 799, 800, 801 and 805, and more preferably SEQ ID NO: 800 and 805 is further fused to the N-terminus or the C-terminus of the BMP protein in the recombinant protein of 1); and 3) a recombinant protein, in which one or more of a histidine tag having an amino acid sequence of SEQ ID NO: 813 is further fused to the N-terminus or the C-terminus of the aMTD in the recombinant protein of 1) or 2).

The BMPs may exhibit a physiological phenomenon-related activity or a therapeutic purpose-related activity by intracellular or in vivo delivery. The recombinant expression vector may include a tag sequence which makes it easy to purify the recombinant protein, for example, consecutive histidine codon, maltose binding protein codon, Myc codon, etc., and further include a fusion partner to enhance solubility of the recombinant protein, etc. Further, for the overall structural and functional stability of the recombinant protein or flexibility of the proteins encoded by respective genes, the recombinant expression vector may further include one or more glycine, proline, and spacer amino acid or polynucleotide sequences including AAY amino acids. Furthermore, the recombinant expression vector may include a sequence specifically digested by an enzyme in order to remove an unnecessary region of the recombinant protein, an expression regulatory sequence, and a marker or reporter gene sequence to verify intracellular delivery, but is not limited thereto.

In still another embodiment of the present invention, the CP-BMP recombinant protein may have a histidine-tag affinity domain additionally fused to one end thereof. Preferably, the histidine-tag may be fused to the N-terminus of BMP, aMTD or SD. More preferably, the histidine-tag may be fused to the N-terminus of aMTD or BMP.

In still another embodiment of the present invention, the histidine-tag affinity domain may have an amino acid sequence of SEQ ID NO: 813.

In still another embodiment of the present invention, the histidine-tag affinity domain may be encoded by a polynucleotide sequence of SEQ ID NO: 814.

In still another embodiment of the present invention, the fusion may be formed via a peptide bond or a chemical bond.

The chemical bond may be preferably selected from the group consisting of disulfide bonds, diamine bonds, sulfide-amine bonds, carboxyl-amine bonds, ester bonds, and covalent bonds.

In still another embodiment of the present invention, the CP-BMP recombinant protein may be used for the regeneration of defected bone. The CP-BMP recombinant protein may act on tissues or bone defected by osteogenesis imperfecta, osteoporosis, fracture and osteotomy to efficiently help cell differentiation, leading to bone regeneration or formation.

Still another embodiment of the present invention provides a polynucleotide sequence encoding the CP-BMP recombinant protein.

The polynucleotide sequence may be present in a vector in which the polynucleotide sequence is operably linked to regulatory sequences capable of providing for the expression of the polynucleotide sequence by a suitable host cell.

According to one embodiment of the present invention, the polynucleotide sequence may be selected from the following groups:

1) a polynucleotide sequence, in which any one polynucleotide sequence selected from the group consisting of SEQ ID NOs: 241 to 481, preferably SEQ ID NOs: 241, 243, 252, 257, 273, 481, 274, 296, 314, 331, 334, 341, 350, 371, 375, 379, 383, 440, 468, 469 and 481, and more preferably SEQ ID NOs: 12 and 341, is operably linked with and a polynucleotide sequence selected from the group consisting of SEQ ID NOs: 815 to 818; and 2) a polynucleotide sequence, in which any one polynucleotide sequence selected from the group consisting of SEQ ID NOs: 806 to 812, preferably SEQ ID NOs: 806, 807, 808 and 812, and more preferably SEQ ID NOs: 807 and 812 is further operably linked to the polynucleotide sequence of 1).

Within the expression vector, the term "operably linked" is intended to mean that the polynucleotide sequence of interest is linked to the regulatory sequence(s) in a manner which allows for expression of the polynucleotide sequence. The term "regulatory sequence" is intended to include promoters, enhancers, and other expression control elements. Such operable linkage with the expression vector can be achieved by conventional gene recombination techniques known in the art, while site-directed DNA cleavage and linkage are carried out by using conventional enzymes known in the art.

The expression vectors may contain a signal sequence or a leader sequence for membrane targeting or secretion, as well as regulatory sequences such as a promoter, an operator, an initiation codon, a termination codon, a polyadenylation signal, an enhancer and the like. The promoter may be a constitutive or an inducible promoter. Further, the expression vector may include one or more selectable marker genes for selecting the host cell containing the expression vector, and may further include a polynucleotide sequence that enables the vector to replicate in the host cell in question.

The expression vector constructed according to the present invention may be the vector where the polynucleotide encoding the CP-BMP recombinant protein (where an aMTD is fused to the N-terminus or C-terminus of a BMP protein) is inserted within the multiple cloning sites (MC S), preferably NdeI/SalI, NdeI/BamHI, NdeI/NotI and NdeI/HindIII site of a pET-22b(+) vector, a pET-26b(+) vector or a pET-28a(+) vector (Novagen, Darmstadt, Germany).

In still another embodiment of the present invention, the polynucleotide encoding the SD being additionally fused to the N-terminus or C-terminus of a BMP protein may be inserted into a cleavage site of restriction enzyme (NdeI, EcoRI, SalI, XhoI, NotI, HindIII, etc.) within the multiple cloning sites (MCS) of a pET-22b(+) vector, a pET-26b(+) vector or a pET-28a(+) vector.

In still another embodiment of the present invention, the polynucleotide is cloned into a pET-22b(+) vector, a pET-26b(+) vector or a pET-28a(+) vector bearing a His-tag sequence so as to fuse six histidine residues to the N-terminus of the CP-BMP recombinant protein to allow easy purification.

According to one embodiment of the present invention, the polynucleotide sequence may be represented by a polynucleotide sequence selected from the group consisting of SEQ ID NOs: 824 and 825.

According to another embodiment of the present invention, the polynucleotide sequence may be further fused with SD, and may be represented by a polynucleotide sequence selected from the group consisting of SEQ ID NOs: 826 and 827.

According to still another embodiment of the present invention, the polynucleotide sequence may be fused with a histidine-tag affinity domain, and may be a polynucleotide sequence of SEQ ID NOs: 828 and 832.

Preferably, the CP-BMP recombinant protein of another embodiment of the present invention may be composed of an amino acid sequence selected from the group consisting of SEQ ID NOs: 824, 826 and 828.

Still another embodiment of the present invention provides a recombinant expression vector including the polynucleotide sequence.

Preferably, the vector may be inserted in a host cell and recombined with the host cell genome, or refers to any nucleic acid including a nucleotide sequence competent to replicate spontaneously as an episome. Such a vector may include a linear nucleic acid, a plasmid, a phagemid, a cosmid, an RNA vector, a viral vector, etc.

Preferably, the vector may be genetically engineered to incorporate the nucleic acid sequence encoding the recombinant protein in an orientation either N-terminal and/or C-terminal to a nucleic acid sequence encoding a peptide, a polypeptide, a protein domain, or a full-length protein of interest, and in the correct reading frame so that the recombinant protein consisting of aMTD, BMP, and preferably SD may be expressed. Expression vectors may be selected from those readily available for use in prokaryotic or eukaryotic expression systems. Preferably, a pET-22b(+) vector, a pET-26b(+) vector or a pET-28a(+) vector may be used.

Standard recombinant nucleic acid methods may be used to express a genetically engineered recombinant protein. The nucleic acid sequence encoding the recombinant protein according to one embodiment of the present invention may be cloned into a nucleic acid expression vector, e.g., with appropriate signal and processing sequences and regulatory sequences for transcription and translation, and the protein may be synthesized using automated organic synthetic methods. Synthetic methods of producing proteins are described in, for example, the literature [Methods in Enzymology, Volume 289: Solid-Phase Peptide Synthesis by Gregg B. Fields (Editor), Sidney P. Colowick, Melvin I. Simon (Editor), Academic Press (1997)].

In order to obtain high level expression of a cloned gene or nucleic acid, for example, a cDNA encoding the recombinant protein of the present invention, the recombinant protein sequence may be typically subcloned into an expression vector that includes a strong promoter for directing transcription, a transcription/translation terminator, and in the case of a nucleic acid encoding a protein, a ribosome binding site for translational initiation. Suitable bacterial promoters are well known in the art and are described, e.g., in the literatures [Sambrook & Russell, Molecular Cloning: A Laboratory Manual, 3d Edition, Cold Spring Harbor Laboratory, N.Y. (2001); and Ausube, et al., Current Protocols in Molecular Biology, Greene Publishing Associates and Wiley Interscience, N. Y. (1989)]. Bacterial expression systems for expression of the recombinant protein of the present invention are available in, e.g., *E. coli, Bacillus* sp., and *Salmonella* (Palva et al., Gene 22: 229-235 (1983); Mosbach et al., Nature 302: 543-545 (1983)). Kits for such expression systems are commercially available. Eukaryotic expression systems for mammalian cells, yeast, and insect cells are well known in the art and are also commercially available. The eukaryotic expression vector may be preferably an adenoviral vector, an adeno-associated vector, or a retroviral vector.

Generally, the expression vector for expressing the cell permeable recombinant protein according to one embodiment of the present invention in which the cargo protein, i.e. BMP, is attached to the N-terminus, C-terminus, or both termini of aMTD may include regulatory sequences including, for example, a promoter, operably attached to a sequence encoding the advanced macromolecule transduction domain. Non-limiting examples of inducible promoters that may be used include steroid-hormone responsive promoters (e.g., ecdysone-responsive, estrogen-responsive, and glutacorticoid-responsive promoters), tetracycline "Tet-On" and "Tet-Off" systems, and metal-responsive promoters.

The recombinant protein may be introduced into an appropriate host cell, e.g., a bacterial cell, a yeast cell, an insect cell, or a tissue culture cell. The recombinant protein may also be introduced into embryonic stem cells in order to generate a transgenic organism. Large numbers of suitable vectors and promoters are known to those skilled in the art and are commercially available for generating the recombinant protein of the present invention.

Known methods may be used to construct vectors including the polynucleotide sequence according to one embodiment of the present invention and appropriate transcriptional/translational control signals. These methods include in vitro recombinant DNA techniques, synthetic techniques, and in vivo recombination/genetic recombination. For example, these techniques are described in the literatures [Sambrook & Russell, Molecular Cloning: A Laboratory Manual, 3d Edition, Cold Spring Harbor Laboratory, N. Y. (2001); and Ausubel et al., Current Protocols in Molecular Biology Greene Publishing Associates and Wiley Interscience, N.Y. (1989)].

Still another embodiment of the present invention provides a transformant transformed with the recombinant expression vector.

The transformation includes transfection, and refers to a process whereby a foreign (extracellular) DNA, with or without an accompanying material, enters into a host cell. The "transfected cell" refers to a cell into which the foreign DNA is introduced into the cell, and thus the cell harbors the foreign DNA. The DNA may be introduced into the cell so that a nucleic acid thereof may be integrated into the chromosome or replicable as an extrachromosomal element. The cell introduced with the foreign DNA, etc. is called a transformant.

As used herein, 'introducing' of a protein, a peptide, an organic compound into a cell may be used interchangeably with the expression of 'carrying,' 'penetrating,' 'transporting,' 'delivering,' 'permeating' or 'passing.'

It is understood that the host cell refers to a eukaryotic or prokaryotic cell into which one or more DNAs or vectors are introduced, and refers not only to the particular subject cell but also to the progeny or potential progeny thereof. Because certain modifications may occur in succeeding generations due to either mutation or environmental influences, such progeny may not, in fact, be identical to the parent cell, but are still included within the scope of the term as used herein.

The host cells may be preferably bacterial cells, and as the bacterial cells, there are, in principle, no limitations. They may be eubacteria (gram-positive or gram-negative) or archaebacteria, as long as they allow genetic manipulation for insertion of a gene of interest, preferably for site-specific integration, and they may be cultured on a manufacturing scale. Preferably, the host cells may have the property to allow cultivation to high cell densities.

Examples of bacterial host cells that may be used in the preparation of the recombinant protein are *E. coli* (Lee, 1996; Hannig and Makrides, 1998), *Bacillus subtilis*, *Pseudomonas fluorescens* (Squires et al., 2004; Retallack et al., 2006) as well as various *Corynebacterium* (US 2006/0003404 A1) and *Lactococcus lactis* (Mierau et al., 2005) strains. Preferably, the host cells are *Escherichia coli* cells.

More preferably, the host cell may include an RNA polymerase capable of binding to a promoter regulating the gene of interest. The RNA polymerase may be endogenous or exogenous to the host cell.

Preferably, host cells with a foreign strong RNA polymerase may be used. For example, *Escherichia coli* strains engineered to carry a foreign RNA polymerase (e.g. like in the case of using a T7 promoter a T7-like RNA polymerase in the so-called "T7 strains") integrated in their genome may be used. Examples of T7 strains, e.g. BL21(DE3), HMS174 (DE3), and their derivatives or relatives (see Novagen, pET System manual, 11$^{th}$ edition), may be widely used and commercially available. Preferably, BL21-CodonPlus (DE3)-RIL or BL21-CodonPlus(DE3)-RIPL (Agilent Technologies) may be used. These strains are DE3 lysogens containing the T7 RNA polymerase gene under control of the lacUV5 promoter. Induction with IPTG allows production of T7 RNA polymerase which then directs the expression of the gene of interest under the control of the T7 promoter.

The host cell strains, *E. coli* BL21(DE3) or HMS174 (DE3), which have received their genome-based T7 RNA polymerase via the phage DE3, are lysogenic. It is preferred that the T7 RNA polymerase contained in the host cell has been integrated by a method which avoids, or preferably excludes, the insertion of residual phage sequences in the host cell genome since lysogenic strains have the disadvantage to potentially exhibit lytic properties, leading to undesirable phage release and cell lysis.

Still another embodiment of the present invention provides a preparing method of the CP-BMP recombinant protein including preparing the recombinant expression vector; preparing the transformant using the recombinant expression vector; culturing the transformant; and recovering the recombinant protein expressed by culturing.

Culturing may be preferably in a mode that employs the addition of a feed medium, this mode being selected from the fed-batch mode, semi-continuous mode, or continuous mode, and the bacterial expression host cells may include a DNA construct, integrated in their genome, carrying the DNA sequence encoding the protein of interest under the control of a promoter that enables expression of said protein.

There are no limitations in the type of the culture medium. The culture medium may be semi-defined, i.e. containing complex media compounds (e.g. yeast extract, soy peptone, casamino acids), or it may be chemically defined, without any complex compounds. Preferably, a defined medium may be used. The defined media (also called minimal or synthetic media) are exclusively composed of chemically defined substances, i.e. carbon sources such as glucose or glycerol, salts, vitamins, and, in view of a possible strain auxotrophy, specific amino acids or other substances such as thiamine. Most preferably, glucose may be used as a carbon source. Usually, the carbon source of the feed medium serves as the growth-limiting component which controls the specific growth rate.

Host cells may be disrupted by any convenient method, including freeze-thaw cycling, sonication, mechanical disruption, or the use of cell lysing agents. The literature [Scopes, Protein Purification: Principles and Practice, New York: Springer-Verlag (1994)] describes a number of general methods for purifying recombinant (and non-recombinant) proteins. The methods may include, e.g., ion-exchange chromatography, size-exclusion chromatography, affinity chromatography, selective precipitation, dialysis, and hydrophobic interaction chromatography. These methods may be adapted to devise a purification strategy for the cell permeable recombinant protein. If the cell permeable recombinant protein includes a purification handle, such as an epitope tag or a metal chelating sequence, affinity chromatography may be used to easily purify the protein.

The amount of the protein produced may be evaluated by detecting the advanced macromolecule transduction domain directly (e.g., using Western analysis) or indirectly (e.g., by assaying materials derived from the cells for specific DNA binding activity, such as by electrophoretic mobility shift assay). Proteins may be detected prior to purification, during any stage of purification, or after purification. In some implementations, purification or complete purification may not be necessary.

The recombinant protein prepared by the method according to one embodiment of the present invention may be an improved cell/tissue-permeable recombinant BMP, and induces differentiation of osteoblasts to regenerate defected bones.

The cell permeable recombinant proteins prepared by the method according to one embodiment of the present invention may be preferably used for regeneration of defected bone, which osteogenesis imperfecta, osteoporosis, bone fracture and osteotomy.

The osteogenesis imperfecta (OI), also known as "brittle bone disease" or Lobstein syndrome, is a debilitating and rare congenital bone disease that affects about one in every 15,000 people. Though phenotypes vary among OI types, common symptoms include incomplete ossification of bones and teeth, reduced bone mass, brittle bones, and pathologic fractures. These common symptoms of OI are thought to be caused by gene mutations which result in deficiencies in Type-I collagen or other proteins involved in bone matrix deposition or homeostasis.

The osteoporosis is a disease in which bones become fragile and more likely to fracture. Usually the bone loses density, which measures the amount of calcium and minerals in the bone. Osteoporosis is the most common type of bone disease. Bone is living tissue. Existing bone is constantly being replaced by new bone. Osteoporosis occurs when the body fails to form enough new bone, when too much existing bone is reabsorbed by the body, or both.

The bone fracture is a medical condition in which there is a damage in the continuity of the bone. A bone fracture can be the result of high force impact or stress, or a minimal trauma injury as a result of certain medical conditions that weaken the bones, such as osteoporosis, bone cancer, or osteogenesis imperfecta, where the fracture is then properly termed a pathologic fracture.

The osteotomy is a surgical operation in which a bone is cut to shorten, lengthen, or change its alignment. In some osteotomies, the bone is cut and an implant is provided in the bone to change the alignment of the bone.

The CP-BMP recombinant proteins according to one embodiment of the present invention may be used to bone regeneration, which the bone including but not limited to a tibia, fibula, femur, pelvis, humerus, ulna, radius, metacarpal and metatarsal.

The cell permeable recombinant proteins may be delivered to the interior of the cell, eliminating the need to transfect or transform the cell with a recombinant vector. The cell permeable recombinant proteins according to one embodiment of the present invention may be used in vitro to investigate protein function or may be used to maintain cells in a desired state.

Still another embodiment of the present invention provides a composition including the CP-BMP recombinant protein as an active ingredient. The composition may include CP-BMP2, CP-BMP7 or both CP-BMP2 and CP-BMP7 as an active ingredient. Preferably, the composition may include CP-BMP 2 or CP-BMP7, and more preferably, both CP-BMP2 and CP-BMP7 for effective bone regeneration.

Still another embodiment of the present invention provides a pharmaceutical composition for regenerating of defected bone including the CP-BMP recombinant protein as an active ingredient; and a pharmaceutically acceptable carrier.

Preferably, the composition may be for injectable (e.g. intraperitoneal, intravenous, subcutaneous, and intra-arterial, etc.) and may include the active ingredient in an amount of 75 to 600 ug/defected site, preferably 75 to 300 ug/defected site, more preferably 75 to 150 ug/defected site.

In the treatment of adult humans, the range of 75 to 150 ug/defected site/day in single or divided dose, is especially preferred. However, it will be understood that the concentration of the CP-BMP recombinant protein actually administered will be determined by a physician, in the light of the relevant circumstances, including the condition to be treated, the chosen route of administration, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Still another embodiment of the present invention provides use of the CP-BMP recombinant protein as a medicament for regenerating of defected bone.

Still another embodiment of the present invention provides a medicament including the CP-BMP recombinant protein.

Still another embodiment of the present invention provides use of the CP-BMP recombinant protein for the preparation of a medicament for regenerating of defected bone.

Still another embodiment of the present invention provides a method of regenerating of defected bone, preparing defected bone; and treating the defected bone with an therapeutically effective amount of the CP-BMP recombinant protein. According to the method, the CP-BMP recombinant protein may be administrated or treated to the site of defected bone, and can induces bone regeneration and formation.

In one embodiment of the present invention, the subject may be preferably a mammal.

The pharmaceutical composition according to one embodiment of the present invention may be prepared by using pharmaceutically suitable and physiologically acceptable additives, in addition to the active ingredient, and the additives may include excipients, disintegrants, sweeteners, binders, coating agents, blowing agents, lubricants, glidants, flavoring agents, etc.

For administration, the pharmaceutical composition may be preferably formulated by further including one or more pharmaceutically acceptable carriers in addition to the above-described active ingredient.

Dosage forms of the pharmaceutical composition may include granules, powders, tablets, coated tablets, capsules, suppositories, liquid formulations, syrups, juice, suspensions, emulsions, drops, injectable liquid formulations, etc. For formulation of the composition into a tablet or capsule, for example, the active ingredient may be combined with any oral, non-toxic pharmaceutically acceptable inert carrier, such as ethanol, glycerol, water, etc. If desired or necessary, suitable binders, lubricants, disintegrants, and colorants may be additionally included as a mixture.

Examples of the suitable binder may include, but are not limited to, starch, gelatin, natural sugars such as glucose or beta-lactose, corn sweeteners, natural and synthetic gums such as acacia, tragacanth, or sodium oleate, sodium stearate, magnesium stearate, sodium benzoate, sodium acetate, sodium chloride, etc. Examples of the disintegrant may include, but are not limited to, starch, methyl cellulose, agar, bentonite, xanthan gum, etc. For formulation of the composition into a liquid preparation, a pharmaceutically acceptable carrier which is sterile and biocompatible may be used, such as saline, sterile water, a Ringer's solution, buffered saline, an albumin infusion solution, a dextrose solution, a maltodextrin solution, glycerol, and ethanol, and these materials may be used alone or in any combination thereof. If necessary, other common additives, such as antioxidants, buffers, bacteriostatic agents, etc., may be added. Further, diluents, dispersants, surfactants, binders, and lubricants may be additionally added to prepare injectable formulations such as aqueous solutions, suspensions, and emulsions, or pills, capsules, granules, or tablets. Furthermore, the composition may be preferably formulated, depending upon diseases and ingredients, using any appropriate method known in the art, as disclosed in Remington's Pharmaceutical Science, Mack Publishing Company, Easton Pa.

Preferably, the treatment or treating mean improving or stabilizing the subject's condition or disease; or preventing or relieving the development or worsening of symptoms associated with the subject's condition or disease.

The subject and patient are used herein interchangeably. They refer to a human or another mammal (e.g., mouse, rat, rabbit, dog, cat, cattle, swine, sheep, horse or primate) that can be afflicted with or is susceptible to a disease or disorder (e.g., PD) but may or may not have the disease or disorder. In certain embodiments, the subject is a human being.

Preferably, the amount effective or effective amount is the amount of an active ingredient or a pharmaceutical composition disclosed herein that when administered to a subject for treating a disease, is sufficient to effect such treatment of the disease. Any improvement in the patient is considered sufficient to achieve treatment. An effective amount of an active ingredient or a pharmaceutical composition disclosed herein, used for the regeneration of defected bone can vary depending upon the manner of administration, the age, body weight, and general health of the patient. Ultimately, the prescribers or researchers will decide the appropriate amount and dosage regimen.

In the treatment or prevention method according to one embodiment of the present invention, the composition including the CP-BMP recombinant protein as an active ingredient may be administered in a common manner via oral, buccal, rectal, intravenous, intra-arterial, intraperitoneal, intramuscular, intrastemal, percutaneous, topical, intraocular or subcutaneous route, more preferably via subcutaneous or intravenous injection route.

Advantageous Effects

One embodiment of the present invention provides artificially constructed aMTD sequences based on the critical factors (CFs) that overcome the limitations of prior arts (MTM/MTS/MTD), such as limited diversity and unpredictable cell-permeability. Based on the CFs that assure the cell-permeability, the aMTD displays these sequences shows up to 109.9 relative fold enhanced ability compared to prior arts thereof to deliver biologically active macromolecules into live cells. Therefore, one embodiment of the present invention would allow their practically effective applications in molecule delivery, drug delivery, protein therapy, intracellular protein therapy, protein replacement therapy, peptide therapy, gene delivery and so on.

With enhanced solubility and yield, aMTD/SD-fused BMP recombinant protein could be produced in large quantities. In addition, effective cell-permeability of the recombinant protein overcomes the limitations of previously developed bone regeneration. Therefore, CP-BMP recombinant protein of the present invention would allow practical applications to efficiently bone regeneration for recovery of bone defected by osteogenesis imperfect, osteoporosis, facture and osteoectomy.

DESCRIPTION OF DRAWINGS

FIG. 1 shows Structure of aMTD- or rPeptide-Fused Recombinant Proteins. A schematic diagram of the His-tagged CRA recombinant proteins is illustrated and constructed according to one embodiment of the present invention. The his-tag for affinity purification (white), aMTD or rPeptide (gray) and cargo A (CRA, black) are shown.

FIGS. 2a to 2c show Construction of Expression Vectors for aMTDs- or rPeptide-Fused Recombinant Proteins. These FIGs. show the agarose gel electrophoresis analysis showing plasmid DNA fragments at 645 bp insert encoding aMTDs or rPeptide-fused CRA cloned into the pET-28a(+) vector according to one embodiment of the present invention.

FIGS. 3a to 3d show Inducible Expression of aMTD- or rPeptide-Fused Recombinant Proteins. Expressed recombinant aMTD- or random peptide-fused CRA recombinant proteins were transformed in E. coli BL21(DE3) strain. Expression of recombinant proteins in E. coli before (−) and after (+) induction with IPTG was monitored by SDS-PAGE, and stained with Coomassie blue.

FIGS. 4a and 4b show Purification of aMTD- or rPeptide-Fused Recombinant Proteins. Expressed recombinant proteins were purified by $Ni^{2+}$ affinity chromatography under the natural condition. Purification of recombinant proteins displayed through SDS-PAGE analysis.

FIGS. 5a to 5u show Determination of aMTD-Mediated Cell-Permeability. Cell-permeability of a negative control (A: rP38) and reference hydrophobic CPPs (MTM12 and MTD85) are shown. The cell-permeability of each aMTD and/or rPeptide is visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins (HMCA) fused to negative control (rP38), reference CPP (MTM12 or MTD85) or new hydrophobic CPP (aMTD) are shown with light thick line and indicated by arrows.

FIGS. 6a to 6c show Determination of rPeptide-Mediated Cell-Permeability. The cell-permeability of each aMTD and/or rPeptide was visually compared to that of the cargo protein lacking peptide sequence (HCA). Gray shaded area represents untreated RAW 264.7 cells (vehicle); thin light gray line represents the cells treated with equal molar concentration of FITC (FITC only); dark thick line indicates the cells treated with FITC-his-tagged CRA protein (HCA); and the cells treated with the FITC-proteins fused to rPeptides are shown with light thick line and indicated by arrows.

FIGS. 7a to 7k shows Visualized Cell-Permeability of aMTD-Fused Recombinant Proteins. NIH3T3 cells were treated with FITC-labeled protein (10 uM) fused to aMTD for 1 hour at 37° C. Cell-permeability of the proteins was visualized by laser scanning confocal microscopy (LSM700 version).

FIG. 8 show Visualized Cell-Permeability of rPeptide-Fused Recombinant Proteins. Cell-permeability of rPeptide-fused recombinant proteins was visualized by laser scanning confocal microscopy (LSM700 version).

FIGS. 9a to 9c show Relative Cell-Permeability of aMTD-Fused Recombinant Proteins Compared to Negative Control (rP38). The FIGs. show graphs comparing the cell-permeability of the recombinant proteins fused to aMTDs and a negative control (A: rP38).

FIGS. 10a to 10c show Relative Cell-Permeability of aMTD-Fused Recombinant Proteins Compared to Reference CPP (MTM12). The FIGs. show graphs comparing the cell-permeability of the recombinant proteins fused to aMTDs and a reference CPP (MTM12).

FIGS. 11a to 11c show Relative Cell-Permeability of aMTD-Fused Recombinant Proteins Compared to Reference CPP (MTD85). The FIGs. show graphs comparing the cell-permeability of the recombinant proteins fused to aMTDs and a reference CPP (MTD85).

FIG. 12 shows Relative Cell-Permeability of rPeptide-Mediated Recombinant Proteins Compared to Average that of aMTDs. The FIG. 12 shows graphs comparing the cell-permeability of the recombinant proteins fused to rPeptides and that (average value: aMTD AVE) of aMTDs.

FIGS. 13a, 13b, 13c, and 13d show Association of Cell-Permeability with Amino Acid Composition in aMTD Sequences, wherein the graphs display delivery potential (Geometric Mean) of aMTDs influenced with amino acid composition of A, I, V and L, respectively.

FIGS. 14a, 14b, 14c, and 14d show Association of Cell-Permeability with Critical Factors in aMTDs, wherein the graphs show the association of cell-permeability with critical factors [bending potential: proline position (PP) (FIG. 14a), rigidity/flexibility: instability index (II) (FIG. 14b), structural feature: aliphatic index (AI) (FIG. 14c) and hydropathy: grand average of hydropathy (GRAVY) (FIG. 14d)].

FIGS. 15a, 15b, 15c, and 15d show Relative Relevance of aMTD-Mediated Cell-Permeability with Critical Factors. Cell-permeability of 10 high and 10 low ranked aMTDs in their delivery potential were examined for their association with the critical factors [bending potential: proline position (PP) (FIG. 15a), rigidity/flexibility: instability index (II) (FIG. 15b), structural feature: aliphatic index (AI) (FIG. 15c) and hydropathy: grand average of hydropathy (GRAVY) (FIG. 15d)].

FIG. 16 shows Relative Relevance of rPeptide-Mediated Cell-Permeability with Hydropathy Range (GRAVY). This graph and a chart illustrate relative relevance of rPeptide-mediated cell-permeability with its hydropathy range (GRAVY).

FIG. 17 shows Structural Features of BMP2 and BMP7. A structural composition of BMP families is illustrated and structure design for BMP2/7 recombinant proteins in present invention is based on their basic structure.

FIG. 18a shows Schematic Diagram of His-Tagged BMP2/7 (M form) Recombinant Proteins. Design of BMP2/7 (M form) recombinant proteins containing histidine tag for affinity purification, BMP2/7 (MP), aMTD$_{24}$, solubilization domain A (SDA), and/or solubilization domain B (SDB).

FIG. 18b shows Schematic Diagram of His-Tagged BMP2/7 (L form) Recombinant Proteins. Design of BMP2/7 (L form) recombinant proteins containing histidine tag for affinity purification, BMP2/7 (LAP+MP), aMTD$_{24}$, solubilization domain A (SDA), and/or solubilization domain B (SDB).

FIG. 19a shows Construction of Expression for His-Tagged BMP2 (M form) Recombinant Proteins. This figure show the agarose gel electrophoresis analysis show plasmid DNA fragments encoding BMP2 (MP) cloned into the pET-28a(+) vector according to one embodiment of the present invention aMTD-fused BMP2 (MP) and SD.

FIG. 19b shows Construction of Expression for His-Tagged BMP7 (M form) Recombinant Proteins. These agarose gel electrophoresis analysis show plasmid DNA fragments encoding BMP7 (MP) cloned into the pET-28a(+) vector according to one embodiment of the present invention aMTD fused BMP7 (MP) and SD.

FIG. 19c shows Construction of Expression for His-Tagged BMP2 (L form) Recombinant Proteins. These agarose gel electrophoresis analysis show plasmid DNA fragments encoding BMP2 (LAP+MP: LP) cloned into the pET-28a(+) vector according to one embodiment of the present invention aMTD fused BMP2 (LP) and SD.

FIG. 19d shows Construction of Expression for His-Tagged BMP7 (L form) Recombinant Proteins. These agarose gel electrophoresis analysis show plasmid DNA fragments encoding BMP7 (LAP+MP: LP) cloned into the pET-28a(+) vector according to one embodiment of the present invention aMTD fused BMP7 (LP) and SD.

FIG. 20a shows Inducible Expression and Purification of BMP2 (M form/L form) Recombinant Proteins. Expression of BMP2 recombinant proteins in E. coli before (−) and after (+) induction with IPTG, and purification by Ni$^{2+}$ affinity chromatography (P) were confirmed by SDS-PAGE which stained with Coomassie Brilliant Blue.

FIG. 20b shows Inducible Expression and Purification of BMP7 (M form/L form) Recombinant Proteins. Expression of BMP7 recombinant proteins in E. coli before (−) and after (+) induction with IPTG, and purification by Ni$^{2+}$ affinity chromatography (P) were confirmed by SDS-PAGE which stained with Coomassie Brilliant Blue.

Figure 21:
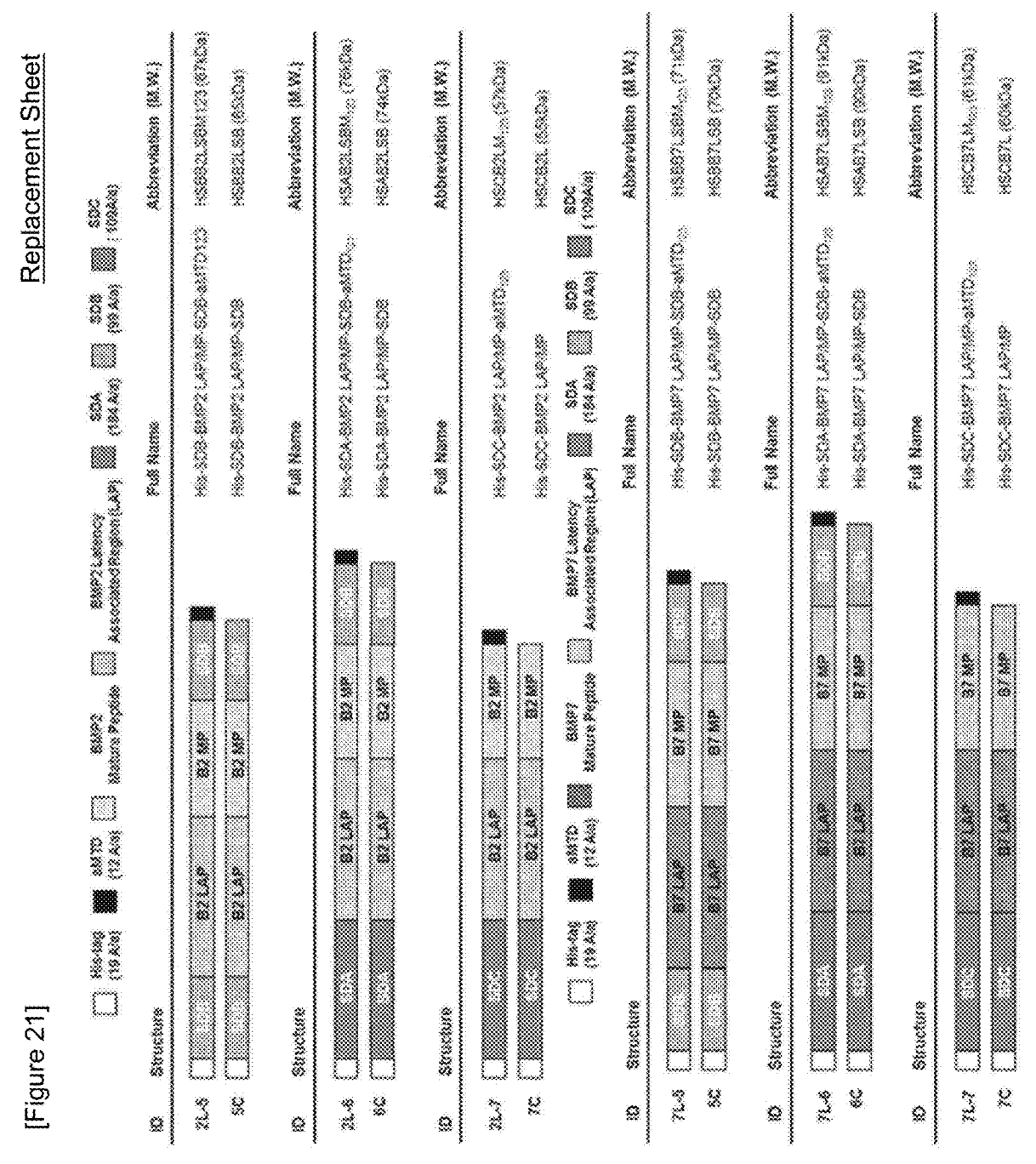

FIG. 21 shows Structural Changes of BMP2/7 (L form) Recombinant Proteins. Additional designs (A, B, C) of BMP2/7 (LAP+MP: LP) recombinant proteins contained histidine tag for affinity purification (white), BMP2/7 (LP), aMTD$_{123}$ (black), solubilization domain A (SDA), and/or solubilization domain B (SDB) or solubilization domain C (SDC).

FIG. 22 shows Construction of Expression for Newly Designed BMP2/7 (L form) Recombinant Proteins. These agarose gel electrophoresis analysis show plasmid DNA fragments encoding newly designed BMP2 (LAP+MP: LP) cloned into the pET-28a(+) vector according to one embodiment of the present invention aMTD fused BMP2 (LP) and SD.

FIG. 23a shows Inducible Expression and Purification of Newly Designed BMP2 (L form) Recombinant Proteins. Expression of BMP2 (L form) recombinant proteins before (−) and after (+) induction with IPTG, and purification by Ni$^{2+}$ affinity chromatography (P) were confirmed by SDS-PAGE analysis which stained with Coomassie Brilliant Blue.

FIG. 23b shows Inducible Expression and Purification of Newly Designed BMP7 (L form) Recombinant Proteins. Expression of BMP7 (L form) recombinant proteins before (−) and after (+) induction with IPTG, and purification by Ni$^{2+}$ affinity chromatography (P) were confirmed by SDS-PAGE analysis which stained with Coomassie Brilliant Blue.

FIG. 24 shows aMTD-Mediated Cell-Permeability of BMP2/7 (M form) Recombinant Proteins. RAW 264.7 cells were exposure to FITC-labeled BMP2/7 recombinant proteins (10 uM) compared with control protein fused with/without aMTD and solubilization domain A or B (10 uM) for 1 hour, treated with proteinase K to remove cell associated but non-internalized proteins and analyzed by FACS. Gray shaded area represents untreated RAW 264.7 cells (vehicle) and equimolar concentration of unconjugated FITC (FITC-only, green)-treated cells were served as control.

FIG. 25 shows aMTD-Mediated Intracellular Delivery and Localization of BMP2/7 (M form) Recombinant Proteins. Fluorescence confocal laser scanning microscopy shows intracellular localization of BMP2/7 (M form) recombinant proteins in NIH3T3 cells after incubated with 10 uM of FITC-conjugated BMP2/7 recombinant proteins, unconjugated FITC (FITC-only) or protein physiological buffer (vehicle) for 1 hour. Nomarski images are provided to show their cell morphology.

FIG. 26 shows Tissue Distribution of CP-BMP2/7 Recombinant Proteins. Cryosection of saline-perfused organs were prepared from mice 1 hour after the intraperitoneal injection of the BMP2/7 recombinant proteins, vehicle, or FITC only. The images from fluorescence microscopy shows distribution of BMP2/7 recombinant proteins in various organs.

FIG. 27 shows Morphological Differentiation in C2C12 Myoblasts with CP-BMP2/7 Recombinant Proteins. The images of cells show the morphology of the C2C12 myoblasts after treatment of BMP2/7 (M form) recombinant proteins with dose variation. (×100 magnification). The C2C12 cells were treated with the BMP2/7 recombinant proteins for 7 days. The proteins were freshly replaced every day. To compare the effect of CP-BMP2/7 recombinant proteins, the morphology is compared with BMP2/7 (M form) recombinant proteins.

FIG. 28 shows Stimulatory Effect of CP-BMP2/7 Recombinant Proteins on Smad Signaling in C2C12 Cells. The C2C12 cells were treated for 15 minutes with 10 uM BMP2/7 (M form) recombinant proteins and then extracted protein in these cells. The cell lysates were analyzed for phosphorylated Smad-1/5/8 and β-actin expression.

FIG. 29 shows Stimulatory Effect of CP-BMP2/7 Recombinant Proteins on ALP Activity in MC3T3-E1 Cells. The BMP2/7 recombinant proteins (10 uM) were continuously treated for 5 days and then measured ALP activity.

FIG. 30 shows Osteogenic Differentiation of C2C12 Myoblasts by Using Combinational Treatment of CP-BMP2 and CP-BMP7 Recombinant Proteins. The images of cells, which were continuously treated with vehicle (control) or 1 uM of CP-BMP2/7 recombinant proteins (×100 magnification) for 7 days.

FIG. 31 shows ALP Activity of C1C12 Myoblasts by Using Combinational Treatment of CP-BMP2 and CP-BMP7 Recombinant Proteins. The CP-BMP2/7 recombinant proteins (10 uM) were continuously treated for 5 days and then measured ALP activity.

FIG. 32 shows Osteoblastic Effect of CP-BMP2/7 Recombinant Protein in Calvarial Injection Mouse Models. Hematoxylin and Eosin (H&E)-stained calvarial bone sections in diluent, BMP2/7 recombinant protein treated groups (×400). Arrows indicate newly formed bone matrix.

FIG. 33 shows Relative Activity of BMP2/7 recombinant proteins on New Bone Formation in Calvarial Injection Mouse Models. The graph compared the newly formed ECM thickness of aMTD/SD-fused CP-BMP2/7 recombinant proteins or aMTD lacking SD-fused BMP2/7 recombinant proteins with protein physiological buffer (diluent).

FIG. 34 shows Structure of CP-BMP2 Recombinant Proteins fused various aMTDs and SDA.

FIGS. 35a and 35b show Inducible Expression and Purification of Newly Designed CP-BMP2 Recombinant Proteins. Expression of CP-BMP2 recombinant proteins before (−) and after (+) induction with IPTG, and purification by $Ni^{2+}$ affinity chromatography (P) were confirmed by SDS-PAGE analysis which stained with Coomassie Brilliant Blue.

FIG. 36a shows aMTD-Mediated Cell-Permeability of CP-BMP2 Recombinant Proteins fused various aMTDs.

FIG. 36b shows Quantitative aMTD-Mediated Cell-Permeability of CP-BMP2 Recombinant Proteins fused various aMTDs.

FIG. 37 shows Stimulatory Effect of CP-BMP2 Recombinant Proteins on ALP Activity in C3H10T1/2 Cells.

FIG. 38 shows aMTD-Mediated Cell-Permeability of CP-BMP2 Recombinant Proteins in RAW 264.7 cells.

FIG. 39 shows aMTD-Mediated Intracellular Delivery and Localization of CP-BMP2/7 Recombinant Proteins.

FIG. 40a shows Schematic Diagram of BMP2 Recombinant Protein Effects in C2C12 Trans-differentiation into Osteoblasts.

FIG. 40b shows CP-BMP2 Recombinant Protein Inhibits Myotube Formation.

FIG. 41 shows CP-BMP2 Recombinant Protein Improves ALP Activity.

FIG. 42 shows CP-BMP2 Recombinant Protein Induces Smad-mediated Osteogenic Differentiation.

FIG. 43 shows CP-BMP2 Recombinant Protein and BMPR II Co-localize in Golgi, ER and/or Nucleus.

FIG. 44a shows CP-BMP2 Recombinant Protein Induces New Bone Formation (Calvarial Injection Assay).

FIG. 44b shows Quantification of New Bone Formation Induced by CP-BMP2 Recombinant Protein (Calvarial Injection Assay).

FIG. 45a shows CP-BMP2 Recombinant Protein Enhances Bone Regeneration (Calvarial Critical-sized Defect Model).

FIG. 45b shows Quantification of Bone Regeneration Induced by CP-BMP2 Recombinant Protein (Calvarial Critical-sized Defect Model).

FIG. 46a shows CP-BMP2 Recombinant Protein Significantly Induces Bone Regeneration with Reduced Administration Frequency.

FIG. 46b shows Quantification of Bone Regeneration Induced by CP-BMP2 Recombinant Protein with Reduced Administration Frequency.

FIG. 47a shows CP-BMP2 Recombinant Protein Induces Bone Regeneration with Dose-dependent Manner.

FIG. 47b shows Quantification of Bone Regeneration Induced by CP-BMP2 Recombinant Protein with Dose-dependent Manner.

FIG. 48 shows Structures of rhBMP2, rBMP2 and CP-BMP2 Recombinant Proteins.

FIG. 49a shows Horses Characteristics Used Equine Bone Defect Model.

FIG. 49b shows Design of Equine Bone Defect Model.

FIG. 50 shows CP-BMP2 Recombinant Protein Have Similar Osteogenic Activity To Original BMP2 And Much Better Therapeutic Applicability Even Without Scaffold.

FIG. 51 shows CP-BMP2 Recombinant Protein Is Very Safe Protein in vivo (Single Dose Acute Toxicity).

FIGS. 52a and 52b show CP-BMP2 Recombinant Protein Is Very Safe Protein in vivo (Repeated Dose Toxicity Assay).

FIG. 53 shows CP-BMP2 Recombinant Protein Shows Longer Persistency Than Plain-BMP2 Recombinant Protein In Vivo Bioavailability.

FIG. 54 shows CP-BMP2 recombinant protein Is More Stable Than Plain-BMP2 Recombinant Protein In Blood.

FIG. 55 shows CP-BMP2 Recombinant Protein Shows Longer Persistence Than Non-CP-BMP2 Recombinant Protein.

MODE FOR INVENTION

1. Analysis of Reference Hydrophobic CPPs to Identify 'Critical Factors' for Development of Advanced MTDs Previously reported MTDs were selected from a screen of more than 1,500 signal peptide sequences. Although the MTDs that have been developed did not have a common sequence or sequence motif, they were all derived from the hydrophobic (H) regions of signal sequences (HRSSs) that also lack common sequences or motifs except their hydrophobicity and the tendency to adopt alpha-helical conformations. The wide variation in H-region sequences may reflect prior evolution for proteins with membrane translocating activity and subsequent adaptation to the SRP/Sec61 machinery, which utilizes a methionine-rich signal peptide binding pocket in SRP to accommodate a wide-variety of signal peptide sequences.

Previously described hydrophobic CPPs (e.g. MTS/MTM and MTD) were derived from the hydrophobic regions present in the signal peptides of secreted and cell surface proteins. The prior art consists first, of ad hoc use of H-region sequences (MTS/MTM), and second, of H-region sequences (with and without modification) with highest CPP activity selected from a screen of 1,500 signal sequences (MTM). Second prior art, the modified H-region derived hydrophobic CPP sequences had advanced in diversity with multiple number of available sequences apart from MTS/MTM derived from fibroblast growth factor (FGF) 4. However, the number of MTDs that could be modified from naturally occurring secreted proteins are somewhat limited. Because there is no set of rules in determining their cell-permeability, no prediction for the cell-permeability of modified MTD sequences can be made before testing them.

The hydrophobic CPPs, like the signal peptides from which they originated, did not conform to a consensus sequence, and they had adverse effects on protein solubility when incorporated into protein cargo. We therefore set out to identify optimal sequence and structural determinants, namely critical factors (CFs), to design new hydrophobic CPPs with enhanced ability to deliver macromolecule cargoes including proteins into the cells and tissues while maintaining protein solubility. These newly developed CPPs, advanced macromolecule transduction domains (aMTDs) allowed almost infinite number of possible designs that could be designed and developed based on the critical factors. Also, their cell-permeability could be predicted by their character analysis before conducting any in vitro and/or in vivo experiments. These critical factors below have been developed by analyzing all published reference hydrophobic CPPs.

1-1. Analysis of Hydrophobic CPPs

Seventeen different hydrophobic CPPs (Table 1) published from 1995 to 2014 (Table 2) were selected. After physiological and chemical properties of selected hydrophobic CPPs were analyzed, 11 different characteristics that may be associated with cell-permeability have been chosen for further analysis. These 11 characteristics are as follows: sequence, amino acid length, molecular weight, pI value, bending potential, rigidity/flexibility, structural feature, hydropathy, residue structure, amino acid composition and secondary structure of the sequences (Table 3).

Table 1 shows the Summary of Published Hydrophobic Cell-Penetrating Peptides which were Chosen.

TABLE 1

| # | Pepides | Origin | Protein | Ref. |
|---|---|---|---|---|
| 1 | MTM | Homo sapiens | NP_001998 Kaposi fibroblast growth factor (K-FGF) | 1 |
| 2 | MTS | Homo sapiens | NP_001998 Kaposi fibroblast growth factor (K-FGF) | 2 |
| 3 | MTD10 | Streptomyces coelicolor | NP_625021 Glycosyl hydrolase | 8 |
| 4 | MTD13 | Streptomyces coelicolor | NP_639877 Putative secreted protein | 3 |
| 5 | MTD47 | Streptomyces coelicolor | NP_627512 Secreted protein | 4 |
| 6 | MTD56 | Homo sapiens | P23274 Peptidyl-prolyl cis-trans isomerase B precursor | 5 |
| 7 | MTD73 | Drosophila metanogaster | AAA17887 Spatzle (spz) protein | 5 |
| 8 | MTD77 | Homo sapiens | NP_003231 Kaposi fibroblast growth factor (K-FGF) | 6 |
| 9 | MTD84 | Phytophthora cactorum | AAK63068 Phytotoxic protein PcF precursor | 4 |
| 10 | MTD85 | Streptomyces coelicolor | NP_629842 Peptide transport system peptide binding protein | 7 |
| 11 | MTD86 | Streptomyces coelicolor | NP_629842 Peptide transport system secreted peptide binding protein | 7 |
| 12 | MTD103 | Homo sapiens | TMBV19 domain Family member B | 8 |
| 13 | MTD132 | Streptomyces coelicolor | NP_628377 P60-family secreted protein | 4 |
| 14 | MTD151 | Streptomyces coelicolor | NP_630126 Secreted chitinase | 8 |
| 15 | MTD173 | Streptomyces coelicolor | NP_624384 Secreted protein | 4 |
| 16 | MTD174 | Streptomyces coelicolor | NP_733505 Large, multifunctional secreted protein | 8 |
| 17 | MTD181 | Neisseria meningitidis Z2491 | CAB84257.1 Putative secreted protein | 4 |

Table 2 shows the Summarizes Reference Information.

TABLE 2

| | | References | | | | |
|---|---|---|---|---|---|---|
| # | Title | Journal | Year | Vol | Issue | Page |
| 1 | Inhibition of Nuclear Translocation of Transcription Factor NF-kB by a Synthetic peptide Containing a Cell Membrane-permeable Motif and Nuclear Localization Sequence | JOURNAL OF BIOLOGICAL CHEMISTRY | 1995 | 270 | 24 | 14255 |
| 2 | Epigenetic Regulation of Gene Structure and Function with a Cell-Permeable Cre Recombinase | NATURE BIO-TECHNO-LOGY | 2001 | 19 | 10 | 929 |
| 3 | Cell-Permeable NM23 Blocks the Maintenance and Progression of Established Pulmonary Metastasis | CANCER RESEARCH | 2011 | 71 | 23 | 7216 |
| 4 | Antitumor Activity of Cell-Permeable p18INK4-c With Enhanced Membrane and Tissue Penetration | MOLECULAR THERAPY | 2012 | 20 | 8 | 1540 |
| 5 | Antitumor Activity of Cell-Permeable RUNX3 Protein in Gastric Cancer Cells | CLINICAL CANCER RESEARCH | 2012 | 19 | 3 | 680 |
| 6 | The Effect of Intracellular Protein Delivery | BIO-MATERIALS | 2013 | 34 | 26 | 6261 |

TABLE 2-continued

| | References | | | | | |
|---|---|---|---|---|---|---|
| # | Title | Journal | Year | Vol | Issue | Page |
| 7 | on the Ant-Tumor Activity of Recombinant Human Endostatin Partial Somatic to Stem Cell Transformations Induced By Cell-Permeable Reprogramming Factors | SCIENTIFIC REPORTS | 2014 | 4 | 10 | 4361 |
| 8 | Cell-Permeable Parkin Proteins Suppress Parkinson Disease-Associated Phenotypes in Cultured Cells and Animals | PLOS ONE | 2014 | 9 | 7 | 17 |

Table 3 shows the Characteristics of Published Hydrophobic Cell-Penetrating Peptides (A) which were Analyzed.

TABLE 3

| # | Peptides | Sequence | Length | Molecular Weight | pI | Bending Potential | Rigidity/Flexibility (Instability Index: II) |
|---|---|---|---|---|---|---|---|
| 1 | MTM | AAVALLPAVLLALLAP | 16 | 1,515.9 | 5.6 | Bending | 45.5 |
| 2 | MTS | AAVLLPVLLAAP | 12 | 1,147.4 | 5.6 | Bending | 57.3 |
| 3 | MTD10 | LGGAVVAAPVAAAVAP | 16 | 1,333.5 | 5.5 | Bending | 47.9 |
| 4 | MTD13 | LAAAALAVLPL | 11 | 1,022.3 | 5.5 | Bending | 26.6 |
| 5 | MTD47 | AAAVPVLVAA | 10 | 881.0 | 5.6 | Bending | 47.5 |
| 6 | MTD56 | VLLAAALIA | 9 | 854.1 | 5.5 | No-Bending | 8.9 |
| 7 | MTD73 | PVLLLLA | 7 | 737.9 | 6.0 | No-Bending | 36.1 |
| 8 | MTD77 | AVALLILAV | 9 | 882.1 | 5.6 | No-Bending | 30.3 |
| 9 | MTD84 | AVALVAVVAVA | 11 | 982.2 | 5.6 | No-Bending | 9.1 |
| 10 | MTD85 | LLAAAAALLLA | 11 | 1,010.2 | 5.5 | No-Bending | 9.1 |
| 11 | MTD86 | LLAAAAALLLA | 11 | 1,010.2 | 5.5 | No-Bending | 9.1 |
| 12 | MTD103 | LALPVLLLA | 9 | 922.2 | 5.5 | Bending | 51.7 |
| 13 | MTD132 | AVVVPAIVLAAP | 12 | 1,119.4 | 5.6 | Bending | 50.3 |
| 14 | MTD151 | AAAPVAAVP | 9 | 1,031.4 | 5.5 | Bending | 73.1 |
| 15 | MTD173 | AVIPILAVP | 9 | 892.1 | 5.6 | Bending | 48.5 |
| 16 | MTD174 | LILLLPAVALP | 12 | 1,011.8 | 5.5 | Bending | 79.1 |
| 17 | MTD181 | AVLLLPAAA | 9 | 838.0 | 5.6 | Bending | 51.7 |
| | AVE | | 10.8 ± 2.4 | 1,011 ± 189.6 | 5.6 ± 0.1 | Proline Presence | 40.1 ± 21.9 |

| # | Structural Feature (Aliphatic Index: AI) | Hydropathy (GRAVY) | Residue Structure | A/a Composition | | | | | | Secondary Structure | Cargo | Ref. |
|---|---|---|---|---|---|---|---|---|---|---|---|---|
| | | | | A | V | L | I | P | G | | | |
| 1 | 220.0 | 2.4 | Aliphatic Ring | 6 | 2 | 6 | 0 | 2 | 0 | Helix | p50 | 1 |
| 2 | 211.7 | 2.3 | — | 4 | 2 | 4 | 0 | 2 | 0 | No-Helix | cRE | 2 |
| 3 | 140.6 | 1.8 | — | 7 | 4 | 1 | 0 | 2 | 2 | Helix | Parkin | 8 |
| 4 | 213.6 | 2.4 | — | 5 | 1 | 4 | 0 | 1 | 0 | No-Helix | RUNX3 | 3 |
| 5 | 176.0 | 2.4 | — | 5 | 3 | 1 | 0 | 1 | 0 | No-Helix | CMYC | 4 |
| 6 | 250.0 | 3.0 | — | 4 | 1 | 3 | 1 | 0 | 0 | Helix | ES | 5 |
| 7 | 278.6 | 2.8 | — | 1 | 1 | 4 | 0 | 1 | 0 | Helix | ES | 5 |
| 8 | 271.1 | 3.3 | — | 3 | 2 | 3 | 1 | 0 | 0 | Helix | NM23 | 6 |
| 9 | 212.7 | 3.1 | — | 5 | 5 | 1 | 0 | 0 | 0 | Helix | OCT4 | 4 |
| 10 | 231.8 | 2.7 | — | 6 | 0 | 5 | 0 | 0 | 0 | No-Helix | RUNX3 | 7 |
| 11 | 231.8 | 2.7 | — | 6 | 0 | 5 | 0 | 0 | 0 | No-Helix | SOX2 | 7 |
| 12 | 271.1 | 2.8 | — | 2 | 1 | 5 | 0 | 1 | 0 | Helix | p18 | 8 |
| 13 | 195.0 | 2.4 | — | 4 | 4 | 1 | 1 | 2 | 0 | No-Helix | LIN28 | 4 |
| 14 | 120.0 | 1.6 | — | | | | | | | No-Helix | Parkin | 8 |
| 15 | 216.7 | 24 | — | 2 | 2 | 1 | 2 | 2 | 0 | Helix | KLF4 | 4 |
| 16 | 257.3 | 2.0 | — | | | | | | | Helix | Parkin | 8 |
| 17 | 206.7 | 2.4 | — | 4 | 1 | 3 | 0 | 1 | 0 | Helix | SOX2 | 4 |
| | 217.9 ± 43.6 | 2.5 ± 0.4 | — | | | | | | | | | |

Two peptide/protein analysis programs were used (ExPasy: SoSui: harrier.nagahama-i-bio.ac.jp/sosui/sosui_submit.html) to determine various indexes and structural features of the peptide sequences and to design new sequence. Followings are important factors analyzed.

1-2. Characteristics of Analyzed Peptides: Length, Molecular Weight and pI Value Average length, molecular weight and pI value of the peptides analyzed were 10.8±2.4, 1,011±189.6 and 5.6±0.1, respectively (Table 4)

Table 4 shows the Summarizes Critical Factors (CFs) of Published Hydrophobic Cell-Penetrating Peptides (A) which were Anal
yzed.

TABLE 4

Length: 10.8 ± 2.4
Molecular Weight: 1,011 ± 189.6
pI: 5.6 ± 0.1
Bending Potential (BP): Proline presences In the middle
and/or the end of peptides, or No Proline.
Instability Index (II): 40.1 ± 21.9
Residue Structure & Aliphatic Index (AI): 217.9 ± 43.6
Hydropathy (GRAVY): 2.5 ± 0.4
Aliphatic Ring: Non-polar hydrophobic & aliphatic amino acid (A, V, L, I).
Secondary Structure: α-Helix is favored but not required.

1-3. Characteristics of Analyzed Peptides: Bending Potential—Proline Position (PP)

Bending potential (bending or no-bending) was determined based on the fact whether proline (P) exists and/or where the amino acid(s) providing bending potential to the peptide in recombinant protein is/are located. Proline differs from the other common amino acids in that its side chain is bonded to the backbone nitrogen atom as well as the alpha-carbon atom. The resulting cyclic structure markedly influences protein architecture which is often found in the bends of folded peptide/protein chain.

Eleven out of 17 were determined as 'Bending' peptide which means that proline is present in the middle of sequence for peptide bending and/or located at the end of the peptide for protein bending. As indicated above, peptide sequences could penetrate the plasma membrane in a "bent" configuration. Therefore, bending or no-bending potential is considered as one of the critical factors for the improvement of current hydrophobic CPPs.

1-4. Characteristics of Analyzed Peptides: Rigidity/Flexibility—Instability Index (II)

Since one of the crucial structural features of any peptide is based on the fact whether the motif is rigid or flexible, which is an intact physicochemical characteristic of the peptide sequence, instability index (II) of the sequence was determined. The index value representing rigidity/flexibility of the peptide was extremely varied (8.9 to 79.1), but average value was 40.1±21.9 which suggested that the peptide should be somehow flexible, but not too much rigid or flexible (Table 3).

1-5. Characteristics of Analyzed Peptides: Structural Features—Structural Feature (Aliphatic Index: AI) and Hydropathy (Grand Average of Hydropathy: GRAVY)

Alanine (V), valine (V), leucine (L) and isoleucine (I) contain aliphatic side chain and are hydrophobic—that is, they have an aversion to water and like to cluster. These amino acids having hydrophobicity and aliphatic residue enable them to pack together to form compact structure with few holes. Analyzed peptide sequence showed that all composing amino acids were hydrophobic (A, V, L and I) except glycine (G) in only one out of 17 (MTD10—Table 3) and aliphatic (A, V, L, I, and P). Their hydropathic index (Grand Average of Hydropathy: GRAVY) and aliphatic index (AI) were 2.5±0.4 and 217.9±43.6, respectively. Their amino acid composition is also indicated in the Table 3.

1-6. Characteristics of Analyzed Peptides: Secondary Structure (Helicity)

As explained above, the CPP sequences may be supposed to penetrate the plasma membrane directly after inserting into the membranes in a "bent" configuration with hydrophobic sequences having α-helical conformation. In addition, our analysis strongly indicated that bending potential was crucial for membrane penetration. Therefore, structural analysis of the peptides was conducted to determine whether the sequences were to form helix or not. Nine peptides were helix and eight were not (Table 3). It seems to suggest that helix structure may not be required.

1-7. Determination of Critical Factors (CFs)

In the 11 characteristics analyzed, the following 6 are selected namely "Critical Factors" for the development of new hydrophobic CPPs—advanced MTDs: amino acid length, bending potential (proline presence and location), rigidity/flexibility (instability index: II), structural feature (aliphatic index: AI), hydropathy (GRAVY) and amino acid composition/residue structure (hydrophobic and aliphatic A/a) (Tables 3 and Table 4).

2. Analysis of Selected Hydrophobic CPPs to Optimize 'Critical Factors'

Since the analyzed data of the 17 different hydrophobic CPPs (analysis A, Tables 3 and 4) previously developed during the past 2 decades showed high variation and were hard to make common- or consensus-features, analysis B (Tables 5 and 6) and C (Tables 7 and 8) were also conducted to optimize the critical factors for better design of improved CPPs—aMTDs. Therefore, 17 hydrophobic CPPs have been grouped into two groups and analyzed the groups for their characteristics in relation to the cell permeable property. The critical factors have been optimized by comparing and contrasting the analytical data of the groups and determining the common homologous features that may be critical for the cell permeable property.

2-1. Selective Analysis (B) of Peptides Used to Biologically Active Cargo Protein for In Vivo In analysis B, eight CPPs were used with each biologically active cargo in vivo. Length was 11±3.2, but 3 out of 8 CPPs possessed little bending potential. Rigidity/Flexibility (instability index: II) was 41±15, but removing one [MTD85: rigid, with minimal II (9.1)] of the peptides increased the overall instability index to 45.6±9.3. This suggested that higher flexibility (40 or higher II) is potentially be better. All other characteristics of the 8 CPPs were similar to the analysis A, including structural feature and hydropathy (Tables 5 and 6).

Table 5 shows the Characteristics of Published Hydrophobic Cell-Penetrating Peptides (B): Selected CPPs That were Used to Each Cargo In Vivo.

TABLE 5

| # | Peptides | Sequence | Length | Molecular Weight | pI | Bending Potential | Rigidity/Flexibility (Instability Index: II) |
|---|---|---|---|---|---|---|---|
| 1 | MTM | AAVALLPAVLLALLAP | 16 | 1,515.9 | 5.6 | Bending | 45.5 |
| 2 | MTS | AAVLLPVLLAAP | 12 | 1,147.4 | 5.6 | Bending | 57.3 |
| 3 | MTD10 | LGGAVVAAPVAAAVAP | 16 | 1,333.5 | 5.5 | Bending | 47.9 |
| 4 | MTD73 | PVLLLLA | 7 | 737.9 | 6.0 | No-Bending | 36.1 |
| 5 | MTD77 | AVALLILAV | 9 | 882.1 | 5.6 | No-Bending | 30.3 |
| 6 | MTD85 | LLAAAAALLLA | 11 | 1,010.2 | 5.5 | No-Bending | 9.1* |
| 7 | MTD103 | LALPVLLLA | 9 | 922.2 | 5.5 | Bending | 51.7 |
| 8 | MTD132 | AVVVPAIVLAAP | 12 | 1,119.4 | 5.6 | Bending | 50.3 |
|   | AVE |  | 11 ± 3.2 | 1,083 ± 252 | 5.6 ± 0.1 | Proline Presence | 41 ± 15 |

| # | Structural Feature (Aliphatic Index: AI) | Hydropathy (GRAVY) | Residue Structure | A/a Composition | | | | | | Secondary Structure | Cargo | Ref. |
|---|---|---|---|---|---|---|---|---|---|---|---|---|
|   |   |   |   | A | V | L | I | P | G |   |   |   |
| 1 | 220.0 | 2.4 | Aliphatic Ring | 6 | 2 | 6 | 0 | 2 | 0 | Helix | p50 | 1 |
| 2 | 211.7 | 2.3 | — | 4 | 2 | 4 | 0 | 2 | 0 | No-Helix | CRE | 2 |
| 3 | 140.6 | 1.8 | — | 7 | 4 | 1 | 0 | 2 | 2 | Helix | Parkin | 8 |
| 4 | 278.6 | 2.8 | — | 1 | 1 | 4 | 0 | 1 | 0 | Helix | ES | 6 |
| 5 | 271.1 | 3.3 | — | 3 | 2 | 3 | 1 | 0 | 0 | Helix | NM23 | 3 |
| 6 | 2318 | 2.7 | — | 6 | 0 | 5 | 0 | 0 | 0 | No-Helix | RUNX3 | 5 |
| 7 | 271.1 | 2.8 | — | 2 | 1 | 5 | 0 | 1 | 0 | Helix | p18 | 4 |
| 8 | 195.0 | 2.4 | — | 4 | 4 | 1 | 1 | 2 | 0 | Helix | LIN28 | 7 |
|   | 227 ± 47 | 2.5 ± 0.4 |   |   |   |   |   |   |   |   |   |   |

Table 6 shows the Summarized Critical Factors of Published Hydrophobic Cell-Penetrating Peptides (B).

TABLE 6

Length: 11 ± 3.2
Molecular Weight: 1,083 ± 252
pI: 5.6 ± 0.1
Bending Potential (BP): Proline presences in the middle and/or the end of peptides, or No Proline.
Instability Index (II): 41.0 ± 15
(*Removing the MTD85 increases II to 45.6 ± 9.3)
Residue Structure & Aliphatic Index (AI): 227 ± 47
Hydropathy (GRAVY): 2.5 ± 0.4
Aliphatic Ring: Non-polar hydrophobic & aliphatic amino acid (A, V, L, I).
Secondary Structure: α-Helix is favored but not required.

2-2. Selective Analysis (C) of Peptides that Provided Bending Potential and Higher Flexibility To optimize the 'Common Range and/or Consensus Feature of Critical Factor' for the practical design of aMTDs and the random peptides (rPs or rPeptides), which were to prove that the 'Critical Factors' determined in the analysis A, B and C were correct to improve the current problems of hydrophobic CPPs—protein aggregation, low solubility/yield, and poor cell-/tissue-permeability of the recombinant proteins fused to the MTS/MTM or MTD, and non-common sequence and non-homologous structure of the peptides, empirically selected peptides were analyzed for their structural features and physicochemical factor indexes.

Hydrophobic CPPs which did not have a bending potential, rigid or too much flexible sequences (too much low or too much high Instability Index), or too low or too high hydrophobic CPPs were unselected, but secondary structure was not considered because helix structure of sequence was not required.

In analysis C, eight selected CPP sequences that could provide a bending potential and higher flexibility were finally analyzed (Table 7 and 8). Common amino acid length is 12 (11.6±3.0). Proline is presence in the middle of and/or the end of sequence. Rigidity/Flexibility (II) is 45.5 to 57.3 (Avg: 50.1±3.6). AI and GRAVY representing structural feature and hydrophobicity of the peptide are 204.7±37.5 and 2.4±0.3, respectively. All peptides are consisted with hydrophobic and aliphatic amino acids (A, V, L, I, and P). Therefore, analysis C was chosen as a standard for the new design of new hydrophobic CPPs—aMTDs.

Table 7 shows the Characteristics of Published Hydrophobic Cell-Penetrating Peptides (C): Selected CPPs that Provided Bending Potential and Higher Flexibility.

TABLE 7

| # | Peptides | Sequence | Length | Molecular Weight | pI | Bending Potential | Rigidity/Flexibility (Instability Index: II) |
|---|---|---|---|---|---|---|---|
| 1 | MTM | AAVALLPAVLLALLAP | 16 | 1515.9 | 5.6 | Bending | 45.5 |
| 2 | MTS | AAVLLPVLLAAP | 12 | 1147.4 | 5.6 | Bending | 57.3 |

TABLE 7-continued

| # | | | | | | | | | |
|---|---|---|---|---|---|---|---|---|---|
| 3 | MTD10 | LGGAVVAAPVAAAVAP | 16 | 1333.5 | | 5.5 | Bending | 47.9 | |
| 4 | MTD47 | AAAVPVLVAA | 10 | 881.0 | | 5.6 | Bending | 47.5 | |
| 5 | MTD103 | LALPVLLLA | 9 | 922.2 | | 5.5 | Bending | 51.7 | |
| 6 | MTD132 | AVVVPAIVLAAP | 12 | 1119.4 | | 5.6 | Bending | 50.3 | |
| 7 | MTD173 | AVIPILAVP | 9 | 892.1 | | 5.6 | Bending | 48.5 | |
| 8 | MTD181 | AVLLLPAAA | 9 | 838.0 | | 5.6 | Bending | 51.7 | |
| | | AVE | 11.6 ± 3.0 | 1081.2 ± 244.6 | | 5.6 ± 0.1 | Proline Presence | 50.1 ± 3.6 | |

| # | Structural Feature (Aliphatic Index: AI) | Hydropathy (GRAVY) | Residue Structure | A/a Composition A | V | L | I | P | G | Secondary Structure | Cargo | Ref. |
|---|---|---|---|---|---|---|---|---|---|---|---|---|
| 1 | 220.0 | 2.4 | Aliphatic Ring | 6 | 2 | 6 | 0 | 2 | 0 | Helix | p50 | 1 |
| 2 | 211.7 | 2.3 | — | 4 | 2 | 4 | 0 | 2 | 0 | No-Helix | CRE | 2 |
| 3 | 140.6 | 1.8 | — | 7 | 4 | 1 | 0 | 2 | 2 | Helix | Parkin | 8 |
| 4 | 176.0 | 2.4 | — | 5 | 3 | 1 | 0 | 1 | 0 | No-Helix | CMYC | 4 |
| 5 | 271.1 | 2.8 | — | 2 | 1 | 5 | 0 | 1 | 0 | Helix | p18 | 8 |
| 6 | 195.0 | 2.4 | — | 4 | 4 | 1 | 1 | 2 | 0 | No-Helix | LIN28 | 4 |
| 7 | 216.7 | 2.4 | — | 2 | 2 | 1 | 2 | 2 | 0 | Helix | KLF4 | 4 |
| 8 | 206.7 | 2.4 | — | 4 | 1 | 3 | 0 | 1 | 0 | No-Helix | SOX2 | 4 |
| | 204.7 ± 37.5 | 2.4 ± 0.3 | | | | | | | | | | |

Table 8 shows the Summarized Critical Factors of Published Hydrophobic Cell-Penetrating Peptides (C).

TABLE 8

Length: 11.6 ± 3.0
Molecular Weight: 1,081.2 ± 224.6
pI: 5.6 ± 0.1
Bending Potential (BP): Proline presences in the middle and/or the end of peptides.
Instability Index (II): 50.1 ± 3.6
Residue Structure & Aliphatic Index (AI): 204.7 ± 37.5
Hydropathy (GRAVY): 2.4 ± 0.3
Aliphatic Ring: Non-polar hydrophobic & aliphatic amino acid (A, V, L, I).
Secondary Structure: α-Helix is favored but not required.

3. New Design of Improved Hydrophobic CPPs—aMTDs Based on the Optimized Critical Factors 3-1. Determination of Common Sequence and/or Common Homologous Structure As mentioned above, H-regions of signal sequence (HOURSS)-derived CPPs (MTS/MTM and MTD) do not have a common sequence, sequence motif, and/or common-structural homologous feature. According to one embodiment of the present invention, the aim is to develop improved hydrophobic CPPs formatted in the common sequence- and structural-motif which satisfy newly determined 'Critical Factors' to have 'Common Function,' namely, to facilitate protein translocation across the membrane with similar mechanism to the analyzed reference CPPs. Based on the analysis A, B and C, the common homologous features have been analyzed to determine the critical factors that influence the cell-permeability. The range value of each critical factor has been determined to include the analyzed index of each critical factor from analysis A, B and C to design novel aMTDs (Table 9). These features have been confirmed experimentally with newly designed aMTDs in their cell-permeability.

Table 9 shows the Comparison The Range/Feature of Each Critical Factor Between The Value of Analyzed CPPs and The Value Determined for New Design of Novel aMTDs Sequences.

TABLE 9

Summarized Critical Factors of aMTD

| Critical Factor | Selected CPPs Range | Newly Designed CPPs Range |
|---|---|---|
| Bending Potential (Proline Position: PP) | Proline presences in the middle and/or at the end of peptides | Proline presences in the middle (5', 6', 7' or 8') and at the end of peptides |
| Rigidity/Flexibility (Instability Index: II) | 45.5-57.3 (50.1 ± 3.6) | 40-60 |
| Structural Feature (Aliphatic Index: AI) | 140.6-220.0 (204.7 ± 37.5) | 180-220 |
| Hydropathy (Grand Average of Hydropathy GRAVY) | 1.8-2.8 (2.4 ± 0.3) | 2.1-2.6 |
| Length (Number of Amino Acid) | 11.6 ± 3.0 | 9-13 |
| Amino acid Composition | A, V, I, L, P | A, V, I, L, P |

In Table 9, universal common features and sequence/structural motif are provided. Length is 9 to 13 amino acids, and bending potential is provided with the presence of proline in the middle of sequence (at 5', 6', 7' or 8' amino acid) for peptide bending and at the end of peptide for recombinant protein bending and Rigidity/Flexibility of aMTDs is II >40 are described in Table 9.

3-2. Critical Factors for Development of Advanced MTDs

Recombinant cell-permeable proteins fused to the hydrophobic CPPs to deliver therapeutically active cargo molecules including proteins into live cells had previously been reported, but the fusion proteins expressed in bacteria system were hard to be purified as a soluble form due to their low solubility and yield. To address the crucial weakness for further clinical development of the cell-permeable proteins as protein-based biotherapeutics, greatly improved form of the hydrophobic CPP, named as advanced MTD (aMTD) has newly been developed through critical factors-based peptide analysis. The critical factors used for the current invention of the aMTDs are herein (Table 9).

1. Amino Acid Length: 9 to 13
2. Bending Potential (Proline Position: PP)
: Proline presences in the middle (from 5' to 8' amino acid) and at the end of sequence
3. Rigidity/Flexibility (Instability Index: II): 40 to 60

4. Structural Feature (Aliphatic Index: AI): 180 to 220
5. Hydropathy (GRAVY): 2.1 to 2.6
6. Amino Acid Composition: Hydrophobic and Aliphatic amino acids to A, V, L, I and P 3-3. Design of Potentially Best aMTDs that all Critical Factors are Considered and Satisfied After careful consideration of six critical factors derived from analysis of unique features of hydrophobic CPPs, advanced macromolecule transduction domains (aMTDs) have been designed and developed based on the common 12 amino acid platform which satisfies the critical factors including amino acid length (9 to 13) determined from the analysis.

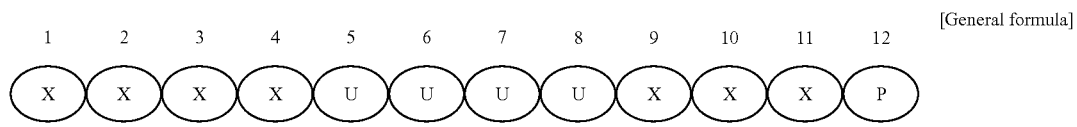

[General formula]

Unlike previously published hydrophobic CPPs that require numerous experiments to determine their cell-permeability, newly developed aMTD sequences could be designed by performing just few steps as follows using above mentioned platform to follow the determined range value/feature of each critical factor.

First, prepare the 12 amino acid sequence platform for aMTD. Second, place proline (P) in the end (12') of sequence and determine where to place proline in one of four U(s) in 5', 6', 7', and 8. Third, alanine (A), valine (V), leucine (L) or isoleucine (I) is placed in either X(s) and/or U(s), where proline is not placed. Lastly, determine whether the amino acid sequences designed based on the platform, satisfy the value or feature of six critical factors to assure the cell permeable property of aMTD sequences. Through these processes, numerous novel aMTD sequences have been constructed. The expression vectors for preparing non-functional cargo recombinant proteins fused to each aMTD, expression vectors have been constructed and forcedly expressed in bacterial cells. These aMTD-fused recombinant proteins have been purified in soluble form and determined their cell-permeability quantitatively. aMTD sequences have been newly designed, numbered from 1 to 240, as shown in Tables 10 to 15. In Tables 10 to 15, sequence ID Number is a sequence listings for reference, and aMTD numbers refer to amino acid listing numbers that actually have been used at the experiments. For further experiments, aMTD numbers have been used. In addition, polynucleotide sequences shown in the sequence lists have been numbered from SEQ ID NO: 241 to SEQ ID NO: 480.

Tables 10 to 15 show the 240 new hydrophobic aMTD sequences that were developed to satisfy all critical factors.

TABLE 10

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 1 | 1 | AAALAPVVLALP | 12 | 57.3 | 187.5 | 2.1 | Aliphatic |
| 2 | 2 | AAAVPLLAVVVP | 12 | 41.3 | 195.0 | 2.4 | Aliphatic |
| 3 | 3 | AALLVPAAVLAP | 12 | 57.3 | 187.5 | 2.1 | Aliphatic |
| 4 | 4 | ALALLPVAALAP | 12 | 57.3 | 195.8 | 2.1 | Aliphatic |
| 5 | 5 | AAALLPVALVAP | 12 | 57.3 | 187.5 | 2.1 | Aliphatic |
| 6 | 11 | VVALAPALAALP | 12 | 57.3 | 187.5 | 2.1 | Aliphatic |
| 7 | 12 | LLAAVPAVLLAP | 12 | 57.3 | 211.7 | 2.3 | Aliphatic |
| 8 | 13 | AAALVPVVALLP | 12 | 57.3 | 203.3 | 2.3 | Aliphatic |
| 9 | 21 | AVALLPALLAVP | 12 | 57.3 | 211.7 | 2.3 | Aliphatic |
| 10 | 22 | AVVLVPVLAAAP | 12 | 57.3 | 195.0 | 2.4 | Aliphatic |
| 11 | 23 | VVLVLPAAAAVP | 12 | 57.3 | 195.0 | 2.4 | Aliphatic |
| 12 | 24 | IALAAPALIVAP | 12 | 50.2 | 195.8 | 2.2 | Aliphatic |
| 13 | 25 | IVAVAPALVALP | 12 | 50.2 | 203.3 | 2.4 | Aliphatic |
| 14 | 42 | VAALPVVAVVAP | 12 | 57.3 | 186.7 | 2.4 | Aliphatic |
| 15 | 43 | LLAAPLVVAAVP | 12 | 41.3 | 187.5 | 2.1 | Aliphatic |

TABLE 10-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 16 | 44 | ALAVPVALLVAP | 12 | 57.3 | 203.3 | 2.3 | Aliphatic |
| 17 | 61 | VAALPVLLAALP | 12 | 57.3 | 211.7 | 2.3 | Aliphatic |
| 18 | 62 | VALLAPVALAVP | 12 | 57.3 | 203.3 | 2.3 | Aliphatic |
| 19 | 63 | AALLVPALVAVP | 12 | 57.3 | 203.3 | 2.3 | Aliphatic |

TABLE 11

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 20 | 64 | AIVALPVAVLAP | 12 | 50.2 | 203.2 | 2.4 | Aliphatic |
| 21 | 65 | IAIVAPVVALAP | 12 | 50.2 | 203.2 | 2.4 | Aliphatic |
| 22 | 81 | AALLPALAALLP | 12 | 57.3 | 204.2 | 2.1 | Aliphatic |
| 23 | 82 | AVVLAPVAAVLP | 12 | 57.3 | 195.0 | 2.4 | Aliphatic |
| 24 | 83 | LAVAAPLALALP | 12 | 41.3 | 195.8 | 2.1 | Aliphatic |
| 25 | 84 | AAVAAPLLLALP | 12 | 41.3 | 195.8 | 2.1 | Aliphatic |
| 26 | 85 | LLVLPAAALAAP | 12 | 57.3 | 195.8 | 2.1 | Aliphatic |
| 27 | 101 | LVALPVAAVLP | 12 | 57.3 | 203.3 | 2.3 | Aliphatic |
| 28 | 102 | LALAPAALALLP | 12 | 57.3 | 204.2 | 2.1 | Aliphatic |
| 29 | 103 | ALIAAPILALAP | 12 | 57.3 | 204.2 | 2.2 | AliphatiC |
| 30 | 104 | AVVAAPLVLALP | 12 | 41.3 | 203.3 | 2.3 | Aliphatic |
| 31 | 105 | LLALAPAALLAP | 12 | 57.3 | 204.1 | 2.1 | Aliphatic |
| 32 | 121 | AIVALPALALAP | 12 | 50.2 | 195.8 | 2.2 | Aliphatic |
| 33 | 123 | AAIIVPAALLAP | 12 | 50.2 | 195.8 | 2.2 | Aliphatic |
| 34 | 124 | IAVALPALIAAP | 12 | 50.3 | 195.8 | 2.2 | Aliphatic |
| 35 | 141 | AVIVLPALAVAP | 12 | 50.2 | 203.3 | 2.4 | Aliphatic |
| 36 | 143 | AVLAVPAVLVAP | 12 | 57.3 | 195.0 | 2.4 | Aliphatic |
| 37 | 144 | VLAIVPAVALAP | 12 | 50.2 | 203.3 | 2.4 | Aliphatic |
| 38 | 145 | LLAVVPAVALAP | 12 | 57.3 | 203.3 | 2.3 | Aliphatic |
| 39 | 161 | AVIALPAL1AAP | 12 | 57.3 | 195.8 | 2.2 | Aliphatic |
| 40 | 162 | AVVALPAALIVP | 12 | 50.2 | 203.3 | 2.4 | Aliphatic |
| 41 | 163 | LALVLPAALAAP | 12 | 57.3 | 195.8 | 2.1 | Aliphatic |
| 42 | 164 | LAAVLPALLAAP | 12 | 57.3 | 195.8 | 2.1 | Aliphatic |
| 43 | 165 | ALAVPVALAIVP | 12 | 50.2 | 203.3 | 2.4 | Aliphatic |
| 44 | 182 | ALIAPVVALVAP | 12 | 57.3 | 203.3 | 2.4 | Aliphatic |
| 45 | 183 | LLAAPVVIALAP | 12 | 57.3 | 211.6 | 2.4 | Aliphatic |
| 46 | 184 | LAAIVPAIIAVP | 12 | 50.2 | 211.6 | 2.4 | Aliphatic |
| 47 | 185 | AALVLPLIIAAP | 12 | 41.3 | 220.0 | 2.4 | Aliphatic |
| 48 | 201 | LALAVPALAALP | 12 | 57.3 | 195.8 | 2.1 | Aliphatic |

TABLE 11-continued

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 49 | 204 LIAALPAVAALP | 12 | 57.3 | 195.8 | 2.2 | Aliphatic |
| 50 | 205 ALALVPAIAALP | 12 | 57.3 | 195.8 | 2.2 | Aliphatic |
| 51 | 221 AAILAPIVALAP | 12 | 50.2 | 195.8 | 2.2 | Aliphatic |
| 52 | 222 ALLIAPAAVIAP | 12 | 57.3 | 195.7 | 2.2 | Aliphatic |
| 53 | 223 AILAVPIAVVAP | 12 | 57.3 | 203.3 | 2.4 | Aliphatic |
| 54 | 224 ILAAVPIALAAP | 12 | 57.3 | 195.8 | 2.2 | Aliphatic |
| 55 | 225 VAALLPAAAVLP | 12 | 57.3 | 187.5 | 2.1 | Aliphatic |
| 56 | 241 AAAVVPVLLVAP | 12 | 57.3 | 195.0 | 2.4 | Aliphatic |
| 57 | 242 AALLVPALVAAP | 12 | 57.3 | 187.5 | 2.1 | Aliphatic |
| 58 | 243 AAVLLPVALAAP | 12 | 57.3 | 187.5 | 2.1 | Aliphatic |
| 59 | 245 AAALAPVLALVP | 12 | 57.3 | 187.5 | 2.1 | Aliphatic |
| 60 | 261 LVLVPLLAAAAP | 12 | 41.3 | 211.6 | 2.3 | Aliphatic |
| 61 | 262 ALIAVPAIIVAP | 12 | 50.2 | 211.6 | 2.4 | Aliphatic |
| 62 | 263 ALAVIPAAAILP | 12 | 54.9 | 195.8 | 2.2 | Aliphatic |
| 63 | 264 LAAAPVVIVIAP | 12 | 50.2 | 203.3 | 2.4 | Aliphatic |
| 64 | 265 VLAIAPLLAAVP | 12 | 41.3 | 211.6 | 2.3 | Aliphatic |
| 65 | 281 ALIVLPAAVAVP | 12 | 50.2 | 203.3 | 2.4 | Aliphatic |
| 66 | 282 VLAVAPALIVAP | 12 | 50.2 | 203.3 | 2.4 | Aliphatic |
| 67 | 283 AALLAPALIVAP | 12 | 50.2 | 195.8 | 2.2 | Aliphatic |
| 68 | 284 ALIAPAVAL1VP | 12 | 50.2 | 211.7 | 2.4 | Aliphatic |
| 69 | 285 AIVLLPAAVVAP | 12 | 50.2 | 203.3 | 2.4 | Aliphatic |

TABLE 12

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 70 | 331 VIAAPVLAVLAP | 12 | 57.3 | 203.3 | 2.4 | Aliphatic |
| 71 | 302 LALAPALALLAP | 12 | 57.3 | 204.2 | 2.1 | Aliphatic |
| 72 | 304 AIILAPIAAIAP | 12 | 57.3 | 204.2 | 2.3 | Aliphatic |
| 73 | 305 IALAAPILLAAP | 12 | 57.3 | 204.2 | 2.2 | Aliphatic |
| 74 | 321 IVAVALPALAVP | 12 | 50.2 | 203.3 | 2.3 | Aliphatic |
| 75 | 322 VVAIVLPALAAP | 12 | 50.2 | 203.3 | 2.3 | Aliphatic |
| 76 | 323 IVAVALPVALAP | 12 | 50.2 | 203.3 | 2.3 | Aliphatic |
| 77 | 324 IVAVALPAALVP | 12 | 50.2 | 203.3 | 2.3 | Aliphatic |
| 78 | 325 IVAVALPAVALP | 12 | 50.2 | 203.3 | 2.3 | Aliphatic |
| 79 | 341 IVAVALPAVLAP | 12 | 50.2 | 203.3 | 2.3 | Aliphatic |
| 80 | 342 VIVALAPAVLAP | 12 | 50.2 | 203.3 | 2.3 | Aliphatic |
| 81 | 343 IVAVALPALVAP | 12 | 50.2 | 203.3 | 2.3 | Aliphatic |
| 82 | 345 ALLIVAPVAVAP | 12 | 50.2 | 203.3 | 2.3 | Aliphatic |

TABLE 12-continued

| Sequence ID Number | aMTD Sequences | Length | Rigidity/ Flexibility (II) | Sturctural Feature (AI) | Hydropathy (GRAVY) | Residue Structure |
|---|---|---|---|---|---|---|
| 83 | 381 AVVIVAPAVIAP | 12 | 50.2 | 195.0 | 2.4 | Aliphatic |
| 84 | 363 AVLAVAPALIVP | 12 | 50.2 | 203.3 | 2.3 | Aliphatic |
| 85 | 364 LVAAVAPALIVP | 12 | 50.2 | 203.3 | 2.3 | Aliphatic |
| 86 | 365 AVIVVAPALLAP | 12 | 50.2 | 203.3 | 2.3 | Aliphatic |
| 87 | 381 VVAIVLPAVAAP | 12 | 50.2 | 195.0 | 2.4 | Aliphatic |
| 88 | 382 AAALVIPAILAP | 12 | 54.9 | 195.8 | 2.2 | Aliphatic |
| 89 | 383 VIVALAPALLAP | 12 | 50.2 | 211.6 | 2.3 | Aliphatic |
| 90 | 384 VIVAIAPALLAP | 12 | 50.2 | 211.6 | 2.4 | Aliphatic |
| 91 | 385 IVAIAVPALVAP | 12 | 50.2 | 203.3 | 2.4 | Aliphatic |
| 92 | 401 AALAVIPAAILP | 12 | 54.9 | 195.8 | 2.2 | Aliphatic |
| 93 | 402 ALAAVIPAAILP | 12 | 54.9 | 195.8 | 2.2 | Aliphatic |
| 94 | 403 AAALVIPAAILP | 12 | 54.9 | 195.8 | 2.2 | Aliphatic |
| 95 | 404 LAAAVIPAAILP | 12 | 54.9 | 195.8 | 2.2 | Aliphatic |
| 96 | 405 LAAAVIPVAILP | 12 | 54.9 | 211.7 | 2.4 | Aliphatic |
| 97 | 421 AAILAAPLIAVP | 12 | 57.3 | 195.8 | 2.2 | Aliphatic |
| 98 | 422 VVAILAPLLAAP | 12 | 57.3 | 211.7 | 2.4 | Aliphatic |
| 99 | 424 AVVVAAPVLALP | 12 | 57.3 | 195.0 | 2.4 | Aliphatic |
| 100 | 425 AVVAIAPVLALP | 12 | 57.3 | 203.3 | 2.4 | Aliphatic |
| 101 | 442 ALAALVPAVLVP | 12 | 57.3 | 203.3 | 2.3 | Aliphatic |
| 102 | 443 ALAALVPVALVP | 12 | 57.3 | 203.3 | 2.3 | Aliphatic |
| 103 | 444 LAAALVPVALVP | 12 | 57.3 | 203.3 | 2.3 | Aliphatic |
| 104 | 445 ALAALVPALVVP | 12 | 57.3 | 203.3 | 2.3 | Aliphatic |
| 105 | 461 IAAVIVPAVALP | 12 | 50.2 | 203.3 | 2.4 | Aliphatic |
| 106 | 462 IAAVLVPAVALP | 12 | 57.3 | 203.3 | 2.4 | Aliphatic |
| 107 | 463 AVAILVPLLAAP | 12 | 57.3 | 211.7 | 2.4 | Aliphatic |
| 108 | 464 AVVIIVPLAAAP | 12 | 57.3 | 203.3 | 2.4 | Aliphatic |
| 109 | 465 IAAVIVPVAALP | 12 | 50.2 | 203.3 | 2.4 | Aliphatic |
| 110 | 481 AIAIAIVPVALP | 12 | 50.2 | 211.6 | 2.4 | Aliphatic |
| 111 | 482 ILAVAAIPVAVP | 12 | 54.9 | 203.3 | 2.4 | Aliphatic |
| 112 | 483 ILAAAIIPAALP | 12 | 54.9 | 204.1 | 2.2 | Aliphatic |
| 113 | 484 LAVVLAAPAIVP | 12 | 50.2 | 203.3 | 2.4 | Aliphatic |
| 114 | 485 AILAAIVPLAVP | 12 | 50.2 | 211.6 | 2.4 | Aliphatic |
| 115 | 501 VIVALAVPALAP | 12 | 50.2 | 203.3 | 2.4 | Aliphatic |
| 116 | 502 AIVALAVPVLAP | 12 | 50.2 | 203.3 | 2.4 | Aliphatic |
| 117 | 503 AAIIIVLPAALP | 12 | 50.2 | 220.0 | 2.4 | Aliphatic |
| 118 | 504 LIVALAVPALAP | 12 | 50.2 | 211.7 | 2.4 | Aliphatic |
| 119 | 505 AIIIVIAPAAAP | 12 | 50.2 | 195.8 | 2.3 | Aliphatic |

TABLE 13

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 120 | 521 LAALIVVPAVAP | 12 | 50.2 | 203.3 | 2.4 | Aliphatic |
| 121 | 522 ALLVIAVPAVAP | 12 | 57.3 | 203.3 | 2.4 | Aliphatic |
| 122 | 524 AVALIVVPALAP | 12 | 50.2 | 203.3 | 2.4 | Aliphatic |
| 123 | 525 ALAIVVAPVAVP | 12 | 50.2 | 195.0 | 2.4 | Aliphatic |
| 124 | 541 LLALIIAPAAAP | 12 | 57.3 | 204.1 | 2.1 | Aliphatic |
| 125 | 542 ALALIIVPAVAP | 12 | 50.2 | 211.6 | 2.4 | Aliphatic |
| 126 | 543 LLAALIAPAALP | 12 | 57.3 | 204.1 | 2.1 | Aliphatic |
| 127 | 544 IVALIVAPAAVP | 12 | 43.1 | 203.3 | 2.4 | Aliphatic |
| 128 | 545 VVLVLAAPAAVP | 12 | 57.3 | 195.0 | 2.3 | Aliphatic |
| 129 | 661 AAVAIVLPAVVP | 12 | 50.2 | 195.0 | 2.4 | Aliphatic |
| 130 | 562 ALIAAIVPALVP | 12 | 50.2 | 211.7 | 2.4 | Aliphatic |
| 131 | 563 ALAVIVVPALAP | 12 | 50.2 | 203.3 | 2.4 | Aliphatic |
| 132 | 564 VAIALIVPALAP | 12 | 50.2 | 211.7 | 2.4 | Aliphatic |
| 133 | 565 VAIVLVAPAVAP | 12 | 50.2 | 195.0 | 2.4 | Aliphatic |
| 134 | 582 VAVALIVPALAP | 12 | 50.2 | 203.3 | 2.4 | Aliphatic |
| 135 | 583 AVILALAPIVAP | 12 | 50.2 | 211.6 | 2.4 | Aliphatic |
| 136 | 585 ALIVAIAPALVP | 12 | 50.2 | 211.6 | 2.4 | Aliphatic |
| 137 | 601 AAILIAVPIAAP | 12 | 57.3 | 195.8 | 2.3 | Aliphatic |
| 138 | 602 VIVALAAPVLAP | 12 | 50.2 | 203.3 | 2.4 | Aliphatic |
| 139 | 603 VLVALAAPVIAP | 12 | 57.3 | 203.3 | 2.4 | Aliphatic |
| 140 | 604 VALIAVAPAVVP | 12 | 57.3 | 195.0 | 2.4 | Aliphatic |
| 141 | 605 VIAAVLAPVAVP | 12 | 57.3 | 195.0 | 2.4 | Aliphatic |
| 142 | 622 ALIVLAAPVAVP | 12 | 50.2 | 203.3 | 2.4 | Aliphatic |
| 143 | 623 VAAAIALPAIVP | 12 | 50.2 | 187.5 | 2.3 | Aliphatic |
| 144 | 625 ILAAAAAPLIVP | 12 | 50.2 | 195.8 | 2.2 | Aliphatic |
| 145 | 643 LALVLAAPAIVP | 12 | 50.2 | 211.6 | 2.4 | Aliphatic |
| 146 | 645 ALAVVALPAIVP | 12 | 50.2 | 203.3 | 2.4 | Aliphatic |
| 147 | 661 AAILAPIVAALP | 12 | 65.2 | 195.8 | 2.2 | Aliphatic |
| 148 | 664 ILIAIAIPAAAP | 12 | 54.9 | 204.1 | 2.3 | Aliphatic |
| 149 | 665 LAIVLAAPVAVP | 12 | 50.2 | 203.3 | 2.3 | Aliphatic |
| 150 | 666 AALAIIAPAIVP | 12 | 50.2 | 195.8 | 2.3 | Aliphatic |
| 151 | 667 LAVAIVAPALVP | 12 | 50.2 | 203.3 | 2.3 | Aliphatic |
| 152 | 683 LAIVLAAPAVLP | 12 | 50.2 | 211.7 | 2.4 | Aliphatic |
| 153 | 684 AAIVLALPAVLP | 12 | 50.2 | 211.7 | 2.4 | Aliphatic |
| 154 | 685 ALLVAVLPAALP | 12 | 57.3 | 211.7 | 2.3 | Aliphatic |
| 155 | ese AALVAVLPVALP | 12 | 57.3 | 203.3 | 2.3 | Aliphatic |
| 156 | 687 AILAVALPLLAP | 12 | 57.3 | 220.0 | 2.3 | Aliphatic |
| 157 | 703 IVAVALVPALAP | 12 | 50.2 | 203.3 | 2.4 | Aliphatic |

TABLE 13-continued

| Sequence ID Number | aMTD Sequences | Length | Rigidity/ Flexibility (II) | Structural Feature (AI) | Hydropathy (GRAVY) | Residue Structure |
|---|---|---|---|---|---|---|
| 158 | 705 IVAVALLPALAP | 12 | 50.2 | 211.7 | 2.4 | AliphatiC |
| 159 | 706 IVAVALLPAVAP | 12 | 50.2 | 203.3 | 2.4 | Aliphatic |
| 160 | 707 IVALAVLPAVAP | 12 | 50.2 | 203.3 | 2.4 | Aliphatic |
| 161 | 724 VAVLAVLPALAP | 12 | 57.3 | 203.3 | 2.3 | Aliphatic |
| 162 | 725 IAVLAVAPAVLP | 12 | 57.3 | 203.3 | 2.3 | Aliphatic |
| 163 | 726 LAVAIIAPAVAP | 12 | 57.3 | 187.5 | 2.2 | Aliphatic |
| 164 | 727 VALAIALPAVLP | 12 | 57.3 | 211.6 | 2.3 | Aliphatic |
| 165 | 743 AlAIALVPVALP | 12 | 57.3 | 211.6 | 2.4 | Aliphatic |
| 166 | 744 AAVVIVAPVALP | 12 | 50.2 | 195.0 | 2.4 | Aliphatic |
| 167 | 746 VAIIVVAPALAP | 12 | 50.2 | 203.3 | 2.4 | Aliphatic |
| 168 | 747 VALLAIAPALAP | 12 | 57.3 | 195.8 | 2.2 | Aliphatic |
| 169 | 763 VAVLIAVPALAP | 12 | 57.3 | 203.3 | 2.3 | Aliphatic |

TABLE 14

| Sequence ID Number | aMTD Sequences | Length | Rigidity/ Flexibility (II) | Sturctural Feature (AI) | Hydropathy (GRAVY) | Residue Structure |
|---|---|---|---|---|---|---|
| 170 | 764 AVALAVLPAVVP | 12 | 57.3 | 195.0 | 2.3 | Aliphatic |
| 171 | 765 AVALAVVPAVLP | 12 | 57.3 | 195.0 | 2.3 | Aliphatic |
| 172 | 766 IVVIAVAPAVAP | 12 | 50.2 | 195.0 | 2.4 | Aliphatic |
| 173 | 767 IVVAAVVPALAP | 12 | 50.2 | 195.0 | 2.4 | Aliphatic |
| 174 | 783 IVALVPAVAIAP | 12 | 50.2 | 203.3 | 2.5 | Aliphatic |
| 175 | 784 VAALPAVALVVP | 12 | 57.3 | 195.0 | 2.4 | Aliphatic |
| 176 | 786 LVAIAPLAVLAP | 12 | 41.3 | 211.7 | 2.4 | Aliphatic |
| 177 | 787 AVALVPVIVAAP | 12 | 50.2 | 195.0 | 2.4 | Aliphatic |
| 178 | 788 AlAVAIAPVALP | 12 | 57.3 | 187.5 | 2.3 | Aliphatic |
| 179 | 803 AIALAVPVLALP | 12 | 57.3 | 211.7 | 2.4 | Aliphatic |
| 180 | 805 LVLIAAAPIALP | 12 | 41.3 | 220.0 | 2.4 | Aliphatic |
| 181 | 806 LVALAVPAAVLP | 12 | 57.3 | 203.3 | 2.3 | Aliphatic |
| 182 | 807 AVALAVPALVLP | 12 | 57.3 | 203.3 | 2.3 | Aliphatic |
| 183 | 808 LVVLAAAPLAVP | 12 | 41.3 | 203.3 | 2.3 | Aliphatic |
| 184 | 809 LIVLAAPALAAP | 12 | 50.2 | 195.8 | 2.2 | Aliphatic |
| 185 | 810 VIVLAAPALAAP | 12 | 50.2 | 187.5 | 2.2 | Aliphatic |
| 186 | 811 AVVLAVPALAVP | 12 | 57.3 | 195.0 | 2.3 | Aliphatic |
| 187 | 824 LIIVAAAPAVAP | 12 | 50.2 | 187.5 | 2.3 | Aliphatic |
| 188 | 825 IVAVIVAPAVAP | 12 | 43.2 | 195.0 | 2.5 | Aliphatic |
| 189 | 826 LVALAAPIIAVP | 12 | 41.3 | 211.7 | 2.4 | Aliphatic |
| 190 | 827 IAAVLAAPALVP | 12 | 57.3 | 187.5 | 2.2 | Aliphatic |
| 191 | 828 IALLAAPIIAVP | 12 | 41.3 | 220.0 | 2.4 | Aliphatic |

TABLE 14-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 192 | 829 | AALALVAPVIVP | 12 | 50.2 | 203.3 | 2.4 | Aliphatic |
| 193 | 830 | IALVAAPVALVP | 12 | 57.3 | 203.3 | 2.4 | Aliphatic |
| 194 | 831 | IIVAVAPAAIVP | 12 | 43.2 | 203.3 | 2.5 | Aliphatic |
| 195 | 832 | AVAAIVPVIVAP | 12 | 43.2 | 195.0 | 2.5 | Aliphatic |
| 196 | 843 | AVLVLVAPAAAP | 12 | 41.3 | 219.2 | 2.5 | Aliphatic |
| 197 | 844 | VVALLAPLIAAP | 12 | 41.3 | 211.8 | 2.4 | Aliphatic |
| 198 | 845 | AAVVIAPLLAVP | 12 | 41.3 | 203.3 | 2.4 | Aliphatic |
| 199 | 846 | IAVAVAAPLLVP | 12 | 41.3 | 203.3 | 2.4 | Aliphatic |
| 200 | 847 | LVAIVVLPAVAP | 12 | 50.2 | 219.2 | 2.6 | Aliphatic |
| 201 | 848 | AVAIVVLPAVAP | 12 | 50.2 | 195.0 | 2.4 | Aliphatic |
| 202 | 849 | AVILLAPLIAAP | 12 | 57.3 | 220.0 | 2.4 | Aliphatic |
| 203 | 850 | LVIALAAPVALP | 12 | 57.3 | 211.7 | 2.4 | Aliphatic |
| 204 | 851 | VLAVVLPAVALP | 12 | 57.3 | 219.2 | 2.5 | Aliphatic |
| 205 | 852 | VLAVAAPAVLLP | 12 | 57.3 | 203.3 | 2.3 | Aliphatic |
| 206 | 863 | AAVVLLPIIAAP | 12 | 41.3 | 211.7 | 2.4 | Aliphatic |
| 207 | 864 | ALLVIAPAIAVP | 12 | 57.3 | 211.7 | 2.4 | Aliphatic |
| 208 | 865 | AVLVIAVPAIAP | 12 | 57.3 | 203.3 | 2.5 | Aliphatic |
| 209 | 867 | ALLVVIAPLAAP | 12 | 41.3 | 211.7 | 2.4 | Aliphatic |
| 210 | 868 | VLVAAILPAAIP | 12 | 54.9 | 211.7 | 2.4 | Aliphatic |
| 211 | 870 | VLVAAVLPIAAP | 12 | 41.3 | 203.3 | 2.4 | Aliphatic |
| 212 | 872 | VLAAAVLPLVVP | 12 | 41.3 | 219.2 | 2.5 | Aliphatic |
| 213 | 875 | AIAIVVPAVAVP | 12 | 50.2 | 195.0 | 2.4 | Aliphatic |
| 214 | 877 | VAIIAVPAVVAP | 12 | 57.3 | 195.0 | 2.4 | Aliphatic |
| 215 | 878 | IVALVAPAAVVP | 12 | 50.2 | 195.0 | 2.4 | Aliphatic |
| 216 | 879 | AAIVLLPAVVVP | 12 | 50.2 | 219.1 | 2.5 | Aliphatic |
| 217 | 881 | AALIVVPAVAVP | 12 | 50.2 | 195.0 | 2.4 | Aliphatic |
| 218 | 882 | AIALVVPAVAVP | 12 | 57.3 | 195.0 | 2.4 | Aliphatic |
| 219 | 883 | LAIVPAAIAALP | 12 | 50.2 | 195.8 | 2.2 | Aliphatic |

TABLE 15

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 220 | 885 | LVAIAPAVAVLP | 12 | 57.3 | 203.3 | 2.4 | Aliphatic |
| 221 | 887 | VLAVAPAVAVLP | 12 | 57.3 | 195.0 | 2.4 | Aliphatic |
| 222 | 888 | ILAVVAIPAAAP | 12 | 54.9 | 187.5 | 2.3 | Aliphatic |
| 223 | 889 | ILVAAAPIAALP | 12 | 57.3 | 195.8 | 2.2 | Aliphatic |
| 224 | 891 | ILAVAAIPAALP | 12 | 54.9 | 195.8 | 2.2 | Aliphatic |

TABLE 15-continued

| Sequence ID Number | aMTD | Sequences | Length | Rigidity/ Flexibility (II) | Structural Feature (AI) | Hydropathy (GRAVY) | Residue Structure |
|---|---|---|---|---|---|---|---|
| 225 | 893 | VIAIPA1LAAAP | 12 | 54.9 | 195.8 | 2.3 | Aliphatic |
| 226 | 895 | AIIIVVPAIAAP | 12 | 50.2 | 211.7 | 2.5 | Aliphatic |
| 227 | 896 | AILIVVAPIAAP | 12 | 50.2 | 211.7 | 2.5 | Aliphatic |
| 228 | 897 | AVIVPVAI1AAP | 12 | 50.2 | 203.3 | 2.5 | Aliphatic |
| 229 | 899 | AVVIALPAVVAP | 12 | 57.3 | 195.0 | 2.4 | Aliphatic |
| 230 | 900 | ALVAVIAPVVAP | 12 | 57.3 | 195.0 | 2.4 | Aliphatic |
| 231 | 901 | ALVAVLPAVAVP | 12 | 57.3 | 195.0 | 2.4 | Aliphatic |
| 232 | 902 | ALVAPLLAVAVP | 12 | 41.3 | 203.3 | 2.3 | Aliphatic |
| 233 | 904 | AVLAVVAPVVAP | 12 | 57.3 | 186.7 | 2.4 | Aliphatic |
| 234 | 905 | AVIAVAPLVVAP | 12 | 41.3 | 195.0 | 2.4 | Aliphatic |
| 235 | 906 | AVIALAPVVVAP | 12 | 57.3 | 195.0 | 2.4 | Aliphatic |
| 236 | 907 | VAIALAPVVVAP | 12 | 57.3 | 195.0 | 2.4 | Aliphatic |
| 237 | 908 | VALALAPVVVAP | 12 | 57.3 | 195.0 | 2.3 | Aliphatic |
| 238 | 910 | VAALLPAVVVAP | 12 | 57.3 | 195.0 | 2.3 | Aliphatic |
| 239 | 911 | VALALPAVVVAP | 12 | 57.3 | 195.0 | 2.3 | Aliphatic |
| 240 | 912 | VALLAPAVVVAP | 12 | 57.3 | 195.0 | 2.3 | Aliphatic |
|  |  |  |  | 52.6 ± 5.1 | 201.7 ± 7.8 | 2.3 ± 0.1 |  |

3-4. Design of the Peptides that Did not Satisfy at Least One Critical Factor To demonstrate that present invention of new hydrophobic CPPs—aMTDs, which satisfy all critical factors described above, are correct and rationally designed, the peptides which do not satisfy at least one critical factor have also been designed. Total of 31 rPeptides (rPs) are designed, developed and categorized as follows: no bending peptides, either no proline in the middle as well at the end and/or no central proline; rigid peptides (II<40); too much flexible peptides; aromatic peptides (aromatic ring presences); hydrophobic, with non-aromatic peptides but have amino acids other than A, V, L, 1, P or additional proline residues; hydrophilic, but non-aliphatic peptides.

3-4-1. Peptides that do not Satisfy the Bending Potential

Table 16 shows the peptides that do not have any proline in the middle (at 5', 6', 7' or 8') and at the end of the sequences. In addition, Table 16 describes the peptides that do not have proline in the middle of the sequences. All these peptides are supposed to have no-bending potential.

TABLE 16

| Group | rPeptide ID | Sequences | Length | Proline Position (PP) | Rigidity/ Flexibility (II) | Structural Feature (AI) | Hydropathy (GRAVY) |
|---|---|---|---|---|---|---|---|
| No-Bending Peptides (No Proline at 5, 6, 7 or 8 and/or 12) | 931 | AVLIAPAILAAA | 12 | 6 | 57.3 | 204.2 | 2.5 |
|  | 936 | ALLILAAAVAAP | 12 | 12 | 41.3 | 204.2 | 2.4 |
|  | 152 | LAAAVAAVAALL | 12 | None | 9.2 | 204.2 | 2.7 |
|  | 27 | LAIVAAAALVA | 12 | None | 2.1 | 204.2 | 2.8 |
|  | 935 | ALLILPAAAVAA | 12 | 6 | 57.3 | 204.2 | 2.4 |
|  | 670 | AULILAAAVAAL | 12 | None | 25.2 | 236.6 | 2.8 |
|  | 934 | LILAPAAVVAAA | 12 | 5 | 57.3 | 195.8 | 2.5 |
|  | 37 | TTCSQQQYCTNG | 12 | None | 53.1 | 0.0 | -1.1 |
|  | 16 | NNSCTTYTNGSQ | 12 | None | 47.4 | 0.0 | -1.4 |
|  | 113 | PVAVALLIAVPP | 12 | 1, 11, 12 | 57.3 | 195.0 | 2.1 |

3-4-2. Peptides that do not Satisfy the Rigidity/Flexibility

To prove that rigidity/flexibility of the sequence is a crucial critical factor, rigid (Avg. II: 21.8±6.6) and too high flexible sequences (Avg. II: 82.3±21.0) were also designed. Rigid peptides that instability index is much lower than that of new aMTDs (II: 41.3 to 57.3, Avg. II: 53.3±5.7) are shown in Table 17. Bending, but too high flexible peptides that II is much higher than that of new aMTDs are also provided in Table 18.

TABLE 17

| Group | rPeptide ID | Sequences | Length | Proline Position (PP) | Rigidity/ Flexibility (II) | Structural Feature (AI) | Hydropathy (GRAVY) |
|---|---|---|---|---|---|---|---|
| Rigid Peptides (II < 50) | 226 | ALVAAIPALAIP | 12 | 6 | 20.4 | 195.8 | 2.2 |
| | 6 | VIAMIPAAFWVA | 12 | 6 | 15.7 | 146.7 | 2.2 |
| | 750 | LALAAIAPLAIP | 12 | 8, 12 | 22.8 | 204.2 | 2.2 |
| | 26 | AAIALAAPLAIV | 12 | 8 | 18.1 | 204.2 | 2.5 |
| | 527 | LVLAAVAPIAIP | 12 | 8, 12 | 22.8 | 211.7 | 2.4 |
| | 466 | IIAAAAPLAIIP | 12 | 7, 12 | 22.8 | 204.2 | 2.3 |
| | 167 | VAIAIPAALAIP | 12 | 6, 12 | 20.4 | 195.8 | 2.3 |
| | 246 | VVAVPLLVAFAA | 12 | 5 | 25.2 | 195.0 | 2.7 |
| | 426 | AAALAIPLAIIP | 12 | 7, 12 | 43.7 | 204.2 | 2.2 |
| | 606 | AAAIAAIPIIIP | 12 | 8, 12 | 4.4 | 204.2 | 2.4 |
| | 66 | AGVLGGPIMGVP | 12 | 7, 12 | 35.5 | 121.7 | 2.3 |
| | 248 | VAAIVPIAALVP | 12 | 6, 12 | 34.2 | 203.3 | 2.5 |
| | 227 | LAAIVPIAAAVP | 12 | 6, 12 | 34.2 | 181.5 | 2.2 |
| | 17 | GGCSAPQTTESN | 12 | 6 | 51.6 | 8.3 | -0.5 |
| | 67 | LDAEVPLADDVP | 12 | 6, 12 | 34.2 | 130.0 | 0.3 |

TABLE 18

| Group | rPeptide ID | Sequences | Length | Proline Position (PP) | Rigidity/ Flexibility (II) | Structural Feature (AI) | Hydropathy (GARVY) |
|---|---|---|---|---|---|---|---|
| Bending Peptides but Too High Flexibility | 692 | PAPLPPVVILAV | 12 | 1, 3, 5,6 | 105.5 | 186.7 | 1.8 |
| | 69 | PVAVLPPAALVP | 12 | 1, 6, 7, 12 | 89.4 | 162.5 | 1.6 |
| | 390 | VPILVPVVPVVP | 12 | 2, 6, 9, 12 | 105.4 | 210.0 | 2.2 |
| | 350 | VPILVPVVPVVP | 12 | 2, 6, 12 | 121.5 | 210.0 | 2.2 |
| | 331 | VPVLVPLVPVVP | 12 | 2, 6, 9, 12 | 105.4 | 210.0 | 2.2 |
| | 9 | VALVPAALILPP | 12 | 5, 11, 12 | 89.4 | 203.3 | 2.1 |
| | 68 | VAPVLPAAPLVP | 12 | 3, 6, 9, 12 | 105.5 | 162 5 | 1.6 |
| | 349 | VPVLVPVVPVVP | 12 | 2, 6, 9, 12 | 121.5 | 201.6 | 2.2 |
| | 937 | VPVLVPLPVPVV | 12 | 2, 6, 8, 10 | 121.5 | 210.0 | 2.2 |
| | 938 | VPVLLPVVVPVP | 12 | 2, 6, 10, 12 | 121.5 | 210.0 | 2.2 |
| | 329 | LPVLVPVVPVVP | 12 | 2, 6, 9, 12 | 121.5 | 210.0 | 2.2 |
| | 49 | VVPAAPAVPVVP | 12 | 3, 6, 9, 12 | 121.5 | 145.8 | 1.7 |
| | 772 | LPVAPVIPIIVP | 12 | 2, 5, 8, 12 | 79.9 | 210.8 | 2.1 |
| | 210 | ALIALPALPALP | 12 | 6, 9, 12 | 89.4 | 195.8 | 1.8 |
| | 28 | AVPLLPLVPAVP | 12 | 3, 6,9, 12 | 89.4 | 186.8 | 1.8 |
| | 693 | AAPVLPVAVPIV | 12 | 3, 6, 10 | 82.3 | 186.7 | 2.1 |
| | 169 | VALVAPALILAP | 12 | 6, 12 | 73.4 | 211.7 | 2.4 |
| | 29 | VLPPLPVLPVLP | 12 | 3, 4, 6, 9, 12 | 121.5 | 202.5 | 1.7 |
| | 190 | AAILAPAVIAPP | 12 | 6, 11, 12 | 89.4 | 163.3 | 1.8 |

3-4-3. Peptides that do not Satisfy the Structural Features

New hydrophobic CPPs—aMTDs are consisted with only hydrophobic and aliphatic amino acids (A, V, L, I and P) with average ranges of the indexes—AI: 180 to 220 and GRAVY: 2.1 to 2.6 (Table 9). Based on the structural indexes, the peptides which contain an aromatic residue (W, F or Y) are shown in Table 19 and the peptides which are hydrophobic with non-aromatic sequences but have amino acids residue other than A, V, L, I, P or additional proline residues are designed (Table 20). Finally, hydrophilic and/or bending peptides which are consisted with non-aliphatic amino acids are shown in Table 21.

TABLE 19

| Group | rPeptide ID | Sequences | Length | Proline Position (PP) | Rigidity/ Flexibility (II) | Structural Feature (AI) | Hydropathy (GRAVY) |
|---|---|---|---|---|---|---|---|
| Aromatic Peptides (Aromatic Ring Presences) | 30 | WFFAGPIMLIWP | 12 | 6, 12 | 9.2 | 105.8 | 1.4 |
| | 33 | AAAILAPAFLAV | 12 | 7 | 57.3 | 171.7 | 2.4 |
| | 131 | WIIAPVWLAWIA | 12 | 5 | 51.6 | 179.2 | 1.9 |
| | 922 | WYVIFVLPLVVP | 12 | 8, 12 | 41.3 | 194.2 | 2.2 |
| | 71 | FMWMWFPFMWYP | 12 | 7, 12 | 71.3 | 0.0 | 0.6 |
| | 921 | IWWFVVLPLVVP | 12 | 8, 12 | 41.3 | 194.2 | 2.2 |

TABLE 20

| Group | rPeptide ID | Sequences | Length | Proline Position (PP) | Rigidity/ Flexibility (II) | Sturctural Feature (AI) | Hydropathy (GARVY) |
|---|---|---|---|---|---|---|---|
| Hydrophobic but Non Aromatic Peptides | 436 | VVMLVVPAVMLP | 12 | 7, 12 | 57.3 | 194.2 | 2.6 |
| | 138 | PPAALLAILAVA | 12 | 1, 2 | 57.3 | 195.8 | 2.2 |
| | 77 | PVALVLVALVAP | 12 | 1, 12 | 41.3 | 219.2 | 2.5 |
| | 577 | MLMIALVPMIAV | 12 | 8 | 18.9 | 195.0 | 2.7 |
| | 97 | ALLAAPPALLAL | 12 | 6, 7 | 57.3 | 204.2 | 2.1 |
| | 214 | ALIVAPALMALP | 12 | 6, 12 | 60.5 | 187.5 | 2.2 |
| | 59 | AVLAAPVVAALA | 12 | 6 | 41.3 | 187.5 | 2.5 |
| | 54 | LAVAAPPVVALL | 12 | 6, 7 | 57.3 | 203.3 | 2.3 |

TABLE 21

| Group | rPeptide ID | Sequences | Length | Proline Position (PP) | Rigidity/ Flexibility (II) | Sturctural Feature (AI) | Hydropathy (GRAVY) |
|---|---|---|---|---|---|---|---|
| Hydrophilic Peptides but Non Aliphatic | 949 | SGNSCOOCGNSS | 12 | None | 41.7 | 0.0 | -1.1 |
| | 39 | CYNTSPCTGCCY | 12 | 6 | 52.5 | 0.0 | 0.0 |
| | 19 | YVSCCTYTNGSO | 12 | None | 47.7 | 0.0 | -1.0 |
| | 947 | CYYNOOSNNNNO | 12 | None | 59.6 | 0.0 | -2.4 |
| | 139 | TGSTNSPTCTST | 12 | 7 | 53.4 | 0.0 | -0.7 |
| | 18 | NYCCTPTINGOS | 12 | 6 | 47.9 | 0.0 | -0.9 |
| | 20 | NYCNTCPTYGOS | 12 | 7 | 47.4 | 0.0 | -0.9 |
| | 635 | GSTGGSOONNOY | 12 | None | 31.9 | 0.0 | -1.9 |
| | 40 | TYNTSCTPGTCY | 12 | 8 | 49.4 | 0.0 | -0.6 |
| | 57 | ONNCHTSSOGGG | 12 | None | 52.4 | 0.0 | -1.6 |
| | 159 | CYSGSTSONOPP | 12 | 11, 12 | 51.0 | 0.0 | -1.3 |
| | 700 | GTSNTCOSNONS | 12 | None | 19.1 | 0.0 | -1.6 |
| | 38 | YYNOSTCGGOCY | 12 | None | 53.8 | 0.0 | -1.0 |

3-5. Summary of Newly Designed Peptides

Total of 457 sequences have been designed based on the critical factors. Designed potentially best aMTDs (hydrophobic, flexible, bending, aliphatic and 12-A/a length peptides) that do satisfy all range/feature of critical factors are 316. Designed rPeptides that do not satisfy at least one of the critical factors are 141 that no bending peptide sequences are 26; rigid peptide (II<40) sequences are 23; too much flexible peptides are 24; aromatic peptides (aromatic ring presences) are 27; hydrophobic, but non-aromatic peptides are 23; and hydrophilic, but non-aliphatic peptides are 18.

4. Preparation of Recombinant Report Proteins Fused to aMTDs and rPeptides

Recombinant proteins fused to aMTDs and others [rPeptides, reference hydrophobic CPP sequences (MTM and MTD)] were expressed in a bacterial system, purified with single-step affinity chromatography and prepared as soluble proteins in physiological condition. These recombinant proteins have been tested for the ability of their cell-permeability by utilizing flow cytometry and laser scanning confocal microscopy.

4-1. Selection of Cargo Protein for Recombinant Proteins Fused to Peptide Sequences For clinical/non-clinical application, aMTD-fused cargo materials would be biologically active molecules that could be one of the following: enzymes, transcription factors, toxic, antigenic peptides, antibodies and antibody fragments. Furthermore, biologically active molecules could be one of these following macromolecules: enzymes, hormones, carriers, immunoglobulin, membrane-bound proteins, transmembrane proteins, internal proteins, external proteins, secreted proteins, virus proteins, native proteins, glycoproteins, fragmented proteins, disulfide bonded proteins, recombinant proteins, chemically modified proteins and prions. In addition, these biologically active molecules could be one of the following: nucleic acid, coding nucleic acid sequence, mRNAs, antisense RNA molecule, carbohydrate, lipid and glycolipid.

According to these pre-required conditions, a non-functional cargo to evaluate aMTD-mediated protein uptake has been selected and called as Cargo A (CRA) that should be soluble and non-functional. The domain (A/a 289 to 840; 184 A/a length) is derived from protein S (Genbank ID: CP000113.1).

4-2. Construction of Expression Vector and Preparation of Recombinant Proteins

Coding sequences for recombinant proteins fused to each aMTD are cloned NdeI (5') and SalI (3') in pET-28a(+) (Novagen, Darmstadt, Germany) from PCR-amplified DNA segments. PCR primers for the recombinant proteins fused to aMTD and rPeptides are represented by SEQ ID NOs: 482 to 798. Structure of the recombinant proteins is displayed in FIG. 1.

The recombinant proteins were forcedly expressed in *E. coli* BL21(DE3) cells grown to an $OD_{600}$ of 0.6 and induced for 2 hours with 0.7 mM isopropyl-β-D-thiogalactopyranoside (IPTG). The proteins were purified by $Ni^{2+}$ affinity chromatography as directed by the supplier (Qiagen, Hilden, Germany) in natural condition. After the purification, purified proteins were dissolved in a physiological buffer such as DMEM medium.

TABLE 22

Potentially Best aMTDs (Hydrophobic, Flexible, Bending, Aliphatic & Helical): 240
Random Peptides: 31
No Bending Peptides (No Proline at 5 or 6 and/or 12): 02
No Bending Peptides (No Central Proline): 01
Rigid Peptides (II < 50): 09
Too Much Flexible Peptides: 09

TABLE 22-continued

Aromatic Peptides (Aromatic Ring Presences): 01
Hydrophobic, But Non-Aromatic Peptides: 02
Hydrophilic, But Non-Aliphatic Peptides: 07

4-3. Expression of aMTD- or Random Peptide (rP)-Fused Recombinant Proteins

The present invention also relates to the development method of aMTD sequences having cell-permeability. Using the standardized six critical factors, 316 aMTD sequences have been designed. In addition, 141 rPeptides are also developed that lack one of these critical factors: no bending peptides: i) absence of proline both in the middle and at the end of sequence or ii) absence of proline either in the middle or at the end of sequence, rigid peptides, too much flexible peptides, aromatic peptides (aromatic ring presence), hydrophobic but non-aromatic peptides, and hydrophilic but non-aliphatic peptides (Table 22).

These rPeptides are devised to be compared and contrasted with aMTDs in order to analyze structure/sequence activity relationship (SAR) of each critical factor with regard to the peptides' intracellular delivery potential. All peptide (aMTD or rPeptide)-containing recombinant proteins have been fused to the CRA to enhance the solubility of the recombinant proteins to be expressed, purified, prepared and analyzed.

These designed 316 aMTDs and 141 rPeptides fused to CRA were all cloned (FIG. 2) and tested for inducible expression in *E. coli* (FIG. 3). Out of these peptides, 240 aMTDs were inducibly expressed, purified and prepared in soluble form (FIG. 4). In addition, 31 rPeptides were also prepared as soluble form (FIG. 4).

To prepare the proteins fused to rPeptides, 60 proteins were expressed that were 10 out of 26 rPeptides in the category of no bending peptides (Table 16); 15 out of 23 in the category of rigid peptides [instability index (II)<40] (Table 17); 19 out of 24 in the category of too much flexible peptides (Table 18); 6 out of 27 in the category of aromatic peptides (Table 19); 8 out of 23 in the category of hydrophobic but non-aromatic peptides (Table 20); and 12 out of 18 in the category of hydrophilic but non-aliphatic peptides (Table 21).

4-4. Quantitative Cell-Permeability of aMTD-Fused Recombinant Proteins

The aMTDs and rPeptides were fluorescently labeled and compared based on the critical factors for cell-permeability by using flow cytometry and confocal laser scanning microscopy (FIGS. 5 to 8). The cellular uptake of the peptide-fused non-functional cargo recombinant proteins could quantitatively be evaluated in flow cytometry, while confocal laser scanning microscopy allows intracellular uptake to be assessed visually. The analysis included recombinant proteins fused to a negative control [rP38] that has opposite characteristics (hydrophilic and aromatic sequence: YYN-QSTCGGQCY) to the aMTDs (hydrophobic and aliphatic sequences). Relative cell-permeability (relative fold) of aMTDs to the negative control was also analyzed (Table 23 and FIG. 9).

Table 23 shows the Comparison Analysis of Cell-Permeability of aMTDs with a Negative Control (A: rP38).

TABLE 23

|  | Negative Control rP38 |
| --- | --- |
| aMTD The Average of 240 aMTDs | 19.6 ± 1.6* (Best: 164.2) |

*Relative Fold (aMTD in Geo Mean in its comparison to rP38)

Relative cell-permeability (relative fold) of aMTDs to the reference CPPs [B: MTM12 (AAVLLPVLLAAP), C: MTD85 (AVALLILAV)] was also analyzed (Tables 40 and 41)

Table 24 shows Comparison Analysis of Cell-Permeability of aMTDs with a Reference CPP (B: MTM12).

TABLE 24

|  | MTM12 |
| --- | --- |
| aMTD The Average of 240 aMTDs | 13.1 ± 1.1* (Best: 109.9) |

*Relative Fold (aMTD in Geo Mean in its comparison to MTM12)

Table 25 shows the Comparison Analysis of Cell-Permeability of aMTDs with a Reference CPP (C: MTD85).

TABLE 25

|  | MTD85 |
| --- | --- |
| aMTD The Average of 240 aMTDs | 6.6 ± 0.5* (Best: 55.5) |

*Relative Fold (aMTD in Geo Mean in its comparison to MTD85)

Geometric means of negative control (histidine-tagged rP38-fused CRA recombinant protein) subtracted by that of naked protein (histidine-tagged CRA protein) lacking any peptide (rP38 or aMTD) was standardized as relative fold of 1. Relative cell-permeability of 240 aMTDs to the negative control (A type) was significantly increased by up to 164 fold, with average increase of 19.6±1.6 (Tables 26 to 31).

TABLE 26

| SEQ ID NO | | aMTD Sequences | Length | Proline Position (PP) | Rigidity/ Flexibility (II) | Structural Feature (AI) | Hydropathy (GRAVY) | Relative Ratio (Fold) | | |
| --- | --- | --- | --- | --- | --- | --- | --- | --- | --- | --- |
| | | | | | | | | A | B | C |
| 229 | 899 | AVVIALPAVVAP | 12 | 7 | 57.3 | 195.0 | 2.4 | 164.2 | 109.9 | 55.5 |
| 237 | 908 | VALALAPVVVAP | 12 | 7 | 57.3 | 195.0 | 2.3 | 150.6 | 100.8 | 50.9 |
| 238 | 910 | VAALLPAVVVAP | 12 | 6 | 57.3 | 195.0 | 2.3 | 148.5 | 99.4 | 50.2 |
| 185 | 810 | VIVLAAPALAAP | 12 | 7 | 50.2 | 187.5 | 2.2 | 120.0 | 80.3 | 40.6 |

TABLE 26-continued

| SEQ ID NO | aMTD Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|---|
| | | | | | | | A | B | C |
| 233 904 | AVLAVVAPVVAP | 12 | 8 | 57.3 | 186.7 | 2.4 | 105.7 | 70.8 | 35.8 |
| 74 321 | IVAVALPALAVP | 12 | 7 | 50.2 | 203.3 | 2.3 | 97.8 | 65.2 | 32.9 |
| 204 851 | VLAVVLPAVALP | 12 | 7 | 57.3 | 219.2 | 2.5 | 96.6 | 64.7 | 32.7 |
| 239 911 | VALALPAVVVAP | 12 | 6 | 57.3 | 195.0 | 2.3 | 84.8 | 56.8 | 28.7 |
| 205 852 | VLAVAAPAVLLP | 12 | 7 | 57.3 | 203.3 | 2.3 | 84.6 | 56.6 | 28.6 |
| 179 803 | AIALAVPVLALP | 12 | 7 | 57.3 | 211.7 | 2.4 | 74.7 | 50.0 | 25.3 |
| 222 888 | ILAVVAIPAAAP | 12 | 8 | 54.9 | 187.5 | 2.3 | 71.0 | 47.5 | 24.0 |
| 188 825 | IVAVIVAPAVAP | 12 | 8 | 43.2 | 195.0 | 2.5 | 69.7 | 46.6 | 23.6 |
| 226 895 | AIIVVPAIAAP | 12 | 7 | 50.2 | 211.7 | 2.5 | 60.8 | 40.7 | 20.6 |
| 227 896 | AILIVVAPIAAP | 12 | 8 | 50.2 | 211.7 | 2.5 | 57.5 | 38.5 | 19.4 |
| 164 727 | VALAIALPAVLP | 12 | 8 | 57.3 | 211.6 | 2.3 | 54.7 | 36.7 | 18.5 |
| 139 603 | VLVALAAPVIAP | 12 | 8 | 57.3 | 203.3 | 2.4 | 54.1 | 36.1 | 18.2 |
| 200 847 | LVAIVVLPAVAP | 12 | 8 | 50.2 | 219.2 | 2.6 | 50.2 | 33.4 | 16.9 |
| 189 826 | LVALAAPIIAVP | 12 | 7 | 41.3 | 211.7 | 2.4 | 49.2 | 32.9 | 16.6 |
| 161 724 | VAVLAVLPALAP | 12 | 8 | 57.3 | 203.3 | 2.3 | 47.5 | 31.8 | 16.1 |
| 131 563 | ALAVIVVPALAP | 12 | 8 | 50.2 | 203.3 | 2.4 | 47.1 | 31.4 | 15.9 |
| 186 811 | AVVLAVPALAVP | 12 | 7 | 57.3 | 195.0 | 2.3 | 46.5 | 31.1 | 15.7 |
| 194 831 | IIVAVAPAAIVP | 12 | 7 | 43.2 | 203.3 | 2.5 | 46.3 | 31.0 | 15.7 |
| 192 829 | AALALVAPVIVP | 12 | 8 | 50.2 | 203.3 | 2.4 | 44.8 | 30.0 | 15.2 |
| 224 891 | ILAVAAIPAALP | 12 | 8 | 54.9 | 195.8 | 2.2 | 44.7 | 29.9 | 15.1 |
| 234 905 | AVIAVAPLVVAP | 12 | 7 | 41.3 | 195.0 | 2.4 | 44.0 | 29.5 | 14.9 |
| 132 564 | VAIALIVPALAP | 12 | 8 | 50.2 | 211.7 | 2.4 | 43.6 | 29.1 | 14.7 |
| 34 124 | IAVALPALIAAP | 12 | 6 | 50.3 | 195.8 | 2.2 | 43.6 | 29.0 | 14.7 |
| 190 827 | IAAVLAAPALVP | 12 | 8 | 57.3 | 187.5 | 2.2 | 43.0 | 28.8 | 14.6 |
| 2 2 | AAAVPLLAVVP | 12 | 5 | 41.3 | 195.0 | 2.4 | 40.9 | 27.2 | 13.8 |
| 91 385 | IVAIAVPALVAP | 12 | 7 | 50.2 | 203.3 | 2.4 | 38.8 | 25.9 | 13.1 |
| 191 828 | IALLAAPIIAVP | 12 | 7 | 41.3 | 220.0 | 2.4 | 36.8 | 24.6 | 12.4 |
| 181 806 | LVALAVPAAVLP | 12 | 7 | 57.3 | 203.3 | 2.3 | 36.7 | 24.6 | 12.4 |
| 198 845 | AAVVIAPLLAVP | 12 | 7 | 41.3 | 203.3 | 2.4 | 35.8 | 24.0 | 12.1 |
| 218 882 | AIALVVPAVAVP | 12 | 7 | 57.3 | 195.0 | 2.4 | 35.0 | 23.4 | 11.8 |
| 128 545 | VVLVLAAPAAVP | 12 | 8 | 57.3 | 195.0 | 2.3 | 34.6 | 23.1 | 11.7 |
| 39 161 | AVIALPALIAAP | 12 | 6 | 57.3 | 195.8 | 2.2 | 34.5 | 23.0 | 11.6 |
| 110 481 | AIAIAIVPVALP | 12 | 8 | 50.2 | 211.6 | 2.4 | 34.3 | 23.0 | 11.6 |
| 230 900 | ALVAVIAPVVAP | 12 | 8 | 57.3 | 195.0 | 2.4 | 34.3 | 22.9 | 11.6 |
| 53 223 | AILAVPIAVVAP | 12 | 6 | 57.3 | 203.3 | 2.4 | 33.0 | 22.1 | 11.2 |
| 187 824 | LIIVAAAPAVAP | 12 | 8 | 50.2 | 187.5 | 2.3 | 32.8 | 21.9 | 11.1 |
| 130 562 | ALIAAIVPALVP | 12 | 8 | 50.2 | 211.7 | 2.4 | 32.7 | 21.8 | 11.0 |

TABLE 26-continued

| SEQ ID NO | aMTD | Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|---|---|
| | | | | | | | | A | B | C |
| 52 | 222 | ALLIAPAAVIAP | 12 | 6 | 57.3 | 195.8 | 2.2 | 32.6 | 21.7 | 11.0 |
| 17 | 61 | VAALPVLLAALP | 12 | 5 | 57.3 | 211.7 | 2.3 | 31.2 | 20.8 | 10.5 |
| 134 | 582 | VAVALIVPALAP | 12 | 8 | 50.2 | 203.3 | 2.4 | 30.6 | 20.4 | 10.3 |
| 223 | 889 | ILVAAAPIAALP | 12 | 7 | 57.3 | 195.8 | 2.2 | 30.3 | 20.3 | 10.3 |
| 177 | 787 | AVALVPVIVAAP | 12 | 6 | 50.2 | 195.0 | 2.4 | 29.3 | 19.6 | 9.9 |
| 157 | 703 | IVAVALVPALAP | 12 | 8 | 50.2 | 203.3 | 2.4 | 29.2 | 19.5 | 9.9 |
| 158 | 705 | IVAVALLPALAP | 12 | 8 | 50.2 | 211.7 | 2.4 | 28.6 | 19.1 | 9.7 |
| 220 | 885 | LVAIAPAVAVLP | 12 | 6 | 57.3 | 203.3 | 2.4 | 28.3 | 19.0 | 9.6 |
| 3 | 3 | AALLVPAAVLAP | 12 | 6 | 57.3 | 187.5 | 2.1 | 27.0 | 18.0 | 9.1 |
| 137 | 601 | AAILIAVPIAAP | 12 | 8 | 57.3 | 195.8 | 2.3 | 26.8 | 17.9 | 9.0 |
| 196 | 843 | AVLVLVAPAAAP | 12 | 8 | 41.3 | 219.2 | 2.5 | 26.4 | 17.7 | 8.9 |
| 94 | 403 | AAALVIPAAILP | 12 | 7 | 54.9 | 195.8 | 2.2 | 25.2 | 16.8 | 8.5 |
| 127 | 544 | IVALIVAPAAVP | 12 | 8 | 43.1 | 203.3 | 2.4 | 23.4 | 15.6 | 7.9 |
| 121 | 522 | ALLVIAVPAVAP | 12 | 8 | 57.3 | 203.3 | 2.4 | 22.7 | 15.2 | 7.7 |

TABLE 27

| SEQ ID NO | aMTD | Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|---|---|
| | | | | | | | | A | B | C |
| 180 | 805 | LVLIAAAPIALP | 12 | 8 | 41.3 | 220.0 | 2.4 | 22.3 | 14.9 | 7.6 |
| 108 | 464 | AVVILVPLAAAP | 12 | 7 | 57.3 | 203.3 | 2.4 | 22.3 | 14.9 | 7.5 |
| 96 | 405 | LAAAVIPVAILP | 12 | 7 | 54.9 | 211.7 | 2.4 | 22.2 | 14.8 | 7.5 |
| 168 | 747 | VALLAIAPALAP | 12 | 8 | 57.3 | 195.8 | 2.2 | 22.0 | 14.8 | 7.5 |
| 115 | 501 | VIVALAVPALAP | 12 | 8 | 50.2 | 203.3 | 2.4 | 21.5 | 14.4 | 7.3 |
| 147 | 661 | AAILAPIVAALP | 12 | 6 | 50.2 | 195.8 | 2.2 | 21.4 | 14.3 | 7.2 |
| 176 | 786 | LVAIAPLAVLAP | 12 | 6 | 41.3 | 211.7 | 2.4 | 21.2 | 14.2 | 7.2 |
| 144 | 625 | ILAAAAPLIVP | 12 | 8 | 50.2 | 195.8 | 2.2 | 20.9 | 13.9 | 7.0 |
| 101 | 442 | ALAALVPAVLVP | 12 | 7 | 57.3 | 203.3 | 2.3 | 20.4 | 13.6 | 6.9 |
| 240 | 912 | VALLAPAVVVAP | 12 | 6 | 57.3 | 195.0 | 2.3 | 19.9 | 13.3 | 6.7 |
| 43 | 165 | ALAVPVALAIVP | 12 | 5 | 50.2 | 203.3 | 2.4 | 19.8 | 13.2 | 6.7 |
| 98 | 422 | VVAILAPLLAAP | 12 | 7 | 57.3 | 211.7 | 2.4 | 19.6 | 13.1 | 6.6 |
| 155 | 686 | AALVAVLPVALP | 12 | 8 | 57.3 | 203.3 | 2.3 | 19.5 | 13.1 | 6.6 |
| 81 | 343 | IVAVALPALVAP | 12 | 7 | 50.2 | 203.3 | 2.3 | 19.4 | 12.9 | 6.5 |
| 76 | 323 | IVAVALPVALAP | 12 | 7 | 50.2 | 203.3 | 2.3 | 19.1 | 12.8 | 6.4 |
| 105 | 461 | IAAVIVPAVALP | 12 | 7 | 50.2 | 203.3 | 2.4 | 19.0 | 12.7 | 6.4 |
| 9 | 21 | AVALLPALLAVP | 12 | 6 | 57.3 | 211.7 | 2.3 | 18.9 | 12.6 | 6.4 |
| 95 | 404 | LAAAVIPAAILP | 12 | 7 | 54.9 | 195.8 | 2.2 | 18.9 | 12.6 | 6.4 |

TABLE 27-continued

| SEQ ID NO | aMTD | Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|---|
| | | | | | | | | A | B | C |
| 60 | 261 | LVLVPLLAAAAP | 12 | 5 | 41.3 | 211.6 | 2.3 | 18.5 | 12.3 | 6.2 |
| 122 | 524 | AVALIVVPALAP | 12 | 8 | 50.2 | 203.3 | 2.4 | 18.3 | 12.2 | 6.2 |
| 55 | 225 | VAALLPAAAVLP | 12 | 6 | 57.3 | 187.5 | 2.1 | 18.3 | 12.2 | 6.2 |
| 63 | 264 | LAAAPVVIVIAP | 12 | 5 | 50.2 | 203.3 | 2.4 | 18.2 | 12.1 | 6.1 |
| 1 | 1 | AAALAPVVLALP | 12 | 6 | 57.3 | 187.5 | 2.1 | 17.7 | 11.8 | 6.0 |
| 88 | 382 | AAALVIPAILAP | 12 | 7 | 54.9 | 195.8 | 2.2 | 17.7 | 11.8 | 6.0 |
| 107 | 463 | AVAILVPLLAAP | 12 | 7 | 57.3 | 211.7 | 2.4 | 17.6 | 11.7 | 5.9 |
| 75 | 322 | VVAIVLPALAAP | 12 | 7 | 50.2 | 203.3 | 2.3 | 17.6 | 11.7 | 5.9 |
| 117 | 503 | AAIIIVLPAALP | 12 | 8 | 50.2 | 220.0 | 2.4 | 17.6 | 11.8 | 5.9 |
| 211 | 870 | VLVAAVLPIAAP | 12 | 8 | 41.3 | 203.3 | 2.4 | 16.6 | 11.1 | 5.6 |
| 56 | 241 | AAAVVPVLLVAP | 12 | 6 | 57.3 | 195.0 | 2.4 | 16.6 | 11.0 | 5.6 |
| 163 | 726 | LAVAIIAPAVAP | 12 | 8 | 57.3 | 187.5 | 2.2 | 16.5 | 11.0 | 5.6 |
| 79 | 341 | IVAVALPAVLAP | 12 | 7 | 50.2 | 203.3 | 2.3 | 16.4 | 10.9 | 5.5 |
| 125 | 542 | ALALIIVPAVAP | 12 | 8 | 50.2 | 211.6 | 2.4 | 16.2 | 10.8 | 5.5 |
| 83 | 361 | AVVIVAPAVIAP | 12 | 7 | 50.2 | 195.0 | 2.4 | 16.0 | 10.7 | 5.4 |
| 54 | 224 | ILAAVPIALAAP | 12 | 6 | 57.3 | 195.8 | 2.2 | 15.8 | 10.6 | 5.3 |
| 20 | 64 | AIVALPVAVLAP | 12 | 6 | 50.2 | 203.3 | 2.4 | 15.8 | 10.6 | 5.3 |
| 111 | 482 | ILAVAAIPVAVP | 12 | 8 | 54.9 | 203.3 | 2.4 | 15.8 | 10.6 | 5.3 |
| 113 | 484 | LAVVLAAPAIVP | 12 | 8 | 50.2 | 203.3 | 2.4 | 15.6 | 10.4 | 5.3 |
| 210 | 868 | VLVAAILPAAIP | 12 | 8 | 54.9 | 211.7 | 2.4 | 14.9 | 10.0 | 5.0 |
| 124 | 541 | LLALIIAPAAAP | 12 | 8 | 57.3 | 204.1 | 2.1 | 14.8 | 9.9 | 5.0 |
| 150 | 666 | AAIAIIAPAIVP | 12 | 8 | 50.2 | 195.8 | 2.3 | 14.7 | 9.9 | 5.0 |
| 149 | 665 | LAIVLAAPVAVP | 12 | 8 | 50.2 | 203.3 | 2.3 | 14.7 | 9.9 | 5.0 |
| 84 | 363 | AVLAVAPALIVP | 12 | 7 | 50.2 | 203.3 | 2.3 | 14.7 | 9.8 | 4.9 |
| 57 | 242 | AALLVPALVAAP | 12 | 6 | 57.3 | 187.5 | 2.1 | 14.6 | 9.7 | 4.9 |
| 90 | 384 | VIVAIAPALLAP | 12 | 7 | 50.2 | 211.6 | 2.4 | 14.0 | 9.4 | 4.7 |
| 214 | 877 | VAIIAVPAVVAP | 12 | 7 | 57.3 | 195.0 | 2.4 | 14.0 | 9.4 | 4.7 |
| 206 | 863 | AAVVLLPIIAAP | 12 | 7 | 41.3 | 211.7 | 2.4 | 13.8 | 9.3 | 4.7 |
| 123 | 525 | ALAIVVAPVAVP | 12 | 8 | 50.2 | 195.0 | 2.4 | 13.8 | 9.2 | 4.7 |
| 213 | 875 | AIAIVVPAVAVP | 12 | 7 | 50.2 | 195.0 | 2.4 | 13.8 | 9.2 | 4.7 |
| 69 | 285 | AIVLLPAAVVAP | 12 | 6 | 50.2 | 203.3 | 2.4 | 13.3 | 8.9 | 4.5 |
| 65 | 281 | ALIVLPAAVAVP | 12 | 6 | 50.2 | 203.3 | 2.4 | 13.3 | 8.9 | 4.5 |
| 209 | 867 | ALLVVIAPLAAP | 12 | 8 | 41.3 | 211.7 | 2.4 | 13.2 | 8.8 | 4.4 |
| 172 | 766 | IVVIAVAPAVAP | 12 | 8 | 50.2 | 195.0 | 2.4 | 12.9 | 8.6 | 4.4 |
| 80 | 342 | VIVALAPAVLAP | 12 | 7 | 50.2 | 203.3 | 2.3 | 12.7 | 8.5 | 4.3 |

TABLE 27-continued

| SEQ ID NO | | aMTD Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|---|
| | | | | | | | | A | B | C |
| 217 | 881 | AALIVVPAVAVP | 12 | 7 | 50.2 | 195.0 | 2.4 | 12.7 | 8.5 | 4.3 |
| 119 | 505 | AIIIVIAPAAAP | 12 | 8 | 50.2 | 195.8 | 2.3 | 12.4 | 8.3 | 4.2 |

TABLE 28

| SEQ ID NO | | aMTD Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|---|
| | | | | | | | | A | B | C |
| 169 | 763 | VAVLIAVPALAP | 12 | 8 | 57.3 | 203.3 | 2.3 | 12.3 | 7.2 | 4.2 |
| 156 | 687 | AILAVALPLLAP | 12 | 8 | 57.3 | 220.0 | 2.3 | 12.0 | 7.0 | 4.1 |
| 159 | 706 | IVAVALLPAVAP | 12 | 8 | 50.2 | 203.3 | 2.4 | 12.0 | 7.0 | 4.1 |
| 145 | 643 | LALVLAAPAIVP | 12 | 8 | 50.2 | 211.6 | 2.4 | 11.8 | 7.9 | 4.0 |
| 66 | 282 | VLAVAPALIVAP | 12 | 6 | 50.2 | 203.3 | 2.4 | 11.8 | 7.9 | 4.0 |
| 126 | 543 | LLAALIAPAALP | 12 | 8 | 57.3 | 204.1 | 2.1 | 11.7 | 7.8 | 4.0 |
| 78 | 325 | IVAVALPAVALP | 12 | 7 | 50.2 | 203.3 | 2.3 | 11.7 | 7.8 | 4.0 |
| 199 | 846 | IAVAVAAPLLVP | 12 | 8 | 41.3 | 203.3 | 2.4 | 11.7 | 6.8 | 4.0 |
| 89 | 383 | VIVALAPALLAP | 12 | 7 | 50.2 | 211.6 | 2.3 | 11.6 | 7.7 | 3.9 |
| 87 | 381 | VVAIVLPAVAAP | 12 | 7 | 50.2 | 195.0 | 2.4 | 11.5 | 7.7 | 3.9 |
| 183 | 808 | LVVLAAAPLAVP | 12 | 8 | 41.3 | 203.3 | 2.3 | 11.5 | 7.6 | 3.9 |
| 208 | 865 | AVLVIAVPAIAP | 12 | 8 | 57.3 | 203.3 | 2.5 | 11.3 | 7.5 | 3.8 |
| 162 | 725 | IAVLAVAPAVLP | 12 | 8 | 57.3 | 203.3 | 2.3 | 11.2 | 7.5 | 3.8 |
| 197 | 844 | VVALLAPLIAAP | 12 | 7 | 41.3 | 211.8 | 2.4 | 11.2 | 7.5 | 3.8 |
| 228 | 897 | AVIVPVAIIAAP | 12 | 5 | 50.2 | 203.3 | 2.5 | 11.2 | 7.5 | 3.8 |
| 141 | 605 | VIAAVLAPVAVP | 12 | 8 | 57.3 | 195.0 | 2.4 | 11.0 | 7.4 | 3.7 |
| 166 | 744 | AAVVIVAPVALP | 12 | 8 | 50.2 | 195.0 | 2.4 | 11.0 | 7.3 | 3.7 |
| 51 | 221 | AAILAPIVALAP | 12 | 6 | 50.2 | 195.8 | 2.2 | 10.9 | 7.3 | 3.7 |
| 142 | 622 | ALIVLAAPVAVP | 12 | 8 | 50.2 | 203.3 | 2.4 | 10.6 | 7.1 | 3.6 |
| 92 | 401 | AALAVIPAAILP | 12 | 7 | 54.9 | 195.8 | 2.2 | 10.6 | 7.1 | 3.6 |
| 77 | 324 | IVAVALPAALVP | 12 | 7 | 50.2 | 203.3 | 2.3 | 10.3 | 6.9 | 3.5 |
| 215 | 878 | IVALVAPAAVVP | 12 | 7 | 50.2 | 195.0 | 2.4 | 10.3 | 6.9 | 3.5 |
| 71 | 302 | LALAPALALLAP | 12 | 5 | 57.3 | 204.2 | 2.1 | 10.2 | 6.8 | 3.4 |
| 154 | 685 | ALLVAVLPAALP | 12 | 8 | 57.3 | 211.7 | 2.3 | 10.2 | 5.9 | 3.4 |
| 201 | 848 | AVAIVVLPAVAP | 12 | 8 | 50.2 | 195.0 | 2.4 | 10.0 | 6.7 | 3.4 |
| 138 | 602 | VIVALAAPVLAP | 12 | 8 | 50.2 | 203.3 | 2.4 | 9.9 | 5.8 | 3.4 |
| 178 | 788 | AIAVAIAPVALP | 12 | 8 | 57.3 | 187.5 | 2.3 | 9.8 | 6.6 | 3.3 |
| 38 | 145 | LLAVVPAVALAP | 12 | 6 | 57.3 | 203.3 | 2.3 | 9.5 | 6.3 | 3.2 |
| 6 | 11 | VVALAPALAALP | 12 | 6 | 57.3 | 187.5 | 2.1 | 9.5 | 6.3 | 3.2 |

TABLE 28-continued

| SEQ ID NO | aMTD | Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|---|---|
| | | | | | | | | A | B | C |
| 35 | 141 | AVIVLPALAVAP | 12 | 6 | 50.2 | 203.3 | 2.4 | 9.4 | 6.3 | 3.2 |
| 120 | 521 | LAALIVVPAVAP | 12 | 8 | 50.2 | 203.3 | 2.4 | 9.4 | 6.3 | 3.2 |
| 100 | 425 | AVVAIAPVLALP | 12 | 7 | 57.3 | 203.3 | 2.4 | 9.4 | 6.3 | 3.2 |
| 86 | 365 | AVIVVAPALLAP | 12 | 7 | 50.2 | 203.3 | 2.3 | 9.3 | 6.2 | 3.1 |
| 62 | 263 | ALAVIPAAAILP | 12 | 6 | 54.9 | 195.8 | 2.2 | 9.0 | 6.0 | 3.0 |
| 82 | 345 | ALLIVAPVAVAP | 12 | 7 | 50.2 | 203.3 | 2.3 | 8.9 | 5.9 | 3.0 |
| 203 | 850 | LVIALAAPVALP | 12 | 8 | 57.3 | 211.7 | 2.4 | 8.8 | 5.9 | 3.0 |
| 37 | 144 | VLAIVPAVALAP | 12 | 6 | 50.2 | 203.3 | 2.4 | 8.8 | 5.9 | 3.0 |
| 173 | 767 | IVVAAVVPALAP | 12 | 8 | 50.2 | 195.0 | 2.4 | 8.5 | 5.0 | 2.9 |
| 47 | 185 | AALVLPLIIAAP | 12 | 6 | 41.3 | 220.0 | 2.4 | 8.5 | 5.7 | 2.9 |
| 202 | 849 | AVILLAPLIAAP | 12 | 7 | 57.3 | 220.0 | 2.4 | 8.3 | 4.8 | 2.8 |
| 40 | 162 | AVVALPAALIVP | 12 | 6 | 50.2 | 203.3 | 2.4 | 8.2 | 5.5 | 2.8 |
| 207 | 864 | ALLVIAPAIAVP | 12 | 7 | 57.3 | 211.7 | 2.4 | 8.2 | 4.8 | 2.8 |
| 42 | 164 | LAAVLPALLAAP | 12 | 6 | 57.3 | 195.8 | 2.1 | 8.2 | 5.5 | 2.8 |
| 236 | 907 | VAIALAPVVVAP | 12 | 7 | 57.3 | 195.0 | 2.4 | 8.1 | 5.4 | 2.8 |
| 103 | 444 | LAAALVPVALVP | 12 | 7 | 57.3 | 203.3 | 2.3 | 8.1 | 5.4 | 2.7 |
| 102 | 443 | ALAALVPVALVP | 12 | 7 | 57.3 | 203.3 | 2.3 | 8.0 | 5.3 | 2.7 |
| 221 | 887 | VLAVAPAVAVLP | 12 | 6 | 57.3 | 195.0 | 2.4 | 7.7 | 5.1 | 2.6 |
| 231 | 901 | ALVAVLPAVAVP | 12 | 7 | 57.3 | 195.0 | 2.4 | 7.7 | 5.1 | 2.6 |
| 167 | 746 | VAIIVVAPALAP | 12 | 8 | 50.2 | 203.3 | 2.4 | 7.6 | 4.4 | 2.6 |
| 232 | 902 | ALVAPLLAVAVP | 12 | 5 | 41.3 | 203.3 | 2.3 | 7.6 | 5.1 | 2.6 |
| 133 | 565 | VAIVLVAPAVAP | 12 | 8 | 50.2 | 195.0 | 2.4 | 7.5 | 5.0 | 2.5 |
| 59 | 245 | AAALAPVLALVP | 12 | 6 | 57.3 | 187.5 | 2.1 | 7.5 | 5.0 | 2.5 |
| 165 | 743 | AIAIALVPVALP | 12 | 8 | 57.3 | 211.6 | 2.4 | 7.4 | 4.9 | 2.5 |
| 109 | 465 | AVVILVPLAAAP | 12 | 7 | 57.3 | 203.3 | 2.4 | 7.4 | 4.9 | 2.5 |
| 30 | 104 | AVVAAPLVLALP | 12 | 6 | 41.3 | 203.3 | 2.3 | 7.3 | 4.9 | 2.5 |

TABLE 29

| SEQ ID NO | aMTD | Sequences | Length | Proline Position (PP) | Rigidity/ Flexibility (II) | Sturctural Feature (AI) | Hydropathy (GRAVY) | Relative Ratio (Fold) | | |
|---|---|---|---|---|---|---|---|---|---|---|
| | | | | | | | | A | B | C |
| 160 | 707 | IVALAVLPAVAP | 12 | 8 | 50.2 | 203.3 | 2.4 | 7.3 | 4.9 | 2.5 |
| 212 | 872 | VLAAVLPLVVP | 12 | 8 | 41.3 | 219.2 | 2.5 | 7.3 | 4.9 | 2.5 |
| 135 | 583 | AVILALAPIVAP | 12 | 8 | 50.2 | 211.6 | 2.4 | 7.3 | 4.8 | 2.4 |
| 216 | 879 | AAIVLLPAVVVP | 12 | 7 | 50.2 | 219.1 | 2.5 | 7.2 | 4.8 | 2.4 |
| 175 | 784 | VAALPAVALVVP | 12 | 5 | 57.3 | 195.0 | 2.4 | 7.1 | 4.7 | 2.4 |
| 225 | 893 | VIAIPAILAAAP | 12 | 5 | 54.9 | 195.8 | 2.3 | 7.0 | 4.7 | 2.4 |

TABLE 29-continued

| SEQ ID NO | aMTD | Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|---|
| | | | | | | | | A | B | C |
| 8 | 13 | AAALVPVVALLP | 12 | 6 | 57.3 | 203.3 | 2.3 | 7.0 | 4.7 | 2.4 |
| 184 | 809 | LIVLAAPALAAP | 12 | 7 | 50.2 | 195.8 | 2.2 | 7.0 | 4.7 | 2.4 |
| 104 | 445 | ALAALVPALVVP | 12 | 7 | 57.3 | 203.3 | 2.3 | 6.9 | 4.6 | 2.3 |
| 22 | 81 | AALLPALAALLP | 12 | 5 | 57.3 | 204.2 | 2.1 | 6.9 | 4.6 | 2.3 |
| 151 | 667 | LAVAIVAPALVP | 12 | 8 | 50.2 | 203.3 | 2.3 | 6.9 | 4.6 | 2.3 |
| 235 | 906 | AVIALAPVVVAP | 12 | 7 | 57.3 | 195.0 | 2.4 | 6.8 | 4.6 | 2.3 |
| 112 | 483 | ILAAAIIPAALP | 12 | 8 | 54.9 | 204.1 | 2.2 | 6.8 | 4.5 | 2.3 |
| 114 | 485 | AILAAIVPLAVP | 12 | 8 | 50.2 | 211.6 | 2.4 | 6.8 | 4.5 | 2.3 |
| 97 | 421 | AAILAAPLIAVP | 12 | 7 | 57.3 | 195.8 | 2.2 | 6.7 | 4.5 | 2.3 |
| 136 | 585 | ALIVAIAPALVP | 12 | 8 | 50.2 | 211.6 | 2.4 | 6.6 | 4.4 | 2.2 |
| 99 | 424 | AVVVAAPVLALP | 12 | 7 | 57.3 | 195.0 | 2.4 | 6.6 | 4.4 | 2.2 |
| 85 | 364 | LVAAVAPALIVP | 12 | 7 | 50.2 | 203.3 | 2.3 | 6.5 | 4.3 | 2.2 |
| 93 | 402 | ALAAVIPAAILP | 12 | 7 | 54.9 | 195.8 | 2.2 | 6.4 | 4.3 | 2.2 |
| 106 | 462 | IAAVLVPAVALP | 12 | 7 | 57.3 | 203.3 | 2.4 | 6.3 | 4.2 | 2.1 |
| 64 | 265 | VLAIAPLLAAVP | 12 | 6 | 41.3 | 211.6 | 2.3 | 6.0 | 4.0 | 2.0 |
| 70 | 301 | VIAAPVLAVLAP | 12 | 6 | 57.3 | 203.3 | 2.4 | 6.0 | 4.0 | 2.0 |
| 45 | 183 | LLAAPVVIALAP | 12 | 6 | 57.3 | 211.6 | 2.4 | 6.0 | 4.0 | 2.0 |
| 58 | 243 | AAVLLPVALAAP | 12 | 6 | 57.3 | 187.5 | 2.1 | 5.9 | 3.9 | 2.0 |
| 148 | 664 | ILIAIAIPAAAP | 12 | 8 | 54.9 | 204.1 | 2.3 | 5.7 | 3.8 | 1.9 |
| 174 | 783 | IVALVPAVAIAP | 12 | 6 | 50.2 | 203.3 | 2.5 | 5.7 | 3.8 | 1.9 |
| 116 | 502 | AIVALAVPVLAP | 12 | 8 | 50.2 | 203.3 | 2.4 | 5.6 | 3.7 | 1.9 |
| 61 | 262 | ALIAVPAIIVAP | 12 | 6 | 50.2 | 211.6 | 2.4 | 5.5 | 3.7 | 1.9 |
| 152 | 683 | LAIVLAAPAVLP | 12 | 8 | 50.2 | 211.7 | 2.4 | 5.5 | 3.2 | 1.9 |
| 193 | 830 | IALVAAPVALVP | 12 | 7 | 57.3 | 203.3 | 2.4 | 5.3 | 3.5 | 1.8 |
| 170 | 764 | AVALAVLPAVVP | 12 | 8 | 57.3 | 195.0 | 2.3 | 5.0 | 3.4 | 1.7 |
| 182 | 807 | AVALAVPALVLP | 12 | 7 | 57.3 | 203.3 | 2.3 | 5.0 | 3.3 | 1.7 |
| 46 | 184 | LAAIVPAIIAVP | 12 | 6 | 50.2 | 211.6 | 2.4 | 4.8 | 3.2 | 1.6 |
| 73 | 305 | IALAAPILLAAP | 12 | 6 | 57.3 | 204.2 | 2.2 | 4.8 | 3.2 | 1.6 |
| 27 | 101 | LVALAPVAAVLP | 12 | 6 | 57.3 | 203.3 | 2.3 | 4.5 | 3.0 | 1.5 |
| 72 | 304 | AIILAPIAAIAP | 12 | 6 | 57.3 | 204.2 | 2.3 | 4.4 | 3.0 | 1.5 |
| 140 | 604 | VALIAVAPVVVP | 12 | 8 | 57.3 | 195.0 | 2.4 | 4.3 | 2.5 | 1.5 |
| 146 | 645 | ALAVVALPAIVP | 12 | 8 | 50.2 | 203.3 | 2.4 | 4.3 | 2.9 | 1.5 |
| 48 | 201 | LALAVPALAALP | 12 | 6 | 57.3 | 195.8 | 2.1 | 4.2 | 2.8 | 1.4 |
| 41 | 163 | LALVLPAALAAP | 12 | 6 | 57.3 | 195.8 | 2.1 | 4.1 | 2.4 | 1.4 |
| 195 | 832 | AVAAIVPVIVAP | 12 | 7 | 43.2 | 195.0 | 2.5 | 4.1 | 2.7 | 1.4 |
| 44 | 182 | ALIAPVVALVAP | 12 | 6 | 57.3 | 203.3 | 2.4 | 4.0 | 2.7 | 1.4 |
| 11 | 23 | VVLVLPAAAAVP | 12 | 6 | 57.3 | 195.0 | 2.4 | 4.0 | 2.6 | 1.3 |

TABLE 29-continued

| SEQ ID NO | aMTD | Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|---|
| | | | | | | | | A | B | C |
| 31 | 105 | LLALAPAALLAP | 12 | 6 | 57.3 | 204.1 | 2.1 | 4.0 | 2.6 | 1.3 |
| 129 | 561 | AAVAIVLPAVVP | 12 | 8 | 50.2 | 195.0 | 2.4 | 3.9 | 2.6 | 1.3 |
| 171 | 765 | AVALAVVPAVLP | 12 | 8 | 57.3 | 195.0 | 2.3 | 3.8 | 2.2 | 1.3 |
| 153 | 684 | AAIVLALPAVLP | 12 | 8 | 50.2 | 211.7 | 2.4 | 3.5 | 2.1 | 1.2 |
| 36 | 143 | AVLAVPAVLVAP | 12 | 6 | 57.3 | 195.0 | 2.4 | 3.3 | 2.2 | 1.1 |
| 118 | 504 | LIVALAVPALAP | 12 | 8 | 50.2 | 211.7 | 2.4 | 3.3 | 2.2 | 1.1 |
| 10 | 22 | AVVLVPVLAAAP | 12 | 6 | 57.3 | 195.0 | 2.4 | 3.1 | 2.1 | 1.1 |
| 5 | 5 | AAALLPVALVAP | 12 | 6 | 57.3 | 187.5 | 2.1 | 3.1 | 2.1 | 1.0 |
| 67 | 283 | AALLAPALIVAP | 12 | 6 | 50.2 | 195.8 | 2.2 | 3.1 | 2.0 | 1.0 |
| 21 | 65 | IAIVAPVVALAP | 12 | 6 | 50.2 | 203.3 | 2.4 | 3.0 | 2.0 | 1.0 |
| 219 | 883 | LAIVPAAIAALP | 12 | 6 | 50.2 | 195.8 | 2.2 | 3.0 | 2.0 | 1.0 |
| 33 | 123 | AAIIVPAALLAP | 12 | 6 | 50.2 | 195.8 | 2.2 | 2.9 | 2.0 | 1.0 |

TABLE 30

| SEQ ID NO | aMTD | Sequences | Length | Proline Position (PP) | Rigidity/ Flexibility (II) | Structural Feature (AI) | Hydropathy (GRAVY) | Relative Ratio (Fold) | | |
|---|---|---|---|---|---|---|---|---|---|---|
| | | | | | | | | A | B | C |
| 68 | 284 | ALIAPAVALIVP | 12 | 5 | 50.2 | 211.7 | 2.4 | 2.8 | 1.8 | 0.9 |
| 50 | 205 | ALALVPAIAALP | 12 | 6 | 57.3 | 195.8 | 2.2 | 2.6 | 1.7 | 0.9 |
| 14 | 42 | VAALPVVAVVAP | 12 | 5 | 57.3 | 186.7 | 2.4 | 2.5 | 1.7 | 0.8 |
| 32 | 121 | AIVALPALALAP | 12 | 6 | 50.2 | 195.8 | 2.2 | 2.5 | 1.7 | 0.8 |
| 13 | 25 | IVAVAPALVALP | 12 | 6 | 50.2 | 203.3 | 2.4 | 2.4 | 1.6 | 0.8 |
| 12 | 24 | IALAAPALIVAP | 12 | 6 | 50.2 | 195.8 | 2.2 | 2.3 | 1.6 | 0.8 |
| 49 | 204 | LIAALPAVAALP | 12 | 6 | 57.3 | 195.8 | 2.2 | 2.2 | 1.5 | 0.8 |
| 7 | 12 | LLAAVPAVLLAP | 12 | 6 | 57.3 | 211.7 | 2.3 | 2.2 | 1.5 | 0.7 |
| 15 | 43 | LLAAPLVVAAVP | 12 | 5 | 41.3 | 187.5 | 2.1 | 2.1 | 1.4 | 0.7 |
| 29 | 103 | ALIAAPILALAP | 12 | 6 | 57.3 | 204.2 | 2.2 | 2.1 | 1.4 | 0.7 |
| 23 | 82 | AVVLAPVAAVLP | 12 | 6 | 57.3 | 195.0 | 2.4 | 2.1 | 1.4 | 0.7 |
| 4 | 4 | ALALLPVAALAP | 12 | 6 | 57.3 | 195.8 | 2.1 | 2.0 | 1.3 | 0.7 |
| 26 | 85 | LLVLPAAALAAP | 12 | 5 | 57.3 | 195.8 | 2.1 | 1.9 | 1.3 | 0.7 |
| 19 | 63 | AALLVPALVAVP | 12 | 6 | 57.3 | 203.3 | 2.3 | 1.9 | 1.3 | 0.7 |
| 16 | 44 | ALAVPVALLVAP | 12 | 5 | 57.3 | 203.3 | 2.3 | 1.6 | 1.1 | 0.5 |
| 25 | 84 | AAVAAPLLLALP | 12 | 6 | 41.3 | 195.8 | 2.1 | 1.5 | 1.0 | 0.5 |
| 18 | 62 | VALLAPVALAVP | 12 | 6 | 57.3 | 203.3 | 2.3 | 1.4 | 0.9 | 0.5 |
| 24 | 83 | LAVAAPLALALP | 12 | 6 | 41.3 | 195.8 | 2.1 | 1.4 | 0.9 | 0.5 |
| 28 | 102 | LALAPAALALLP | 12 | 5 | 57.3 | 204.2 | 2.1 | 1.4 | 0.9 | 0.5 |

TABLE 30-continued

| SEQ ID NO | aMTD | Sequences | Length | Proline Position (PP) | Rigidity/ Flexi- bility (II) | Sturc- tural Feature (AI) | Hydro- pathy (GRAVY) | Relative Ratio (Fold) A | B | C |
|---|---|---|---|---|---|---|---|---|---|---|
| 143 | 623 | VAAAIALPAIVP | 12 | 8 | 50.2 | 187.5 | 2.3 | 0.8 | 0.6 | 0.3 |
| | | | | | | | | 19.6 ± 1.6 | 13.1 ± 1.1 | 6.6 ± 0.5 |

Moreover, compared to reference CPPs (B type: MTM12 and C type: MTD85), novel 240 aMTDs averaged of 13±1.1 (maximum 109.9) and 6.6±0.5 (maximum 55.5) fold higher cell-permeability, respectively (Tables 26 to 31).

TABLE 31

| | Negative Control rP38 | MTM12 | MTD85 |
|---|---|---|---|
| aMTD The Average of 240 aMTDs | 19.6 ± 1.6* (Best: 164.2) | 13.1 ± 1.1* (Best: 109.9) | 6.6 ± 0.5* (Best: 55.5) |

*Relative Fold (aMTD in Geo Mean in its comparison to rP38, MTM12 or MTD85)

In addition, cell-permeabilities of 31 rPeptides have been compared with that of 240 aMTDs (0.3±0.04; Tables 32 and 33).

TABLE 32

| Sequence ID Number | rPeptide ID | Sequences | Length | Proline Position (PP) | Rigidity/ Flexi- bility (II) | Sturctural Feature (AI) | Hydro- pathy (GRAVY) | Relative Ratio to aMTD AVE |
|---|---|---|---|---|---|---|---|---|
| 875 | 692 | PAPLPPVVILAV | 12 | 1, 3, 5, 6 | 105.5 | 186.7 | 1.8 | 0.74 |
| 863 | 26 | AAIALAAPLAIV | 12 | 8 | 18.1 | 204.2 | 2.5 | 0.65 |
| 859 | 113 | PVAVALLIAVPP | 12 | 1, 11, 12 | 57.3 | 195.0 | 2.1 | 0.61 |
| 865 | 466 | IIAAAAPLAIIP | 12 | 7, 12 | 22.8 | 204.2 | 2.3 | 0.52 |
| 866 | 167 | VAIAIPAALAIP | 12 | 6, 12 | 20.4 | 195.8 | 2.3 | 0.50 |
| 904 | 97 | ALLAAPPALLAL | 12 | 6, 7 | 57.3 | 204.2 | 2.1 | 0.41 |
| 877 | 390 | VPLLVPVVPVVP | 12 | 2, 6, 9, 12 | 105.4 | 210.0 | 2.2 | 0.41 |
| 868 | 426 | AAALAIPLAIIP | 12 | 7, 12 | 4.37 | 204.2 | 2.2 | 0.40 |
| 905 | 214 | ALIVAPALMALP | 12 | 6, 12 | 60.5 | 187.5 | 2.2 | 0.33 |
| 881 | 68 | VAPVLPAAPLVP | 12 | 3, 6, 9, 12 | 105.5 | 162.5 | 1.6 | 0.32 |

TABLE 32-continued

| Sequence ID Number | rPeptide ID | Sequences | Length | Proline Position (PP) | Rigidity/ Flexibility (II) | Structural Feature (AI) | Hydropathy (GRAVY) | Relative Ratio to aMTD AVE |
|---|---|---|---|---|---|---|---|---|
| 909 | 39 | CYNTSPCTGCCY | 12 | 6 | 52.5 | 0.0 | 0.0 | 0.29 |
| 856 | 934 | LILAPAAVVAAA | 12 | 5 | 57.3 | 195.8 | 2.5 | 0.28 |
| 884 | 938 | VPVLLPVVVPVP | 12 | 2, 6, 10, 12 | 121.5 | 210.0 | 2.2 | 0.28 |
| 885 | 329 | LPVLVPVVPVVP | 12 | 2, 6, 9, 12 | 121.5 | 210.0 | 2.2 | 0.23 |
| 869 | 606 | AAAIAAIPIIIP | 12 | 8, 12 | 4.4 | 204.2 | 2.4 | 0.20 |
| 886 | 49 | VVPAAPAVPVVP | 12 | 3, 6, 9, 12 | 121.5 | 145.8 | 1.7 | 0.18 |
| 912 | 139 | TGSTNSPTCTST | 12 | 7 | 53.4 | 0.0 | -0.7 | 0.17 |
| 887 | 772 | LPVAPVIPIIVP | 12 | 2, 5, 8, 12 | 79.9 | 210.8 | 2.1 | 0.16 |
| 899 | 921 | IWWFVVLPLVVP | 12 | 8, 12 | 41.3 | 194.2 | 2.2 | 0.14 |
| 870 | 66 | AGVLGGPIMGVP | 12 | 7, 12 | 35.5 | 121.7 | 1.3 | 0.13 |
| 890 | 693 | AAPVLPVAVPIV | 12 | 3, 6, 10 | 82.3 | 186.7 | 2.1 | 0.13 |
| 913 | 18 | NYCCTPTTNGQS | 12 | 6 | 47.9 | 0.0 | -0.9 | 0.10 |
| 858 | 16 | NNSCTTYTNGSQ | 12 | None | 47.4 | 0.0 | -1.4 | 0.08 |
| 872 | 227 | LAAIVPIAAAVP | 12 | 6, 12 | 34.2 | 187.5 | 2.2 | 0.08 |
| 873 | 17 | GGCSAPQTTCSN | 12 | 6 | 51.6 | 8.3 | -0.5 | 0.08 |
| 874 | 67 | LDAEVPLADDVP | 12 | 6, 12 | 34.2 | 130 | 0.3 | 0.08 |
| 915 | 635 | GSTGGSQQNNQY | 12 | None | 31.9 | 0.0 | -1.9 | 0.07 |
| 892 | 29 | VLPPLPVLPVLP | 12 | 3, 4, 6, 9, 12 | 121.5 | 202.5 | 1.7 | 0.07 |
| 917 | 57 | QNNCNTSSQGGG | 12 | None | 52.4 | 0.0 | -1.6 | 0.06 |
| 919 | 700 | GTSNTCQSNQNS | 12 | None | 19.1 | 0.0 | -1.6 | 0.05 |
| 920 | 38 | YNQSTCGGQCY | 12 | ND | 53.8 | 0.0 | -1.0 | 0.05 |
| | | | | | | | AVE | 0.3 ± 0.04 |

TABLE 33

|  | Relative Ratio to aMTD AVE* |
|---|---|
| rPeptide | 0.3 ± 0.04 |
| The Average of 31 aMTDs | |

*Out of 240 aMTDs, average relative fold of aMTD had been 19.6 fold compared to type A (rP38).

In summary, relatively cell-permeability of aMTDs has shown maximum of 164.0, 109.9 and 55.5 fold higher to rP38, MTM12 and MTD85, respectively. In average of total 240 aMTD sequences, 19.6±1.6, 13.1±1.1 and 6.6±0.5 fold higher cell-permeability are shown to the rP38, MTM12 and MTD85, respectively (Tables 26 to 31). Relative cell-permeability of negative control (rP38) to the 240 aMTDs is only 0.3±0.04 fold.

4-5. Intracellular Delivery and Localization of aMTD-Fused Recombinant Proteins

Recombinant proteins fused to the aMTDs were tested to determine their intracellular delivery and localization by laser scanning confocal microscopy with a negative control (rP38) and previous published CPPs (MTM12 and MTD85) as the positive control references. NIH3T3 cells were exposed to 10 uM of FITC-labeled protein for 1 hour at 37° C., and nuclei were counterstained with DAPI. Then, cells were examined by confocal laser scanning microscopy (FIG. 7). Recombinant proteins fused to aMTDs clearly display intracellular delivery and cytoplasmic localization (FIG. 7) that are typically higher than the reference CPPs (MTM12 and MTD85). The rP38-fused recombinant protein did not show internalized fluorescence signal (FIG. 7a). In addition, as seen in FIG. 8, rPeptides (his-tagged CRA recombinant proteins fused to each rPeptide) display lower- or non-cell-permeability.

4-6. Summary of Quantitative and Visual Cell-Permeability of Newly Developed aMTDs Histidine-tagged aMTD-fused cargo recombinant proteins have been greatly enhanced in their solubility and yield. Thus, FITC-conjugated recombinant proteins have also been tested to quantitate and visualize intracellular localization of the proteins and demonstrated higher cell-permeability compared to the reference CPPs.

In the previous studies using the hydrophobic signal-sequence-derived CPPs—MTS/MTM or MTDs, 17 published sequences have been identified and analyzed in various characteristics such as length, molecular weight, pI value, bending potential, rigidity, flexibility, structural feature, hydropathy, amino acid residue and composition, and secondary structure of the peptides. Based on these analytical data of the sequences, novel artificial and non-natural peptide sequences designated as advanced MTDs (aMTDs) have been invented and determined their functional activity in intracellular delivery potential with aMTD-fused recombinant proteins.

aMTD-fused recombinant proteins have promoted the ability of protein transduction into the cells compared to the recombinant proteins containing rPeptides and/or reference hydrophobic CPPs (MTM12 and MTD85). According to the results, it has been demonstrated that critical factors of cell-penetrating peptide sequences play a major role to determine peptide-mediated intracellular delivery by penetrating plasma membrane. In addition, cell-permeability can considerably be improved by following the rational that all satisfy the critical factors.

5. Structure/Sequence Activity Relationship (SAR) of aMTDs on Delivery Potential After determining the cell-permeability of novel aMTDs, structure/sequence activity relationship (SAR) has been analyzed for each critical factor in selected some of and all of novel aMTDs (FIGS. 13 to 16 and Table 34).

TABLE 34

| Rank of Delivery Potential | Rigidity/ Flexibility (II) | Sturctural Feature (AI) | Hydropathy (GRAVY) | Relative Ratio (Fold) | | | Amino Acid Composition | | | |
|---|---|---|---|---|---|---|---|---|---|---|
| | | | | A | B | C | A | V | I | L |
| 1~10 | 55.9 | 199.2 | 2.3 | 112.7 | 75.5 | 38.1 | 4.0 | 3.5 | 0.4 | 2.1 |
| 11~20 | 51.2 | 205.8 | 2.4 | 56.2 | 37.6 | 19.0 | 4.0 | 2.7 | 1.7 | 1.6 |
| 21~30 | 49.1 | 199.2 | 2.3 | 43.6 | 28.9 | 14.6 | 4.3 | 2.7 | 1.4 | 1.6 |
| 31~40 | 52.7 | 201.0 | 24 | 34.8 | 23.3 | 11.8 | 4.2 | 2.7 | 1.5 | 1.6 |
| 41~50 | 53.8 | 201.9 | 2.3 | 30.0 | 20.0 | 10.1 | 4.3 | 2.3 | 1.1 | 2.3 |
| 51~60 | 51.5 | 205.2 | 2.4 | 23.5 | 15.7 | 7.9 | 4.4 | 2.1 | 1.5 | 2.0 |
| 222~231 | 52.2 | 197.2 | 2.3 | 2.2 | 1.5 | 0.8 | 4.5 | 2.1 | 1.0 | 2.4 |
| 232~241 | 54.1 | 199.7 | 2.2 | 1.7 | 1.2 | 0.6 | 4.6 | 1.7 | 0.2 | 3.5 |

5-1. Proline Position:

In regards to the bending potential (proline position: PP), aMTDs with its proline at 7' or 8' amino acid in their sequences have much higher cell-permeability compared to the sequences in which their proline position is at 5' or 6' (FIGS. 14a, 14b, 15a and 15b).

5-2. Hydropathy:

In addition, when the aMTDs have GRAVY (Grand Average of Hydropathy) ranging in 2.1 to 2.2, these sequences display relatively lower cell-permeability, while the aMTDs with 2.3 to 2.6 GRAVY are shown significantly higher one (FIGS. 14b, 15b, 15c and 15d).

5-3. rPeptide SAR:

To the SAR of aMTDs, rPeptides have shown similar SAR correlations in the cell-permeability, pertaining to their proline position (PP) and hydropathy (GRAVY). These results confirm that rPeptides with high GRAVY (2.4 to 2.6) have better cell-permeability (FIG. 16).

5-4. Analysis of Amino Acid Composition:

In addition to proline position and hydropathy, the difference of amino acid composition is also analyzed. Since aMTDs are designed based on critical factors, each aMTD-fused recombinant protein has equally two proline sequences in the composition. Other hydrophobic and aliphatic amino acids—alanine, isoleucine, leucine and valine—are combined to form the rest of aMTD peptide sequences.

Alanine: In the composition of amino acids, the result does not show a significant difference by the number of alanine in terms of the aMTD's delivery potential because all of the aMTDs have three to five alanines. However, four alanine compositions show the most effective delivery potential (geometric mean) (FIG. 13a).

Leucine and Isoleucine: Also, the compositions of isoleucine and leucine in the aMTD sequences show inverse relationship between the number of amino acid (I and L) and delivery potential of aMTDs. Lower number of isoleucine and leucine in the sequences tends to have higher delivery potential (geometric mean) (FIGS. 13a to 13b).

Valine: Conversely, the composition of valine of aMTD sequences shows positive correlation with their cell-permeability. When the number of valine in the sequence is low, the delivery potential of aMTD is also relatively low (FIG. 13b).

Ten aMTDs having the highest cell-permeability are selected (average geometric mean: 2584±126). Their average number of valine in the sequences is 3.5; 10 aMTDs having relatively low cell-permeability (average geometric mean: 80±4) had average of 1.9 valine amino acids. The average number of valine in the sequences is lowered as their cell-permeability is also lowered as shown in FIG. 13b. Compared to higher cell-permeable aMTDs group, lower sequences had average of 1.9 in their valine composition. Therefore, to obtain high cell-permeable sequence, an average of 2-4 valines should be composed in the sequence.

5-5. Conclusion of SAR Analysis:

As seen in FIG. 15, all 240 aMTDs have been examined for these association of the cell-permeability and the critical factors: bending potential (PP), rigidity/flexibility (II), structure feature (AI), and hydropathy (GRAVY), amino acid length and composition. Through this analysis, cell-permeability of aMTDs tends to be lower when their central proline position is at 5' or 6' and GRAVY is 2.1 or lower (FIG. 15). Moreover, after investigating 10 higher and 10 lower cell-permeable aMTDs, these trends are clearly shown to confirm the association of cell-permeability with the central proline position and hydropathy.

6. Experimental Confirmation of Index Range/Feature of Critical Factors

The range and feature of five out of six critical factors have been empirically and experimentally determined that are also included in the index range and feature of the critical factors initially proposed before conducting the experiments and SAR analysis. In terms of index range and feature of critical factors of newly developed 240 aMTDs, the bending potential (proline position: PP), rigidity/flexibility (Instability Index: II), structural feature (Aliphatic Index: AI), hydropathy (GRAVY), amino acid length and composition are all within the characteristics of the critical factors derived from analysis of reference hydrophobic CPPs.

Therefore, our hypothesis to design and develop new hydrophobic CPP sequences as advanced MTDs is empirically and experimentally proved and demonstrated that critical factor-based new aMTD rational design is correct.

TABLE 35

Summarized Critical Factors of aMTD

| Critical Factor | Newly Designed CPPs Range | Analysis of Experimental Results Range |
|---|---|---|
| Bending Potential (Proline Position: PP) | Proline presences in the middle (5', 6', 7' or 8') and at the end of peptides | Proline presences in the middle (5', 6', 7' or 8') and at the end of peptides |

TABLE 35-continued

Summarized Critical Factors of aMTD

| Critical Factor | Newly Designed CPPs Range | Analysis of Experimental Results Range |
|---|---|---|
| Rigidity/Flexibility (Instability Index: II) | 40-60 | 41.3-57.3 |
| Structural Feature (Aliphatic Index: AI) | 180-220 | 187.5-220.0 |
| Hydropathy (Grand Average of Hydropathy GRAVY) | 2.1-2.6 | 2.2-2.6 |
| Length (Number of Amino Acid) | 9-13 | 12 |
| Amino acid Composition | A, V, I, L, P | A, V, I, L, P |

7. Discovery and Development of Protein-Based New Biotherapeutics with MITT Enabled by aMTDs for Protein Therapy 240 aMTD sequences have been designed and developed based on the critical factors. Quantitative and visual cell-permeability of 240 aMTDs (hydrophobic, flexible, bending, aliphatic and 12 a/a-length peptides) are all practically determined.

To measure the cell-permeability of aMTDs, rPeptides have also been designed and tested. As seen in FIGS. 13a to 15d, there are vivid association of cell-permeability and the critical factors of the peptides. Out of these critical factors, we are able to configure that the most effective cell-permeable aMTDs have the amino acid length of 12; composition of A, V, L, I and P; multiple proline located at either 7' or 8' and at the end (12'); instability index ranged of 41.3 to 57.3; aliphatic index ranged of 187.5 to 220.0; and hydropathy (GRAVY) ranged of 2.2 to 2.6.

These examined critical factors are within the range that we have set for our critical factors; therefore, we are able to confirm that the aMTDs that satisfy these critical factors have relatively high cell-permeability and much higher intracellular delivery potential compared to reference hydrophobic CPPs reported during the past two decades.

It has been widely evident that many human diseases are caused by proteins with deficiency or over-expression that causes mutations such as gain-of-function or loss-of-function. If biologically active proteins could be delivered for replacing abnormal proteins within a short time frame, possibly within an hour or two, in a quantitative manner, the dosage may be regulated depending on when and how proteins may be needed. By significantly improving the solubility and yield of novel aMTD in present invention (Table 31), one could expect its practical potential as an agent to effectively deliver therapeutic macromolecules such as proteins, peptides, nucleic acids, and other chemical compounds into live cells as well as live mammals including human. Therefore, newly developed MITT utilizing the pool (240) of novel aMTDs can be used as a platform technology for discovery and development of protein-based biotherapeutics to apprehend intracellular protein therapy after determining the optimal cargo-aMTD relationship.

8. Novel Hydrophobic CPPs—aMTDs for Development of CP-BMP2/7 Recombinant Proteins 8-1. Selection of aMTD for Cell-Permeability From 240 aMTDs and, 2 aMTDs were selected and used for the construction of CP-BMP2/7 recombinant proteins. 2 aMTDs used are shown in the following Table 36.

Various hydrophobic CPPs—aMTDs have been used to enhance the delivery of cargo proteins (BMP2 or BMP7) to mammalian cells and tissues.

TABLE 36

| SEQ ID NO | aMTD ID | Amino Acid Sequences |
|---|---|---|
| 12 | 24 | IALAAPALIVAP |
| 33 | 123 | AAIIVPAALLAP |

8-2. Selection of Solubilization Domain (SD) for Structural Stability

Recombinant cargo protein (BMP2 or BMP7) fused to hydrophobic CPP could be expressed in bacteria system, purified with single-step affinity chromatography, but protein dissolved in physiological buffers (e.g. PBS, DMEM or RPMI1640 etc.) was highly insoluble and had extremely low yield as a soluble form. Therefore, an additional non-functional protein domain (solubilization domain: SD) has been applied to fuse with the recombinant protein for improving the solubility, yield and eventually cell and tissue permeability.

According to the specific aim, the selected domains are SDA to SDF (Table 37). The aMTD/SD-fused BMP2/7 recombinant proteins have been determined for their stability.

The solubilization domains (SDs) and aMTDs have greatly influenced in increasing solubility/yield and cell-/tissue-permeability of the protein. Therefore, we have developed highly soluble and highly stable BMP2/7 recombinant protein fused with SD(s) (SDA, SDB or/and SDC) and aMTDs.

Table 37 shows the Characteristics of Solubilization Domains.

TABLE 37

| SD | Genbank ID | Origin | Protein (kDa) | pI | Instability Index (II) | GRAVY |
|---|---|---|---|---|---|---|
| A | CP000113.1 | Bacteria | 23 | 4.6 | 48.1 | −0.1 |
| B | BC086945.1 | Rat | 11 | 4.9 | 43.2 | −0.9 |
| C | CP012127.1 | Human | 12 | 5.8 | 30.7 | −0.1 |
| D | CP012127.1 | Bacteria | 23 | 5.9 | 26.3 | −0.1 |
| E | CP011550.1 | Human | 11 | 5.3 | 44.4 | −0.9 |
| F | NG_034970 | Human | 34 | 7.1 | 56.1 | −0.2 |

8-3. Construction of Expression Vector

BMP2 and BMP7 are synthesized as pre-pro peptides consisting of a signal peptide (SP), latency associated peptide (LAP) and mature peptide (MP). After the synthesis, SP and LAP are later processed by enzymatic cleavage, where the C-terminal mature domain is released and secreted (FIG. 17). In one embodiment of the present invention, BMP2 and BMP7 may be prepared an L form consisting of LAP and MP, and an M form consisting of only MP. 16 different types of recombinant protein with or without the aMTD and solubilization domains (SDs) for BMP2/7 were designed.

BMP2 recombinant protein structures for M form were labeled as follows: (2M-1) a BMP2 fused with His-tag, (2M-2) a BMP2 fused with His-tag and aMTD, (2M-3) a BMP2 fused with His-tag, aMTD and SDA, (2M-3C) a BMP2 fused with His-tag and SDA, (2M-4) a BMP2 fused with His-tag, aMTD and SDB, and (2M-4C) a BMP2 fused with His-tag and SDB, and BMP7 recombinant protein structures for M form were labeled as follows: (7M-1) a BMP7 fused with His-tag, (7M-2) a BMP7 fused with His-tag and aMTD, (7M-3) a BMP7 fused with His-tag, aMTD and SDA, (7M-3C) a BMP7 fused with His-tag and SDA, (7M-4) a BMP7 fused with His-tag, aMTD and SDB, and (7M-4C) a BMP7 fused with His-tag and SDB (FIG. 18a). Among them, (2/7M-3) and (2/7M-4) structures were used as candidate proteins having the biological efficacy of CP-BMP recombinant protein, and (2/7M-1), (2/7M-2), (2/7M-3C) and (2/7M-4C) were used as control groups (Non-CP-BMP) with respect to (2/7M-3) and (2/7M-4).

BMP2 recombinant protein structures for L form were labeled as follows: (2L-1) a BMP2 fused with His-tag, (2L-2) a BMP2 fused with His-tag and aMTD, (2L-3) a BMP2 fused with His-tag, aMTD and SDA, (2L-4) a BMP2 fused with His-tag, aMTD and SDB, (2L-5) a BMP2 fused with His-tag, aMTD and two SDB, (2L-5C) a BMP2 fused with His-tag and two SDB, (2L-6) a BMP2 fused with His-tag, aMTD, SDA and SDB, (2L-6C) a BMP2 fused with His-tag, SDA and SDB, (2L-7) a BMP2 fused with His-tag, aMTD and SDC, and (2L-7C) a BMP2 fused with His-tag and SDC, and BMP7 recombinant protein structure for L form were labeled as follows: (7L-1) a BMP7 fused with His-tag, (7L-2) a BMP7 fused with His-tag and aMTD, (7L-3) a BMP7 fused with His-tag, aMTD and SDA, (7L-4) a BMP7 fused with His-tag, aMTD and SDB, (7L-5) a BMP7 fused with His-tag, aMTD and two SDB, (7L-5C) a BMP7 fused with His-tag and two SDB, (7L-6) a BMP7 fused with His-tag, aMTD, SDA and SDB, (7L-6C) a BMP7 fused with His-tag, SDA and SDB, (7L-7) a BMP7 fused with His-tag, aMTD and SDC, and (7L-7C) a BMP7 fused with His-tag and SDC (FIGS. 18b and 23b). Among them, (2/7L-3), (2/7L-4), (2/7L-5), (2/7L-6) and (2/7L-7) structures were used as candidate proteins having the biological efficacy of CP-BMP2/7 recombinant protein, and (2/7L-1), (2/7L-2), (2/7L-5C), (2/7L-6C) and (2/7L-7C) were used as control groups (Non-CP-BMP) with respect to (2/7L-3), (2/7L-4), (2/7L-5), (2/7L-6) and (2/7L-7). 8-4. Preparation of BMP2/7 Recombinant Proteins The BMP2/7 recombinant proteins were successfully induced by adding IPTG and purified. The solubility and yield of the BMP2/7 recombinant proteins were determined.

The solubility and yields of BMP2/7 (M form) recombinant proteins fused with SD (2/7M-3 and 2/7M-4) were significant increased, which compared to a BMP2/7 (M form) recombinant proteins without SDs (2/7M-1 and 2/7M-2) (FIGS. 20a and 20b). The solubility and yields of BMP2/7 (L form) recombinant proteins fused with SDs (2/7L-5 and 2/7L-6) were significant increased, which BMP (L form) recombinant proteins without SD (L-1 and L-2) or with SDs (2/7L-3, 2/7L-4 and 2/7L-7) (FIGS. 20a, 20b, 23a and 23b). The results suggested that the BMP2/7 recombinant proteins fused with SDA or/and SDB displayed a significant improvement of solubility and yields.

Taken together, since L form consisting of LAP and MP has a larger size than M form consisting of MP, the BMP recombinant proteins fused with same aMTD and SD may be different cell-permeability depending on L form or M form. BMP requires MP to act on cells, and therefore, in this experiment, BMP recombinant protein consisting of MP (BMP (M form) recombinant protein) was used.

9. Determination of Cell-Permeability of BMP2/7 (M Form) Recombinant Proteins

The cell-permeability of the BMP2/7 (M form) recombinant proteins was investigated. BMP2/7 (M form) recombinant proteins were labeled fluorescence dye, FITC (fluorescein isothiocyanate), then cell permeability of the BMP2/7 (M form) recombinant proteins was evaluated in RAW 264.7 cells and NIH3T3 cells. The RAW 264.7 cells and the NIH3T3 cells were cultured in DMEM containing 10% fetal bovine serum (FBS) and 500 mg/mL of 5% penicillin/streptomycin (P/S). The RAW 264.7 cells analyzed by FACS (fluorescence-activated cell sorting) showed a gain in fluorescence, indicative of the presence of FITC-labeled BMP2/7 (M form) recombinant proteins as compared with control that only FITC or vehicle (diluent). For FACS analysis, cells ($1\times10^4$) were analyzed using a CellQues Pro cytometric analysis software (FACS Calibur, Beckton-Dickinson, San Diego Calif., USA). The cell-permeability of aMTD/SD-fused BMP2/7 (M form) recombinant proteins was examined, respectively (FIG. 24).

In the NIH3T3 cells, the cell-permeability and intracellular localization of the fluorescent signal was determined by confocal laser scanning microscopy (LSM700, Zeiss, Germany; FIG. 25). The intracellular localization of the fluorescent signal was determined by confocal laser scanning microscopy and by Nomarski interference microscope image of the same cells (LSM700, Zeiss, Germany). These results suggest that the BMP2/7 (M form) recombinant protein attaching aMTD is enhanced its cell-permeability and therefore, aMTD is critical for systemic delivery of the protein in vitro.

Accordingly, BMP2/7 recombinant proteins (2M-3, 7M-3, 2M-4 and 7M-4) having superior cell permeability were selected as candidates with biological efficacy (cell-permeability BMP2/7 recombinant protein, CP-BMP2/7).

10. Determination of Tissue-Permeability of CP-BMP2/7 Recombinant Proteins

Tissue-permeability of CP-BMP2/7 recombinant proteins was investigated by intraperitoneal injection of a FITC-labeled aMTD/SD-fused BMP2/7 recombinant protein into ICR mouse. Tissues obtained from each organ (brain, heart, lung, liver, spleen and kidney) after the injection of the protein show that the aMTD-fused CP-BMP2/7 recombinant protein is delivered into each organ (FIG. 26). Thus, these results suggest that the CP-BMP2/7 recombinant protein attaching aMTD is enhanced its tissue-permeability and therefore, aMTD is critical for systemic delivery of the protein in vivo.

11. Determination of Biological Activity of CP-BMP2/7 Recombinant Proteins In Vitro To investigate biological activity of the CP-BMP2/7 recombinant protein, MC3T3-E1 cell (preosteoblast), C3H10T-1/2 cell (multiple mesenchymal stem cell) and C2C12 cell (myoblast) were examined for osteogenic differentiation in vitro.

11-1. Inhibition of Myotube Formation

C2C12 myoblasts are known to differentiate into myotubes under the starvation condition (<2% of FBS or horse serum in media), and the treatment of BMPs suppress myogenesis and lead to osteogenesis (FIG. 40a). To examine the effect of CP-BMP2/7 recombinant proteins on the osteogenic differentiation, the C2C12 cells incubated with various dose of the CP-BMP2/7 recombinant proteins in serum free condition for 2 hours, and continuously exposed in 2% FBS media for 7 days (FIG. 27). These results suggest that the CP-BMP2/7 recombinant proteins inhibit myotube formation of the C2C12 cells.

11-2. Activation of Smad Signaling Pathway

To confirm biological activity of CP-BMP2/7 recombinant proteins, the activation of Smad-signaling was investigated. For starvation of cells, confluent C2C12 cells were incubated with serum free DMEM media, and then 10 uM of CP-BMP2/7 recombinant proteins were separately treated for 15 minutes. The cells were lysed, and Smad phosphorylation was examined (FIG. 28). Further, C3H10T1/2 mesenchymal stem cells and MC3T3-E1 preosteoblasts were treated with the BMP2/7 recombinant proteins, and activation of Smad-signaling was examined in the cells. These results indicate that the CP-BMP2/7 recombinant proteins activate Smad.

11-3. Alkaline Phosphatase (ALP) Activity

Alkaline phosphatase (ALP) is a widely accepted bone marker and activated by BMP stimulation. To confirm biological activity of CP-BMP2/7 recombinant proteins, ALP activity of the MC3T3-E1 cells was investigated (FIG. 29). Further, C3H10T1/2 mesenchymal stem cells and C2C12 cells were treated with the BMP2/7 recombinant proteins, and ALP activity was examined in the cells. These results indicate that the CP-BMP2/7 recombinant proteins increase ALP activity.

11-4. Combinational Treatment of CP-BMP2 and CP-BMP7 Recombinant Proteins

Synergistic effect of CP-BMP2 and CP-BMP7 recombinant proteins on osteogenic differentiation of C2C12 myoblasts was evaluated with inhibition effect of myotube formation and ALP activity (FIGS. 30 and 31). Further, C3H10T1/2 mesenchymal stem cells and MC3T3-E1 preosteoblasts were treated with the BMP2 or CP-BMP7 recombinant protein, and ALP activity was examined in the cells. These results indicate that combination treatment of the CP-BMP2 and CP-BMP7 recombinant proteins remarkably increase alkaline phosphatase (ALP) expression and significantly inhibit myotube formation, compared to single treatment of CP-BMP2/7 recombinant proteins.

12. Determination of Biological Activity of CP-BMP2/7 Recombinant Proteins In Vivo To investigate the effect of CP-BMP2/7 recombinant proteins on new bone formation of calvaria in vivo, CP-BMP2/7 recombinant proteins were locally injected to defected calvaria of mouse by subcutaneous injection. After 4 weeks, new bone formation was determined by using H&E staining (FIGS. 32 and 33). These results indicate that the CP-BMP2/7 recombinant proteins activate differentiation of osteoblast to form new bone.

13. Determination of Optimal aMTD for CP-BMP2 Recombinant Protein 13-1. Selection of aMTD for Cell-Permeability To improve cell-permeability and activity of the CP-BMP2 recombinant protein, CP-BMP2 recombinant proteins fused with different aMTDs were prepared (FIG. 34). From 240 aMTDs, 17 aMTDs were selected and used for the construction of CP-BMP2 recombinant proteins. 17 aMTDs used are shown in the following Table 38. However, the aMTD$_{481}$-fused CP-BMP2 recombinant protein was not prepared.

TABLE 38

| SEQ ID NO | aMTD ID | Amino Acid Sequences |
|---|---|---|
| 1 | 1 | AAALAPVVLALP |
| 3 | 3 | AALLVPAAVLAP |
| 17 | 61 | VAALPVLLALP |
| 34 | 124 | IAVALPALIAAP |
| 74 | 321 | IVAVALPALAVP |
| 91 | 385 | IVAIAVPALVAP |

TABLE 38-continued

| SEQ ID NO | aMTD ID | Amino Acid Sequences |
|---|---|---|
| 94 | 403 | AAALVIPAAILP |
| 101 | 442 | ALAALVPAVLVP |
| 110 | 481 | AIAIAIVPVALP |
| 131 | 563 | ALAVIVVPALAP |
| 136 | 585 | ALIVAIAPALVP |
| 139 | 603 | VLVALAAPVIAP |
| 143 | 623 | VAAAIALPAIVP |
| 200 | 847 | LVAIVVLPAVAP |
| 228 | 897 | AVIVPVAIIAAP |
| 229 | 899 | AVVIALPAVVAP |

13-2. Preparation of CP-BMP2 Recombinant Proteins

The 12 different types of CP-BMP2 recombinant proteins with the aMTD and SD were successfully induced by adding IPTG and purified (FIGS. 35a and 35b). These results indicate that different aMTDs-fused CP-BMP2 recombinant proteins expressed, and have high solubility and yield. However, the aMTD$_1$, aMTD$_{847}$ or aMTD$_{899}$-fused CP-BMP2 recombinant protein was not expressed.

13-3. Determination of Cell-Permeability of CP-BMP2 Recombinant Proteins

The cell-permeability of the 13 different types of CP-BMP2 recombinant proteins was investigated (FIGS. 36a and 36b). These results indicate that 13 different types of CP-BMP2 recombinant protein have high cell-permeability.

13-4. Determination of Biological Activity of CP-BMP2 Recombinant Proteins

The biological activity of the 4 different types of CP-BMP2 recombinant proteins was investigated (FIG. 37). ALP activity of CP-BMP2 recombinant proteins was determined in C3H10T1/2 mesenchymal stem cells (FIG. 37). The 4 different types of CP-BMP2 recombinant proteins are each CP-BMP2 recombinant proteins fused with aMTD$_{24}$, aMTD$_{442}$, aMTD$_{563}$ and aMTD$_{623}$. Further, C2C12 myoblasts and MC3T3-E1 preosteoblasts were treated with the 4 different types of CP-BMP2 recombinant protein, and ALP activity was examined in the cells. These results indicate that the aMTD$_{442}$-fused CP-BMP2 recombinant protein has the most excellent ALP activity.

In conclusion, CP-BMP2 recombinant protein attaching aMTD$_{442}$ having the excellent cell permeability was determined as an optimal CP-BMP2 recombinant protein.

14. Determination of Cell-Permeability of CP-BMP2 Recombinant Proteins

The cell-permeability of CP-BMP2 recombinant protein attaching aMTD$_{442}$ was investigated (FIGS. 38 and 39). These results suggest that the CP-BMP2 recombinant protein attaching aMTD$_{442}$ is enhanced its cell-permeability and therefore, aMTD$_{442}$ is critical for systemic delivery of the BMP.

15. Determination of Biological Activity of CP-BMP2 Recombinant Protein In Vitro To reinvestigate the biological activity of the CP-BMP2 recombinant protein which showed excellent effects on bone formation or regeneration, osteogenic differentiation was examined in vitro.

C2C12 myoblasts were treated with the CP-BMP2 recombinant protein, and inhibition of myotube formation in the cells was observed (FIG. 40b). C3H10T1/2 mesenchymal stem cells were treated with the CP-BMP2 recombinant protein, and ALP activity of the cells was examined (FIG. 41). Further, C2C12 myoblasts and MC3T3-E1 preosteoblasts were treated with the CP-BMP2 recombinant protein, and inhibition of myotube formation and ALP activity were examined in the cells.

These results suggest that the CP-BMP2 recombinant protein has excellent ability of osteogenic differentiation.

16. Determination of Mechanism of CP-BMP2 Recombinant Protein

To investigate the mechanism of the CP-BMP2 recombinant protein, C2C12 myoblasts were treated with the CP-BMP2 recombinant protein, and then signal intensity of Smad was examined (FIG. 42). Further, the C3H10T1/2 mesenchymal stem cells and MC3T3-E1 preosteoblasts were treated with the CP-BMP2 recombinant protein, and then signal intensity of Smad was examined in the cells. As a result, strong Smad activity was observed in the cells treated with the CP-BMP2 recombinant protein (CP-BMP2), compared to the cells treated with the BMP2 recombinant protein lacking aMTD (Non-CP-BMP2).

To investigate why the Smad signal induced by the CP-BMP2 recombinant protein is stronger than that of the control protein (Non-CP-BMP2), binding of CP-BMP2 recombinant protein and BMP2 receptor was examined in MC3T3-E1 preosteoblasts (FIG. 43). Further, the C2C12 myoblasts and MC3T3-E1 preosteoblasts were treated with the CP-BMP2 recombinant protein, and then signal intensity of Smad was examined in the cells. As a result, since the CP-BMP2 recombinant proteins permeating cells strongly bind to BMP receptors in intracellular ER (Endoplasmic reticulum) and golgi, strong Smad activity by the CP-BMP2 recombinant protein was observed.

17. Determination of Effect of CP-BMP2 Recombinant Protein In Vivo

To investigate the effect of CP-BMP2 recombinant proteins on new bone formation, the CP-BMP2 recombinant proteins were locally injected to calvaria of mouse by subcutaneous injection. After 4 weeks, new bone formation was determined by using H&E staining (FIGS. 44a and 44b).

To investigate the effect of CP-BMP2 recombinant proteins on bone regeneration, calvarial critical-sized defect model was designed in mouse. The CP-BMP2 recombinant proteins were locally injected to defected calvaria of mouse by subcutaneous injection. After 8 weeks, new bone formation was determined by using H&E staining (FIGS. 45a and 45b). Effective administration conditions of CP-BMP2 recombinant protein for bone regeneration were determined by changing administration frequency and dose of the CP-BMP2 recombinant protein (FIGS. 46a, 46b, 47a and 47b).

To investigate the effect of CP-BMP2 recombinant proteins on bone regeneration, equine bone defect model was designed in horse (FIG. 49b). The CP-BMP2 recombinant proteins showed in FIG. 48 were locally injected to defected hind limb of horses by subcutaneous injection. After 9 weeks, new bone formation was determined by using CT (FIGS. 48a, 49b and 50).

As a result, it was confirmed that the CP-BMP2 recombinant protein activated differentiation of osteoblast, leading to effective regeneration of defected bone, suggesting that the CP-BMP2 recombinant protein exhibits excellent effects on recovery of defected bone.

18. Determination of Toxicity of CP-BMP2 Recombinant Protein

To investigate toxicity of the CP-BMP2 recombinant protein in vivo, a toxicity assay was performed. In a single dose acute toxicity assay, a high concentration of the CP-BMP2 recombinant protein was intravenously administered to a mouse once, and the toxicity assay was performed for 2 weeks (FIG. 51). In a repeated dose toxicity assay, different concentrations of the CP-BMP2 recombinant protein were intravenously administered to a mouse once daily, and the toxicity assay was performed for 2 weeks (FIGS. 52a and 52b). As a result, even though high concentrations of CP-BMP2 recombinant protein were administered, no toxicity was observed.

19. Determination of Pharmacokinetics of CP-BMP2 Recombinant Protein

To determinate of pharmacokinetics of CP-BMP2 recombinant proteins, CP-BMP2 recombinant protein was labeled with FITC.

30 mg/kg of FITC-labeled CP-BMP2 recombinant protein were intravenously administered to mouse. At each time point, PBMCs were separated from the blood and splenocytes were separated from the spleen of the mouse. The CP-BMP2 recombinant proteins were measured in the PBMCs and splenocytes (FIG. 53). Further, the blood that separated from mouse and the CP-BMP2 recombinant protein were mixed, and the concentration of CP-BMP2 recombinant protein was measured at each time point (FIG. 54). As a result, it was confirmed that the CP-BMP2 recombinant protein was stably maintained in the blood for a long period of time.

15 mg/kg of FITC-labeled CP-BMP2 recombinant proteins were subcutaneously injected into the calvarial bone of mouse, and FITC signals expressed in the calvarial bone of the mouse were measured at each time point (FIG. 55). As a result, it was confirmed that the CP-BMP2 recombinant protein was maintained in the blood and organ for a long period of time. These results suggest that the CP-BMP2 recombinant protein may exist in vivo for a long period of time, and the CP-BMP2 recombinant protein may also maintain its effect persistently.

The following examples are presented to aid practitioners of the invention, to provide experimental support for the invention, and to provide model protocols. In no way are these examples to be understood to limit the invention.

Example 1. Development of Novel Advanced Macromolecule Transduction Domain (aMTD)

H-regions of signal sequences (HOURSP)-derived CPPs (MTS/MTM and MTD) do not have a common sequence, a sequence motif, and/or a common structural homologous feature. According to one embodiment of the present invention, the aim is to develop improved hydrophobic CPPs formatted in the common sequence and structural motif that satisfy newly determined 'critical factors' to have a 'common function,' to facilitate protein translocation across the plasma membrane with similar mechanism to the analyzed CPPs.

The structural motif as follows:

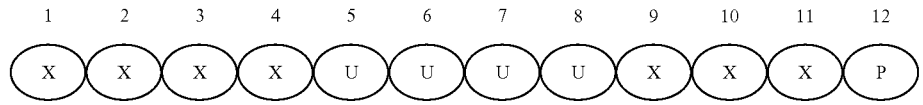

wherein X(s) refers to Alanine (A), Valine (V), Leucine (L) or Isoleucine (I); one of U refers to proline and the other U(s) refer to A, V, L or I; and P refers to proline.

In Table 9, universal common sequence/structural motif is provided as follows. The amino acid length of the peptides according to one embodiment of the present invention ranges from 9 to 13 amino acids, mostly 12 amino acids, and their bending potentials are dependent with the presence and location of proline in the middle of sequence (at 5', 6', 7' or 8' amino acid) and at the end of peptide (at 12') for recombinant protein bending. Instability index (II) for rigidity/flexibility of aMTDs is II<40, grand average of hydropathy (GRAVY) for hydropathy is around 2.2, and aliphatic index (AI) for structural features is around 200 (Table 9). Based on these standardized critical factors, new hydrophobic peptide sequences, namely advanced macromolecule transduction domain peptides (aMTDs), according to one embodiment of the present invention have been developed and summarized in Tables 10 to 15.

Example 2. Construction of Expression Vectors for Recombinant Proteins Fused to aMTDs Our newly developed technology has enabled us to expand the method for making cell-permeable recombinant proteins. The expression vectors were designed for histidine-tagged CRA proteins fused with aMTDs or rPeptides. To construct expression vectors for recombinant proteins, polymerase chain reaction (PCR) had been devised to amplify each designed aMTD or rPeptide fused to CRA.

The PCR reactions (100 ng genomic DNA, 10 pmol each primer, each 0.2 mM dNTP mixture, 1× reaction buffer and 2.5 U Pfu(+) DNA polymerase (Doctor protein, Korea) was digested on the restriction enzyme site between Nde I (5') and Sal I (3') involving 35 cycles of denaturation (95° C.), annealing (62° C.), and extension (72° C.) for 30 seconds each. For the last extension cycle, the PCR reactions remained for 5 minutes at 72° C. Then, they were cloned into the site of pET-28a(+) vectors (Novagen, Darmstadt, Germany). DNA ligation was performed using T4 DNA ligase at 4° C. overnight. These plasmids were mixed with competent cells of E. coli DH5-alpha strain on the ice for 10 minutes. This mixture was placed on the ice for 2 minutes after it was heat shocked in the water bath at 42° C. for 90 seconds. Then, the mixture added with LB broth media was recovered in 37° C. shaking incubator for 1 hour. Transformant was plated on LB broth agar plate with kanamycin (50 ug/mL) (Biopure, Johnson City, Tenn., USA) before incubating at 37° C. overnight. From a single colony, plasmid DNA was extracted, and after the digestion of Nde I and Sal I restriction enzymes, digested DNA was confirmed at 645 bp by using 1.2% agarose gels electrophoresis (FIG. 2). PCR primers for the CRA recombinant proteins fused to aMTD and random peptides (rPeptide) are summarized in Tables 23 to 30. Amino acid sequences of aMTD and rPeptide primers are shown in Tables 31 to 38.

Example 3. Inducible Expression, Purification and Preparation of Recombinant Proteins Fused to aMTDs and rPeptides To express recombinant proteins, pET-28a(+) vectors for the expression of CRA proteins fused to a negative control [rPeptide 38 (rP38)], reference hydrophobic CPPs (MTM$_{12}$ and MTD$_{85}$) and aMTDs were transformed in E. coli BL21 (DE3) strains. Cells were grown at 37° C. in LB medium containing kanamycin (50 ug/mL) with a vigorous shaking and induced at OD$_{600}$=0.6 by adding 0.7 mM IPTG (Biopure) for 2 hours at 37° C. Induced recombinant proteins were loaded on 15% SDS-PAGE gel and stained with Coomassie Brilliant Blue (InstantBlue, Expedeon, Novexin, UK) (FIG. 3).

The E. coli cultures were harvested by centrifugation at 8,000 rpm for 10 minutes, and the supernatant was discarded. The pellet was re-suspended in the lysis buffer (50 mM NaH$_2$PO$_4$, 10 mM Imidazol, 300 mM NaCl, pH 8.0). The cell lysates were sonicated on ice using a sonicator (Sonics and Materials, Inc., Newtown, Conn., USA) equipped with a probe. After centrifuging the cell lysates at 8,000 rpm for 10 minutes to pellet the cellular debris, the supernatant was incubated with lysis buffer-equilibrated Ni-NTA resin (Qiagen, Hilden, Germany) gently by open-column system (Bio-rad, Hercules, Calif., USA). After washing protein-bound resin with 200 mL wash buffer (50 mM NaH$_2$PO$_4$, 20 mM Imidazol, 300 mM NaCl, pH 8.0), the bounded proteins were eluted with elution buffer (50 mM NaH$_2$PO$_4$, 250 mM Imidazol, 300 mM NaCl, pH 8.0).

Recombinant proteins purified under natural condition were analyzed on 15% SDS-PAGE gel and stained with Coomassie Brilliant Blue (FIG. 4). All of the recombinant proteins were dialyzed for 8 hours and overnight against physiological buffer, a 1:1 mixture of cell culture medium (Dulbecco's Modified Eagle's Medium: DMEM, Hyclone, Logan, Utah, USA) and Dulbecco's phosphate buffered saline (DPBS, Gibco, Grand Island, N.Y., USA). From 316 aMTDs and 141 rPeptides cloned, 240 aMTD- and 31 rPeptide-fused recombinant proteins were induced, purified, prepared and analyzed for their cell-permeability.

Example 4. Determination of Quantitative Cell-Permeability of Recombinant

Proteins

For quantitative cell-permeability, the aMTD- or rPeptide-fused recombinant proteins were conjugated to fluorescein isothiocyanate (FITC) according to the manufacturer's instructions (Sigma-Aldrich, St. Louis, Mo., USA). RAW 264.7 cells were treated with 10 uM FITC-labeled recombinant proteins for 1 hour at 37° C., washed three times with cold PBS, treated with 0.25% tripsin/EDTA (Sigma-Aldrich, St. Louis, Mo.) for 20 minutes at 37° C. to remove cell-surface bound proteins. Cell-permeability of these recombinant proteins were analyzed by flow cytometry (Guava, Millipore, Darmstadt, Germany) using the FlowJo cytometric analysis software (FIGS. 5 to 6). The relative cell-permeability of aMTDs were measured and compared with the negative control (rP38) and reference hydrophobic CPPs (MTM12 and MTD85) (Table 31).

Example 5. Determination of Cell-Permeability and Intracellular Localization of Recombinant Proteins For a visual reference of cell-permeability, NIH3T3 cells were cultured for 24 hours on coverslip in 24-wells chamber slides, treated with 10 uM FITC-conjugated recombinant proteins for 1 hour at 37° C., and washed three times with cold PBS. Treated cells were fixed in 4% paraformaldehyde (PFA, Junsei, Tokyo, JP) for 10 minutes at room temperature, washed three times with PBS, and mounted with VECTASHIELD Mounting Medium (Vector laboratories, Burlingame, Calif., USA), and counter stained with DAPI (4',6-diamidino-2-phenylindole). The intracellular localization of the fluorescent signal was determined by confocal laser scanning microscopy (LSM700, Zeiss, Germany; FIGS. 7 and 8).

Example 6. Expression of BMP2/7 Recombinant Proteins

<6-1> Construction of Expression Vectors for BMP2/7 Recombinant Proteins

Full-length cDNA for human BMP2 (RC214586) and BMP7 (RC203813) were purchased from Origene. Our newly developed technology, aMTD-based MITT, has enabled us to improve the method for developing cell-permeable recombinant proteins. The expression vectors were designed for BMP2/7 (M Form) recombinant proteins fused with aMTD/SD (2/7M-3 and 2/7M-4) and control proteins without aMTD- or/and SD (2/7M-1, 2/7M-2, 2/7M-3C and 2/7M-4C), and BMP2/7 (L Form) recombinant proteins fused with aMTD/SD (2/7L-3 and 2/7L-4) and control proteins without aMTD or/and SD (2/7L-1, 2/7L-2, 2/7M-3C and 2/7M-4C).

To acquire expression vectors for BMP2/7 recombinant proteins, polymerase chain reaction (PCR) had been devised to amplify these recombinant proteins. The PCR reactions (100 ng genomic DNA, 10 pmol each primer, each 0.2 mM dNTP mixture, 1× reaction buffer and 2.5 U Pfu(+) DNA polymerase (Doctor Protein, Korea) was digested on the different restriction enzyme site involving 40 cycles of denaturation (95° C.), annealing (58° C.), and extension (72° C.) for 30 seconds each. For the last extension cycle, the PCR reactions remained for 10 minutes at 72° C. Then, they were cloned into the site of pET-28a(+) vectors (Novagen, Darmstadt, Germany). DNA ligation was performed using T4 DNA ligase (NEB, USA) at 4° C. overnight. These plasmids were mixed with competent cells of E. coli (BL21 (DE3) codon plus RIL) strain (ATCC, USA) on the ice for 10 minutes. This mixture was placed on the ice for 2 minutes after it was heat-shocked in the water bath at 42° C. for 90 seconds. Then, the mixture added with LB broth media (ELPIS, Korea) was recovered in 37° C. shaking incubator for 1 hour. Transformant was plated on LB broth agar plate with kanamycin (50 ug/mL). From a single colony, plasmid DNA was extracted, and after the digestion of BamHI and HindIII restriction enzymes (NEB, USA), digested DNA was confirmed by using 1.2% agarose gels electrophoresis (FIGS. 19a to 19d). PCR primers for the His-tagged (or not His-tagged) BMP recombinant proteins fused to aMTD and SD are summarized in Table 39 to 42.

As shown in FIGS. 19a to 19d, respective BMP2/7 (M form) recombinant expression vectors were expressed respective BMP2/7 recombinant proteins (2/7M-1, 2/7M-2, 2/7M-3, 2/7M-3C, 2/7M-4 and 2/7M-4C), and respective BMP2/7 (L form) recombinant expression vectors were expressed respective BMP2/7 recombinant protein (2/7L-1, 2/7L-2, 2/7L-3 and 2/7L-4).

TABLE 39

| Clone ID | Abbreviation | | Primer Sequence (5'→3') |
|---|---|---|---|
| 2M-1 | HB2M | Forward | ATTTATCATATGCAAGCCAAACACAAACAGCGG |
| | | Reverse | GGTATTGGATCCCTAGCGACACCCACA |
| 2M-2 | HM$_{24}$B2M | Forward | ATTTATCATATGATTGCGCTGGCGGCGCCGGCGTGATTGTGGCGCCGCAAGCCAAACACAAACAGCGG |
| | | Reverse | GGTATTGGATCCCTAGCGACACCCACA |
| 2M-3 | HM$_{24}$B2MSA | Forward | ATTTATCATATGATTGCGCTGGCGGCGCCGGCGTGATTGTGGCGCCGCAAGCCAAACACAAACAGCGG |
| | | Reverse | TATGTTGGATCCGTAGCGACACCCACA |
| | | Forward | CCCGGATCCATGCAAATATTACCGTTTTCTATAACGAA |
| | | Reverse | CGCGTCGACTTACCTCGGCTGCACCGGCACGGAGATGAC |
| 2M-3C | HB2MSA | Forward | ATTTATCATATGCAAGCCAAACACAAACAGCGG |
| | | Reverse | CGCGTCGACTTACCTCGGCTGCACCGGCACGGAGATGAC |
| 2M-4 | HM$_{24}$B2MSB | Forward | ATTTATCATATGATTGCGCTGGCGGCGCCGGCGTGATTGTGGCGCCGCAAGCCAAACACAAACAGCGG |
| | | Reverse | TATGTTGGATCCGTAGCGACACCCACA |
| | | Forward | CCCGGATCCATGGCAGAACAAAGCGACAAGGATGTGAAG |
| | | Reverse | CGCGTCGACTTAAAGGGTTTCCGAAGGCTTGGCTATCTT |
| 2M-4C | HB2MSB | Forward | ATTTATCATATGCAAGCCAAACACAAACAGCGG |
| | | Reverse | CGCGTCGACTTAAAGGGTTTCCGAAGGCTTGGCTATCTT |

TABLE 40

| Clone ID | Abbreviation | | Primer Sequence (5'→3') |
|---|---|---|---|
| 7M-1 | HB7M | Forward | ATTTATCATATGACGCCCAAGAACCAGGAAGCC |
| | | Reverse | ATAAATGGATCCCTAGTGGCAGCCACA |
| 7M-2 | HM$_{24}$B7M | Forward | ATTTATCATATGATTGCGCTGGCGGCGCCGGCGCTGATTGTGGCGCCGACGCCCAAGAACCAGGAAGCC |
| | | Reverse | ATAAATGGATCCCTAGTGGCAGCCACA |
| 7M-3 | HM$_{24}$B7MSA | Forward | ATTTATCATATGATTGCGCTGGCGGCGCCGGCGCTGATTGTGGCGCCGACGCCCAAGAACCAGGAAGCC |
| | | Reverse | ATAAATGGATCCCTAGTGGCAGCCACA |
| | | Forward | CCCGGATCCATGCAAATATTACCGTTTTCTATAACGAA |
| | | Reverse | CGCGTCGACTTACCTCGGCTGCACCGGCACGGAGATGAC |

TABLE 40-continued

| Clone ID | Abbreviation | | Primer Sequence (5'→3') |
|---|---|---|---|
| 7M-3C | HB7MSA | Forward | ATTTATCATATGACGCCCAAGAACCAGGAAGCC |
| | | Reverse | CGCGTCGACTTACCTCGGCTGCACCGGCACGGAGATGAC |
| 7M-4 | HM$_{24}$B7MSB | Forward | ATTTATCATATGATTGCGCTGGCGGCGCCGGCGCTGATTGTGGCGCCGACGCCCAAGAACCAGGAAGCC |
| | | Reverse | ATAAATGGATCCCTAGTGGCAGCCACA |
| | | Forward | CCCGGATCCATGGCAGAACAAAGCGACAAGGATGTGAAG |
| | | Reverse | CGCGTCGACTTAAAGGGTTTCCGAAGGCTTGGCTATCTT |
| 7M-4C | HB7MSB | Forward | ATTTATCATATGACGCCCAAGAACCAGGAAGCC |
| | | Reverse | CGCGTCGACTTAAAGGGTTTCCGAAGGCTTGGCTATCTT |

TABLE 41

| Clone ID | Abbreviation | | Primer Sequence (5'→3') |
|---|---|---|---|
| 2L-1 | HB2L | Forward | ATTTATCATATGCTCGTTCCGGAGCTGGGCCGC |
| | | Reverse | GGTATTGGATCCCTAGCGACACCCACA |
| 2L-2 | HM$_{24}$B2L | Forward | ATTTATCATATGATTGCGCTGGCGGCGCCGGCGCTGATTGTGGCGCCGCTCGTTCCGGAGCTGGGCCGC |
| | | Reverse | GGTATTGGATCCCTAGCGACACCCACA |
| 2L-3 | HM$_{24}$B2LSA | Forward | ATTTATCATATGATTGCGCTGGCGGCGCCGGCGCTGATTGTGGCGCCGCTCGTTCCGGAGCTGGGCCGC |
| | | Reverse | TATGTTGGATCCGTAGCGACACCCACA |
| | | Forward | CCCGGATCCATGCAAATATTACCGTTTTCTATAACGAA |
| | | Reverse | CGCGTCGACTTACCTCGGCTGCACCGGCACGGAGATGAC |
| 2L-4 | HM$_{24}$B2LSB | Forward | ATTTATCATATGATTGCGCTGGCGGCGCCGGCGCTGATTGTGGCGCCGCTCGTTCCGGAGCTGGGCCGC |
| | | Reverse | TATGTTGGATCCGTAGCGACACCCACA |
| | | Forward | CCCGGATCCATGGCAGAACAAAGCGACAAGGATGTGAAG |
| | | Reverse | CGCGTCGACTTAAAGGGTTTCCGAAGGCTTGGCTATCTT |

TABLE 42

| Clone ID | Abbreviation | | Primer Sequence (5'→3') |
|---|---|---|---|
| 7L-1 | HB7L | Forward | ATTTATCATATGTCCGCCCTGGCCGACTTCAGC |
| | | Reverse | ATAAATGGATCCCTAGTGGCAGCCACA |

TABLE 42-continued

| Clone ID | Abbreviation | | Primer Sequence (5'→3') |
|---|---|---|---|
| 7L-2 | HM$_{24}$B7L | Forward | ATTTATCATATGATTGCGCTGGCGGCG CCGGCGCTGATTGTGGCGCCGTCCGCC CTGGCCGACTTCAGC |
| | | Reverse | GGTATTGGATCCCCTAGCGACACCCACA |
| 7L-3 | HM$_{24}$B7LSA | Forward | ATTTATCATATGATTGCGCTGGCGGCG CCGGCGCTGATTGTGGCGCCGTCCGCC CTGGCCGACTTCAGC |
| | | Reverse | ATAAATGGATCCCTAGTGGCAGCCACA |
| | | Forward | CCCGGATCCATGCAAATATTACCGTTT TCTATAACGAA |
| | | Reverse | CGCGTCGACTTACCTCGGCTGCACCGG CACGGAGATGAC |
| 7M-4 | HM$_{24}$B7LSB | Forward | ATTTATCATATGATTGCGCTGGCGGCG CCGGCGCTGATTGTGGCGCCGTCCGCC CTGGCCGACTTCAGC |
| | | Reverse | ATAAATGGATCCCTAGTGGCAGCCACA |
| | | Forward | CCCGGATCCATGGCAGAACAAAGCGAC AAGGATGTGAAG |
| | | Reverse | CGCGTCGACTTAAAGGGTTTCCGAAGG CTTGGCTATCTT |

<6-2> Expression and Purification of Histidine-tagged BMP2/7 Recombinant Proteins

*E. coli* containing the recombinant expression vectors was incubated within 1 mL of LB medium at 37° C. overnight, and then inoculated in 700 mL of LB medium, followed by incubation at 37° C., until OD$_{600}$ reached 0.5 to 0.7 mM of isopropyl-β-D-thiogalactoside (IPTG) as a protein expression inducer was added to this culture medium, and then further incubated at 37° C. for 3 hours. This culture medium was centrifuged at 4° C. and 8,000 rpm for 15 minutes, and a supernatant was discarded to recover a cell pellet. The cell pellet thus recovered was suspended in a lysis buffer (50 mM NaH$_2$PO$_4$, 300 mM NaCl, pH 8.0), and then cells were disrupted by sonication. The cells were centrifuged at 15,000 rpm for 10 minutes to obtain an insoluble fraction containing recombinant proteins. Denatured recombinant proteins were lysed using denature lysis buffer (8 M Urea, 10 mM Tris, 100 mM NaH$_2$PO$_4$) and purified by adding Ni-NTA resin. Resin bound to proteins were washed 3 times with 30 mL of denature washing buffer (8 M Urea, 10 mM Tris, 20 m imidazole, 100 mM NaH$_2$PO$_4$). BMP2/7 recombinant proteins (2/7M-1, 2/7M-2, 2/7M-3, 2/7M-3C, 2/7M-4, 2/7M-4C, 2/7L-1, 2/7L-2, 2/7L-3 and 2/7L-4) were eluted 3 times with 30 mL of denature elution buffer (8 M Urea, 10 mM Tris, 250 mM imidazole). After purification, they were dialyzed twice against a refolding buffer (550 mM Guanidine-HCl, 440 mM L-Arginine, 50 mM Tris, 100 mM NDSB, 150 mM NaCl, 2 mM reduced glutathione and 0.2 mM oxidized glutathione). Finally, they were dialyzed against a physiological buffer such as DMEM at 4° C. until the dialysis was over 300×10$^5$ times. Concentration of purified proteins was quantified using Bradford assay according to the manufacturer's instructions. After purification, they were dialyzed against DMEM as indicated above. Finally, SDS-PAGE analysis of cell lysates before (−) and after (+) IPTG induction; aliquots of Ni$^{2+}$ affinity purified BMP2/7 recombinant proteins (P); and molecular weight standards (M) were conducted to confirm the presence of target protein.

<6-3> Determination of Solubility/Yield of BMP2/7 Recombinant Proteins

The aMTD-fused BMP2/7 recombinant proteins containing SDA or SDB are cloned, expressed, purified, and prepared in a soluble form under the denatural condition. Each BMP2/7 recombinant protein fused to aMTD and/or SD (2/7M-1, 2/7M-2, 2/7M-3, 2/7M-4, 2/7L-1, 2/7L-2, 2/7L-3 and 2/7L-4) was determined for their size (number of amino acids), yield (mg/L) and solubility on 10% SDS-PAGE gel and stained with Coomassie Brilliant Blue. Solubility was scored on a 5-point scale ranging from highly soluble proteins with little tendency to precipitate (+++++) to largely insoluble proteins (+) by measuring their turbidity (A450). Yield (mg/L) in physiological buffer condition of each recombinant protein was also determined. The cell-permeable BMP2/7 recombinant proteins were observed as a single band, where the amount of the final purified protein was up to 10 mg/mL in this protein purification procedure. As shown in FIGS. 20a and 20b, each type of BMP2/7 recombinant proteins were successfully expressed and purified. The solubility and yield of 2/7M-3 and 2/7M-4 were significantly increased compared to control protein (2/7M-1 and 2/7M-2). In contrast, 2/7L-3 and 2/7L-4 showed lower solubility and yield than 2/7M-3 and 2/7M-4, and little solubility, like the control proteins (2/7L-1 and 2/7L-2).

Example 7. Expression of New BMP2/7 (L form) Recombinant Proteins

To solve the problem with low solubility and yields of BMP2/7 (L form) recombinant protein, the type of aMTD and location of SD were changed in the aMTD/SD-fused BMP2/7 recombinant proteins. The expression vectors were designed for BMP2/7 (L Form) recombinant proteins fused with aMTD/SD (2/7L-5, 2/7L-6 and 2/7L-7) and control proteins without aMTD (2/7L-5C, 2/7L-6C and 2/7L-7C). In the same manner as in Example 6, the recombinant expression vectors prepared by using primers described in Tables 43 and 44 were identified by gel electrophoresis, and each of the BMP recombinant proteins were expressed and purified from each of the recombinant expression vectors, and solubility and yield were measured.

PCR primers for the His-tagged (or not His-tagged) BMP2/7 (L form) recombinant proteins fused to aMTD and SD are summarized in Tables 43 and 44.

As shown in FIG. 22, the respective BMP2/7 (L form) recombinant expression vectors were expressed respective BMP2/7 (L form) recombinant proteins (2/7L-5, 2/7L-5C, 2/7L-6, 2/7L-6C, 2/7L-7 and 2/7L-7C).

TABLE 43

| Clone ID | Abbreviation | | Primer Sequence (5'→3') |
|---|---|---|---|
| 2L-5 | HSBB2LSBM$_{123}$ | Forward | TCTTGTCATATGGCAGAACAAAG CGACAAG |
| | | Reverse | TAAGTTGCGGCCGCTTACGCCAG CAGCGCCGCCGGCACAATAATCG CCGCCGGAAGGGTTTTCCGAAGG |
| 2L-5C | HSBB2LSB | Forward | TCTTGTCATATGGCAGAACAAAG CGACAAG |

TABLE 43-continued

| Clone ID | Abbreviation | | Primer Sequence (5'→3') |
|---|---|---|---|
| | | Reverse | AATAACGCGGCCGCTTAAAAGGG TTTCCGAAGG |
| 2L-6 | HSAB2LSBM$_{123}$ | Forward | GGGTTTCATATGATGGCAAATAT TACCGTTTTC |
| | | Reverse | TAAGTTGCGGCCGCTTACGCCAG CAGCGCCGCCGGCACAATAATCG CCGCCGGAAGGGTTTTCCGAAGG |
| 2L-6C | HSAB2LSB | Forward | GGGTTTCATATGATGGCAAATAT TACCGTTTTC |
| | | Reverse | AATAACGCGGCCGCTTAAAAGGG TTTCCGAAGG |
| 2L-7 | SCHB2LM$_{123}$ | Forward | AATATAGGATCCCTCGTTCCGGA GCTGGGC |
| | | Reverse | TAAGTTGCGGCCGCTTACGCCAG CAGCGCCGCCGGCACAATAATCG CCGCCGGAAGGGTTTTCCGAAGG |
| 2L-7C | SCHB2L | Forward | AATATAGGATCCCTCGTTCCGGA GCTGGGC |
| | | Reverse | GTATTGGTCGACTTAGCGACACC CACAACC |

TABLE 44

| Clone ID | Abbreviation | | Primer Sequence (5'→3') |
|---|---|---|---|
| 7L-5 | HSBB7LSBM$_{123}$ | Forward | TCTTGTCATATGGCAGAACAAAG CGACAAG |
| | | Reverse | TAAGTTGCGGCCGCTTACGCCAG CAGCGCCGCCGGCACAATAATCG CCGCCGGAAGGGTTTTCCGAAGG |
| 7L-5C | HSBB7LSB | Forward | TCTTGTCATATGGCAGAACAAAG CGACAAG |
| | | Reverse | AATAACGCGGCCGCTTAAAGGGT TTTCCGAAGG |
| 7L-6 | HSAB7LSBM$_{123}$ | Forward | GGGTTTCATATGATGGCAAATAT TACCGTTTTC |
| | | Reverse | TAAGTTGCGGCCGCTTACGCCAG CAGCGCCGCCGGCACAATAATCG CCGCCGGAAGGGTTTTCCGAAGG |
| 7L-6C | HSAB7LSB | Forward | GGGTTTCATATGATGGCAAATAT TACCGTTTTC |
| | | Reverse | AATAACGCGGCCGCTTAAAGGGT TTTCCGAAGG |
| 7L-7 | SCHB7LM$_{123}$ | Forward | AATGATGGATCCTCCGCCCTGGC CGACTTC |
| | | Reverse | TAAGTTGCGGCCGCTTACGCCAG CAGCGCCGCCGGCACAATAATCG CCGCCGGAAGGGTTTTCCGAAGG |
| 7L-7C | SCHB7L | Forward | AATGATGGATCCTCCGCCCTGGC CGACTTC |
| | | Reverse | TAATATGTCGACTTAGTGGCAGC CACAGGC |

As shown in FIGS. 23a and 23b, each type of BMP2/7 (L form) recombinant proteins were successfully expressed and purified. 2L-5, 7L-5, 2L-6 and 7L-6 were successfully expressed and purified with significantly improved solubility and yield. But, 2L-7 and 7L-7 showed very limited solubility and yield. These results demonstrate that the combinational fusion of SDA and/or SDB to BMP2/7 (L form) recombinant proteins significantly improve their solubility, while SDC fused BMP2/7 (L form) recombinant proteins showed indifference.

Example 8. Determination of Cell-Permeability of BMP2/7 Recombinant Protein

Because we first secured full set of purified BMP2/7 (M form) recombinant proteins, BMP2/7 (M form) recombinant proteins were used for further investigations including cell-/tissue-permeability and biological activity.

For quantitative cell-permeability, 50 ul of 0.1 M sodium carbonate (Biosesang) was added to the each 10 mL of 10 uM aMTD/SD-fused BMP2/7 recombinant proteins (2/7M-1, 2/7M-2, 2/7M-3 and 2/7M-4), vehicle or FITC only. 50 ul/mL of 10 uM fluorescein isothiocynate (FITC, Sigma, F7250) was added, and left in a 4° C. shaker overnight. The FITC-aMTD/SD-fused BMP2/7 recombinant proteins were put in a dialysis membrane (Thermo), and 1 L of buffer was added thereto. For 2/7M-1, DMEM was used as a buffer, and for 2/7M-2, 2/7M-3 and 2/7M-4, saline (0.9% sodium chloride) was used as a buffer. The membranes were incubated on a 4° C. stir plate for 3 hours. The buffer was changed, followed by further incubation for 3 hours. The buffer was changed again, followed by overnight incubation. The buffer was changed again, followed by incubation for 2 hours. The proteins were filtered using a 0.2 urn syringe filter, and then aliquoted and stored at −70° C. before use.

RAW 264.7 cells (ATCC, USA) were treated with 10 uM of the FITC-labeled BMP2/7 recombinant proteins (2/7M-1, 2/7M-2, 2/7M-3 and 2/7M-4) for 1 hour at 37° C., washed three times with cold PBS, treated with proteinase K (10 ug/mL) for 20 minutes at 37° C. to remove cell-surface bound proteins and subjected to fluorescence-activated cell sorting (FACS) analysis (FACSCalibur; BD, Franklin Lakes, N.J.).

As shown in FIG. 24, the aMTD/SD-fused CP-BMP2/7 recombinant proteins (2/7M-3 and 2/7M-4) exhibited superior cell permeability, compared to the BMP2/7 recombinant proteins lacking aMTD or SD (2/7M-1 and 2/7M-2). In particular, 2M-4 and 7M-4 were found to have the highest cell permeability.

For a visual reference of cell-permeability, NIH3T3 cells (ATCC, USA) were cultured for 24 hours on a coverslip in 24-wells chamber slides, treated with 10 uM of vehicle (culture medium, DMEM), FITC only or FITC-conjugated BMP2/7 recombinant proteins (2/7M-1, 2/7M-2, 2/7M-3 and 2/7M-4) for 1 hour at 37° C., and washed three times with cold PBS. Treated cells were fixed in 4% paraformaldehyde (PFA, Junsei, Tokyo, Japan) for 10 minutes at room temperature, washed three times with PBS, and mounted with VECTASHIELD Mounting Medium (Vector laboratories, Burlingame, Calif., USA) with DAPI (4′,6-diamidino-2-phenylindole) for nuclear staining. The intracellular localization of the fluorescent signal was determined by confocal laser scanning microscopy (top) and by Nomarski interference microscope image of the same cells (LSM700, Zeiss, Germany).

As shown in FIG. 25, the aMTD/SD-fused BMP2/7 recombinant proteins (2/7M-3 and 2/7M-4) exhibited superior cell permeability, compared to the BMP2/7 recombinant proteins lacking aMTD or SD (2/7M-1 and 2/7M-2). In particular, 2M-4 and 7M-4 were found to have the highest cell permeability.

Consequently, 2M-3, 7M-3, 2M-4 and 7M-4 showing excellent cell permeability as well as excellent solubility and yield were determined as CP-BMP2/7 recombinant proteins.

Example 9. Determination of Tissue-Permeability of CP-BMP2/7 Recombinant

Proteins

For tissue-permeability, ICR mouse (6-week-old, male) were injected intraperitoneally (600 ug/head) with vehicle, FITC only or FITC-conjugated BMP2/7 recombinant proteins (2M-4, 2M-4C, 7M-4 and 7M-4C). After 2 hours, the organs (brain, heart, lung, liver, spleen and kidney) were isolated, washed with O.C.T. compound (Sakura), and frozen in deep freezer. Cryosections (15 um thickness) were analyzed by fluorescence microscopy.

As shown in FIG. 26, the aMTD/SD-fused CP-BMP2/7 recombinant proteins (2M-4 and 7M-4) expressed FITC signals in many organs (brain, hear, lung, liver, spleen and kidney), compared to the BMP recombinant proteins lacking aMTD (2M-4C and 7M-4C). As a result, it was confirmed that the BMP2/7 recombinant protein has cell permeability by aMTD.

Example 10. Determination of Biological Activity of CP-BMP2/7 Recombinant Proteins In Vitro <10-1> Inhibition of Myotube Formation C2C12 myoblasts (ATCC, USA) were cultured with high glucose DMEM (Hyclone) and 10% fetal bovine serum (FBS, Hyclone) at 37° C. for growth and expansion. The C2C12 cells were plated on 24-well culture plate ($1\times10^5$ cells/well) in the growth media for 24 hours. To induce the differentiation, the cells were exposed to a starvation condition with 2% of FBS in a culture media with or without BMP2/7 recombinant proteins. The BMP2/7 recombinant proteins (2M-1, 7M-1, 2M-4 and 7M-4) were treated with different concentration (0.1, 0.5, 0, 5 uM). After 3 days and 7 days of culture, the cell morphologies were photographed to determine the differentiation into either myotube formation.

As shown in FIG. 27, the inhibitory effects on myotube formation of C2C12 cells were not shown at the low concentrations (0.1 and 0.5 uM) of 2M-1, 7M-1, 2M-4 and 7M-4. However, treatment of 2M-1 or 7M-1 at 1 uM significantly inhibited the myotube formation, which manifests the transition of lineage differentiation from myogenic to osteogenic. Highest concentration 5 uM of 2M-1 has shown weak cytotoxicity, while same dose of 7M-1 has shown strong inhibition of myotubes formation without any cytotoxic effect. Unlike what has been previously expected, 2M-4 and 7M-4 did not affect and differentiation of the C2C12 cells even at the high doses (1 and 5 uM). Therefore, we have selected 1 uM of BMP2/7 recombinant protein as the effective concentration for further experiments.

<10-2> Activation of Smad Signaling Pathway

To investigate the activation of BMP-Smad signaling, C2C12 cells were cultured with high glucose DMEM (Hyclone) and 10% fetal bovine serum (FBS, Hyclone) at 37° C. for growth and expansion. The cells were plated on 24-well culture plate ($1\times10^5$ cells/well) in the growth media for 24 hours. The cells were incubated with serum-free medium alone (α-MEM or DMEM) containing 10 uM of BMP2/7 recombinant proteins (2/7M-3, 2/7M-3C, 2/7M-4 and 2/7M-4C) of indicated concentration for 15 minutes. The cells treated BMP2/7 recombinant proteins were lysed in a lysis buffer (RIPA buffer) containing a protease cocktail and phosphatase inhibitor cocktail (Sigam). Equal amounts of cell lysate protein were subjected to SDS-PAGE and transferred to nitrocellulose membranes. The protein transferred membranes were incubated to block non-specific binding sites in immersing the membrane in 5% skim milk. The membranes were incubated with anti-phosphorylated Smad1/5/8 (Cellsignaling) overnight at 4° C. and anti-6-actin (Santacruz) at room temperature (RT) and then incubated with the appropriate horseradish peroxidase-conjugated secondary antibodies for 1 hour at RT. The blots were developed using a chemiluminescence detection system and exposed to an x-ray film.

As shown in FIG. 28, p-Smad 1/5/8 activities of 2M-4 and 7M-4 were similar to that of vehicle, and 2M-3 and 7M-3 showed the excellent p-Smad 1/5/8 activity.

<10-3> ALP Activity

To investigate whether the CP-BMP2/7 recombinant proteins directly affect osteogenic activity, an ALP activity assay was performed.

Mouse pre-osteoblast, MC3T3-E1 cells were cultured in the minimum essential medium (MEM) alpha modification (Hyclone) with 10% FBS and 1% penicillin/streptomycin. ALP activity was measured with cell lysate, according to the manufacturer's protocol. Briefly, supernatant of cell lysate was used after 13000 rpm of centrifugation for 10 min, and 10 ul of supernatant was reacted with 200 ul of ALP substrate solution for 30 minutes at 37° C. After 30 minutes, the optical density (O.D) was measured by using microplate reader at 405 nm of wave length. Different concentrations of p-Nitrophenyl Phosphate were used as standards for ALP activity, and calculated ALP activities were normalized by total protein concentration, which was obtained from bradford (Bio-rad) protein assay.

As shown in FIG. 29, the treatment of CP-BMP2/7 recombinant proteins (2M-3, 7M-3, 2M-4 and 7M-4) showed ALP activity, compared to treatment of the control proteins (2/7M-3C and 2/7M-4C). In particular, 2M-3 as the BMP2 recombinant protein showed 3-folds higher ALP activity than 2M-4, and both 7M-3 and 7M-4 as the BMP7 recombinant protein showed excellent ALP activity.

<10-4> Combinational Treatment of CP-BMP2 and CP-BMP7 Recombinant Proteins

To evaluated synergistic effect of CP-BMP2 and CP-BMP7 recombinant proteins on osteogenic differentiation of C2C12 myoblasts, inhibitory of myotube formation and ALP activity were investigated.

In the same manner as in Example <10-1>, single treatment or co-treatment with each 1 uM of CP-BMP2 and/or CP-BMP7 recombinant proteins (2M-4 and 7M-4) was performed in the C2C12 cells. After 3 days and 7 days of culture, cell morphologies were photographed to determine the differentiation into either myotube formation or osteogenesis.

As shown in FIG. 30, it was confirmed that co-treatment of the CP-BMP2 and CP-BMP7 recombinant proteins (2M-4 and 7M-4) inhibited myotube formation, compared to single treatment of the CP-BMP2 or CP-BMP7 recombinant protein (2M-4 or 7M-4).

In the same manner as in Example <10-3>, single treatment or co-treatment with each 1 uM of CP-BMP2 and CP-BMP7 recombinant proteins (2M-4 and 7M-4) was performed ALP activity assay in the MC3T3-E1 cells.

As shown in FIG. 31, it was confirmed that co-treatment of the CP-BMP2 and CP-BMP7 recombinant proteins (2M-4 and 7M-4) significantly increased in ALP activity, compared to single treatment of CP-BMP2 or CP-BMP7 recombinant protein (2M-4 or 7M-4).

These results showed that sufficient exposure time of CP-BMP2/7 recombinant proteins is required for effective osteogenic differentiation. Further, combinational treatment of CP-BMP2 and CP-BMP7 synergistically induced the osteogenic differentiation of the cells.

Example 11. Determination of Biological Activity of CP-BMP2/7 Recombinant

Proteins in vivo 7.5 mg/kg of BMP2/7 recombinant proteins (2M-3, 7M-3, 2M-3C and 7M-3C) were subcutaneously injected into the calvarial bone of the B6 mouse (6 weeks, male) for 4 weeks three times a week. After 4 weeks, the calvarial bone was separated. Also, samples were decalcified using Rapidcal for 2 weeks (BBC Biochemical, Mount Vernon, Wash., USA) by replacing the solution every 2 days. Samples were dehydrated with graded EtOH (70 to 100%), toluene, and paraffin. Dehydrated samples were embedded in paraffin wax and hardened into a paraffin block for sectioning. Specimens were cut to 6 urn using a microtome (Shandon, Runcorn, Cheshire, GB). Sections underwent deparaffinization and hydration and stained nuclei and cytosol with Harris hematoxylin and eosin solution (H&E staining). Goldner's trichrome staining method was used to determined detailed bone tissue morphology such as mineralized collagen. Following dehydration, samples were mounted with mounting medium (Richard-Allan Scientific, Kalamazoo, Mich., USA) and observed under an optical microscope (Nikon 2000, Japan).

As shown in FIG. 32, only few lining cells were observed on the surface of calvarial bone tissue in diluent treated group. In 2M-3C or 7M-3C treated group, the BMP2/7 recombinant protein without aMTD, showed increase of extra cellular matrix (ECM) formation on the surface of calvaria tissue, which indicated that the immature bone matrix formation. On the other hands, the significant increase of ECM formation was observed in 2M-3 or 7M-3 treated group, the BMP2/7 recombinant protein fused with aMTD.

As shown in FIG. 33, the new bone formation was quantified by measuring their newly formed ECM thickness. Although the 2M-3C or 7M-3C treated group showed more than 5 folds greater relative activity, 2M-3 or 7M-3 treated group showed more than 20 folds greater relative activity which compare to diluent treated group.

These results showed that the fusion of aMTD to BMP2 or BMP7 recombinant proteins, CP-BMP2/7 recombinant proteins, resulted in great increase of their bioactivity such as new bone formation.

Example 12. Determination of Biological Activity of CP-BMP2 Recombinant Proteins In Vitro <12-1> Expression and Purification of CP-BMP2 Recombinant Proteins To improve cell-permeability and activity of the CP-BMP2 recombinant protein, different aMTD-fused CP-BMP2 recombinant proteins were prepared (FIG. 34).

First, the expression vectors were designed for CP-BMP2 recombinant proteins fused with $aMTD_1$, $aMTD_3$, $aMTD_{61}$, $aMTD_{124}$, $aMTD_{241}$, $aMTD_{321}$, $aMTD_{385}$, $aMTD_{403}$, $aMTD_{442}$, $aMTD_{481}$, $aMTD_{563}$, $aMTD_{585}$, $aMTD_{603}$, $aMTD_{623}$, $aMTD_{847}$, $aMTD_{897}$, $aMTD_{899}$. The expression vectors were expressed in the same manner as in Example <6-1>, PCR primers for CP-BMP2 recombinant proteins fused with aMTD and SD are summarized in Table 45.

As a result, it was confirmed that the expression vectors which CP-BMP2 recombinant protein fused with $aMTD_1$, $aMTD_3$, $aMTD_{61}$, $aMTD_{124}$, $aMTD_{241}$, $aMTD_{321}$, $aMTD_{385}$, $aMTD_{403}$, $aMTD_{442}$, aMTD563, $aMTD_{585}$, $aMTD_{603}$, $aMTD_{623}$, $aMTD_{847}$, $aMTD_{897}$ and $aMTD_{899}$, except for $aMTD_{481}$, were prepared.

TABLE 45

| No. | Abbreviation | Primer Sequence (5'→3') Forword | Reverse |
|---|---|---|---|
| 1 | HM$_1$B2MSA | ATTTATCATATGGCGGCGGCGCTGGCGCCGGTGGTGCTGGCGCTGCCGCACGCGTCGACTTACCTCGGCTAGCCAAACACAAACAGCGG | GCACCGGCACGGAGATGAC |
| 2 | HM$_3$B2MSA | ATTTATCATATGGCGGCGGCGCTGGCGCCGGTGGTGCTGGCGCTGCCGCAAGCCAAACACAAACAGCGG | |
| 3 | HM$_{61}$B2MSA | ATTTATCATATGGTGGCGGCGCTGCCGGTGCTGCTGGCGGCGCTGCCGCAAGCCAAACACAAACAGCGG | |
| 4 | HM$_{124}$B2MSA | ATTTATCATATGATTGCGGTGGCGCTGCCGGCGCTGATTGCGGCGCCGCAAGCCAAACACAAACAGCGG | |
| 5 | HM$_{241}$B2MSA | ATTTATCATATGGCGGCGGCGGTGGTGCCGGTGCTGCTGGTGGCGCCGCAAGCCAAACACAAACAGCGG | |
| 6 | HM$_{321}$B2MSA | ATTTATCATATGATTGTGGCGGTGGCGCTGCCGGCGCTGGCGGTGCCGCAAGCCAAACACAAACAGCGG | |
| 7 | HM$_{385}$B2MSA | ATTTATCATATGATTGTGGCGATTGCGGTGCCGGCGCTGGTGGCGCCGCAAGCCAAACACAAACAGCGG | |
| 8 | HM$_{403}$B2MSA | ATTTATCATATGGCGGCGGCGCTGGTGATTCCGGCGGCGATTCTGCCGCAAGCCAAACACAAACAGCGG | |
| 9 | HM$_{442}$B2MSA | ATTTATCATATGGCGCTGGCGGCGCTGGTGCCGGCGGTGCTGGTGCCGCAAGCCAAACACAAACAGCGG | |

TABLE 45-continued

| No. | Abbreviation | Primer Sequence (5'→3') Forword / Reverse |
|---|---|---|
| 10 | HM₆₀₃B2MSA | ATTTATCATATGGTGCTGGTGGCGCTGGCGGCGCCGGTGATTGCGCCGCA AGCCAAACACAAACAGCGG |
| 11 | HM₅₆₃B2MSA | ATTTATCATATGGCGCTGGCGGTGATTGTGGTGCCGGCGCTGGCGCCGCA AGCCAAACACAAACAGCGG |
| 12 | HM₄₈₁B2MSA | ATTTATCATATGGCGATTGCGATTGCGATTGTGCCGGTGGCGCTGCCGCA AGCCAAACACAAACAGCGG |
| 13 | HM₅₈₅B2MSA | ATTTATCATATGGCGCTGATTGTGGCGATTGCGCCGGCGCTGGTGCCGCA AGCCAAACACAAACAGCGG |
| 14 | HM₆₂₃B2MSA | ATTTATCATATGGTGGCGGCGGCGATTGCGCTGCCGGCGATTGTGCCGCA AGCCAAACACAAACAGCGG |
| 15 | HM₈₄₇B2MSA | ATTTATCATATGCTGGTGGCGATTGTGGTGCTGCCGGCGGTGGCGCCGCA AGCCAAACACAAACAGCGG |
| 16 | HM₈₉₇B2MSA | ATTTATCATATGGCGGTGATTGTGCCGGTGGCGATTATTGCGGCGCCGCA AGCCAAACACAAACAGCGG |
| 17 | HM₈₉₉B2MSA | ATTTATCATATGGCGGTGGTGATTGCGCTGCCGGCGGTGGTGGCGCCGCA AGCCAAACACAAACAGCGG |

The expression vectors expressed respective CP-BMP2 recombinant proteins, in the same manner as in Example <6-2>. The 12 different types of CP-BMP2 recombinant protein, except for recombinant proteins fused with aMTD$_1$, aMTD$_{842}$, aMTD$_{899}$, were expressed. Solubility and yield of the 12 different CP-BMP2 recombinant proteins were measured in the same manner as in Example <6-3>.

As shown in FIGS. 35a and 35b, the 12 different types of CP-BMP2 recombinant proteins were successfully expressed and purified, and the solubility and yield of the CP-BMP2 recombinant proteins were increased. In particular, the CP-BMP2 recombinant proteins fused with aMTD$_{24}$, aMTD$_{442}$, aMTD$_{563}$ and aMTD$_{623}$ were found to have high solubility.

<12-2> Determination of Cell-Permeability of CP-BMP2 Recombinant Proteins

The cell-permeability of the 13 different types of CP-BMP2 recombinant proteins was investigated in the same manner as in Example 8. RAW 264.7 cells were treated with the 13 different types of CP-BMP2 recombinant proteins, vehicle or only FITC.

As shown in FIGS. 36a and 36b, aMTD-fused CP-BMP2 recombinant proteins have excellent cell permeability. In particular, CP-BMP2 recombinant proteins fused with aMTD$_{24}$, aMTD$_{442}$, aMTD$_{563}$ and aMTD$_{623}$ were found to have high cell permeability.

<12-3> Determination of Biological Activity of CP-BMP2 Recombinant Proteins

To determine biological activity of 4 different types of CP-BMP2 recombinant protein having excellent cell permeability, an ALP assay was performed in the same manner as in Example <10-3>. C3H10T1/2 mesenchymal stem cells were treated with CP-BMP2 recombinant proteins fused with aMTD$_{24}$, aMTD$_{442}$, aMTD$_{563}$ and aMTD$_{623}$, or control (vehicle).

As shown in FIG. 37, treatment of the CP-BMP2 recombinant protein showed ALP activity, compared to treatment of the control (vehicle). In particular, aMTD$_{442}$-fused CP-BMP2 recombinant protein was showed higher ALP activity. Further, in C2C12 myoblasts and MC3T3-E1 preosteoblasts, treatment of CP-BMP2 recombinant proteins fused with aMTD$_{442}$ showed higher ALP activity.

As in the following Table 46, solubility, cell-permeability and biological activity of each of the CP-BMP2 recombinant proteins fused with different aMTDs (aMTD$_1$, aMTD$_3$, aMTD$_{61}$, aMTD$_{124}$, aMTD$_{241}$, aMTD$_{321}$, aMTD$_{385}$, aMTD$_{403}$, aMTD$_{442}$, aMTD$_{481}$, aMTD$_{563}$, aMTD$_{585}$, aMTD$_{603}$, aMTD$_{623}$, aMTD$_{847}$, aMTD$_{897}$, aMTD$_{899}$) were compared.

TABLE 46

| | Solubility | | Cell-Permeabillity | | | Biological Activity | |
|---|---|---|---|---|---|---|---|
| Rank | aMTD | Yield (mg/L) | Rank | aMTD | Rel. fold | Rank | aMTD | ALP activity |
| 1 | 623 | 51 | 1 | 623 | 19.9 | 1 | 449 | 6.92 |
| 2 | 563 | 48 | 2 | 442 | 11.5 | 2 | 563 | 5.24 |
| 3 | 442 | 47 | 3 | 24 | 8.5 | 3 | 623 | 5.23 |
| 4 | 24 | 42 | 4 | 563 | 7.9 | 4 | 24 | 2.97 |

The aMTD$_{442}$-fused CP-BMP2 recombinant protein showing the most excellent biological activity as well as excellent solubility and cell-permeability was determined as an optimal CP-BMP2 recombinant protein, and this aMTD$_{442}$-fused CP-BMP2 recombinant protein was subjected to subsequent experiments.

Example 13. Determination of Cell-Permeability of CP-BMP2 Recombinant Protein

To investigate cell-permeability of the aMTD$_{442}$-fused CP-BMP2 recombinant protein, RAW 264.7 cells and NIH3T3 cells were used in the same manner as in Example 8. The RAW 264.7 cells and NIH3T3 cells were treated with the FITC-labeled CP-BMP2 recombinant proteins, vehicle, FITC only or control protein (BMP2).

As shown in FIGS. 38 and 39, it was confirmed that aMTD/SD-fused CP-BMP2 recombinant protein (CP-BMP2) exhibited superior cell-permeability, compared to the BMP2 which lacking aMTD/SD. These results suggest that the CP-BMP2 recombinant protein fused with aMTD$_{442}$ is enhanced its cell-permeability and therefore, aMTD$_{442}$ is critical for systemic delivery of the BMP.

Example 14. Determination of Biological Activity of CP-BMP2 Recombinant Protein In Vitro To reinvestigate the biological activity of the CP-BMP2 recombinant protein which showed excellent effects on bone formation in vivo, osteogenic differentiations were examined in the C2C12 myoblasts, C3H10T1/2 mesenchymal stem cells and MC3T3-E1 preosteoblasts.

<14-1> Inhibition of Myotube Formation

In the same manner as in Example <10-1>, the C2C12 myoblasts were incubated with serum-free medium containing 1 uM of CP-BMP2 recombinant proteins or vehicle for 2 hours, and washed out with PBS. Then, the cells incubated for 7 days under 2% FBS media without any additional treatment of CP-BMP2 recombinant proteins. The cell morphologies were photographed to determine the differentiation into either myotube formation.

As shown in FIG. 40b, treatment of the CP-BMP2 recombinant proteins showed inhibition of myotube formation, compared to treatment of the vehicle.

<14-2> ALP Activity

C3H10T1/2 mesenchymal stem cells (ATCC, USA) were maintained in the Roswell Park Memorial Institute medium (RPMI) 1640 (Hyclone) with 10% FBS and 1% penicillin/streptomycin. To induce the osteogenic differentiation, the cells were exposed to a starvation condition with a serum-free culture media. The cells were incubated with serum-free medium containing 1 uM of CP-BMP2 recombinant proteins (CP-BMP2), control protein (Non-CP-BMP2; BMP2 recombinant protein fused with his-tag and SD) or vehicle for 2 hours and washed out with PBS. The culture media changed with 10% FBS. After 7 days of culture, ALP activity was measured in the same manner as in Example <10-3>.

As shown in FIG. 41, treatment of CP-BMP2 recombinant proteins (CP-BMP2) showed 11-folds higher ALP activity than treatment of the vehicle, and 3-folds higher ALP activity than treatment of the control protein (Non-CP-BMP2).

C2C12 myoblasts were incubated with serum-free medium containing 1 uM of CP-BMP2 recombinant proteins or vehicle for 2 hours, and washed out with PBS. Then, the cells incubated for 7 days under 2% FBS media without any additional treatment of 1 uM of CP-BMP2 recombinant proteins (CP-BMP2), control protein (Non-CP-BMP2; BMP2 recombinant protein fused with his-tag and SD) or vehicle for 2 hours and washed out with PBS. The culture media changed with 10% FBS. After 7 days of culture, ALP activity was measured in the same manner as in Example <10-3>.

MC3T3-E1 preosteoblasts (ATCC, USA) were maintained in Alpha Modification of Eagle's Minimum Essential Media (α-MEM) (Hyclone) with 10% FBS and 1% penicillin/streptomycin. To induce the osteogenic differentiation, the cells were exposed to a starvation condition with a serum-free culture media included 50 mg/mL ascorbic acid, 10 mM β-glycerophosphate (SFOM). The cells were incubated with SFOM containing I uM of CP-BMP2 recombinant proteins (CP-BMP2), control protein (Non-CP-BMP2) or vehicle for 2 hours and washed out with PBS. After 7 days of culture, ALP activity was measured in the same manner as in Example <10-3>.

As a result, in C2C12 myoblasts and MC3T3-E1 preosteoblasts, treatment of CP-BMP2 recombinant proteins (CP-BMP2) showed higher ALP activity than treatment of the vehicle and control protein (Non-CP-BMP2).

Example 15. Determination of Mechanism of CP-BMP2 Recombinant Proteins

To investigate the mechanism of the CP-BMP2 recombinant protein, intracellular activity and binding of the CP-BMP2 recombinant protein were examined.

<15-1> Activation of Smad Signaling Pathway

To investigate the activation of Smad signaling, C2C12 cells were incubated with 1 M of CP-BMP2 recombinant proteins (CP-BMP2), control protein (Non-CP-BMP2) or vehicle in the same manner as in Example <10-2>.

As shown in FIG. 42, treatment of the CP-BMP2 recombinant proteins showed p-Smad 1/5/8 phosphorylation. And, treatment of the CP-BMP2 recombinant proteins showed significantly increased p-Smad 1/5/8 phosphorylation, compared to treatment of the control protein (non-CP-BMP2).

To investigate the activation of Smad signaling, C3H10T1/2 mesenchymal stem cells and MC3T3-E1 preosteoblasts were incubated with 1 M of CP-BMP2 recombinant proteins (CP-BMP2), control protein (Non-CP-BMP2) and vehicle in the same manner as in Example <10-2>.

As a result, in C2C12 myoblasts and MC3T3-E1 preosteoblasts, treatment of the CP-BMP2 recombinant proteins showed p-Smad 1/5/8 phosphorylation. And, treatment of the CP-BMP2 recombinant proteins showed significantly increased p-Smad 1/5/8 phosphorylation, compared to treatment of the control protein (non-CP-BMP2).

<15-2> Binding of CP-BMP2 Recombinant Protein and BMP Receptor

To investigate why the Smad signal of the CP-BMP2 recombinant proteins is stronger than that of the control protein, co-localization of BMP2 and BMP receptor was examined.

MC3T3-E1 preosteoblasts were cultured in 10% FBS-supplemented α-MEM (Modification). The cells were seeded in an 8-well slide chamber at a density of 5×10$^3$ cells/well, and incubated for 24 hours. The cells were incubated in serum-free media (α-MEM) for 2 hours, and treated with 1 uM of FITC-labeled Plain-BMP2 recombinant proteins (Plain-BMP2, BMP2 fused with his-tag only), FITC-labeled CP-BMP2 recombinant proteins (CP-BMP2) or vehicle, followed by incubation for 2 hours. The cells were washed with PBS three times, and fixed in 4% paraformaldehyde for 20 minutes. The cells were washed with PBS three times, followed by permeabilization with 0.5% Triton X-100 for 15 minutes and incubation in a blocking buffer (3% BSA-0.05% Triton X-100) for 30 minutes. Anti-BMP receptor II Ab (santa cruz, dilution 1:100) was diluted with an Ab reaction buffer (1% BSA and 0.05% Triton X-100), and 100 ul thereof was treated to cells, followed by incubation for 1 hour. The cells were washed with PBS, and then incubated for 30 minutes in a PE-conjugated anti-goat IgG Ab (Bioss, dilution 1:100)-diluted Ab reaction buffer. Then, the cells were washed with PBS and treated with Cy-5.5-conjugated anti-PDI Ab (Bioss, ER marker) or Cy-5-conjugated anti-giantin Ab (Bioss, gogi marker), followed by incubation for 1 hour. The cells mounted with VECTASHIELD Mounting (with DAPI) (Vector laboratories, Burlingame, Calif., USA), and the intracellular localization of the fluorescent signal was determined by confocal laser scanning microscopy (LSM800, Zeiss, Germany)

As shown in FIG. 43, the CP-BMP2 recombinant protein including aMTD permeated cells, and thus co-localized with ER or golgi. However, it was confirmed that the control protein (Plain-BMP2) and vehicle did not permeate cells.

As a result, since the aMTD-fused BMP (CP-BMP2 recombinant protein) is co-localized with BMP receptors in intracellular ER and golgi, strong Smad activity by CP-BMP2 recombinant protein is observed.

Example 16. Determination of Effect of CP-BMP2 Recombinant Proteins In Vivo

The effect of CP-BMP2 recombinant proteins on bone formation and regeneration was investigated.

<16-1> New Bone Formation 7.5 mg/kg of CP-BMP2 recombinant proteins (CP-BMP2), vehicle (diluent) or control protein (Non-CP-BMP2) were subcutaneously injected into the calvarial bone of the B6 mouse (6 weeks, male) for 4 weeks three times a week. After 4 weeks, the calvarial bone was separated, followed by decalcification for 3 weeks. Paraffin blocks of the calvarial bone were prepared, followed by sectioning. After deparaffination of the sections, new bone formation was determined by using Hematoxylin and Eosin (H&E) staining.

As shown in FIG. 44a, only few lining cells were observed on the surface of calvarial bone tissue in diluent treated group. In non-CP-BMP2 recombinant proteins treated group, the BMP2 protein without aMTD, showed increase of extra cellular matrix (ECM) formation on the surface of calvaria tissue, which indicated that the immature bone matrix formation. On the other hands, the significant increase of ECM formation was observed in CP-BMP2 recombinant proteins treated group, the BMP2 protein fused with aMTD.

As shown in FIG. 44b, the new bone formation was quantified by measuring newly formed ECM thickness. Although the non-CP-BMP2 recombinant proteins treated group showed more than 6 folds greater relative activity ($P<0.001$), CP-BMP2 recombinant proteins treated group showed more than 22 folds greater relative activity which compare to diluent treated group ($P<0.001$).

<16-2> Calvarial Critical-Sized Defect Model

The effect of CP-BMP2 recombinant proteins for bone regeneration in vivo was investigated by calvarial critical sized defect model using ICR mouse (6 weeks) (Dooyeol biothec, Seoul, Korea). The mice were anesthetized with Zoletil (60 mg/kg) and Xylazine (20 mg/kg) and exposed incision area by shaving scalp hair. For defect creation, head skin incision was performed; two defects on both sides of the calvaria were made by using 4 mm-diameter surgical trephine bur. Surgery sites were sutured and treated with Povidone iodine. After 24 hours of surgery, the CP-BMP2, non-CP-BMP2 or diluent was locally injected to surgery site, and the injection was repeated for 8 weeks three times a week during experimental periods. All mice were sacrificed after 9 weeks, and the calvarial bone was separated and bone regeneration was examined by x-ray and Micro-CT. The fixed calvarial tissues were exposed to soft X-rays (CMP-2, Softex Co., Tokyo, Japan) under optimized exposure condition (23 kV, 2 mA, 90 s). The exposed results were obtained by the developing film. Three-dimensional images from micro-CT scanning were analyzed with Adobe Photoshop CS6 (Adobe Systems, CA, USA) to measure regenerated bone areas.

As shown in FIGS. 45a and 45b, the group treated with CP-BMP2 recombinant protein (CP-BMP2) showed 8 times higher bone regeneration than the group treated with vehicle (diluent).

To determine administration frequency of the CP-BMP2 recombinant protein, to 4 groups of ICR mouse (6 weeks), each group having 6 mice, 7.5 mg/kg of CP-BMP2 recombinant proteins (CP-BMP2), vehicle (diluent) or control protein (Non-CP-BMP2) were subcutaneously injected once or three times a week for 8 weeks. The calvarial bone was separated and bone regeneration was examined by X-ray and Micro-CT.

As shown in FIGS. 46a and 46b, bond regeneration was observed in all groups treated with the CP-BMP2 recombinant protein once a week or three times a week. The administration frequency was determined as once a week for 8 weeks.

To determine the administration concentration of the CP-BMP2 recombinant protein, 0, 0.75, 3.75, 7.5, 15, 75, or 150 mg/kg of CP-BMP2 recombinant proteins (CP-BMP2) were subcutaneously injected to 7 groups of ICR mouse (6 weeks), each group having 10 mice, once a week for 8 weeks. The calvarial bone was separated and bone regeneration was examined by X-ray and Micro-CT.

As shown in FIGS. 47a and 47b, bond regeneration was observed in all groups treated with the CP-BMP2 recombinant protein. Excellent bone regeneration effect was also observed in the groups treated with low concentration (7.5 mg/kg). Thus, the administration concentration was determined as 7.5 mg/kg.

As a result, when 7.5 mg/kg of the CP-BMP2 recombinant protein was administered once a week for 8 weeks, excellent bone regeneration effect may be expected in mouse.

<16-3> Equine Bone Defect Model

To investigate the efficacy of the CP-BMP2 recombinant protein in a large animal, 3rd metatarsal bones of both hind limbs of a horse was drilled (diameter 4.5 mm×depth 10 mm) to prepare an equine hind limb hole defect model (FIGS. 48 and 49b). rBMP2 (BMP2; Korea) or CP-BMP2 recombinant protein (CP-BMP2) was subcutaneously injected to the defected site of the left limb, once a week for 8 weeks. Further, to compare the BMP2 administration method using a scaffold, rhBMP2 (Original; Cowell®, Korea) or CP-BMP2 recombinant protein (CP-BMP2), together with a collagen scaffold, were injected to the defected site of the right limb during operation. After operation, bone regeneration was examined by portable X-ray every week, and at 9 weeks, and the horse was sacrificed, followed by CT examination.

Structures of rBMP2 (BMP2), rhBMP2 (Original), and CP-BMP2 recombinant protein (CP-BMP2) were showed in FIG. 48, and information about the horse was showed in FIG. 49a, and images of X-ray and CT were showed in FIG. 49b.

As shown in FIG. 50, in the group with scaffold, the CP-BMP2 recombinant proteins (CP-BMP2) confirmed the bone regeneration effect similar to rhBMP2 (Original) (original: 1±0.35, CP-BMP2: 0.81±0.31, p=0.345). In the group without scaffold, the CP-BMP2 recombinant proteins (CP-BMP2) confirmed about 8.6-folds higher bone regeneration effect than rBMP2 (BMP2) (BMP2: 1±0.36, CP-BMP2: 8.68±1.31, $p<0.05$).

As shown in FIG. 49b, completely bone regeneration by treatment of the CP-BMP2 recombinant proteins was observed from CT at 9 weeks.

As a result, the CP-BMP2 recombinant protein confirmed excellent bone regeneration effect on mouse and horse, compared to the BMP2 recombinant protein lacking aMTD, suggesting efficient intracellular delivery of BMP2 by aMTD and effective regeneration of defected bone by the CP-BMP2 recombinant protein.

Example 17. Determination of Toxicity of CP-BMP2 Recombinant Proteins

To investigate toxicity of the CP-BMP2 recombinant protein in vivo, a toxicity assay was performed.

<17-1> Single Dose Acute Toxicity Assay

A toxicity assay was performed after single administration of ICR mouse (5 weeks) with high concentration of CP-BMP2 recombinant protein. A group was comprised of 5 male mice and 5 female mice. Each 75, 100, 150, or 200 mg/kg of the CP-BMP2 recombinant protein was intravenously administered once, or 1000 mg/kg thereof was subcutaneously administered. The survival of mouse was examined for 2 weeks. A control group was administered with a vehicle at a volume equal to the CP-BMP2 recombinant protein.

In FIG. 51, the survival rate for only 5 days was for acute toxicity of CP-BMP2 recombinant protein, but the examination was actually performed for 2 weeks.

As shown in FIG. 51, death of only one female mouse was observed in the group intravenously administered with 200 mg/kg of the CP-BMP2 recombinant protein, and all mice survived in other groups. Reduction in voluntary exercise was observed in the group subcutaneously administered with 1000 mg/kg of CP-BMP2 recombinant protein, but this symptom was not observed at 1 day after administration.

<17-2> Repeated Dose Toxicity Assay

A toxicity assay was performed after repeated subcutaneous administration of ICR mouse (6 weeks) with the CP-BMP2 recombinant protein for 2 weeks. A group was comprised of 5 male mice and 5 female mice.

The group treated with CP-BMP2 recombinant protein was administered with each 1.875, 3.75, or 7.5 mg/kg/day of the CP-BMP2 recombinant protein, and a control group was administered with a vehicle at a volume equal to the CP-BMP2 recombinant protein. For 2 weeks after administration, the mice were weighed. After 2 weeks, all mice were sacrificed, and measured the weights of the organs (brain, liver, heart, spleen, and kidney).

As shown in FIGS. 52a and 52b, all mice in the group treated with CP-BMP2 recombinant protein and the control group survived, and there were no significant weight changes in the body weight and organs.

As a result, it was confirmed that the CP-BMP2 recombinant protein has no in vivo toxicity.

Example 18. Determination of Pharmacokinetics of CP-BMP2 Recombinant

Proteins

To determinate of pharmacokinetics of CP-BMP2 recombinant proteins, bioavailability of the CP-BMP2 recombinant proteins was investigated in vitro and in vivo.

<18-1> Bioavailability in vivo

ICR mouse (male, 6 weeks) were intravenously administered with 30 mg/kg of FITC-labeled CP-BMP2 recombinant protein (CP-BMP2) or control protein; rBMP2 (BMP2), and then the blood was collected every 10 minutes, and the spleen was separated every 2 hours.

The blood was immediately put in an EDTA tube and mixed well, followed by centrifugation at 4,000 rpm and 4° C. for 5 minutes. Plasma was removed from the centrifuged blood, and only buffy coat was collected in a new microtube. 0.5 mL of RBC lysis buffer was put in the microtube, followed by vortexing. The microtube was left at room temperature for 5 minutes, followed by centrifugation at 4,000 rpm and 4° C. for 5 minutes. (When RBCs were not completely removed, 0.5 mL of RBC lysis buffer was put again, followed by vortexing). After removing a supernatant, a pellet was peripheral blood mononuclear cells (PBMCs), and added 0.3 mL of PBS, followed by pipetting.

The spleen was separated into single cells using a slide glass or cell strainer in the presence of PBS. The cells were collected in a microtube, followed by centrifugation at 4,000 rpm and 4° C. for 5 minutes. After removing a supernatant, 0.5 mL of RBC lysis buffer was added thereto, followed by vortexing. The microtube was left at room temperature for 5 minutes, followed by centrifugation at 4,000 rpm and 4° C. for 5 minutes. (When RBCs were not completely removed, 0.5 mL of RBC lysis buffer was put again, followed by vortexing). After removing a supernatant, a pellet was splenocytes, and added 0.5 mL of PBS, followed by pipetting. The PBMC and splenocyte were subjected to fluorescence-activated cell sorting (FACS) analysis (FACSCalibur; BD, Franklin Lakes, N.J.).

As shown in FIG. 53, in the PBMCs, the highest peak of the CP-BMP2 recombinant protein (CP-BMP2) was detected at 10 minutes, but no control protein (BMP2) was detected. In the splenocytes, the highest peak of the CP-BMP2 recombinant protein (CP-BMP2) was detected at 2 hours, whereas the highest peak of the control protein (BMP2) was detected at 10 minutes, but the peak was lower than that of the CP-BMP2 recombinant protein (CP-BMP2). High concentration of the CP-BMP2 recombinant protein (CP-BMP2) was detected and maintained for 8 hours, compared to the control protein (BMP2).

<18-2> Bioavailability Ex Vivo

The whole blood was obtained from ICR mouse (6 weeks), and then mixed with respective CP-BMP2 recombinant proteins (CP-BMP2) or control protein (BMP2; Plain-BMP2). A ratio of blood and protein was 7.5 ug of protein per 1 mL of blood, based on in vivo study. The blood and each protein were allowed to react at each time point. After reaction, plasma was separated from the blood, and histidine included in the plasma was detected by His-ELISA (Genscript Co.).

As shown in FIG. 54, in ex vivo, high concentration was also detected for a long period of time upon treatment of CP-BMP2, compared to treatment of BMP2 (Plain-BMP2).

<18-3> Bioavailability for Duration Time In Vivo 15 mg/kg of Cy5-labeled CP-BMP2 recombinant protein (CP-BMP2) or control protein (Non-CP-BMP2) were subcutaneously injected into the calvarial bone of ICR mouse (6 weeks). Distribution of Cy5-labeled proteins was measured at each time point by using a bio-imaging analyzer (KODAK Image Station 4000MM).

As shown in FIG. 55, high concentration of the CP-BMP2 recombinant proteins (CP-BMP2) was detected for a long period of time, compared to the control protein (Non-CP-BMP2).

As a result, the CP-BMP2 recombinant protein was stably maintained in vivo for a long period of time, indicating that when the CP-BMP2 recombinant protein is applied to drugs, it is maintained for a long period of time to efficiently activity and functions of BMP2 in vivo.

Those skilled in the art to which embodiments of the present invention pertain will appreciate that the embodiments of the present invention may be implemented in different forms without departing from the essential characteristics thereof. Therefore, it should be understood that the disclosed embodiments are not limitative, but illustrative in all embodiments. The scope of the present invention is made to the appended claims rather than to the foregoing description, and all variations which come within the range of equivalency of the claims are therefore intended to be embraced therein.

The invention claimed is:

1. A recombinant protein, which comprises a BMP being one of BMP2 and BMP7, and an advanced macromolecule transduction domain (aMTD) being composed of 9 to 13 amino acid residues and having improved cell or tissue permeability,
   wherein the aMTD is fused to one end or both ends of the BMP, and
   wherein the aMTD has the amino acid sequence of SEQ ID NO: 101.

2. The recombinant protein according to claim 1, which further comprises one or more solubilization domain (SD)(s) fused to the end(s) of one or more of the BMP and the aMTD, wherein the SD(s) independently have an amino acid sequence selected from the group consisting of SEQ ID NOs: 799 to 805.

3. The recombinant protein according to claim 2, wherein the recombinant protein is represented by any one of the following structural formula:
   A-B-C, A-C-B, B-A-C, B-C-A, C-A-B, C-B-A and A-C-B-C
   wherein A is the aMTD, B is the BMP having one of BMP2 and BMP7, and C is the SD.

4. The recombinant protein according to claim 1, wherein the BMP has an amino acid sequence selected from the group consisting of SEQ ID NOs: 815 to 818.

5. The recombinant protein according to claim 4, wherein the BMP is encoded by a polynucleotide sequence selected from the group consisting of SEQ ID NOs: 819 to 823.

6. The recombinant protein according to claim 1, wherein the aMTD is encoded by the polynucleotide sequence of SEQ ID NO: 341.

7. The recombinant protein of claim 2, wherein the SD(s), independently, are encoded by a polynucleotide sequence selected from the group consisting of SEQ ID NOs: 806 to 812.

8. The recombinant protein according to claim 1, wherein the fusion is formed via a peptide bond or a chemical bond.

9. The recombinant protein according to claim 1, wherein the recombinant protein is used for the regeneration of defected bone.

10. A method for preparing the recombinant protein of claim 1, comprising:
    culturing a transformant transformed with a recombinant expression vector comprising a polynucleotide that encodes the recombinant protein in a culture medium to produce the recombinant protein; and
    recovering the recombinant protein expressed by the culturing.

11. A pharmaceutical composition comprising the recombinant protein of claim 1 as an active ingredient; and a pharmaceutically acceptable carrier.

12. A method of regenerating of defected bone in a subject in need thereof comprising:
   administering to the subject a therapeutically effective amount of the recombinant protein according to claim 1.

* * * * *